(12) United States Patent
Park et al.

(10) Patent No.: US 11,753,431 B2
(45) Date of Patent: Sep. 12, 2023

(54) COMPOUNDS COMPRISING CLEAVABLE LINKER AND USES THEREOF

(71) Applicant: IntoCell, Inc., Daejeon (KR)

(72) Inventors: Taekyo Park, Daejeon (KR); Sung Ho Woo, Sejong-Si (KR); Sunyoung Kim, Daejeon (KR); Suho Park, Daejeon (KR); Jongun Cho, Daejeon (KR); Doohwan Jung, Daejeon (KR); Donghoon Seo, Daejeon (KR); Jaeho Lee, Sejong-Si (KR); Sangkwang Lee, Daejeon (KR); Sanghyeon Yun, Daejeon (KR); Hyang Sook Lee, Daejeon (KR); Okku Park, Daejeon (KR); Beomseok Seo, Daejeon (KR)

(73) Assignee: IntoCell, Inc., Daejeon (KR)

( * ) Notice: Subject to any disclaimer, the term of this patent is extended or adjusted under 35 U.S.C. 154(b) by 518 days.

(21) Appl. No.: 16/628,482

(22) PCT Filed: Jul. 3, 2018

(86) PCT No.: PCT/IB2018/000847
§ 371 (c)(1),
(2) Date: Jan. 3, 2020

(87) PCT Pub. No.: WO2019/008441
PCT Pub. Date: Jan. 10, 2019

(65) Prior Publication Data
US 2021/0388017 A1 Dec. 16, 2021

Related U.S. Application Data

(60) Provisional application No. 62/597,226, filed on Dec. 11, 2017.

(30) Foreign Application Priority Data

Jul. 4, 2017 (KR) .......................... 10-2017-0084805

(51) Int. Cl.
| | |
|---|---|
| *C07H 15/207* | (2006.01) |
| *A61K 47/68* | (2017.01) |
| *A61P 35/00* | (2006.01) |
| *A61K 51/04* | (2006.01) |
| *A61K 47/54* | (2017.01) |

(52) U.S. Cl.
CPC ......... *C07H 15/207* (2013.01); *A61K 47/549* (2017.08); *A61K 47/6803* (2017.08); *A61K 47/6835* (2017.08); *A61K 51/04* (2013.01); *A61P 35/00* (2018.01)

(58) Field of Classification Search
CPC .... C07H 15/207; A61K 47/68; A61K 47/549; A61K 51/04; A61P 35/00
See application file for complete search history.

(56) References Cited

U.S. PATENT DOCUMENTS

| | | | |
|---|---|---|---|
| 3,954,743 | A | 5/1976 | Koch |
| 4,540,828 | A | 9/1985 | Yang |
| 4,550,118 | A | 10/1985 | Sugino et al. |
| 5,070,096 | A | 12/1991 | Mohrs et al. |
| 5,279,920 | A | 1/1994 | Onodera et al. |
| 5,981,559 | A | 11/1999 | Nagaoka et al. |
| 2009/0233876 | A1 | 9/2009 | Auriol et al. |
| 2014/0249099 | A1 | 9/2014 | White et al. |
| 2014/0303376 | A1 | 10/2014 | Pang et al. |
| 2014/0309390 | A1 | 10/2014 | Yan |
| 2016/0159377 | A1 | 6/2016 | Wright |
| 2016/0184451 | A1 | 6/2016 | Kim et al. |
| 2017/0157262 | A1 | 6/2017 | Zhao et al. |
| 2018/0110874 | A1 | 4/2018 | Li |
| 2018/0222853 | A1 | 8/2018 | Wang et al. |
| 2021/0388017 | A1 | 12/2021 | Park et al. |
| 2021/0393795 | A1 | 12/2021 | Park et al. |
| 2022/0118104 | A1 | 4/2022 | Park et al. |

FOREIGN PATENT DOCUMENTS

| | | |
|---|---|---|
| DE | 1182232 B | 11/1964 |
| JP | 2005/291974 A | 10/2005 |
| KR | 10-2017-0031307 A | 3/2017 |

(Continued)

OTHER PUBLICATIONS

Aver'yanov et al., "Oxidation of aromatic compounds. III. Oxidation of substituted phenols and their O-derivatives in the HSO3F—PbO2 system," Zhurnal Organicheskoi Khimii, 31(8):1197-1207 (1995).
Benassi et al., "Howglucosylation triggers physical-chemical properties of curcumin: an experimental and theoretical study," Journal of Physical Organic Chemistry, 24(4):199-310 (2011).
CAS Registry No. 1087396-71-1.
CAS Registry No. 18001-14-4.
CAS Registry No. 2094867-09-9.
CAS Registry No. 2094950.01-1.
CAS Registry No. 2094951-37-6.
CAS Registry No. 716-42-7.
CAS Registry No. 80858-87-3.
CAS Registry No. 88-75-5.

(Continued)

*Primary Examiner* — Michael G. Hartley
*Assistant Examiner* — Jagadishwar R Samala
(74) *Attorney, Agent, or Firm* — Foley Hoag LLP; David P. Halstead

(57) ABSTRACT

Provided are a compound including a cleavable linker, a use thereof, and an intermediate compound for preparing the same, and more particularly, the compound including a cleavable linker of the present invention may include an active agent (for example, a drug, a toxin, a ligand, a probe for detection, etc.) having a specific function or activity, a $SO_2$ functional group which is capable of selectively releasing the active agent, and a functional group which triggers a chemical reaction, a physicochemical reaction and/or a biological reaction by external stimulation, and may further include a ligand (for example, oligopeptide, polypeptide, antibody, etc.) having binding specificity for a desired target receptor.

20 Claims, 7 Drawing Sheets

(56) References Cited

FOREIGN PATENT DOCUMENTS

| WO | WO-2014/134202 A1 | 9/2014 |
|----|-------------------|--------|
| WO | WO-2016/029324 A1 | 3/2016 |
| WO | WO-2016/118770 A1 | 7/2016 |
| WO | WO-2017/044043 A1 | 3/2017 |
| WO | WO-2019/008441 A1 | 1/2019 |
| WO | WO-2020/141459 A1 | 7/2020 |
| WO | WO-2020/141460 A2 | 7/2020 |

OTHER PUBLICATIONS

Chen et al., "Product class 7: aryl hypohalites, aryl peroxides, and aryloxy sulfur compounds," Science of Synthesis, 31:665-704 (2007).
Coelho et al., "Adipocyte secretome increases radioresistance of malignany melanocytes by improving cell survival and decreasing oxidative status," Radiation Research, 187(5):581-588 (2017).
Elsohly et al., "Synthetically Modified Viral Capsids as Versatile Carriers for Use in Antibody-Based Cell Targeting," Bioconjug Chem., 26(8):1590-1596 (2015).
Finnegan et al., "The lipopolysaccharide-induced metabolome signature in *Arabidopsis thaliana* reveals dynamic reprogramming of phytoalexin and phytoanticipin pathways," Plos One, 11(9):e0163572 (2016).
Gouasmat et al., "Catalytic Iron (III) Chloride Mediated Site-Selective Protection of Mono- and Disaccharides and One Trisaccharide," European Journal of Organic Chemistry, 2017(23):3355-3361 (2017).
Hakamata et al., "N-linked oligosaccharide processing enzymes as molecular targets for drug discovery," Journal of Applied Glycoscience, 53: 149-154 (2006).
International Search Report and Written Opinion for International Application No. PCT/IB2018/000847 dated Oct. 31, 2018.
International Search Report and Written Opinion for International Application No. PCT/IB2020/000018 dated May 27, 2020.
International Search Report and Written Opinion for International Application No. PCT/IB2020/000019 dated Jul. 8, 2020.
Kawa et al., "Glycosylation of a newly functionalized orthoester derivative," Molecules, 19(2):2602-2611 (2014).
Paquet et al., "Synthesis and in vitro biological properties of novel cationic derivatives of amphotericin B," Chemistry—A European Journal, 14(8):2465-2481 (2008).
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker," Bioconjugate Chemistry, 30: 1957-1968 (2019).
Park et al., "Introduction of Para-Hydroxy Benzyl Spacer Greatly Expands the Utility of Ortho-Hydroxy-Protected Aryl Sulfate System: Application to Nonphenolic Payloads," Bioconjugate Chemistry, 30: 1969-1978 (2019).
Reuillon et al., "Efficacious N-protection of O-aryl sulfamates with 2, 4-dimethoxybenzyl Groups," Organic & Biomolecular Chemistry, 10(37):7610-7617 (2012).
Strancar et al., "Phosphinate Inhibitors of UDP-N-Acetylmuramoyl-LAlanyl-D-Glutamate: L-Lysine Ligase (MurE)," Arch Pharm Chemistry in Life Sciences, 340: 127-134 (2007).
Turpin et al., "Synthesis and Biological Properties of Novel Pyridinioalkanoyl Thioesters (PATE) as Anti-HIV-1 Agents That Target the Viral Nucleocapsid Protein Zinc Fingers," Journal of Medicinal Chemistry, 42: 67-86 (1999).
Zhang et al., "Flavonoid metabolism: the synthesis of phenolic glucuronides and sulfates as candidate metabolites for bioactivity studies of dietary flavonoids," Tetrahedron, 68(22):4194-4201 (2012).
Ashton J et al., "Synthesis, Characterization, and Bioactivity of the Photoisomerizable Tubulin Polymerization Inhibitor azo-Combretastatin A4," Organic Letters, 17(18): 4546-4549 (2015).
Dyson G. and May P., "Chemistry of synthetic Drugs", Mir, 1964, pp. 12-19 w/ English Translation.
Lin et al., "Structural Identification of Chemical Constituents from Scutellaria biacalensis by HPLC-ESI-MS/MS and NMR Spectroscopy," Asian Journal of Chemistry, 25: 3799-3805 (2013).
Liu et al., "Zinc-mediated chain extension reaction of o-phenolic-1,3-diketone to o-phenolic-1,4-diketone," Letters in Organic Chemistry, 10(3): 216-222 (2013).
PubChem CD 102590900; "2-Nitro-4-(1H-1,2,3-triazole-1-ylmethyl)phenol" retrieved online <https://pubchem.ncbi.nlm.nih.gov/compound/102590900>: 6 pages (Create Date: Jan. 4, 2016).
Shi et al., "One-Pot UV Triggered o-Nitrobenzyl Dopamine Polymerization and Coating for Surface Antibacterial Applications," ACS Applied Materials and Interfaces, 8(48): 33131-33138 (2016).
Young et al., "Reactions of Organic Peroxides. Part IX.* Hydroperoxides of Some Alkyltetralins," Journal of the Chemical Society, 1958, p. 2288-2292.
CAS Registry No. 176312-66-6 Entered STN: May 16, 1996.
CAS Registry No. 621-44-3 Entered STN: Nov. 16, 1984.
Extended European Search Report for EP Application No. EP 18828726 dated Jul. 30, 2021.
International Preliminary Report on Patentability for International Application No. PCT/IB2020/000018 dated Jul. 15, 2021.
International Preliminary Report on Patentability for International Application No. PCT/IB2020/000019 dated Jul. 15, 2021.
Park et al., "Sulfonate Version of OHPAS Linker has Two Distinct Pathways of Breakdown: Elimination Route Allows Para-Hydroxy-Protected Benzylsulfonate (PHP-BS) to Serve as an Alternative Self-Immolative Group," Bioconjugate Chem., Manuscript (2020).
Extended European Search Report for EP Application No. EP20736028 dated Feb. 2, 2023.
Registry[online], Columbus, Ohio, US, STN Search Report US Registry, pp. 1-4 (Publication Date: May 3, 2017).

COMPOUNDS COMPRISING CLEAVABLE LINKER AND USES THEREOF

RELATED APPLICATIONS

This application is a United States National Stage of International Patent Application No. PCT/IB18/00847, filed on Jul. 3, 2018, which claims the benefit of U.S. Provisional Patent Application No. 62/597,226, filed on Dec. 11, 2017, and Korean Patent Application No. 10-2017-0084805, filed on Jul. 4, 2017. The contents of each of these applications is hereby incorporated by reference in its entirety.

BACKGROUND

Antibody-drug conjugates (ADCs) are emerging as a powerful class of anti-tumor agents with efficacy across a range of cancers. ADCs are commonly composed of three distinct features: a cell-binding agent or targeting moiety; a linker; and a cytotoxic agent. The linker component of ADC is an important feature in developing targeted anti-cancer agents that possess a desirable target-specificity, i.e., high activity in tumor cells, but with low activity in healthy cells.

Therefore, there is a need for improved linkers useful for preparing ADCs.

SUMMARY

Provided herein are conjugates of Formula (I'):

$$(D-L)_n\text{-}(CB)_{cb} \qquad (I')$$

or a pharmaceutically acceptable salt thereof,
wherein:
CB is a targeting moiety;
cb and n are each independently integers having a value of 1 to about 20, preferably from 1 to about 10;
each D-L independently is a group having the structure of Formula (I"):

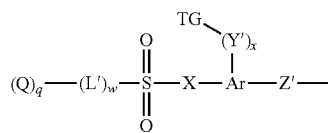

(I")

Q is an active agent linked to L' via a heteroatom, preferably O or N;
Z' is a linking group;
L' is a spacer moiety attached to the $SO_2$ via a heteroatom selected from O, S, and N, preferably O or N, and is selected such that cleavage of the bond between L' and $SO_2$ promotes cleavage of the bond between L' and Q to release the active agent;
X is —O—, —$C(R^b)_2$—, or —N(R')—, preferably —O—;
Ar represents a ring, such as aryl, heteroaryl, cycloalkyl, or heterocycloalkyl, preferably aryl or heteroaryl;
Y' is —$(CR^b{}_2)_y N(R^a)$—, —$(CR^b{}_2)_y O$—, or —$(CR^b{}_2)_y S$—, positioned such that the N, O, or S atom is attached to TG if y is 1;
X and Y' are positioned on adjacent atoms of Ar;
TG is a triggering group that, when activated, generates an N, O, or S atom capable of reacting with the $SO_2$ to displace $(Q)_q\text{-}(L')_w$ and form a 5- or 6-membered ring including X—$SO_2$ and the intervening atoms of Ar;

q is an integer having a value from 1 to about 20, preferably from 1 to about 10;
w, x, and y are each independently an integer having a value of 0 or 1;
each $R^a$ and $R^c$ is independently hydrogen or lower alkyl; and
each $R^b$ is independently hydrogen or lower alkyl; or
two $R^b$, together with the atom to which they are attached, form a 3-5-membered ring, preferably a 3-4-membered ring;
provided that when w is 0, q is 1.

The present invention also relates to compositions (e.g., pharmaceutical compositions) comprising a compound of Formula (I') and a carrier (e.g., a pharmaceutically acceptable carrier).

In one aspect, the invention provides conjugates of Formula (I'), and compositions comprising such conjugates, e.g., for use in therapy, imaging, as sensors, as molecular switches, as molecular machines, and/or as nanomachines.

In another aspect, the invention further provides conjugates of Formula (I') and pharmaceutical compositions thereof, for use in a method for delivering an active agent to a cell, wherein the targeting moiety is selected to bind to a molecule associated with a target cell. In particular, the present compounds, conjugates, and compositions may be useful for inhibiting abnormal cell growth or treating a proliferative disorder in a mammal (e.g., a human), such as where the target cell is a cancer cell and the targeting moiety is selected to bind to a molecule associated with the cancer cell (and not associated with healthy cells, or at least preferentially associated with tumor cells rather than healthy cells).

The present conjugates of Formula (I') and pharmaceutical compositions thereof may be useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

DETAILED DESCRIPTION

Figure 1:
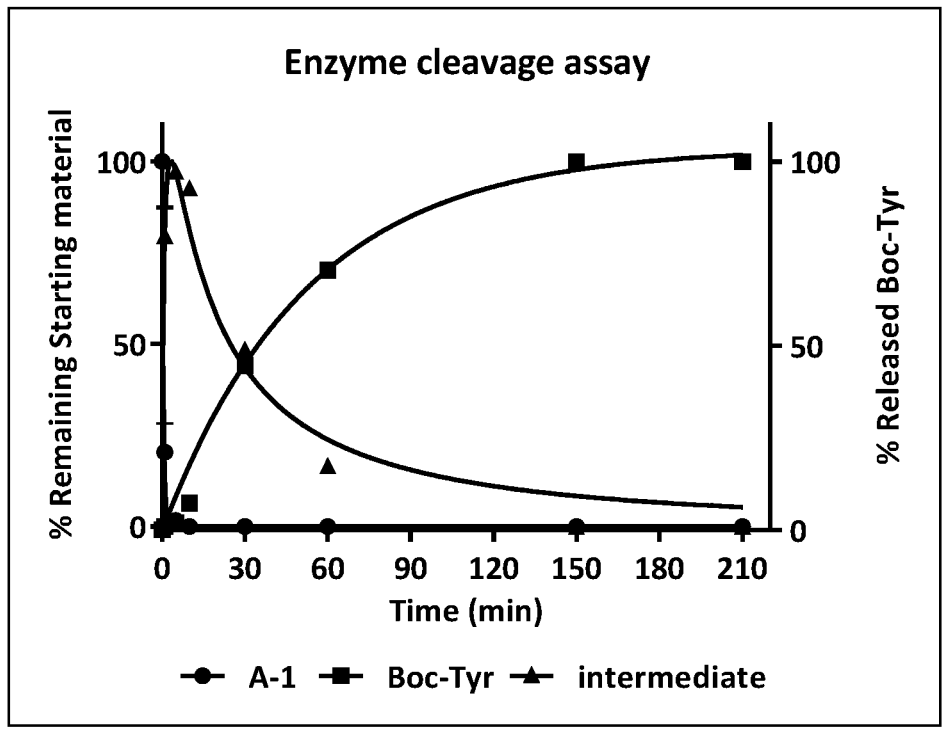
FIG. 1 shows results of an enzymatic cleavage assay of Compound A-1.
Figure 2:
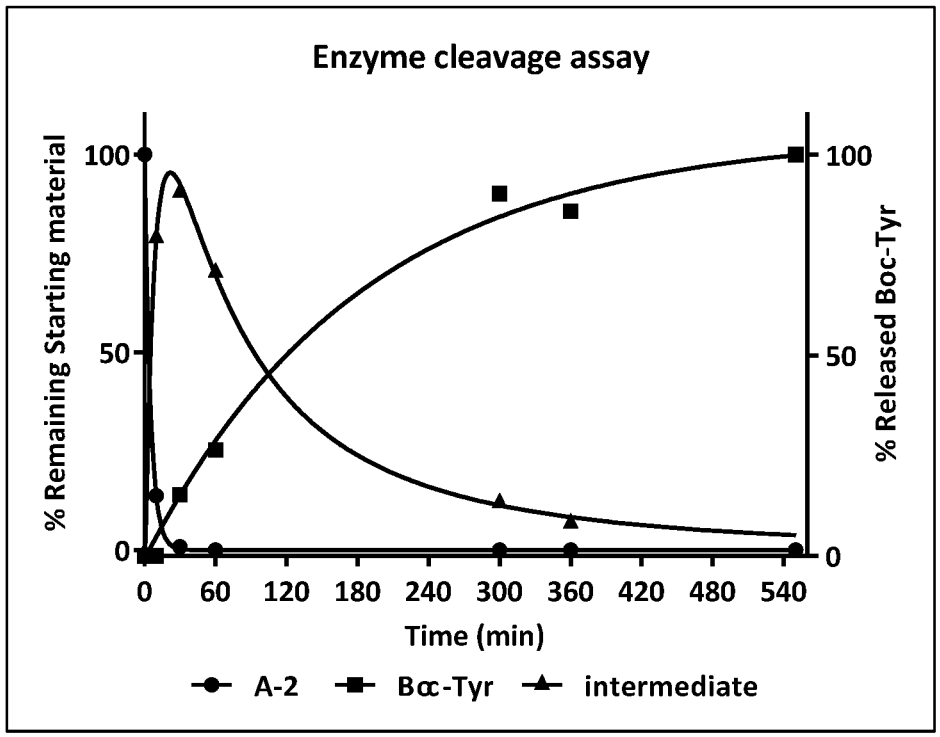
FIG. 2 shows results of an enzymatic cleavage assay of Compound A-2.
Figure 3:
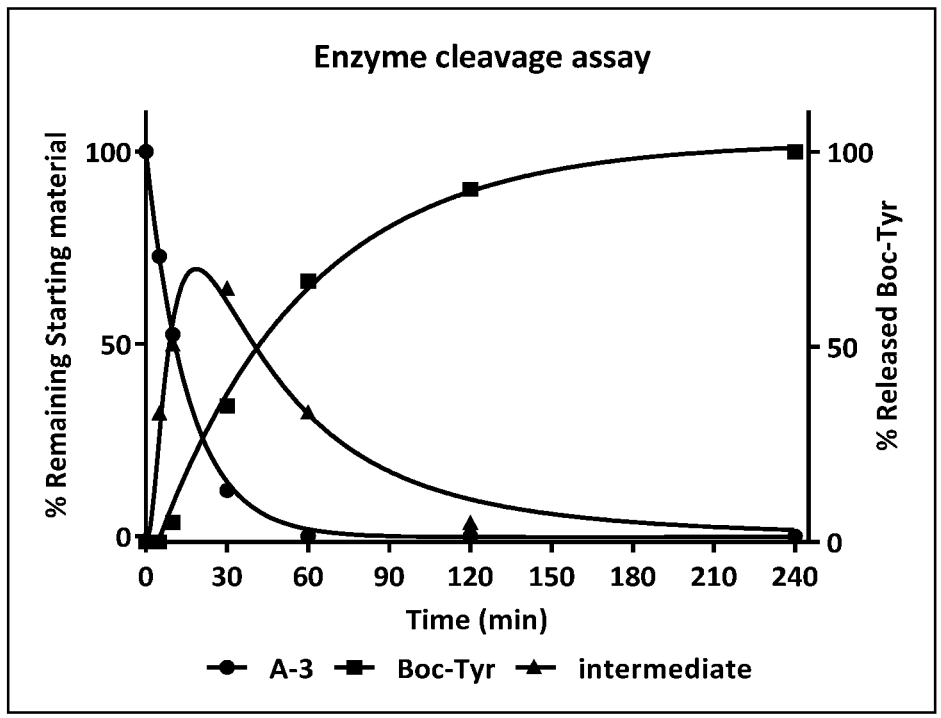
FIG. 3 shows results of an enzymatic cleavage assay of Compound A-3.
Figure 4:
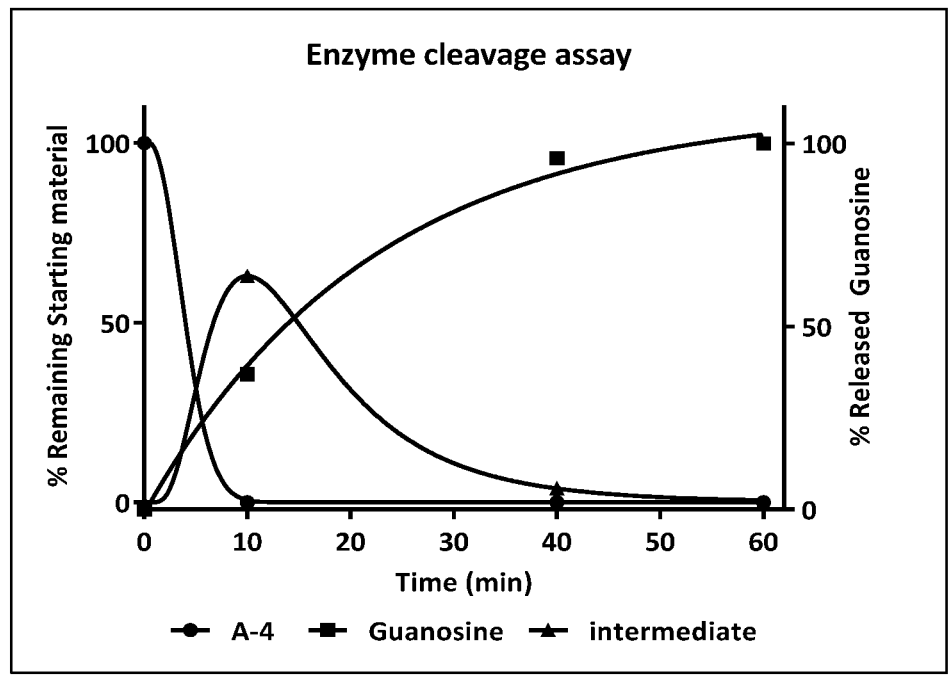
FIG. 4 shows results of an enzymatic cleavage assay of Compound A-4.
Figure 5:
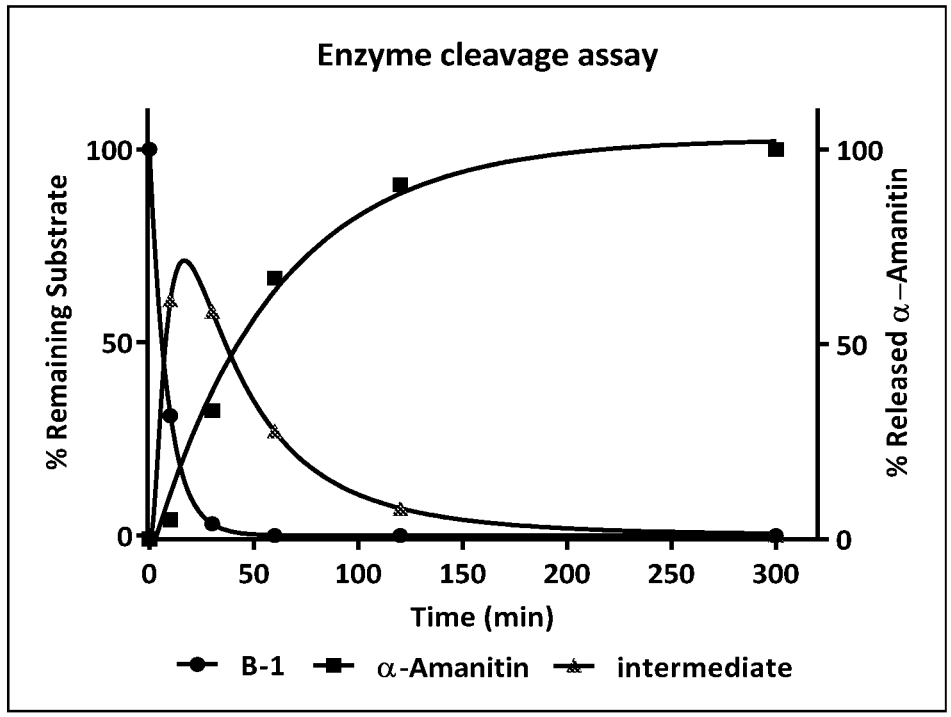
FIG. 5 shows results of an enzymatic cleavage assay of Compound B-1.
Figure 6:
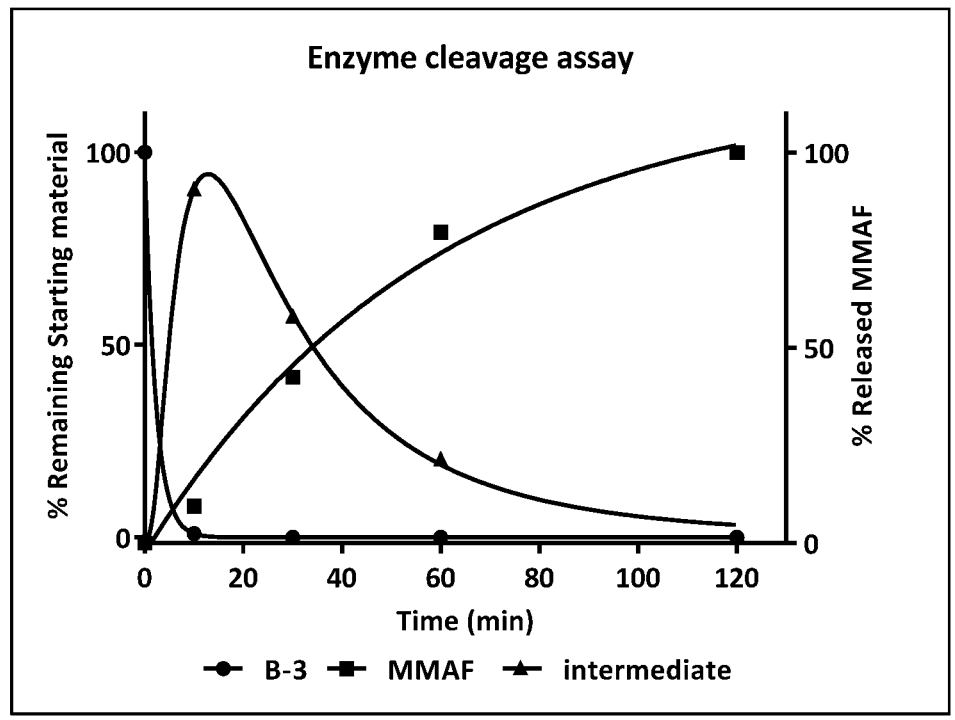
FIG. 6 shows results of an enzymatic cleavage assay of Compound B-3.
Figure 7:
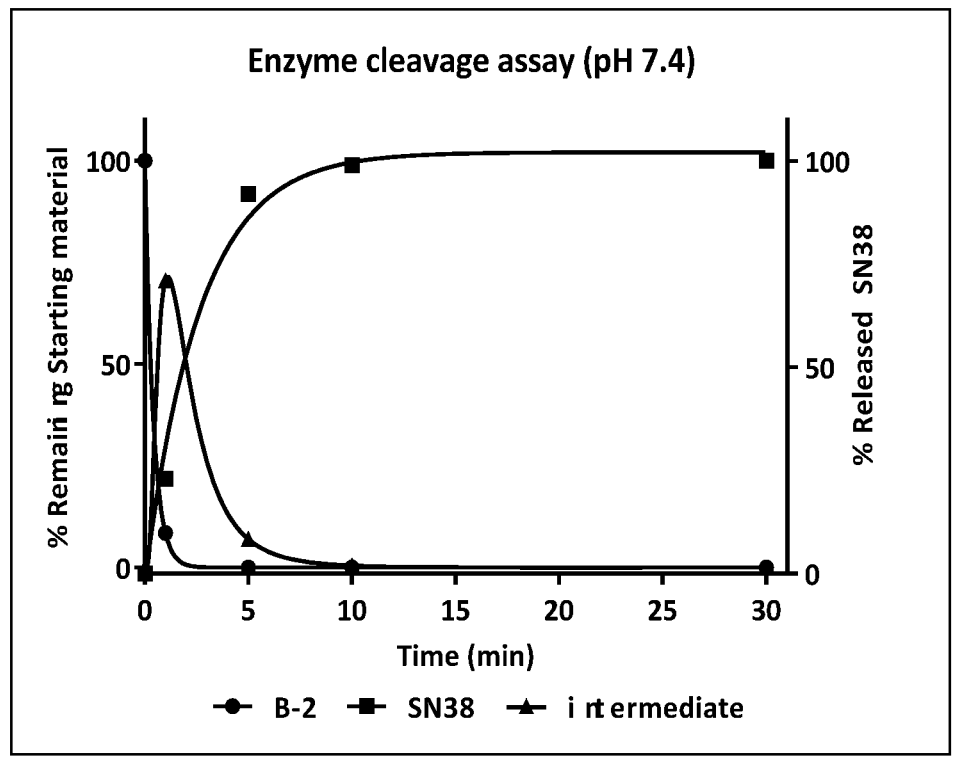
FIG. 7 shows results of an enzymatic cleavage assay (pH 7.4) of Compound B-2.
Figure 8:
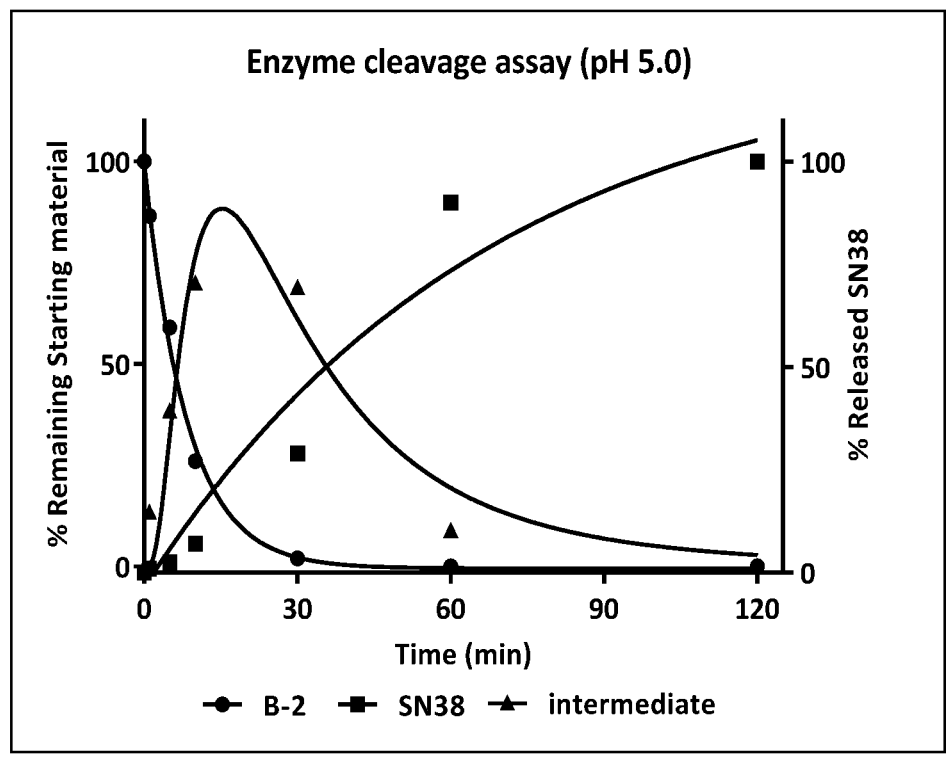
FIG. 8 shows results of an enzymatic cleavage assay (pH 5.0) of Compound B-2.
Figure 9:
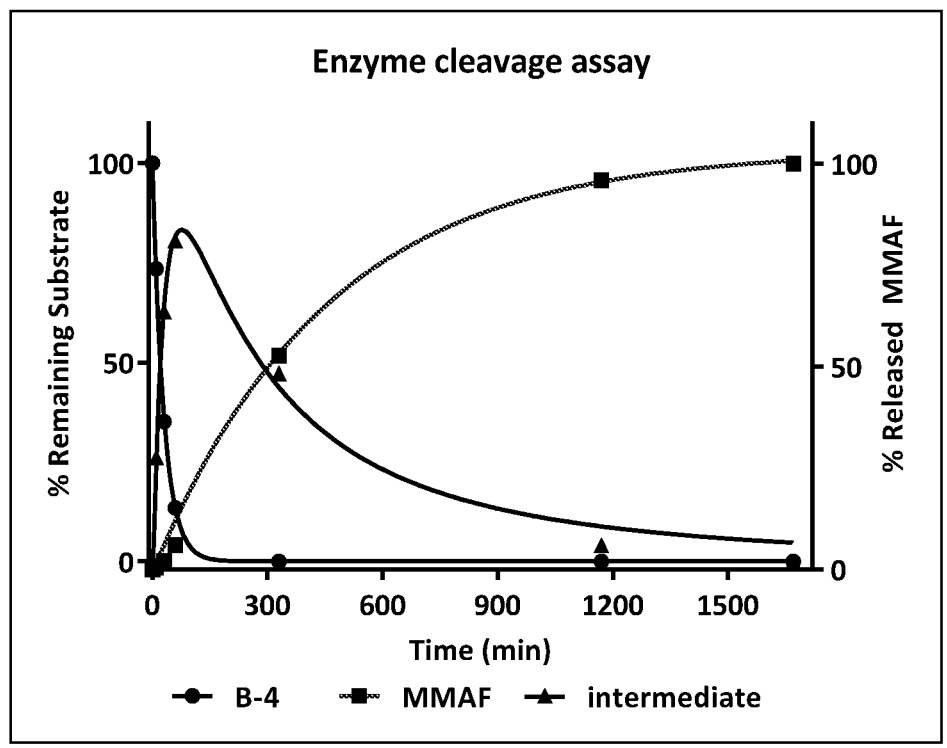
FIG. 9 shows results of an enzymatic cleavage assay of Compound B-4.
Figure 10:
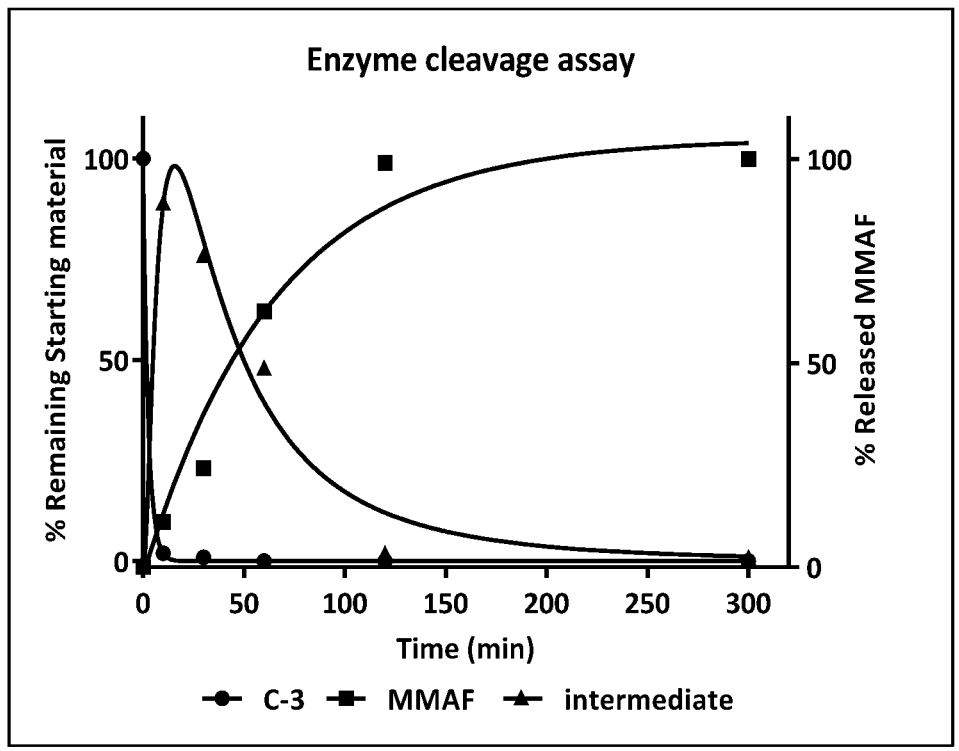
FIG. 10 shows results of an enzymatic cleavage assay of Compound C-3.
Figure 11:
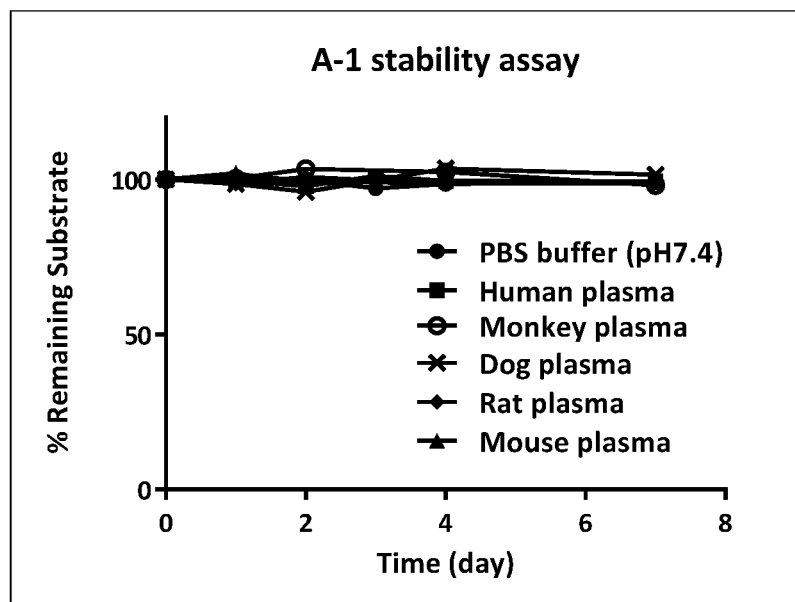
FIG. 11 shows results of stability analysis of Compound A-1.

The present invention relates to compounds and conjugates comprising a cleavable linker and uses thereof. Representative compounds and conjugates disclosed herein comprise an active agent (e.g., a chemical factor, a biological factor, a hormone, an oligonucleotide, a drug, a toxin, a ligand, a probe for detection, etc.) having a desired function or activity, a functional group that undergoes a chemical reaction (e.g., a physicochemical reaction and/or a biological reaction) under predetermined conditions to release a nucleophilic heteroatom, and an $SO_2$ functional group positioned proximal to the nucleophilic heteroatom so that it can react with the nucleophilic heteroatom in an intramolecular cyclization reaction to release the active agent. In some embodiments, the compounds and conjugates disclosed herein further comprise a targeting moiety (e.g., oligopeptide, polypeptide, antibody, etc.) having binding specificity for a desired target receptor or other molecule associated with a target cell.

Definitions

The meaning of the term "alkyl" is understood in the art. For example, "alkyl" used alone or as part of a larger moiety, such as "alkoxy", "haloalkyl", "cycloalkyl", "heterocycloalkyl", and the like, may refer to a straight chain or branched hydrocarbon which is completely saturated. Typically, a straight chain or branched alkyl group is an acyclic group having from 1 to about 20 carbon atoms, preferably from 1 to about 10 carbon atoms, unless otherwise defined. Examples of straight chain and branched alkyl groups include, but are not limited to, methyl, ethyl, propyl, isopropyl, n-butyl, sec-butyl, tert-butyl, n-pentyl, n-hexyl, n-heptyl, and n-octyl. A $C_1$-$C_6$ straight chain or branched alkyl group is also referred to as a "lower alkyl" group. Alkyl groups having two open valences are sometimes referred to with an "ene" suffix, as in alkylene. Exemplary alkylene groups include methylene, ethylene, propylene, and the like.

Moreover, the term "alkyl" (or "lower alkyl") may include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. The skilled artisan will understand that the moieties substituted on the hydrocarbon chain can themselves be substituted, if appropriate. For example, the substituents of a substituted alkyl may include substituted and unsubstituted forms of alkyl, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_x$-$C_y$" when used in conjunction with a chemical moiety, such as, for example, acyl, acyloxy, alkyl, alkenyl, alkynyl, or alkoxy may include groups that contain from x to y carbons in the chain, wherein "x" and "y" are integers selected from 1 to about 20, and wherein x is an integer of lesser value than y, and x and y are not the same value. For example, the term "$C_x$-$C_y$-alkyl" refers to substituted or unsubstituted saturated hydrocarbon groups, including straight-chain alkyl and branched-chain alkyl groups that contain from x to y number of carbons in the chain, including haloalkyl groups such as trifluoromethyl and 2,2,2-tirfluoroethyl, etc. The terms "$C_2$-$C_y$-alkenyl" and "$C_2$-$C_y$-alkynyl" refer to substituted or unsubstituted unsaturated aliphatic groups analogous in length and possible substitution to the alkyls described above, but that contain at least one double or triple bond respectively. As applied to heteroalkyls, "$C_x$-$C_y$," indicates that the group contains from x to y number of carbons and heteroatoms in the chain. As applied to carbocyclic structures, such as aryl and cycloalkyl groups, "$C_x$-$C_y$" indicates that the ring comprises x to y number of carbon atoms in the ring.

The meaning of the term "alkoxy" is understood in the art, and, for example, may refer to an alkyl group, preferably a lower alkyl group, having an oxygen attached thereto. Representative alkoxy groups include methoxy, ethoxy, propoxy, tert-butoxy and the like.

The terms "hal", "halo", and "halogen" are used interchangeably throughout, and refer to fluorine or fluoro (F), chlorine or chloro (Cl), bromine or bromo (Br), or iodine or iodo (I).

The meaning of the term "cycloalkyl" is understood in the art, and, for example, may refer to a substituted or unsubstituted cyclic hydrocarbon which is completely saturated. Cycloalkyl includes monocyclic and bicyclic rings. Typically, a monocyclic cycloalkyl group has from 3 to about 10 carbon atoms, more typically 3 to 8 carbon atoms, unless otherwise defined. The second ring of a bicyclic cycloalkyl may be selected from saturated, unsaturated, and aromatic rings. Cycloalkyl includes bicyclic molecules in which one, two, or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The meaning of the term "aryl" is understood in the art, and, for example, may refer to substituted or unsubstituted single-ring aromatic groups in which each atom of the ring is carbon. Preferably, the ring is a 5-to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkyls, aryls, heteroaryls, and/or heterocyclyls. Aryl groups include benzene, naphthalene, phenanthrene, phenol, aniline, and the like.

The meaning of the terms "heterocyclyl" and "heterocycle" are understood in the art, and, for example, may refer to substituted or unsubstituted non-aromatic ring structures, preferably 3-to 10-membered rings, more preferably 3-to 7-membered rings, whose ring structures include at least one heteroatom, preferably one to four heteroatoms, more preferably one or two heteroatoms. Such heterocycles also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkyls, aryls, heteroaryls, and/or heterocyclyls. Heterocyclyl groups include, for example, piperidine, piperazine, pyrrolidine, morpholine, lactones, lactams, and the like.

The meaning of the term "heteroaryl" is understood in the art, and, for example, may refer to substituted or unsubstituted aromatic single ring structures, preferably 5-to 7-membered rings, more preferably 5-to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or heteroatoms of the moiety. The skilled artisan will understand that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In some embodiments, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, such as, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an alkyl, an aralkyl, or an aromatic or heteroaromatic moiety. The skilled artisan will understand that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

The term "subject" to which administration is contemplated includes, for example, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition can, for example, refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

In certain embodiments, compounds and conjugates disclosed herein may be used alone or conjointly administered with another type of therapeutic compound or agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds and conjugates can be administered either in the same formulation or in a separate formulation, either concomitantly or sequentially. In certain embodiments, the different therapeutic compounds and conjugates can be administered within one hour, 12 hours, 24 hours, 36 hours, 48 hours, 72 hours, or a week of one another. Thus, a subject who receives such treatment can benefit from a combined effect of different therapeutic compounds and conjugates.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

Compounds and Conjugates of the Invention

The present disclosure provides conjugates of Formula (I'):

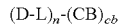 (I')

or a pharmaceutically acceptable salt thereof,
wherein:
CB is a targeting moiety;
cb and n are each independently integers having a value of 1 to about 20, preferably from 1 to about 10;
each D-L independently is a group having the structure of Formula (I"):

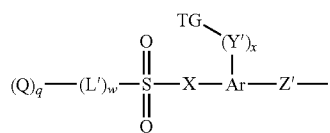 (I")

each Q is, independently, an active agent linked to L' via a heteroatom, preferably O or N;
Z' is a linking group;
L' is a spacer moiety attached to the $SO_2$ via a heteroatom selected from O, S, and N, preferably O or N, and is selected such that cleavage of the bond between L' and $SO_2$ promotes cleavage of the bond between L' and Q to release the active agent;
X is —O—, —C($R^b$)$_2$—, or —N(R')—, preferably —O—;
Ar represents a ring, such as aryl, heteroaryl, cycloalkyl, or heterocycloalkyl, preferably aryl or heteroaryl;
Y' is —(C$R^b_2$)$_y$N($R^a$)—, —(C$R^b_2$)$_y$O—, or —(C$R^b_2$)$_y$S—, positioned such that the N, O, or S atom is attached to TG if y is 1;
X and Y' are positioned on adjacent atoms of Ar;
TG is a triggering group that, when activated, generates an N, O, or S atom capable of reacting with the $SO_2$ to displace (Q)$_q$-(L')$_w$ and form a 5-6-membered ring including X—$SO_2$ and the intervening atoms of Ar;
q is an integer having a value from 1 to about 20, preferably from 1 to about 10;
w, x, and y are each independently an integer having a value of 0 or 1;
each $R^a$ and $R^c$ is independently hydrogen or lower alkyl; and
each $R^b$ is independently hydrogen or lower alkyl; or
two $R^b$, together with the atom to which they are attached, form a 3-5-membered ring, preferably a 3-4-membered ring,
provided that when w is 0, q is 1.

Each active agent can be any suitable active agent, as described in greater detail below. While many traditional conjugation methods require having certain functional groups, such as amines or hydroxyl groups, to form a stable linkage, the disclosure herein provides strategies for forming connections using functional groups, such as phenols and tertiary amines, to form stable linkages in the conjugates disclosed herein, while still permitting release under the predetermined conditions that activate the triggering group.

Many suitable triggering groups are known in the art, and exemplary triggering groups and the conditions that activate them are discussed below, such as moieties described for Y below. Some triggering groups include the N, O, or S atom, but in a non-nucleophilic form. For example, an $NO_2$ group is a triggering group that, under reductive conditions, is reduced to an $NH_2$ or NHOH group that can react with the $SO_2$, and an acetate group is a triggering group that, under hydrolytic conditions, is hydrolyzed to a hydroxyl group that can react with the $SO_2$. Other triggering groups do not include the N, O, or S atom, but when activated are converted to a nucleophilic N, O, or S atom. For example, a boronate group is a triggering group that, under oxidative conditions (such as peroxide), is converted to a hydroxyl group that can react with the $SO_2$. Preferably, the triggering group is selected such that the conditions that activate it do so selectively, without cleaving or degrading other portions of the conjugate, such as the targeting moiety. Once the nucleophilic N, O, or S atom is generated, that atom intramolecularly attacks the $SO_2$ moiety to form a ring, expelling the moiety (Q)$_q$-(L')$_w$-H, where the H is bonded to the heteroatom of Q or L' that was formerly attached to the $SO_2$ moiety.

In embodiments where w is 0, q is 1 and Q is directly attached to the $SO_2$ via a heteroatom. Accordingly, activating the triggering group generates a nucleophilic heteroatom that intramolecularly attacks the $SO_2$ moiety to form a ring, expelling the active agent Q-H, where the H is bonded to the heteroatom formerly attached to $SO_2$.

In embodiments where w is 1, L' may be selected to permit attachment of multiple occurrences of Q, which may be the same or different. Accordingly, each instance of Q is indirectly attached to the $SO_2$ via a spacer moiety. In such embodiments, activating the triggering group generates a nucleophilic heteroatom that intramolecularly attacks the $SO_2$ moiety to form a ring, expelling the moiety (Q)$_q$-L'-H, where the H is bonded to the heteroatom in L' that was formerly attached to $SO_2$. In such embodiments, the released heteroatom triggers an intramolecular reaction that expels the active agent(s) Q (such as if Q has a tertiary amine that was attached to L' as a quaternary ammonium) or Q-H. For example, the heteroatom may undergo an intramolecular cyclization reaction with an ester moiety formed with a hydroxyl of Q-H, forming a ring and ejecting the active agent Q-H. Alternatively, the heteroatom may undergo an intramolecular tautomerization that expels the active agent Q or Q-H.

Ar can be any suitable ring, including a ring of a bicycle or other polycycle, so that the moieties that undergo intramolecular cyclization are held in close proximity to facilitate that reaction after activation of the triggering group. The planar character of aromatic and heteroaromatic rings is preferred, as the rigid geometry of substituents on such rings ensures favorable placement of the reactive moieties, although other types of rings, such as cycloalkenyl or heterocycloalkyl, can enforce similar geometries. A five- or six-membered ring, and/or the number or identities of heteroatoms in the ring, and/or substituents (e.g., electron-donating or electron-withdrawing substituents) on other the ring, may be selected to modulate the rate of cyclization based on the resulting bond angles of the ring. Similarly, the more flexible conformations of cycloalkyl and heterocyclyl rings can be useful when it is desired to slow the rate of intramolecular cyclization.

Z' can be any suitable linking group that connects Ar to one or more CB groups. Typically, the linking group should be sufficiently hydrophilic to promote water-solubility and discourage aggregation of the conjugate, such as by including moieties such as polyethylene glycol moieties, peptide sequences, charge-bearing moieties (such as carboxylates, amines, nitrogen-containing rings, etc.), etc. to balance the hydrophobic character of any alkyl chains that may be included. Because it is often advantageous to prepare conjugates in a modular fashion, Z' may contain a linking unit, a functional group that results from the conjugation of one reactive moiety to another. Representative linking units are discussed in greater detail below (e.g., in connection with the variable Z), and common linking groups include amides, triazoles, oximes, carbamates, etc. Representative Z' groups include $L^{1'}$-Z groups as discussed in greater detail below. In some embodiments, all of the D-L groups attached to each CB are identical, while in other embodiments, each CB may be attached to two or more distinct D-L groups. For example, some D-L groups may have a triggering group that is activated under a first condition, while other D-L groups may have a triggering group that is activated under a second condition, so that, for example, one active agent can be selectively released under the first condition, but a second active agent can be selectively released under the second condition.

The disclosure also provides compounds that may serve as intermediates or reagents in the formation of group D-L in formula (I'), as described in Formula (I"). Thus, in some embodiments, provided herein are compounds of Formula (Ia):

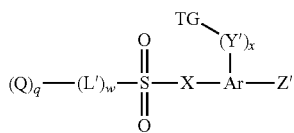

(Ia)

or a pharmaceutically acceptable salt thereof, wherein:
each Q is, independently, an active agent linked to L' via a heteroatom, preferably O or N;
Z' is absent or a linking group;
L' is a spacer moiety attached to the $SO_2$ via a heteroatom selected from O, S, and N, preferably O or N, and is selected such that cleavage of the bond between L' and $SO_2$ promotes cleavage of the bond between L' and Q to release the active agent;
X is —O—, —$CR^a{}_2$—, or —NR'—, preferably —O—;
Ar represents a ring, such as aryl, heteroaryl, cycloalkyl, or heterocycloalkyl, preferably aryl or heteroaryl;
Y' is —$(CR^b{}_2)_y$N($R^a$)—, —$(CR^b{}_2)_y$O—, or —$(CR^b{}_2)_y$S—, positioned such that the N, O, or S atom is attached to TG if y is 1;
X and Y' are positioned on adjacent atoms of Ar;
TG is a triggering group that, when activated, generates an N, O, or S atom capable of reacting with the $SO_2$ to displace $(Q)_q$-$(L')_w$ and form a 5-6-membered ring including X—$SO^2$ and the intervening atoms of Ar;
q is an integer having a value from 1 to about 20, preferably from 1 to about 10;
w, x, and y are each independently an integer having a value of 0 or 1;

each $R^a$ and $R^c$ is independently hydrogen or lower alkyl; and
each $R^b$ is independently hydrogen or lower alkyl; or
two $R^b$, together with the carbon atom to which they are attached, form a 3-5-membered ring, preferably a 3-4-membered ring.

In certain embodiments of Formulas (I') and (Ia), —Y' is —$(CH_2)_y$NR"—, —$(CH_2)_y$O— or —$(CH_2)_y$S—, positioned such that the N, O, or S atom is attached to TG if y is 1; R" is hydrogen or $C_1$-$C_6$-alkyl; and y is an integer having a value of 0 or 1. In some such embodiments, TG is a β-galactoside, β-glucuronide, or a combination of β-galactoside and β-glucuronide.

In some embodiments of Formulas (I') and (Ia), (L')W links each Q to the —$SO_2$—; and each Q is an active agent linked to one of the L' groups through a heteroatom, preferably O or N, and forming an —O—, an —OC(O)—, an —OC(O)O— or an —OC(O)NH— linkage including the heteroatom of Q.

In other embodiments, $(Q)_q$-$(L')_w$-is selected from:

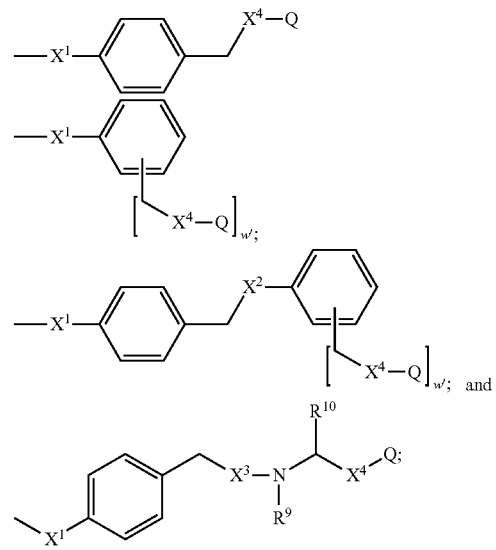

wherein:
Q is an active agent linked to L' through a heteroatom, preferably O or N,
$X^4$ is absent or forms an —O—, an —OC(O)—, an —OC(O)O— or an —OC(O)NH— linkage including the heteroatom of Q;
$X^1$ is —O— or —$NR^a$—;
$X^2$ is —O—, —OC(O)—, —OC(O)O— or —OC(O)NH—;
$X^3$ is —OC(=O)—;
w' is an integer having a value of 1, 2, 3, 4, or 5;
$R^9$ and $R^{10}$ are each independently hydrogen, alkyl, aryl, or heteroaryl, wherein alkyl, aryl, and heteroaryl are unsubstituted or substituted with one or more substituents, e.g., selected from alkyl, —$(CH_2)_u$$NH_2$, —$(CH_2)_u$$NR^{u1}R^{u2}$, and —$(CH_2)_u$$SO_2R^{u3}$;
$R^{u1}$, $R^{u2}$, and $R^{u3}$ are each independently hydrogen, alkyl, aryl, or heteroaryl; and
u is an integer having a value of 1 to about 10.

In some such embodiments, $(Q)_q$-$(L')_w$-is selected from:

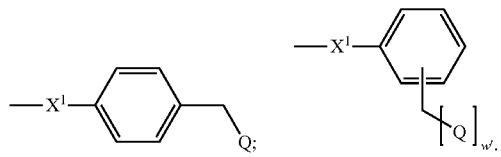

Further, the invention provides intermediates for preparing conjugates according to Formula (I') or compounds according to Formula (Ia), wherein $(Q)_q$-$(L')_w$ in those Formulas is replaced by a leaving group, such as a halogen (preferably fluorine), to permit attachment of $(Q)_q$-$(L')_w$.

In certain such embodiments, Z' includes a reactive group (e.g., a precursor group, as discussed in greater detail below with respect to Z) that can be used to attach the compound to a triggering agent, such as a CB (e.g., to prepare a compound of Formula (I') as discussed in greater detail above), to a solid surface (e.g., to form a solid-supported array, or sensor particles), or to any other molecule or support of interest. In certain preferred embodiments, the compound of Formula (I') is selected from:

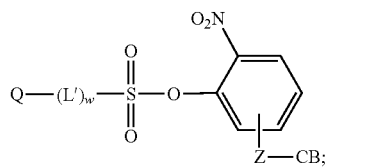

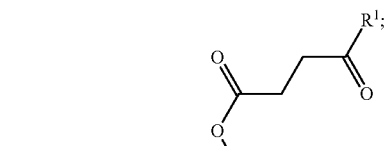

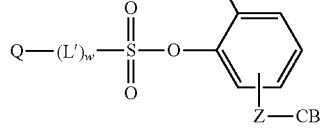

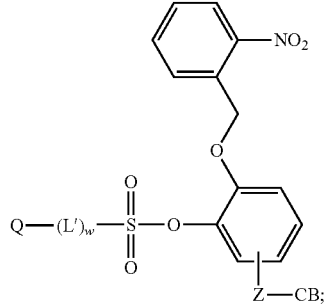

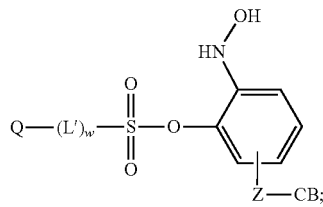

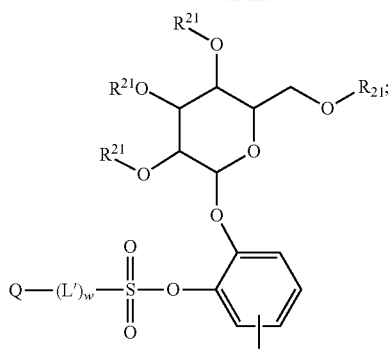

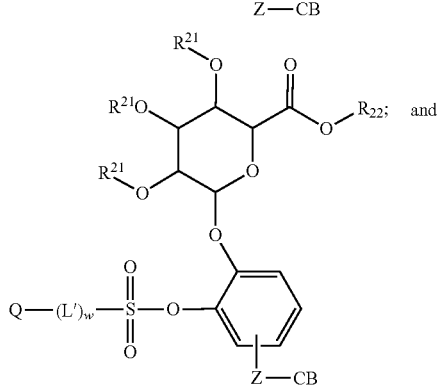

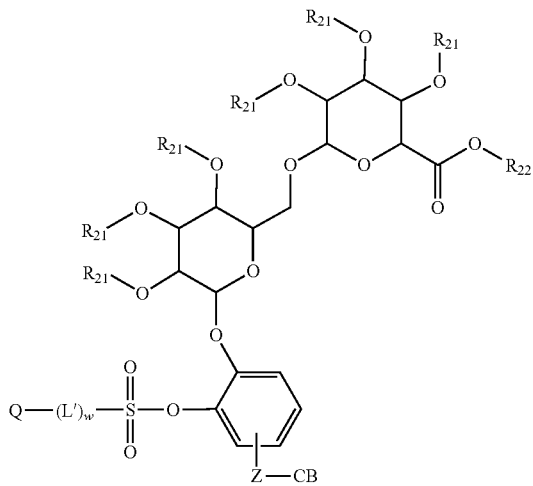

wherein:

$R^1$ is $C_1$-$C_6$ alkyl; and $R^{21}$ and $R^{22}$ are each independently hydrogen or $C_1$-$C_6$-alkyl.

In other embodiments, the compound of Formula (I') is selected from:

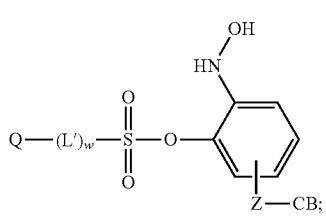

-continued
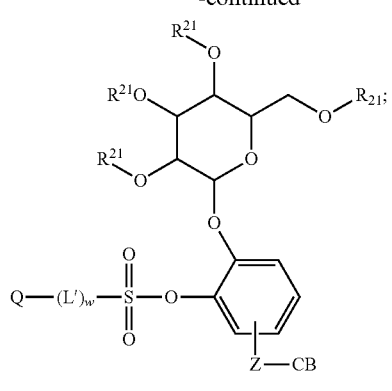
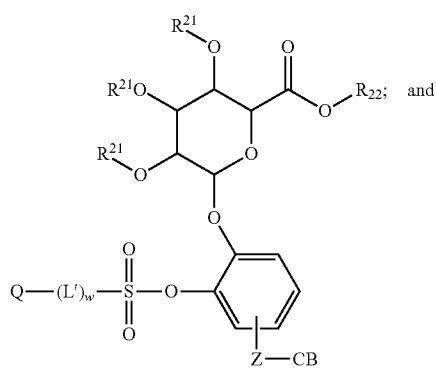
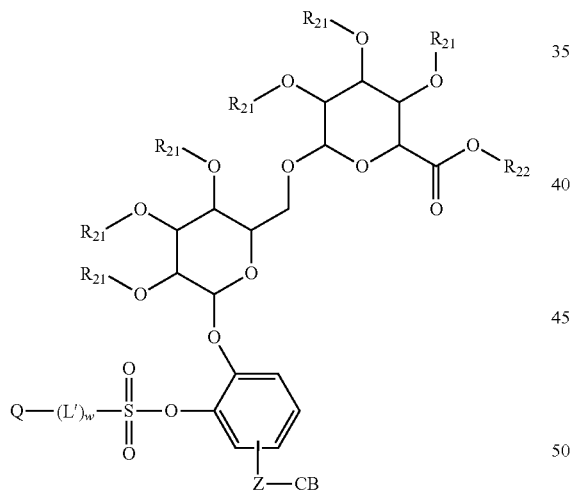
In still other embodiments, the compound of Formula (I') is selected from:
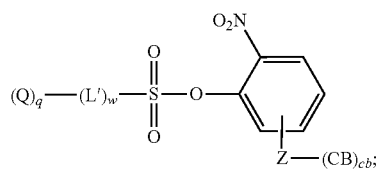
-continued
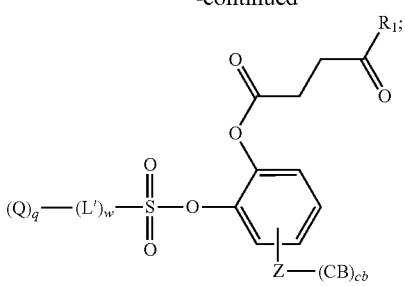
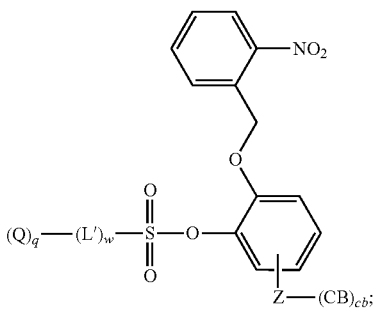
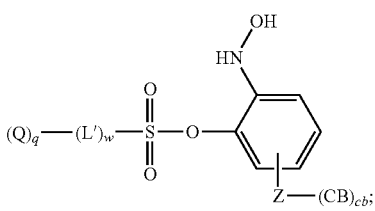
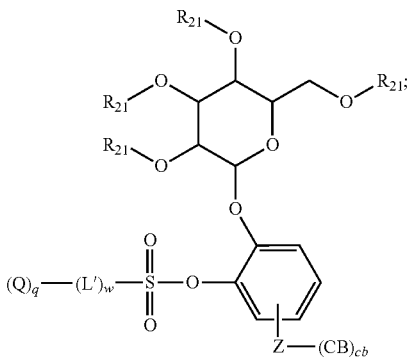
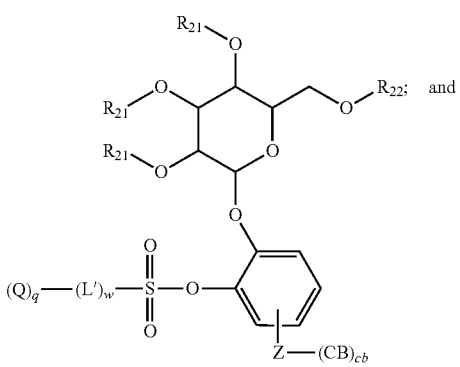

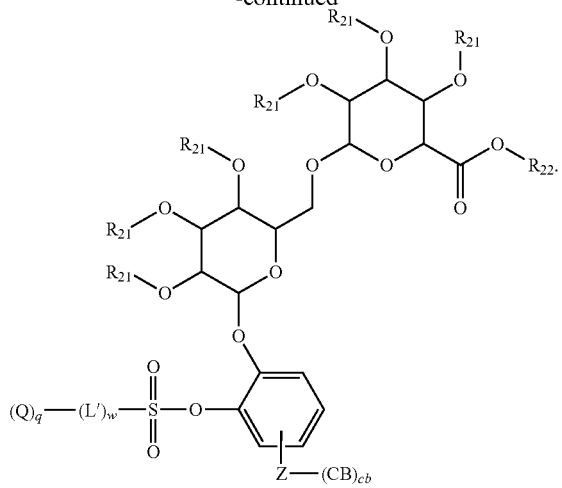
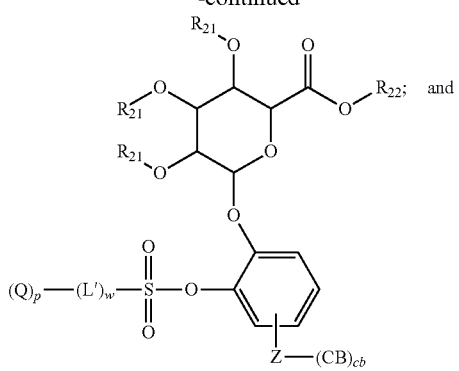
In other embodiments, the compound of Formula (I') is selected from:
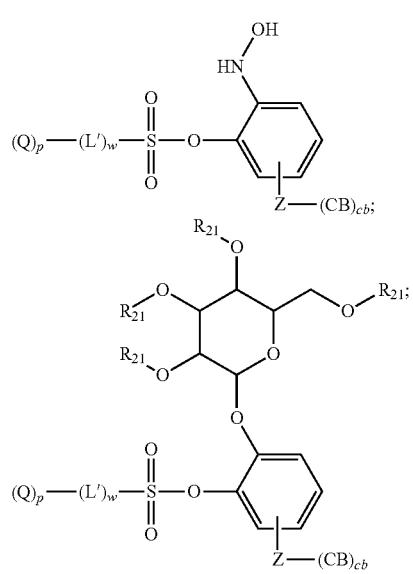
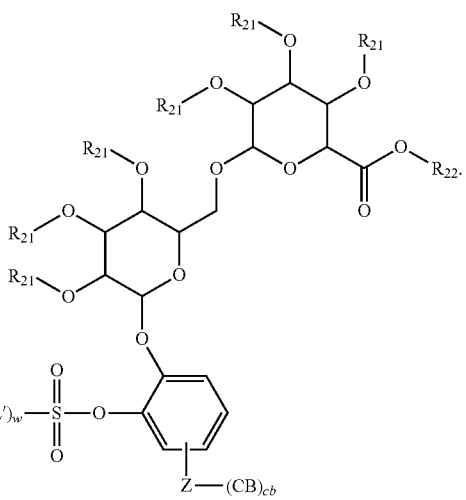
In certain preferred embodiments, Z is a linking group having a structure of Formula (F), (G), (H), (J), (K), (L), (M), or (N):
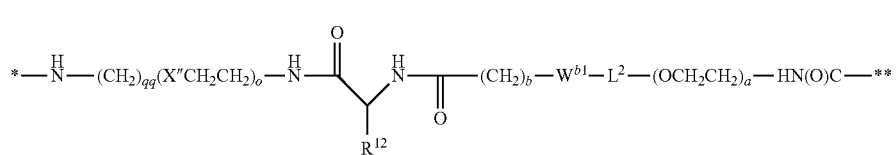
(F)
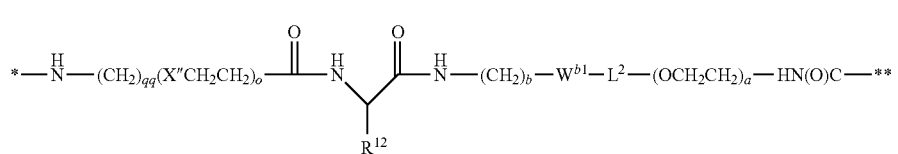
(G)

-continued

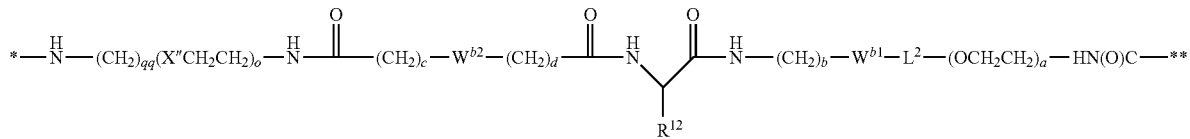
(H)

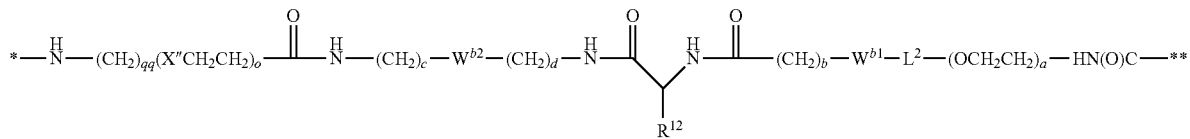
(J)

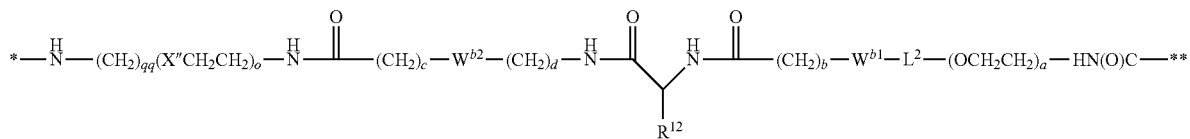
(K)

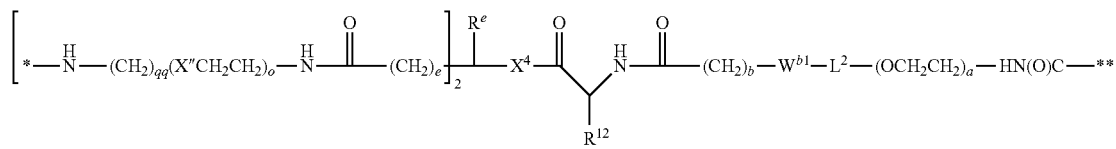
(L)

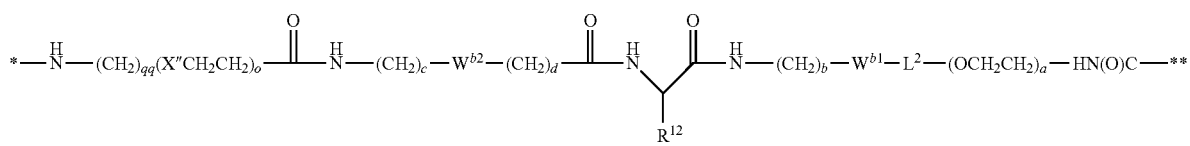
(M)

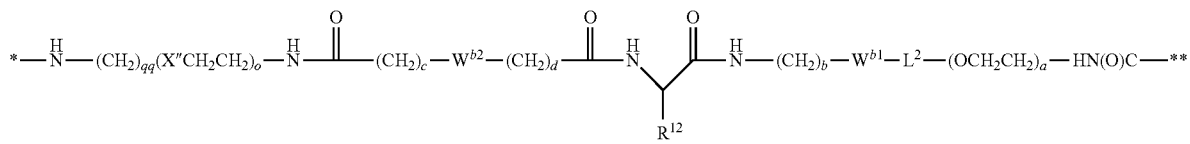
(N)

wherein:
* is the point of attachment to CB;
** is point of attachment to Ar;
$R^e$ is alkyl;
X" is —O—, —S—, —NH—, or —CH$_2$—;
$X^4$ is —NHC(O)—(CH$_2$)$_g$—NH— or —C(O)NH—(CH$_2$)$_h$—NH—;
$W^{b1}$ and $W^{b2}$ are each independently —C(O)NH—, —NHC(O)—,

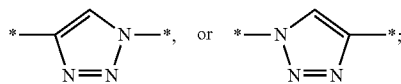

$L^2$ is an optionally present spacer moiety, and may be further substituted with one or more substituents, such as $C_1$-$C_6$ alkyl, $C_5$-$C_{14}$ aryl, and $C_3$-$C_8$ heteroaryl, wherein the alkyl, aryl and heteroaryl may be further substituted, e.g., with one or more substituents selected from the group consisting of $C_1$-$C_{10}$ alkyl, —(CH$_2$)$_u$NH$_2$, —(CH$_2$)$_u$NR$^{u1}$R$^{u2}$, —(CH$_2$)$_u$CO$_2$H, —(CH$_2$)$_u$CO$_2$R$^{u1}$, and —(CH$_2$)$_u$SO$_2$R$^{u3}$, wherein $R^{u1}$, $R^{u2}$, and $R^{u3}$ are each independently hydrogen, $C_1$-$C_{15}$ alkyl, $C_6$-$C_{20}$ aryl or $C_3$-$C_{10}$ heteroaryl; and u is an integer having a value of 1 to about 10;
$R^{12}$ is hydrogen, $C_1$-$C_8$ alkyl, or an amino acid moiety, such as a natural amino acid moiety;
b, c, d, e, g, h, o, and qq are each independently an integer having a value of 1 to about 10; and
s' is an integer having a value of 1 to about 10.

In other embodiments, Z is a linking group having a structure of Formula (F'), (G'), (H'), (J'), (K'), (L'), (M'), or (N'):
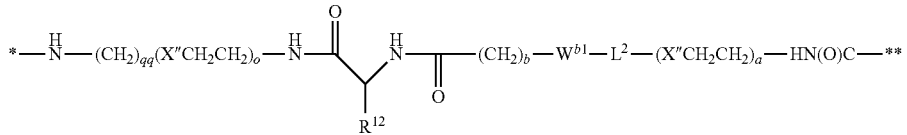
(F')
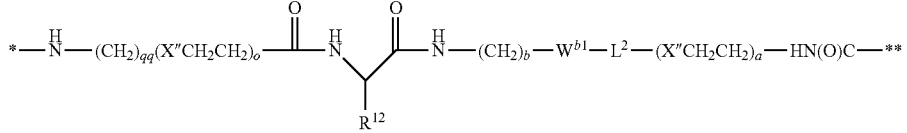
(G')
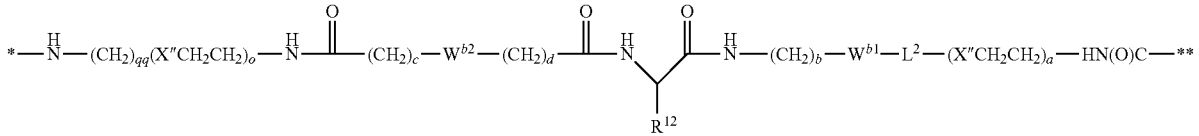
(H')
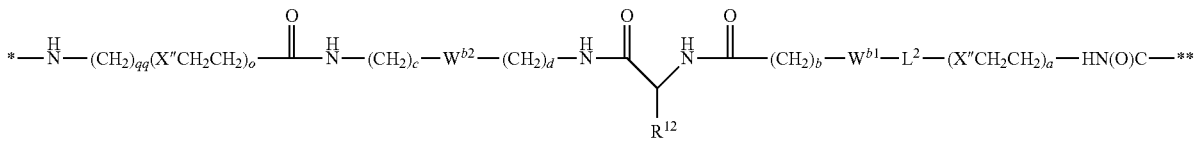
(J')
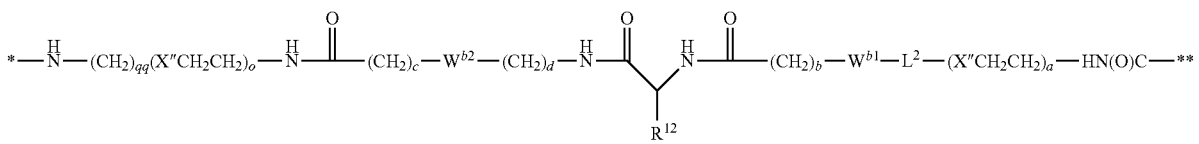
(K')
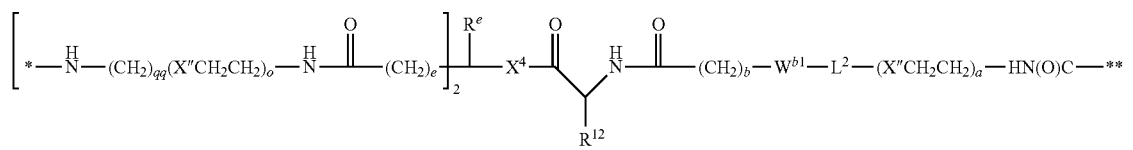
(L')
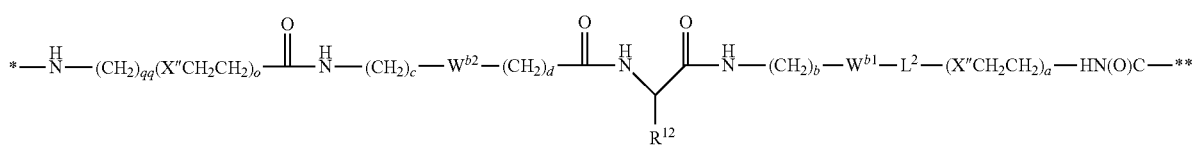
(M')
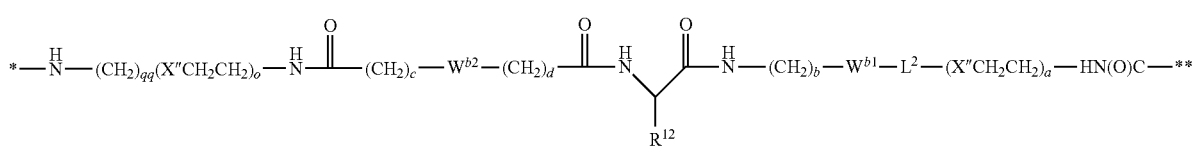
(N')

In certain preferred embodiments, CB is selected from:
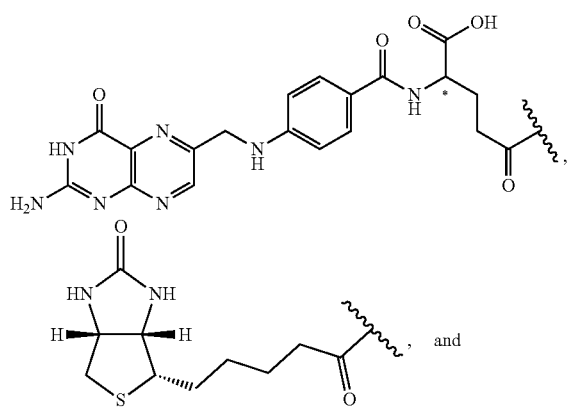
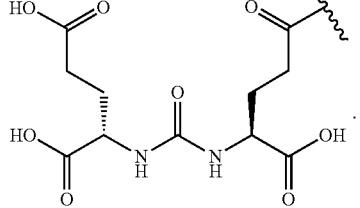
In certain preferred embodiments, $(Q)_q\text{-}(L')_w$ is selected from:
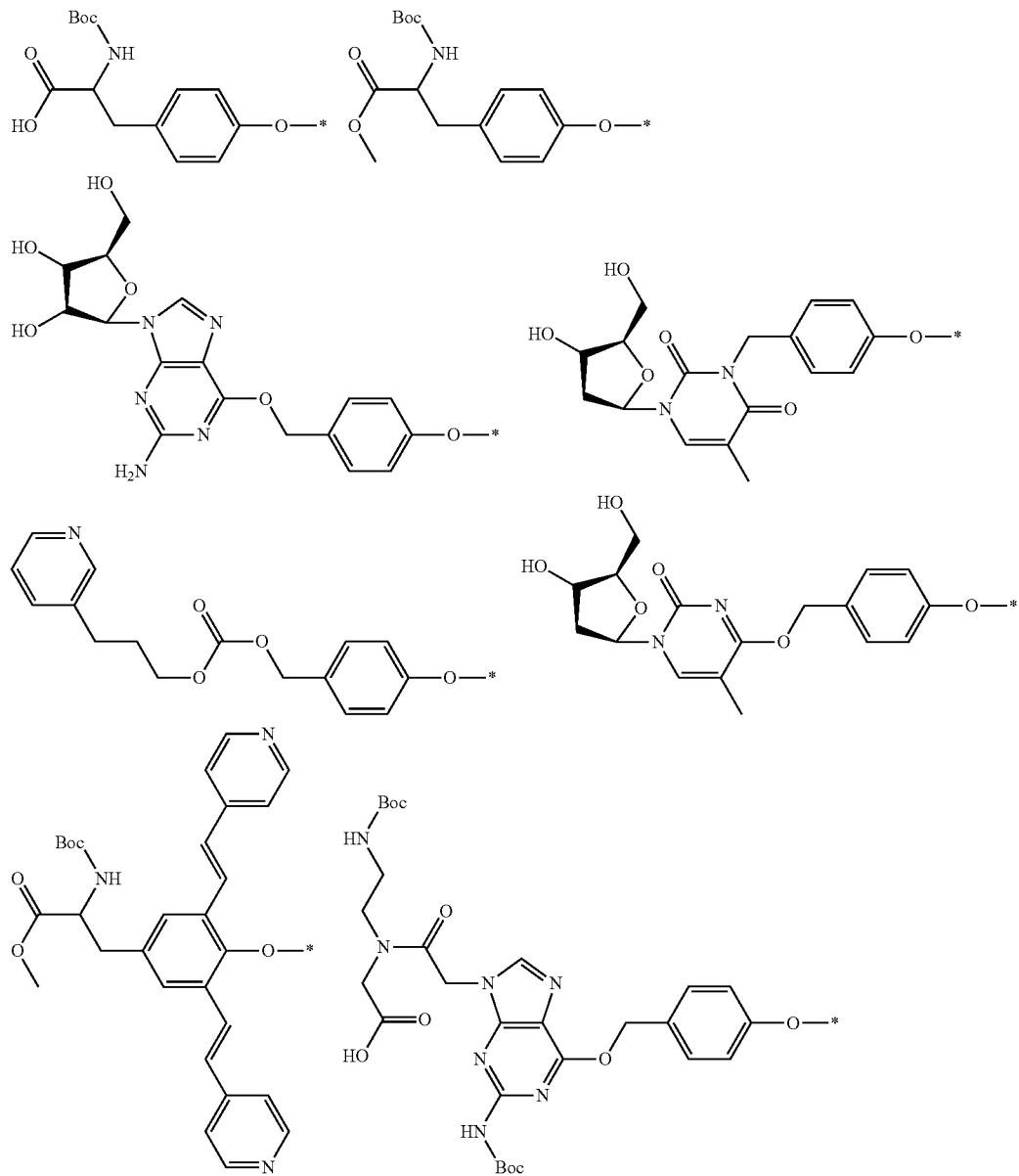

-continued
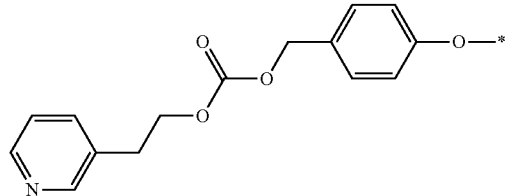
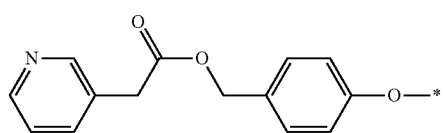
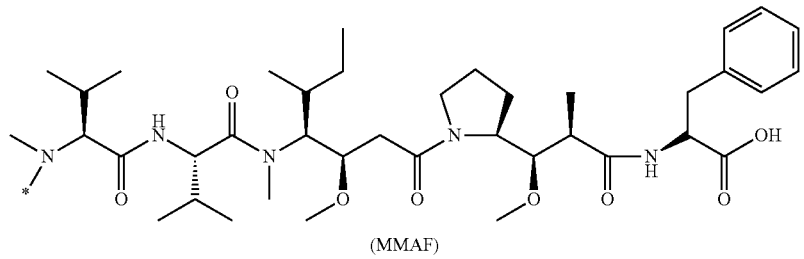
(MMAF)
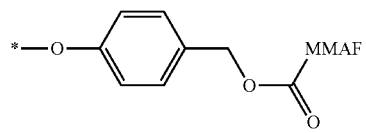
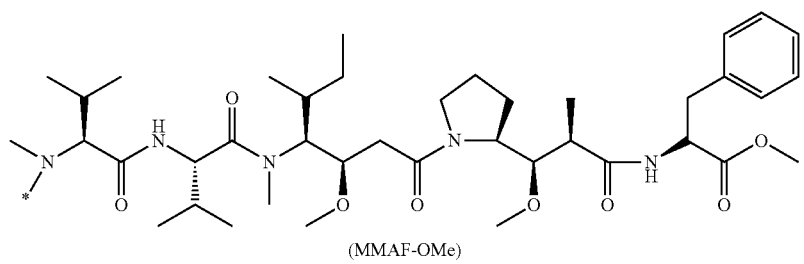
(MMAF-OMe)
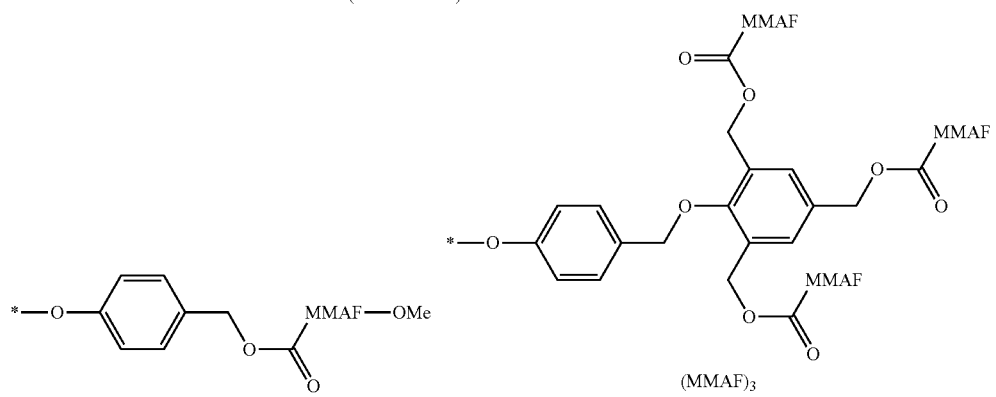
(MMAF)₃
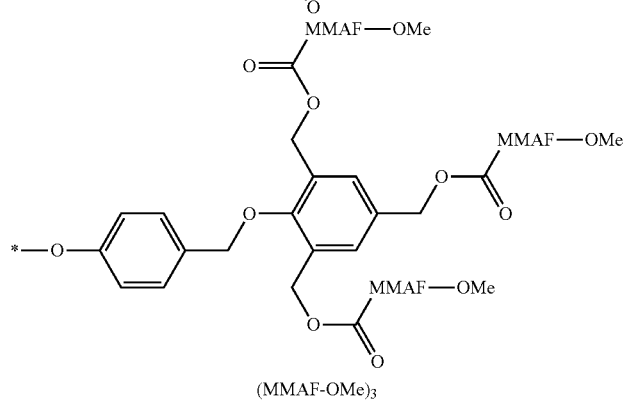
(MMAF-OMe)₃

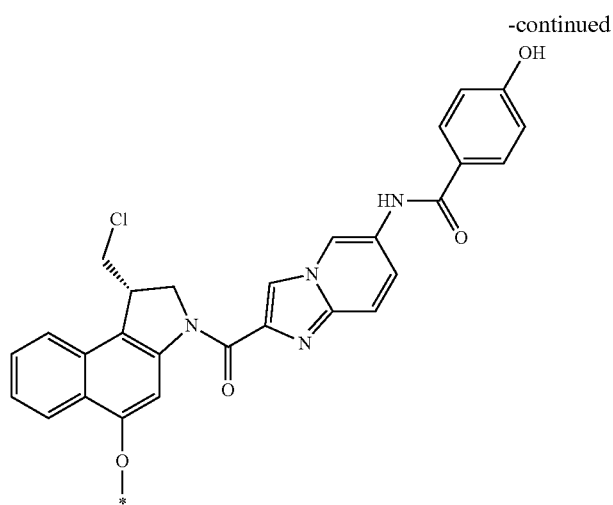
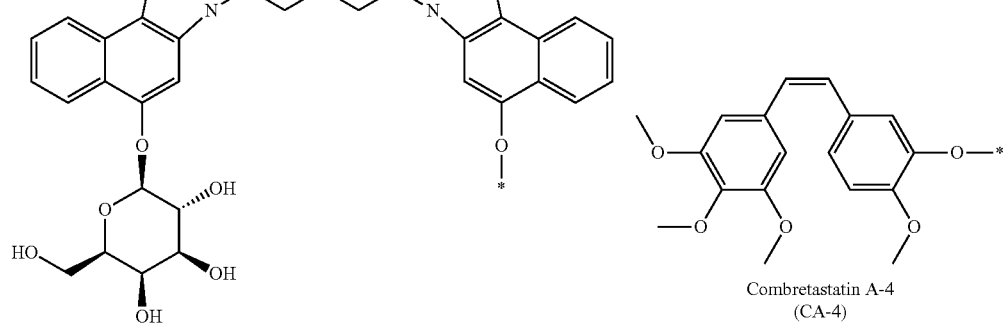
Combretastatin A-4
(CA-4)
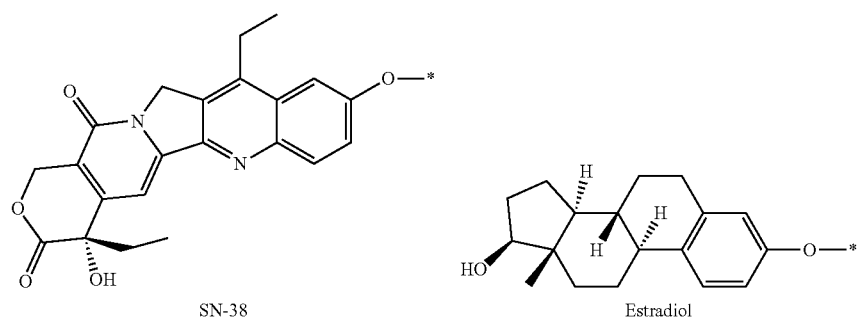
SN-38
Estradiol

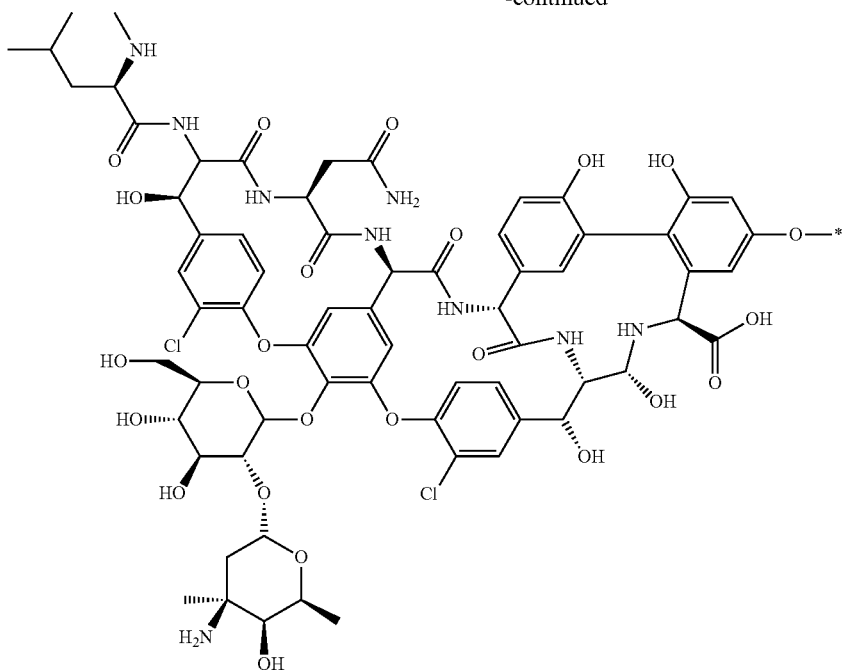
Vancomycin
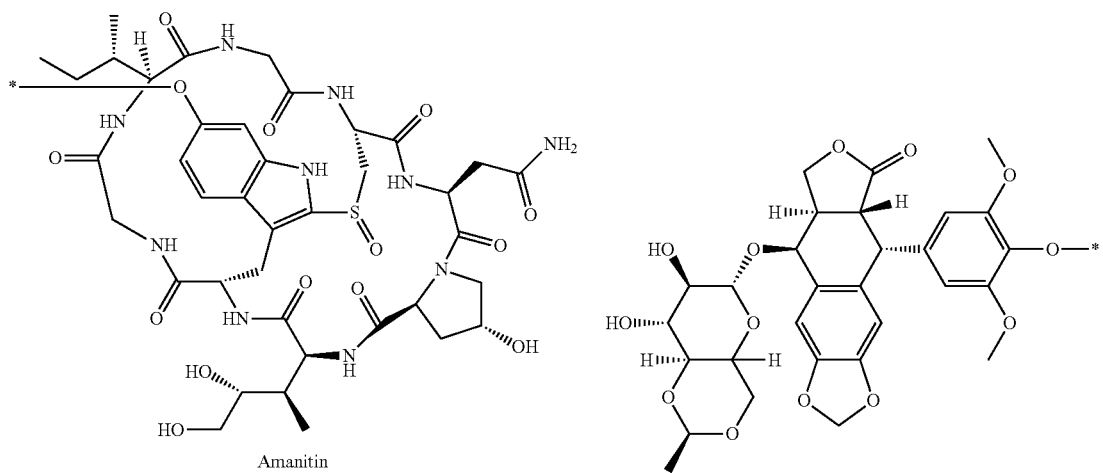
Amanitin
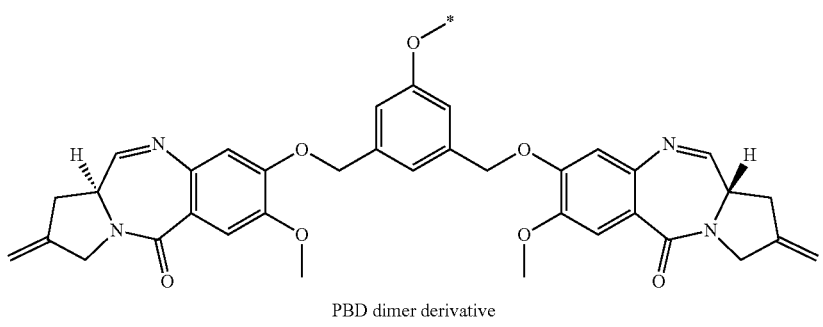
PBD dimer derivative

-continued
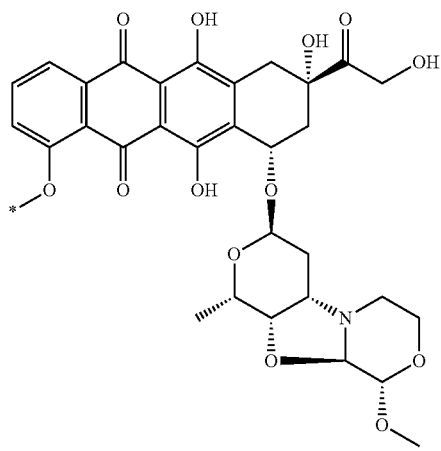
PNU-159682
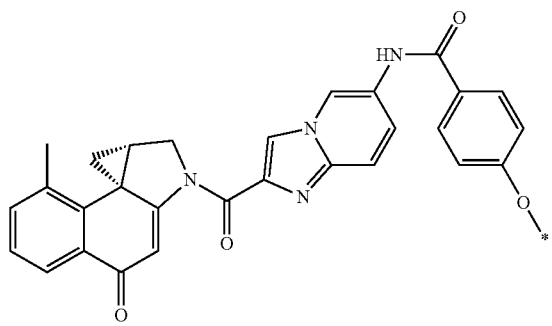
Duocarmycin analog
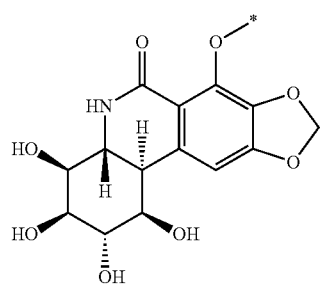
Pancratistatin
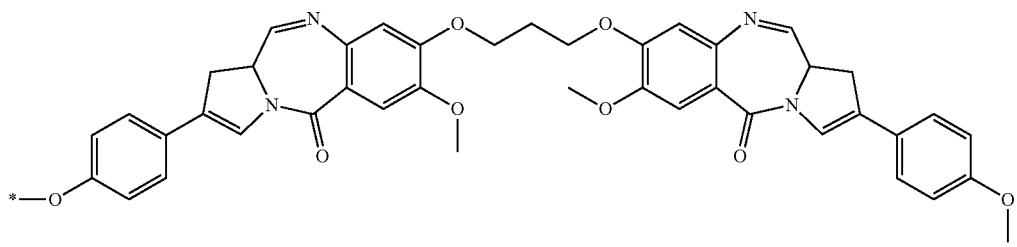
PBD-dimer
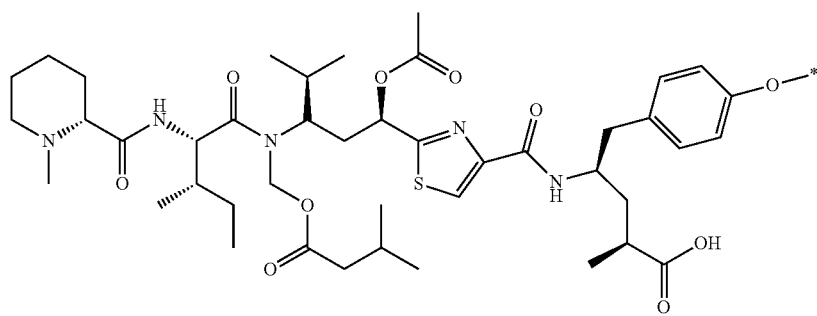
Tubulysin B -continued
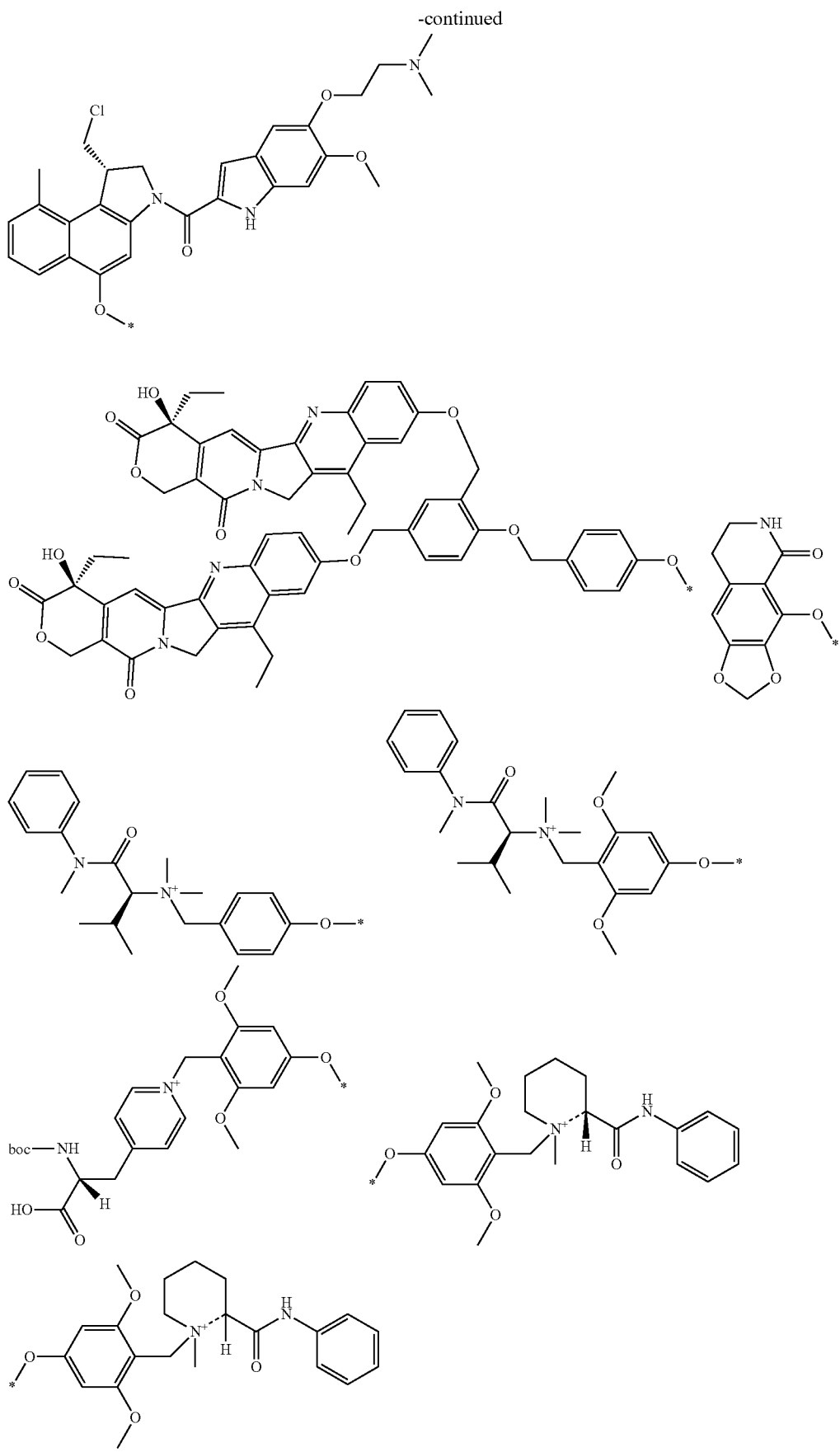

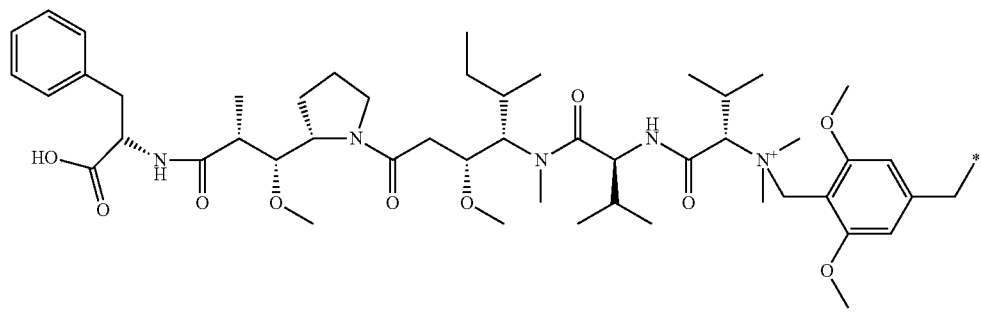
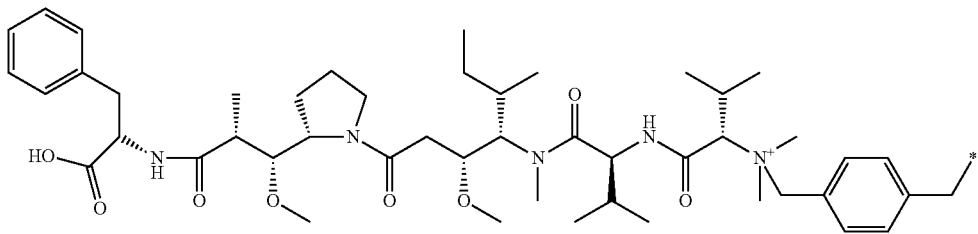
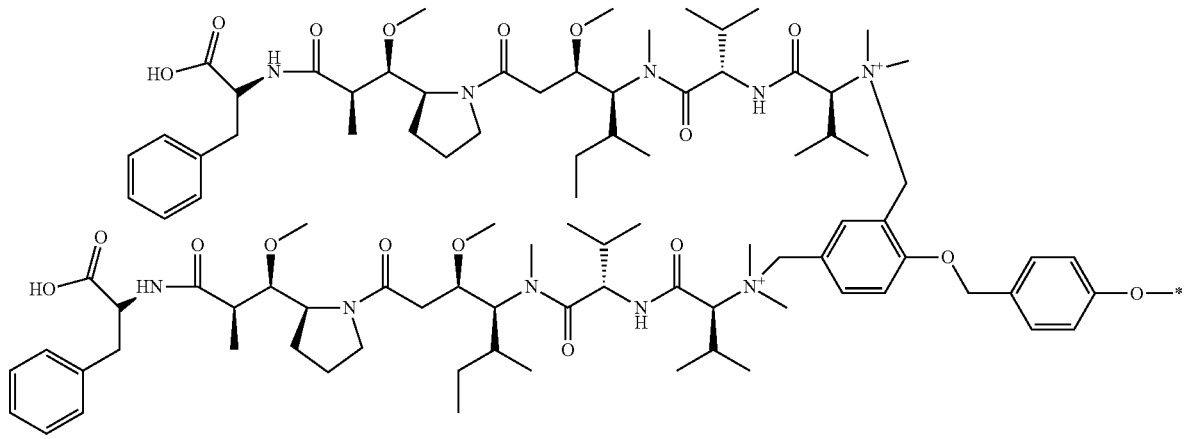
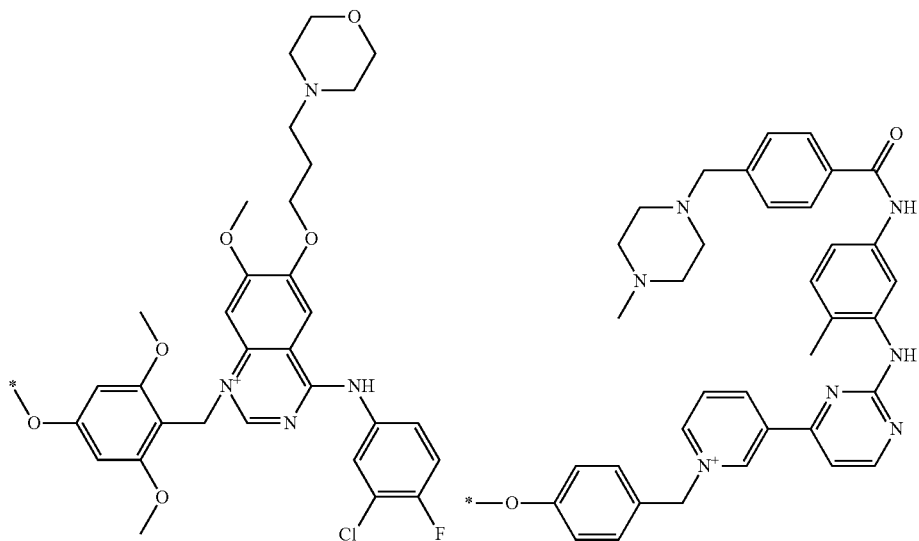

-continued

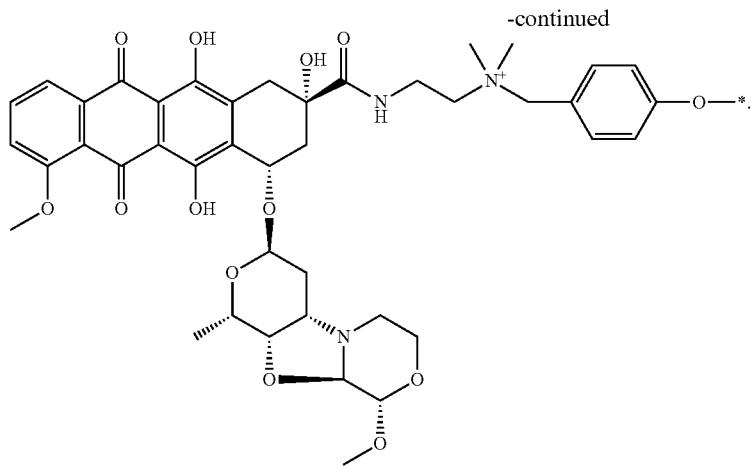

Also provided herein are compounds of Formula (I):

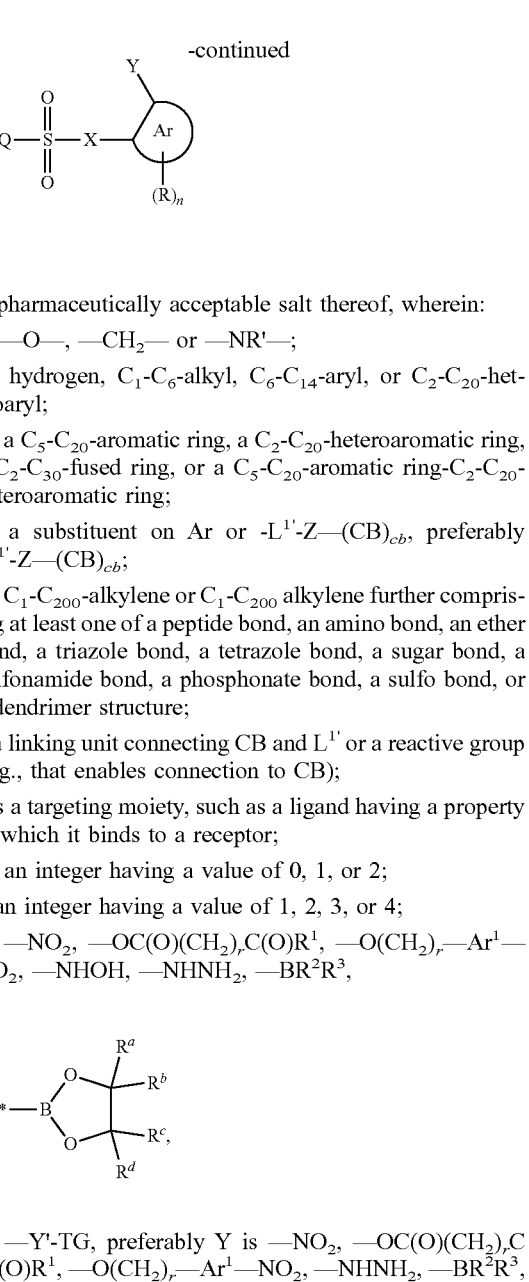

or a pharmaceutically acceptable salt thereof, wherein:

X is —O—, —CH$_2$— or —NR'—;

R' is hydrogen, $C_1$-$C_6$-alkyl, $C_6$-$C_{14}$-aryl, or $C_2$-$C_{20}$-heteroaryl;

Ar is a $C_5$-$C_{20}$-aromatic ring, a $C_2$-$C_{20}$-heteroaromatic ring, a $C_2$-$C_{30}$-fused ring, or a $C_5$-$C_{20}$-aromatic ring-$C_2$-$C_{20}$-heteroaromatic ring;

R is a substituent on Ar or -$L^{1'}$-Z—(CB)$_{cb}$, preferably -$L^{1'}$-Z—(CB)$_{cb}$;

$L^{1'}$ is $C_1$-$C_{200}$-alkylene or $C_1$-$C_{200}$ alkylene further comprising at least one of a peptide bond, an amino bond, an ether bond, a triazole bond, a tetrazole bond, a sugar bond, a sulfonamide bond, a phosphonate bond, a sulfo bond, or a dendrimer structure;

Z is a linking unit connecting CB and $L^{1'}$ or a reactive group (e.g., that enables connection to CB);

CB is a targeting moiety, such as a ligand having a property in which it binds to a receptor;

cb is an integer having a value of 0, 1, or 2;

n is an integer having a value of 1, 2, 3, or 4;

Y is —NO$_2$, —OC(O)(CH$_2$)$_r$C(O)R$^1$, —O(CH$_2$)$_r$—Ar$^1$—NO$_2$, —NHOH, —NHNH$_2$, —BR$^2$R$^3$,

[structure with B, O, O, R$^a$, R$^b$, R$^c$, R$^d$]

or —Y'-TG, preferably Y is —NO$_2$, —OC(O)(CH$_2$)$_r$C(O)R$^1$, —O(CH$_2$)$_r$—Ar$^1$—NO$_2$, —NHNH$_2$, —BR$^2$R$^3$,

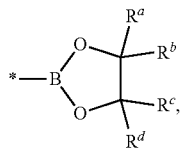

or —Y'-TG;
$R^1$ is $C_1$-$C_6$ alkyl;
r is an integer having a value of 1, 2, 3, 4, or 5;
$Ar^1$ is $C_6$-$C_{20}$ arylene;
$R^2$ and $R^3$ are each independently hydrogen, $C_1$-$C_6$-alkyl, $C_1$-$C_6$-alkoxy, or hydroxy;
$R^a$, $R^b$, $R^c$, and $R^d$ are each independently hydrogen or $C_1$-$C_6$ alkyl;
Y' is —$(CH_2)_xNR''$—, —$(CH_2)_xO$—, or —$(CH_2)_xS$—;
R" is hydrogen or $C_1$-$C_6$ alkyl;
x is an integer having a value of 0 or 1;
TG is a triggering group;
Q is -$Q^1$ or -L'-$(Q')_w$;
L' is a $C_7$-$C_{30}$-hydrocarbon spacer having —O— or —NR'''— at one end and —O—, —OC(O)—, —O(CO)O—, —OC(O)NR'''— or —OC(O)NR⁴CH₂O— at the other end, wherein —O—, —OC(O)—, —O(CO)O— or —OC(O)NR''''— may be further included in the $C_7$-$C_{30}$ hydrocarbon spacer, the $C_7$-$C_{30}$ hydrocarbon spacer being further substituted with one or more substituents, such as $C_1$-$C_6$ alkyl, $C_5$-$C_{14}$ aryl, and $C_3$-$C_8$ heteroaryl, wherein the alkyl, aryl and heteroaryl may be further substituted, e.g., with one or more substituents selected from the group consisting of $C_1$-$C_{10}$ alkyl, —$(CH_2)_uNH_2$, —$(CH_2)_uNR^{u1}R^{u2}$, —$(CH_2)_uCO_2H$, —$(CH_2)_uCO_2R^{u1}$, and —$(CH_2)_uSO_2R^{u3}$, wherein $R^{u1}$, $R^{u2}$, and $R^{u3}$ are each independently hydrogen, $C_1$-$C_{15}$ alkyl, $C_6$-$C_{20}$ aryl or $C_3$-$C_{10}$ heteroaryl; and u is an integer having a value of 1 to about 10;
$Q^1$ is an active agent including at least one functional group of —OH, —NH—, —$NR_5R_6$, —SH, —$SO_2NH_2$, or —COOH;
$R^4$ is hydrogen, $C_1$-$C_6$-alkyl, $C_5$-$C_{14}$-aryl, or $C_3$-$C_8$-heteroaryl, wherein alkyl, aryl, and heteroaryl are substituted or unsubstituted;
$R^5$ and $R^6$ are each independently $C_1$-$C_6$-alkyl, $C_3$-$C_9$-cycloalkyl or $C_5$-$C_{10}$-heteroaryl, wherein heteroaryl is substituted or unsubstituted;
R''' and R'''' are each independently hydrogen or $C_1$-$C_6$-alkyl; and
w is an integer having a value of 1, 2, 3, 4, or 5.

In some embodiments, the compound of Formula (I) comprises a functional group (e.g., Y) capable of inducing intramolecular cyclization by external stimulation. In certain embodiments, said functional group is introduced at an ortho-position with respect to X.

In some embodiments, R' is $C_1$-$C_6$-alkyl, $C_6$-$C_{14}$-aryl, or $C_2$-$C_{20}$-heteroaryl.

In some embodiments, Ar is a $C_5$-$C_{20}$-aromatic ring, a $C_2$-$C_2O$-heteroaromatic ring, a $C_2$-$C_{30}$-fused ring, or a $C_5$-$C_{20}$-aromatic ring-$C_2$-$C_{20}$-heteroaromatic ring. For example, Ar may be a benzene ring, a naphthalene ring, a pyridine ring, or a quinolone ring. Preferably, Ar is a benzene ring or a naphthalene ring. In some embodiments, the compound of Formula (I) is a compound having a structure according to Formula (II):

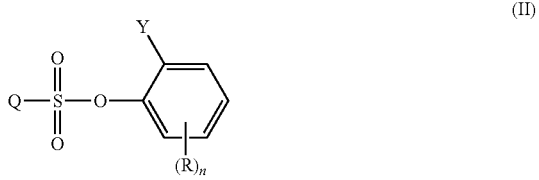

or a pharmaceutically acceptable salt thereof.

In other embodiments, the compound of Formula (I) is a compound having a structure according to Formula (III):

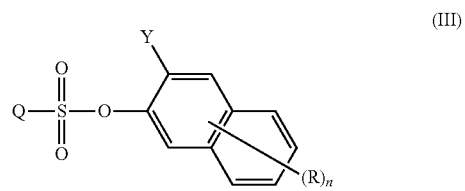

or a pharmaceutically acceptable salt thereof.

In some embodiments, the compound is a compound of Formula (I), (II), or (III), wherein R is selected from hydrogen, halogen (hal), aldehyde, acetal, ketal, —R*, —OR*, —SR*, —NR*R**, —C(hal)₃, —CN, —OCN, —SCN, —N=C=O, —NCS, —NO, —NO₂, —N₃, —NC, —C(O)R*, —OC(O)R*, —OS(O)R*, —S(O)₂R*, —S(O)₂OR*, —OS(O)OR*, —OS(O)₂OR*, —S(O)NR*R**, —S(O)₂NR*R**, —S(O)R*, —OP(O)(OR*)₂, —P(O)(OR*)₂, —OP(OR*)₂, —OP(OR*)N(R**)₂, —OP(O)(OR*)N(R**)₂, —PR*, —P(O)₂, —P(O)R*, —C(O)hal, —C(S)R*, —CO₂R*, —C(S)OR*, —C(O)SR*, —C(S)SR*, —C(O)NR*R**, —C(S)NR*R**, —C(=NR*)NR*R**, —NR*C(O)R**, —NR*S(O)₂OR**, —NR*S(O)R**, —NR*C(O)NR**, —SS—R*, or —R*SSR**, wherein: R* and R** are each independently hydrogen, $C_1$-$C_{18}$ alkyl, $C_6$-$C_{20}$ aryl, $C_3$-$C_{15}$ heterocycle or $C_3$-$C_{20}$ heteroaryl.

In some embodiments, the compound is a compound of Formula (I), (II), or (III), wherein R is hydrogen or *-($L^a$-$A_1$-$L^b$-$L^c$-Z)$_m$—CB; wherein:
$L^a$ is a single bond or $C_1$-$C_2O$-alkylene;
$A^l$ is —C(O)NR*—, —NR*C(O)—, —NR*—, —O—, —PO₃—, —OPO₃—, —SO—, —SO₂— or —SO₃—;
$L^b$ is —(CH₂CH₂O)ₐ— or —(CH₂)ₐ—;
R* is hydrogen, $C_1$-$C_{18}$-alkyl, $C_6$-$C_{20}$-aryl, $C_3$-$C_{15}$-heterocycle, or $C_3$-$C_{20}$ heteroaryl;
a is an integer having a value of 1 to about 20;
$L^c$ is a single bond or $C_1$-$C_2O$-alkylene;
n is an integer having a value of 1 or 2; and
Z is a linking unit connecting CB and L'; or
Z is a precursor selected from isocyanide, isothiocyanide, 2-pyridyl disulfide, haloacetamide (—NHC(O)CH₂-hal), maleimide, diene, alkene, halide, tosylate (TsO⁻), aldehyde, sulfonate (R—SO₃⁻),

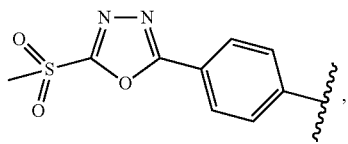

-continued

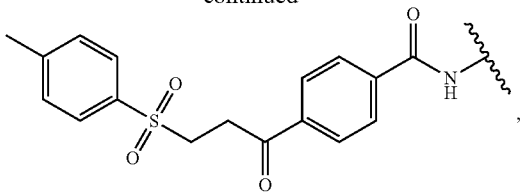
, phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$);

CB is a targeting moiety, such as a ligand capable of binding to a receptor; and m is an integer having a value of 0, 1, or 2.

In some embodiments, the compound is a compound of Formula (I), (II), or (III), wherein R is hydrogen or *-L$^a$-A$_1$-L$^b$-L$^c$-Z; wherein:

L$^a$ is a single bond or C$_1$-C$_2$O-alkylene;
A$^1$ is —C(O)NR*—, —NR*C(O)—, —NR*—, —O—, —PO$_3$—, —PO$_4$—, —SO—, —SO$_2$—, or —SO$_3$—;
L$^b$ is —(CH$_2$CH$_2$O)$_a$— or —(CH$_2$)$_a$—;
R* is hydrogen, C$_1$-C$_{18}$-alkyl, C$_6$-C$_{20}$-aryl, C$_3$-C$_{15}$-heterocycle, or C$_3$-C$_{20}$-heteroaryl;
a is an integer having a value of 1 to about 20;
L$^c$ is a single bond or C$_1$-C$_2$O-alkylene;
n is an integer having a value of 1 or 2; and
Z is a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

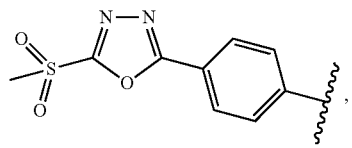
,

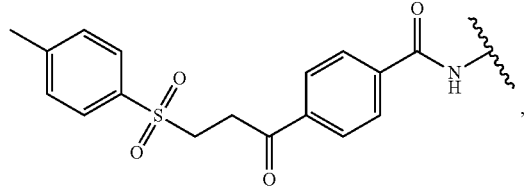
, phosphonic acid (—P(=O)(OH)$_2$), ketone, C$_5$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In some embodiments, the compound is a compound of Formula (I), (II), or (III), wherein R is *(-L$^a$-A$_1$-L$^b$-L$^c$-Z)$_m$—CB; wherein:

L$^a$ is a single bond or C$_1$-C$_2$O-alkylene;
A$^1$ is —C(O)NR—, —NR*C(O)—, —NR*—, —O—, —PO$_3$—, —PO$_4$—, —SO—, —SO$_2$— or —SO$_3$—;
L$^b$ is —(CH$_2$CH$_2$O)$_a$— or —(CH$_2$)$_a$—;
R* is hydrogen, C$_1$-C$_{18}$-alkyl, C$_6$-C$_{20}$-aryl, C$_3$-C$_{15}$-heterocycle, or C$_3$-C$_{20}$-heteroaryl;
a is an integer having a value of 1 to about 20;

L$^c$ is a single bond or C$_1$-C$_{20}$-alkylene;
n is an integer having a value of 1 or 2;
Z is a linking unit connecting CB and L';
CB is a targeting moiety, such as a ligand having a property in which it binds to a receptor; and
m is an integer having a value of 1 to 2.

In some embodiments, the compound is a compound of Formula (I), (II), or (III), wherein L' is a C$_7$-C$_{30}$ hydrocarbon spacer further comprising —O—, —OC(O)—, —O(CO)O— or —OC(O)NR''''.

In some embodiments, the compound is a compound of Formula (I), (II), or (III), wherein Q is -L'-(Q$^1$)$_w$ selected from:

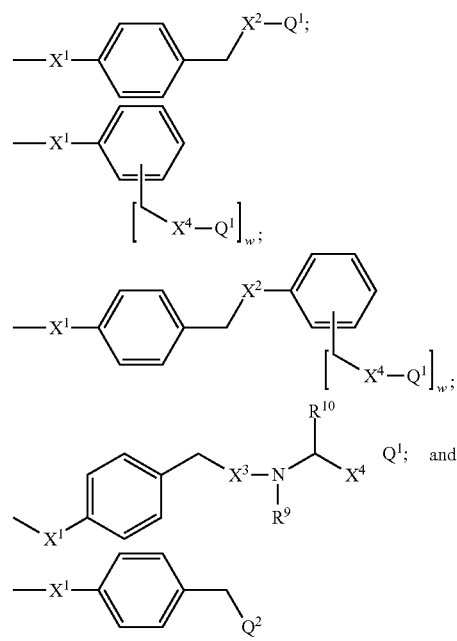

wherein:
Q$^1$ is an active agent comprising at least one functional group selected from —OH, —NR$^5$R$^6$, —SH, and —COOH;
Q$^2$ is an active agent comprising —NR$^5$R$^6$;
X$^1$ is —O— or —NR'''—;
X$^2$ and X$^4$ are each independently absent or selected from —O—, —OC(O)—, —OC(O)O—, and —OC(O)NH—;
X$^3$ is —OC(=O)—;
R$^5$ and R$^6$ are the same as defined above;
R$^9$ and R$^{10}$ are each independently hydrogen, C$_1$-C$_6$ alkyl, C$_6$-C$_{14}$ aryl or C$_3$-C$_9$ heteroaryl, the alkyl, aryl, and heteroaryl of the R$_9$ and R$_{10}$ may be further substituted with one or more substituents selected from the group consisting of C$_1$-C$_{10}$ alkyl, —(CH$_2$)$_u$NH$_2$, —(CH$_2$)$_u$NR$^{u1}$R$^{u2}$, and —(CH$_2$)$_u$SO$_2$R$^{u3}$, and the R$^{u1}$, R$^{u2}$, and R$^{u3}$ are each independently hydrogen, C$_1$-C$_{15}$ alkyl, C$_6$-C$_{20}$ aryl or C$_3$-C$_{10}$ heteroaryl; and u is an integer having a value of 1 to about 10;
R''' is hydrogen or C$_1$-C$_6$-alkyl; and
w is an integer having a value of 1, 2, 3, 4, or 5.

In certain embodiments, -L'-(Q$^1$)$_w$ is selected from

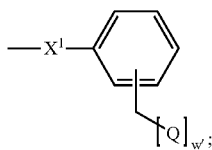

The at least one functional group of Q, Q$^1$, or Q$^2$ selected from —OH, —NR$^5$R$^6$, —SH, and —COOH serves as a connection point of the active agent to L'. The functional group may exist as part of an ester, thioester, carbonate, carbamate, amide, sulfonamide, sulfonate, sulfate, or other suitable linkage; that is, the —OH, —NR$^5$R$^6$, —SH, and —COOH moiety does not exist as such while the active agent is part of the conjugate.

In some embodiments, Q$^2$ is an active agent comprising —NR$^5$R$^6$, wherein the active agent is capable of binding in a quaternary amine structure, for instance the —NR$^5$R$^6$ moiety in the active agent is capable of forming a quaternary amine linkage with L'.

In some embodiments of Formulas (I"), (Ia), (I), (II), and (III), R$^4$ is substituted alkyl, aryl, or heteroaryl. In some such embodiments, R$^4$ is substituted with one or more substituents selected from C$_1$-C$_{10}$ alkyl, —(CH$_2$)$_u$NH$_2$, —(CH$_2$)$_u$NR$^{u1}$R$^{u2}$, —(CH$_2$)$_u$CO$_2$H, —(CH$_2$)$_u$CO$_2$R$^{u1}$, and —(CH$_2$)$_u$SO$_2$R$^{u3}$, wherein R$^{u1}$, R$^{u2}$, and R$^{u3}$ are each independently hydrogen, C$_1$-C$_{15}$-alkyl, C$_6$-C$_{20}$-aryl, or C$_3$-C$_{10}$-heteroaryl; and u is an integer having a value of 1 to about 10.

In some embodiments of Formulas (I"), (Ia), (I), (II), and (III), R$^5$ and/or R$^6$ is heteroaryl substituted with —NR$^7$R$^8$, wherein R$^7$ and R$^8$ are each independently hydrogen, C$_1$-C$_6$-alkyl, C$_3$-C$_9$-cycloalkyl, or C$_5$-C$_{14}$-aryl.

In some embodiments of Formulas (I"), (Ia), (I), (II), and (III), Q or -(L')$_w$-(Q)$_q$ is selected from:

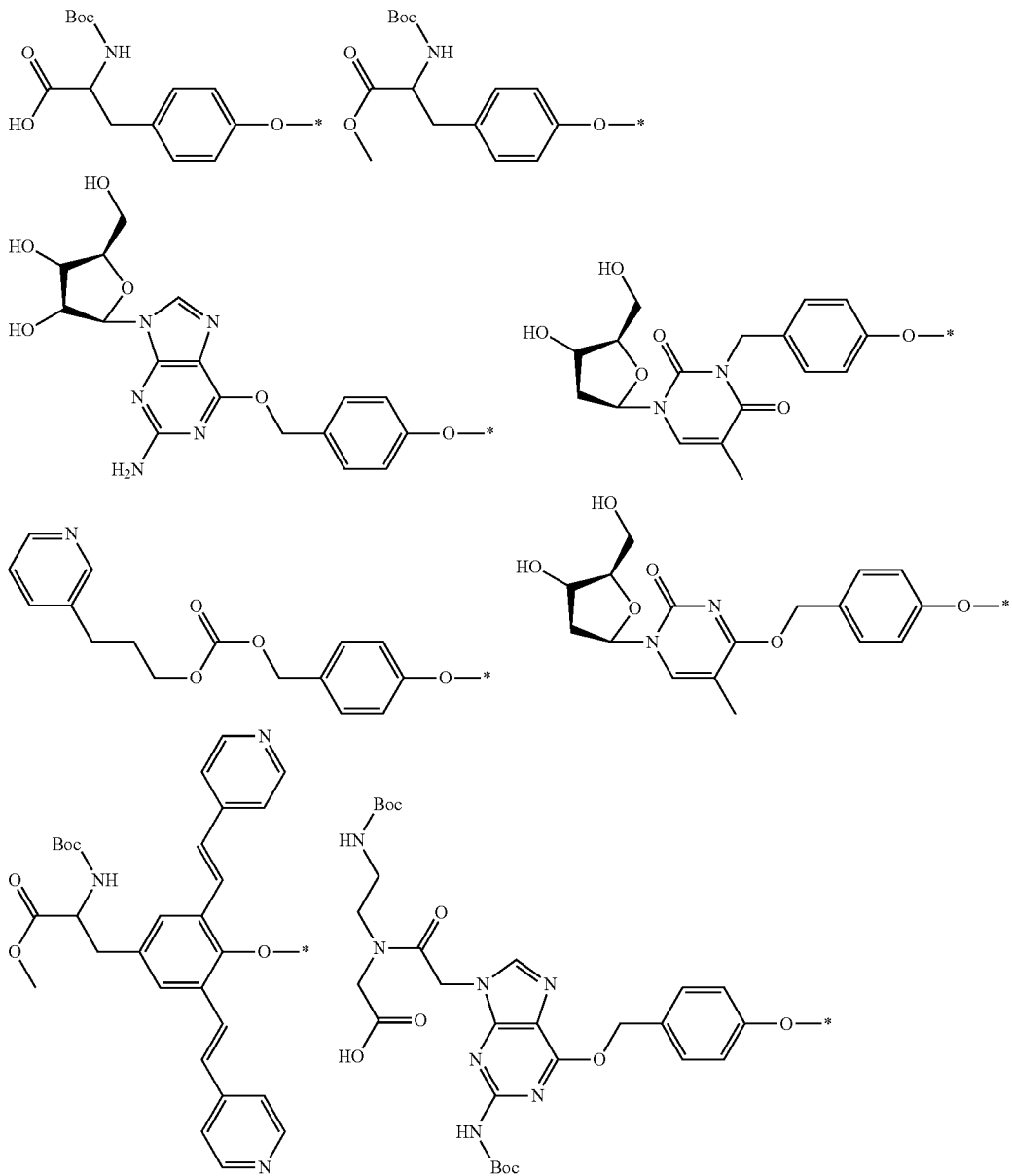

-continued
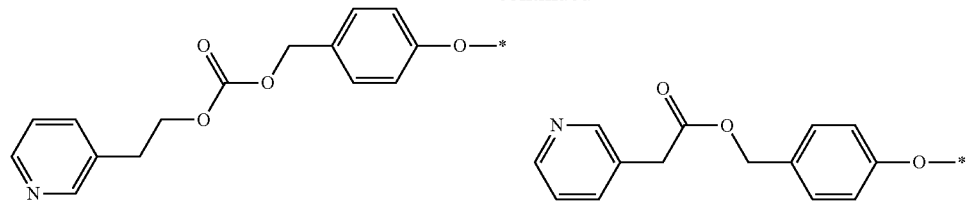
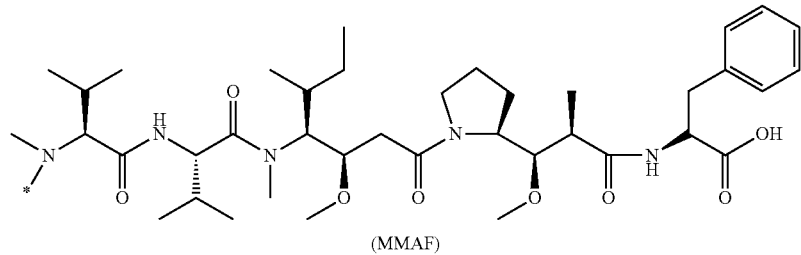
(MMAF)
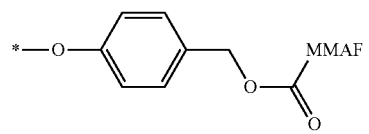
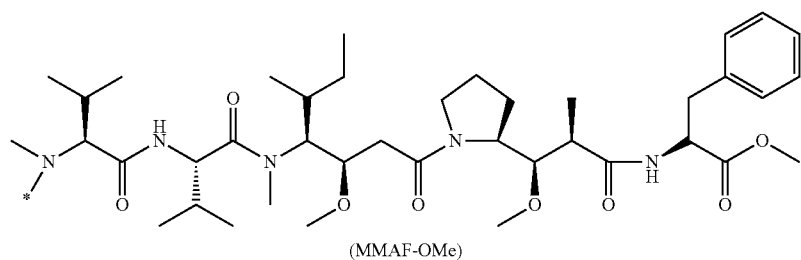
(MMAF-OMe)
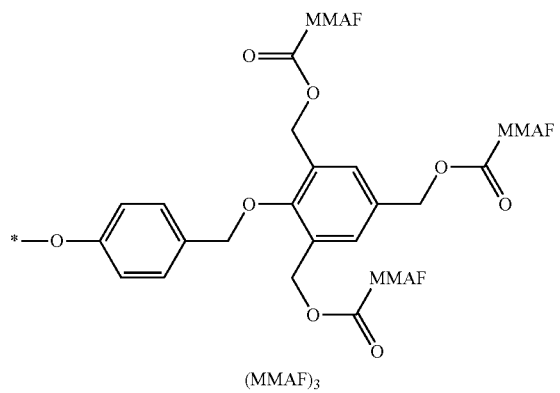
(MMAF)₃
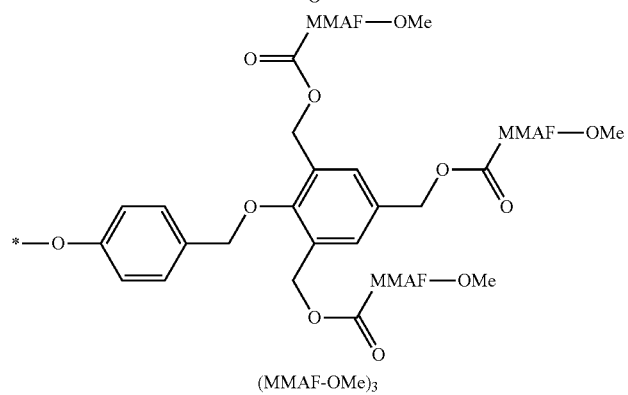
(MMAF-OMe)₃

-continued
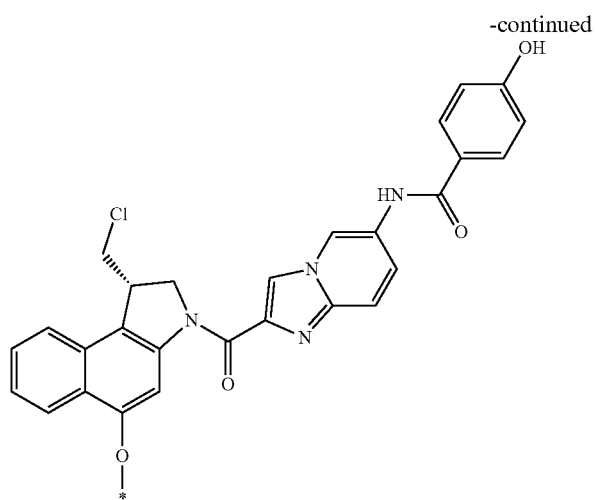
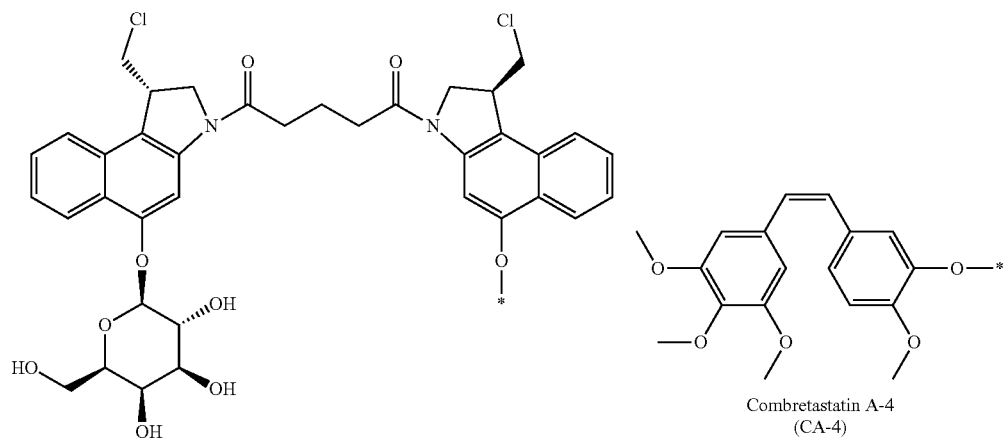
Combretastatin A-4
(CA-4)
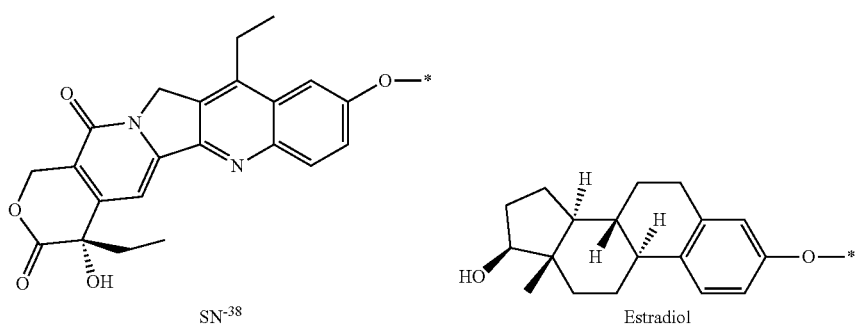
SN-38
Estradiol -continued
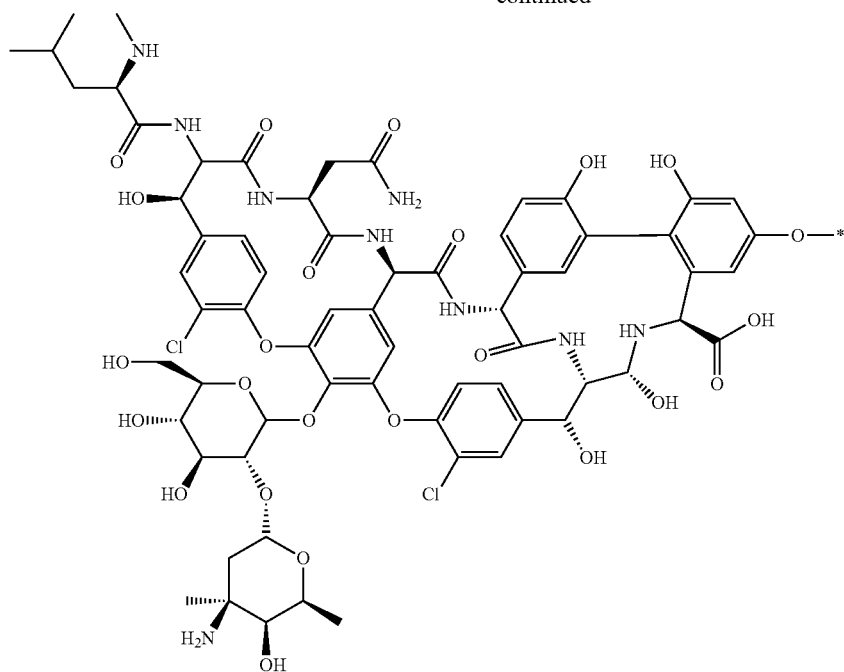
Vancomycin
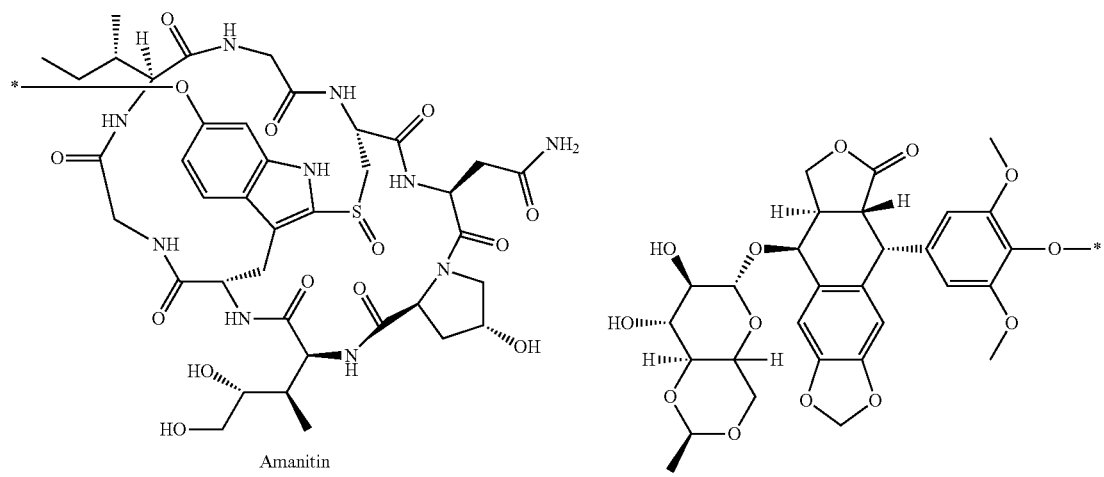
Amanitin
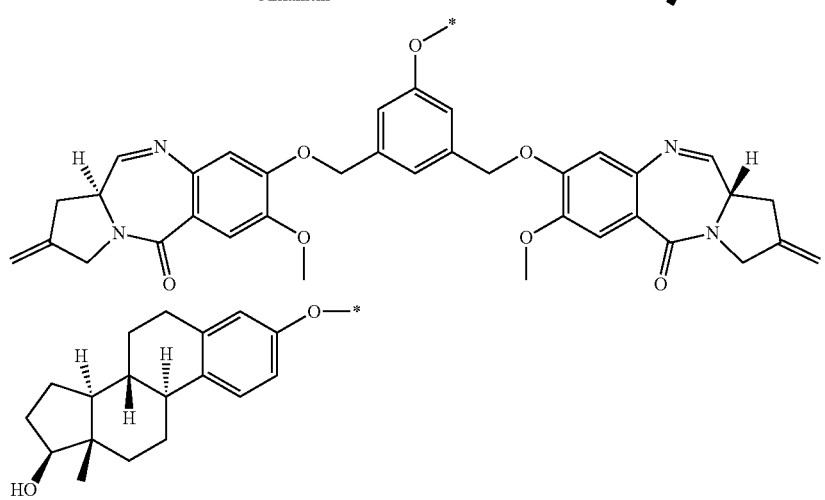

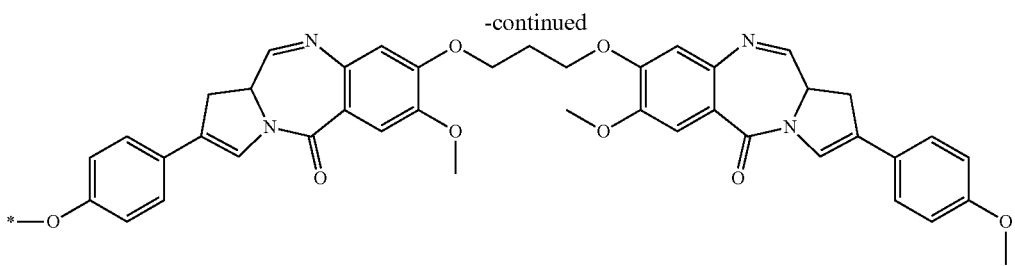

PBD-dimer

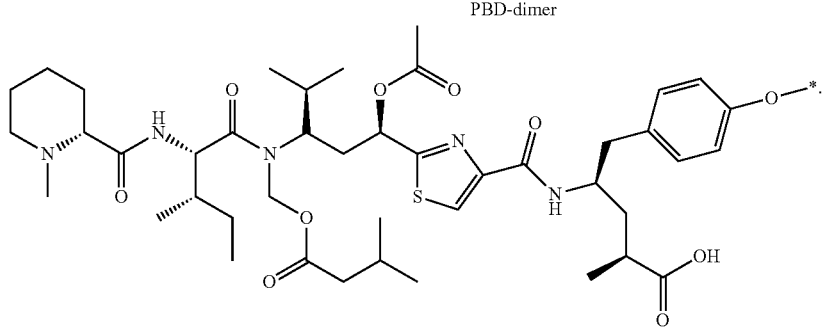

Tubulysin B

In certain embodiments, provided herein is a compound of Formula (I), (II), or (III), wherein:

Y is —NO$_2$, —OC(O)(CH$_2$)$_r$C(O)R$^1$, —O(CH$_2$)$_r$—Ar$^1$—NO$_2$, —NHOH, —BR$^2$R$^3$ or —Y'-TG, preferably Y is —NO$_2$, —OC(O)(CH$_2$)$_r$C(O)R$^1$, —O(CH$_2$)$_r$—Ar$^1$—NO$_2$, —BR$^2$R$^3$ or —Y'-TG;

R$^1$ is C$_1$-C$_6$ alkyl;

r is an integer having a value of 1, 2, 3, 4, or 5;

Ar$^1$ is phenylene, biphenylene, or naphthylene;

R$^2$ and R$^3$ are each independently hydrogen, C$_1$-C$_6$-alkyl, C$_1$-C$_6$-alkoxy, or hydroxy;

Y' is —(CH$_2$)$_x$NR''—, —(CH$_2$)$_x$O— or —(CH$_2$)$_x$S—;

R'' is hydrogen or C$_1$-C$_6$-alkyl;

x is an integer having a value of 0 or 1;

R'' is hydrogen or C$_1$-C$_6$-alkyl; and

TG is a triggering group, such as a β-galactoside, β-glucuronide, or a combination of β-galactoside and β-glucuronide.

In certain embodiments, the compound of Formula (I), (II), or (III) is selected from:

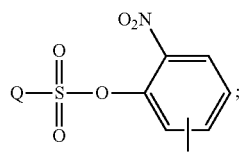

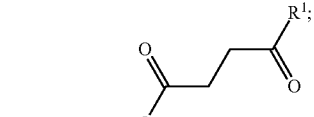

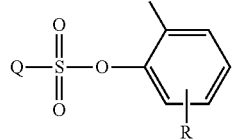

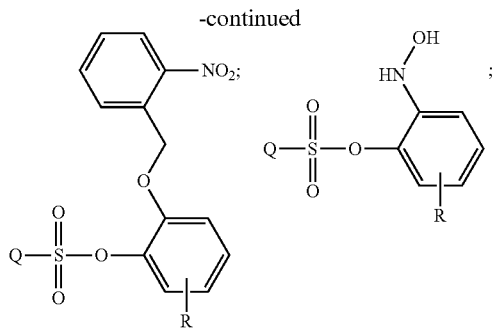

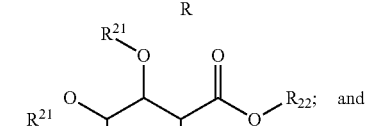

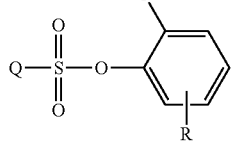

-continued
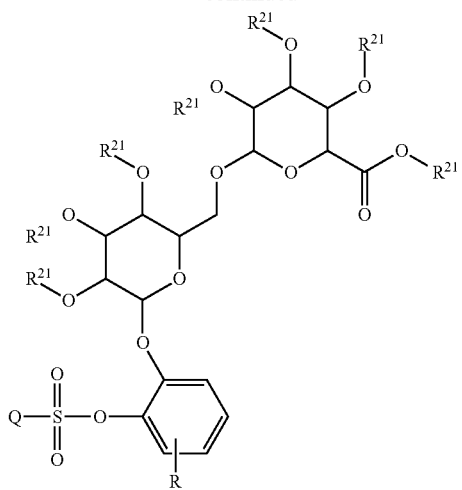
wherein:
R$^1$ is C$_1$-C$_6$ alkyl;
R$^{21}$ and R$^{22}$ are each independently hydrogen or acetyl;
R is hydrogen, *-L$^a$-A$_1$-L$^b$-L$^c$-Z, or a group having a structure of Formula (F), (G), (H), (J), (K), (L), (M), or (N):
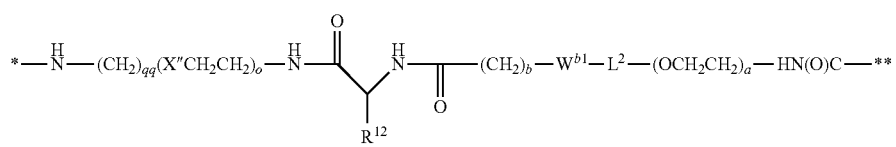
(F)
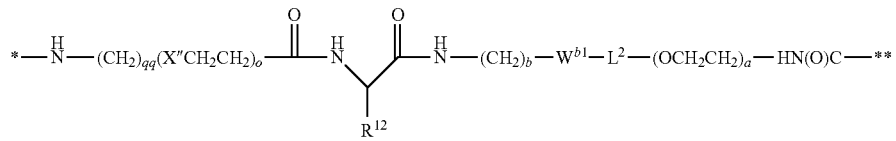
(G)
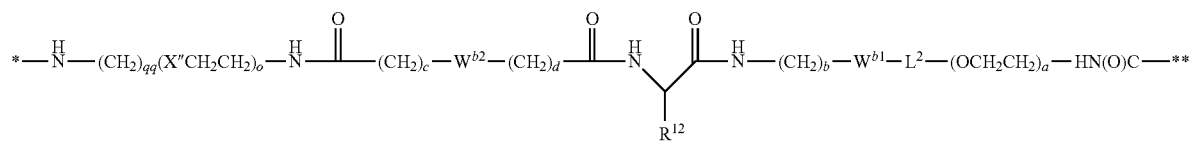
(H)
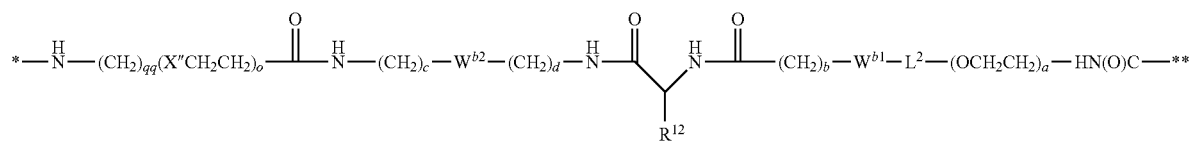
(J)
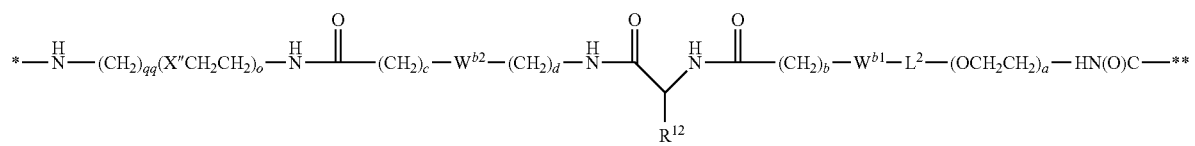
(K)

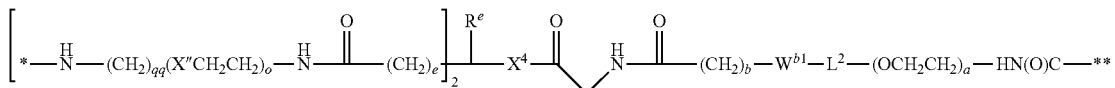

(L)

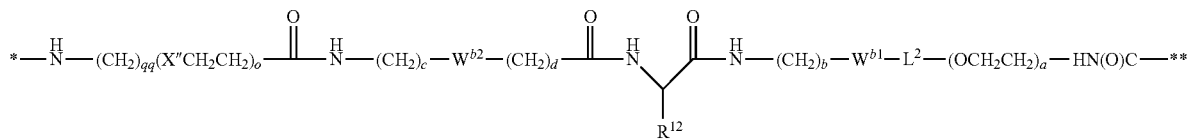

(M)

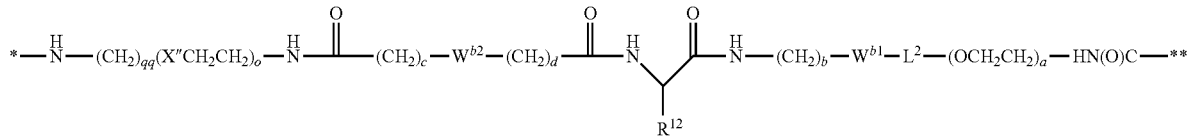

(N)

$L^a$ is a single bond or $C_1$-$C_{20}$ alkylene;
$A^1$ is —C(O)NH—, —NHC(O)—, —NH—, —O—, —PO_3—, —PO_4—, —SO—, —SO_2— or —SO_3—;
$L^b$ is —(CH_2CH_2O)_a— or —(CH_2)_a—;
a is an integer having a value of 1 to about 20;
L' is $C_1$-$C_{20}$ alkylene;
X" is —O—, —S—, —NH—, or —CH_2—;
$W^{b1}$ and $W^{b2}$ are each independently —C(O)NH—, —NHC(O)—,

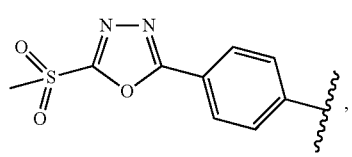

$R^{12}$ is hydrogen, $C_1$-$C_8$ alkyl, an amino acid moiety, —(CH_2)_sCOR^{13}, or —(CH_2)_pNR^{14}R^{15};
$R^{13}$ is OH or —NH(CH_2)_s(X"CH_2CH_2)_{s"}Z;
$R^{14}$ and $R^{15}$ are each independently hydrogen or —(C(O) (CH_2)_{s'}(X"CH_2CH_2)_{s"}Z)_m—CB;
X" is —O—, —S—, —NH—, or —CH_2—;
$R^e$ is $C_1$-$C_8$-alkyl or -(L^{1'}-Z)_m—CB;
$X^4$ is —NHC(O)—(CH_2)_g—NH— or —C(O)NH—(CH_2)_h—NH—;
b, c, d, e, g, h, o, and q are each independently an integer having a value of 1 to about 10;
p is an integer having a value of 1 to about 10;
s and s" are each independently an integer having a value of 0 to about 10;
s' is an integer having a value of 1 to about 10;
m is an integer having a value of 0 or 1;
Z is isocyanide, isothiocyanide, 2-pyridyl disulfide, haloacetamide (—NHC(O)CH_2-hal), maleimide, diene, alkene, halide, tosylate (TsO⁻), aldehyde, sulfonate (R—SO_3⁻), phosphonic acid (—P(=O)(OH)_2), ketone, $C_5$-$C_{10}$-cycloalkynyl, —OH, —NHOH, —NHNH_2, —SH, carboxylic acid (—COOH), acetylene (—C≡CH), azide (—N_3), amino (—NH_2), sulfonic acid (—SO_3H), an alkynone derivative (—C(O)C≡C—R^a, wherein $R^a$ is $C_1$-$C_{10}$ alkyl), or dihydrogen phosphate (—OP(=O)(OH)_2);
CB is a ligand selected from:

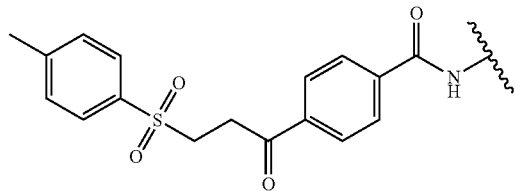

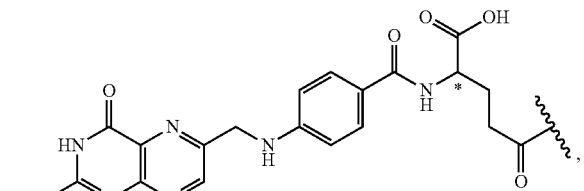

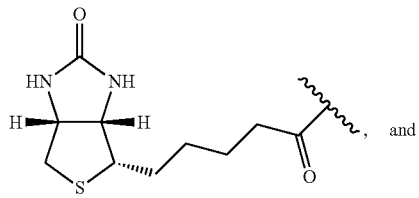, and

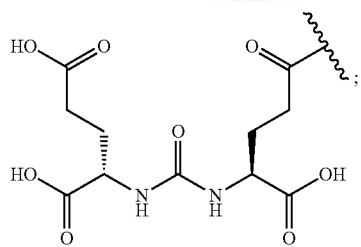
and
Q is selected from:
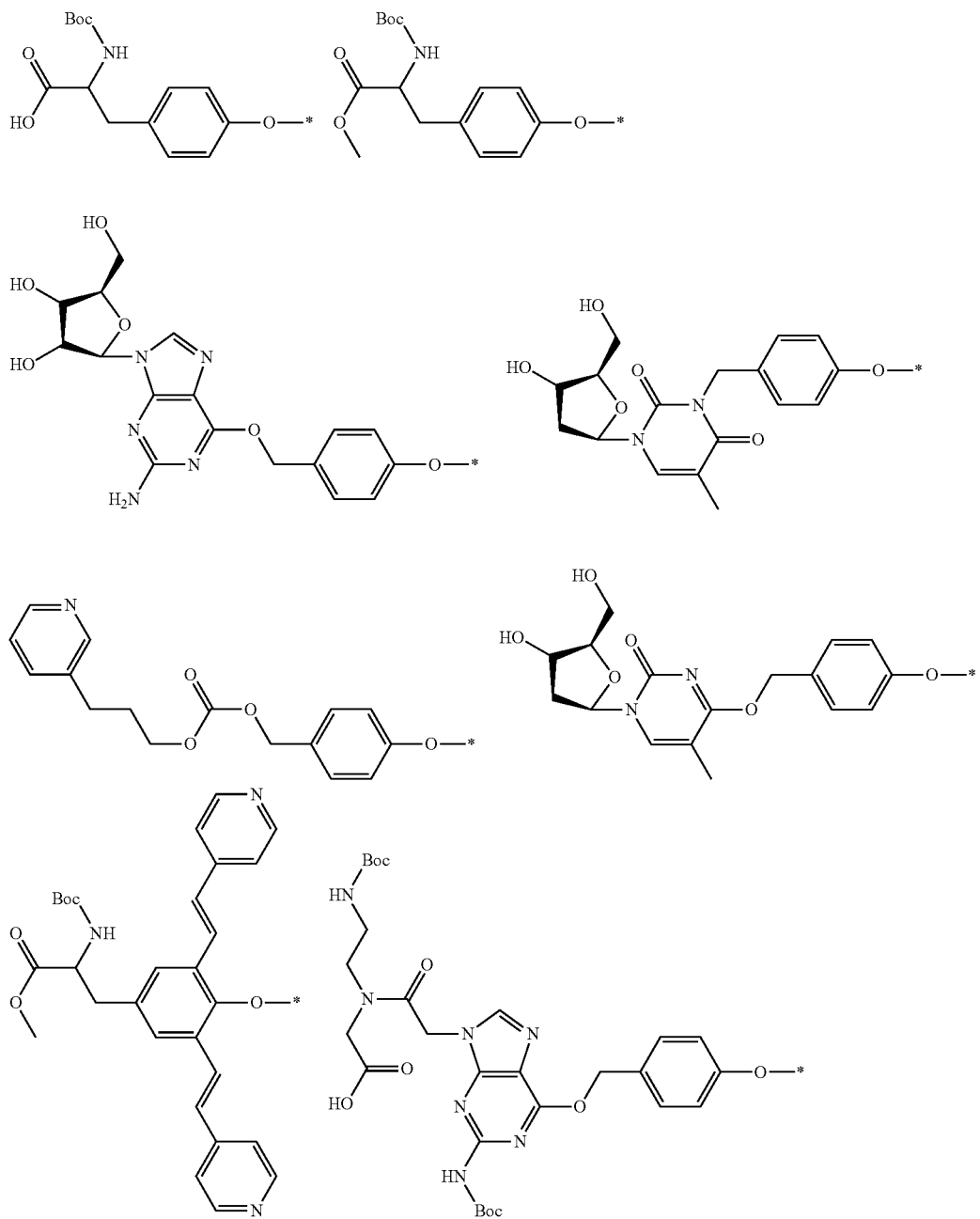

-continued
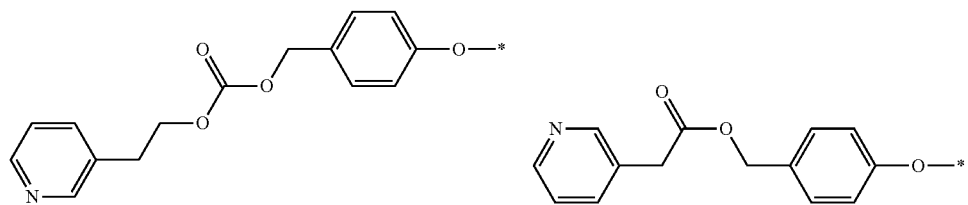
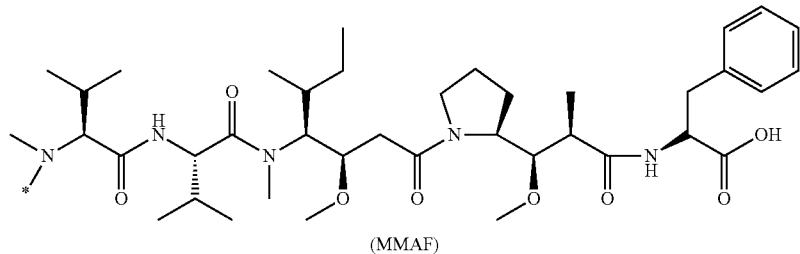
(MMAF)
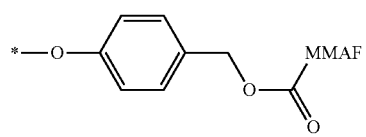
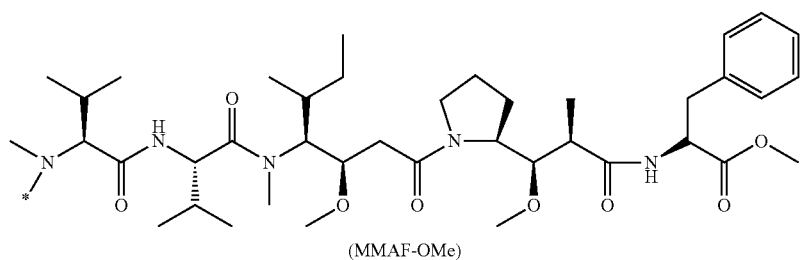
(MMAF-OMe)
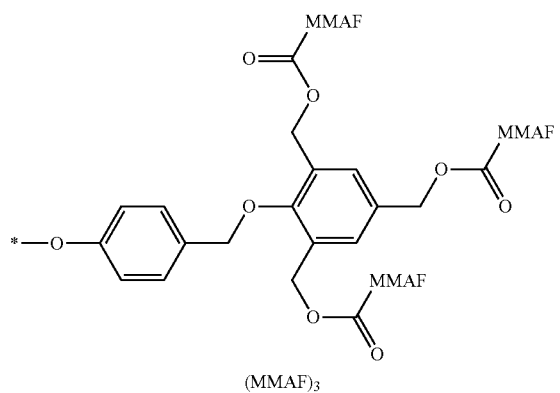
(MMAF)₃
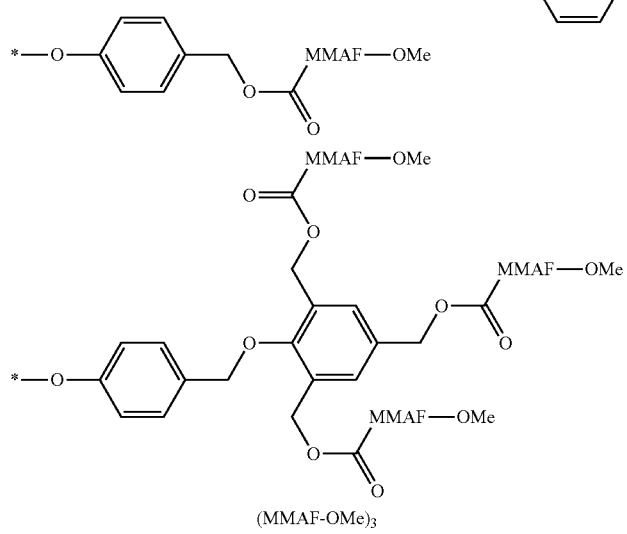
(MMAF-OMe)₃

-continued
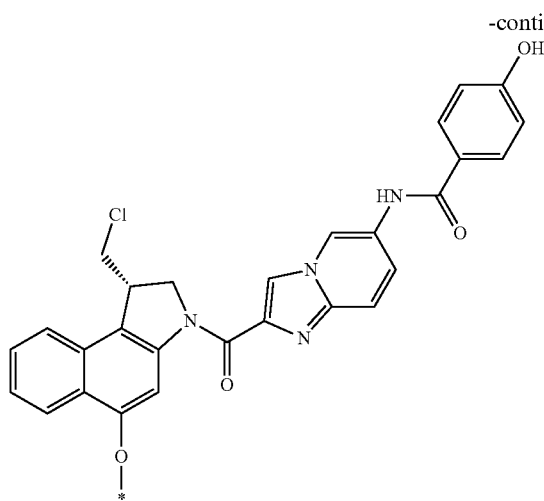
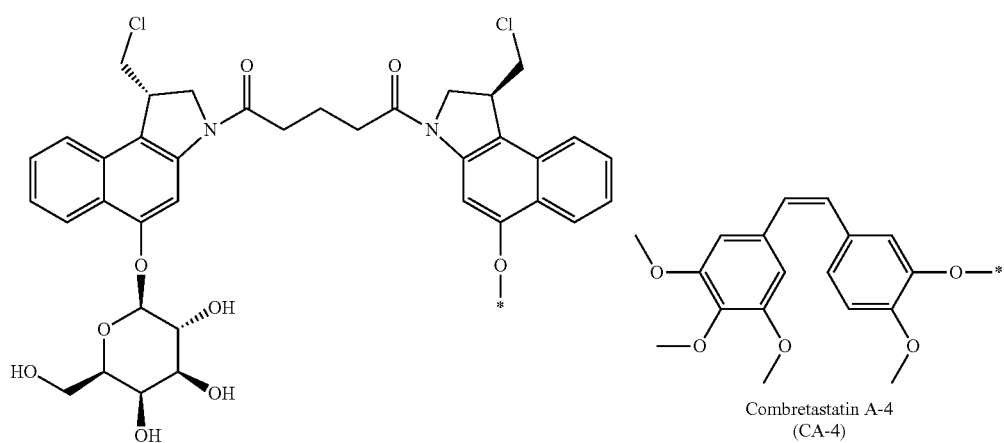
Combretastatin A-4
(CA-4)
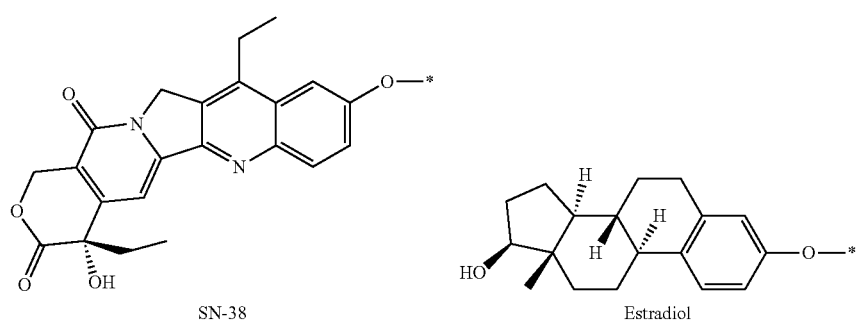
SN-38
Estradiol -continued
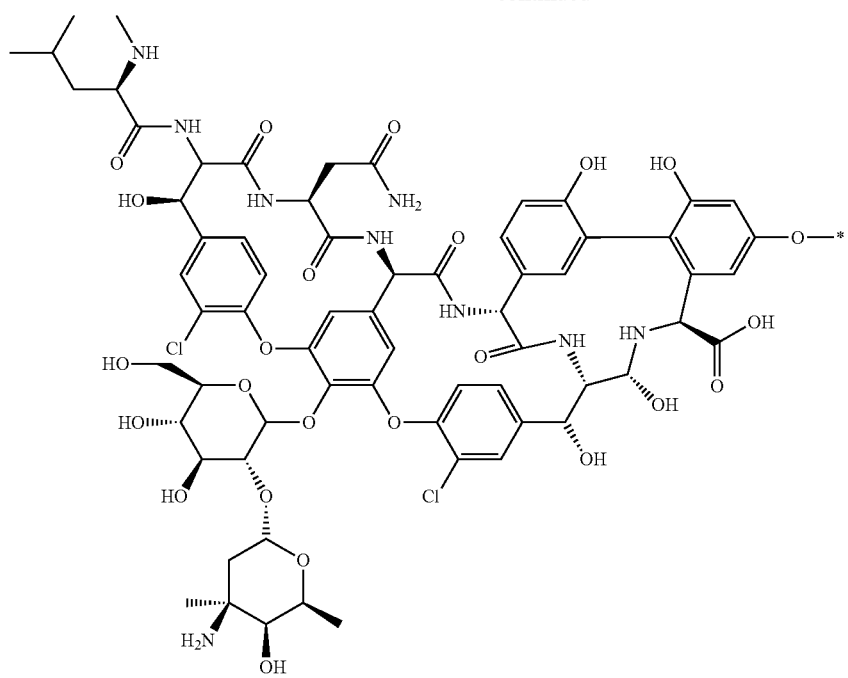
Vancomycin
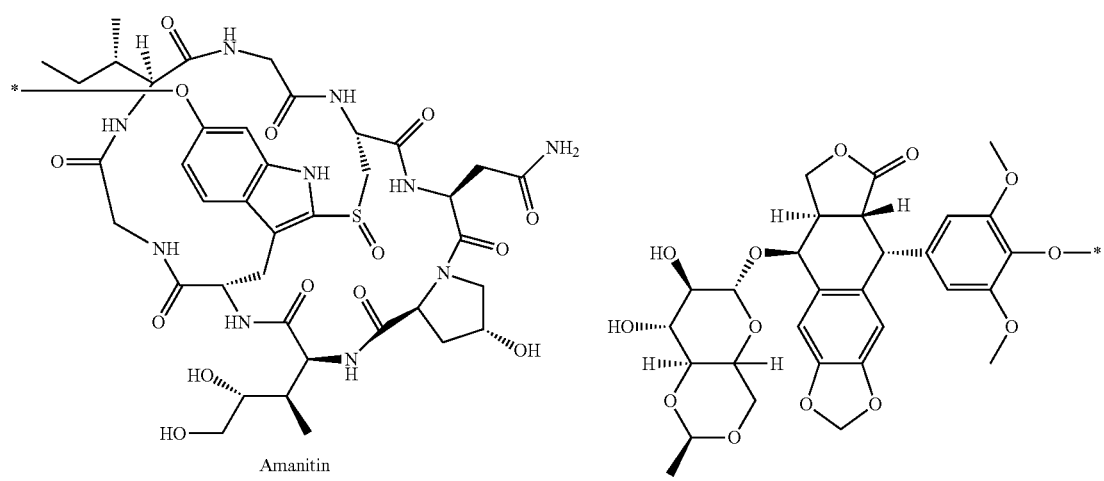
Amanitin
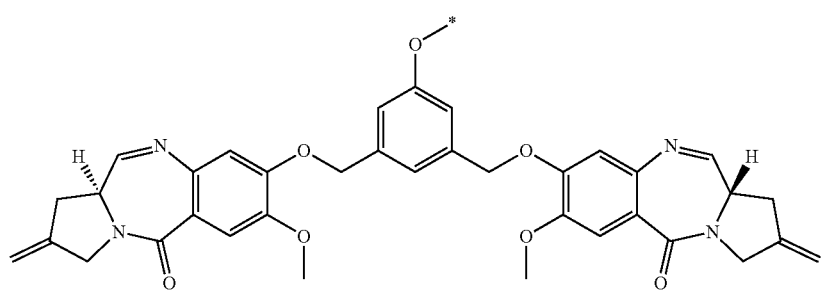
PBD dimer derivative

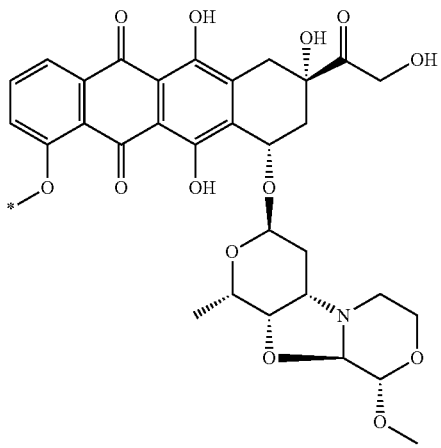

PNU-159682

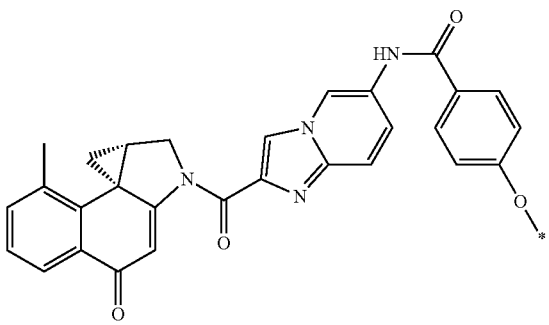

Duocarmycin analog

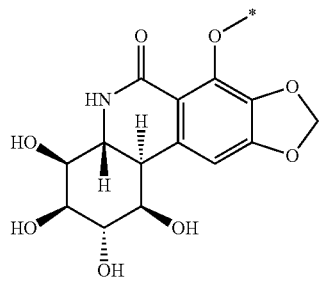

Pancratistatin

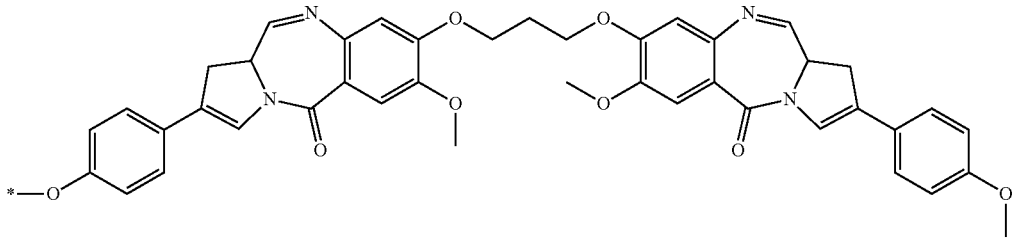

PBD-dimer

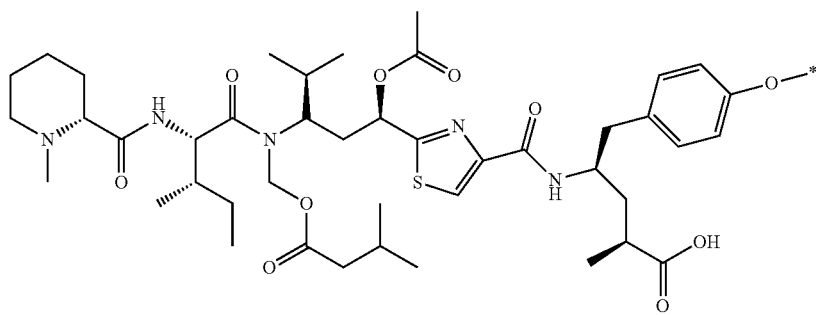

Tubulysin B

Release of the Active Agent

As described above, in certain embodiments, the compounds and conjugates disclosed herein are capable of dissociating one or more active agents (represented by Q, $Q^1$, $Q^2$) through an intramolecular cyclization reaction following a chemical reaction that activates the triggering group. In certain embodiments, the chemical reaction is a physicochemical reaction and/or a biochemical reaction.

In some embodiments, the compounds and conjugates disclosed herein comprise a nucleophilic functional group (Y or Y') introduced at an adjacent atom on Ar with respect to X (e.g., O). Typically, the nucleophilic functional group is masked by a triggering group (TG), as further detailed below. Upon activation, the triggering group releases the nucleophilic functional group to react with the nearby $SO_2$ moiety in an intramolecular cyclization, ultimately releasing the one or more active agents (Q, $Q^1$, or $Q^2$). In some such embodiments, one or more active agents are released through an intramolecular cyclization reaction after a chemical reaction, a physicochemical reaction and/or a biochemical reaction (see, for example, Reaction Scheme 1), or the active agent is released through 1,6-elimination or 1,4- elimination after the intramolecular cyclization reaction (see, for example, Reaction Scheme 2).

As an example, the mechanism when Y is —Y'-TG is shown in Reaction Scheme 1:

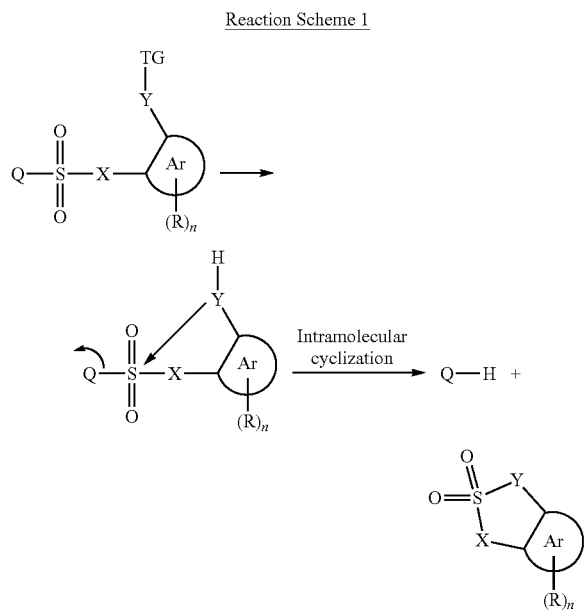

The mechanism when Q is

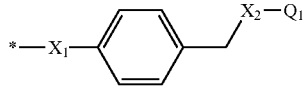

is shown in Reaction Scheme 2:

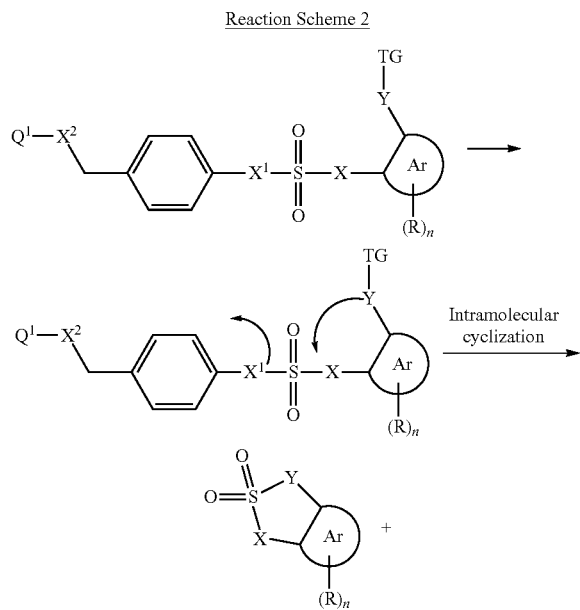

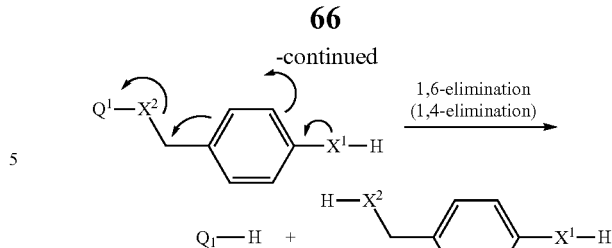

In some embodiments, $Q^1$ when released is an active agent comprising at least one functional group selected from —OH, —NH—, —SH and —COOH. According to these embodiments, as further described herein, $Q^1$ is conjugated to a compound as described herein by the —OH, —NH—, —SH and —COOH, for instance through a functional group selected from ester, amide, thioester, carbamate, urea, oxime, hydrazone, etc. In some such embodiments, $Q^2$ is used in place of $Q^1$, and $Q^2$ is an amine group-containing drug. In other embodiments, $Q^2$ is an active agent capable of binding with an ammonium unit. In still other embodiments, $Q^2$ is capable of being dissociated in its original form having an amine group upon release of $Q^2$ release, wherein the active agent may be a drug, a toxin, an affinity ligand, a probe for detection, or a combination thereof.

In some embodiments, the compounds and conjugates disclosed herein are chemically and physiologically stable. In some such embodiments, the compounds and conjugates disclosed herein reach a desired target cell in a state wherein there is little dissociation of the active agent in the blood, thereby selectively releasing the drug.

Triggering Groups (TGs)

In some embodiments, the conjugates of the present invention include a triggering group (TG). TGs are groups capable of being cleaved, preferably selectively cleaved, by a chemical reaction, such as a biological reaction. Generally, triggering groups serve to mask the nucleophilic nature of the Y or Y' group, thereby providing stability (e.g., by preventing self-immolation or intramolecular cyclization prior to the conjugate reaching a target location or experiencing a predetermined trigger condition) to the compounds and conjugates disclosed herein. Upon activation, the triggering group releases the nucleophilic Y or Y' group and allows for self-immolation or intramolecular cyclization to occur, as described above.

In some embodiments, the TG comprises a sequence (such as a peptide sequence) or a moiety recognized by TEV, trypsin, thrombin, cathepsin B, cathespin D, cathepsin K, caspase 1, matrix metalloproteinase (MMP), and the like, which can be hydrolyzed by an enzyme (e.g., an oxidoreductase, a transferase, a hydrolase, a lyase, an isomerase, a ligase, etc.) and/or may include a moiety selected from a phosphodiester, a phospholipid, an ester, a β-galactose, a β-glucose, a fucose, an oligosugar, and the like.

In some embodiments, the TG comprises a reactive chemical moiety or functional group that can be cleaved under nucleophilic reagent conditions (e.g., a silyl ether, a 2-N-acyl nitrobenzenesulfonamide, an unsaturated vinyl sulfide, a sulfonamide after activation, a malondialdehyde-indole derivative, a levulinoyl ester, a hydrazone, or an acyl hydrazone).

In some embodiments, the TG may comprise a reactive chemical moiety or functional group that can be cleaved under basic reagent conditions (e.g., a 2-cyanoethyl ester, an ethylene glycolyl disuccinate, a 2-sulfonylethyl ester, an alkyl thioester, or a thiophenyl ester).

In some embodiments, the TG may comprise a reactive chemical moiety or functional group that can be cleaved by photo-irradiation (e.g., 2-nitrobenzyl derivative, phenacyl ester, 8-quinolinyl benzenesulfonate, coumarin, phosphotriester, bis-arylhydrazone, or bimane bi-thiopropionic acid derivative).

In some embodiments, the TG may comprise a reactive chemical moiety or functional group that can be cleaved by reducing agent conditions (e.g., hydroxylamine, disulfide, levulinate, nitro, or 4-nitrobenzyl derivative).

In some embodiments, the TG may comprise a reactive chemical moiety or a functional group that can be cleaved using acidic conditions (e.g., saccharides, tert-butylcarbamate analogue, dialkyl or diaryl dialkoxysilane, orthoester, acetal, aconityl, hydrazone, (3-thiopropionate, phosphoramidate, imine, trityl, vinyl ether, polyketal, and alkyl 2-(diphenylphosphino)benzoate derivative; alkyl ester, 8-hydroxyquinoline ester, and picolinate ester).

In some embodiments, the TG may comprise a reactive chemical moiety or functional group that can be cleaved under oxidative conditions (e.g., a boronate, a vicinal diol, paramethoxybenzyl derivative, or a selenium compound).

In certain preferred embodiments, the TG comprises a saccharide, which can be cleaved under acidic or enzymatic conditions. In certain preferred embodiments, the triggering group is —NO$_2$, which can be cleaved under reducing conditions. In certain preferred embodiments, the triggering group is a boronate, which can be cleaved under oxidative conditions. In certain preferred embodiments, the triggering group is an ester, which can be cleaved under acidic, basic, or enzymatic conditions. In certain preferred embodiments, the triggering group is a hydrazone, which can be cleaved under nucleophilic conditions or under acidic conditions. In certain preferred embodiments, the triggering group is a hydroxylamine, which can be cleaved under reducing conditions.

Saccharide Triggering Groups

In some embodiments, the compounds and conjugates disclosed herein comprise a saccharide triggering group, for instance a triggering group selected from:

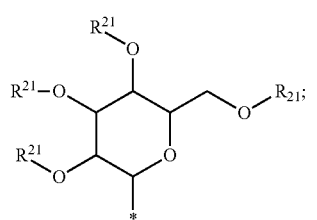

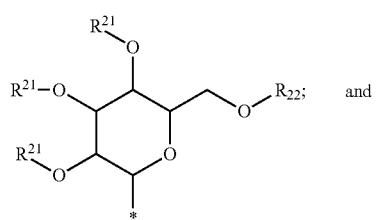
and

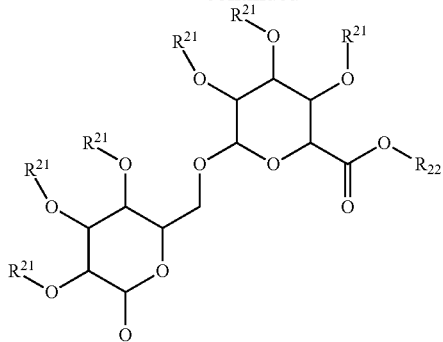

wherein each $R^{21}$ is independently hydrogen or is selected such that O—$R^{21}$ is a hydroxy protecting group (e.g., acetyl); and $R^{22}$ is hydrogen or lower alkyl (e.g., $C_1$-$C_6$-alkyl). In certain embodiments, the hydroxy protecting group is capable of being used in organic synthesis, including but not limited to: methyl ether, methoxymethyl ether, methylthiomethyl ether, 2-methoxyethoxymethyl ether, bis(2-chloroethoxy)methyl ether, tetrahydropyranyl ether, tetrahydrothiopyranyl ether, 4-methoxytetrahydropyranyl ether, 4-methoxytetrahydrothiopyranyl ether, tetrahydrofuranyl ether, 1-ethoxyethyl ether, 1-methyl-1-methoxyethyl ether, 2-(phenylselenyl)ethyl ether, t-butyl ether, allyl ether, benzyl ether, o-nitrobenzyl ether, triphenyl methyl ether, α-naphthyldiphenyl methyl ether, p-methoxyphenyldiphenylmethyl ether, 9-(9-phenyl-10-oxo)anthryl ether, trimethylsilyl ether, isopropyldimethylsilyl ether, t-butyldimethylsilyl ether, t-butyldiphenylsilyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethylbenzoate ester, methyl carbonate, 2,2,2-trichloroethyl carbonate, allyl carbonate, p-nitrophenyl carbonate, benzyl carbonate, p-nitrobenzyl carbonate, S-benzylthiocarbonate, N-phenylcarbamate, nitrate ester, 2,4-dinitrophenylsulfenate ester, etc., but is not limited thereto.

Protecting Groups as Triggering Groups

In some embodiments, TG is a group that is capable of being cleaved by a chemical reaction, a physicochemical reaction, and/or a biological reaction. In certain embodiments, TG is a protecting group. In some such embodiments, the protecting group is an amine group protecting group, an alcohol protecting group, or a thiol protecting group.

Amine Protecting Groups

In certain embodiments, the amine protecting group is a general protecting group that is capable of being used in organic synthesis, including but not limited to: m-nitrophenyl carbamate, 3,5-dimethoxybenzyl carbamate, o-nitrobenzyl carbamate, phenyl(o-nitrophenyl)methyl carbamate, alkyl carbamate, 9-fluorenylmethyl carbamate, 2,2,2-trichloroethyl carbamate, 2-trimethylsilylethyl carbamate (Teoc), t-butyl carbamate(Boc), vinyl carbamate (Voc), allyl carbamate (Alloc), 1-isopropylallyl carbamate (Ipaoc), 8-quinolyl carbamate, N-hydroxypiperidinyl carbamate, benzyl carbamate, p-methoxybenzyl carbamate, p-nitrobenzyl carbamate, diphenyl methyl carbamate, acetamide, chloroacetamide, trichloroacetamide, phenylacetamide, benzamide, N-phthalimide, N-2,3-diphenylmaleimide, N-2,5-dimethylpyrrole, N-1,1-dimethylthiomethyleneamine, N-benzylideneamine, benzenesulfenamide, o-nitrobenzenesulfenamide, triphenylmethylsulfenamide, p-toluenesulfonamide, methanesulfonamide, etc., but is not limited thereto.

Alcohol Protecting Groups

In certain embodiments, the alcohol protecting group is a general protecting group that is capable of being used in organic synthesis, including but not limited to: methyl ether, methoxymethyl ether (MOM ether), benzyloxymethyl ether (BOM ether), 2-(trimethylsilyl)ethoxymethyl ether (SEM ether), phenylthiomethyl ether (PTM ether), 2,2-dichloro-1,1-difluoroethyl ether, p-bromophenacyl ether, chloropropylmethyl ether, isopropyl ether, cyclohexyl ether, 4-methoxybenzyl, 2,6-dichlorobenzyl ether, 4-(dimethylaminocarbonyl)benzyl ether, 9-anthrylmethyl ether, 4-picolyl ether, methylthiomethyl ether (MTM ether), 2-methoxyethoxymethyl ether (MEM ether), bis(2-chloroethoxy)methyl ether, tetrahydropyranyl ether (THP ether), tetrahydrothiopyranyl ether, 4-methoxytetrahydropyranyl ether, 4-methoxytetrahydrothiopyranyl ether, tetrahydrofuranyl ether, 1-ethoxyethyl ether, 1-methyl-1-methoxyethyl ether, 2-(phenylselenyl)ethyl ether), t-butyl ether, allyl ether, benzyl ether, o-nitrobenzyl ether, triphenylmethyl ether, α-naphthyldiphenylmethyl ether, p-methoxyphenyldiphenylmethyl ether, 9-(9-phenyl-10-oxo)anthryl ether, trimethylsilyl ether (TMS ether), isopropyldimethylsilyl ether, t-butyldimethylsilyl ether (TBDMS ether), t-butyldiphenyl silyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethylbenzoate(Mesitoate) ester, methyl carbonate, 2,2,2-trichloroethyl carbonate, allyl carbonate, p-nitrophenyl carbonate, benzyl carbonate, p-nitrobenzyl carbonate, S-benzyl thiocarbonate, N-phenylcarbamate, nitrate ester, 2,4-dinitrophenylsulfenate ester, dimethylphosphinyl ester (DMP ester), dimethylthiophosphinyl ester (MPT ester), aryl methanesulfonate, aryl toluenesulfonate, etc., but is not limited thereto.

Thiol Protecting Groups

In certain embodiments, the thiol protecting group is capable of being used in organic synthesis, including but not limited to: S-benzyl thioether, S-p-methoxybenzyl thioether, S-o- or p-hydroxyl or acetoxybenzyl thioether, S-p-nitrobenzyl thioether, S-4-picolyl thioether, S-2-picolyl N-oxide thioether, S-9-anthrylmethyl thioether, S-9-fluorenylmethyl thioether, S-methoxymethyl monothioacetal, A-acetyl derivative, S-benzoyl derivative, S—(N-ethylcarbamate), S—(N-methoxymethylcarbamate), etc., but is not limited thereto.

Linking Group

In some embodiments, the compounds and conjugates disclosed herein comprise a linking group connecting each CB and Ar through a covalent bond. Typical linking groups are stable, non-hydrolyzable moieties, such as, for example a $C_{10}$-$C_{100}$ linear or branched, saturated or unsaturated alkylene. In certain embodiments, the linking unit satisfies at least two, and more preferably at least three, out of four of the following criteria:

(i) at least one —$CH_2$— in the alkylene moiety is substituted with (i.e., is replaced by) one or more heteroatoms selected from —NH—, —C(=O)—, —O—, —S— and —P—;

(ii) at least one heteroarylene is included in the alkylene moiety;

(iii) at least one amino acid moiety, sugar bond, peptide bond, or amide bond is included in the alkylene moiety; and (iv) the alkylene may be further substituted with one or more substituents selected from the group consisting of $C_1$-$C_{20}$ alkyl, $C_6$-$C_{20}$ aryl $C_1$-$C_8$ alkyl, —$(CH_2)_s$COOH, and —$(CH_2)_p$$NH_2$, wherein s is an integer having a value of 0 to 10, and p is an integer having a value of 1 to about 10.

In certain embodiments, the linking unit comprises at least two, and more preferably at least three, of the following:

(i) at least one heteroatom selected from —NH—, —C(=O), —O—, —S— and —P—;

(ii) at least one heteroarylene;

(iii) at least one amino acid moiety, sugar bond, peptide bond, or amide bond; and (iv) the alkylene may be further substituted with one or more substituents selected from the group consisting of $C_1$-$C_{20}$ alkyl, $C_6$-$C_{20}$ aryl $C_1$-$C_8$ alkyl, —$(CH_2)_s$COOH, and —$(CH_2)_p$$NH_2$, wherein s is an integer having a value of 0 to 10, and p is an integer having a value of 1 to about 10.

In other embodiments, the linking group connecting each CB and Ar comprises a functional group produced through a click chemical reaction.

In alternative embodiments, the linking unit comprises a reactive functional group capable of participating in a click chemical reaction.

A click chemical reaction is a reaction that can be performed under mild conditions, and is extremely selective for functional groups that are not commonly found in biological molecules (e.g., an azide group, an acetylene group, etc.). Accordingly, this reaction can be carried out in the presence of complex triggering groups, targeting moieties, etc. Further, click chemistry has high reaction specificity. For example, the click chemical reaction between an azide group and an acetylene group proceeds selectively without interference from other functional groups present in the molecule. For example, azide-acetylene click chemistry may afford a triazole moiety in high yield.

Thus, in some embodiments, the linking group connecting each CB and Ar comprises

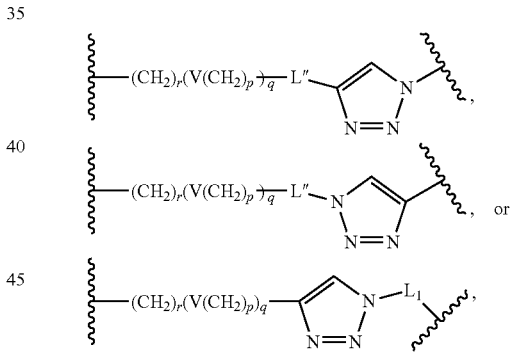

V may be a single bond, —O—, —S—, —$NR^{21}$—, —C(O)$NR^{22}$—, —$NR^{23}$C(O)—, —$NR^{24}SO_2$—, or —$SO_2NR^{25}$—, $R^{21}$ to $R^{25}$ may be each independently hydrogen, ($C_1$-$C_6$) alkyl, ($C_1$-$C_6$)alkyl($C_6$-$C_{20}$)aryl, or ($C_1$-$C_6$)alkyl($C_3$-$C_{20}$) heteroaryl, r may be an integer having a value of 1 to about 10, p may be an integer having a value of 0 to about 10, q may be an integer having a value of 1 to about 10, and L" may be a single bond.

In other embodiments, the linking unit connecting each CB and Ar is a linking group represented by Formula (A):

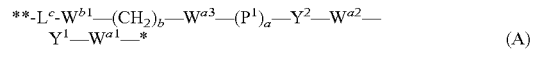

wherein:

is the point of attachment to CB;

* is point of attachment to Ar;

$W^{a1}$, $W^{a2}$, and $W^{a3}$ are each independently —NH—, —C(=O)—, or (—$CH_2$—)$_b$;

$W^{b1}$ is an amide bond or triazolylene;

$P^1$ is a linker connecting $W^{a3}$ and $Y^2$, and is an amino acid moiety, a peptide bond, or an amide bond;

L' is alkylene;

$Y^2$ is a single bond, $-W^{a4}-(CH_2)_c-W^{b2}-(CH_2)_d-W^{a5}-$, or $-W^{a6}-(CH_2)_e-CR^eR^f-X-$;

$R^e$ is $C_1$-$C_8$ alkyl or $CB-W^{a7}-Y_3-W_{c1}-(CH_2)_f-$;

$R^f$ is $B-W^{a7}-Y^3-W^{c1}-(CH_2)_f-$;

X is $-NHC(=O)-(CH_2)_g-W^{a8}-$ or $-C(=O)NH-(CH_2)_h-W^{a9}-$;

$W^{a4}$, $W^{a5}$, $W^{a6}$, $W^{a7}$, $W^{a8}$, and $W^{a9}$ are each independently $-NH-$, $-C(=O)-$, or $-CH_2-$;

$W^{b2}$ is an amide bond or triazolylene;

$W^{c1}$ is $-NHC(=O)-$ or $-C(=O)NH-$;

$Y^3$ is $-(CH_2)_i-(X'CH_2CH_2)_j-(CH_2)_k-$;

X' is $-O-$, $-S-$, $-NH-$, or $-CH_2-$;

CB is the same as defined above;

b, c, d, e, f, g, h, i, and j are each independently an integer having a value of 1 to about 10;

k and y are each independently an integer having a value of 0 to about 10;

$Y^1$ is $-(CH_2)_q-(CH_2CH_2X'')_o-$ or $-(CH_2)_q-(X''CH_2CH_2)_o-$;

X'' is $-O-$, $-S-$, $-NH-$, or $-CH_2-$; and and q are an integer having a value of 1 to about 10.

In some embodiments, $P^1$ comprises at least one unit represented by Formula (B) or (C):

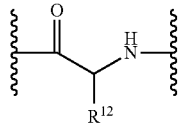
(B)

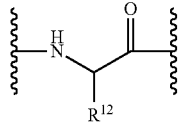
(C)

wherein:

$R^{12}$ is hydrogen, $C_1$-$C_8$-alkyl, an amino acid side chain, such as a natural amino acid side chain (e.g., H, methyl, isopropyl, isobutyl, sec-butyl, S-methyl thioether, benzyl, indole, pyrollidine, pyrroline, hydroxymethyl, tyrosyl, lysyl, imidazole, glycyl, glutamyl, carbamoylbutanoic acid, carboxamide, aspartic acid, 1-hydroxyethyl, and 2-hydroxyethyl), $-(CH_2)_sCOR^{13}$ or $-(CH_2)_pNR^{14}R^{15}$;

$R^{13}$ is OH or $-NH(CH_2)_s(X''CH_2CH_2)_{s''}Z$;

$R^{14}$ and $R^{15}$ are each independently hydrogen or $-(C(O)(CH_2)_s(X''CH_2CH_2)_{s''}Z)_m-CB$;

X'' is $-O-$, $-S-$, $-NH-$, or $-CH_2-$;

Z and CB are the same as defined above;

p is an integer having a value of 1 to about 10;

s and s'' are an integer having a value of 0 to about 10;

s' is an integer having a value of 1 to about 10; and m is an integer having a value of 0 or 1.

In some embodiments of formula (B) or (C):

$R^{12}$ is hydrogen, alkyl, an amino acid side chain, $-(CH_2)_sC(O)R^{13}$ or $-(CH_2)_pNR^{14}R^{15}$;

p is an integer having a value of 1 to about 10;

s is an integer having a value of 0 to about 10;

$R^{13}$ is OH or $-NH(CH_2)_s(X'''CH_2CH_2)_{s'}-Z-(CB)_m$;

$R^{14}$ and $R^{15}$ are each independently hydrogen or $-C(O)(CH_2)_s(X'''CH_2CH_2)_{s''}Z-(CB)_m$;

s'' is an integer having a value of 0 to about 10;

s' is an integer having a value of 1 to about 10;

m is an integer having a value of 0 or 1;

X''' is $-O-$, $-S-$, $-NH-$, or $-CH_2-$; and

Z'' is a linking group connecting CB to the remainder of $R^{14}$ or $R^{15}$; or Z'' is a linking group comprising a reactive group.

In some such embodiments of formula (B) or (C):

$R^{13}$ is OH or $-NH(CH_2)_s(X'''CH_2CH_2)_{s''}Z''$;

$R^{14}$ and $R^{15}$ are each independently hydrogen or $-C(O)(CH_2)_s(X'''CH_2CH_2)_{s''}Z''$; and Z'' is a reactive precursor of a linking unit selected from isocyanide, isothiocyanide, 2-pyridyl disulfide, haloacetamide ($-NHC(O)CH_2$-hal), maleimide, diene, alkene, halide, tosylate (TsO⁻), aldehyde, sulfonate (R$-SO_3^-$),

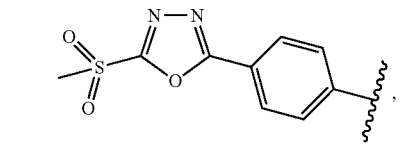

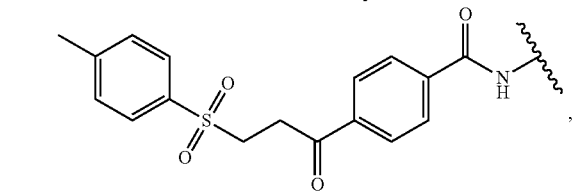

phosphonic acid ($-P(=O)(OH)_2$), ketone, $C_8$-$C_{10}$ cycloalkynyl, $-OH$, $-NHOH$, $-NHNH_2$, $-SH$, carboxylic acid ($-COOH$), acetylene ($-C\equiv CH$), azide ($-N_3$), amino ($-NH_2$), sulfonic acid ($-SO_3H$), an alkynone derivative ($-C(O)C\equiv C-R^a$, wherein $R^a$ is $C_1$-$C_{10}$-alkyl), and dihydrogen phosphate ($-OP(=O)(OH)_2$).

In other such embodiments of formula (B) or (C):

$R^{13}$ is OH or $-NH(CH_2)_s(X'''CH_2CH_2)_{s''}-Z''CB$;

$R^{14}$ and $R^{15}$ are each independently hydrogen or $-C(O)(CH_2)_s(X'''CH_2CH_2)s$-Z''CB; and Z'' is a linking unit connecting CB to the remainder of $R^{14}$ or $R^{15}$ formed from a precursor selected from isocyanide, isothiocyanide, 2-pyridyl disulfide, haloacetamide ($-NHC(O)CH_2$-hal), maleimide, diene, alkene, halide, tosylate (TsO⁻), aldehyde, sulfonate (R$-SO_3^-$),

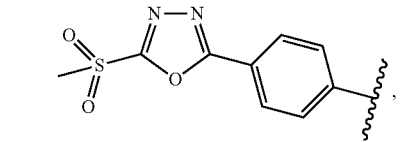

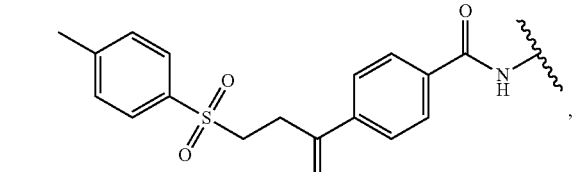

phosphonic acid ($-P(=O)(OH)_2$), ketone, $C_8$-$C_{10}$ cycloalkynyl, $-OH$, $-NHOH$, $-NHNH_2$, $-SH$, carboxylic acid ($-COOH$), acetylene ($-C\equiv CH$), azide ($-N_3$), amino ($-NH_2$), sulfonic acid ($-SO_3H$), an alkynone derivative (—C(O)C≡C—R$^a$, wherein R$^a$ is C$_1$-C$_{10}$-alkyl), and dihydrogen phosphate (—OP(=O)(OH)$_2$).

In some embodiments, Y$^2$ is a single bond or is selected from:

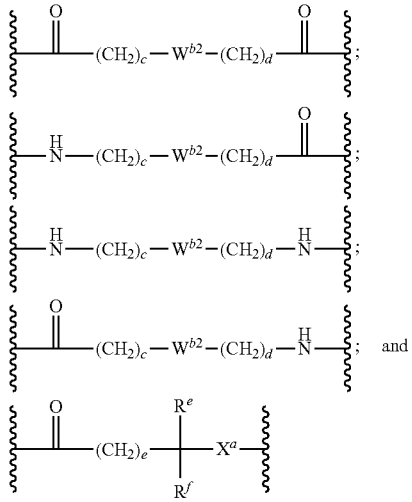

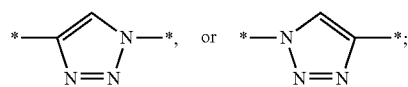

wherein:
W$^{b2}$ is —C(O)NH—, —NHC(O)—,

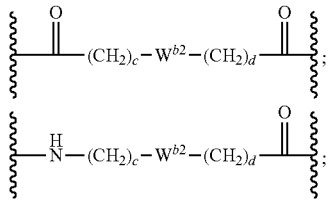

R$^e$ is C$_1$-C$_8$-alkyl or -(L$^{1'}$-Z—)$_m$CB;
R$^f$ is B—W$^{b2'}$—(CH$_2$)$_i$—(X"CH$_2$CH$_2$)$_j$—NH—C(=O)—(CH$_2$)$_f$—;
X$^a$ is —NHC(=O)—(CH$_2$)$_g$—NH— or —C(O)NH—(CH$_2$)$_h$—NH—;
W$^{b2'}$ is —C(O)NH— or —NHC(=O)—;
c, d, e, f, g, h, i, and j are each independently an integer having a value of 1 to about 10;
X" is —O—, —S—, —NH—, or —CH$_2$—; and
L$^{1'}$, Z, m, and B are the same as defined above.

In certain embodiments, the linking unit connecting each CB and Ar is a linking group comprising (CH$_2$)$_b$, L$^c$, (P$^1$)$_a$, W$^{a1}$, W$^{a2}$, W$^{a3}$, Y$^1$, and Y$^2$ groups connected to each other by covalent bonds, wherein:
W$^{a1}$, W$^{a2}$, and W$^{a3}$ are each independently —NH—, —C(O)—, or —CH$_2$—;
W$^{b1}$ is an amide bond or triazolylene;
P$^1$ is an amide bond, an amino acid residue, or a peptide;
L$^c$ is alkylene;
Y$^1$ is —(CH$_2$)$_q$—(CH$_2$CH$_2$X")$_o$— or —(CH$_2$)$_q$—(X"CH$_2$CH$_2$)$_o$—;
X" is —O—, —S—, —NH— or —CH$_2$—;
Y$^2$ is a single bond or a group selected from:

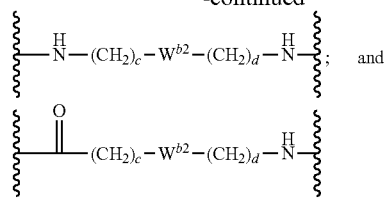

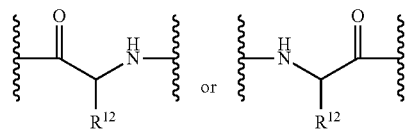

W$^{b2}$ is an amide bond or triazolylene;
a is 0 to 10;
b, c, and d are each independently an integer having a value of 1 to about 10; and
o and q are each independently an integer having a value of 1 to about 10.

In some embodiments, R$^{12}$ is a natural amino acid side chain. In other embodiments, R$^{12}$ is non-natural amino acid side chain.

In some embodiments, the linking unit connecting each CB and Ar is a linking group represented by Formula (A):

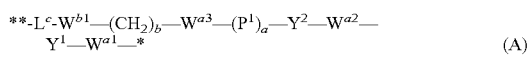

wherein:
* is the point of attachment to CB; and
** is point of attachment to Ar.

In some such embodiments, P$^1$ is

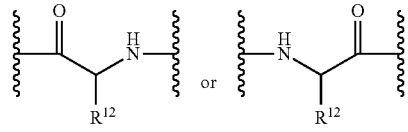

wherein:
R$^{12}$ is hydrogen, alkyl, an amino acid side chain, —(CH$_2$)$_s$COOH or —(CH$_2$)$_p$NH$_2$;
p is an integer having a value of 1 to about 10; and
s and s" are each independently an integer having a value of 0 to about 10.

In some embodiments P$^1$ is

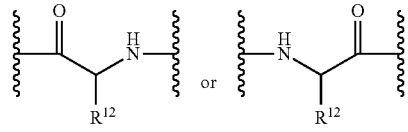

wherein:
R$^{12}$ is hydrogen, alkyl, an amino acid side chain, —(CH$_2$)$_s$C(O)R$^{13}$ or —(CH$_2$)$_p$NR$^{14}$R$^{15}$;
p is an integer having a value of 1 to about 10;
s is an integer having a value of 0 to about 10;
R$^{13}$ is OH or —NH(CH$_2$)$_{s'}$(X'''CH$_2$CH$_2$)$_{s''}$Z"—(CB)$_m$;
R$^{14}$ and R$^{15}$ are each independently hydrogen or —C(O)(CH$_2$)$_{s'}$(X'''CH$_2$CH$_2$)$_{s''}$Z"—(CB)$_m$;
s" is an integer having a value of 0 to about 10;
s' is an integer having a value of 1 to about 10;
m is an integer having a value of 0 or 1;
X''' is —O—, —S—, —NH—, or —CH$_2$—; and
Z" is a linking group connecting CB to the remainder of R$^{14}$ or R$^{15}$; or Z" is a linking group comprising a reactive group.

In some such embodiments of $P^1$:

$R^{13}$ is OH or —NH(CH$_2$)$_s$(X'''CH$_2$CH$_2$)$_{s'}$-Z'';

$R^{14}$ and $R^{15}$ are each independently hydrogen or —C(O)(CH$_2$)$_{s'}$(X'''CH$_2$CH$_2$)$_{s''}$Z''; and Z'' is a reactive precursor of a linking unit selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

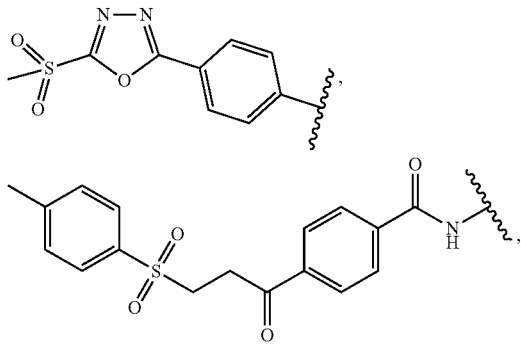

phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In other such embodiments of $P^1$:

$R^{13}$ is OH or —NH(CH$_2$)$_s$(X'''CH$_2$CH$_2$)$_{s''}$Z''CB;

$R^{14}$ and $R^{15}$ are each independently hydrogen or —C(O)(CH$_2$)$_s$(X'''CH$_2$CH$_2$)$_{s''}$Z''CB; and Z'' is a linking unit connecting CB to the remainder of $R^{14}$ or $R^{15}$ formed from a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

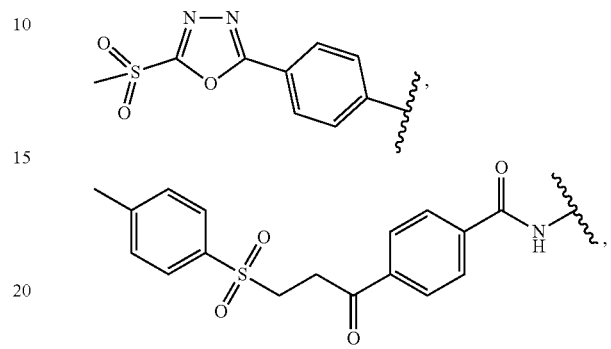

phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In alternative embodiments, the linking unit connecting CB and Ar is a linking group represented by Formula (F), (G), (H), (J), (K), (L), (M), or (N):

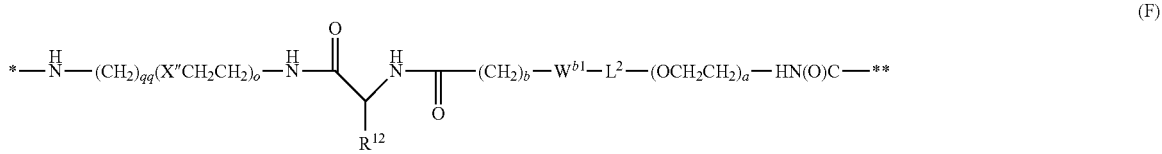

(F)

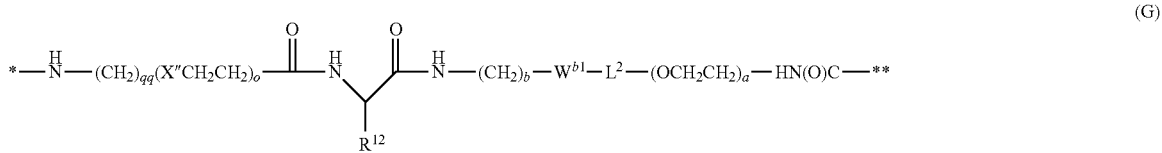

(G)

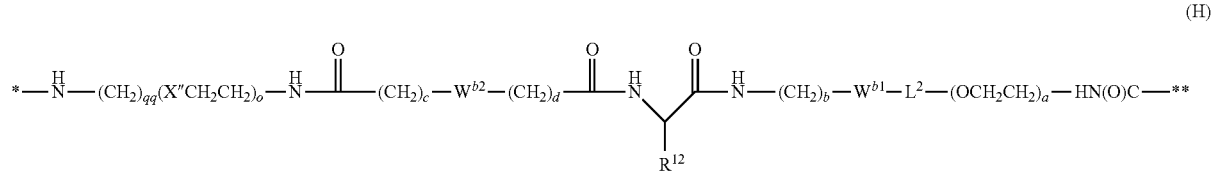

(H)

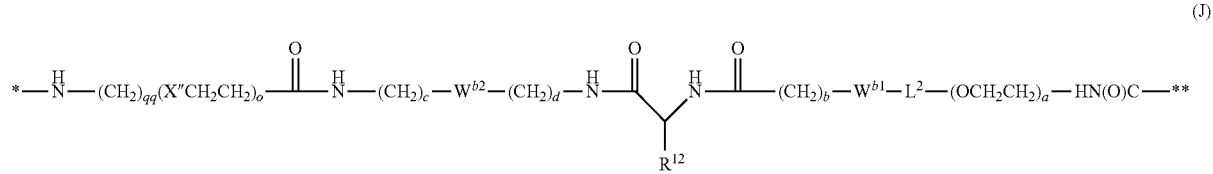

(J)

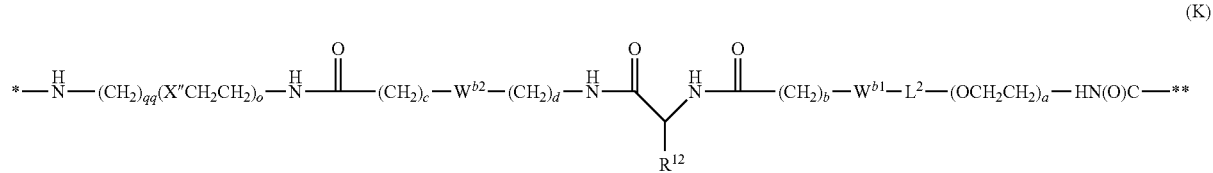

(K)

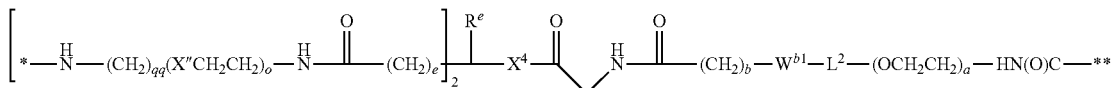
(L)

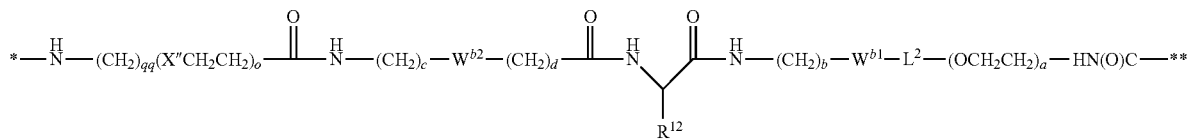
(M)

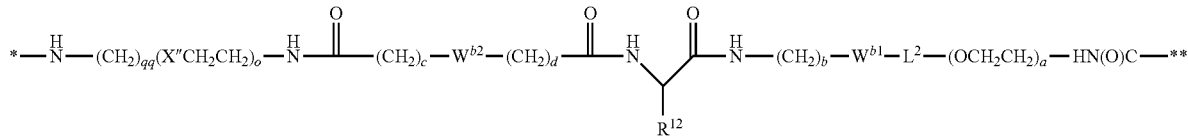
(N)

wherein:

$R^e$ is alkyl;

$X^4$ is —NHC(O)—$(CH_2)_g$—NH— or —C(O)NH—$(CH_2)_h$—NH—;

e, g, and h are each independently an integer having a value of 1 to about 10; and s' is an integer having a value of 1 to about 10.

In some embodiments of Formula (F), (G), (H), (I), (J), (K), (L), or (M):

$R^{12}$ is hydrogen, alkyl, an amino acid side chain, —$(CH_2)_s$C(O)$R^{13}$ or —$(CH_2)_p NR^{14}R^{15}$;

p is an integer having a value of 1 to about 10;

s is an integer having a value of 0 to about 10;

$R^{13}$ is OH or —NH$(CH_2)_{s'}$(X'''CH$_2$CH$_2$)s-Z''—$(CB)_m$;

$R^{14}$ and $R^{15}$ are each independently hydrogen or —C(O)$(CH_2)_{s'}$(X'''CH$_2$CH$_2)_{s''}$-Z''—$(CB)_m$;

s'' is an integer having a value of 0 to about 10;

s' is an integer having a value of 1 to about 10;

m is an integer having a value of 0 or 1;

X''' is —O—, —S—, —NH—, or —CH$_2$—; and

Z'' is a linking group connecting CB to the remainder of $R^{14}$ or $R^{15}$; or Z'' is a linking group comprising a reactive group.

In some such embodiments of Formula (F), (G), (H), (I), (J), (K), (L), or (M):

$R^{13}$ is OH or —NH$(CH_2)_{s'}$(X'''CH$_2$CH$_2)_{s''}$Z'';

$R^{14}$ and $R^{15}$ are each independently hydrogen or —C(O)$(CH_2)_{s'}$(X'''CH$_2$CH$_2)_{s''}$Z''; and Z'' is a reactive precursor of a linking unit selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

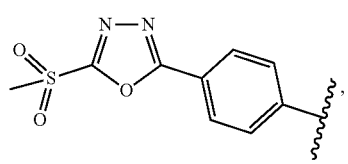

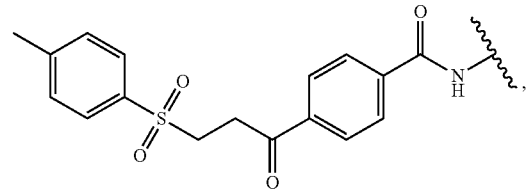

phosphonic acid (—P(=O)(OH)$_2$), ketone, $C_8$-$C_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—$R^a$, wherein $R^a$ is $C_1$-$C_{10}$-alkyl), and dihydrogen phosphate (—OP(=O)(OH)$_2$).

In some embodiments of Formula (F), (G), (H), (I), (J), (K), (L), or (M):

$R^{13}$ is OH or —NH$(CH_2)_{s'}$(X'''CH$_2$CH$_2)$s-Z''CB;

$R^{14}$ and $R^{15}$ are each independently hydrogen or —C(O)$(CH_2)_{s'}$(X'''CH$_2$CH$_2)_{s''}$—Z''CB; and Z'' is a linking unit connecting CB to the remainder of $R^{14}$ or $R^{15}$ formed from a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

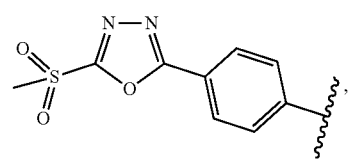

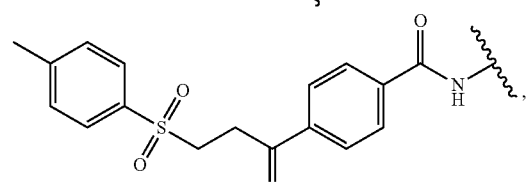

phosphonic acid (—P(=O)(OH)$_2$), ketone, $C_8$-$C_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

Targeting Moieties

The compounds and conjugates of the present invention can further comprise a ligand or targeting moiety, CB. In some embodiments, the ligand or targeting moiety is any molecular recognition element, which can undergo a specific interaction with at least one other molecular through, e.g., noncovalent bonding such as hydrogen bonding, metal coordination, hydrophobic forces, van der Waals forces, π-π interactions, halogen bonding, electrostatic, and/or electromagnetic effects. In certain embodiments, CB is selected from a nanoparticle, an immunoglobulin, a nucleic acid, a protein, an oligopeptide, a polypeptide, an antibody, a fragment of an antigenic polypeptide, a repebody, and the like.

The compounds and conjugates of the present invention may comprise one or more targeting moieties. That is, the variable cb may have an integer value selected from 1, 2, 3, 4, 5, 1-10, or 1-20.

In some embodiments, CB comprises two or more independently selected natural amino acids or non-natural amino acids conjugated by covalent bonds (e.g., peptide bonds), and the peptide may include 2, 3, 4, 5, 6, 7, 8, 9, 10, 11, 12, 13, 14, 15, 16, 17, 18, 19, 20, or more natural amino acids or non-natural amino acids that are conjugated by peptide bonds. In some embodiments, the ligand comprises shorter amino acid sequences (e.g., fragments of natural proteins or synthetic polypeptide fragments) as well as full-length proteins (e.g., pre-engineered proteins).

In some embodiments, CB is selected from an antibody, a hormone, a drug, an antibody analogue (e.g., non-IgG), protein, an oligopeptide, a polypeptide, etc., which bind to a receptor. In certain embodiments, CB selectively targets the drug in a specific organ, tissue, or cell. In other embodiments, CB specifically binds to a receptor over-expressed in cancer cells as compared to normal cells, and may be classified into a monoclonal antibody (mAb) or an antibody fragment and a low-molecular non-antibody. Preferably, CB is selected from peptides, tumor cell-specific peptides, tumor cell-specific aptamers, tumor cell-specific carbohydrates, tumor cell-specific monoclonal antibodies, polyclonal antibodies, and antibody fragments that are identified in a library screen.

Exemplary ligands or targeting moieties include, but are not limited to, carnitine, inositol, lipoic acid, pyridoxal, ascorbic acid, niacin, pantothenic acid, folic acid, riboflavin, thiamine, biotin, vitamin B$_{12}$, other water-soluble vitamins (vitamin B), fat-soluble vitamins (vitamin A, D, E, K), RGD (Arg-Gly-Asp), NGR (Asn-Gly-Arg), transferrin, VIP (vasoactive intestinal peptide) receptor, APRPG (Ala-Pro-Arg-Pro-Gly) peptide, TRX-20 (thioredoxin-20), integrin, nucleolin, aminopeptidase N (CD13), endoglin, vascular epithelial growth factor receptor, low density lipoprotein receptor, transferrin receptor, somatostatin receptor, bombesin, neuropeptide Y, luteinizing hormone releasing hormone receptor, folic acid receptor, epidermal growth factor receptor, transforming growth factor, fibroblast growth factor receptor, asialoglycoprotein receptor, galectin-3 receptor, E-selectin receptor, hyaluronic acid receptor, prostate-specific membrane antigen (PSMA), cholecystokinin A receptor, cholecystokinin B receptor, discoidin domain receptor, mucin receptor, opioid receptor, plasminogen receptor, bradykinin receptor, insulin receptor, insulin-like growth factor receptor, angiotensin AT1 receptor, angiotensin AT2 receptor, granulocyte macrophage colony stimulating factor receptor (GM-CSF receptor), galactosamine receptor, sigma-2 receptor, delta-like 3 (DLL-3), aminopeptidase P, melanotransferrin, leptin, tetanus toxin Tet1, tetanus toxin G23, RVG (Rabies Virus Glycoprotein) peptide, HER2 (human epidermal growth factor receptor 2), GPNMB (glycoprotein non-metastatic b), Ley, CA6, CanAng, SLC44A4 (Solute carrier family 44 member 4), CEACAM5 (Carcinoembryonic antigen-related cell adhesion molecule 5), Nectin-4, Carbonic Anhydrase 9, TNNB2, 5T4, CD30, CD37, CD74, CD70, PMEL17, EphA2(EphrinA2 receptor), Trop-2, SC-16, Tissue factor, ENPP-3(AGS-16), SLITRK6 (SLIT and NTRK like family member 6), CD27, Lewis Y antigen, LIV1, GPR161 (G Protein-Coupled Receptor 161), PBR (peripheral-type benzodiazeoine receptor), MERTK (Mer receptor tyrosine kinase) receptor, CD71, LLT1 (Lectin-like transcript 1 or CLED2D), interleukin-22 receptor, sigma 1 receptor, peroxisome proliferator-activated receptor, DLL3, C4.4a, cKIT, EphrinA, CTLA4 (Cytotoxic T-Lymphocyte Associated Protein 4), FGFR2b (fibroblast growth factor receptor 2b), N-acetylcholine receptor, gonadotropin releasing hormone receptor, gastrin-releasing peptide receptor, bone morphogenetic protein receptor-type 1B (BMPR1B), E16 (LAT1, SLC7A5), STEAP1 (six transmembrane epithelial antigen of prostate), 0772P (CA125, MUC16), MPF (MSLN, mesothelin), Napi3b (SLC34A2), Sema5b (semaphorin 5b), ETBR(Endothelin type B receptor), MSG783(RNF124), STEAP2 (six transmembrane epithelial antigen of prostate 2), TrpM4 (transient receptor potential cation 5 channel, subfamily M, member 4), CRIPTO (teratocarcinoma-derived growth factor), CD21, CD79b, FcRH2 (IFGP4), HER2 (ErbB2), NCA (CEACM6), MDP (DPEP1), IL20R-alpha (IN20Ra), Brevican (BCAN), EphB2R, ASLG659 (B7h), CD276, PSCA (prostate stem cell antigen precursor), GEDA, BAFF-R (BR3), CD22 (BL-CAM), CD79a, CXCR5, HLA-DOB, P2X5, CD72, LY64, FcRH1, IRTA2, TENB2, SSTR2, SSTR5, SSTR1, SSTR3, SSTR4, ITGAV (Integrin, alpha 5), ITGB6 (Integrin, beta 6), MET, MUC1, EGFRvIII, CD33, CD19, IL2RA (interleukin 2 receptor, alpha), AXL, BCMA, CTA (cancer tetis antigens), CD174, CLEC14A, GPR78, CD25, CD32, LGR5 (GPR49), CD133 (Prominin), ASG5, ENPP3 (ectonucleotide Pyrophosphatase/Phosphodiesterase 3), PRR4 (proline-rich protein 4), GCC (guanylate cyclase 2C), Liv-1 (SLC39A6), CD56, CanAg, TIM-1, RG-1, B7-H4, PTK7, CD138, Claudins, Her3 (ErbB3), RON (MST1R), CD20, TNC (Tenascin C), FAP, DKK-1, CD52, CS1 (SLAMF7), Annexin A1, V-CAM, gp100, MART-1, MAGE-1 (melanoma antigen-encoding gene-1), MAGE-3 (melanoma-associated antigen 3), BAGE, GAGE-1, MUM-1 (multiple myeloma oncogene 1), CDK4, TRP-1(gp75), TAG-72 (tumor-associated glycoprotein-72), ganglioside GD2, GD3, GM2, GM3, VEP8, VEP9, My1, VIM-D5, D156-22, OX40, RNAK, PD-L1, TNFR1, TNFR2, etc.

Targets

In some embodiments, the target or targets of the molecular recognition element are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1,000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

In some embodiments, a substance is considered to be "targeted" if it specifically binds to a targeting moiety, such as a nucleic acid targeting moiety. In some embodiments, a targeting moiety, such as a nucleic acid targeting moiety, specifically binds to a target under stringent conditions.

In certain embodiments, the conjugates and compounds described herein comprise a targeting moiety that specifically binds to one or more targets (e.g., antigens) associated with an organ, tissue, cell, extracellular matrix component, and/or intracellular compartment. In some embodiments, the conjugates and compounds described herein comprise a targeting moiety that specifically binds to targets associated with a particular organ or organ system. In some embodiments, the conjugates and compounds described herein comprise a targeting moiety that specifically binds to one or more intracellular targets (e.g., organelle, intracellular protein). In some embodiments, the conjugates and compounds described herein comprise a targeting moiety which specifically binds to targets associated with diseased organs, tissues, cells, extracellular matrix components, and/or intracellular compartments. In some embodiments, the conjugates and compounds described herein comprise a targeting moiety that specifically binds to targets associated with particular cell types (e.g., endothelial cells, cancer cells, malignant cells, prostate cancer cells, etc.).

In some embodiments, the conjugates and compounds described herein comprise a targeting moiety that binds to a target that is specific for one or more particular tissue types (e.g., liver tissue vs. prostate tissue). In some embodiments, the conjugates and compounds described herein comprise a targeting moiety that binds to a target that is specific for one or more particular cell types (e.g., T cells vs. B cells). In some embodiments, the conjugates and compounds described herein comprise a targeting moiety that binds to a target that is specific for one or more particular disease states (e.g., tumor cells vs. healthy cells). In some embodiments, the conjugates and compounds described herein comprise a targeting moiety that binds to a target that is specific for one or more particular developmental stages (e.g., stem cells vs. differentiated cells).

In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing cells from a plurality (e.g., 5-10 or more) of different tissues or organs in approximately equal amounts. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types.

In some embodiments, a target comprises a protein, a carbohydrate, a lipid, and/or a nucleic acid. In some embodiments, a target comprises a protein and/or characteristic portion thereof, such as a tumor marker, integrin, cell surface receptor, transmembrane protein, intercellular protein, ion channel, membrane transporter protein, enzyme, antibody, chimeric protein, glycoprotein, etc. In some embodiments, a target comprises a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells), etc. In some embodiments, a target comprises a lipid and/or characteristic portion thereof, such as an oil, fatty acid, glyceride, hormone, steroid (e.g., cholesterol, bile acid), vitamin (e.g., vitamin E), phospholipid, sphingolipid, lipoprotein, etc. In some embodiments, a target comprises a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA.

Numerous markers are known in the art. Typical markers include cell surface proteins, e.g., receptors. Exemplary receptors include, but are not limited to, the transferrin receptor; LDL receptor; growth factor receptors such as epidermal growth factor receptor family members (e.g., EGFR, Her2, Her3, Her4) or vascular endothelial growth factor receptors, cytokine receptors, cell adhesion molecules, integrins, selectins, and CD molecules. The marker can be a molecule that is present exclusively or in higher amounts on a malignant cell, e.g., a tumor antigen.

Nanoparticles

In some embodiments, the targeting moiety comprises a particle (e.g., target particle), preferably a nanoparticle, optionally a targeted nanoparticle attached to a targeting molecule that can binds specifically or preferably to a target. In some embodiments, the targeting particle by itself guides the compound of the present invention (such as by enrichment in tumor cells or tissue) and there is no additional targeting molecules attached therein.

By "nanoparticle" herein is meant any particle having a diameter of less than 1000 nm. In some embodiments, a therapeutic agent and/or targeting molecule can be associated with the body of the particle, for instance in a polymeric matrix. In some embodiments, the targeting molecule can be covalently associated with the surface of the polymeric matrix. In some embodiments, the covalent association is mediated by a linker. In some embodiments, the therapeutic agent can be associated with the surface of, encapsulated within, surrounded by, and/or dispersed throughout the polymeric matrix. See, for example, U.S. Pat. No. 8,246,968, which is incorporated herein in its entirely.

In general, nanoparticles of the present invention comprise any type of particle. Any particle can be used in accordance with the present invention. In some embodiments, particles are biodegradable and biocompatible. In general, a biocompatible substance is not toxic to cells. In some embodiments, a substance is considered to be biocompatible if its addition to cells results in less than a certain threshold of cell death. In some embodiments, a substance is considered to be biocompatible if its addition to cells does not induce adverse effects. In general, a biodegradable substance is one that undergoes breakdown under physiological conditions over the course of a therapeutically relevant time period (e.g., weeks, months, or years). In some embodiments, a biodegradable substance is a substance that can be broken down by cellular machinery. In some embodiments, a biodegradable substance is a substance that can be broken down by chemical processes. In some embodiments, a particle is a substance that is both biocompatible and biodegradable. In some embodiments, a particle is a substance that is biocompatible, but not biodegradable. In some embodiments, a particle is a substance that is biodegradable, but not biocompatible.

It is often desirable to use a population of particles that is relatively uniform in terms of size, shape, and/or composition so that each particle has similar properties. For example, at least 80%, at least 90%, or at least 95% of the particles may have a diameter or greatest dimension that falls within 5%, 10%, or 20% of the average diameter or greatest dimension. In some embodiments, a population of particles may be heterogeneous with respect to size, shape, and/or composition. A variety of different particles can be used in accordance with the present invention. In some embodiments, particles are spheres or spheroids. In some embodiments, particles are spheres or spheroids. In some embodiments, particles are flat or plate-shaped. In some embodiments, particles are cubes or cuboids. In some embodiments, particles are ovals or ellipses. In some embodiments, particles are cylinders, cones, or pyramids.

In some embodiments, particles are microparticles (e.g., microspheres). In general, a "microparticle" refers to any particle having a diameter of less than 1000 μm. In some embodiments, particles are picoparticles (e.g., picospheres). In general, a "picoparticle" refers to any particle having a diameter of less than 1 nm. In some embodiments, particles are liposomes. In some embodiments, particles are micelles.

Particles can be solid or hollow and can comprise one or more layers (e.g., nanoshells, nanorings). In some embodiments, each layer has a unique composition and unique properties relative to the other layer(s). For example, particles may have a core/shell structure, wherein the core is one layer and the shell is a second layer. Particles may comprise a plurality of different layers. In some embodiments, one layer may be substantially crosslinked, a second layer is not substantially cross-linked, and so forth. In some embodiments, one, a few, or all of the different layers may comprise one or more therapeutic or diagnostic agents to be delivered. In some embodiments, one layer comprises an agent to be delivered, a second layer does not comprise an agent to be delivered, and so forth. In some embodiments, each individual layer comprises a different agent or set of agents to be delivered.

In some embodiments, a particle is porous, by which is meant that the particle contains holes or channels, which are typically small compared with the size of a particle. For example a particle may be a porous silica particle, e.g., a mesoporous silica nanoparticle or may have a coating of mesoporous silica (Lin et al., 2005, J. Am. Chem. Soc, 17:4570). Particles may have pores ranging from about 1 nm to about 50 nm in diameter, e.g., between about 1 and 20 nm in diameter. Between about 10% and 95% of the volume of a particle may consist of voids within the pores or channels.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other nanoparticles that can be associated with inventive nanoparticles, etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties.

Examples of polymers include polyalkylenes (e.g., polyethylenes), polycarbonates (e.g., poly(1,3-dioxan-2-one)), polyanhydrides (e.g., poly(sebacic anhydride)), polyhydroxyacids (e.g., poly(3-hydroxyalkanoate)), polyfumarates, polycaprolactones, polyamides (e.g., polycaprolactam), polyacetals, polyethers, polyesters (e.g., polylactide, polyglycolide), poly(orthoesters), polyvinyl alcohols, polyurethanes, polyphosphazenes, polyacrylates, polymethacrylates, polycyanoacrylates, polyureas, polystyrenes, and polyamines. In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, polyglycolic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; and polycyanoacrylates.

In some embodiments, particles can be non-polymeric particles (e.g., metal particles, quantum dots, ceramic particles, polymers comprising inorganic materials, bone-derived materials, bone substitutes, viral particles, etc.). In some embodiments, a therapeutic or diagnostic agent to be delivered can be associated with the surface of such a non-polymeric particle. In some embodiments, a non-polymeric particle is an aggregate of non-polymeric components, such as an aggregate of metal atoms (e.g., gold atoms). In some embodiments, a therapeutic or diagnostic agent to be delivered can be associated with the surface of and/or encapsulated within, surrounded by, and/or dispersed throughout an aggregate of non-polymeric components.

Particles (e.g., nanoparticles, microparticles) may be prepared using any method known in the art. For example, particulate formulations can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other suitable methods. Alternatively or additionally, aqueous and organic solvent syntheses for monodisperse semiconductor, conductive, magnetic, organic, and other nanoparticles have been described (Pellegrino et al., 2005, Small, 1:48; Murray et al., 2000, Ann. Rev. Mat. Sci., 30:545; and Trindade et al., 2001, Chem. Mat., 13:3843).

Methods for making microparticles for delivery of encapsulated agents are described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6: 275; and Mathiowitz et al., 1988, J. Appl. Polymer Sci., 35:755).

Nucleic Acid Targeting Moieties

In some embodiments, the targeting moiety comprises an nucleic acid targeting moiety.

In general, a nucleic acid targeting moiety is any polynucleotide that binds to a component associated with an organ, tissue, cell, extracellular matrix component, and/or intracellular compartment (the target).

In some embodiments, nucleic acid targeting moieties are aptamers. An aptamer is typically a polynucleotide that binds to a specific target structure that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g., hairpin loops) that disrupt base pairing.

In some embodiments, nucleic acid targeting moieties are spiegelmers (PCT Publications WO 98/08856, WO 02/100442, and WO 06/117217). In general, spiegelmers are synthetic, mirror-image nucleic acids that can specifically bind to a target (i.e., mirror image aptamers). Spiegelmers are characterized by structural features that make them not susceptible to exo- and endo-nucleases.

One of ordinary skill in the art will recognize that any nucleic acid targeting moiety (e.g., aptamer or spiegelmer) that is capable of specifically binding to a target can be used in accordance with the present invention. In some embodiments, nucleic acid targeting moieties to be used in accordance with the present invention may target a marker associated with a disease, disorder, and/or condition. In some embodiments, nucleic acid targeting moieties to be used in accordance with the present invention may target cancer-associated targets. In some embodiments, nucleic acid targeting moieties to be used in accordance with the present invention may target tumor markers. Any type of cancer and/or any tumor marker may be targeted using nucleic acid targeting moieties in accordance with the present invention. To give but a few examples, nucleic acid targeting moieties may target markers associated with prostate cancer, lung cancer, breast cancer, colorectal cancer, bladder cancer, pancreatic cancer, endometrial cancer, ovarian cancer, bone cancer, esophageal cancer, liver cancer, stomach cancer, brain tumors, cutaneous melanoma, and/or leukemia.

Nucleic acids of the present invention (including nucleic acid nucleic acid targeting moieties and/or functional RNAs to be delivered, e.g., RNAi-inducing entities, ribozymes, tRNAs, etc., described in further detail below) may be prepared according to any available technique including, but not limited to chemical synthesis, enzymatic synthesis, enzymatic or chemical cleavage of a longer precursor, etc.

Methods of synthesizing RNAs are known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in molecular biology, v. 288 (Clifton, N.J.) Totowa, N.J.: Humana Press, 2005).

The nucleic acid that forms the nucleic acid nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid nucleic acid targeting moiety can be replaced with a hydrocarbon linker or a polyether linker provided that the binding affinity and selectivity of the nucleic acid nucleic acid targeting moiety is not substantially reduced by the substitution (e.g., the dissociation constant of the nucleic acid nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) Antisense Drug Technology: Principles, Strategies, and Applications (1 st ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, SR, NH$_2$, NHR, NR$_2$ or CN, wherein R is C$_1$-C$_6$ alkyl, alkenyl, or alkynyl, and halo is F, Cl, Br, or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 0(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g., exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of a nucleic acid targeting moiety such that the ability of the nucleic acid targeting moiety to specifically bind to the target is not substantially affected. The modified region may be at the 5'-end and/or the 3'-end of one or both strands. For example, modified nucleic acid targeting moieties in which approximately 1-5 residues at the 5' and/or 3' end of either of both strands are nucleotide analogs and/or have a backbone modification have been employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Application Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic or diagnostic agent, improved specific binding of an nucleic acid targeting moiety to a target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the nucleic acid targeting moiety are inverted to yield a linkage such as a 3'-3' linkage or a 5'-5' linkage.

In some embodiments, nucleic acids in accordance with the present invention are not synthetic, but are naturally-occurring entities that have been isolated from their natural environments.

Any method can be used to design novel nucleic acid targeting moieties (see, e.g., U.S. Pat. Nos. 6,716,583; 6,465,189; 6,482,594; 6,458,543; 6,458,539; 6,376,190; 6,344,318; 6,242,246; 6,184,364; 6,001,577; 5,958,691; 5,874,218; 5,853,984; 5,843,732; 5,843,653; 5,817,785; 5,789,163; 5,763,177; 5,696,249; 5,660,985; 5,595,877; 5,567,588; and 5,270,163; and U.S. Patent Application Publications 2005/0069910, 2004/0072234, 2004/0043923, 2003/0087301, 2003/0054360, and 2002/0064780).

Nucleic acid targeting moieties that bind to a protein, a carbohydrate, a lipid, and/or a nucleic acid can be designed and/or identified. In some embodiments, nucleic acid targeting moieties can be designed and/or identified for use in the complexes of the invention that bind to proteins and/or characteristic portions thereof, such as tumor-markers, integrins, cell surface receptors, transmembrane proteins, intercellular proteins, ion channels, membrane transporter proteins, enzymes, antibodies, chimeric proteins etc. In some embodiments, nucleic acid targeting moieties can be designed and/or identified for use in the complexes of the invention that bind to carbohydrates and/or characteristic portions thereof, such as glycoproteins, sugars (e.g., monosaccharides, disaccharides and polysaccharides), glycocalyx (i.e., the carbohydrate-rich peripheral zone on the outside surface of most eukaryotic cells) etc. In some embodiments, nucleic acid targeting moieties can be designed and/or identified for use in the complexes of the invention that bind to lipids and/or characteristic portions thereof, such as oils, saturated fatty acids, unsaturated fatty acids, glycerides, hormones, steroids (e.g., cholesterol, bile acids), vitamins (e.g., vitamin E), phospholipids, sphingolipids, lipoproteins etc. In some embodiments, nucleic acid targeting moieties can be designed and/or identified for use in the complexes of the invention that bind to nucleic acids and/or characteristic portions thereof, such as DNA nucleic acids; RNA nucleic acids; modified DNA nucleic acids; modified RNA nucleic acids; and nucleic acids that include any combination of DNA, RNA, modified DNA, and modified RNA; etc.

Nucleic acid targeting moieties (e.g., aptamers or spiegelmers) may be designed and/or identified using any available method. In some embodiments, nucleic acid targeting moieties are designed and/or identified by identifying nucleic acid targeting moieties from a candidate mixture of nucleic acids.

Methods of Preparing the Compounds of the Invention

The compounds and conjugates disclosed herein can be prepared via simple preparation methods (see, e.g., Examples 1-78). Such preparation methods enable easy purification.

Thus, also provided herein are methods for preparing the compounds of the invention. For example, compounds of the invention can be prepared as shown in any one of Reaction Schemes 3, 4, 5, 6, or 7:

Reaction Scheme 3

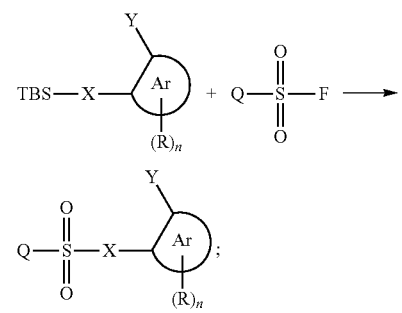

Reaction Scheme 4

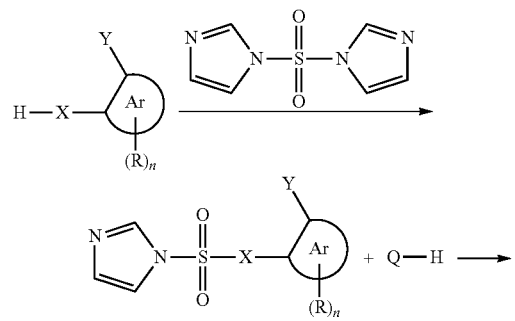

-continued

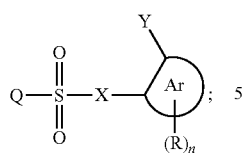; 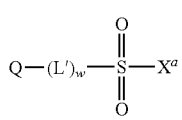

or a pharmaceutically acceptable salt thereof, with a sulfonyl halide:

$$Q-(L')_w-\overset{\overset{O}{\|}}{\underset{\|}{S}}-X^a$$

to provide a compound of Formula Iaa):

$$Q-(L')_w-\overset{\overset{O}{\|}}{\underset{\underset{O}{\|}}{S}}-O-\underset{Z'}{Ar}-\overset{TG}{\underset{(Y')_x}{|}}$$ (Iaa)

Reaction Scheme 5

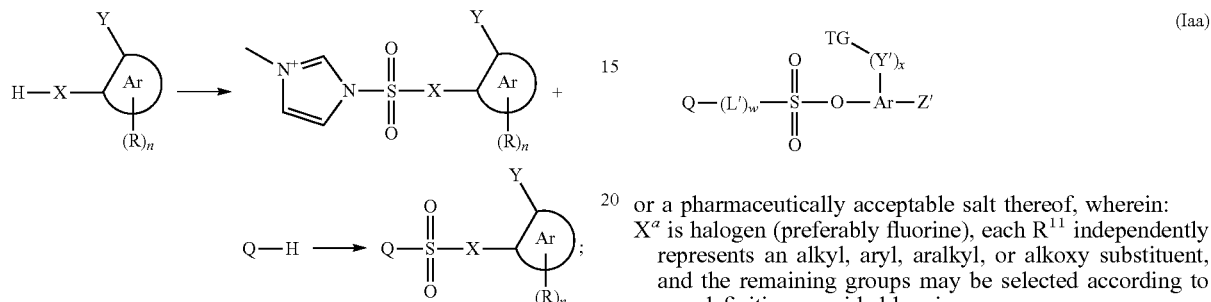

or a pharmaceutically acceptable salt thereof, wherein:
$X^a$ is halogen (preferably fluorine), each $R^{11}$ independently represents an alkyl, aryl, aralkyl, or alkoxy substituent, and the remaining groups may be selected according to any definition provided herein.

For example, in certain such embodiments,
Q is an active agent linked to L' by a heteroatom, preferably O or N;
Z' is absent or a linking group comprising at least one reactive group, such as a precursor described above in connection with Z;
L' is a spacer moiety attached to the $SO_2$ via a heteroatom selected from O, S, and N, preferably O or N, and is selected such that cleavage of the bond between L' and $SO_2$ promotes cleavage of the bond between L' and Q to release the active agent;
Ar is aryl, heteroaryl, cycloalkyl, or heterocycloalkyl, preferably aryl or heteroaryl;
Y' is $-(CR^b_2)_yN(R^a)-$, $-(CR^b_2)_yO-$, or $-(CR^b_2)_yS-$, such that the N, O, or S atom is attached to TG if y is 1; and Y' are positioned on adjacent atoms of Ar;
TG is a triggering group that, when activated, results in formation of an N, O, or S atom capable of reacting with the $SO_2$ to displace $(Q)_q-(L')_w$ and form a 5-6-membered ring including $X-SO^2$ and the intervening atoms of Ar;
w, x, and y are each independently an integer having a value of 0 or 1;
each $R^a$ and R' is independently hydrogen or lower alkyl; and
each $R^b$ is independently hydrogen or lower alkyl; or
two $R^b$, together with the carbon atom to which they are attached, form a 3-5-membered ring, preferably a 3-4-membered ring.

Reaction Scheme 6

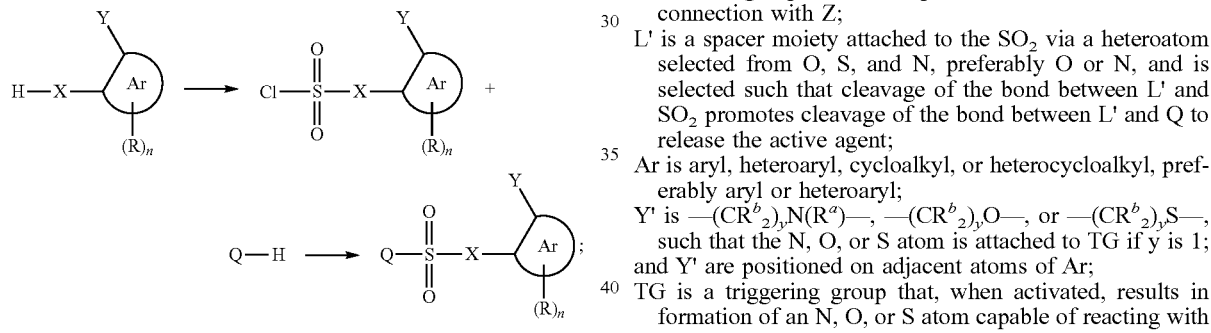

Reaction Scheme 7

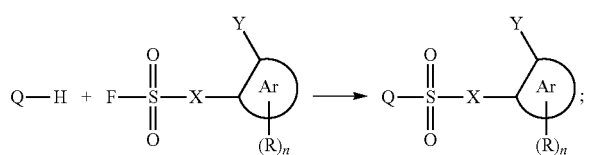

wherein X, Y, Ar, R, and n are the same as defined above.

Also provided herein are methods for preparing a compound, comprising reacting a compound of Formula (IIc):

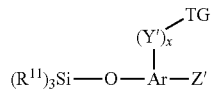 (IIc)

The reactive group of the linking group can be a moiety capable of participating in 1,3-dipolar cycloaddition reactions, hetero-Diels-Alder reactions, nucleophilic substitution reactions, non-aldol type carbonyl reactions, additions to carbon-carbon multiple bonds, oxidation reactions, click reactions, or any other intermolecular coupling reaction. Preferably, the reactive group is selected to participate in a selective reaction with a reacting partner that is not common in biological molecules, such as a 1,3-dipolar cycloaddition, hetero-Diels-Alder, oxime/hydrazone condensation, or click reaction.

In certain preferred embodiments, the linking group may comprise an alkyne or azide (which react to form a triazole), an alkyne and a nitrile oxide (which react to form an isoxazole), or a carbonyl (e.g., an aldehyde or ketone) or a hydrazine or hydroxylamine (which react to form an oxime or a hydrazone).

In other embodiments, provided herein are methods for preparing a compound, comprising:
(a) reacting a compound of Formula (IIa):

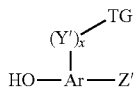

(IIa)

or a pharmaceutically acceptable salt thereof, with 1,1'-sulfonylbis(1H-imidazole):

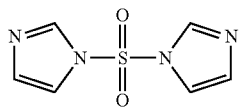 [SMILES: O=S(=O)(n1ccnc1)n1ccnc1]

to provide a compound of Formula (IIbb):

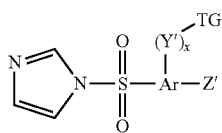

(IIbb)

or a pharmaceutically acceptable salt thereof, wherein the variables may be selected according to any definition provided herein.

For example, in certain such embodiments,

Z' is absent or a linking group comprising a reactive group as discussed in greater detail above;

Ar is aryl, heteroaryl, cycloalkyl, or heterocycloalkyl, preferably aryl or heteroaryl;

Y' is $-(CR^b_2)_yN(R^a)-$, $-(CR^b_2)_yO-$, or $-(CR^b_2)_yS-$, positioned such that the N, O, or S atom is attached to TG if y is 1;

$-SO_2-$ and Y' are positioned on adjacent atoms of Ar;

TG is a triggering group that, when activated, results in formation of an N, O, or S atom capable of reacting with the $SO_2$ to displace $(Q)_q-(L')_w$ and form a 5-6-membered ring including $X-SO^2$ and the intervening atoms of Ar;

w, x, and y are each independently an integer having a value of 0 or 1;

each $R^a$ and R' is independently hydrogen or lower alkyl; and each $R^b$ is independently hydrogen or lower alkyl; or two $R^b$, together with the carbon atom to which they are attached, form a 3-5-membered ring, preferably a 3-4-membered ring.

A compound of Formula (IIbb) may then be further reacted with a compound of Formula (Ia'), Q-(L')$_w$—H, or a pharmaceutically acceptable salt thereof, to provide a compound (Ia):

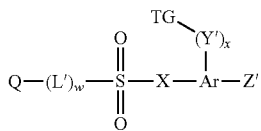

(Ia)

or a pharmaceutically acceptable salt thereof, wherein the variables may be selected according to any definition provided herein.

For example, in certain embodiments,

X is O;

Q is an active agent linked to L' by a heteroatom, preferably O or N;

L' is a linking group attached to the $SO_2$ via a heteroatom selected from O, S, and N, preferably O or N, and is selected such that cleavage of the bond between L' and $SO_2$ promotes cleavage of the bond between L' and Q to release the active agent; and w is 0 or 1.

In some embodiments, the methods utilize an intermediate compound of Formula (IIa), (IIb), or (IIc) to provide a compound of Formula (Iaa), wherein Ar, TG, Y' Z' and $R^a$ are as defined above for the conjugates of Formula (I') or the compounds of Formula (Ia).

The invention further provides the compounds described above, which are useful in these methods.

Intermediate Compounds

In some embodiments, the compounds and conjugates disclosed herein can be prepared by a method that utilizes an intermediate compound having the structure according to Formula (IV):

(IV)

or a pharmaceutically acceptable salt thereof, wherein:

W is hydrogen, $-SiR^{16}R^{17}R^{18}$ or $-SO_2$-G;

$R^{16}$, $R^{17}$, and $R^{18}$ are each independently $C_1$-$C_6$-alkyl;

G is halogen (preferably fluorine), imidazole, or N-methyl imidazolium;

R is a substituent or -L$^{1'}$-Z;

L$^{1'}$ is a $C_1$-$C_{200}$-alkylene that optionally comprises at least one of a peptide bond, an amino bond, an ether bond, a triazole bond, a tetrazole bond, a sugar bond, a sulfonamide bond, a phosphonate bond, a sulfo bond, or a dendrimer structure;

Z is a precursor selected from isocyanide, isothiocyanide, 2-pyridyl disulfide, haloacetamide ($-NHC(O)CH_2$-hal), maleimide, diene, alkene, halide, tosylate (TsO$^-$), aldehyde, sulfonate (R$-SO_3^-$),

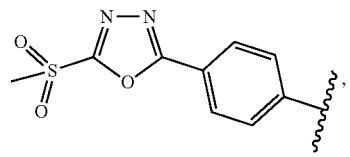

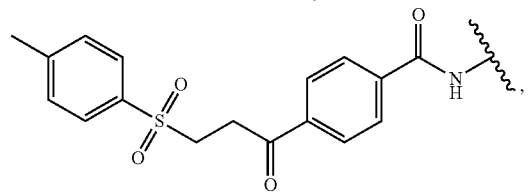

phosphonic acid (—P(=O)(OH)$_2$), ketone, C$_8$-C$_{10}$ cycloalkyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$ alkyl), and dihydrogen phosphate (—OP(=O)(OH)$_2$);

n is an integer having a value of 1 to 4;

Y is —NO$_2$, —OC(O)(CH$_2$)$_r$C(O)R$^1$, —O(CH$_2$)$_r$—Ar$_1$—NO$_2$, —NHOH, —NHNH$_2$, —BR$_2$R$^3$,

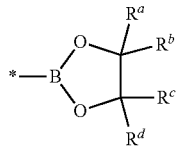

or —Y'-TG, such as —NO$_2$, —OC(O)(CH$_2$)$_r$C(O)R$^1$, —O(CH$_2$)$_r$—Ar$_1$—NO$_2$, —NHNH$_2$, —BR$_2$R$^3$,

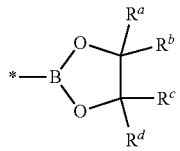

or —Y'-TG;

R$^1$ is C$_1$-C$_6$ alkyl;

r is an integer of 1 to 5;

Ar$^l$ is C$_6$-C$_{20}$-arylene;

R$^2$ and R$^3$ are each independently hydrogen, C$_1$-C$_6$-alkyl, C$_1$-C$_6$-alkoxy, or hydroxy;

R$^a$, R$^b$, R$^c$, and R$^d$ are each independently hydrogen or C$_1$-C$_6$ alkyl;

Y' is —(CH$_2$)$_x$NR''—, —(CH$_2$)$_x$O—, or —(CH$_2$)$_x$S—;

R'' is hydrogen or C$_1$-C$_6$ alkyl;

x is an integer of 0 or 1; and

TG is a triggering group.

In some embodiments, the compounds and conjugates disclosed herein can be prepared by a method that utilizes an intermediate compound having the structure according to Formula (V):

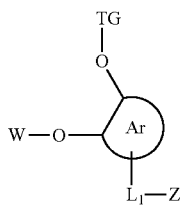

or a pharmaceutically acceptable salt thereof, wherein:

W, L$^1$, and Z are the same as defined for Formula (IV); and

TG is a triggering group, such as a β-galactoside, β-glucuronide, or a combination of β-galactoside and β-glucuronide.

In other embodiments, the compounds and conjugates disclosed herein can be prepared by a method that utilizes an intermediate compound having the structure according to Formula (VI):

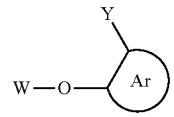

or a pharmaceutically acceptable salt thereof, wherein:

W is the same as defined for Formula (IV);

Y is —NO$_2$, —OC(O)(CH$_2$)$_r$C(O)R$^1$, —O(CH$_2$)$_r$—Ar$^1$—NO$_2$, —NHOH, —NHNH$_2$, —BR$^2$R$^3$, or —O-TG;

R$^1$ is C$_1$-C$_6$-alkyl, such as NO$_2$, —OC(O)(CH$_2$)$_r$C(O)R$^1$, —O(CH$_2$)$_r$—Ar$^1$—NO$_2$, —NHOH, —NHNH$_2$, —BR$^2$R$^3$, or —O-TG;

R$^1$ is C$_1$-C$_6$-alkyl;

r is an integer of 1 to 5;

Ar$^1$ is phenylene, biphenylene, or naphthalene;

R$^2$ and R$^3$ are each independently hydrogen, C$_1$-C$_6$-alkyl, C$_1$-C$_6$-alkoxy, or hydroxy;

R$^a$, R$^b$, R$^c$, and R$^d$ are each independently hydrogen or C$_1$-C$_6$-alkyl; and TG is a triggering group, β-galactoside, β-glucuronide, or a combination of β-galactoside and β-glucuronide.

Also provided herein are intermediate compounds of Formula (IIa), (IIb), or (IIc):

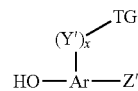

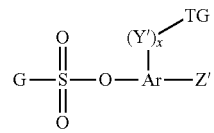

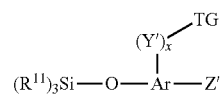

or a pharmaceutically acceptable salt thereof, wherein:

G is halogen, imidazole, or N-methyl imidazolium;

each R$^{11}$ is independently C$_1$-C$_6$-alkyl;

Ar is aryl, heteroaryl, cycloalkyl, or heterocycloalkyl;

TG is a triggering group that, when activated, results in formation of an N, O, or S atom capable of forming a 5-6-membered ring including X—SO$^2$ and the intervening atoms of Ar;

Y' is —(CR$^b_2$)$_y$N(R$^a$)—, —(CR$^b_2$)$_y$O—, or —(CR$^b_2$)$_y$S—, positioned such that the N, O, or S atom is attached to TG if y is 1;

O and Y' are positioned on adjacent atoms of Ar;

x and y are each independently an integer having a value of 0 or 1;

Z' is absent or a linking unit comprising, e.g., a reactive or binding unit; and each R$^a$ is independently hydrogen or alkyl; or two R$^a$, together with the carbon atom to which they are attached, form a three-membered ring.

In some embodiments, the intermediate compound is a compound of Formula (IIa), (IIb), or (IIc), wherein Ar, TG, Y'Z' and R$^a$ are as defined above for the conjugates of Formula (I') or the compounds of Formula (Ia).

In preferred embodiments, the intermediate compound is a compound of Formula (IIa), (IIb), or (IIc), wherein Ar is aryl (e.g., phenyl or naphthyl).

In some embodiments, provided herein is an intermediate compound is a compound of Formula (IIa), (IIb), or (IIc), wherein Z' is a linking group comprising one or more groups selected from isocyanide, isothiocyanide, 2-pyridyl disulfide, haloacetamide (—NHC(O)CH$_2$-halo), maleimide, diene, alkene, halide, tosylate (TsO$^-$), aldehyde, sulfonate (R—SO$_3^-$),

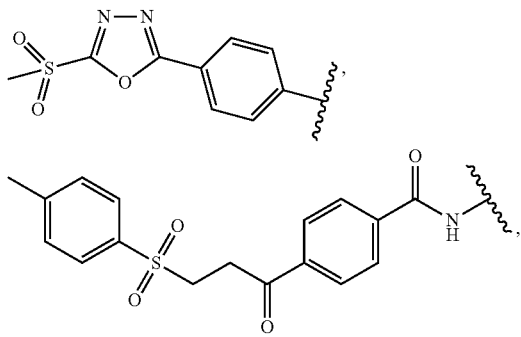

phosphonic acid (—P(=O)(OH)$_2$), ketone, C$_5$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$), and dihydrogen phosphate (—OP(=O)(OH)$_2$.

In other embodiments, the intermediate compound is a compound of Formula (IIa), (IIb), or (IIc), wherein x is 0. In some such embodiments, TG is —NO$_2$, —OC(O)(CH$_2$)$_r$C(O)R$^1$, —NHOH, —NHNH$_2$, —BR$^2$R$^3$,

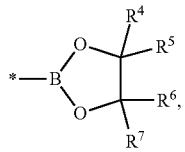

such as NO$_2$, —OC(O)(CH$_2$)$_r$C(O)R$^1$, —NHNH$_2$, —BR$^2$R$^3$,

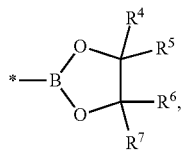

wherein:
R$^1$ is C$_1$-C$_6$ alkyl;
R$^2$ and R$^3$ are each independently hydrogen, C$_1$-C$_6$ alkyl, C$_1$-C$_6$ alkoxy, or hydroxy;
R$^4$, R$^5$, R$^6$, and R$^7$ are each independently hydrogen or C$_1$-C$_6$ alkyl; and
r is an integer having a value of 1, 2, 3, 4, or 5.

In alternative embodiments, the intermediate compound is a compound of Formula (IIa), (IIb), or (IIc), wherein TG is a triggering group comprising β-galactoside, β-glucuronide, or a combination of β-galactoside and β-glucuronide.

In particular embodiments, the intermediate compound is:

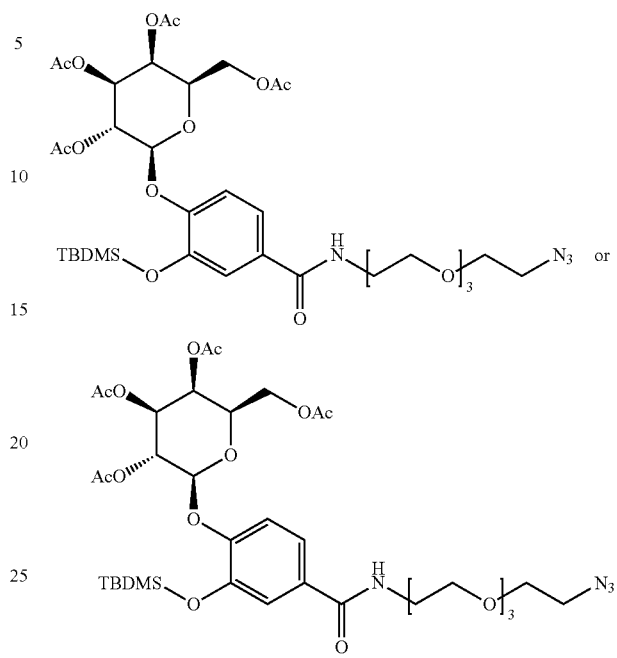

or a pharmaceutically acceptable salt thereof.

In certain other embodiments, the intermediate compound is:

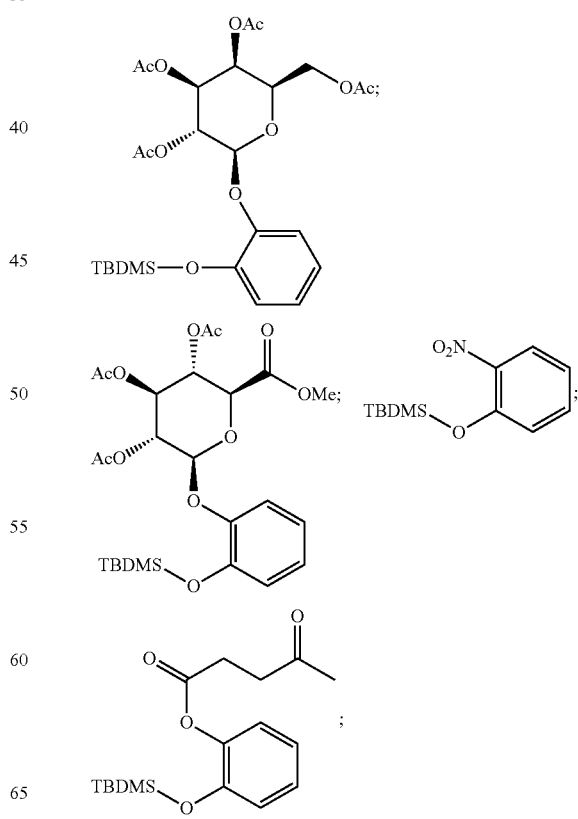

-continued

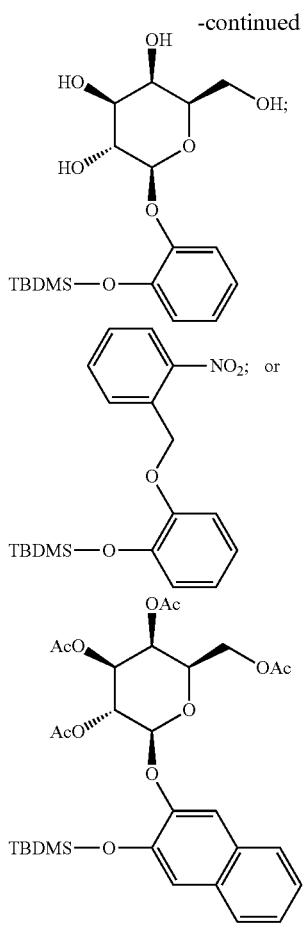

or a pharmaceutically acceptable salt thereof.

Antibody-Drug Conjugates (ADCs)

In some embodiments, CB is an antibody, and Q is a drug. Accordingly, the compounds and conjugates disclosed herein may be used to conjugate an antibody to a drug moiety to form an antibody-drug conjugate (ADC). Antibody-drug conjugates (ADCs) may increase therapeutic efficacy in treating disease, e.g., cancer, due to the ability of the ADC to selectively deliver one or more drug moiety(s) to target tissues, such as a tumor-associated antigen. Thus, in certain embodiments, the invention provides ADCs for therapeutic use, e.g., treatment of cancer.

ADCs of the invention comprise an antibody linked to one or more drug moieties. The specificity of the ADC is defined by the specificity of the antibody. In one embodiment, an antibody is linked to one or more cytotoxic drug(s), which is delivered internally to a cancer cell.

Examples of drugs that may be used in the ADC of the invention are provided below. The terms "drug", "agent", and "drug moiety" are used interchangeably herein. The terms "linked" and "conjugated" are also used interchangeably herein and indicate that the antibody and moiety are covalently linked.

In some embodiments, the ADC has the following formula (Formula VII):

(D-L)$_n$-Ab     (VII)

wherein Ab is the antibody and (D-L) is a Linker-Drug moiety. The Linker-Drug moiety is made of a linker L and a drug moiety D. The drug moiety may have, for example, cytostatic, cytotoxic, or otherwise therapeutic activity against a target cell. n is an integer having a value of 1 to about 20, preferably from 1 to about 10. Preferably, D-L is has the structure of Formula (I''):

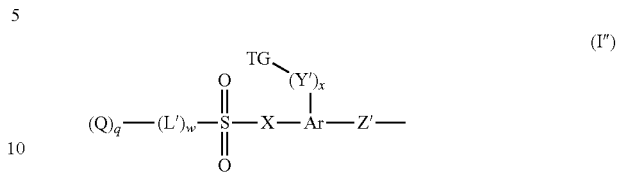

Q is an active agent linked to L' by a heteroatom, preferably O or N;

Z' is a linking group;

L' is a spacer moiety attached to the SO$_2$ via a heteroatom selected from O, S, and N, preferably O or N, and is selected such that cleavage of the bond between L' and SO$_2$ promotes cleavage of the bond between L' and Q to release the active agent;

X is —O—, —C(R$^b$)$_2$—, or —N(R')—, preferably —O—;

Ar is aryl, heteroaryl, cycloalkyl, or heterocycloalkyl, preferably aryl or heteroaryl;

Y' is —(CR$^b$$_2$)$_y$N(R$^a$)—, —(CR$^b$$_2$)$_y$O—, or —(CR$^b$$_2$)$_y$S—, positioned such that the N, O, or S atom is attached to TG if y is 1;

X and Y' are positioned on adjacent atoms of Ar;

TG is a triggering group that, when activated, results in formation of an N, O, or S atom capable of reacting with the SO$_2$ to displace (Q)$_q$-(L')$_w$ and form a 5-6-membered ring including X—SO$^2$ and the intervening atoms of Ar;

w, x, and y are each independently an integer having a value of 0 or 1;

each R$^a$ and R' is independently hydrogen or lower alkyl; and each R$^b$ is independently hydrogen or lower alkyl; or two R$^b$, together with the atom to which they are attached, form a 3-5-membered ring, preferably a 3-4-membered ring.

In some embodiments, n has a value ranging from 1 to 8, 1 to 7, 1 to 6, 1 to 5, 1 to 4, 1 to 3, 1 to 2, or is an integer having a value of 1. When cb is 1 and n is 1, the drug-to-antibody ratio (DAR) of an ADC is equivalent to the number of drugs present in (D-L). When cb is other than 1, the drug-to-antibody ratio (DAR) of an ADC is equivalent to ratio of the number of drugs present in (D-L) to the number of antibodies present in the conjugate.

Exemplary Drugs for Conjugation

The ADCs of the invention provide a targeted therapy that may, for example, reduce the side effects often seen with anti-cancer therapies, as the one or more active agent(s) or drug(s) is delivered to a specific cell.

For example, the drug may be selected from the group consisting of erlotinib (TARCEVA; Genentech/OSI Pharm.); bortezomib (VELCADE; MilleniumPharm.); fulvestrant (FASLODEX; AstraZeneca); sutent (SU11248; Pfizer); letrozole (FEMARA; Novartis); imatinib mesylate (GLEEVEC; Novartis); PTK787/ZK 222584 (Novartis); oxaliplatin (Eloxatin; Sanofi); 5-fluorouracil (5-FU); leucovorin; rapamycin (Sirolimus, RAPAMUNE; Wyeth); lapatinib (TYKERB, GSK572016; GlaxoSmithKline); lonafarnib (SCH 66336); sorafenib (BAY43-9006; Bayer Labs.); gefitinib (IRESSA; Astrazeneca); AG1478, AG1571 (SU 5271; Sugen); alkylating agent (e.g., thiotepa or CYTOXAN® cyclophosphamide); alkyl sulfonate (e.g., busulfan, improsulfan or piposulfan); aziridine (e.g., benzodopa, carboquone, meturedopa or uredopa); ethylenimine, methylmelamine, altretamine, triethylenemelamine, triethylenephosphoramide, triethylenethiophosphoramide, trimethylolmelamine; acetogenins (e.g., bullatacin or bullatacinone); camptothecin including synthetic analogue topotecan; bryostatin; callystatin; CC-1065 (including adozelesin, carzelesin or bizelesin synthetic analogues thereof); cryptophycins (e.g., cryptophycin 1 or cryptophycin 8); dolastatin; duocarmycin (including a synthetic analogue, KW-2189, and CB1-TM1); eleutherobin; pancratistatin; sarcodictyin; spongistatin; nitrogen mustard (e.g., chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard); nitrousurea (e.g., carmustine, chlorozotocin, fotemustine, lomustine, nimustine or ranimnustine); antibiotics (e.g., calicheamicin selected from calicheamycin gammal I and calicheamycin omega 11 or dynemicin including dynemicin A as enediyne antibiotics); bisphosphonate (e.g., clodronate); esperamicin, neocarzinostatin chromophore or related chromoprotein enediyne antibiotic chromophores, aclacinomycin, actinomycin, antramycin, azaserine, bleomycin, cactinomycin, carabicin, carninomycin, carzinophilin, chromomycin, dactinomycin, daunorubicin, detorubucin, 6-diazo-5-oxo-L-norleucine, ADRLIMYCIN® doxorubicin (e.g., morpholino-doxorubicin, cyanomorpholino-doxorubicin, 2-pyrrolino-doxorubicin, liposomal doxorubicin or deoxydoxorubicin), epirubicin, esorubicin, marcellomycin, mitomycin (e.g., mitomycin C, mycophenolic acid, nogalamycin, olivomycin, peplomycin, potfiromycin, puromycin, quelamycin, rodorubicin, streptomigrin, streptozocin, tubercidin, ubenimex, zinostatin or zorubicin); anti-metabolites (e.g., 5-fluorouracil (5-FU)); folic acid analogues (e.g., denopterin, methotrexate, pteropterin or trimetrexate); purine analogs (e.g., fludarabine, 6-mercaptopurine, thiamiprine or thiguanine); pyrimidine analogs (e.g., ancitabine, azacitidine, 6-azauridine, carmofur, cytarabine, dideoxyuridine, doxifluridine, enocitabine or floxuridine); androgen (e.g., calusterone, dromostanolone propionate, epitiostanol, mepitiostane or testolactone); anti-adrenal (e.g., aminoglutethimide, mitotane or trilostane); folic acid replenisher (e.g., folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoid (e.g., maytansine or ansamitocin; trichothecene (e.g., T-2 toxin, verracurin A, roridin A or anguidine); mitoguazone; mitoxantrone; mopidanmol; nitraerine; pentostatin; phenamet; pirarubicin; losoxantrone; 2-ethylhydrazide; procarbazine; PSK® polysaccharide; razoxane; rhizoxin; sizofiran; spirogermanium; tenuazonic acid; triaziquone; 2,2',2"-trichlorotriethylamine; trichothecene (particularly, T-2 toxin, verracurin A, roridin A or anguidine); urethane; vindesine; dacarbazine; mannomustine; mitobronitol; mitolactol; pipobroman; gacytosine; arabinoside ('Ara-C'); cyclophosphamide; thiotepa; taxoids (e.g., TAXOL® paclitaxel (Bristol-Myers Squibb Oncology, Princeton, N. J.), ABRAXANE™ cremophor-free, albumin-engineered nanoparticle formulation of paclitaxel, American Pharmaceutical Partners, Schaumber, Ill. or TAXOTERE® doxetaxel ((Rhone-Poulenc Rorer, Antony, France))); chlorambucil; gemcitabine; 6-thioguanine; mercaptopurine; platinum analog (e.g., cisplatin or carboplatin); vinblastine; platinum; etoposide, ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DFMO); retinoid (e.g., retinoic acid); capecitabine; and a pharmaceutically acceptable salt thereof, a solvate thereof, an acid thereof or a derivative thereof.

Mitotic Inhibitors

In some embodiments, linkers of the invention may be used to conjugate an antibody to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by affecting microtubule polymerization or microtubule depolymerization. Thus, in certain embodiments, an antibody is conjugated to one or more mitotic inhibitor(s) that disrupts microtubule formation by inhibiting tubulin polymerization. In one embodiment, the mitotic inhibitor used in the ADCs of the invention is Taxol® (paclitaxel), Taxotere® (docetaxel), or Ixempra® (ixabepilone). Examples of mitotic inhibitors that may be used in the ADCs disclosed herein are provided below. Included in the genus of mitotic inhibitors are auristatins, described above.

Auristatins

The linkers of the invention may be used to conjugate an antibody to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

Dolastatins

The linkers of the invention may be used to conjugate an antibody to at least one dolastatin to form an ADC. Dolastatins are short peptidic compounds isolated from the Indian Ocean sea hare *Dolabella auricularia* (see Pettit et al., *J. Am. Chem. Soc.,* 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the ADC of the invention comprises an antibody, a linker as described herein, and at least one dolastatin. Auristatins, described above, are synthetic derivatives of dolastatin 10.

Maytansinoids

The linkers of the invention may be used to conjugate an antibody to at least one maytansinoid to form an ADC. Maytansinoids are potent antitumor agents that were originally isolated from members of the higher plant families Celastraceae, Rhamnaceae and Euphorbiaceae, as well as some species of mosses (Kupchan et al, J. Am. Chem. Soc. 94:1354-1356 [1972]; Wani et al, J. Chem. Soc. Chem. Commun 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441, 163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. The structure of an exemplary maytansinoid, mertansine (DM1), is provided below.

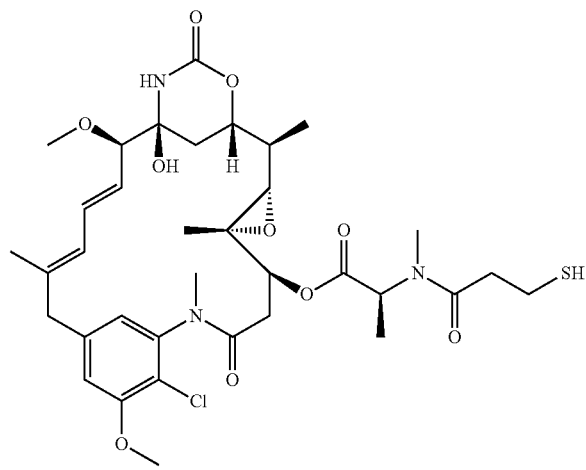

Mertansine (DM1)

Representative examples of maytansinoids include, but are not limited, to DM1 (N2'-deacetyl-N2'-(3-mercapto-1-oxopropyl)-maytansine; also referred to as mertansine, drug maytansinoid 1; ImmunoGen, Inc.; see also Chari et al. (1992) Cancer Res 52:127), DM2, DM3 (N2'-deacetyl-N2'-(4-mercapto-1-oxopentyl)-maytansine), DM4 (4-methyl-4-mercapto-1-oxopentyl)-maytansine) and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

Plant Alkaloids

The linkers of the invention may be used to conjugate an antibody to at least one plant alkaloid, e.g., a taxane or vinca alkaloid. Plant alkaloids are chemotherapy treatments derived made from certain types of plants. The vinca alkaloids are made from the periwinkle plant *catharanthus rosea*), whereas the taxanes are made from the bark of the Pacific Yew tree taxus).

Both the vinca alkaloids and taxanes are also known as antimicrotubule agents, and are described in more detail below.

Taxanes

The linkers of the invention may be used to conjugate an antibody to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (Taxotere®; Sanofi Aventis), paclitaxel (Abraxane® or Taxol®; Abraxis Oncology), and nanoparticle paclitaxel (ABI-007/Abraxene®; Abraxis Bioscience).

In one embodiment, the linkers of the invention may be used to conjugate an antibody to at least one docetaxel. In one embodiment, the linkers of the invention may be used to conjugate an antibody to at least one paclitaxel.

Vinca Alkaloids

In one embodiment, the linkers of the invention may be used to conjugate an antibody to at least one vinca alkaloid. Vinca alkaloids are a class of cell-cycle-specific drugs that work by inhibiting the ability of cancer cells to divide by acting upon tubulin and preventing the formation of microtubules. Examples of vinca alkaloids that may be used in the ADCs of the invention include, but are not limited to, vindesine sulfate, vincristine, vinblastine and vinorelbine.

Antitumor Antibiotics

The linkers of the invention may be used to conjugate an antibody to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the ADCs disclosed herein include, but are not limited to, actinomycines (e.g., pyrrolo[2,1-c][1,4]benzodiazepines), anthracyclines, calicheamicins, and duocarmycins, described in more detail below.

Actinomycines

The linkers of the invention may be used to conjugate an antibody to at least one actinomycine. Actinomycines are a subclass of antitumor antibiotics isolated from bacteria of the genus *Streptomyces*. Representative examples actinomycines include, but are not limited to, actinomycin D (Cosmegen [also known as actinomycin, dactinomycin, actinomycin IV, actinomycin C1], Lundbeck, Inc.), anthramycin, chicamycin A, DC-81, mazethramycin, neothramycin A, neothramycin B, porothramycin, prothracarcin B, SG2285, sibanomicin, sibiromycin and tomaymycin. In one embodiment, D is pyrrolobenzodiazepine (PBD). Examples of PBDs include, but are not limited to, anthramycin, chicamycin A, DC-81, mazethramycin, neothramycin A, neothramycin B, porothramycin, prothracarcin B, SG2000 (SJG-136), SG2202 (ZC-207), SG2285 (ZC-423), sibanomicin, sibiromycin and tomaymycin. Thus, in one embodiment, D is actinomycine, e.g., actinomycin D, or PBD, e.g., a pyrrolobenzodiazepine (PBD) dimer.

The structures of PBDs can be found, for example, in U.S. Patent Application Pub. Nos. 2013/0028917 and 2013/0028919, and in WO 2011/130598 A1, each of which are incorporated herein by reference in their entirety. The generic structure of a PBD is provided below.

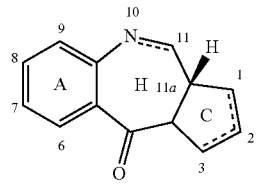

PBDs differ in the number, type and position of substituents, in both their aromatic A rings and pyrrolo C rings, and in the degree of saturation of the C ring. In the B-ring, there is generally an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11α position which provides them with a right-handed twist when viewed from the C ring towards the A ring. Further examples of PBDs which may be conjugated to antibodies via the linkers disclosed herein can be found, for example, in U.S. Patent Application Publication Nos. 2013/0028917 A1 and 2013/0028919 A1, in U.S. Pat. No. 7,741,319 B2, and in WO 2011/130598 A1 and WO 2006/111759 A1, each of which are incorporated herein by reference in their entirety.

Anthracyclines

The linkers of the invention may be used to conjugate an antibody to at least one anthracycline. Anthracyclines are a subclass of antitumor antibiotics isolated from bacteria of the genus *Streptomyces*. Representative examples include, but are not limited to daunorubicin (Cerubidine, Bedford Laboratories), doxorubicin (Adriamycin, Bedford Laboratories; also referred to as doxorubicin hydrochloride, hydroxydaunorubicin, and Rubex), epirubicin (Ellence, Pfizer), and idarubicin (Idamycin; Pfizer Inc.). Thus, in one embodiment, D is anthracycline, e.g., doxorubicin.

Calicheamicins

The linkers of the invention may be used to conjugate an antibody to at least one calicheamicin. Calicheamicins are a family of enediyne antibiotics derived from the soil organism *Micromonospora echinospora*. Calicheamicins bind the minor groove of DNA and induce double-stranded DNA breaks, resulting in cell death with a 100 fold increase over other chemotherapeutics (Damle et al. (2003) Curr Opin Pharmacol 3:386). Preparation of calicheamicins that may be used as drug conjugates in the invention have been described, see U.S. Pat. Nos. 5,712,374; 5,714,586; 5,739,116; 5,767,285; 5,770,701; 5,770,710; 5,773,001; and 5,877,296. Structural analogues of calicheamicin which may be used include, but are not limited to, γ1 I, α2 I, α3 I, N-acetyl-γ1 I, PSAG and θI 1 (Hinman et al., Cancer Research 53:3336-3342 (1993), Lode et al., Cancer Research 58:2925-2928 (1998) and the aforementioned U.S. Pat. Nos. 5,712,374; 5,714,586; 5,739,116; 5,767,285; 5,770,701; 5,770,710; 5,773,001; and 5,877,296). Thus, in one embodiment, D is calicheamicin.

Duocarmycins

The linkers of the invention may be used to conjugate an antibody to at least one duocarmycin. Duocarmycins are a subclass of antitumor antibiotics isolated from bacteria of the genus *Streptomyces*. (see Nagamura and Saito (1998) Chemistry of Heterocyclic Compounds, Vol. 34, No. 12). Duocarmycins bind to the minor groove of DNA and alkylate the nucleobase adenine at the $N_3$ position (Boger (1993) Pure and Appl Chem 65(6):1123; and Boger and Johnson (1995) PNAS USA 92:3642). Synthetic analogs of duocarmycins include, but are not limited to, adozelesin, bizelesin, and carzelesin. Thus, in one embodiment, the D is duocarmycin.

Other Antitumor Antibiotics

In addition to the foregoing, additional antitumor antibiotics that may be used in the ADCs of the invention include bleomycin (Blenoxane, Bristol-Myers Squibb), mitomycin, and plicamycin (also known as mithramycin).

Immunomodulating Agents

In some embodiments, the linkers of the invention may be used to conjugate an antibody to at least one immunomodulating agent. As used herein, the term "immunomodulating agent" refers to an agent that can stimulate or modify an immune response. In one embodiment, an immunomodulating agent is an immunostimuator which enhances a subject's immune response. In some embodiments, an immunomodulating agent is an immunosuppressant, which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs of the invention include, but are not limited to, cancer vaccines, cytokines, and immunomodulating gene therapy.

Cancer Vaccines

The linkers of the invention may be used to conjugate an antibody to a cancer vaccine. As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant invention, administering an ADC comprising anantibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the ADCs disclosed herein include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, D is a cancer vaccine that is either an immunostimulator or is an immunosuppressant.

Cytokines

The linkers of the invention may be used to conjugate an antibody at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) Cancers 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs of the invention include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, D is a cytokine.

Colony-Stimulating Factors (CSFs)

The linkers of the invention may be used to conjugate an antibody to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in ADCs disclosed herein include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, D is a CSF.

Gene Therapy

The linkers of the invention may be used to conjugate an antibody to at least one nucleic acid (directly or indirectly via a carrier) for gene therapy. Gene therapy generally refers to the introduction of genetic material into a cell whereby the genetic material is designed to treat a disease. As it pertains to immunomoduatory agents, gene therapy is used to stimulate a subject's natural ability to inhibit cancer cell proliferation or kill cancer cells. In one embodiment, the ADC of the invention comprises a nucleic acid encoding a functional, therapeutic gene that is used to replace a mutated or otherwise dysfuntional (e.g., truncated) gene associated with cancer. In other embodiments, the ADC of the invention comprises a nucleic acid that encodes for or otherwise provides for the production of a therapeutic protein to treat cancer. The nucleic acid that encodes the therapeutic gene may be directly conjugated to the antibody, or alternatively, may be conjugated to the antibody through a carrier. Examples of carriers that may be used to deliver a nucleic acid for gene therapy include, but are not limited to, viral vectors or liposomes.

Alkylating Agents

The linkers of the invention may be used to conjugate an antibody to one or more alkylating agent(s). Alkylating agents are a class of antineoplastic compounds that attaches an alkyl group to DNA. Examples of alkylating agents that may be used in the ADCs of the invention include, but are not limited to, alkyl sulfonates, ethylenimimes, methylamine derivatives, epoxides, nitrogen mustards, nitrosoureas, triazines and hydrazines.

Alkyl Sulfonates

The linkers of the invention may be used to conjugate an antibody to at least one alkyl sulfonate. Alkyl sulfonates are a subclass of alkylating agents with a general formula: $R-SO_2-O-R^1$, wherein R and $R^1$ are typically alkyl or aryl groups. A representative example of an alkyl sulfonate is busulfan (Myleran®, GlaxoSmithKline; Busulfex IV®, PDL BioPharma, Inc.).

Nitrogen Mustards

The linkers of the invention may be used to conjugate an antibody to at least one nitrogen mustard. Representative examples of this subclass of anti-cancer compounds include, but are not limited to chlorambucil (Leukeran®, GlaxoSmithKline), cyclophosphamide (Cytoxan®, Bristol-Myers Squibb; Neosar, Pfizer, Inc.), estramustine (estramustine phosphate sodium or Estracyt®), Pfizer, Inc.), ifosfamide (Ifex®, Bristol-Myers Squibb), mechlorethamine (Mustargen®, Lundbeck Inc.), and melphalan (Alkeran® or L-Pam® or phenylalanine mustard; GlaxoSmithKline).

Nitrosoureas

The linkers of the invention may be used to conjugate an antibody to at least one nitrosourea. Nitrosoureas are a subclass of alkylating agents that are lipid soluble. Representative examples include, but are not limited to, carmustine (BCNU [also known as BiCNU, N,N-bis(2-chloroethyl)-N-nitrosourea, or 1,3-bis(2-chloroethyl)-1-nitrosourea], Bristol-Myers Squibb), fotemustine (also known as Muphoran®), lomustine (CCNU or 1-(2-chloroethyl)-3-cyclohexyl-1-nitrosourea, Bristol-Myers Squibb), nimustine (also known as ACNU), and streptozocin (Zanosar*, Teva Pharmaceuticals).

Triazines and Hydrazines

The linkers of the invention may be used to conjugate an antibody to at least one triazine or hydrazine. Triazines and hydrazines are a subclass of nitrogen-containing alkylating agents. In some embodiments, these compounds spontaneously decompose or can be metabolized to produce alkyl diazonium intermediates that facilitate the transfer of an alkyl group to nucleic acids, peptides, and/or polypeptides, thereby causing mutagenic, carcinogenic, or cytotoxic effects. Representative examples include, but are not limited to dacarbazine (DTIC-Dome, Bayer Healthcare Pharmaceuticals Inc.), procarbazine (Mutalane®, Sigma-Tau Pharmaceuticals, Inc.), and temozolomide (Temodar®, Schering Plough).

Other Alkylating Agents

The linkers of the invention may be used to conjugate an antibody to at least one ethylenimine, methylamine derivative, or epoxide. Ethylenimines are a subclass of alkylating agents that typically containing at least one aziridine ring. Epoxides represent a subclass of alkylating agents that are characterized as cyclic ethers with only three ring atoms.

Representatives examples of ethylenimines include, but are not limited to thiopeta (Thioplex, Amgen), diaziquone (also known as aziridinyl benzoquinone (AZQ)), and mitomycin C. Mitomycin C is a natural product that contains an aziridine ring and appears to induce cytoxicity through cross-linking DNA (Dorr R T, et al. Cancer Res. 1985; 45:3510; Kennedy K A, et al Cancer Res. 1985; 45:3541). Representative examples of methylamine derivatives and their analogs include, but are not limited to, altretamine (Hexalen, MGI Pharma, Inc.), which is also known as hexamethylamine and hexastat. Representative examples of epoxides of this class of anti-cancer compound include, but are not limited to dianhydrogalactitol. Dianhydrogalactitol (1,2:5,6-dianhydrodulcitol) is chemically related to the aziridines and generally facilitate the transfer of an alkyl group through a similar mechanism as described above. Dibromodulcitol is hydrolyzed to dianhydrogalactitol and thus is a pro-drug to an epoxide (Sellei C, et al. Cancer Chemother Rep. 1969; 53:377).

Antiangiogenic Agents

In some embodiments, the linkers of the invention may be used to conjugate an antibody to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs of the invention include, but are not limited to, angiostatin, ABX EGF, C1-1033, PKI-166, EGF vaccine, EKB-569, GW2016, ICR-62, EMD 55900, CP358, PD153035, AG1478, IMC-$C_{225}$ (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S—24, vitaxin, dimethylxanthenone acetic acid, IM862, Interleukin-12, Interleukin-2, NM-3, HuMV833, PTK787, RhuMab, angiozyme (ribozyme), IMC-$1C_{11}$, Neovastat, marimstat, prinomastat, BMS—275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

Antimetabolites

The linkers of the invention may be used to conjugate an antibody to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs of the invention include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

Antifolates

The linkers of the invention may be used to conjugate an antibody to at least one antifolate. Antifolates are a subclass of antimetabolites that are structurally similar to folate. Representative examples include, but are not limited to, methotrexate, 4-amino-folic acid (also known as aminopterin and 4-aminopteroic acid), lometrexol (LMTX), pemetrexed (Alimpta, Eli Lilly and Company), and trimetrexate (Neutrexin, Ben Venue Laboratories, Inc.)

Purine Antagonists

The linkers of the invention may be used to conjugate an antibody to at least one purine antagonist. Purine analogs are a subclass of antimetabolites that are structurally similar to the group of compounds known as purines. Representative examples of purine antagonists include, but are not limited to, azathioprine (Azasan, Salix; Imuran, GlaxoSmithKline), cladribine (Leustatin [also known as 2-CdA], Janssen Biotech, Inc.), mercaptopurine (Purinethol [also known as 6-mercaptoethanol], GlaxoSmithKline), fludarabine (Fludara, Genzyme Corporation), pentostatin (Nipent, also known as 2'-deoxycoformycin (DCF)), 6-thioguanine (Lanvis [also known as thioguanine], GlaxoSmithKline).

Pyrimidine Antagonists

The linkers of the invention may be used to conjugate an antibody to at least one pyrimidine antagonist. Pyrimidine antagonists are a subclass of antimetabolites that are structurally similar to the group of compounds known as purines. Representative examples of pyrimidine antagonists include, but are not limited to azacitidine (Vidaza, Celgene Corporation), capecitabine (Xeloda, Roche Laboratories), Cytarabine (also known as cytosine arabinoside and arabinosylcytosine, Bedford Laboratories), decitabine (Dacogen, Eisai Pharmaceuticals), 5-fluorouracil (Adrucil, Teva Pharmaceuticals; Efudex, Valeant Pharmaceuticals, Inc), 5-fluoro-2'-deoxyuridine 5'-phosphate (FdUMP), 5-fluorouridine triphosphate, and gemcitabine (Gemzar, Eli Lilly and Company).

Boron-Containing Agents

The linkers of the invention may be used to conjugate an antibody to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

Chemoprotective Agents

The linkers of the invention may be used to conjugate an antibody to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

Hormone Agents

The linkers of the invention may be used to conjugate an antibody to at least one hormone agent. A hormone agent (including synthetic hormones) is a compound that interferes with the production or activity of endogenously produced hormones of the endocrine system. In some embodiments, these compounds interfere with cell growth or produce a cytotoxic effect. Non-limiting examples include androgens, estrogens, medroxyprogesterone acetate (Provera, Pfizer, Inc.), and progestins.

Antihormone Agents

The linkers of the invention may be used to conjugate an antibody to at least one antihormone agent. An "antihormone" agent is an agent that suppresses the production of and/or prevents the function of certain endogenous hormones. In one embodiment, the antihormone agent interferes with the activity of a hormone selected from the group comprising androgens, estrogens, progesterone, and goanadotropin-releasing hormone, thereby interfering with the growth of various cancer cells. Representative examples of antihormone agents include, but are not limited to, aminoglutethimide, anastrozole (Arimidex, AstraZeneca Pharmaceuticals), bicalutamide (Casodex, AstraZeneca Pharmaceuticals), cyproterone acetate (Cyprostat, Bayer PLC), degarelix (Firmagon, Ferring Pharmaceuticals), exemestane (Aromasin, Pfizer Inc.), flutamide (Drogenil, Schering-Plough Ltd), fulvestrant (Faslodex, AstraZeneca Pharmaceuticals), goserelin (Zolodex, AstraZeneca Pharmaceuticals), letrozole (Femara, Novartis Pharmaceuticals Corporation), leuprolide (Prostap), lupron, medroxyprogesterone acetate (Provera, Pfizer Inc.), Megestrol acetate (Megace, Bristol-Myers Squibb Company), tamoxifen (Nolvadex, AstraZeneca Pharmaceuticals), and triptorelin (Decapetyl, Ferring).

Corticosteroids

The linkers of the invention may be used to conjugate an antibody to at least one corticosteroid. Corticosteroids may be used in the ADCs of the invention to decrease inflammation. An example of a corticosteroid includes, but is not limited to, a glucocorticoid, for example, prednisone (Deltasone, Pharmacia & Upjohn Company, a division of Pfizer, Inc.).

Photoactive Therapeutic Agents

The linkers of the invention may be used to conjugate an antibody to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

Oligonucleotides

The linkers of the invention may be used to conjugate an antibody to at least one oligonucleotide. Oligonucleotides are made of short nucleic acid chains that work by interfering with the processing of genetic information. In some embodiments, the oligonucleotides for use in ADCs are unmodified single-stranded and/or double-stranded DNA or RNA molecules, while in other embodiments, these therapeutic oligonucleotides are chemically-modified single-stranded and/or double-stranded DNA or RNA molecules. In one embodiment, the oligonucleotides used in the ADCs are relatively short (19-25 nucleotides) and hybridize to a unique nucleic acid sequence in the total pool of nucleic acid targets present in cells. Some of the important oligonucleotide technologies include the antisense oligonucleotides (including RNA interference (RNAi)), aptamers, CpG oligonucleotides, and ribozymes.

Antisense Oligonucleotides

The linkers of the invention may be used to conjugate an antibody to at least one antisense oligonucleotide. Antisense oligonucleotides are designed to bind to RNA through Watson-Crick hybridization. In some embodiments the antisense oligonucleotide is complementary to a nucleotide encoding a region, domain, portion, or segment of the conjugated antibody. In some embodiments, the antisense oligonucleotide comprises from about 5 to about 100 nucleotides, from about 10 to about 50 nucleotides, from about 12 to about 35, and from about 18 to about 25 nucleotides There are multiple mechanisms that can be exploited to inhibit the function of the RNA once the oligonucleotide binds to the target RNA (Crooke S T. (1999). Biochim. Biophys. Acta, 1489, 30-42). The best-characterized antisense mechanism results in cleavage of the targeted RNA by endogenous cellular nucleases, such as RNase H or the nuclease associated with the RNA interference mechanism. However, oligonucleotides that inhibit expression of the target gene by non-catalytic mechanisms, such as modulation of splicing or translation arrest, can also be potent and selective modulators of gene function.

Another RNase-dependent antisense mechanism that has recently received much attention is RNAi (Fire et al. (1998). Nature, 391, 806-811; Zamore P D. (2002). Science, 296, 1265-1269.). RNA interference (RNAi) is a post-transcriptional process where a double stranded RNA inhibits gene expression in a sequence specific fashion. In some embodiments, the RNAi effect is achieved through the introduction of relatively longer double-stranded RNA (dsRNA), while in preferred embodiments, this RNAi effect is achieved by the introduction of shorter double-stranded RNAs, e g small interfering RNA (siRNA) and/or microRNA (miRNA). In yet another embodiment, RNAi can also be achieved by introducing of plasmid that generate dsRNA complementary to target gene. In each of the foregoing embodiments, the double-stranded RNA is designed to interfere with the gene expression of a particular the target sequence within cells. Generally, the mechanism involves conversion of dsRNA into short RNAs that direct ribonucleases to homologous mRNA targets (summarized, Ruvkun, Science 2294:797 (2001)), which then degrades the corresponding endogenous mRNA, thereby resulting in the modulation of gene expression. Notably, dsRNA has been reported to have anti-proliferative properties, which makes it possible also to envisage therapeutic applications (Aubel et al., Proc. Natl. Acad. Sci., USA 88:906 (1991)). For example, synthetic dsRNA has been shown to inhibit tumor growth in mice (Levy et al. Proc. Nat. Acad. Sci. USA, 62:357-361 (1969)), is active in the treatment of leukemic mice (Zeleznick et al., Proc. Soc. Exp. Biol. Med. 130:126-128 (1969)), and inhibits chemically induced tumorigenesis in mouse skin (Gelboin et al., Science 167:205-207 (1970)). Thus, in preferred embodiments, the invention provides for the use of antisense oligonucleotides in ADCs for the treatment of breast cancer. In other embodiments, the invention provides compositions and methods for initiating antisense oligo-nucleotide treatment, wherein dsRNA interferes with target cell expression of EGFR at the mRNA level. dsRNA, as used above, refers to naturally-occurring RNA, partially purified RNA, recombinantly produced RNA, synthetic RNA, as well as altered RNA that differs from naturally-occurring RNA by the inclusion of non-standard nucleotides, non-nucleotide material, nucleotide analogs (e.g. locked nucleic acid (LNA)), deoxyribonucleotides, and any combination thereof. RNA of the invention need only be sufficiently similar to natural RNA that it has the ability to mediate the antisense oligonucleotide-based modulation described herein.

Aptamers

The linkers of the invention may be used to conjugate an antibody to at least one aptamer. An aptamer is a nucleic acid molecule that has been selected from random pools based on its ability to bind other molecules. Like antibodies, aptamers can bind target molecules with extraordinary affinity and specificity. In many embodiments, aptamers assume complex, sequence-dependent, three-dimensional shapes that allow them to interact with a target protein, resulting in a tightly bound complex analogous to an antibody-antigen interaction, thereby interfering with the function of said protein. The particular capacity of aptamers to bind tightly and specifically to their target protein underlines their potential as targeted molecular therapies.

CpG Oligonucleotides

The linkers of the invention may be used to conjugate an antibody to at least one CpG oligonucleotide. Bacterial and viral DNA are known to be a strong activators of both the innate and specific immunity in humans. These immunologic characteristics have been associated with unmethylated CpG dinucleotide motifs found in bacterial DNA. Owing to the fact that these motifs are rare in humans, the human immune system has evolved the ability to recognize these motifs as an early indication of infection and subsequently initiate immune responses. Therefore, oligonucleotides containing this CpG motif can be exploited to initiate an antitumor immune response.

Ribozymes

The linkers of the invention may be used to conjugate an antibody to at least one ribozyme. Ribozymes are catalytic RNA molecules ranging from about 40 to 155 nucleotides in length. The ability of ribozymes to recognize and cut specific RNA molecules makes them potential candidates for therapeutics. A representative example includes angiozyme.

Radionuclide Agents (Radioactive Isotopes)

The linkers of the invention may be used to conjugate an antibody to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of 111In, 177Lu, 212Bi, 213Bi, 211At, 62Cu, 64Cu, 67Cu, 90Y, 125I, 131I, 32P, 33P, 47Sc, 111Ag, 67Ga, 142Pr, 153Sm, 161Tb, 166Dy, 166Ho, 186Re, 188Re, 189Re, 212Pb, 223$R^a$, 225Ac, 59Fe, 75Se, 77As, 89Sr, 99Mo, 105Rh, 109Pd, 143Pr, 149Pm, 169Er, 194Ir, 198Au, 199Au, and 211Pb. Also preferred are radionuclides that substantially decay with Auger-emitting particles. For example, Co-58, Ga-67, Br-80m, Tc-99m, Rh-103m, Pt-109, In-1111, Sb-119, 1-125, Ho-161, Os-189m and Ir-192. Decay energies of useful beta-particle-emitting nuclides are preferably Dy-152, At-211, Bi-212, $R^a$-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include 11C, 13N, 15O, 75Br, 198Au, 95Ru, 97Ru, 103Ru, 105Ru, 107Hg, 203Hg, 121mTe, 122mTe, 125mTe, 165Tm, 167Tm, 168Tm, 197Pt, 109Pd, 105Rh, 142Pr, 143Pr, 161Tb, 166Ho, 199Au, 57Co, 58Co, 51Cr, 59Fe, 75Se, 201Tl, 225Ac, 76Br, 169Yb, and the like.

Radiosensitizers

The linkers of the invention may be used to conjugate an antibody to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin®, benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

Topoisomerase Inhibitors

The linkers of the invention may be used to conjugate an antibody to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

Tyrosine Kinase Inhibitors

The linkers of the invention may be used to conjugate an antibody to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs of the invention include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

Other Agents

Examples of other agents that may be used in the ADCs of the invention include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the ADCs of the invention are not exclusive, in that certain examples of drugs may be found in more than one category, e.g., ansamitocins are both mitotic inhibitors and antitumor antibiotics.

All stereoisomers of the above drug moieties are contemplated for the compounds of the invention, i.e. any combination of R and S configurations at the chiral carbons of D.

A "detectable moiety" or a "marker" refers to a composition that is detectable by spectroscopic, photochemical, biochemical, immunochemical, radioactive or chemical means. For example, a useful label includes $^{32}P$, $^{35}S$, fluorescent dyes, electron-dense reagents, enzymes (e.g., enzymes that are generally used in ELISA), biotin-streptavidin, dioxigenin, hapten, and proteins for which antisera or monoclonal antibodies are available, or nucleic acid molecules with a sequence complementary to a target. The detectable moiety often generates a measurable signal, e.g., a radioactive signal, a color signal or a fluorescent signal, which is usable to quantify an amount of the detectable moiety that binds in the sample. Quantification of the signal may be accomplished by, for example, scintillation counting, density gauge, flow cell analysis, ELISA, or direct analysis by mass spectroscopy of circular or subsequently digested peptides (one or more peptides may be assayed). Those skilled in the art are familiar with techniques and detection means for a label compound of interest. These techniques and methods are conventional and well known in the art.

The probe for detection refers to (i) a material capable of providing a detectable signal, (ii) a material capable of interacting with a first probe or a second probe to change a detectable signal provided by the first probe or the second probe, such as fluorescence resonance energy transfer (FRET), (iii) a material capable of stabilizing an interaction with an antigen or a ligand or increasing binding affinity, (iv) a material capable of affecting electric mobility or cell-invasive action by physical parameters such as charge, hydrophobicity, etc., or (v) a material capable of adjusting ligand affinity, antigen-antibody binding or ion complex formation.

Antibodies

The antibody of an ADC may be any antibody that binds, typically but not necessarily specifically, an antigen expressed on the surface of a target cell of interest. The antigen need not, but in some embodiments, is capable of internalizing an ADC bound thereto into the cell. Target cells of interest may include cells where induction of apoptosis is desirable. Target antigens may be any protein, glycoprotein, polysaccharide, lipoprotein, etc. expressed on the target cell of interest, but will typically be proteins that are either uniquely expressed on the target cell and not on normal or healthy cells, or that are over-expressed on the target cell as compared to normal or healthy cells, such that the ADCs selectively target specific cells of interest, such as, for example, tumor cells. As will be appreciated by skilled artisans, the specific antigen, and hence antibody, selected will depend upon the identity of the desired target cell of interest. In specific embodiments, the antibody of the ADC is an antibody suitable for administration to humans.

Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at its other end.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab.

The term "antibody" herein is used in the broadest sense and refers to an immunoglobulin molecule that specifically binds to, or is immunologically reactive with, a particular antigen, and includes polyclonal, monoclonal, genetically engineered and otherwise modified forms of antibodies, including but not limited to murine, chimeric antibodies, humanized antibodies, heteroconjugate antibodies (e.g., bispecific antibodies, diabodies, triabodies, and tetrabodies), and antigen binding fragments of antibodies, including e.g., Fab', F(ab')2, Fab, Fv, rIgG, and scFv fragments. The term "scFv" refers to a single chain Fv antibody in which the variable domains of the heavy chain and the light chain from a traditional antibody have been joined to form one chain.

Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment" refers to a portion of a full-length antibody, generally the target binding or variable region. Examples of antibody fragments include Fab, Fab', F(ab')$_2$ and Fv fragments. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target. "Single-chain Fv" or "scFv" antibody fragments comprise the VH and VL domains of an antibody in a single polypeptide chain. Generally, the Fv polypeptide further comprises a polypeptide linker between the VH and VL domains which enables the scFv to form the desired structure for target binding. "Single domain antibodies" are composed of a single VH or VL domains which exhibit sufficient affinity to the target. In a specific embodiment, the single domain antibody is a camelized antibody (see, e.g., Riechmann, 1999, Journal of Immunological Methods 231:25-38).

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')2 pepsin digestion product. Additional chemical couplings of antibody fragments are known to those of ordinary skill in the art.

Both the light chain and the heavy chain variable domains have complementarity determining regions (CDRs), also known as hypervariable regions. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The CDRs in each chain are held together in close proximity by the FR regions and, with the CDRs from the other chain, contribute to the formation of the target binding site of antibodies (see Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al., unless otherwise indicated.

In certain embodiments, the antibodies of the ADCs of the present disclosure are monoclonal antibodies. The term "monoclonal antibody" (mAb) refers to an antibody that is derived from a single copy or clone, including e.g., any eukaryotic, prokaryotic, or phage clone, and not the method by which it is produced. Preferably, a monoclonal antibody of the disclosure exists in a homogeneous or substantially homogeneous population. Monoclonal antibody includes both intact molecules, as well as, antibody fragments (such as, for example, Fab and F(ab')2 fragments), which are capable of specifically binding to a protein. Fab and F(ab')2 fragments lack the Fc fragment of intact antibody, clear more rapidly from the circulation of the animal, and may have less non-specific tissue binding than an intact antibody (Wahl et al., 1983, *J. Nucl. Med* 24:316). Monoclonal antibodies useful with the present disclosure can be prepared using a wide variety of techniques known in the art including the use of hybridoma, recombinant, and phage display technologies, or a combination thereof. The antibodies of the disclosure include chimeric, primatized, humanized, or human antibodies.

While in most instances antibodies are composed of only the genetically-encoded amino acids, in some embodiments non-encoded amino acids may be incorporated at specific. Examples of non-encoded amino acids that may be incorporated into antibodies for use in controlling stoichiometry and attachment location, as well as methods for making such modified antibodies are discussed in Tian et al., 2014, *Proc Nat'l Acad Sci USA* 111(5):1766-1771 and Axup et al., 2012, *Proc Nat'l Acad Sci USA* 109(40):16101-16106 the entire contents of which are incorporated herein by reference.

In certain embodiments, the antibody of the ADCs described herein is a chimeric antibody. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, *Science* 229(4719):1202-7; Oi et al., 1986, *BioTechniques* 4:214-221; Gillies et al., 1985, *J. Immunol. Methods* 125:191-202; U.S. Pat. Nos. 5,807,715; 4,816,567; and 4,816397, which are incorporated herein by reference in their entireties.

In certain embodiments, the antibody of the ADCs described herein is a humanized antibody. "Humanized" forms of non-human (e.g., murine) antibodies are chimeric immunoglobulins, immunoglobulin chains or fragments thereof (such as Fv, Fab, Fab', F(ab')2 or other target-binding subdomains of antibodies), which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, *Mol. Immunol.*, 28:489-498; Studnicka et al., 1994, *Prot. Eng.* 7:805-814; Roguska et al., 1994, *Proc. Natl. Acad Sci. USA* 91:969-973; and U.S. Pat. No. 5,565,332, all of which are hereby incorporated by reference in their entireties.

In certain embodiments, the antibody of the ADCs described herein is a human antibody. Completely "human" antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 4,716,111, 6,114,598, 6,207,418, 6,235,883, 7,227,002, 8,809,151 and U.S. Published Application No. 2013/189218, the contents of which are incorporated herein by reference in their entireties. Human antibodies can also be produced using transgenic mice which are incapable of expressing functional endogenous immunoglobulins, but which can express human immunoglobulin genes. See, e.g., U.S. Pat. Nos. 5,413,923; 5,625,126; 5,633,425; 5,569,825; 5,661,016; 5,545,806; 5,814,318; 5,885,793; 5,916,771; 5,939,598; 7,723,270; 8,809,051 and U.S. Published Application No. 2013/117871, which are incorporated by reference herein in their entireties. In addition, companies such as Medarex (Princeton, N.J.), Astellas Pharma (Deerfield, Ill.), and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, *Biotechnology* 12:899-903).

In certain embodiments, the antibody of the ADCs described herein is a primatized antibody. The term "primatized antibody" refers to an antibody comprising monkey variable regions and human constant regions. Methods for producing primatized antibodies are known in the art. See, e.g., U.S. Pat. Nos. 5,658,570; 5,681,722; and 5,693,780, which are incorporated by reference in their entireties.

In certain embodiments, the antibody of the ADCs described herein is a bispecific antibody or a dual variable domain antibody (DVD). Bispecific and DVD antibodies are monoclonal, often human or humanized, antibodies that have binding specificities for at least two different antigens. DVDs are described, for example, in U.S. Pat. No. 7,612,181, the disclosure of which is incorporated herein by reference.

In certain embodiments, the antibody of the ADCs described herein is a derivatized antibody. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (see, e.g., Wolfson, 2006, Chem. Biol. 13(10):1011-2).

In certain embodiments, the antibody of the ADCs described herein has a sequence that has been modified to alter at least one constant region-mediated biological effector function relative to the corresponding wild type sequence. For example, in some embodiments, the antibody can be modified to reduce at least one constant region-mediated biological effector function relative to an unmodified antibody, e.g., reduced binding to the Fc receptor (FcR). FcR binding can be reduced by mutating the immunoglobulin constant region segment of the antibody at particular regions necessary for FcR interactions (see, e.g., Canfield and Morrison, 1991, *J. Exp. Med* 173:1483-1491; and Lund et al., 1991, *J. Immunol.* 147:2657-2662).

In certain embodiments, the antibody of the ADCs described herein is modified to acquire or improve at least one constant region-mediated biological effector function relative to an unmodified antibody, e.g., to enhance FcγR interactions (see, e.g., US 2006/0134709). For example, an antibody with a constant region that binds FcγRIIA, FcγRIIB and/or FcγRIIIA with greater affinity than the corresponding wild type constant region can be produced according to the methods described herein.

In certain specific embodiments, the antibody of the ADCs described herein is an antibody that binds tumor cells, such as an antibody against a cell surface receptor or a tumor-associated antigen (TAA). In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to the surface of the no-cancerous cells. Such cell surface receptor and tumor-associated antigens are known in the art, and can prepared for use in generating antibodies using methods and information which are well known in the art.

Exemplary Cell Surface Receptors and TAAs

Examples of cell surface receptor and TAAs to which the antibody of the ADCs described herein may be targeted include, but are not limited to, the various receptors and TAAs listed below in Table 1. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to the listed cell surface receptors and TAAs are available in public databases such as GenBank.

TABLE 1

4-1BB
5AC
5T4
Alpha-fetoprtein
angiopoietin 2
ASLG659
TCL1
BMPR1B
Brevican (BCAN, BEHAB)
C2-42 antigen
C5
CA-125
CA-125 (imitation)
CA-IX (Carbonic anhydrase 9)
CCR4
CD140a
CD152
CD19
CD20
CD200
CD21 (C3DR) 1)

TABLE 1-continued

CD22 (B-cell receptor CD22-B isoform)
CD221
CD23 (gE receptor)
CD28
CD30 (TNFRSF8)
CD33
CD37
CD38 (cyclic ADP ribose hydrolase)
CD4
CD40
CD44 v6
CD51
CD52
CD56
CD70
CD72 (Lyb-2, B-cell differentiation antigen CD72)
CD74
CD79a (CD79A, CD79α, immunoglobulin-associated alpha) Genbank accession No. NP_001774.10)
CD79b (CD79B, CD79β, B29)
CD80
CEA
CEA-related antigen
ch4D5
CLDN18.2
CRIPTO (CR, CR1, CRGF, TDGF1 teratocarcinoma-derived growth factor)
CTLA-4
CXCR5
DLL4
DR5
E16 (LAT1, SLC7A5) EGFL7
EGFR
EpCAM
EphB2R (DRT, ERK, Hek5, EPHT3, Tyro5)
Episialin
ERBB3
ETBR (Endothelin type B receptor)
FCRH1 (Fc receptor-like protein 1)
FcRH2 (IFGP4, IRTA4, SPAP1, SPAP1B, SPAP1C, SH2 domain containing phosphatase anchor protein
Fibronectin extra domain-B
Folate receptor 1
Frizzled receptor
GD2
[0260]
GD3 ganglioside
GEDA
GPNMB
HER1
HER2 (ErbB2)
HER2/neu
HER3
HGF
HLA-DOB
HLA-DR
Human scatter factor receptor kinase
IGF-1 receptor
IgG4
IL-13
IL20Rα (IL20Ra, ZCYTOR7)
IL-6
ILGF2
ILFR1R
integrin α
integrin α5β1
integrin αvβ3
IRTA2 (Immunoglobulin superfamily receptor translocation associated 2, Gene Chromosome 1q21)
Lewis-Y antigen
LY64 (RP105)
MCP-1
MDP (DPEP1)
MPF (MSLN, SMR, mesothelin, megkaryocyte potentiating factor)
MS4A1
MSG783 (RNF124, hypothetical protein FLJ20315)
MUC1
Mucin CanAg
Napi3 (NAPI-3B, NPTIIb, SLC34A2, type II sodium-dependent phosphate transporter 3b)

TABLE 1-continued

NCA (CEACAM6)
P2X5 (Purinergic receptor P2X ligand-gated ion channel 5)
PD-1
PDCD1
PDGF-R α
Prostate specific membrane antigen
PSCA (Prostate stem cell antigen precursor)
PSCA hlg
RANKL
RON
SDC1
Sema 5b
SLAMF7 (CS-1)
STEAP1
STEAP2 (HGNC_8639, PCANAP1, STAMP1, STEAP2, STMP, prostate cancer associated gene 1)
TAG-72
TEM1
Tenascin C
TENB2, (TMEFF2, tomoregulin, TPEF, HPP1, TR)
TGF-β
TRAIL-E2
TRAIL-R1
TRAIL-R2
TrpM4 (BR22450, FLJ20041, TRPM4, TRPM4B, transient receptor potential cation channel subfmlily M, member 4)
TA CTAA16.88
TWEAK-R
TYRP1 (glycoprotein 75)
VEGF
VEGF-A
EGFR-1
VEGFR-2
Vimentin Exemplary Antibodies Exemplary antibodies to be used with ADCs of the disclosure include but are not limited to 3F8 (GD2), Abagovomab (CA-125 (imitation)), Adecatumumab (EpCAM), Afutuzumab (CD20), Alacizumab pegol (VEGFR2), ALD518 (IL-6), Alemtuzumnab (CD52), Altumomab pentetate (CEA), Amatuximab (Mesothelin), Anatumomnab mafenatox (TAG-72), Apolizumab (HLA-DR), Arcitumomab (CEA), Bavituximab (Phosphatidylserine), Bectumomab (CD22), Belimumab (BAFF), Besilesomab (CEA-related antigen), Bevacizumab (VEGF-A), Bivatuzumab mertansine (CD44 v6), Blinatumomab (CD19), Brentuximab vedotin ((CD30 (TNFRSF8)), Cantuzumab mertansine (Mucin CanAg), Cantuzumab ravtansine (MUC1), Capromab pendetide (Prostatic carcinoma cells), Carlumab (MCP-1), Catumaxomab (EpCAM, CD3), CC49 (Tag-72), cBR96-DOX ADC (Lewis-Y antigen), Cetuximab (EGFR), Citatuzumab bogatox (EpCAM), Cixutumumab (IGF-1 receptor), Clivatuzumab tetraxetan(MUC1), Conatumumab (TRAIL-E2), Dacetuzumab (CD40), Dalotuzumab (Insulin-like growth factor 1 receptor), Deratumumab ((CD38 (cyclic ADP ribose hydrolase)), Demcizumab (DLL4), Denosumab (RANKL), Detumomab (B-lymphoma cell), Drozitumab (DR5), Dusigitumab (ILGF2), Ecromeximab (D3 ganglioside), Eculizumab ($C_5$), Edrecolomab (EpCAM), Elotuzumab (SLAMF7), Elsilimomab (IL-6), Enavatuzumab (TWEAK receptor), Enoticumab (DLL4), Ensituximab (5AC), Epitumomab cituxetan (Episialin), Epratuzumab (CD22), Ertumaxomab ((HER2/neu, CD3)), Etancizumab (Integrin av$3), Farletuzumab (Folate receptor 1), FBTA05 (CD20), Ficlatuzumab (HGF), Figitumumab (IGF-1 receptor), Flanvotumab ((TYRP1 (glycoprotein 75)), Fresolimumab (TGF-1), Galiximab (CD80), Ganitumab (IGF-I), Gemtuzumab ozogamicin (CD33), Girentuximab ((Carbonic anhydrase 9 (CA-IX)), Glembatumumab vedotin (GPNMB), Ibritumomab tiuxetan (CD20) Icrucumab (VEGFR-1), Igovomab (CA-125), IMAB362 (CLDN18.2), Imgatuzumab (EGFR), Indatuximab ravtansine (SDC1), Intetumumab (CD51), Inotuzumab ozogamicin (CD22), Ipilimumab (CD152), Iratumumab ((CD30 (TNFRSF8)), Labetuzumab (CEA), Lambrolizumab (PDCD1), Lexatumumab (TRAIL-R2), Lintuzumab (CD33), Lorvotuzumab mertansine (CD56), Lucatumumab (CD40), Lumiliximab ((CD23 (IgE receptor)), Mapatumumab (TRAIL-R1), Margetuximab (ch4DS), Matuzumab (EGFR), Milatuzumab (CD74), Mitumomab (GD3 ganglioside), Mogamulizumab (CCR4), Moxetumomab pasudotox (CD22), Nacolomab tafenatox (C2-42 antigen), Naptumomab estafenatox (5T4), Narnatumab (RON), Natalizumab (integrin a4), Necitumumab (EGFR), Nesvacumab (angiopoietin 2), Nimotuzumab (EGFR), Nivolumab (IgG4), Ocaratuzumab (CD20), Ofatumumab (CD20), Olaratumab (PDGF-R a), Onartuzumab (Human scatter factor receptor kinase), Ontuxizumab (TEM1), Oportuzumab monato (EpCAM), Oregovomab (CA-125), Otlertuzumab (CD37), Panitumumab (EGFR) Pankomab (Tumor specific glycosylation of MUC1), Parsatuzumab (EGFL7), Patritumab (HER3), Pemtumomab (MUC1), Pertuzumab (HER2/neu), Pidilizumab (PD-1), Pinatuzumab vedotin (CD22), Pritumumab (Vimentin), Racotumomab (N-glycolylneuraminic acid), Radretumab (Fibronectin extra domain-B), Ramucirumab (VEGFR2), Rilotumumab (HGF), Rituximab (CD20), Robatumumab (IGF-1 receptor), Samalizumab (CD200), Satumomab pendetide (TAG-72), Seribantumab (ERBB3), Sibrotuzumab (FAP), SGN-CD19A (CD19), SGN-CD33A (CD33), Siltuximab (IL-6), Solitomab (EpCAM), Sonepcizumab (Sphingosine-1-phosphate), Tabalumb (BAFF), Tacatuzumab tetraxetan (Alpha-fetoprotein), Taplitumomab paptox (CD19), Tenatumomab (Tenascin C), Teprotumumab (CD221), TGN1412 (CD28), Ticilimumab (CTLA-4), Tigatuzumab (TRAIL-R2), TNX-650 (IL-13), Tovetumab (CD40a), Trastuzumab (HER2/neu), TRBS07 (GD2), Tremelimumab (CTLA-4), Tucotuzumab celmoleukin (EpCAM), Ublituximab (MS4A), Urelumab (4-1BB), Vandetanib (VEGF), Vantictumab (Frizzled receptor), Volociximab (integrin α5β1), Vorsetuzumab mafodotin (CD70), Votumumab (Tumor antigen CTAA16.88), Zalutumumab (EGFR), Zanolimumab (CD4), and Zatuximab (HER1).

Methods of Making Antibodies

The antibody of an ADC can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel, F. M. et al., eds., Greene Publishing Associates, 1989) and in U.S. Pat. No. 4,816,397.

In one embodiment, the Fc variant antibodies are similar to their wild-type equivalents but for changes in their Fc domains. To generate nucleic acids encoding such Fc variant antibodies, a DNA fragment encoding the Fc domain or a portion of the Fc domain of the wild-type antibody (referred to as the "wild-type Fc domain") can be synthesized and used as a template for mutagenesis to generate an antibody as described herein using routine mutagenesis techniques; alternatively, a DNA fragment encoding the antibody can be directly synthesized.

Once DNA fragments encoding wild-type Fc domains are obtained, these DNA fragments can be further manipulated by standard recombinant DNA techniques, for example, to convert the constant region genes to full-length antibody chain genes. In these manipulations, a CH-encoding DNA fragment is operatively linked to another DNA fragment encoding another protein, such as an antibody variable region or a flexible linker. The term "operatively linked," as used in this context, is intended to mean that the two DNA fragments are joined such that the amino acid sequences encoded by the two DNA fragments remain in-frame.

To express the Fc variant antibodies, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. A variant antibody light chain gne and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the variant Fc domain sequences, the expression vector can already carry antibody variable region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all to Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR-host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection, and the like.

It is possible to express the antibodies in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies include Chinese Hamster Ovary (CHO cells) (including DHFR-CHO cells, described in Urlaub and Chasin, 1980, *Proc. Natl. Acad. Sci. USA* 77:4216-4220, used with a DHFR selectable marker, e.g., as described in Kaufman and Sharp, 1982, Mol. Biol. 159:601-621), NSO myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules.

In some embodiments, the antibody of an ADC can be a bifunctional antibody. Such antibodies, in which one heavy and one light chain are specific for one antigen and the other heavy and light chain are specific for a second antigen, can be produced by crosslinking an antibody to a second antibody by standard chemical crosslinking methods. Bifunctional antibodies can also be made by expressing a nucleic acid engineered to encode a bifunctional antibody.

In certain embodiments, dual specific antibodies, i.e. antibodies that bind one antigen and a second, unrelated antigen using the same binding site, can be produced by mutating amino acid residues in the light chain and/or heavy chain CDRs. Exemplary second antigens include a proinflammatory cytokine (such as, for example, lymphotoxin, interferon-7, or interleukin-1). Dual specific antibodies can be produced, e.g., by mutating amino acid residues in the periphery of the antigen binding site (see, e.g., Bostrom et al., 2009, *Science* 323:1610-1614). Dual functional antibodies can be made by expressing a nucleic acid engineered to encode a dual specific antibody.

Antibodies can also be produced by chemical synthesis (e.g., by the methods described in *Solid Phase Peptide Synthesis*, 2nd ed., 1984 The Pierce Chemical Co., Rockford, Ill.). Antibodies can also be generated using a cell-free platform (see, e.g., Chu et al., *Biochemia No. 2*, 2001 (Roche Molecular Biologicals)).

Methods for recombinant expression of Fc fusion proteins are described in Flanagan et al., *Methods in Molecular Biology*, vol. 378: Monoclonal Antibodies: Methods and Protocols.

Once an antibody has been produced by recombinant expression, it can be purified by any method known in the art for purification of an immunoglobulin molecule, for example, by chromatography (e.g., ion exchange, affinity, particularly by affinity for antigen after Protein A or Protein G selection, and sizing column chromatography), centrifugation, differential solubility, or by any other standard technique for the purification of proteins.

Once isolated, an antibody can, if desired, be further purified, e.g., by high performance liquid chromatography (see, e.g., Fisher, *Laboratory Techniques In Biochemistry And Molecular Biology* (Work and Burdon, eds., Elsevier, 1980)), or by gel filtration chromatography on a Superdex™ 75 column (Pharmacia Biotech AB, Uppsala, Sweden).

Imaging Compounds and Sensors

In certain embodiments, provided herein are uses for the disclosed compounds in imaging compositions and as sensors.

The sensor may be a biosensor, a chemical sensor, or a molecular switch. Biosensors are capable of identifying the presence or the amount of a specific material by reacting specific materials (e.g., cancer cells, viruses, various chemicals, etc.) with bio-receptors (portions designed to be capable of adsorbing and reacting with biomaterials such as DNA, RNA, antibodies, enzyme proteins, cells, biological membranes, hormone receptors, etc.) having selection specificity, and performing measurement using a signal transducer (a device that converts reaction between the specific material and a biological receptor into an electrical signal using various methods), and may be utilized for medical, environmental, process industries, military (chemical warfare), research, food, etc. (see, e.g., *Biosensors and Bioelectronics*, 2016, 32-45; Pol. J. Environ. Stud. 2015, 19-25; *Analytica Chimica Acta* 568 (2006) 200-210; *Biosensors and Bioelectronics* 2017, 217-231; *ACS Appl. Mater. Interfaces* 2015, 7, 20190-20199; *Journal of Coastal Life Medicine* 2016; 4(3): 200-202; *Artificial Cells, Blood Substitutes, and Biotechnology*, 39: 281-288; *Journal of Controlled Release* 159 (2012) 154-163).

Chemical sensors quickly and accurately monitor specific materials in many fields such as clinical diagnosis, medical research, chemical material measurement, environmental measurement, etc., by a method of using electrical properties such as electricity, resistance, potential difference, etc., and optical properties such as color, fluorescence, etc., and includes a gas sensor (hydrogen, oxygen, carbon monoxide), an ion sensor (cation, anion, gas sensitive ion), a component sensor (vapor phase, liquid phase, luminescent component), a humidity sensor (relative humidity, absolute humidity, condensation), dust/soot sensor (floating dust, dirt dust, soot, turbidity), etc. (see, e.g., *Chem. Soc. Rev.*, 2015, 44, 3358; *Journal of the Korean Chemical Society*, 2010, 451-459; *Chem. Sci.*, 2015, 6, 1150-1158; KR 10-1549347; *J. Phys. Chem. B* 2016, 120, 7053-7061; *ACS Appl. Mater. Interfaces* 2015, 7, 704-712; *J. Am. Chem. Soc.* 2011, 133, 10960-10965; *J. Am. Chem. Soc.* 2012, 134, 20412-20420; *Org. Lett.* 2014, 16, 1680-1683; *J. Org. Chem.* 2013, 78, 702-705; *J. Org. Chem.* 2015, 80, 12129-12136; *ACS Macro Lett.* 2014, 3, 1191-1195; *New J. Chem.*, 2012, 36, 386-393; *Chem. Commun.*, 2010, 46, 6575-6577; 2013).

A molecular switch is a molecule that can be reversibly switched between two or more stable states. The molecules may be switched between states in response to environmental stimuli, such as changes in chemical environment (such as pH), light irradiation (for example, light of a particular wavelength), temperature, an electric current, microenvironment, or the presence of a ligand. In some cases, switching between states may be dependent on a combination of stimuli. The oldest forms of synthetic molecular switches are pH indicators, which display distinct colors as a function of pH. Synthetic molecular switches may be applied in molecular computers or responsive drug delivery systems. Molecular switches are also important in biology because many biological functions are based on them, for instance allosteric regulation and vision.

Such biosensors, chemical sensors, and molecular switches may further comprise additional photoreactive moieties, such as rhodamine, phenol red, orange azo dye, papa red, non-sulfonated cyanine, sulfonated cyanine, chemiluminescent fluoride sensor (1,2-dioxetane derivative), and D2A dyes (NIR fluorescence dyes). Alternatively, the photoreactive moiety may be selected from a compound having functional groups and structures similar to the following:

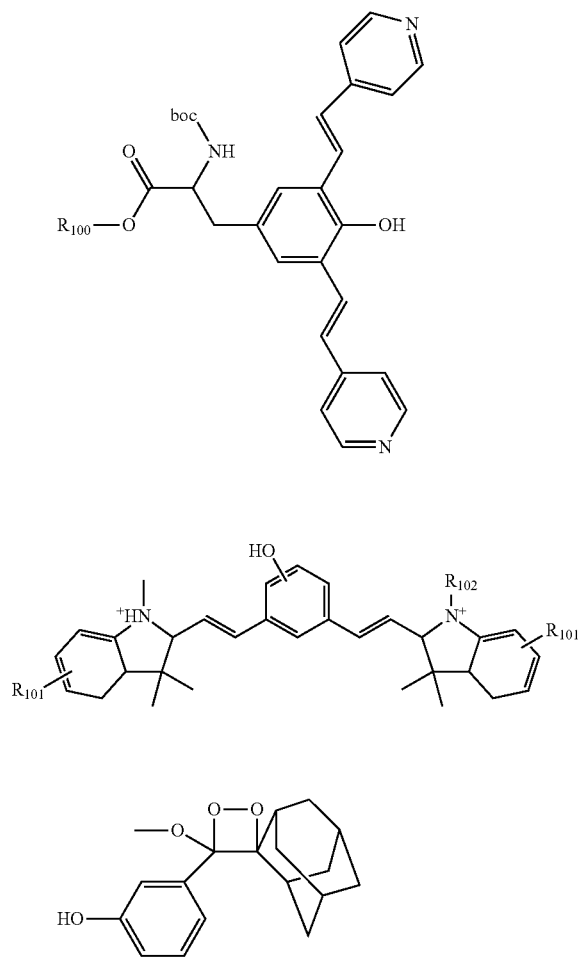

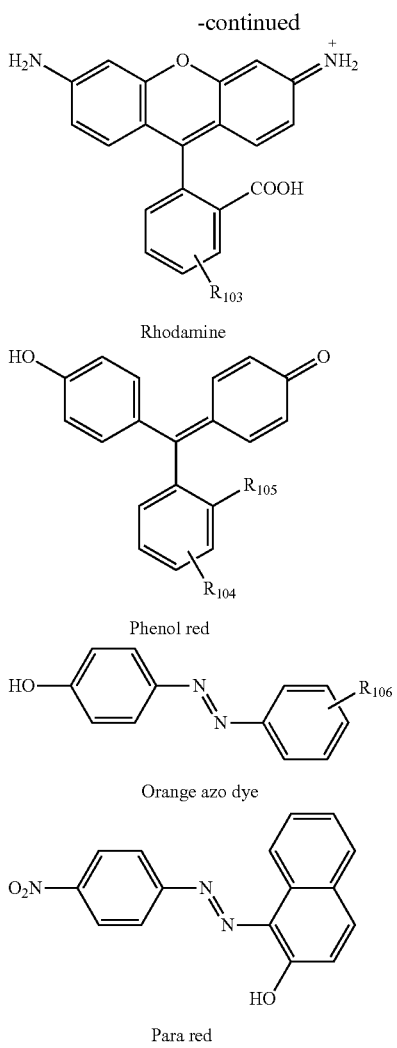

Rhodamine

Phenol red

Orange azo dye

Para red wherein:
$R_{100}$ is H or $C_1$-$C_6$-alkyl;
$R_{101}$ is H or $SO_3H$; $R_{102}$ is $C_1$-$C_6$-alkyl or —$(CH_2)_z$COOH;
z is an integer of 3 to 8;
$R_{103}$ and $R_{104}$ are each independently H or $C_1$-$C_6$ alkyl; and
$R_{105}$ and $R_{106}$ are each independently hydrogen, COOH or $SO_3H$.

Additional photoreactive moieties are known in the art. See, e.g., Org. Lett. 2014, 16, 1680-1683; J. Am. Chem. Soc. 2011, 133, 10960-10965; Dye Lasers, 3rd Ed. (Springer-Verlag, Berlin, 1990); J. Am. Chem. Soc. 2012, 134, 20412-20420).

Methods of Treatment

Target-Oriented Treatments

The targeting moiety of the conjugate may be recognized by a cell, thereby providing a so-called target-oriented treatment.

In some embodiments, the conjugate comprises an active agent for use in a target-oriented treatment for treating an autoimmune disease. In some such embodiments, active agents is selected from: cyclosporine, cyclosporine A, mycophenylate mofetil, sirolimus, tacrolimus, enanercept, prednisone, azathioprine, methotrexate cyclophosphamide, aminocaproic acid, chloroquine, hydroxychloroquine, hydrocortisone, dexamethasone, chlororambucil, DHEA, danazol, bromocriptine, meloxicam, infliximab, etc.

In some embodiments, the compound comprises an active agent Q for use in a target-oriented treatment for treating an infectious disease. In some such embodiments, Q is selected from: beta-lactam series (penicillin G, penicillin V, cloxacillin, dicloxacillin, methicillin, nafcillin, oxacillin, ampicillin, amoxicillin, becampicillin, azlocillin, carbenicillin, mezlocillin, piperacillin, ticarcillin), aminoglycoside series (amikacin, gentamycin, kanamycin, neomycin, netilmicin, streptomycin, tobramycin), macrolide series (azithromycin, clarithromycin, erythromycin, lincomycin, clindamycin), tetracycline series (demeclocycline, doxycyline, minocycline, tetracycline), quinolone series (cinoxacin, nalidixic acid), fluoroquinolone series (ciprofloxacin, enoxacin, grepafloxacin, levofloxacin, lomefloxacin, norfloxacin, ofloxacin, sparfloxacin, trovafloxicin), polypeptide series (bacitracin, colistin, polymyxin B), sulfonamide series (sulfisoxazole, sulfamethoxazole, sulfadiazine, sulfamethizole, sulfacetamide), other antibiotics (trimethoprim, sylfamethazole, chloramphenicol, vancomycin, metronidazole, quinupristin, dalfopristin, rifampicin, spectinomycin, nitrofurantoin), general anti-viral agent (idoxuradine, vidarabine, acyclovir, famcicyclovir, pencicyclovir, valacyclovir, gancicyclovir, foscarnet, ribavirin, amantadine, rimantadine, cidofovir, Antisense oligonucleotides, Immunoglobumins, interfeones), HIV infection therapeutic agent (tenofovir, emtricitabine, zidovudine, didanosine, zalcitabine, stavudine, lamivudine, nevirapine, delaviridine, saquinavir, ritonavir, indinavir, nelfinavir), etc.

In some embodiments, the compounds and conjugates disclosed herein comprise an active agent Q for use in a method for delivering an active agent to a cell for treating a tumor, wherein the targeting moiety is selected to bind with a target cell (i.e., a cancer cell). In particular, the present compounds, conjugates, and compositions may be useful for inhibiting abnormal cell growth or treating a proliferative disorder in a mammal (e.g., a human), such as where the target cell is a cancer cell and the targeting moiety is selected to bind to molecule associated with the cancer cell (and not associated with healthy cells, or at least preferentially associated with tumor cells rather than healthy cells).

In some such embodiments, the active agent is selected from: a cytotoxic or immunomodulatory agent, an anticancer agent, an anti-tublin agent, a cytotoxic agent, etc. Preferably, the cytotoxic or immunomodulatory agent includes an anti-tubulin agent, auristatin, a DNA minor groove binder, a DNA transcription inhibitor, an alkylating agent, anthracycline, antibitiotic, antifolate, antimetabolite, a calmodulin inhibitor, a chemotherapy sensitizer, duocarmycin, etoposide, fluorindated pyrimidine, ionophore, lexitropsin, maytansinoid, nitrosourea, platinol, a pore-forming compound, purine antimetabolite, puromycin, radiation sensitizer, rapamycin, steroid, taxane, topoisomerase inhibitor, vinca alkaloid, etc.; the anti-cancer agent includes methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, proocarbizine, topotecan, nitrogen mustards, cytoxan, etoposide, 5-fluorouracil, BCNU, irinotecan, camptothecins, bleomycin, doxorubicin, idaribicin, daunorubicin, dactinomycin, plicamycin, mitoxantrone, asparaginase, vinblastine, vincristine, vinorelbine, paclitaxel, docetaxel, etc.; the anti-tublin agent includes taxane (e.g., paclitaxel, docetaxel), T67, vinca alkyloid (e.g., vincristine, vinblastine, vindesine, vinorelbine), a baccatin derivative, a taxane derivative, epothiolone (e.g., epothilone A, epothilone B), nocodazole, colchicine, colcimid, estramustine, crytophycins, cemadotin, maytansinoids, combrestatins, discodermolide, eleutherobin, an auristatin derivative (AFP, MMAF, MMAE), etc.; the cytotoxic agent includes androgen, anthramycin(AMC), asparaginase, 5-azacytidine, azathioprine, bleomycin, busulfan, buthionine sulfoximine, calicheamicin, calicheamicin derivative, camptothecin, carboplatin, carmustine(BSNU), CC-1065, chlorambucin, cisplatin, colchicine, cyclophosphamide, cytarabine, cytidine arabinoside, cytochalasin B, dacarbazine, dactinomycin(actinomycin), daunorubicin, decarbazine, DM1, DM4, docetaxel, doxorubicin, etoposide, estrogen, 5-fluordeoxyuridine, 5-fluorouracil, gemcitabine, gramicidin D, hydroxyurea, idaribicin, ifosfamide, irinotecan, lomustine(CCNU), maytansine, mechlorethamine, melphalan, 6-merceptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16, VM-26; DNA minor groove binder (e.g., enediyne, lexitropsin, CBI compound), duocarmycin, taxane (e.g., paclitaxel, docetaxel), puromycins, *vinca* alkaloids, CC-1065, SN-38, topotecan, morpholino-doxorubicin, rhizoxin, cyanomorpholino-doxorubicin, echinomycin, combretastatin, netropsin, epothilone A, epothilone B, estramustine, cryptophycins, cemadotin, maytansinoids, discodermolide, eleutherobin, mitoxantrone, etc.

Cellular Proliferation and Apoptosis

The compounds and conjugates disclosed herein may be used in methods to induce apoptosis in cells.

Dysregulated apoptosis has been implicated in a variety of diseases, including, for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., breast cancer, lung cancer), viral infections (e.g., herpes, papilloma, or HIV), and other conditions, such as osteoarthritis and atherosclerosis. The compounds, conjugates, and compositions described herein may be used to treat or ameliorate any of these diseases. Such treatments generally involve administering to a subject suffering from the disease an amount of a compound, conjugate, or composition described herein sufficient to provide therapeutic benefit. The identity of the antibody of the compound, conjugate, or composition administered will depend upon the disease being treated—thus the antibody should bind a cell-surface antigen expressed in the cell type where inhibition would be beneficial. The therapeutic benefit achieved will also depend upon the specific disease being treated. In certain instances, the compounds and compositions disclosed herein may treat or ameliorate the disease itself, or symptoms of the disease, when administered as monotherapy. In other instances, the compounds and compositions disclosed herein may be part of an overall treatment regimen including other agents that, together with the inhibitor or the compounds and compositions disclosed herein, treat or ameliorate the disease being treated, or symptoms of the disease. Agents useful to treat or ameliorate specific diseases that may be administered adjunctive to, or with, the the compounds and compositions disclosed herein will be apparent to those of skill in the art.

Although absolute cure is always desirable in any therapeutic regimen, achieving a cure is not required to provide therapeutic benefit. Therapeutic benefit may include halting or slowing the progression of the disease, regressing the disease without curing, and/or ameliorating or slowing the progression of symptoms of the disease. Prolonged survival as compared to statistical averages and/or improved quality of life may also be considered therapeutic benefit.

One particular class of diseases that involve dysregulated apoptosis and that are significant health burden world-wide are cancers. In a specific embodiment, the the compounds and compositions disclosed herein may be used to treat cancers. The cancer may be, for example, solid tumors or hematological tumors. Cancers that may be treated with the compounds and compositions disclosed herein include, but are not limited to bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer and spleen cancer. The compounds and compositions disclosed herein may be especially beneficial in the treatment of cancers because the antibody can be used to target the tumor cell specifically, thereby potentially avoiding or ameliorating undesirable side-effects and/or toxicities that may be associated with systemic administration of unconjugated inhibitors. One embodiment pertains to a method of treating a disease involving dysregulated intrinsic apoptosis, comprising administering to a subject having a disease involving dysregulated apotosis an amount of a compound and composition disclosed herein effective to provide therapeutic benefit, wherein the ligand of the compounds and compositions disclosed herein binds a cell surface receptor on a cell whose intrinsic apoptosis is dysregulated. One embodiment pertains to a method of treating cancer, comprising administering to a subject having cancer a compound and composition disclosed herein, wherein the ligand is capable of binding a cell surface receptor or a tumor associated antigen expressed on the surface of the cancer cells, in an amount effective to provide therapeutic benefit.

In the context of tumorigenic cancers, therapeutic benefit, in addition to including the effects discussed above, may also specifically include halting or slowing progression of tumor growth, regressing tumor growth, eradicating one or more tumors and/or increasing patient survival as compared to statistical averages for the type and stage of the cancer being treated. In one embodiment, the cancer being treated is a tumorigenic cancer.

The compounds and conjugates disclosed herein may be administered as monotherapy to provide therapeutic benefit, or may be administered adjunctive to, or with, other chemotherapeutic agents and/or radiation therapy. Chemotherapeutic agents to which the compounds and compositions disclosed herein may be utilized as adjunctive therapy may be targeted (for example, ADCs, protein kinase inhibitors, etc.) or non-targeted (for example, non-specific cytotoxic agents such as radionucleotides, alkylating agents and intercalating agents). Non-targeted chemotherapeutic agents with which the compounds and compositions disclosed herein may be adjunctively administered include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, Cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, calicheamicin, and docetaxel.

The compounds and conjugates disclosed herein that may not be effective as monotherapy to treat cancer may be administered adjunctive to, or with, other chemotherapeutic agents or radiation therapy to provide therapeutic benefit. One embodiment pertains to a method in which a compound or composition disclosed herein is administered in an amount effective to sensitize the tumor cells to standard chemotherapy and/or radiation therapy. Accordingly, in the context of treating cancers, "therapeutic benefit" includes administering the compounds and compositions disclosed herein adjunctive to, or with, chemotherapeutic agents and/or radiation therapy, either in patients who have not yet begin such therapy or who have but have not yet exhibited signs of resistance, or in patients who have begun to exhibit signs of resistance, as a means of sensitizing the tumors to the chemo and/or radiation therapy.

Pharmaceutical Compositions and Administration Thereof

The compounds and conjugates disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a disclosed compound and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compounds, conjugates, or compositions thereof may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697, and 2005/004074; and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to about 99.5% (more preferably, about 0.5 to about 90.0%) of active ingredient in combination with a pharmaceutically acceptable carrier.

In some embodiments of the invention, a compound of the invention is conjointly administered with one or more additional compounds/agents.

In certain such embodiments, the conjoint administration is simultaneous. In certain such embodiments, the compound of the invention is co-formulated with the one or more additional compounds. In certain other such embodiments, the compound of the invention is administered separately but simultaneously with the one or more additional compounds. In certain such embodiments, the conjoint administration is sequential, with administration of the compound of the invention preceding or following the administration of the one or more additional compound by minutes or hours.

Methods of introduction of a compound of the invention may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound, conjugate or combination of compounds and/or conjugates employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. "Therapeutically effective amount" refers to the concentration of a compound that is sufficient to elicit the desired therapeutic effect. It is generally understood that the effective amount of the compound will vary according to the weight, sex, age, and medical history of the subject. Other factors that influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound or conjugate may be administered as one, two, three, four, five, six, or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds or conjugates disclosed herein may be used alone or conjointly administered with another type of therapeutic agent. As used herein, the phrase "conjoint administration" refers to any form of administration of two or more different therapeutic compounds or conjugates such that the second compound or conjugate is administered while the previously administered therapeutic compound or conjugate is still effective in the body (e.g., the two compounds or conjugates are simultaneously effective in the patient, which may include synergistic effects of the two compounds or conjugates). For example, the different therapeutic compounds or conjugates can be administered either in the same formulation or in a separate formulation, either concomitantly or sequentially. In certain embodiments, the different therapeutic compounds or conjugates can be administered within one hour, 12 hours, 24 hours, 36 hours, 48 hours, 72 hours, a week, or more of one another. Thus, an individual who receives such treatment can benefit from a combined effect of different therapeutic compounds or conjugates.

This invention includes the use of pharmaceutically acceptable salts of compounds or conjugates disclosed herein. In certain embodiments, contemplated salts of the invention include, but are not limited to, alkyl, dialkyl, trialkyl, or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples, which are included merely for purposes of illustration of certain aspects and embodiments of the present invention, and are not intended to limit the invention.

EXEMPLIFICATION

Synthetic Protocols

Abbreviations

AcO: acetyl
AcOH: acetic acid
EA: ethyl acetate
DCM: dichloromethane
m-CPBA: meta-chloroperoxybenzoic acid
TBDMSOTf: tert-butyldimethylsilyl triflate
TBDMS: tert-Butyldimethylsilyl
DMF: Dimethylformamide
EDCI: 1-Ethyl-3-(3-dimethylaminopropyl)carbodiimide
HOBt: 1-Hydroxybenzotriazole hydrate
ACN: Acetonitrile
TBDMS-Cl: tert-Butyldimethylsilyl chloride
DBU: 1,8-Diazabicyclo[5.4.0]undec-7-ene
THF: Tetrahydrofuran
DCC: N,N'-Dicyclohexylcarbodiimide
DMAP: 4-Dimethylaminopyridine
NHS: N-Hydroxysuccinimide
DIPEA: Diisopropylethylamine
TEA: triethylamine
DEAD: diethyl azodicarboxylate
Boc: tert-butyloxycarbonyl
LAH: lithium aluminium hydride
CDI: 1,1'-Carbonyldiimidazole
BEMP: 2-tert-Butylimino-2-diethylamino-1,3-dimethylperhydro-1,3,2-diazaphosphorine
TPSCl: Triphenylchlorosilane
tfa: Trifluoroacetyl PyBop: benzotriazol-1-yl-oxytripyrrolidinophosphonium hexafluorophosphate
HBTU: N,N,N',N'-Tetramethyl-O-(1H-benzotriazol-1-yl)uronium hexafluorophosphate
TFA: Trifluoroacetic acid
DIC: N,N'-Diisopropylcarbodiimide
DMPA: 2,2-Dimethoxy-2-phenylacetophenone
TBAF: Tetra-n-butylammonium fluoride
AgOTf: Silver trifluoromethanesulfonate
(BimC4A)$_3$: Tripotassium 5,5',5''-[2,2',2''-nitrilotris(methylene)tris(1H-benzimidazole-2,1-diyl)]tripentanoate hydrate

[Example 1] Preparation of BGal-Br (Hereinafter, Referred to as 'Int-TG')

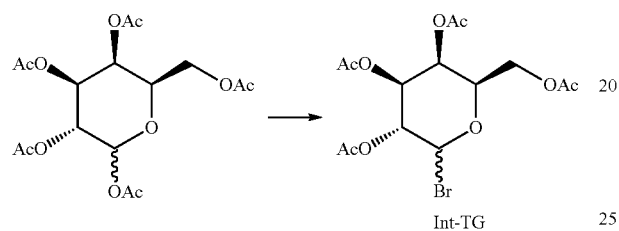

β-D-galactose pentaacetate (Alfa, CAS 4163-60-4, 5.0 g, 12.81 mmol) was dissolved in 33% HBr in AcOH (20 mL) at 0° C. under N$_2$ atmosphere. The mixture was warmed to room temperature. After stirring at room temperature for 4 hours, the mixture was concentrated under reduced pressure, and then EA (1000 mL) and saturated sodium bicarbonate (1000 mL) were added. The organic layer was dried over anhydrous Na$_2$SO$_4$, filtered, and concentrated under reduced pressure. The residue was purified by column chromatography to obtain compound Int-TG (5.2 g, 99%).

$^1$H NMR (400 MHz, CDCl$_3$) δ 6.70 (d, J=4.0 Hz, 1H), 5.52 (d, J=2.4 Hz, 1H), 5.41 (dd, J=7.6, 2.8 Hz, 1H), 5.05 (dd, J=6.4, 4.0 Hz, 1H), 4.49 (t, J=6.4 Hz, 1H), 4.22-4.09 (m, 2H), 2.16-2.01 (m, 12H).

[Example 2] Preparation of Compound Int-TG1

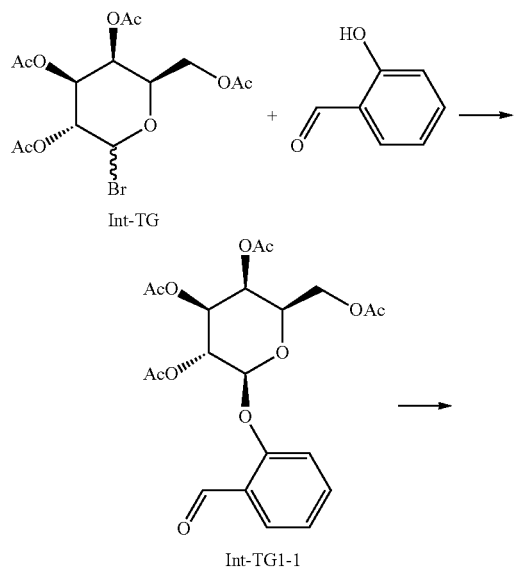

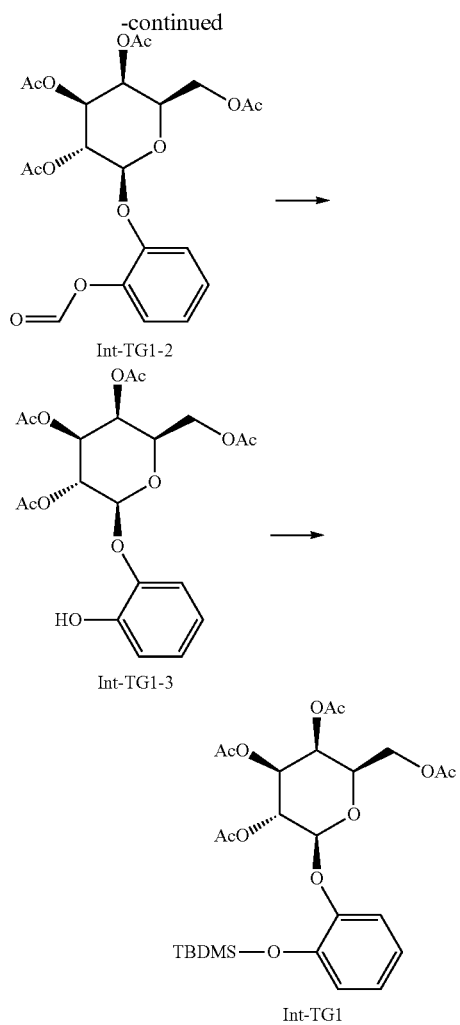

Preparation of Compound Int-TG1-1

To a solution of salicylaldehyde (Aldrich, CAS 90-02-8, 148 mg, 1.22 mmol) and compound Int-TG (0.5 g, 1.22 mmol) in acetonitrile (10 mL) were added dried molecular sieve (2.5 g) and Ag$_2$O (845 mg, 3.65 mmol) under N$_2$ atmosphere. After stirring at room temperature for 1 hour, distilled water (50 mL) and EA (50 mL×2) were added. The organic layer was dried over anhydrous Na$_2$SO$_4$, filtered and concentrated under reduced pressure. The residue was purified by column chromatography to obtain compound Int-TG1-1 (441 mg, 81%).

$^1$H NMR (400 MHz, CDCl$_3$) δ 10.37 (s, 1H), 7.88 (t, J=7.6 Hz, 1H), 7.21 (t, J=7.4 Hz, 1H), 7.14 (t, J=8.4 Hz, 1H), 5.62 (m, 1H), 5.48 (m, 1H), 5.16 (d, J=7.2 Hz, 2H), 4.27-4.23 (m, 1H), 4.18-4.09 (m, 2H)$_m$ 2.21 (s, 3H), 2.07 (s, 6H), 2.03 (s, 3H).

Preparation of Compound Int-TG1-2

To a solution of compound Int-TG1-1 (260 mg, 0.575 mmol) in DCM (3 mL) was added m-CPBA (283 mg, 1.149 mmol) at 0° C. under N$_2$ atmosphere. After 5 hours, the mixture was concentrated under reduced pressure. Then EA (50 mL×2) and a sodium bicarbonate aqueous solution (30 mL) were added. The obtained organic layer was dried over anhydrous Na$_2$SO$_4$, filtered and concentrated under reduced pressure to obtain compound Int-TG1-2 (270 mg, quant.). Compound Int-TG1-2 was used directly in the next reaction without purification.

$^1$H NMR (400 MHz, CDCl$_3$) δ 8.18 (s, 1H), 7.90 (d, J=8.0 Hz, 1H), 7.64 (d, J=8.0 Hz, 1H), 7.46 (t, J=7.6 Hz, 1H), 7.15 (d, J=8.4 Hz, 1H), 5.51 (m, 2H), 5.11 (d, J=8.8 Hz, 1H), 5.04 (d, J=8.0 Hz, 1H), 4.24 (m, 1H), 4.16 (m, 1H), 4.08 (m, 1H), 2.18 (s, 3H), 2.09 (s, 3H), 2.07 (s, 3H), 2.02 (s, 3H). EI-MS m/z: 491 (M$^+$+Na).

Preparation of Compound Int-TG1-3

To a solution of compound Int-TG1-2 in CHCl$_3$ (3 mL) was added hydrazine-hydrate (21 μL, 0.427 mmol) at 0° C. under N$_2$ atmosphere. After stirring at 0° C. for 0.5 hours, EA (30 mL×2) and 1M HCl aqueous solution (10 mL) were added. The obtained organic layer was dried over anhydrous Na$_2$SO$_4$, filtered and concentrated under reduced pressure to obtain compound Int-TG1-3 (161 mg, 86%).

$^1$H NMR (400 MHz, CDCl$_3$) δ 7.03 (t, J=8.0 Hz, 1H), 6.98-6.95 (m, 2H), 6.83 (t, J=7.6 Hz, 1H), 6.02 (s, 1H), 5.47 (d, J=3.2 Hz, 2H), 5.13 (dd, J=10.8, 2.8 Hz, 1H), 4.93 (d, J=7.6 Hz, 1H), 4.26 (m, 1H), 4.19-4.09 (m, 2H), 4.06 (m, 1H), 2.21 (s, 3H), 2.13 (s, 3H), 2.08 (s, 3H), 2.03 (s, 3H). EI-MS m/z: 463 (M$^+$+Na).

Preparation of Compound Int-TG1

To a solution of compound Int-TG1-3 (161 mg, 0.366 mmol) in DCM (3 mL) was added Et$_3$N (102 μL, 0.732 mmol) and TBDMS-OTf (126 μL, 0.549 mmol) at 0° C. under N$_2$ atmosphere. The mixture was stirred at room temperature for 2 hours. Then DCM (30 mL×2) and 1M HCl aqueous solution (10 mL) was added. The obtained organic layer was dried over anhydrous Na$_2$SO$_4$, filtered, and concentrated under reduced pressure. The residue was purified by column chromatography to obtain compound Int-TG1 (147 mg, 91%).

$^1$H NMR (400 MHz, CDCl$_3$) δ 7.02 (d, J=7.6 Hz, 1H), 6.95-6.84 (m, 3H), 5.48-5.43 (m, 2H), 5.15 (d, J=8.0 Hz, 1H), 5.10 (d, J=10.4 Hz, 1H), 4.21-4.11 (m, 2H), 4.03-3.99 (m, 1H), 2.19 (s, 3H), 2.04 (s, 3H), 2.02 (s, 3H), 2.00 (s, 3H), 0.99 (s, 9H), 0.20 (s, 3H), 0.16 (s, 3H). EI-MS m/z: 555 (M$^+$).

[Example 3] Preparation of Compound Int-TG2

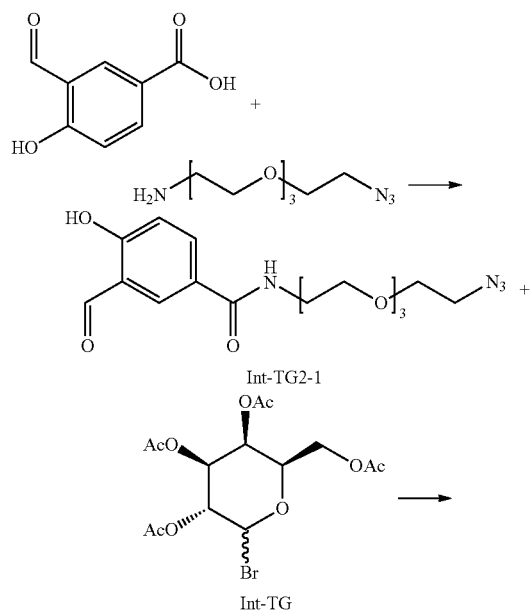

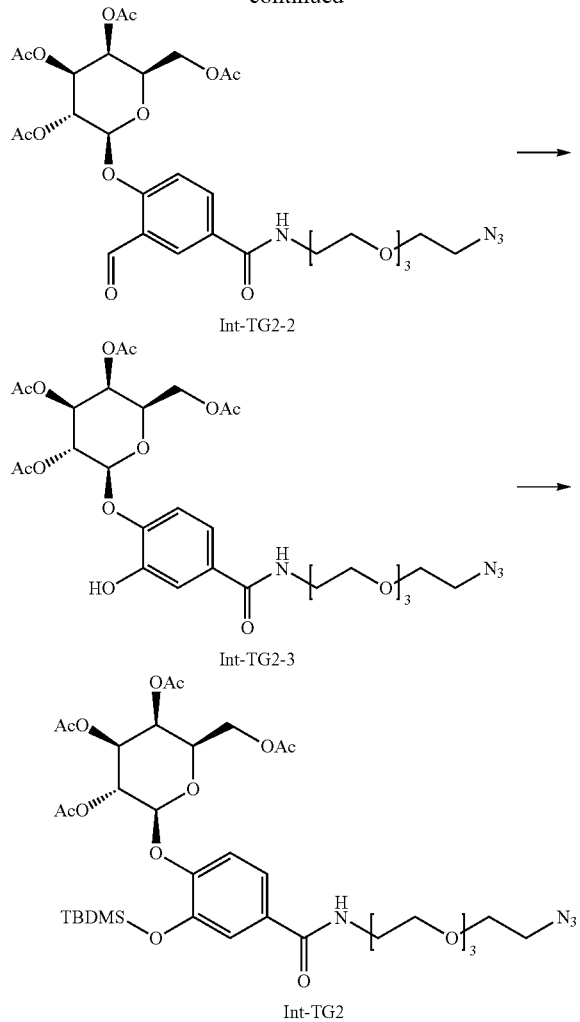

Preparation of Compound Int-TG2-1

To a solution of the 3-Formyl-4-hydroxybenzoic acid (3 g, 18.06 mmol) and 11-azido-3,6,9-trioxaundecan-1-amine (Aldrich, CAS 134179-38-7, 5.98 g, 23.48 mmol) in DMF (20 mL) were added EDCI (5.19 g, 27.09 mmol), HOBt (4.15 g, 27.09 mmol) and Et$_3$N (10.1 mL, 72.24 mmol) at 0° C. under N$_2$ atmosphere. The mixture was stirred overnight at room temperature under N$_2$ atmosphere. The reaction was quenched with EA (60 mL×2) and citric acid (60 mL). The organic layer was extracted with sodium bicarbonate aqueous solution (80 mL). The obtained organic layer was dried over anhydrous Na$_2$SO$_4$, filtered, and concentrated under reduced pressure. The residue was purified by column chromatography to obtain compound Int-TG2-1 (2.56 g, 39%).

$^1$H NMR (400 MHz, CDCl$_3$) δ 11.26 (s, 1H), 9.96 (s, 1H), 8.16 (s, 1H), 7.98-7.96 (d, J=8.4 Hz, 1H), 7.04-7.02 (d, J=9.2 Hz, 1H), 6.91 (s, 1H), 3.68-3.61 (m, 14H), 3.37-3.34 (m, 2H), EI-MS m/z: 367 (M$^+$).

Preparation of Compound Int-TG2-2

To a solution of compound Int-TG2-1 (1.41 g, 3.85 mmol) and compound Int-TG (1.74 g, 4.24 mmol) in anhydrous ADC (20 mL) were added molecular sieve (8 g) and Ag$_2$O (2.68 g, 11.55 mmol) at room temperature under N$_2$ atmosphere. The mixture was stirred at room temperature for 3 hours, then filtered by celite. The organic layer was dried over Na$_2$SO$_4$, filtered and concentrated under reduced pressure. The residue was purified by column chromatography to obtain compound Int-TG2-2 (1.88 g, 70%).

$^1$H NMR (400 MHz, CDCl$_3$) δ 10.35 (s, 1H), 8.20-8.17 (m, 2H), 7.26 (s, 1H), 7.20-7.18 (d, J=9.2 Hz, 1H), 6.96 (s, 1H), 5.63-5.58 (m, 1H), 5.50-5.49 (m, 1H), 5.23-5.21 (m, 1H), 5.18-5.14 (m, 1H), 4.24-4.14 (m, 3H), 3.69-3.64 (m, 14H), 3.37-3.35 (m, 2H), 2.21 (s, 3H), 2.08-2.07 (m, 6H), 2.03 (s, 3H). EI-MS m/z: 697 (M$^+$).

Preparation of Compound Int-TG2-3

To a solution of compound Int-TG2-2 (1.69 g, 2.42 mmol) in DCM (15 mL) was added m-CPBA (2.4 g, 9.70 mmol) at 0° C. under N$_2$ atmosphere. After stirring for 7 hours at 0° C., the mixture was quenched by addition of saturated sodium bicarbonate (40 mL×2). The mixture was separated and the organic layers were washed with brine, dried over Na$_2$SO$_4$, filtered, and concentrated under reduced pressure. The residue was purified by column chromatography to obtain compound Int-TG2-3 (1.25 g, 76%).

$^1$H NMR (400 MHz, CDCl$_3$) δ 7.36-7.33 (m, 2H), 7.01-6.99 (d, J=8.4 Hz, 1H), 6.71 (m, 1H), 6.06 (s, 1H), 5.49-5.44 (m, 2H), 5.15-5.12 (m, 1H), 4.99-4.97 (d, J=8.0 Hz, 1H), 4.24-4.09 (m, 3H), 3.69-3.63 (m, 14H), 3.37-3.34 (m, 2H), 2.20 (s, 3H), 2.13 (s, 3H), 2.12 (s, 3H), 2.03 (s, 3H), EI-MS m/z: 685 (M$^+$).

Preparation of Compound Int-TG2

To a solution of compound Int-TG2-3 (750 mg, 1.09 mmol) in DCM (10 mL) was added TBDMS-OTf (504 μL, 2.19 mmol) and Et$_3$N (458 μL, 3.29 mmol) at 0° C. under N$_2$ atmosphere. The mixture was stirred overnight at room temperature, and then quenched by addition of citric acid (20 ml). The organic layer was washed with brine (20 mL), dried over Na$_2$SO$_4$, filtered and concentrated under reduced pressure. The residue was purified by column chromatography to obtain compound Int-TG2 (799 mg, 91%).

$^1$H NMR (400 MHz, CDCl$_3$) δ 7.35 (d, J=2.4 Hz, 1H), 7.30 (dd, J=8.4, 2.0 Hz, 1H), 7.02 (d, J=8.0 Hz, 1H), 6.65 (t, J=5.2 Hz, 1H), 5.49-5.44 (m, 2H), 5.20 (d, J=7.6 Hz, 1H), 5.12 (dd, J=10.0, 3.6 Hz, 1H), 4.20-4.11 (m, 2H), 4.06-4.03 (m, 1H), 3.69-3.62 (m, 15H), 3.37 (t, J=5.2 Hz, 2H), 2.19 (s, 3H), 2.05 (s, 3H), 2.02 (s, 3H), 2.01 (s, 3H), 1.01 (s, 9H), 0.22 (s, 3H), 0.18 (s, 3H). EI-MS m/z: 799 (M$^+$).

[Example 4] Preparation of Compound Int-TG3

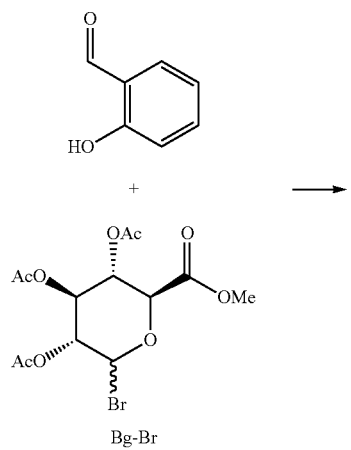

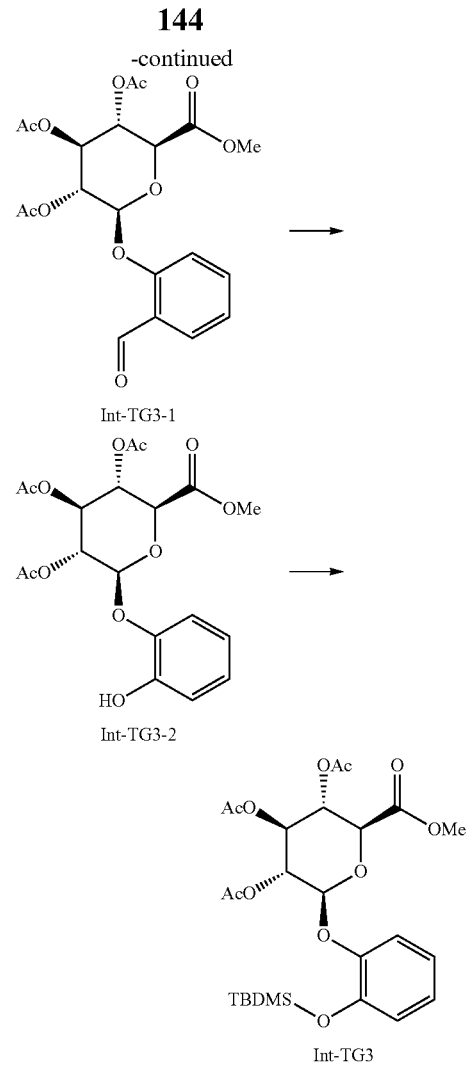

Preparation of Compound Int-TG3-1

To a solution of salicylaldehyde (Aldrich, 200 mg, 1.64 mmol) and compound Bg-Br (813 mg, 1.64 mmol) in acetonitrile (12 mL) was added dried molecular sieve (1.0 g) and Ag$_2$O (1.42 g, 4.92 mmol) at room temperature. The mixture was stirred overnight and distilled water (50 mL) and EA (50 mL×2) were added. The organic layer was dried over anhydrous Na$_2$SO$_4$, filtered and concentrated under reduced pressure. The residue was purified by column chromatography to obtain compound Int-TG-3-1 (218 mg, 30%).

$^1$H NMR (400 MHz, CDCl$_3$) δ 10.35 (s, 1H), 7.86 (dd, J=6.0, 1.6 Hz, 1H), 7.56 (td, J=7.6, 1.6 Hz, 1H), 7.20 (t, J=7.6 Hz, 1H), 7.13 (d, J=8.8 Hz, 1H), 5.39-5.31 (m, 3H), 5.27-5.25 (m, 1H), 5.24-4.19 (m, 1H), 3.75 (s, 3H), 2.07-2.04 (m, 9H). EI-MS m/z: 461 (M$^+$+Na).

Preparation of Compound Int-TG3-2

To a solution of compound Int-TG3-1 (217.6 mg, 0.50 mmol) in DCM (10 mL) was added m-CPBA (367.1 mg, 1.50 mmol) at 0° C. under atmosphere. The mixture was stirred overnight at room temperature and 40 mL of DCM was added. The organic layer was washed saturated sodium bicarbonate (10 mL) and dried over anhydrous Na$_2$SO$_4$, filtered, concentrated under reduced pressure.

The residue was dissolved again in CHCl₃ (5 ml). Then hydrazine (36.2 μL, 0.74 mmol) was added. After 30 minutes, DCM (20 mL×2) and water (10 mL) were added. The obtained organic layer was dried over anhydrous Na₂SO₄, filtered and concentrated under reduced pressure, and the residue was purified by column chromatography to obtain compound Int-TG1-3-2 (195 mg, 92%).

¹H NMR (400 MHz, CDCl₃) δ 7.09 (t, J=8.0 Hz, 1H), 7.00-6.95 (m, 2H), 6.83 (td, J=6.8, 1.6 Hz, 1H), 5.38-5.24 (m, 4H), 4.19-4.13 (m, 1H), 3.75 (s, 3H), 2.06-2.02 (m, 9H). EI-MS m/z: 449 (M⁺+Na).

Preparation of Compound Int-TG3

To a solution of compound Int-TG3-2 (194 mg, 0.46 mmol) in DCM (5 mL) was added Et₃N (190.8 μL, 1.37 mmol) and TBDMS-OTf (209.8 μL, 0.91 mmol) at 0° C. under N₂ atmosphere. After stirring at 0° C. for 1 hour, DCM (30 mL×2) and water (10 mL) were added. The obtained organic layer was dried over anhydrous Na₂SO₄, filtered, and concentrated under reduced pressure. The residue was purified by column chromatography to obtain compound Int-TG3 (188.6 mg, 76%).

¹H NMR (400 MHz, CDCl₃) δ 7.00 (dd, J=6.0, 1.6 Hz, 1H), 6.94-6.88 (m, 2H), 6.84 (dd, J=6.0, 2.0 Hz, 1H), 5.38-5.21 (m, 5H), 3.72 (s, 3H), 2.03 (d, J=6.8 Hz, 9H), 0.98 (s, 9H), 0.18 (s, 3H), 0.15 (s, 3H). EI-MS m/z: 563 (M⁺+Na).

[Example 5] Preparation of Compound Int-TG4

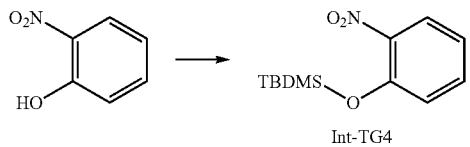

To a solution of 2-Nitrophenol (500 mg, 3.59 mmol) in anhydrous pyridine (20 mL) was added TBDMS-Cl (650 mg, 4.31 mmol) at room temperature under N₂ atmosphere. The mixture was stirred overnight at room temperature and DCM (30 mL×2) and water (20 mL) were added. The obtained organic layer was washed with 2N HCl aqueous solution, dried over anhydrous Na₂SO₄, filtered, and concentrated under reduced pressure. The residue was purified by column chromatography to obtain compound Int-TG4 (410 mg, 94%).

¹H NMR (400 MHz, CDCl₃) δ 7.80 (dd, J=6.8, 0.8 Hz, 1H), 7.43 (t, J=7.2 Hz, 1H), 7.04-6.97 (m, 2H), 1.01 (s, 9H), 0.26 (s, 6H).

[Example 6] Preparation of Compound Int-TG5

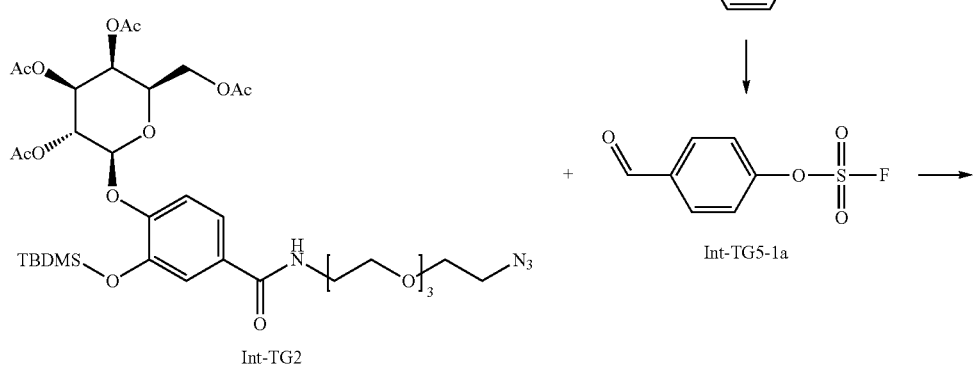

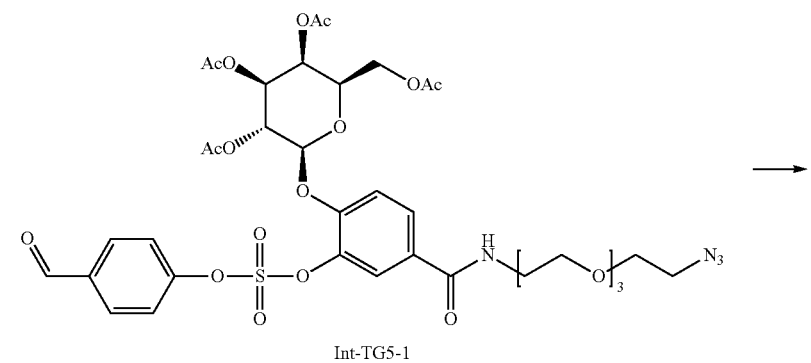

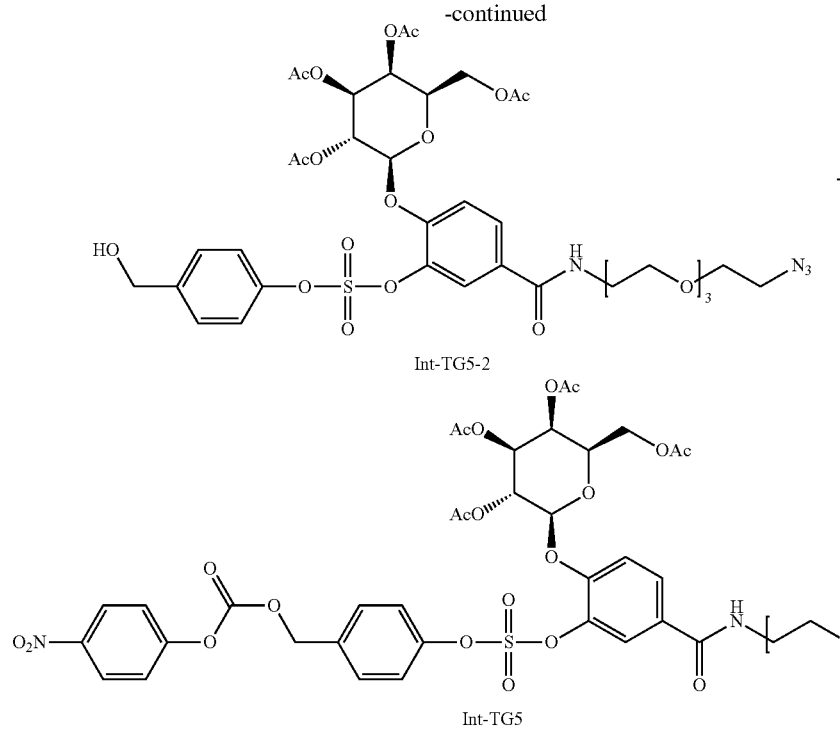

Int-TG5-2

Int-TG5

Preparation of Compound Int-TG5-1a

To a solution of 4-Hydroxybenzaldehyde (1 g, 8.19 mmol) in DCM (3 mL) was added Et₃N (2.28 mL, 16.38 mmol) at room temperature under N₂ atmosphere. SO₂F₂ gas was introduced via balloon, and the mixture was stirred at room temperature for 2 hours. Then the mixture was washed with DCM (30 mL×3) and brine (30 mL), the organic layer was dried over anhydrous Na₂SO₄, filtered and concentrated under reduced pressure. The residue was purified by column chromatography to obtain compound Int-TG5-1a (790 mg, 63%).

$^1$H NMR (400 MHz, CDCl₃) δ 10.06 (s, 1H), 8.05 (d, J=8.0 Hz, 2H), 7.55 (d, J=8.8 Hz, 2H).

Preparation of Compound Int-TG5-1

To a solution of compound Int-TG2 (100 mg, 0.13 mmol) and compound Int-TG5-1a (26 mg, 0.13 mmol) in anhydrous ACN (3 mL) were added DBU (4 μL, 25 μmol). The mixture was stirred at room temperature for 1 hour and was washed with distilled water (10 mL) and EA (10 mL×2). The organic layer was dried over anhydrous Na₂SO₄, filtered and concentrated under reduced pressure. The residue was purified by column chromatography to obtain compound Int-TG5-1 (103 mg, 94%).

EI-MS m/z: 869 (M⁺).

Preparation of Compound Int-TG5-2

To a solution of compound Int-TG5-1 (103 mg, 0.12 mmol) in THF (8 mL) was added NaBH₄ (9 mg, 0.24 mmol) at 0° C. under N₂ atmosphere. After stirring at room temperature for 2 hours, distilled water (10 mL) and EA (10 mL×2) were added. The organic layer was dried over anhydrous Na₂SO₄, filtered and concentrated under reduced pressure to obtain compound Int-TG5-2 (101 mg, 98%).

EI-MS m/z: 871 (M⁺).

Preparation of Compound Int-TG5

To a solution of compound Int-TG5-2 (47 mg, 54 μmol) in DMF (2 mL) was added bis(4-nitrophenyl) carbonate (25 mg, 81 μmol) and DIPEA (14 μL, 81 μmol) at room temperature under a nitrogen atmosphere. The mixture was stirred overnight at room temperature. Then distilled water (10 mL) and EA (10 mL×2) were added, the organic layer was dried over anhydrous Na₂SO₄, filtered and concentrated under reduced pressure. The residue was purified by column chromatography to obtain compound Int-TG5 (53 mg, 94%).

EI-MS m/z: 1036 (M⁺).

[Example 7] Preparation of Compound Int-TG6

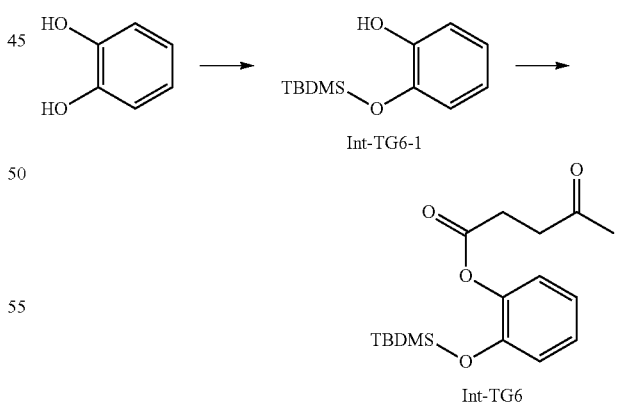

Int-TG6-1

Int-TG6

Preparation of Compound Int-TG6-1

To a solution of 1,2-Dihydroxybenzene (1.0 g, 9.08 mmol) in DMF (15 mL) was added TBDMS-Cl (1.64 g, 10.88 mmol) and imidazole (1.24 g, 18.21 mmol) at 0° C. under N₂ atmosphere. The mixture was stirred at room temperature for 2 hours. EA (30 mL×2) and distilled water (20 mL) were added. The obtained organic layer was washed with brine aqueous solution again, dried over anhydrous Na₂SO₄, filtered, and concentrated under reduced pressure. The residue was purified by column chromatography to obtain compound Int-TG6-1 (1.27 g, 64%).

¹H NMR (400 MHz, CDCl₃) δ 6.94 (d, J=8.0 Hz, 1H), 6.89-6.82 (m, 2H), 6.76 (t, J=7.6 Hz, 1H), 5.48 (s, 1H), 1.02 (s, 9H), 0.28 (s, 6H).

Preparation of Compound Int-TG6

To a solution of the Int-TG6-1 (300 mg, 1.34 mmol) and levulinic acid (310.5 mg, 2.67 mmol) in 1,4-dioxane (12 mL) were added DCC (551.7 mg, 2.67 mmol) and DMAP (13.07 mg, 0.11 mmol). The mixture was stirred at room temperature for 3 hours. Then distilled water (50 mL) and EA (50 mL×2) were added, and the organic layer was dried over anhydrous Na₂SO₄, filtered and concentrated under reduced pressure. The residue was purified by column chromatography to obtain compound Int-TG6 (380.1 mg, 88%).

¹H NMR (400 MHz, CDCl₃) δ 7.09 (td, J=6.0, 1.6 Hz, 1H), 7.03 (dd, J=6.4, 1.6 Hz, 1H) 6.95-6.88 (m, 2H), 2.84 (s, 4H), 2.22 (s, 3H), 0.98 (s, 9H), 0.20 (s, 6H).

[Example 8] Preparation of Compound Int-TG7

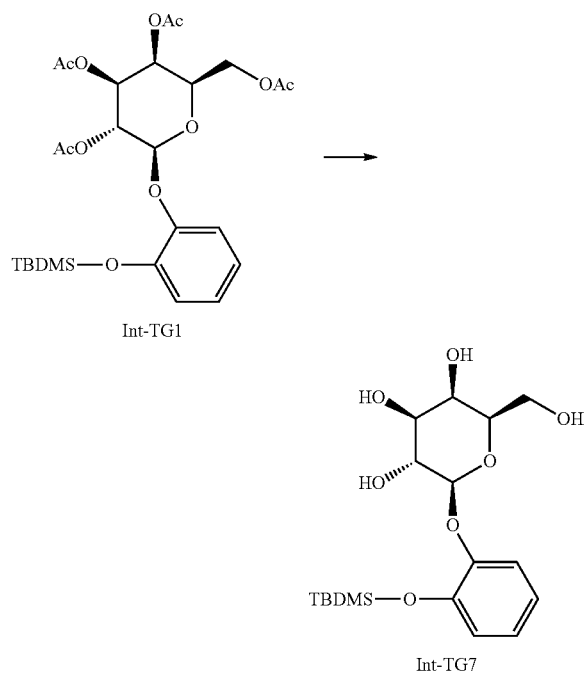

Compound Int-TG1 (80 mg, 0.14 mmol) was dissolved in anhydrous methanol (2 mL), K₂CO₃ (99.7 mg, 0.72 mmol) was added thereto at 0° C. The mixture was stirred at 0° C. for 1 hour. The residue was diluted with EA (10 mL×2), the organic layer was washed with 1N aqueous HCl (2 mL), and water (10 mL). The obtained organic layer was dried over anhydrous Na₂SO₄, filtered, and concentrated under reduced pressure. The residue was subjected to Prep-TLC to obtain compound Int-TG7 (17.4 mg, 31%).

¹H NMR (400 MHz, CDCl₃) δ 7.12 (d, J=8.0 Hz, 1H), 6.95-6.85 (m, 3H), 4.74 (d, J=7.2 Hz, 1H), 4.05 (d, J=3.2 Hz, 1H), 3.97 (dd, J=6.0, 5.6 Hz, 1H), 3.90-3.85 (m, 2H), 3.68 (dd, J=6.8, 2.8 Hz, 1H), 3.63 (t, J=5.6 Hz, 1H), 3.48 (s, 1H), 1.03 (s, 9H), 0.20 (d, J=12.0 Hz, 6H).

EI-MS m/z: 409 (M⁺+Na).

[Example 9] Preparation of Compound Int-TG8

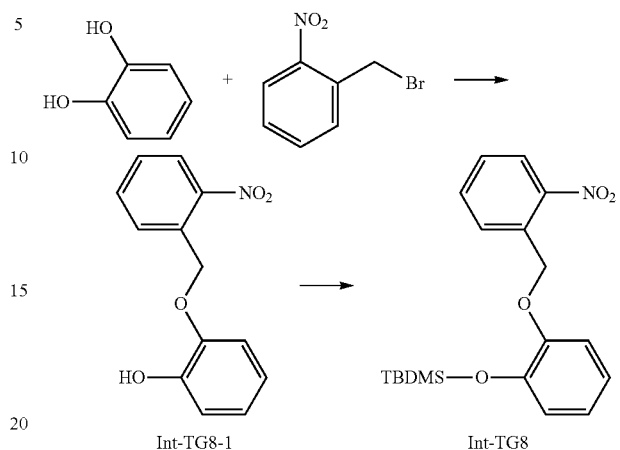

Preparation of Compound Int-TG8-1

To a solution of Catechol (500 mg, 0.4.54 mmol) and 2-nitrobenzyl bromide (333.5 mg, 1.54 mmol) in acetone (30 mL) were added K₂CO₃ (401.6 mg, 2.91 mmol). The mixture was refluxed for 15 hours. After cooling to room temperature, the mixture was concentrated under reduced pressure and was diluted with EA (50 mL×2) and 1N NaOH aqueous solution (20 mL). The obtained organic layer was dried over anhydrous Na₂SO₄, filtered, and concentrated under reduced pressure. The residue was purified by column chromatography to obtain compound Int-TG8-1 (300.3 mg, 79%).

¹H NMR (400 MHz, CDCl₃) δ 8.19 (dd, J=6.8, 1.2 Hz, 1H), 7.75 (d, J=7.6 Hz, 1H), 7.69 (td, J=7.2, 1.2 Hz, 1H), 7.53 (td, J=6.8, 1.6 Hz, 1H), 6.99 (dd, J=7.2, 1.2 Hz, 1H), 6.93 (td, J=5.2, 2.4 Hz, 1H), 6.85-6.79 (m, 2H), 5.64 (s, 1H), 5.58 (s, 2H).

Preparation of Compound Int-TG8

To a solution of compound Int-TG8-1 (300 mg, 1.22 mmol) in DCM (5 mL) was added Et₃N (342 μL, 2.50 mmol) and TBDMS-OTf (421.8 μL, 1.83 mmol) at 0° C. under N₂ atmosphere. The mixture was stirred at room temperature for 3 hours and was diluted with DCM (30 mL×2) and 2N HCl aqueous solution (10 mL). The obtained organic layer was dried over anhydrous Na₂SO₄, filtered, and concentrated under reduced pressure. The residue was purified by column chromatography to obtain compound Int-TG8 (410 mg, 94%).

¹H NMR (400 MHz, CDCl₃) δ 8.19 (dd, J=6.8, 1.2 Hz, 1H), 8.01 (dd, J=8.0, 0.8 Hz, 1H), 7.67 (td, J=6.4, 1.2 Hz, 1H), 7.48 (t, J=7.6 Hz, 1H), 6.92-6.87 (m, 4H), 5.49 (s, 2H), 1.01 (s, 9H), 0.18 (s, 6H).

[Example 10] Preparation of Compound Int-TG9

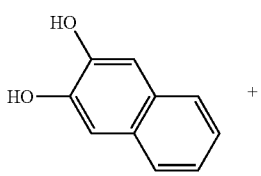

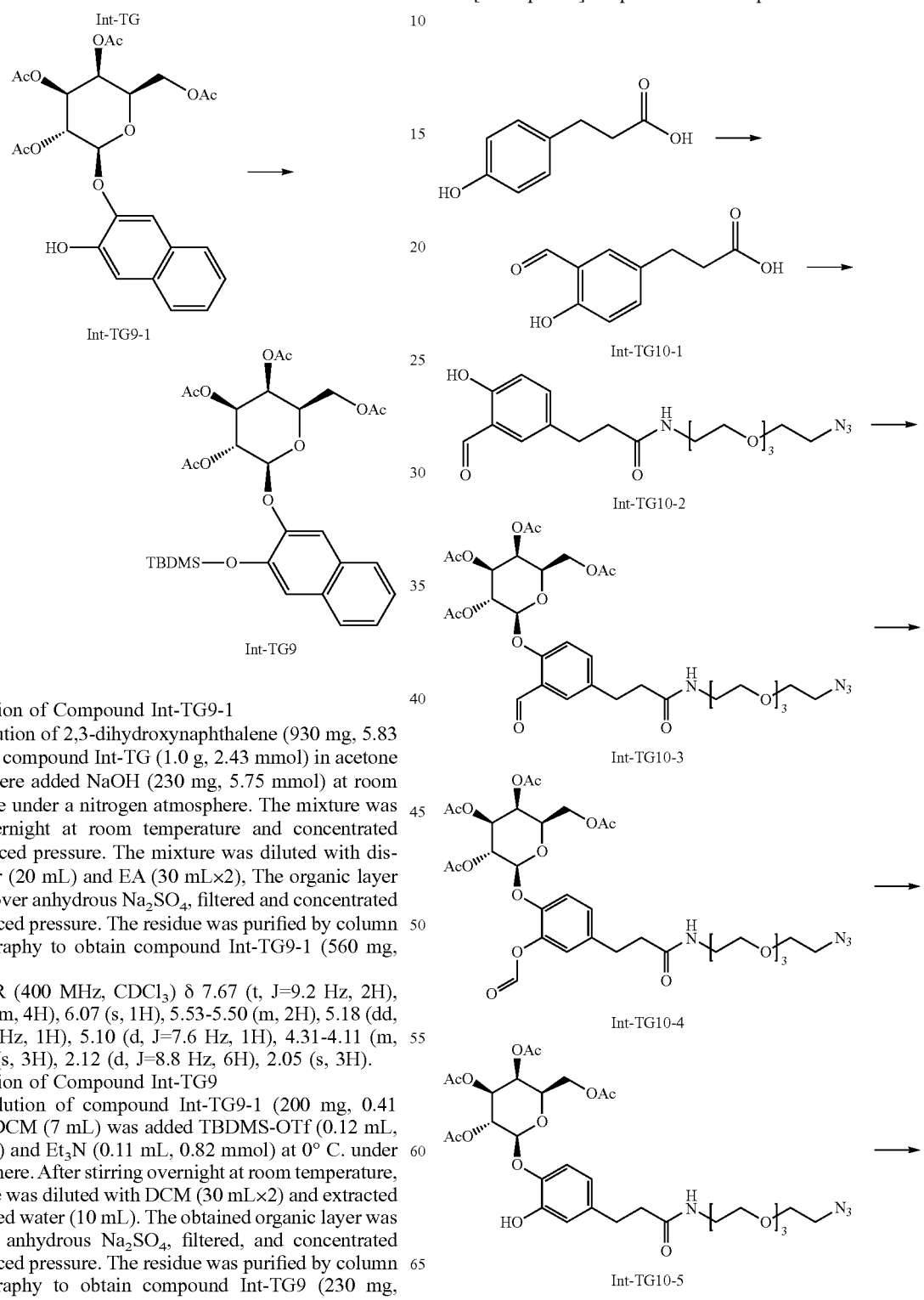

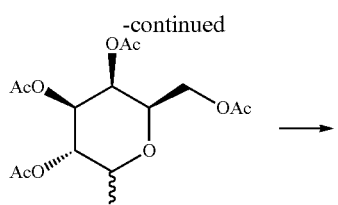

Preparation of Compound Int-TG9-1

To a solution of 2,3-dihydroxynaphthalene (930 mg, 5.83 mmol) and compound Int-TG (1.0 g, 2.43 mmol) in acetone (10 mL) were added NaOH (230 mg, 5.75 mmol) at room temperature under a nitrogen atmosphere. The mixture was stirred overnight at room temperature and concentrated under reduced pressure. The mixture was diluted with distilled water (20 mL) and EA (30 mL×2), The organic layer was dried over anhydrous $Na_2SO_4$, filtered and concentrated under reduced pressure. The residue was purified by column chromatography to obtain compound Int-TG9-1 (560 mg, 47%).

$^1$H NMR (400 MHz, CDCl$_3$) δ 7.67 (t, J=9.2 Hz, 2H), 7.39-7.29 (m, 4H), 6.07 (s, 1H), 5.53-5.50 (m, 2H), 5.18 (dd, J=7.2, 3.6 Hz, 1H), 5.10 (d, J=7.6 Hz, 1H), 4.31-4.11 (m, 3H), 2.21 (s, 3H), 2.12 (d, J=8.8 Hz, 6H), 2.05 (s, 3H).

Preparation of Compound Int-TG9

To a solution of compound Int-TG9-1 (200 mg, 0.41 mmol) in DCM (7 mL) was added TBDMS-OTf (0.12 mL, 0.53 mmol) and Et$_3$N (0.11 mL, 0.82 mmol) at 0° C. under N$_2$ atmosphere. After stirring overnight at room temperature, the mixture was diluted with DCM (30 mL×2) and extracted with distilled water (10 mL). The obtained organic layer was dried over anhydrous $Na_2SO_4$, filtered, and concentrated under reduced pressure. The residue was purified by column chromatography to obtain compound Int-TG9 (230 mg, 96%).

$^1$H NMR (400 MHz, CDCl$_3$) δ 7.67-7.63 (m, 2H), 7.36-7.33 (m, 3H), 7.20 (s, 1H), 5.52 (dd, J=8.4, 2.0 Hz, 1H), 5.47 (d, J=3.2 Hz, 1H), 5.31 (d, J=8.0 Hz, 1H), 5.15 (dd, J=6.8, 3.6 Hz, 1H), 4.23-4.13 (m, 3H), 2.20 (s, 3H), 2.05 (s, 3H) 2.02 (d, J=3.6 Hz, 6H), 1.03 (s, 9H), 0.26 (s, 3H), 0.22 (s, 3H).

[Example 11] Preparation of Compound Int-TG10

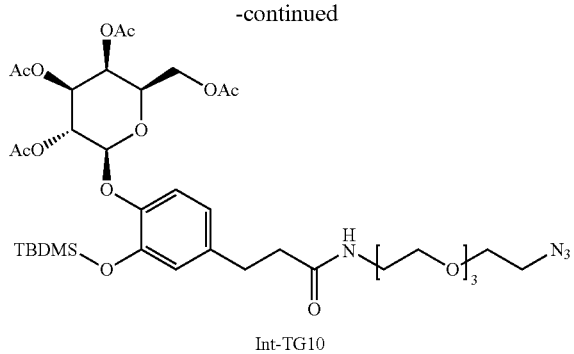

Int-TG10

Preparation of Compound Int-TG10-1

To a solution of 3-(4-Hydroxyphenyl)propionic acid (500 mg, 3.01 mmol) in CHCl$_3$ (10 mL) was added 4M NaOH (7.5 mL, 30 mmol) and then refluxed for 6 hours. After the reaction was completed, the mixture was acidified with 4M HCl and concentrated to remove CHCl$_3$. EA (30 mL×3), H$_2$O (20 mL), and brine (20 mL) were added to perform extraction, and the obtained organic layer was dried over anhydrous Na$_2$SO$_4$, filtered and concentrated under reduced pressure. The residue was purified by column chromatography to obtain compound Int-TG10-1 (408 mg, product: SM=4:6 by HPLC).

$^1$H NMR (400 MHz, CDCl$_3$) δ 10.90 (s, 1H), 9.87 (s, 1H), 7.41-7.38 (m, 2H), 6.94 (d, J=9.6 Hz, 1H), 2.96 (t, J=7.4 Hz, 2H), 2.69 (t, J=7.4 Hz, 2H).

Preparation of Compound Int-TG10-2

To a solution of compound Int-TG10-1 (408 mg, 2.1 mmol) in DMF (10 mL) was added NHS (363 mg, 3.15 mmol) and EDCI (604 mg, 3.15 mmol) and stirred overnight at room temperature. Then 11-azido-3,6,9-trioxaundecan-1-amine (636 mg, 2.5 mmol) dissolved in DMF (3 mL) and DIPEA (3.66 mL, 21 mmol) were added and stirred at room temperature for 1 hour. After the reaction was completed, the mixture was acidified with 4M HCl, diluted with EA (30 mL×5) and washed with H$_2$O (30 mL) and brine (30 mL). The obtained organic layer was dried over anhydrous Na$_2$SO$_4$, filtered and concentrated under reduced pressure. The residue was purified by column chromatography to obtain compound Int-TG10-2 (288 mg, 50% purity by HPLC).

EI-MS m/z: 395 (M$^+$).

Preparation of Compound Int-TG10-3

To a solution of compound Int-TG10-2 (288 mg, 0.73 mmol) and compound Int-TG (303 mg, 0.74 mmol) in ACN (10 mL) were added molecular sieve (1.5 g) under N$_2$ atmosphere. After stirring 10 minutes at room temperature, Ag$_2$O (508 mg, 2.19 mmol) was added thereto. The mixture was stirred at room temperature for 3 hours and diluted with H$_2$O (5 mL), followed by filtration using celite. The filtrate was washed with EA (20 mL×2), H$_2$O (20 mL), and brine (20 mL). The obtained organic layer was dried over anhydrous Na$_2$SO$_4$, filtered and concentrated under reduced pressure. The residue was purified by column chromatography to obtain compound Int-TG10-3 (195 mg).

EI-MS m/z: 725 (M$^+$).

Preparation of Compound Int-TG10-4

To a solution of compound Int-TG10-3 (195 mg, 0.27 mmol) in DCM (5 mL) was added 70% m-CPBA (133 mg, 0.54 mmol) at 0° C. under N$_2$ atmosphere. The mixture was stirred at 0° C. for 3 hours. Then, 70% m-CPBA (66 mg, 0.27 mmol) was further added thereto, and the mixture was stirred overnight at 0° C. The reaction was quenched with saturated NaHCO$_3$ (20 mL×3) and diluted with DCM (20 mL). The organic layer was washed with brine (20 mL) and dried over anhydrous Na$_2$SO$_4$, filtered, concentrated under reduced pressure. Compound Int-TG10-4 was used directly in the next reaction without purification (199 mg, crude).

EI-MS m/z: 741 (M$^+$).

Preparation of Compound Int-TG10-5

To a solution of compound Int-TG10-4 (199 mg, 0.27 mmol) in CHCl$_3$ (4 mL) was added NH$_2$NH$_2$·H$_2$O (133 mg, 0.54 mmol) at 0° C. under N$_2$ atmosphere. After stirring at room temperature for 30 minutes, the mixture was quenched with EA (20 mL) and saturated citric acid (20 mL). The obtained organic layer was dried over anhydrous Na$_2$SO$_4$, filtered and concentrated under reduced pressure. The residue was purified by column chromatography to obtain compound Int-TG10-5 (146 mg).

EI-MS m/z: 713 (M$^+$).

Preparation of Compound Int-TG10

To a solution of compound Int-TG10-5 (146 mg, 0.21 mmol) in DMF (2 mL) was added TEA (133 μL, 0.62 mmol) and TBDMS-OTf (94 μL, 0.41 mmol) at 0° C. under N$_2$ atmosphere. The mixture was stirred at 0° C. for 20 minutes, and continued to be stirred at room temperature for 3 hours. The mixture was extracted with EA (20 mL), saturated citric acid (20 mL), and brine (30 mL). The obtained organic layer was dried over anhydrous Na$_2$SO$_4$, filtered and concentrated under reduced pressure. The residue was purified by column chromatography, followed by Prep TLC to obtain compound Int-TG10 (32 mg, 19%).

EI-MS m/z: 827 (M$^+$).

[Example 12] Preparation of Compound IntA-Q1

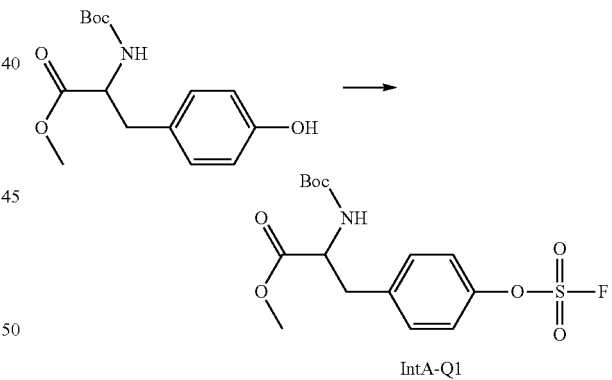

IntA-Q1

To a solution of Boc-Tyr-OMe (300 mg, 1.02 mmol) in DCM (3 mL) was added Et$_3$N (212 μL, 1.52 mmol) at room temperature under N$_2$ atmosphere. SO$_2$F$_2$ gas was introduced via balloon, and the mixture was stirred at room temperature for 2 hours under SO$_2$F$_2$. The mixture was extracted with DCM (30 mL×3) and brine (30 mL). The obtained organic layer was dried over anhydrous Na$_2$SO$_4$, filtered and concentrated under reduced pressure. The residue was purified by column chromatography to obtain compound IntA-Q1 (363 mg, 95%).

$^1$H NMR (400 MHz, CDCl$_3$) δ 7.26 (s, 4H), 5.03 (d, J=8.0 Hz, 1H), 4.62 (m, 1H), 3.73 (s, 3H), 3.21 (dd, J=13.2, 4.8 Hz, 1H), 3.07 (dd, J=13.2, 6.0 Hz, 1H), 1.41 (s, 9H). EI-MS m/z: 400 (M$^+$+Na).

[Example 13] Preparation of Compound IntA-Q2

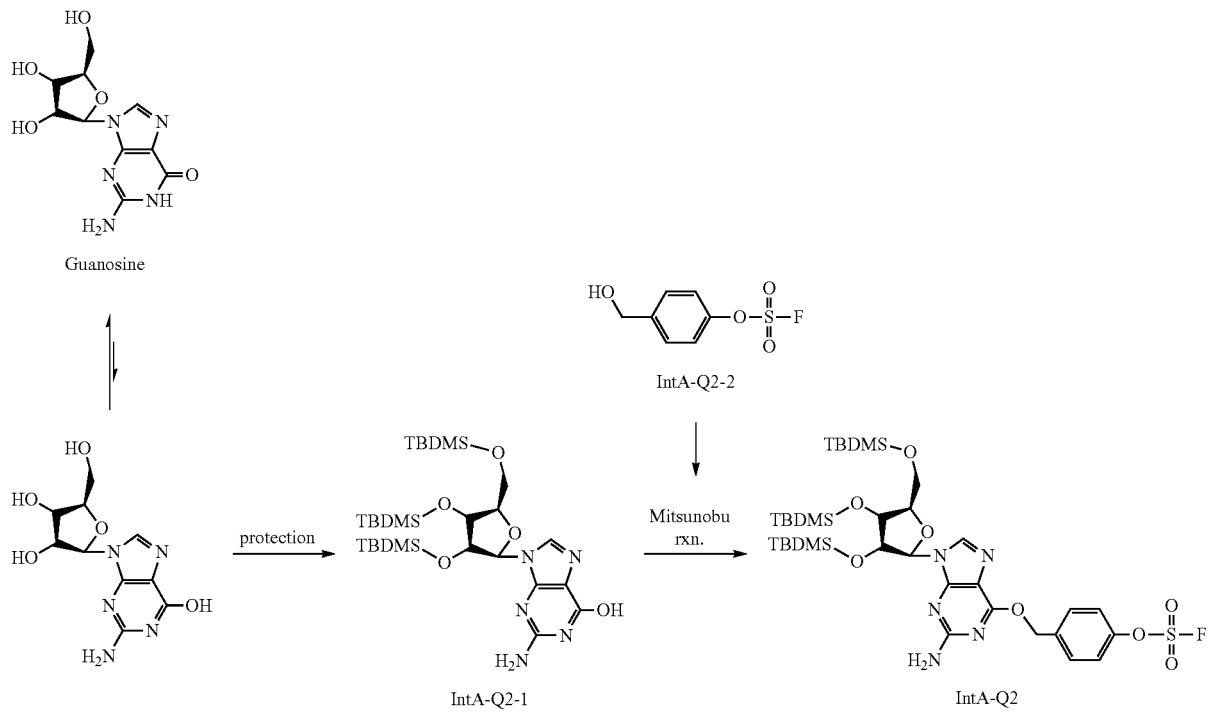

Preparation of Compound IntA-Q2-1

To a solution of Guanosine (1 g, 3.53 mmol) in DMF (30 mL) was added imidazole (1.92 g, 28.45 mmol) and TBDMS-Cl (3.193 g, 21.18 mmol) at room temperature. The mixture was stirred overnight at room temperature and extracted with EA (100 mL×3), $H_2O$ (100 mL), $NH_4Cl$ (100 mL), and brine (100 mL). The obtained organic layer was dried over anhydrous $Na_2SO_4$, filtered and concentrated under reduced pressure. The residue was purified by column chromatography to obtain compound IntA-Q2-1 (1.56 g, 70%).

$^1$H NMR (400 MHz, $CDCl_3$) δ 12.05 (s, 1H), 7.89 (s, 1H), 6.40 (brs, 1H), 5.82-5.79 (m, 1H), 4.44-4.38 (m, 1H), 4.29-4.26 (m, 1H), 4.10-4.09 (m, 1H), 4.02-3.99 (m, 1H), 3.80-3.77 (m, 1H), 0.96 (s, 9H), 0.92 (s, 9H), 0.87 (s, 9H), 0.14 (s, 3H), 0.13 (s, 3H), 0.09 (s, 3H), 0.08 (s, 3H), 0.02 (s, 3H), −0.02 (s, 3H). EI-MS m/z: 627 ($M^+$).

Preparation of Compound IntA-Q2-2

To a solution of 4-hydroxy benzyl alcohol (1.00 g, 8.06 mmol) in DCM (40 mL) and $H_2O$ (40 mL) was added $Et_3N$ (1.70 mL, 12.085 mmol) at room temperature under $N_2$ atmosphere. $SO_2F_2$ gas was introduced via balloon, and the mixture was stirred at room temperature for 5 hours. After the reaction was completed, the mixture was concentrated under reduced pressure, and the residue was purified by column chromatography to obtain compound IntA-Q2-2 (711 mg, 43%).

$^1$H NMR (400 MHz, $CDCl_3$) δ 7.49 (d, J=8.4 Hz, 2H), 7.34 (d, J=8.0 Hz, 2H), 4.76 (d, J=6.0 Hz, 2H), 1.80 (t, J=4.2 Hz, 1H).

Preparation of Compound IntA-Q2

To a solution of compound IntA-Q2-1 (350 mg, 0.56 mmol) in THF (10 mL) was added compound IntA-Q2-2 (253 mg, 1.23 mmol) and $PPh_3$ (235 mg, 0.90 mmol) at room temperature under $N_2$ atmosphere. After the mixture was cooled to 0° C., DEAD (0.41 mL, 0.9 mmol) was added dropwise and stirred at 0° C. for 3 hours. The mixture was extracted with EA (30 mL×3), $H_2O$ (30 mL), and brine (30 mL). The obtained organic layer was dried over anhydrous $Na_2SO_4$, filtered and concentrated under reduced pressure. The residue was separated and purified once by Prep-HPLC, and then purified by column chromatography to obtain compound IntA-Q2 (62 mg, 14%).

$^1$H NMR (400 MHz, $CDCl_3$) δ 8.00 (s, 1H), 7.62 (d, J=8.4 Hz, 2H), 7.33 (d, J=8.4 Hz, 2H), 5.91 (d, J=5.2 Hz, 1H), 5.57 (s, 2H), 4.82-4.78 (m, 2H), 4.52-4.50 (m, 1H), 4.30-4.28 (m, 1H), 4.12-4.08 (m, 1H), 3.98 (dd, J=11.2, 3.6 Hz, 1H), 3.93 (dd, J=11.2, 2.4 Hz, 1H), 0.94 (s, 9H), 0.93 (s, 9H), 0.82 (s, 9H), 0.13 (s, 3H), 0.12 (s, 3H), 0.10 (s, 3H), 0.09 (s, 3H), −0.02 (s, 3H), −0.15 (s, 3H). EI-MS m/z: 815 ($M^+$).

[Example 14] Preparation of Compound IntA-Q3

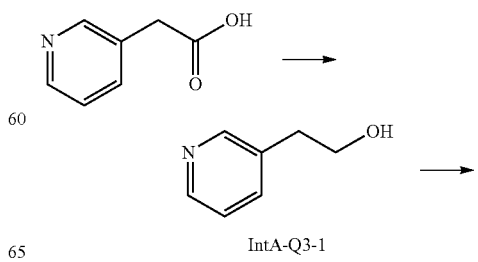

-continued

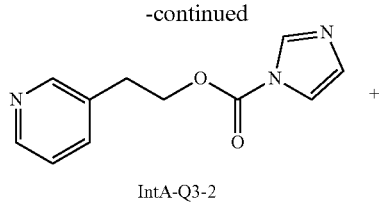

IntA-Q3-2

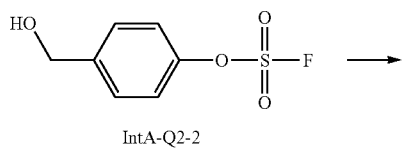

IntA-Q2-2

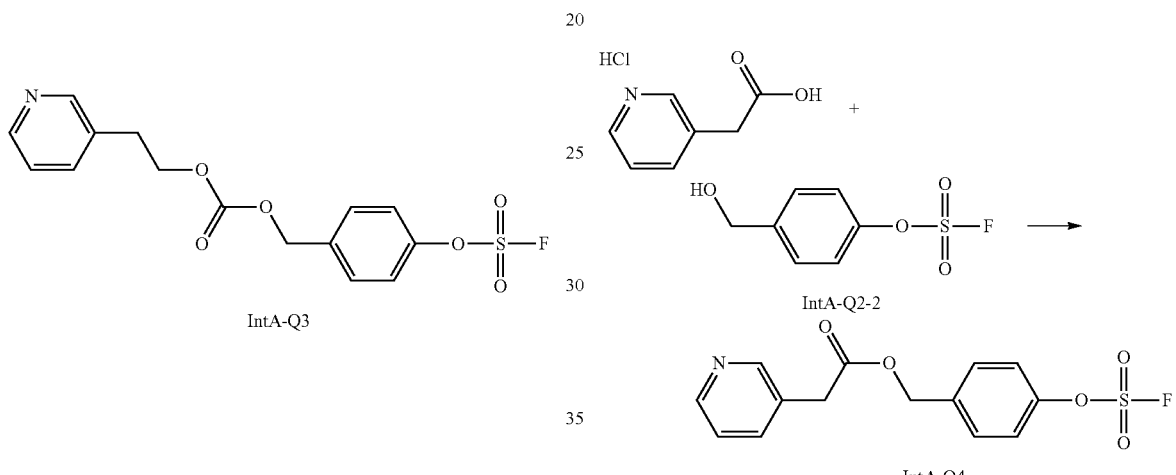

IntA-Q3

Preparation of Compound IntA-Q3

To a solution of 3-Pyridylacetic acid-hydrochloride (1.0 g, 5.76 mmol) in THF (20 mL) was added LAH (1.1 g, 28.8 mmol) at 0° C. under $N_2$ atmosphere. The mixture was warmed up to room temperature and refluxed for 24 hours. The mixture was quenched by addition of methanol (10 mL) and water (20 mL). The aqueous layer was subjected to extraction with ether (50 mL×2), and the obtained organic layer was dried over anhydrous $Na_2SO_4$, filtered, and concentrated under reduced pressure. The residue was purified by column chromatography to obtain compound Int-Q3a (396.3 mg, 56%).

$^1$H NMR (400 MHz, $CDCl_3$) δ 8.48-8.45 (m, 2H), 7.58-7.56 (m, 1H) 7.25-7.22 (m, 2H), 3.89 (t, J=6.8 Hz, 2H), 2.87 (t, J=6.8 Hz, 2H). EI-MS m/z: 124 ($M^+$+1).

Preparation of Compound Int-Q3b

A solution of compound Int-Q3a (260 mg, 2.11 mmol) and CDI (684.6 mg, 4.22 mmol) in DCM (5 mL) was stirred overnight at 50° C. under $N_2$ atmosphere. After the reaction was completed, the mixture was cooled to room temperature, followed by extraction with DCM (20 mL×2) and water (10 mL). The obtained organic layer was dried over anhydrous $Na_2SO_4$, filtered, and concentrated under reduced pressure. The residue was purified by column chromatography to obtain compound Int-Q3b (296.5 mg, 65%).

$^1$H NMR (400 MHz, $CDCl_3$) δ 8.53 (dd, J=3.6, 1.6 Hz, 2H), 8.08 (s, 1H), 7.59-7.57 (m, 1H), 7.37 (s, 1H), 7.29-7.26 (m, 1H), 7.06 (s, 1H), 4.63 (t, J=6.8 Hz, 2H), 3.12 (t, J=6.8 Hz, 1H). EI-MS m/z: 218 ($M^+$+1).

Preparation Method of Compound IntA-Q3

To a solution of compound Int-Q3b (47.6 mg, 0.22 mmol) and compound IntA-Q2-2 (45.2 mg, 0.22 mmol) in THF (400 μL) were added NaH (2.6 mg, 0.07 mmol) at 0° C. under $N_2$ atmosphere. After stirring at 0° C. for 30 minutes, the mixture was extracted with diethyl ether (10 mL×2) and water (5 mL). The obtained organic layer was dried over anhydrous $Na_2SO_4$, filtered, and concentrated under reduced pressure. The residue was purified by column chromatography to obtain compound Int-Q3 (296.5 mg, 65%).

$^1$H NMR (400 MHz, $CDCl_3$) δ 8.50-8.49 (m, 2H), 7.56-7.54 (m, 1H), 7.48 (d, J=8.8 Hz, 2H), 7.35 (d, J=8.8 Hz, 2H), 7.24-7.22 (m, 1H), 5.30 (s, 2H), 4.38 (t, J=6.4 Hz, 2H), 3.00 (t, J=6.8 Hz, 1H). EI-MS m/z: 356 ($M^+$+1).

[Example 15] Preparation of Compound IntA-Q4

Compound IntA-Q4 (178.2 mg, 0.86 mmol) was prepared from compound IntA-Q2-2 (178.2 mg, 0.86 mmol) and 3-Pyridylacetic acid-hydrochloride (100 mg, 0.58 mmol) by a similar method of preparing Int-TG5-1a in Example 6. (161 mg, 86%).

$^1$H NMR (400 MHz, $CDCl_3$) δ 8.55-8.54 (m, 2H), 7.65-7.62 (m, 1H), 7.58 (d, J=8.4 Hz, 2H), 7.33 (d, J=8.4 Hz, 2H), 7.29-7.27 (m, 1H), 5.20 (s, 2H), 3.70 (s, 2H). EI-MS m/z: 326 ($M^+$+1).

[Example 16] Preparation of Compound IntA-Q5

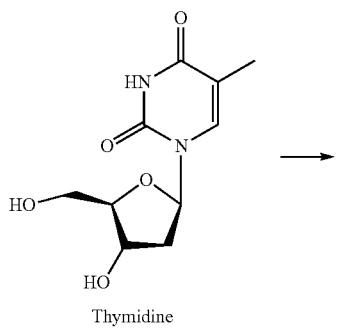

Thymidine

-continued

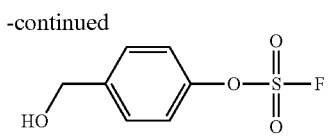

IntA-Q2-2

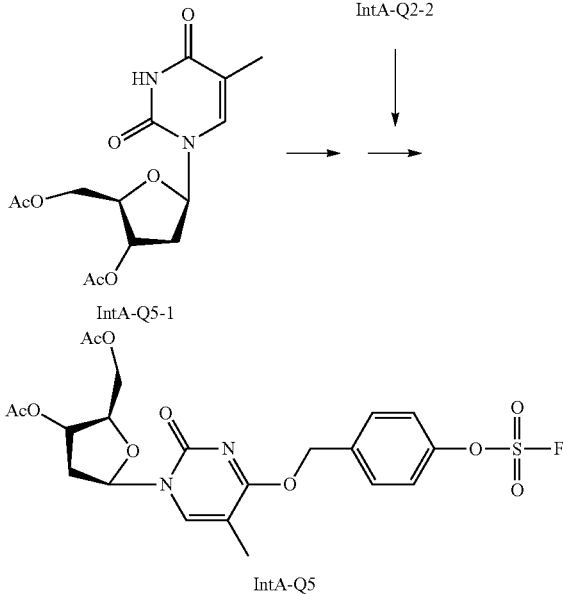

IntA-Q5-1

IntA-Q5

Preparation of Compound IntB-Q5-1

The compound IntA-Q2-2 (230 mg, 1.12 mmol) was dissolved in ether (10 mL), and 1M PBr₃ (446 μl, 0.45 mmol) dissolved in DCM was added and stirred at 0° C. for 2 hours. After the reaction was completed, ether (50 mL) and sodium bicarbonate aqueous solution (50 mL) were added to perform extraction. The organic layer was dried over anhydrous Na₂SO₄, filtered and concentrated under reduced pressure to obtain a compound IntB-Q5-1 (201 mg, 67%).

$^1$H NMR (400 Hz, CDCl₃) δ 7.51 (d, J=8.4 Hz, 2H), 7.33 (d, J=8.4 Hz, 2H), 4.49 (s, 2H).

Preparation of Compound IntA-Q5-1

Thymidine (100 mg, 0.41 mmol) and 60% NaH (25 mg, 0.62 mmol) were dissolved in DMF (3 mL) under a nitrogen atmosphere, and the mixture was cooled to 0° C. The compound IntB-Q5-1 (167 mg, 0.62 mmol) was added at 0° C., and the mixture was stirred at the same temperature for 1 hour. After the reaction was completed, EA (30 mL×3) and citric acid aqueous solution (30 mL) were added to perform extraction, and the obtained organic layer was dried over anhydrous Na₂SO₄, filtered and concentrated under reduced pressure. The residue was purified by column chromatography to obtain a compound IntA-Q5-1 (79 mg, 45%).

$^1$H NMR (400 MHz, DMSO-d₆) δ 7.84 (s, 1H), 7.54 (d, J=8.8 Hz, 2H), 7.47 (d, J=8.8 Hz, 2H), 6.20 (t, J=6.8 Hz, 1H), 5.25 (d, J=4 Hz, 1H), 5.07-5.02 (m, 3H), 4.28-4.22 (m, 1H), 3.78-3.76 (m, 1H), 3.64-3.54 (m, 2H), 2.16-2.11 (m, 2H), 1.84 (s, 3H). EI-MS m/z: 431 (M⁺).

Preparation of Compound IntA-Q5-2

The compound IntA-Q5-1 (40 mg, 0.09 mmol) and the compound Int-TG1 (62 mg, 0.11 mmol) were dissolved in ACN (3 mL) under a nitrogen atmosphere, and then BEMP (14 l, 0.05 mmol) was added thereto. The mixture was stirred overnight at room temperature, DBU (7 μL, 0.05 mmol) was further added thereto, and the mixture was stirred at the same temperature for 1 hour. After the reaction was completed, EA (20 mL×3), citric acid aqueous solution (20 mL), and brine (20 mL) were added to perform extraction, and the obtained organic layer was dried over anhydrous Na₂SO₄, filtered and concentrated under reduced pressure. The residue was purified by column chromatography to obtain a compound IntA-Q5-2 (26 mg, 33%).

EI-MS m/z: 851 (M⁺).

Preparation of Compound IntA-Q5

The compound IntA-Q5-2 (16 mg, 0.02 mmol) was dissolved in MeOH (2 mL) under a nitrogen atmosphere and then cooled to 0° C. K₂CO₃ (13 mg, 0.09 mmol) was added at 0° C., and the mixture was stirred at the same temperature for 1 hour. After the reaction was completed, the reaction solution was subjected to Prep-HPLC to obtain a compound IntA-Q5 (10.3 mg, 80%).

EI-MS m/z: 705 (M⁺+Na).

[Example 17] Preparation of Compound IntA-Q6

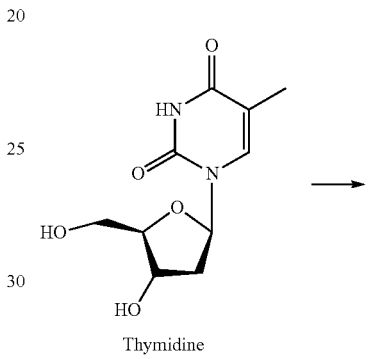

Thymidine

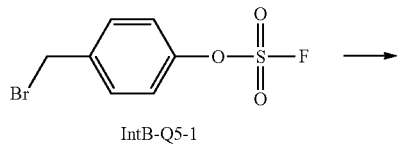

IntB-Q5-1

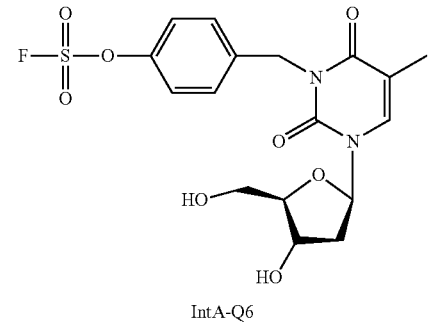

IntA-Q6

60% NaH (25 mg, 0.62 mmol) was added to a stirred solution of thymidine (100 mg, 0.41 mmol) in DMF (3 mL) under N₂ atmosphere. The mixture was cooled to 0° C., and compound IntB-Q5-1 (167 mg, 0.62 mmol) was added. The mixture was stirred for 1 hour. After the reaction was completed, the reaction was quenched by addition of EA (30 mL×3) and saturated citric acid (30 mL). The obtained organic layer was to obtain compound IntA-Q5-1 (79 mg, 45%).

[Example 18] Preparation of Compound IntB-Q1

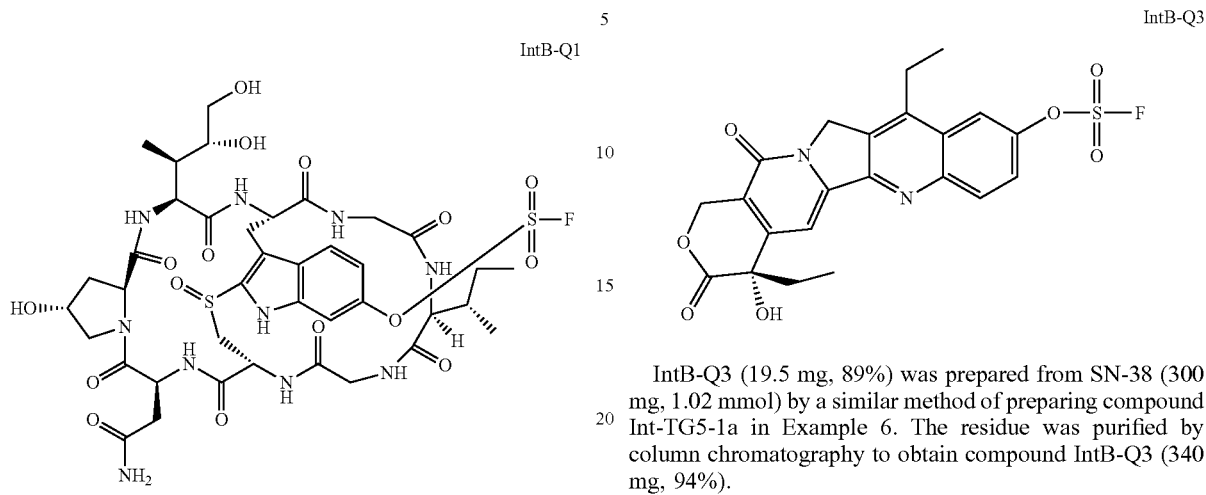

IntB-Q1

IntB-Q1 (19.5 mg, 89%) was prepared from Amanitin (20 mg, 0.022 mmol) by a similar method of preparing compound Int-TG5-1a in Example 6.

EI-MS m/z: 1002 (M$^+$).

[Example 19] Preparation of Compound IntB-Q3

IntB-Q3

IntB-Q3 (19.5 mg, 89%) was prepared from SN-38 (300 mg, 1.02 mmol) by a similar method of preparing compound Int-TG5-1a in Example 6. The residue was purified by column chromatography to obtain compound IntB-Q3 (340 mg, 94%).

$^1$H NMR (400 MHz, CDCl$_3$) δ 8.60 (d, J=2.4 Hz, 1H), 8.39 (d, J=9.2 Hz, 1H), 8.09 (dd, J=9.2, 2.4 Hz, 1H), 7.37 (s, 1H), 6.56 (s, 1H), 5.45 (s, 2H), 5.38 (s, 2H), 3.25 (m, 2H), 1.91-1.84 (m, 2H), 1.32 (t, J=7.6 Hz, 3H), 0.89 (t, J=6.8 Hz, 3H). EI-MS m/z: 475 (M$^+$).

[Example 20] Preparation of Compound IntB-Q4

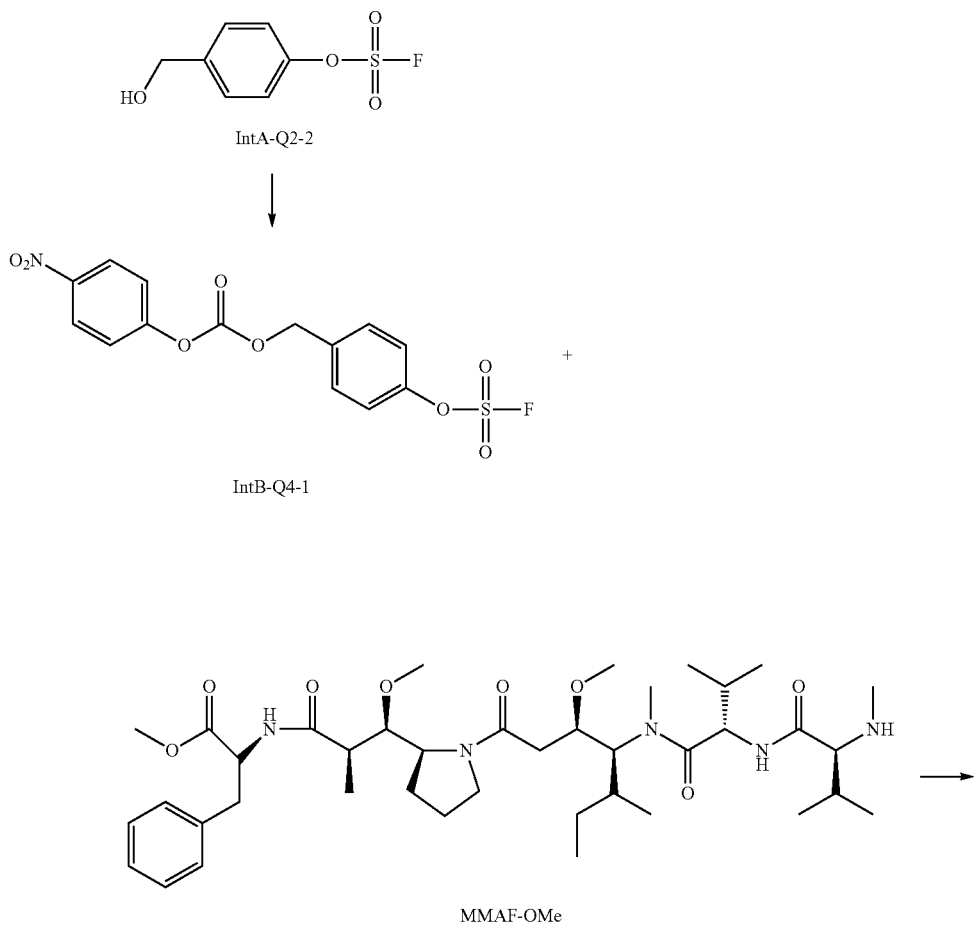

IntA-Q2-2

IntB-Q4-1

MMAF-OMe

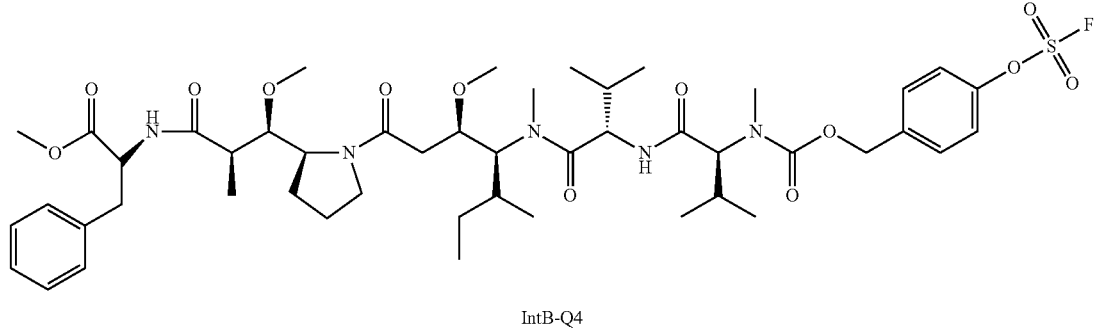

IntB-Q4

Preparation of Compound IntB-Q4-1

To a solution of compound IntA-Q2-2 (110 mg, 0.53 mmol) in DMF (3 mL) was added bis(4-nitrophenyl) carbonate (179 mg, 0.59 mmol) and DIPEA (139 μL, 0.80 mmol) at room temperature. After stirring 15 hours, the mixture was extracted with distilled water (10 mL) and EA (10 mL×2). The organic layer was washed with brine (10 mL), dried over anhydrous Na$_2$SO$_4$, filtered and concentrated under reduced pressure. The residue was purified by column chromatography to obtain compound IntB-Q4-1 (184 mg, 93%).

$^1$H NMR (400 MHz, CDCl$_3$) δ 8.29-8.27 (d, J=8.4 Hz, 2H), 7.58-7.56 (d, J=8.8 Hz, 2H), 7.41-7.38 (m, 4H), 5.32 (s, 2H).

Preparation of Compound IntB-Q4

Compound IntB-Q4-1 (36 mg, 0.097 mmol) and MMAF-OMe (80 mg, 0.107 mmol) that was prepared by a similar method to the method described in ChemPharmBull, 1995, 43(10), 1706-1718 were dissolved in DMF (1 mL) at room temperature under a nitrogen atmosphere. Then, HOBt (3 mg, 0.019 mmol), DIPEA (19 μL, 0.107 mmol) and pyridine (330 μL) were added thereto and stirred overnight. The mixture was adjusted to have pH of 2 to 3 with 1N HCl and then diluted with distilled water (8 mL) and EA (8 mL×2). The organic layer was washed with brine (12 mL), dried over anhydrous Na$_2$SO$_4$, filtered and concentrated under reduced pressure. The residue was purified by column chromatography to obtain compound IntB-Q4 (62 mg, 65%).

EI-MS m/z: 979 (M$^+$).

[Example 21] Preparation of Compound IntB-Q5

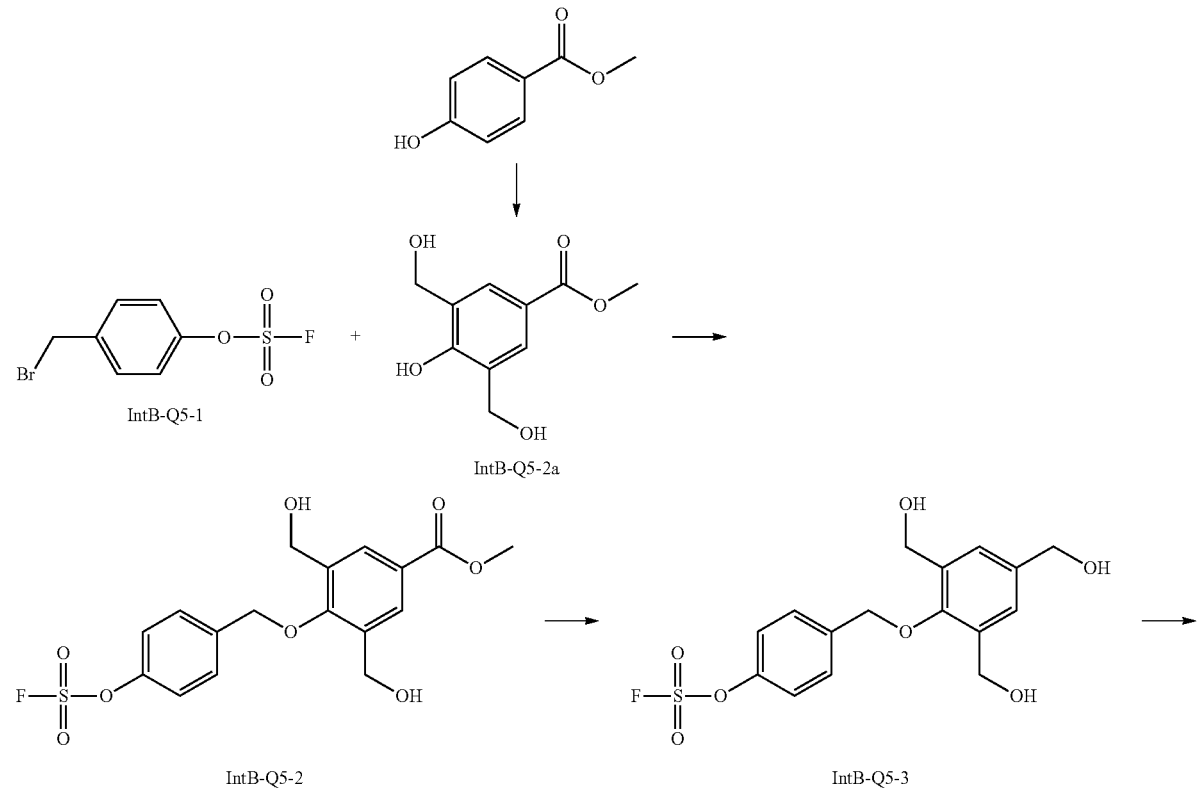

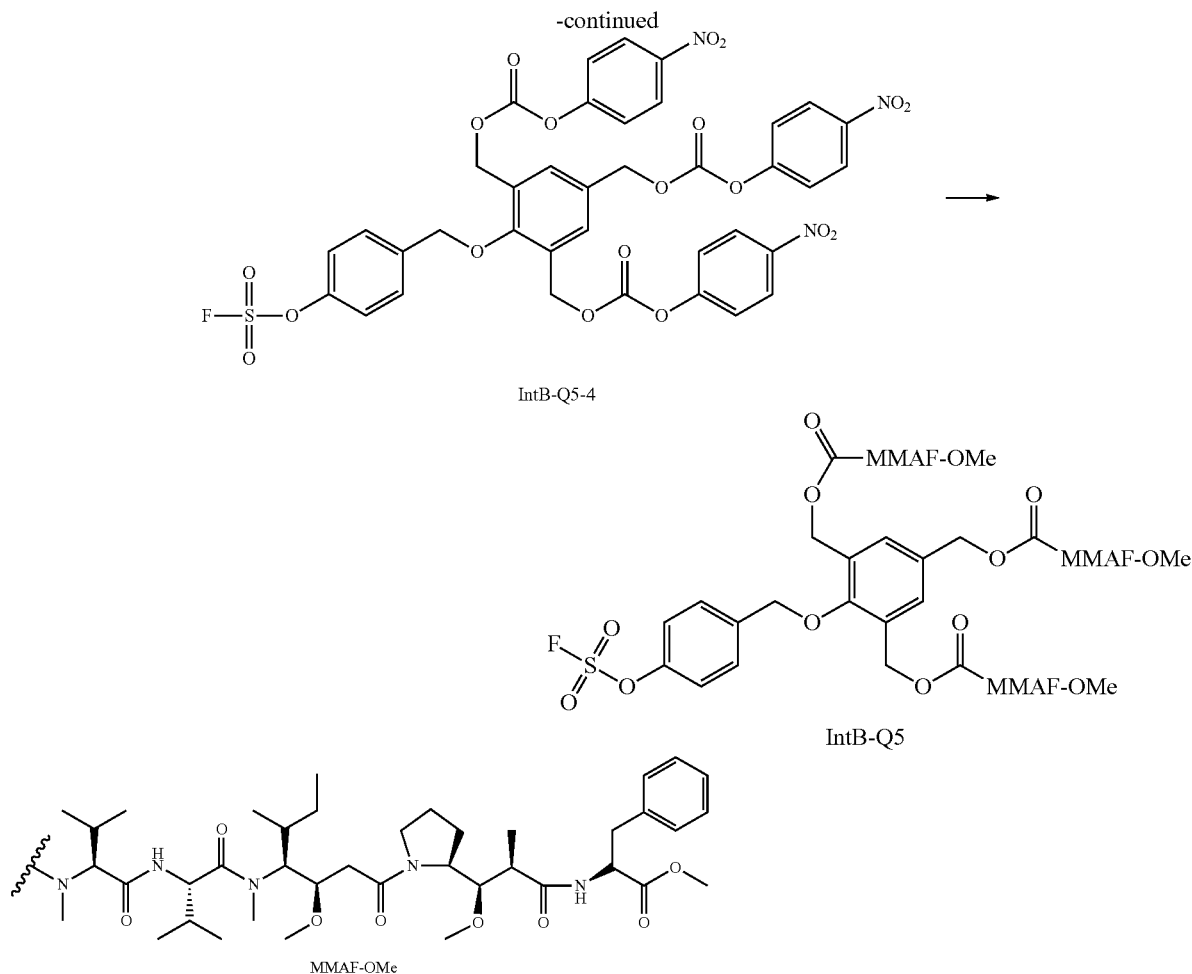

Preparation of Compound IntB-Q5-2a

To a solution of compound methyl 4-hydroxy benzoate (3.00 g, 19.72 mmol) in 12% NaOH aqueous solution (20 mL) was added 40% formaldehyde aqueous solution (20 mL) at room temperature under $N_2$ atmosphere. The mixture was stirred at 50° C. for 3 days. After the reaction was completed, the mixture was extracted with EA (200 mL) and saturated $NH_4Cl$ (200 mL). The organic layer was dried over anhydrous $Na_2SO_4$, filtered and concentrated under reduced pressure. The residue was purified by column chromatography to obtain compound IntB-Q5-2a (2.30 g, 55%).

$^1$H NMR (400 Hz, DMSO-$d_6$) δ 7.84 (s, 2H), 4.56 (s, 4H), 3.80 (s, 3H).

Preparation of Compound IntB-Q5-2

To a solution of compound IntB-Q5-1 (300 mg, 1.12 mmol) and compound IntB-Q5-2a (237 mg, 1.12 mmol) in DMF (10 mL) were added $K_2CO_3$ (308 mg, 2.23 mmol) at room temperature under $N_2$ atmosphere. After stirring for 6 hours, the mixture was diluted with EA (100 mL) and washed 2N HCl aqueous solution (30 mL). The organic layer was dried over anhydrous $Na_2SO_4$, filtered and concentrated under reduced pressure. The residue was purified by column chromatography to obtain compound IntB-Q5-2 (140 mg, 32%).

$^1$H NMR (400 MHz, $CDCl_3$) δ 8.07 (s, 2H), 7.58 (d, J=8.4 Hz, 2H), 7.39 (d, J=8.4 Hz, 2H), 5.07 (s, 2H), 4.73 (s, 4H), 3.91 (s, 3H).

Preparation of Compound IntB-Q5-3

To a solution of compound IntB-Q5-2 (68.8 mg, 1.12 mmol) in THF (2 mL) was added 4M $LiBH_4$ (3.8 mL, 15.20 mmol) dissolved in THF at room temperature. The mixture was stirred for 19 hours and added EA (50 mL). The organic layer was washed with saturated $NH_4Cl$ (50 mL), dried over anhydrous $Na_2SO_4$, filtered and concentrated under reduced pressure. The residue was purified by column chromatography to obtain compound IntB-Q5-3 (23 mg, 36%).

$^1$H NMR (400 MHz, $CDCl_3$+$CD_3OD$) δ 7.59 (d, J=8.8 Hz, 2H), 7.38 (d, J=8.0 Hz, 2H), 7.32 (s, 2H), 4.94 (s, 2H), 4.65 (s, 4H), 4.56 (s, 2H).

Preparation of Compound IntB-Q5-4

To a solution of compound IntB-Q5-3 (33 mg, 0.09 mmol) in THF (4 mL) was added 4-nitrophenyl chloroformate (536 mg, 2.66 mmol) and pyridine (0.20 mL, 2.66 mmol) at 0° C. under $N_2$ atmosphere. The mixture was stirred for 3 hours and diluted with EA (50 mL). The organic layer was washed with 2N aqueous HCl (50 mL), dried over anhydrous $Na_2SO_4$, filtered and concentrated under reduced pressure. The residue was purified by column chromatography to obtain compound IntB-Q5-4 (57 mg, 72%).

$^1$H NMR (400 MHz, $CDCl_3$) δ 8.27 (d, J=8.8 Hz, 6H), 7.68 (s, 2H), 7.64 (d, J=8.0 Hz, 2H), 7.43-7.34 (m, 8H), 5.41 (s, 4H), 5.33 (s, 2H), 5.13 (s, 2H).

Preparation of Compound IntB-Q5

To a solution of compound IntB-Q5-4 (55 mg, 0.06 mmol) and MMAF-OMe (142 mg, 0.19 mmol) in DMF (3 mL)

were added HOBt (24 mg, 0.16 mmol), pyridine (1.5 mL) and DIPEA (55 μL, 0.32 mmol) at room temperature under $N_2$ atmosphere. The mixture was stirred for 15 hours and diluted with EA (100 mL). The organic layer was washed with 2N aqueous HCl (50 mL), dried over anhydrous $Na_2SO_4$, filtered, and concentrated under reduced pressure, followed by separation and purification using Prep-HPLC to obtain compound IntB-Q5 (92 mg, 54%).

EI-MS m/z: 2689 (M⁺).

[Example 22] Preparation of Compound IntB-Q6

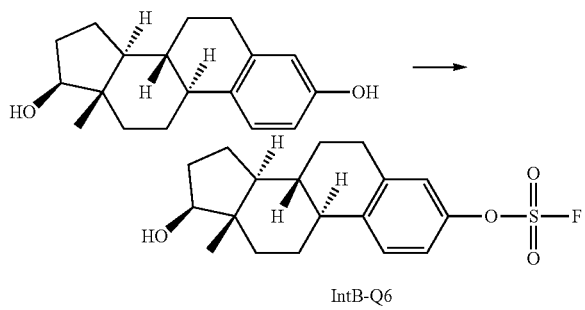

IntB-Q6

To a solution of β-Estradiol (300 mg, 1.10 mmol) in DCM (3 mL), $H_2O$ (2 mL), and DMF (2 mL) was added TEA (230 μL, 1.65 mmol) under a nitrogen atmosphere. The mixture was stirred overnight at room temperature while injecting $SO_2F_2$ gas. After the reaction was competed, it was confirmed that the product and the starting material were present at a ratio of 1:1 on HPLC, followed by Prep-HPLC to obtain compound IntB-Q6 (120 mg, 31%, 134 mg of starting material was obtained).

$^1$H NMR (400 Hz, DMSO-$d_6$) δ 7.45 (d, J=8.8 Hz, 1H), 7.29-7.24 (m, 2H), 5.01 (brs, 1H), 4.93-4.89 (m, 1H), 3.52 (t, J=8.4 Hz, 1H), 2.32-2.16 (m, 2H), 1.93-1.77 (m, 3H), 1.63-1.54 (m, 1H), 1.47-1.07 (m, 8H), 0.66 (s, 3H). EI-MS m/z: 378 (M⁺+Na).

[Example 23] Preparation of Compound IntB-Q7

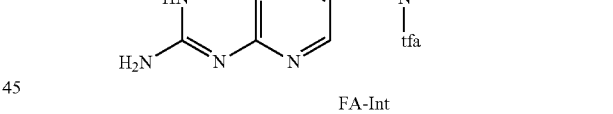

IntB-Q7

Combretastatin A4 (18 mg, 0.057 mmol) was dissolved in DCM (3 mL) under a nitrogen atmosphere, TEA (88 μL, 0.57 mmol) was added thereto, and the mixture was stirred at room temperature for 3 hours while injecting $SO_2F_2$ gas. After the reaction was completed, a saturated citric acid aqueous solution (6 mL) and DCM (6 mL) were added to extract an organic layer, and the organic layer was dried over anhydrous $Na_2SO_4$, filtered and concentrated under reduced pressure. The residue was purified by column chromatography to obtain compound IntB-Q7 (22 mg, 97%).

EI-MS m/z: 399 (M⁺).

[Example 24] Preparation of Compound FA-Int

FA-Int

Compound FA-Int was obtained by performing a reaction in a similar method described in U.S. Patent Application Publication No. 20070276018.

[Example 25] Preparation of Compound IntC-L-1

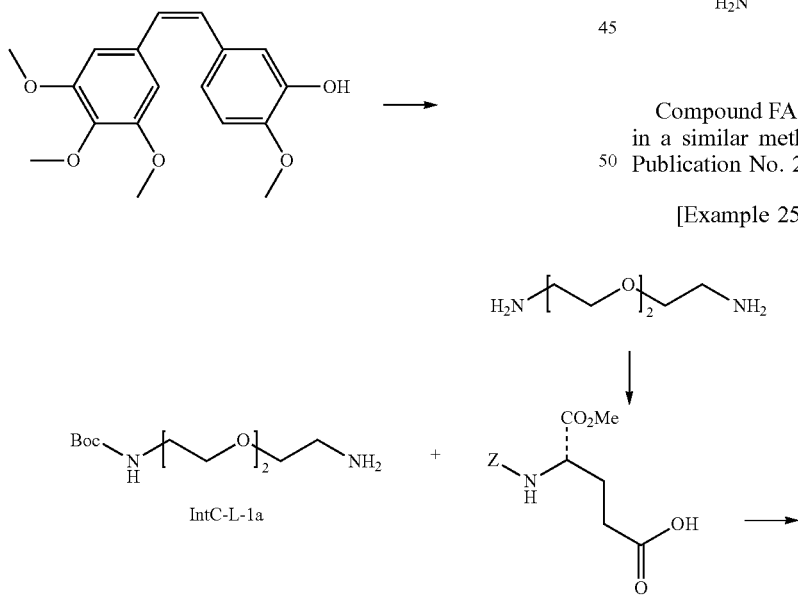

-continued

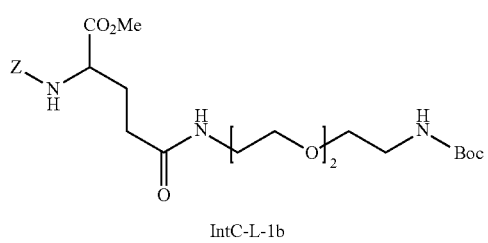

IntC-L-1b

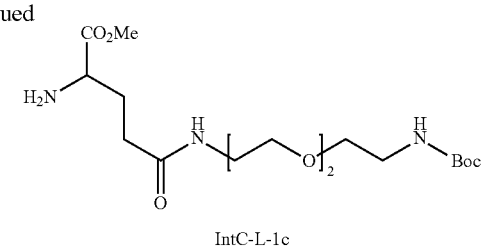

IntC-L-1c

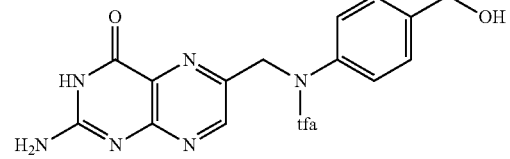

FA-Int

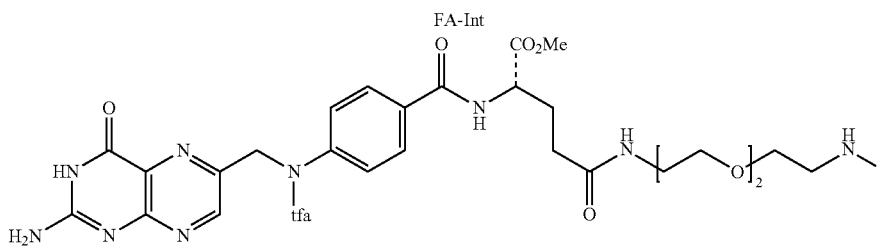

IntC-L-1d

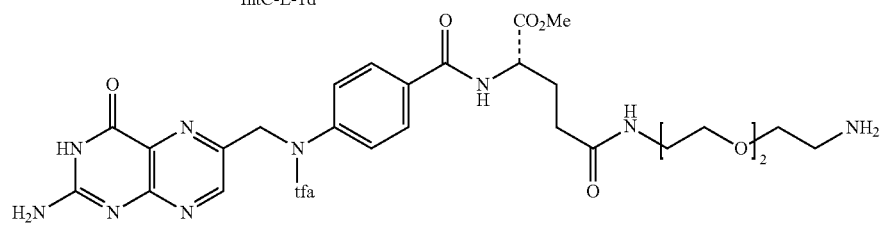

IntC-L-1

Preparation of Compound IntCl-L-1a

To a solution of 2,2-(ethylenedioxy)bis(ethylamine) (50 g, 337.4 mmol) in DCM (300 mL) was added Boc$_2$O (14.7 g, 67.47 mmol) dissolved in DCM (200 mL) under N$_2$ atmosphere. The mixture was stirred overnight at room temperature and quenched with H$_2$O (500 mL) and brine (150 mL×3). The organic layer was dried over anhydrous Na$_2$SO$_4$, filtered and concentrated under reduced pressure. After concentration, compound IntCl-L-1a was used directly in the next reaction without purification (13.01 g, 78%).

$^1$H NMR (400 MHz, CDCl$_3$) δ 5.20 (s, 1H), 3.62-3.62 (m, 4H), 3.55-3.51 (m, 4H), 3.35-3.25 (m, 2H), 2.90-2.87 (m, 2H), 1.45 (s, 9H).

Preparation of Compound IntCl-L-1b

To a solution of compound IntCl-L-1a (6 g, 24.16 mmol) and z-L-Glu-OMe (5.94 g, 20.13 mmol) in DMF (30 mL) was added PyBOP (15.72 g, 30.20 mmol) and DIPEA (10.52 mL, 60.39 mmol) at 0° C. under N$_2$ atmosphere. The mixture was stirred at room temperature for 2 hours. EA (20 mL×6), H$_2$O (20 mL), and brine (200 mL) were added to the mixture. The organic layer was dried over anhydrous Na$_2$SO$_4$, filtered and concentrated under reduced pressure. The residue was purified by column chromatography to obtain compound IntCl-L-1b (10.6 g, quant.).

$^1$H NMR (400 MHz, CDCl$_3$) δ 7.40-7.28 (m, 5H), 6.32 (s, 1H), 5.80 (s, 1H), 5.11 (s, 2H), 5.02 (s, 1H), 4.36 (s, 1H), 3.74 (s, 3H), 3.60 (s, 4H), 3.54 (s, 4H), 3.44-3.43 (m, 2H), 3.38-3.21 (m, 2H), 2.30-2.20 (m, 3H), 2.04-2.00 (m, 1H), 1.76 (s, 1H), 1.44 (s, 9H). EI-MS m/z: 526 (M$^+$).

Preparation of Compound IntCl-L-1c

To a solution of compound IntCl-L-1b (3 g, 5.71 mmol) in MeOH (25 mL) was added Pd/C (900 mg) at room temperature under H$_2$. The mixture was stirred for 3 hours and filtered by celite, and then concentrated under reduced pressure. The compound IntCl-L-1c was used directly in the next step without further purification (2.23 g, crude).

$^1$H NMR (400 MHz, CDCl$_3$) δ 6.56 (s, 1H), 5.20 (s, 1H), 3.73 (s, 3H), 3.61 (s, 4H), 3.57-3.55 (m, 4H), 3.53-3.50 (m, 1H), 3.48-3.44 (m, 4H), 2.40-2.32 (m, 2H), 2.18-2.10 (m, 1H), 1.88-1.81 (m, 1H), 1.44 (s, 9H). EI-MS m/z: 392 (M$^+$).

Preparation of Compound IntCl-L-1d

To a solution of compound IntCl-L-1c (2.23 g, 5.71 mmol) and compound FA-Int (2.12 g, 5.19 mmol) in DMF (15 mL) was added HBTU (2.36 g, 6.23 mmol) and DIPEA (1.36 mL, 7.78 mmol) at 0° C. under N$_2$ atmosphere. The mixture was stirred at room temperature for 2.5 hour and EA (100 mL×7) and H$_2$O (100 mL) were added. The organic layer was dried over anhydrous Na$_2$SO$_4$, filtered and concentrated under reduced pressure. The residue was purified by column chromatography to obtain compound IntCl-L-1d (4.06 g, quant.).

$^1$H NMR (400 Hz, DMSO-$d_6$) δ 8.89 (d, J=7.6 Hz, 1H), 8.63 (s, 1H), 7.90 (d, J=8 Hz, 2H), 7.64 (d, J=8.4 Hz, 2H), 6.76-6.75 (m, 1H), 5.12 (s, 1H), 4.41-4.36 (m, 1H), 3.64 (s, 3H), 3.47 (s, 4H), 3.39-3.35 (m, 4H), 3.20-3.12 (m, 2H), 3.07-3.02 (m, 2H), 2.23 (t, J=7.4 Hz, 2H), 2.09-2.06 (m, 1H), 1.96-1.91 (m, 1H), 1.36 (s, 9H). EI-MS m/z: 782 (M$^+$).

Preparation of Compound IntCl-L-1

To a solution of compound IntCl-L-1d (4.68 g, 5.99 mmol) in DCM (50 mL) was added dropwise TFA (10 mL) at 0° C. The reaction was allowed to warm to room temperature and stirred for 3 hours. The mixture was concentrated under reduced pressure and used directly in the next step without further purification (4.08 g, crude).

EI-MS m/z: 682 (M$^+$).

[Example 26] Preparation of Compound IntC-L

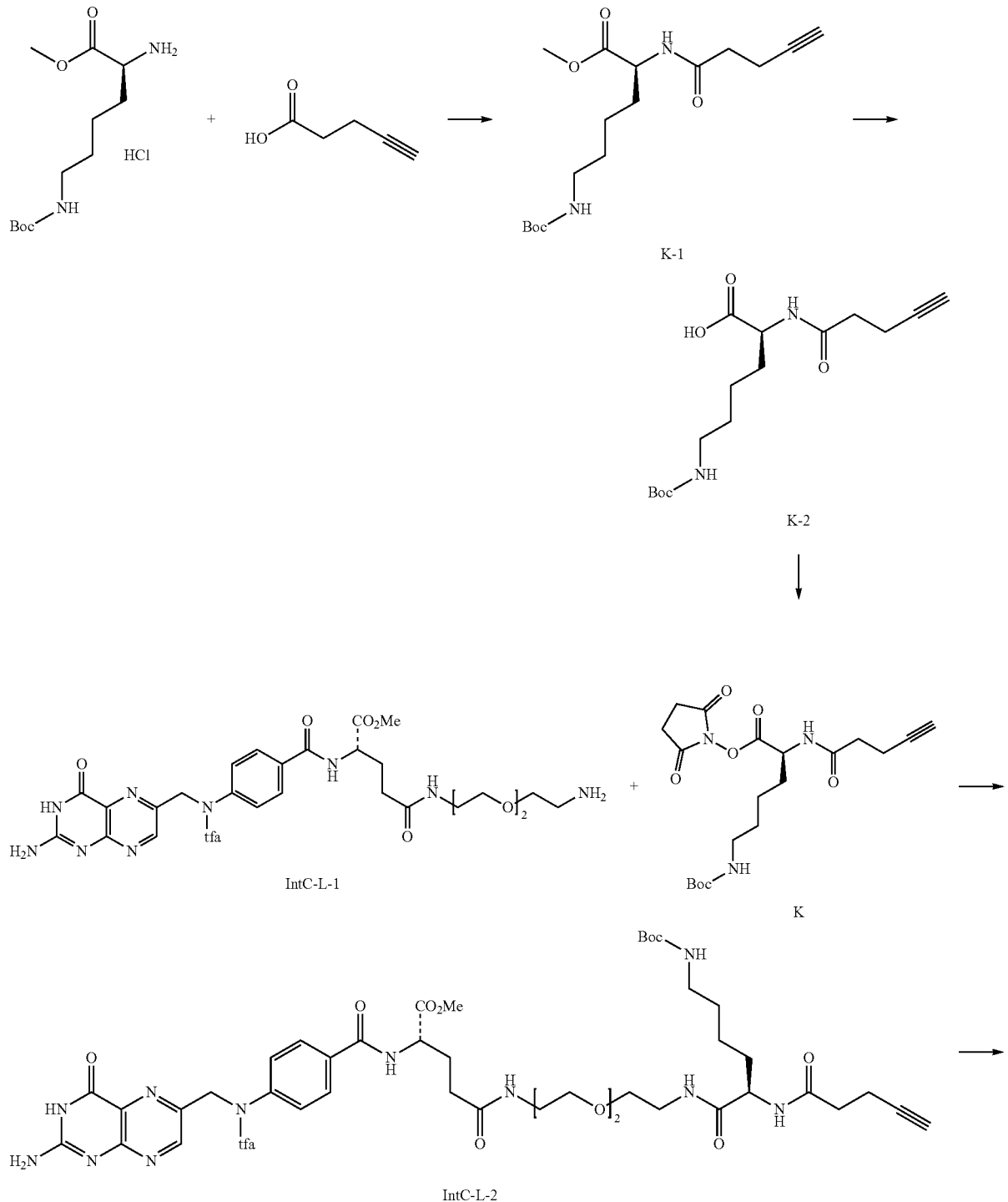

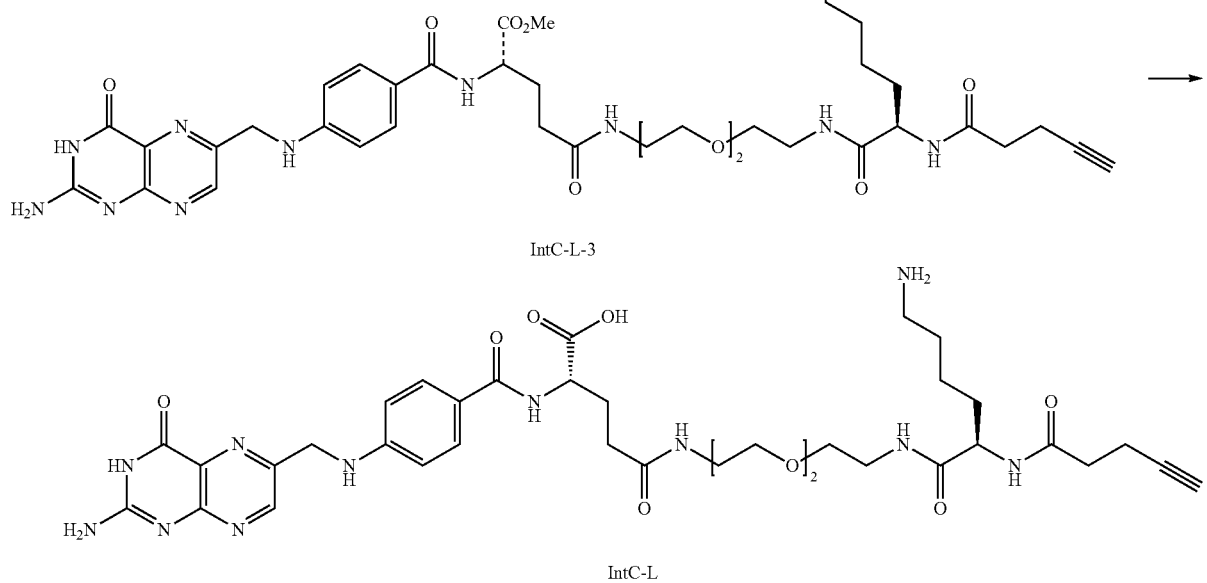

IntC-L-3

IntC-L

Preparation of Compound K-1

To a solution of L-Lys(Boc)-OMe (3 g, 10.11 mmol) and 4-pentynoic acid (992 mg, 10.11 mmol) in DMF (30 mL) was added in one portion PyBop (7.89 g, 15.16 mmol) followed by DIPEA (5.26 mL, 30.32 mmol) at 0° C. under $N_2$ atmosphere. The mixture was stirred overnight at room temperature. EA (80 mL×4) and saturated citric acid (60 mL) were added to the mixture and organic layer was washed with $NaHCO_3$ (120 mL), brine (100 mL), dried over anhydrous $Na_2SO_4$, filtered and concentrated under reduced pressure. The residue was purified by column chromatography to obtain compound K-1 (3.29 g, 95%).

EI-MS m/z: 341 (M+).

Preparation of Compound K-2

To a solution of compound K-1 (3.29 g, 9.66 mmol) in MeOH (15 mL) was added LiOH·$H_2O$ (2.03 g, 48.32 mmol) dissolved in $H_2O$ (15 mL) at 0° C. under $N_2$ atmosphere.

The mixture was stirred at 0° C. for 30 minutes, and warm up to room temperature for 2 hours. The mixture was acidified with saturated citric acid aqueous solution, and EA (40 mL×2) was added to the mixture. The organic layer was washed with $H_2O$ (30 mL) and brine (30 mL), dried over anhydrous $Na_2SO_4$, filtered and concentrated under reduced pressure. Compound K-2 was used directly in the next step without further purification (3.15 g, crude).

EI-MS m/z: 327 (M+).

Preparation of Compound K

To a solution of compound K-2 (3.69 g, 11.31 mmol) in DMF (20 mL) was added NHS (1.69 mg, 14.7 mmol) and EDCI (2.93 g, 15.26 mmol) under $N_2$ atmosphere. The mixture was stirred overnight at room temperature and concentrated. The residue, compound K was used directly in the next step without further purification (4.79 g, crude).

EI-MS m/z: 446 (M+ +Na).

Preparation of Compound IntC-L-2

To a solution of compound IntC-L-1 (4.08 g, 5.99 mmol) and compound K (4.79 g, 11.31 mmol) in DMF (25 mL) was added DIPEA (5.21 mL, 29.93 mmol) under $N_2$ atmosphere.

The mixture was stirred overnight at room temperature. $H_2O$ (70 mL) and brine (60 mL) were added to the mixture and extracted with EA (70 mL×7). And the organic layer was dried over anhydrous $Na_2SO_4$, filtered and concentrated under reduced pressure. The residue was purified by column chromatography to obtain compound IntC-L-2 (1.12 g, 19%).

EI-MS m/z: 991 (M+).

Preparation of Compound IntC-L-3

To a solution of compound IntA-L-2 (1.12 g, 1.13 mmol) in MeOH (27 mL) was added LiOH·$H_2O$ (356 mg, 8.48 mmol) dissolved in $H_2O$ (10 mL) at 0° C. under $N_2$ atmosphere. The mixture was stirred at 0° C. for 30 minutes, and warmed up to room temperature for 3 hours. The mixture was acidified with 2M HCl and concentrated under reduced pressure. The residue, compound IntC-L-3 was used directly in the next step without further purification (996 mg, crude).

EI-MS m/z: 880 (M+).

Preparation of Compound IntC-L

To a solution of compound IntC-L-3 (996 mg, 1.13 mmol) in DCM (30 mL) was added TFA (8 mL) at 0° C. under $N_2$ atmosphere. After stirring at 0° C. for 1 hour, the mixture was concentrated under reduced pressure. The residue was dissolved in DMSO (5 mL) and purified by Prep-HPLC, which produced compound IntC-L (409 mg, 32%).

EI-MS m/z: 780 (M+).

[Example 27] Preparation of Compound MPS-D1

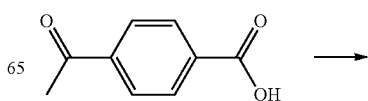

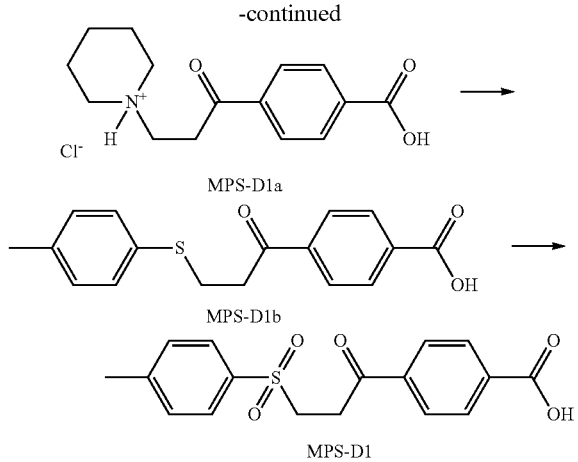

Preparation of Compound MPS-D1a

To a solution of 4-acetylbenzoic acid (9 g, 54.82 mmol) in EtOH (50 mL) was added Piperidine hydrochloride (6.66 g, 54.82 mmol), paraformaldehyde (4.95 g, 164.5 mmol), and conc. HCl (0.6 mL) at room temperature under $N_2$ atmosphere. The mixture was stirred at 100° C. for 16 hours and cooled to room temperature, acetone (90 mL) was added dropwise thereto. The mixture was stirred at 0° C. for 1 hour. The solid was filtered and washed with diethyl ether (30 mL×2) to obtain compound MPS-D1a (6.11 g, 38%).

$^1$H NMR (400 MHz, DMSO-$d_6$) δ 8.08 (s, 4H), 5.73 (s, 1H), 3.65 (t, J=7.2 Hz, 2H), 3.35 (t, J=7.2 Hz, 2H), 3.31 (m, 6H), 1.74 (s, 4H).

Preparation of Compound MPS-D1b

To a solution of MPS-D1a (6.11 g, 20.52 mmol) in EtOH (40 mL) and MeOH (26 mL) was added 4-methoxybenzenethiol (2.55 g, 20.52 mmol) and piperidine (0.3 mL, 3.08 mmol) at room temperature. The mixture was stirred at 100° C. for 16 hours and cooled to 0° C. and additionally stirred for 1 hour. The solid was filtered and washed with ether (30 mL×2) to obtain compound MPS-D1b (5.56 g, 90%).

$^1$H NMR (400 MHz, CDCl$_3$) δ 8.04-7.99 (m, 4H), 7.27 (d, J=8.4 Hz, 2H), 7.15 (d, J=7.6 Hz, 2H), 3.39-3.36 (m, 2H), 3.25-3.21 (m, 2H), 2.27 (s, 3H).

Preparation of Compound MPS-D1

To a solution of MPS-D1b (5.56 g, 18.51 mmol) in MeOH (90 mL) and distilled water (90 mL) was added oxone (25.03 g, 40.72 mmol) at 0° C. under $N_2$ atmosphere. After stirring at room temperature for 14 hours, the mixture was quenched with distilled water (100 mL) and chloroform (150 mL×3). The organic layer was washed with brine (200 mL), dried over anhydrous Na$_2$SO$_4$, filtered and concentrated under reduced pressure to obtain compound MPS-D1 (5.29 g, 86%).

$^1$H NMR (400 MHz, CDCl$_3$) δ 8.04-7.99 (m, 4H), 7.81 (d, J=8.4 Hz, 2H), 7.46 (d, J=8.4 Hz, 2H), 3.63 (t, J=7.2 Hz, 2H), 3.41 (t, J=7.2 Hz, 2H), 2.44 (s, 3H). EI-MS m/z: 333 (M$^+$).

[Example 28] Preparation of Compound MPS-D2

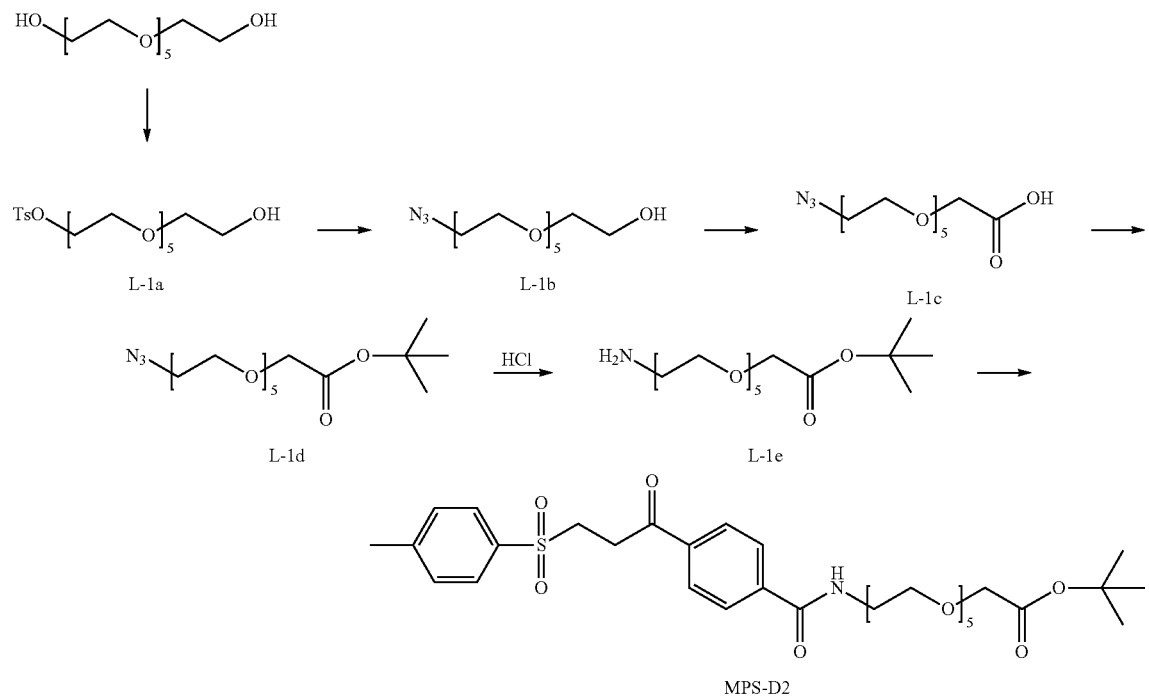

Preparation of Compound L-1a

To a solution of hexaethylene glycol (5.0 g, 17.71 mmol) in anhydrous DCM (178 mL) was added KI (294 mg, 1.77 mmol) and Ag$_2$O (4.92 g, 19.48 mmol) under $N_2$ atmosphere. The mixture was stirred overnight at room temperature. After the reaction was completed, the mixture was filtered through celite and washed with DCM (100 mL). The filtrate was concentrated under reduced pressure. The residue was purified by column chromatography to obtain compound L-1a (5.98 g, 73%).

¹H NMR (400 MHz, CDCl₃) δ 7.80 (d, J=8.4 Hz, 2H), 7.35 (d, J=8.4 Hz, 2H), 4.16 (t, J=4.8 Hz, 2H), 3.71-3.58 (m, 22H), 2.88 (br, 1H), 2.45 (s, 3H).

Preparation of Compound L-1b

To a solution of compound L-1a (5.98 g, 13.7 mmol) in DMF (30 mL) was added NaN₃ (1.34 g, 20.55 mmol) under N₂ atmosphere. The mixture was stirred at 110° C. for 1 hour and concentrated under reduced pressure. The residue was purified by column chromatography to obtain compound L-1b (4.1 g, 97%).

¹H NMR (400 MHz, CDCl₃) δ 3.72-3.60 (m, 22H), 3.39 (t, J=4.8 Hz, 2H), 2.78 (br, 1H).

Preparation of Compound L-1c

To a solution of compound L-1b (2 g, 6.51 mmol) in acetone (56 mL) was slowly added dropwise Jone's reagent solution (5 mL) at −5° C. under N₂ atmosphere. The mixture was stirred at room temperature for 2 hours and filtered through celite, and the filtrate was concentrated under reduced pressure. The filtrate was diluted with DCM (20 mL×2) and water (5 mL). The organic layer was dried over anhydrous Na₂SO₄, filtered, and concentrated under reduced pressure. The residue was purified by column chromatography to obtain compound L-1c (1.85 g, 89%).

¹H NMR (400 MHz, CDCl₃) δ 4.15 (s, 2H), 3.76-3.67 (m, 18H), 3.40 (t, J=4.8 Hz, 2H).

Preparation of Compound L-1d

To a solution of compound L-1c (500 mg, 1.56 mmol) in DCM (10 mL) was added t-BuOH (305 μL, 3.11 mmol), DIC (292.5 μL, 1.87 mmol), and DMAP (19 mg, 0.16 mmol) under N₂ atmosphere. The mixture was stirred at room temperature for 4 hours and diluted with DCM (30 mL×2). The organic layer was washed with water (5 mL), dried over anhydrous Na₂SO₄, filtered, and concentrated under reduced pressure. The residue was purified by column chromatography to obtain compound L-1d (278.5 mg, 47%).

¹H NMR (400 MHz, CDCl₃) δ 4.01 (s, 2H), 3.70-3.66 (m, 18H), 3.38 (t, J=4.8 Hz, 2H), 1.47 (s, 9H).

Preparation of Compound L-1e

To a solution of compound L-1d (278 mg, 0.74 mmol) in EtOH (5 mL) was added Pd/C (236 mg, 0.11 mmol) and 4M-HCl (in 1,4-dioxane) under N₂ atmosphere. The mixture was stirred at room temperature for 1 hour. The mixture was filtered through celite to remove Pd/C, and concentrated to obtain compound L-1e (255.3 mg, 89.2%).

¹H NMR (400 MHz, DMSO-d₆) δ 8.32 (s, 1H), 3.98 (s, 2H), 3.55-3.40 (m, 18H), 3.86 (t, J=5.6 Hz, 2H), 2.70-2.64 (m, 2H), 1.42 (s, 9H).

Preparation of Compound MPS-D2

To a solution of compound L-1e (255.3 mg, 0.66 mmol) and compound MPS-D1 (240.6 mg, 0.72 mmol) in DMF (6 mL) was added HBTU (300 mg, 0.79 mmol) and DIPEA (229.3 μL, 1.32 mmol) under a nitrogen atmosphere. The mixture was stirred at room temperature for 2 hours and diluted with EA (20 mL×2) and water (5 mL). The organic layer was dried over anhydrous Na₂SO₄, filtered, and concentrated under reduced pressure. The residue was purified by column chromatography to obtain compound MPS-D2 (306 mg, 71%).

¹H NMR (400 MHz, CDCl₃) δ 7.95 (s, 4H), 7.82 (d, J=8.0 Hz, 2H), 7.38 (d, J=8.0 Hz, 2H), 7.33-7.30 (m, 1H), 3.98 (s, 2H), 3.68-3.63 (m, 18H), 3.55-3.53 (m, 2H), 3.49-3.47 (m, 2H), 2.95 (s, 1H), 2.88 (s, 1H), 2.46 (s, 3H) 1.46 (s, 9H). EI-MS m/z: 666 (M⁺+1).

[Example 29] Preparation of Compound MPS-D4

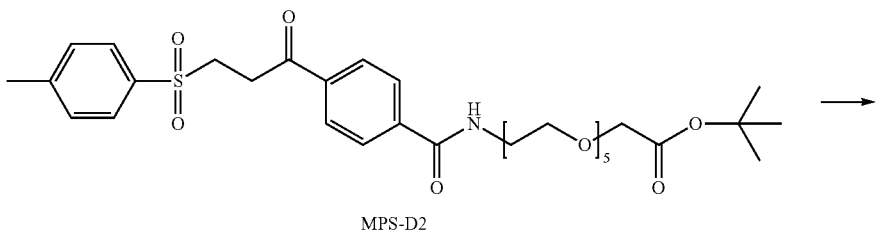

MPS-D2

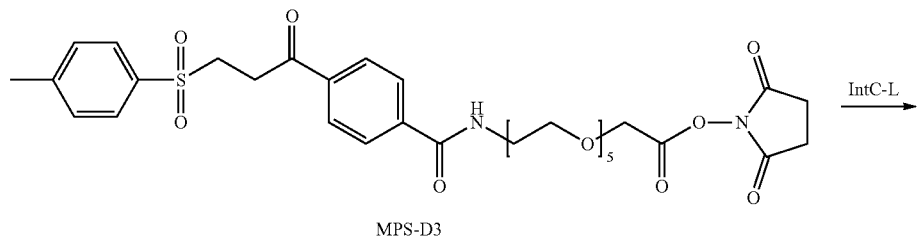

MPS-D3

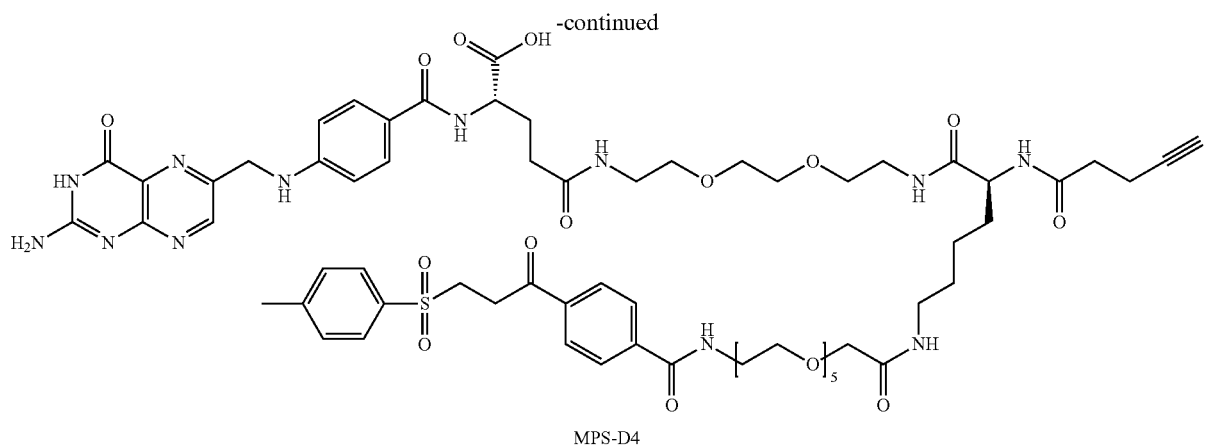

MPS-D4

Preparation of Compound MPS-D3

To a solution of compound MPS-D2 (120 mg, 0.18 mmol) in DCM (8 mL) was added TFA (4 mL) at 0° C. The reaction was allowed to warm to room temperature over 2 hours under $N_2$ atmosphere. After the reaction was completed, the mixture was concentrated under reduced pressure three times by using toluene as a co-solvent, thereby removing TFA. Then, the mixture was dissolved in DMF again, and NHS (31 mg, 0.27 mmol) and EDCI (52 mg, 0.27 mmol) were added thereto. The mixture was stirred overnight at room temperature. After the reaction was completed, compound MPS-D3 was used directly in the next step without further purification (127 mg, crude).

EI-MS m/z: 707 ($M^+$).

Preparation of Compound MPS-D4

To a solution of compound IntC-L (60 mg, 0.08 mmol) and compound MPS-D3 (82 mg, 0.12 mmol) in DMF (6 mL) was added DIPEA (112 μL, 0.64 mmol) under $N_2$ atmosphere. The mixture was stirred for 30 minutes and dissolved in DMSO (3 mL) and purified by HPLC, which produced compound MPS-D4 (77 mg, 73%).

EI-MS m/z: 1373 (M').

[Example 30] Preparation of Compound MPS-D5 mmol) at room temperature under $N_2$ atmosphere. The reaction was cooled to 0° C. and PyBop (1.17 g, 2.26 mmol) and DIPEA (524 μL, 3.01 mmol) were added thereto. The mixture was stirred at room temperature for 2 hours and diluted with EA (30 mL×2) and distilled water (20 mL). The organic layer was extracted and washed with brine (50 mL), dried over anhydrous $Na_2SO_4$, filtered, and concentrated under reduced pressure. The residue was purified by column chromatography to obtain compound MPS-D5 (510 mg, 92%).

$^1$H NMR (400 MHz, $CDCl_3$) δ 9.11 (t, J=5.2 Hz, 1H), 7.98-7.89 (m, 4H), 7.79 (d, J=8.0 Hz, 2H), 7.43 (d, J=8.4 Hz, 2H), 4.05-4.03 (m, 2H), 3.60 (t, J=7.6 Hz, 2H), 3.39 (t, J=7.2 Hz, 2H), 3.12 (s, 1H), 2.38 (s, 3H).

[Example 31] Preparation of Compound IntA-Q7

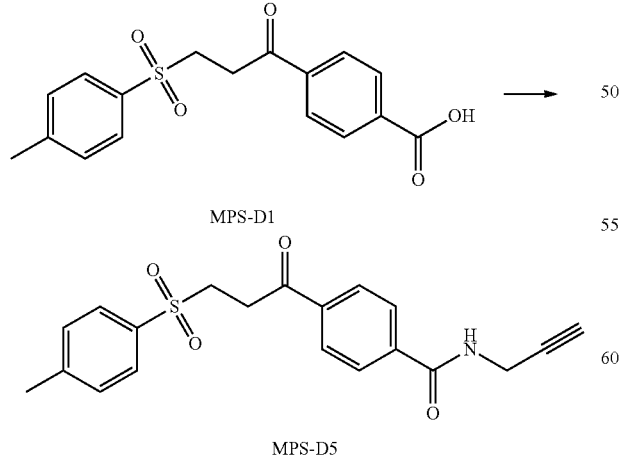

To a solution of compound MPS-D1 (500 mg, 1.50 mmol) in DMF (8 mL) was added propargyl amine (106 μL, 1.65

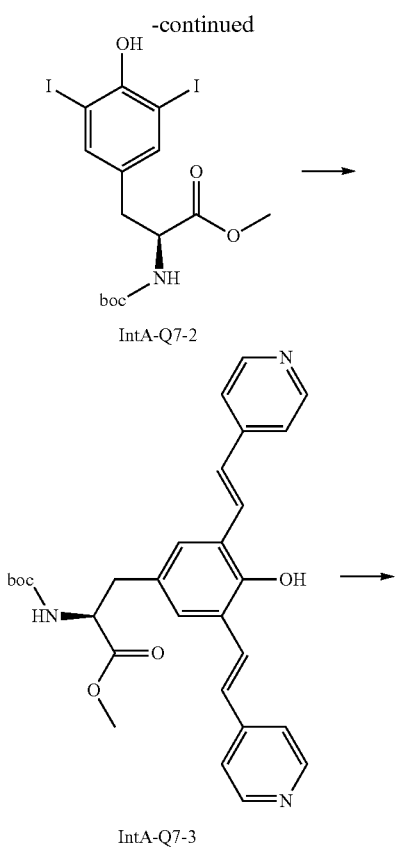

The organic layer was extracted and washed with brine (50 mL), dried over anhydrous Na$_2$SO$_4$, filtered and concentrated under reduced pressure to obtain compound IntA-Q7-2 (1.22 g, quant.).

$^1$H NMR (400 MHz, DMSO-d$_6$) δ 9.38 (s, 1H), 7.60 (s, 2H), 7.30 (d, J=8.4 Hz, 1H), 4.15 (m, 1H), 3.63 (s, 3H), 2.76-2.62 (m, 2H), 1.33 (s, 9H).

Preparation of Compound IntA-Q7-3

To a solution of compound IntA-Q7-2 (1.1 g, 2.01 mmol) and 4-vinylpyridine (650 μL, 6.30 mmol) in DMF (12 mL) was added Pd(OAc)$_2$ (23 mg, 0.101 mmol), P (o-tol)$_3$ (43 mg, 0.141 mmol), and DIPEA (1.75 mL) at room temperature under N$_2$ atmosphere. The mixture was stirred at 100° C. for 3 hours. The mixture was cooled to room temperature, followed by celite filtration, and then washed with EA (20 mL). The filtrate was concentrated under reduced pressure, and the residue was purified by column chromatography to obtain compound IntA-Q7-3 (790 mg, 78%).

EI-MS m/z: 502 (M$^+$).

Preparation of Compound IntA-Q7

To a solution of compound IntA-Q7-3 (100 mg, 0.2 mmol) in ACN (6 mL) and DMF (3 mL) was added Et$_3$N (280 μL, 2.0 mmol) at room temperature under N$_2$ atmosphere. SO$_2$F$_2$ gas was introduced via balloon, and the mixture was stirred at room temperature for 3 hours. The mixture was quenched with saturated NaHCO$_3$ (10 mL×2) and diluted with EA (20 mL). The organic layer was extracted with brine (10 mL), dried over anhydrous Na$_2$SO$_4$, filtered, concentrated under reduced pressure. The residue was purified by column chromatography to obtain compound IntA-Q7 (75 mg, 65%).

EI-MS m/z: 584 (M$^+$).

[Example 32] Preparation of Compound A-15-1

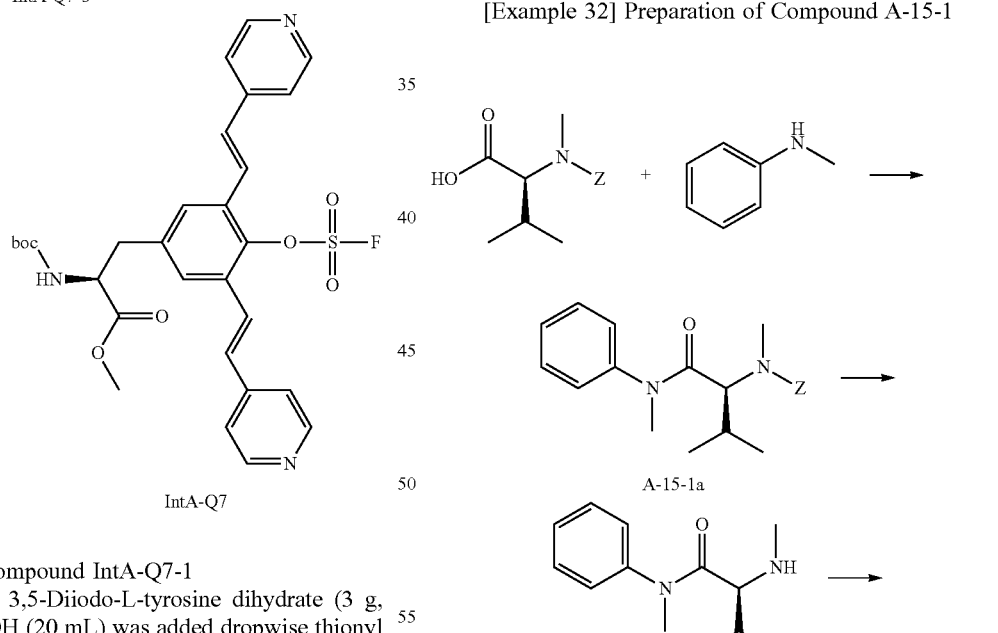

Preparation of Compound IntA-Q7-1

To a solution of 3,5-Diiodo-L-tyrosine dihydrate (3 g, 6.39 mmol) in MeOH (20 mL) was added dropwise thionyl chloride (836 μL, 11.5 mmol) at 0° C. under N$_2$ atmosphere. The mixture was stirred overnight at room temperature. After the reaction was completed, the mixture was concentrated to produce compound IntA-Q7-1 (2.86 g, quant.).

EI-MS m/z: 448 (M$^+$).

Preparation of Compound IntA-Q7-2

To a solution of compound IntA-Q7-1 (1 g, 2.24 mmol) in ACN (10 mL) was added Boc$_2$O (730 mg, 3.36 mmol) and Et$_3$N (940 μL, 6.72 mmol) at 0° C. under N$_2$ atmosphere. The mixture was stirred at room temperature for 15 hours and quenched with EA (30 mL×2) and citric acid (30 mL).

Preparation of Compound A-15-1a

To a solution of z-Valine (1.01 g, 3.81 mmol) and N-methylaniline (412 μL, 3.81 mmol) in DCM (15 mL) was added DCC (1.18 g, 5.71 mmol) and DMAP (92 mg, 0.76 mmol) at room temperature under $N_2$ atmosphere, followed by stirring at room temperature for 3 hours. The mixture was filtered through celite and concentrated under reduced pressure. The residue was purified by column chromatography to obtain compound A-15-1a (1.05 g, 78%).

EI-MS m/z: 584 (M+).

Preparation of Compound A-15-1b

Compound A-15-1a (1.05 g, 2.96 mmol) was dissolved in MeOH (15 mL) under a nitrogen atmosphere, Pd/C (378 mg, 0.18 mmol) was added. After stirring at room temperature for 2 hours under $H_2$, the mixture was filtered through celite and washed with MeOH (30 mL). The filtrate was concentrated to obtain compound A-15-1b (560 mg, 86.0%).

$^1$H NMR (400 MHz, CDCl$_3$) δ 7.45-7.41 (m, 2H), 7.38-7.36 (m, 1H), 7.19 (d, J=7.6 Hz, 1H), 3.32 (s, 3H), 2.88 (d, J=6.0 Hz, 1H), 2.33 (s, 3H), 1.73 (q, J=6.8 Hz, 1H), 0.86 (d, J=6.8 Hz, 3H), 0.80 (d, J=6.8 Hz, 3H).

Preparation of Compound A-15-1

To a solution of compound A-15-1b (220 mg, 0.99 mmol) in DMF (8 mL) was added 37% formaldehyde (223 μL, 2.99 mmol) and AcOH (1.14 mL, 19.8 mmol) under $N_2$ atmosphere. After stirring at room temperature for 5 minutes, NaCNBH$_3$ (125 mg, 1.98 mmol) was added. The mixture was stirred at room temperature for 2 hours and quenched with saturated NaHCO$_3$ (15 mL×2). To the mixture was added EA (20 mL×2) and brine (20 mL). The organic layer was dried over anhydrous Na$_2$SO$_4$, filtered, concentrated under reduced pressure. The residue was purified by column chromatography to obtain compound A-15-1 (189 mg, 81%).

EI-MS m/z: 235 (M+).

[Example 33] Preparation of Compound IntA-Q8

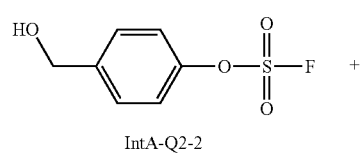

IntA-Q2-2

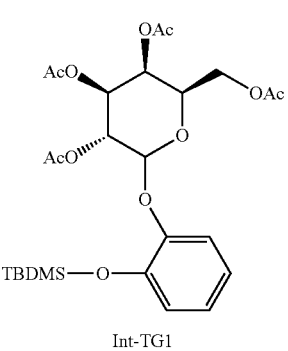

Int-TG1

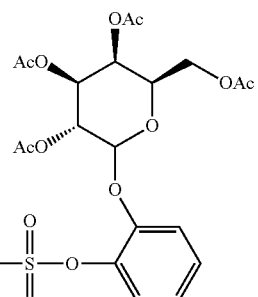

IntA-Q8-1

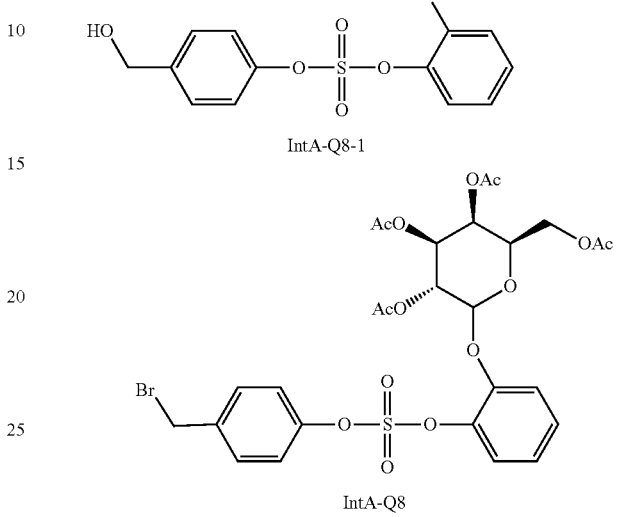

IntA-Q8

Preparation of Compound IntA-Q8-1

To a solution of compound Int-TG1 (Example 2, 120 mg, 0.22 mmol) and IntA-Q2-2 (Example 13, 50 mg, 0.24 mmol) in ACN (2 mL) under $N_2$ atmosphere was added dropwise BEMP (13 μL, 44 μmol). The mixture was stirred at room temperature for 2 hours and added EA (10 mL×2) and citric acid (15 mL). The organic layer was washed with brine (50 mL), dried over anhydrous Na$_2$SO$_4$, filtered and concentrated under reduced pressure. The residue was purified by column chromatography to obtain compound IntA-Q8-1 (72 mg, 54%).

EI-MS m/z: 649 (M++Na).

Preparation of Compound IntA-Q8

To a solution of compound IntA-Q8-1 (72 mg, 0.12 mmol) in THF (4 mL) was added NBS (31 mg, 0.18 mmol) and PPh$_3$ (45 mg, 0.18 mmol) under $N_2$ atmosphere. The mixture was stirred at room temperature for 3 hours and concentrated under reduced pressure. The residue was purified by column chromatography to obtain compound IntA-Q8 (53 mg, 67%).

EI-MS m/z: 713 (M++Na).

[Example 34] Preparation of Compound IntA-Q9

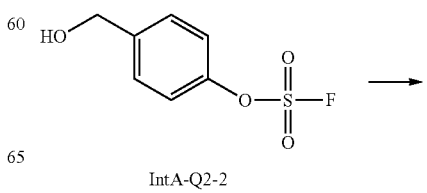

IntA-Q2-2

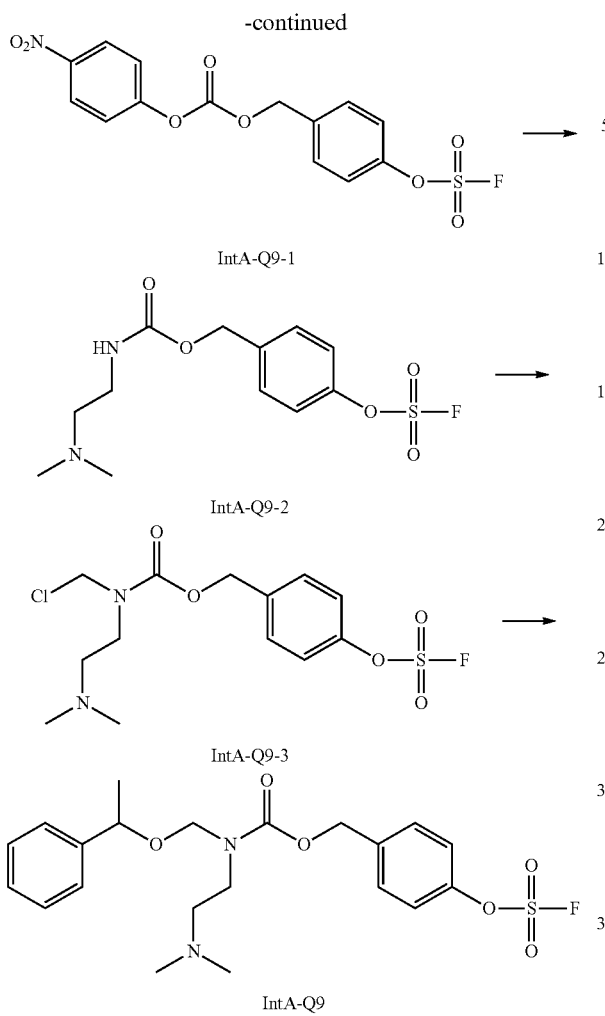

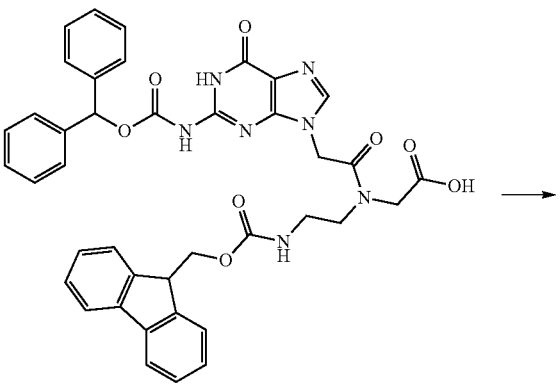

PNA

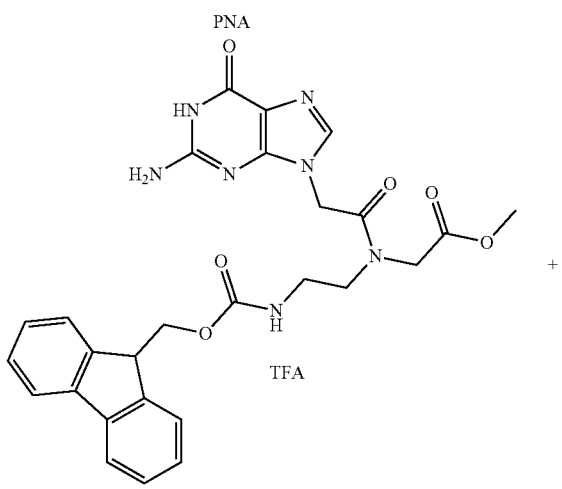

IntB-Q2-1

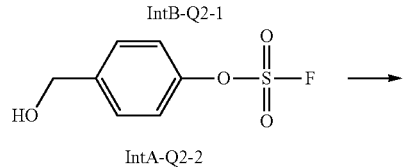

IntA-Q2-2

Preparation of Compound IntA-Q9-1

To a solution of compound IntA-Q2-2 (Example 13, 300 mg, 1.45 mmol) in DMF (5 mL) was added 4-nitrophenyl chloroformate (664 mg, 2.18 mmol) and DIPEA (0.51 mL, 2.91 mmol) at room temperature under $N_2$ atmosphere. After stirring overnight, EA (50 mL) and water (50 mL) were added. The obtained organic layer was dried over anhydrous $Na_2SO_4$, filtered and concentrated under reduced pressure. The residue was purified by column chromatography to obtain compound IntA-Q9-1 (461.3 mg, 85%).

$^1$H NMR (400 MHz, CDCl$_3$) δ 8.29 (d, J=9.2 Hz, 2H), 7.58 (d, J=8.8 Hz, 2H), 7.42-7.38 (m, 4H), 5.33 (s, 2H).

Preparation of Compound IntA-Q9-2

To a solution of compound IntA-Q9-1 (461.3 mg, 1.24 mmol) in DMF (10 mL) and pyridine (2 mL) was added 4-N,N-dimethylethylenediamine (0.14 mL, 1.24 mmol), HOBT (38 mg, 0.25 mmol), and DIPEA (0.22 mL, 1.24 mmol) at room temperature under $N_2$ atmosphere. After stirring for 3 hours, EA (60 mL) and water (60 mL) were added. The obtained organic layer was dried over anhydrous $Na_2SO_4$, filtered and concentrated under reduced pressure. The residue was purified by column chromatography to obtain compound IntA-Q9-2 (337 mg, 89%).

$^1$H NMR (400 MHz, CDCl$_3$) δ 7.48 (d, J=8.8 Hz, 2H), 7.33 (d, J=8.4 Hz, 2H), 5.35 (br, 1H), 5.12 (s, 2H), 3.30 (q, J=5.6, 5.2 Hz, 2H), 2.43 (t, J=5.6 Hz, 2H), 2.24 (s, 6H).

EI-MS m/z: 321 (M$^+$).

Preparation of Compound IntA-Q9-3

To a solution of compound IntA-Q9-2 (100 mg, 0.31 mmol) in anhydrous DCM (3 mL) was added paraformaldehyde (13.1 mg, 0.437 mmol) and TMS-Cl (0.06 mL, 0.47 mmol) at room temperature under $N_2$ atmosphere. After stirring for 3 hours, paraformaldehyde and TMS-Cl each having an amount of 10 equivalents were further added thereto, and the mixture was stirred at 50° C. for 30 minutes.

The crude compound IntA-Q9-3 was used directly in the next step without further purification.

EI-MS m/z: 365 (M$^+$).

Preparation of Compound IntA-Q9

To a solution of compound IntA-Q9-3 (20 mg, 0.054 mmol) in anhydrous DCM (1.5 mL) was added an excessive amount of phenylethyl alcohol and DIPEA at room temperature under $N_2$ atmosphere. After stirring for 2 hours, the mixture was concentrated under reduced pressure. The residue was dissolved in DMSO (4 mL) and purified by prep-HPLC, which produced the compound IntA-Q9 (11.8 mg, 48%).

EI-MS m/z: 455 (M$^+$).

[Example 35] Preparation of Compound IntB-Q2

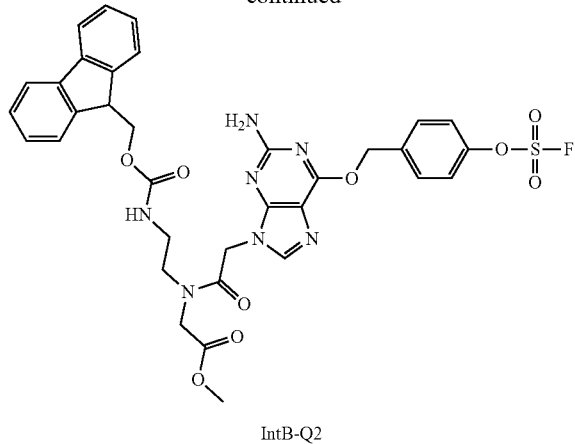

IntB-Q2

Preparation of Compound IntB-Q2-1

To a solution of PNA (380 mg, 0.51 mmol) in MeOH (4 mL) was added dropwise SOCl$_2$ (112 μL, 1.54 mmol) under N$_2$ atmosphere. After stirring overnight at 40° C., SOCl$_2$ (112 μL, 1.54 mmol) was further added thereto, followed by stirring at 40° C. for 3 hours. The mixture was concentrated under reduced pressure. The residue was dissolved in DMSO and purified by prep-HPLC, which produced the compound IntB-Q2-1 (233 mg, 69%).

EI-MS m/z: 546 (M$^+$).

Preparation of Compound IntB-Q2

To a solution of compound IntB-Q2-1 (233 mg, 0.35 mmol) in THF (2 mL) was added compound IntA-Q2-2 (Example 13, 160 mg, 0.78 mmol) and PPh$_3$ (148 mg, 0.57 mmol) under N$_2$ atmosphere. The mixture was cooled to 0° C. DEAD was added dropwise and the mixture was stirred for 3 hours and diluted with EA (50 mL×1). The organic layer was washed with H$_2$O (50 mL×2), and brine (30 mL), dried over anhydrous Na$_2$SO$_4$, filtered and concentrated under reduced pressure. The residue was purified by column chromatography to obtain compound IntB-Q2 (118 mg, 38%).

EI-MS m/z: 734 (M$^+$).

[Example 36] Preparation of Compound POS-D1

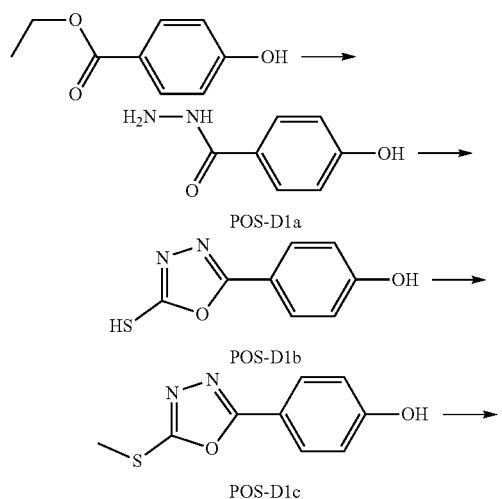

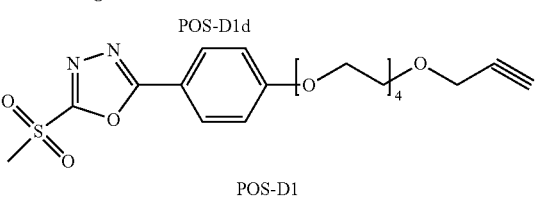

POS-D1d

POS-D1

Preparation of Compound POS-D1a

To a solution of Ethyl 4-hydrobenzoate (20 g, 120.35 mmol) in EtOH (60 mL) was added NH$_2$NH$_2$—H$_2$O (88 mL, 1805.4 mmol) under N$_2$ atmosphere. The mixture was stirred overnight at reflux. After the reaction was completed, the mixture was cooled to room temperature, and concentrated under reduced pressure, followed by EtOH trituration, thereby obtaining compound POS-D1a (17.539 g, 96%).

$^1$H NMR (400 MHz, DMSO-d$_6$) δ 9.50 (s, 1H), 7.68 (d, J=8.4 Hz, 2H), 6.78 (d, J=8.8 Hz, 2H), 4.37 (s, 2H). EI-MS m/z: 431 (M$^+$).

Preparation of compound POS-D1b

To a solution of compound POS-D1a (17.54 g, 115.28 mmol) in EtOH (200 mL) and DMF (100 mL) was added CS$_2$ (45 mL, 749.32 mmol) and KOH (6.5 g, 115.28 mmol) under N$_2$ atmosphere. After stirring at 85° C. for 18 hours, EA (500 mL) and H$_2$O (500 mL) were added and acidified with 1M HCl. The organic layer was washed with H$_2$O (500 mL), and brine (500 mL), dried over anhydrous Na$_2$SO$_4$, filtered and concentrated under reduced pressure. The residue was subjected to ether/HX trituration to obtain compound POS-D1b (20.7 g, 93%).

$^1$H NMR (400 MHz, DMSO-d$_6$) δ 10.44 (s, 1H), 7.72 (d, J=8.4 Hz, 2H), 6.94 (d, J=8.0 Hz, 2H). EI-MS m/z: 195 (M$^+$).

Preparation of Compound POS-D1c

To a solution of compound POS-D1b (5 g, 25.75 mmol) in THF (100 mL) was added dropwise Et$_3$N (4.3 mL, 30.9 mmol) and MeI (1.76 mL, 28.33 mmol) at 0° C. After stirring at 0° C. for 10 minutes, the mixture was warm to room temperature. And then the mixture was stirred for 2 hours and diluted with EA (100 mL×2) The organic layer was washed with H$_2$O (100 mL), and brine (100 mL), dried over anhydrous Na$_2$SO$_4$, filtered and concentrated under reduced pressure. The residue was subjected to ether trituration to obtain compound POS-D1c (5.15 g, 96%).

$^1$H NMR (400 MHz, DMSO-d$_6$) δ 7.80 (d, J=8.4 Hz, 2H), 6.94 (d, J=8.4 Hz, 2H), 2.74 (s, 3H). EI-MS m/z: 209 (M$^+$).

Preparation of Compound POS-D1d

To a solution of compound POS-D1c (3.2 g, 15.37 mmol) in EtOH (150 mL) was added 70% m-CPBA (11.4 g, 46.11 mmol) at 0° C. under N$_2$ atmosphere. After stirring at room temperature for 5 hours, 70% m-CPBA (11.4 g, 46.11 mmol) was further added. Then the mixture was stirred overnight at room temperature and quenched with H$_2$O (500 mL), saturated NaHCO$_3$ (300 mL), diluted with EA (500 mL×2). The organic layer was washed with brine (300 mL), dried over anhydrous Na$_2$SO$_4$, filtered and concentrated under reduced pressure. The residue was subjected to HX/EA=1:1 (100 mL) trituration to obtain compound POS-D1d (3.2 mg, 89%).

¹H NMR (400 MHz, DMSO-d₆) δ 7.95 (d, J=8.8 Hz, 2H), 7.01 (d, J=8.8 Hz, 2H), 3.69 (4 s, 3H). EI-MS m/z: 241 (M⁺).

Preparation of Compound POS-D1

To a solution of tetraethylene glycol (17.3 ml, 0.10 mol) in THF (50 mL) was added dropwise NaH (2.6 g, 0.065 mmol) at 0° C. After stirring at 0° C. for 1 hour, propargyl bromide (5.95 g, 0.05 mol) was added. The mixture was stirred overnight at room temperature and quenched with ice/water, diluted with EA (100 mL×2). The organic layer was washed with H₂O (100 mL), and brine (100 mL), dried over anhydrous Na₂SO₄, filtered and concentrated under reduced pressure. 660 mg (2.84 mmol) of compound obtained by ether trituration from the residue, i.e., 3,6,9,12-tetraoxapentadec-14-yn-1-ol (5.87 g, 51%, ¹H NMR (400 MHz, CDCl₃) δ 4.21 (s, 2H), 3.73-3.66 (m, 14H), 3.59-3.61 (m, 2H), 2.60 (s, 1H), 2.42 (t, J=2.4 Hz, 1H)) and compound D-4-5 (310 mg, 1.29 mmol) were dissolved in THF (8 mL) and DMF (0.8 mL), and PPh₃ (667 mg, 2.58 mmol) was added. The mixture was cooled to 0° C. 2.2M DEAD (1.17 mL, 2.58 mmol) was added thereto, and the mixture was stirred at 0° C. for 3 hours. After the reaction was completed, EA (15 mL×2) and distilled water (15 mL) were added, and the organic layer was extracted and washed with brine (20 mL). The obtained organic layer was dried over anhydrous Na₂SO₄, filtered and concentrated under reduced pressure to obtain compound POS-D1 (205 mg, 30%).

EI-MS m/z: 455 (M⁺).

[Example 37] Preparation of Compound Int-TG11

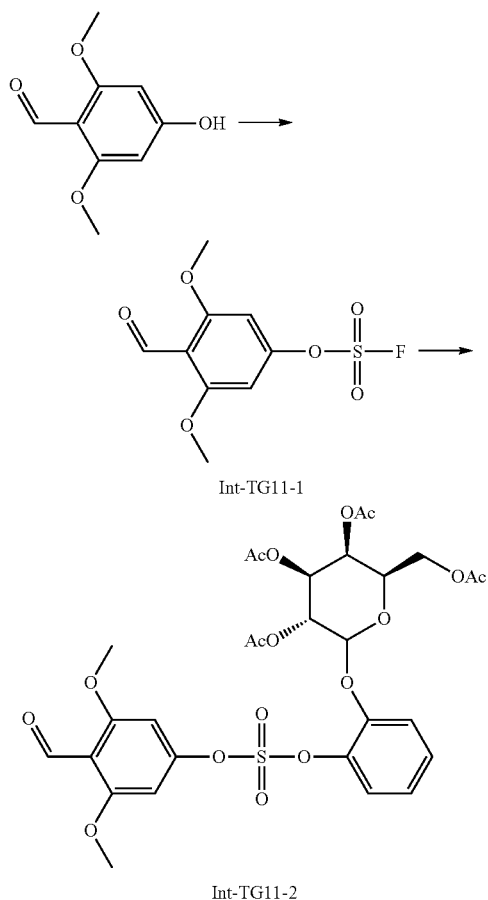

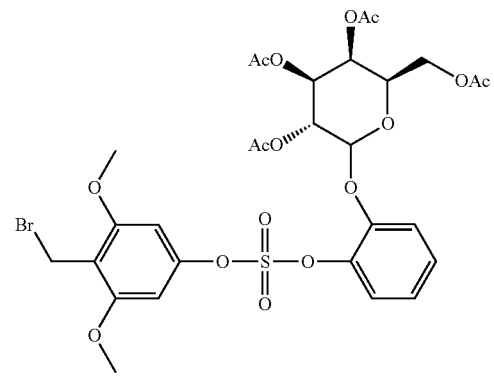

Int-TG11-3 was synthesized via a similar synthetic route as described in Example 6 and Example 33.

Preparation of Compound Int-TG11-1

Yield 99%

EI-MS m/z: 265 (M⁺). 1H-NMR (400 MHz, CDCl₃) δ 10.41 (s, 1H), 6.54 (s, 2H), 3.91 (s, 6H).

Preparation of Compound Int-TG11-2

Yield 99%

EI-MS m/z: 685 (M⁺). 1H-NMR (400 MHz, CDCl₃) δ 10.42 (s, 1H), 7.37 (d, J=8 Hz, 1H), 7.31-7.26 (m, 2H), 7.15-7.11 (m, 1H), 6.58 (s, 2H), 5.54-5.45 (m, 2H), 5.09 (t, J=8.4 Hz, 2H), 4.27-4.22 (m, 1H), 4.16-4.05 (m, 2H), 3.89 (s, 6H), 2.19 (s, 3H), 2.08 (s, 3H), 2.06 (s, 3H), 2.01 (s, 3H)

Preparation of Compound Int-TG11-3

Yield 97%. EI-MS m/z: 669 (M').

¹H-NMR (400 MHz, CDCl₃) δ 7.41 (d, J=8 Hz, 1H), 7.27 (t, J=5.2 Hz, 2H), 7.15-7.11 (m, 1H), 6.53 (s, 2H), 5.53-5.44 (m, 2H), 5.29 (s, 1H), 5.11-5.06 (m, 1H), 4.99 (d, J=8 Hz, 1H), 4.77 (s, 2H), 4.26-4.22 (m, 1H), 4.15-4.11 (m, 1H), 4.06-4.02 (m, 1H), 3.87 (s, 6H), 2.19 (s, 3H), 2.06-2.03 (m, 6H), 1.99 (s, 3H)

Preparation of Compound Int-TG11

To a solution of compound Int-TG11-3 (137 mg, 0.199 mmol) in dry THF (5 ml) was added NBS (53 mg, 0.299 mmol) and triphenylphosphine (78 mg, 0.299 mmol) at room temperature. After stirring 2 hours, the mixture was concentrated under reduced pressure. The residue was purified by column chromatography to produce compound Int-TG11 (129 mg, 86%).

EI-MS m/z: 750 (M⁺¹). 1H-NMR (400 MHz, CDCl₃) δ 7.36 (m, 1H), 7.29-7.28 (m, 2H), 6.56 (s, 1H), 6.53 (s, 1H), 5.58-5.51 (m, 1H), 5.46 (d, J=2.8 Hz, 1H), 5.12-5.06 (m, 2H), 4.60 (s, 2H), 4.27-4.23 (m, 1H), 4.17-4.11 (m, 1H), 4.08-4.05 (m, 1H), 3.88 (s, 3H), 3.86 (s, 3H), 2.20 (s, 3H), 2.09 (s, 3H), 2.08 (s, 3H), 2.01 (s, 3H)

[Example 38] Preparation of Compound Int-TG12

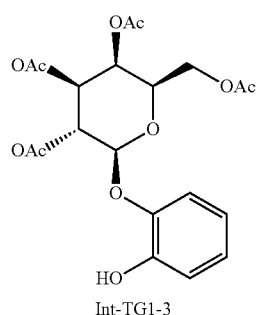

Int-TG1-3

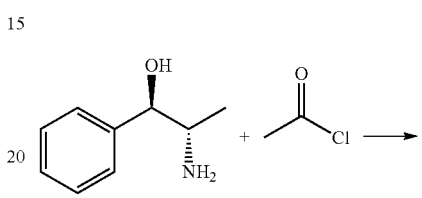

Int-TG12

To a solution of compound Int-TG1-3 (530 mg, 1.2 mmol) in dry THF (25 ml) was added 1,1'-Sulfonyldiimidazole (477 mg, 2.4 mmol) and $Cs_2CO_3$ (196 mg, 0.6 mmol). After 18 hours under reflux, the mixture was quenched with 2 N aq. HCl (100 mL). The organic layer was extracted with EtOAc (2×20 mL), dried over anhydrous MgSO4, filtered and concentrated. The residue was purified by column chromatography to produce the compound Int-TG12 (396 mg, 58%).

$^1$H-NMR (400 MHz, $CDCl_3$) δ 7.84 (s, 1H), 7.35 (s, 1H), 7.34-7.31 (m, 1H), 7.20-7.16 (m, 2H), 7.05 (t, 1H), 6.86 (m, 1H), 5.51-5.45 (m, 2H), 5.10 (dd, J=3.6 Hz, 1H), 4.98 (d, J=8 Hz, 1H), 2.24 (s, 3H), 2.13 (s, 3H), 2.07 (s, 3H), 2.04 (s, 3H).

[Example 39] Preparation of Compound Int-TG13

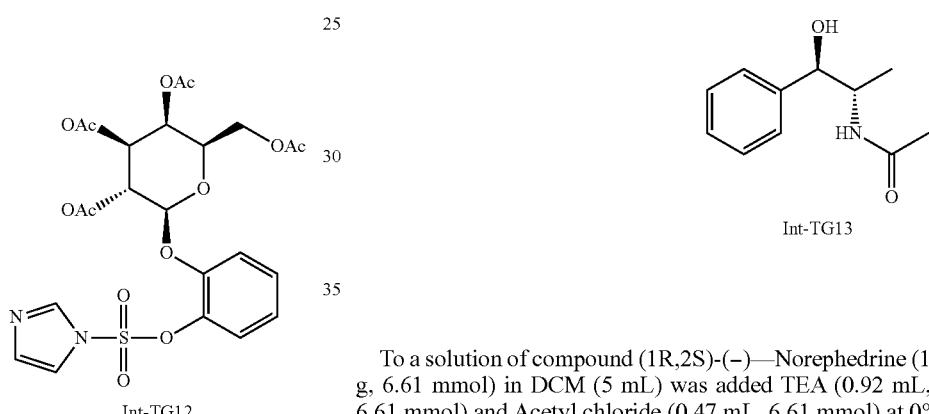

Int-TG13

To a solution of compound (1R,2S)-(−)—Norephedrine (1 g, 6.61 mmol) in DCM (5 mL) was added TEA (0.92 mL, 6.61 mmol) and Acetyl chloride (0.47 mL, 6.61 mmol) at 0° C. under $N_2$ atmosphere. After stirring at room temperature for 2 hours, the mixture was quenched with $H_2O$ (7 mL). The organic layer was extracted with DCM (2×8 mL, dried over anhydrous $MgSO_4$, filtered and concentrated. The residue was purified by column chromatography to produce compound Int-TG13 (987 mg, 78%).

$^1$H-NMR (400 MHz, $CDCl_3$) δ 7.28 (m, 5H), 5.70 (m, 1H), 4.86 (s, 1H), 4.34-4.30 (m, 1H), 3.65 (m, 1H), 2.00 (s, 3H), 1.01 (d, J=7.2 Hz, 3H)

[Example 40] Preparation of Compound Int-TG14

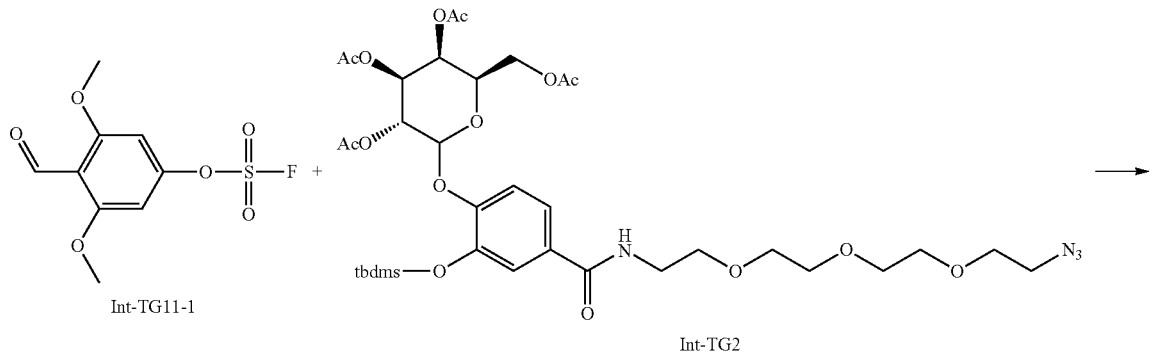

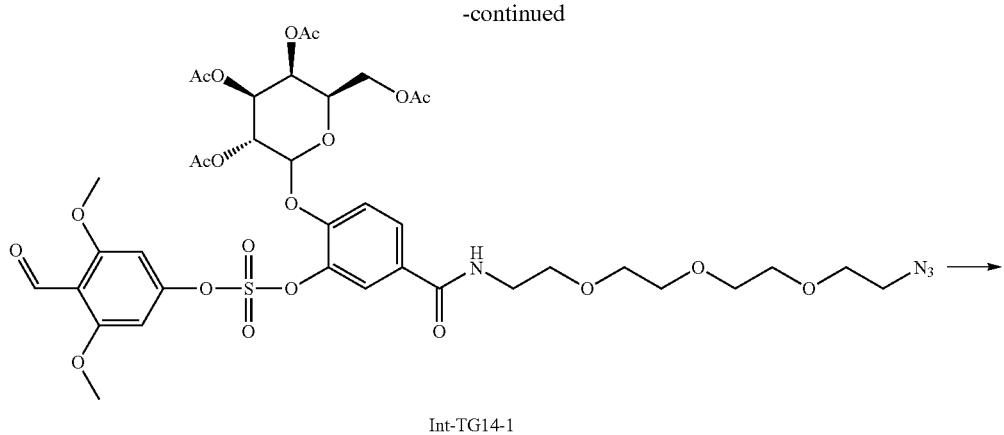
Int-TG14-1
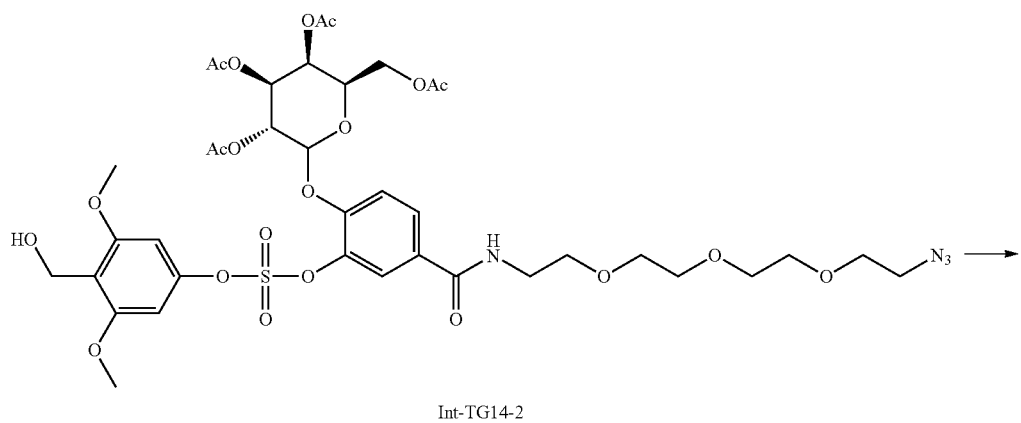
Int-TG14-2
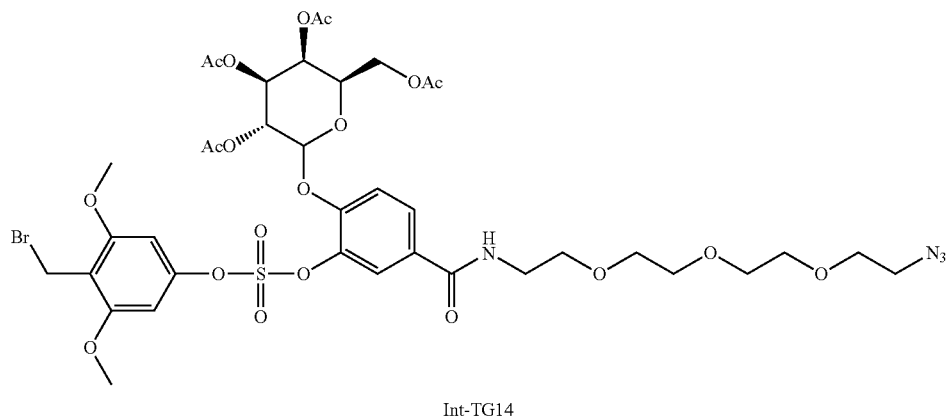
Int-TG14
Compound Int-TG14 was synthesized via a similar synthetic route as described in Example 6 and Example 37.
Preparation of Compound Int-TG14-1
Yield 99%; EI-MS m/z: 929 (M$^{+1}$).
Preparation of Compound Int-TG14-2
Yield 96%; EI-MS m/z: 931 (M$^{+1}$).
Preparation of Compound Int-TG14
Yield 75%; EI-MS m/z: 750 (M$^{+1}$).

[Example 41] Preparation of Compound IntB-Q3

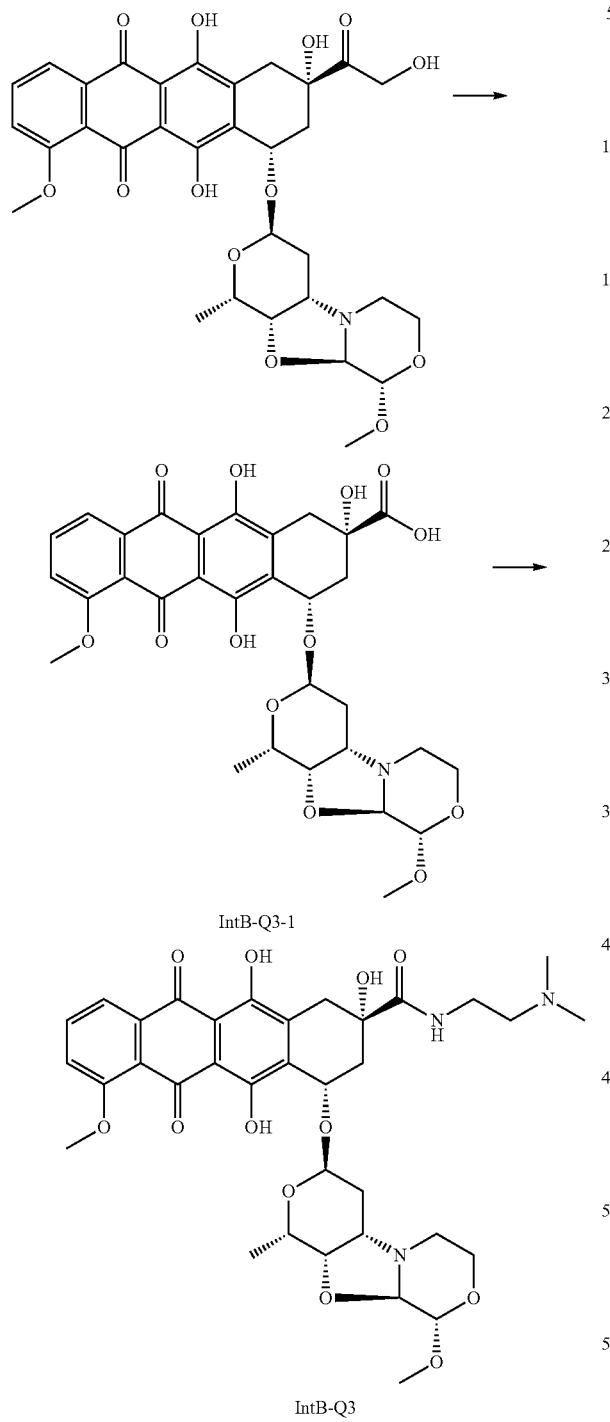

Preparation of Compound IntB-Q3-1

To a solution of PNU-1529682 (52 mg, 0.081 mmol) in MeOH (5 ml)/distilled water (3 mL) was added NaIO₄ (18 mg, 0.081 mmol) at room temperature. After stirring 2 hours, the mixture was concentrated under reduced pressure, which produced the crude compound IntB-Q3-1 (51 mg, 99%). EI-MS m/z: 628 (M$^{+1}$).

Preparation of Compound IntB-Q3

To a solution of compound IntB-Q3-1 (51 mg, 0.081 mmol) in dry DCM (5 mL) was added 2-(Dimethylamino) ethyl amine (6.1 μl, 0.089 mmol) and TEA (34 μl, 0.243 mmol), TBTU (52 mg, 0.162 mmol) at room temperature. After stirring 1 hours, the mixture was diluted with DCM (2×8 mL). The organic layer was washed with H₂O (8 mL), died over anhydrous Na₂SO₄, filtered and concentrated under reduced pressure. The residue was purified by column chromatography to produce compound IntB-Q3 (38 mg, 67%).

EI-MS m/z: 698 (M$^{+1}$).

[Example 42] Preparation of Compound IntB-Q4

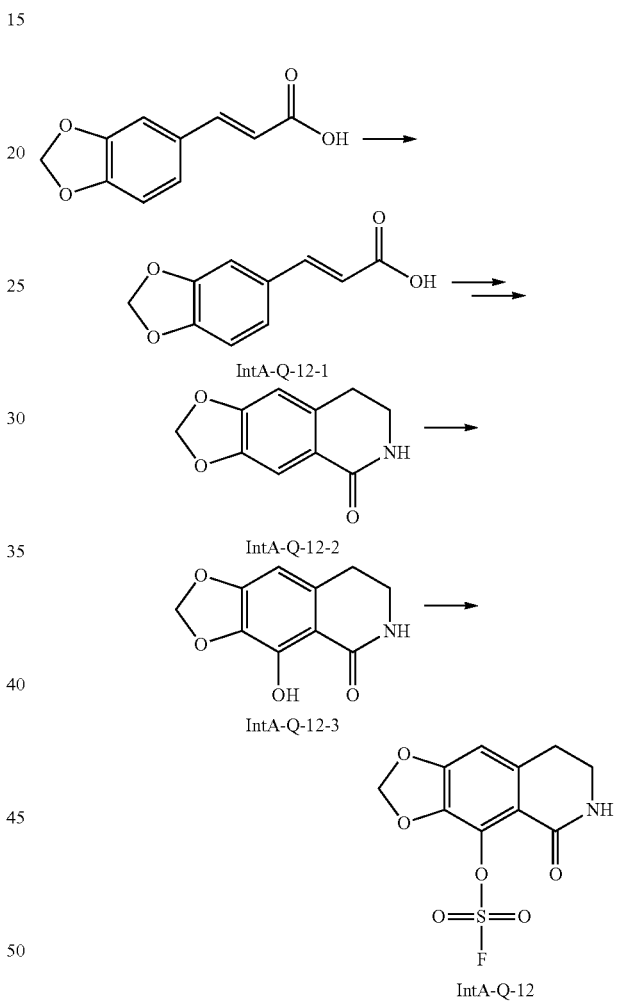

Preparation of Compound IntA-Q-12-1

To a solution of (3,4-methylenedioxy)-cinnamic acid (1.5 g, 7.8 mmol) in MeOH (200 mL), acetic acid (10 mL) was added 10% Pd/C (500 mg) under N₂ atmosphere. The mixture was stirred at room temperature for 22 hours under H₂ atmosphere. Then the mixture was filtered through celite and washed with MeOH (200 mL). The filtrate was concentrated to give compound IntA-Q-12-1 as off-white crystalline solid (1.51 g, 99%).

¹H NMR (400 MHz, CDCl₃) δ 6.74-6.64 (m, 3H), 5.92 (s, 2H), 2.87 (t, J=7.8 Hz, 2H), 2.63 (t, J=7.2 Hz, 2H).

Preparation of Compound IntA-Q-12-2

To a solution of compound IntA-Q-12-2 (750 mg, 3.86 mmol) and TEA (540 μL, 3.86 mmol) in anhydrous toluene (15 mL) was added dropwise diphenylphosphoryl azide (832 µL, 3.86 mmol) at room temperature under N₂ atmosphere. The mixture was warmed to 90° C. for 90 min. After the reaction was completed, Most of the solvent was removed under reduced pressure. The residue was cooled to 0° C. under N₂ atmosphere. BF₃·OEt₂ (2.4 mL, 5.79 mmol) was added dropwise to the stirred mixture, and then stirred at room temperature for 1 hour. The mixture was diluted with EA (50 mL) and washed with saturated aqueous NaHCO₃ (100 mL). The organic layer was dried over MgSO₄, filtered and concentrated under reduced pressure. The residue was purified by column chromatography to obtain compound IntA-Q-12-2 (650 mg, 88%).

$^1$H NMR (400 MHz, CDCl₃) δ 7.51 (s, 1H), 6.65 (s, 1H), 6.06 (brs, 1H), 6.00 (s, 2H), 3.51 (m, 2H), 2.90 (t, J=6.8 Hz, 2H). EI-MS m/z: 192 (M$^{+1}$).

Preparation of Compound IntA-Q-12-4

To a solution of compound IntA-Q-12-3 (38 mg, 0.184 mmol) in THF (3 mL) was added 1 M-tBuOK (1 M in THF, 220 µL, 0.220 mmol) at room temperature. The mixture was stirred at room temperature for 1 hour under SO₂F₂, quenched with 10% HCl aqueous solution until the pH 7, and diluted with EA (50 mL). The organic layer was saturated aqueous NaCl (100 mL), dried over Na₂SO₄, filtered and concentrated under reduced pressure. The residue was purified by column chromatography to obtain a compound IntA-Q-12-4 (17 mg, 32%).

$^1$H NMR (400 MHz, CDCl₃) δ 6.71 (s, 1H), 6.15 (s, 2H), 5.77 (m, 1H), 3.50 (m, 2H), 2.93 (t, J=6.8 Hz, 2H). EI-MS m/z: 290 (M$^{+1}$)

[Example 43] Preparation of Compound Int-TG15

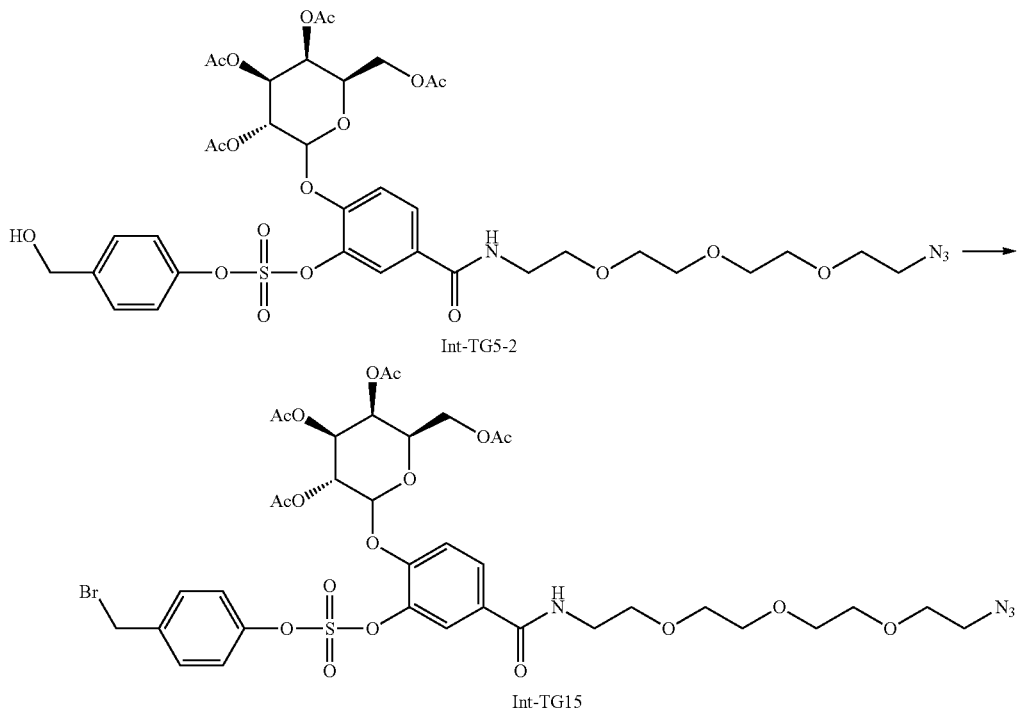

Preparation of Compound IntA-Q-12-3

To a solution of compound IntA-Q-12-2 (200 mg, 1.04 mmol) in THF (10 mL) was added dropwise n-BuLi (2.5 M in Hexane, 1 mL) at −78° C. under N₂ atmosphere. The light purple solution was stirred at −78° C. for 30 minutes and B(OMe)₃ (200 µL, 1.77 mmol) was added. The reaction was warmed to 0° C., then AcOH (154 µL) was added followed by slowly addition of 35% H₂O₂ (230 µL). After stirring at room temperature for 5 hours, diluted with EA (50 mL). The organic layer was washed with saturated aqueous NaCl (100 mL), dried over MgSO₄, filtered and concentrated under reduced pressure. The residue was purified by column chromatography to obtain a compound IntA-Q-12-3 (60 mg, 27%).

$^1$H NMR (400 MHz, CDCl₃) δ 12.33 (s, 1H), 6.29 (s, 1H), 6.03 (s, 2H), 5.89 (brs, 1H), 3.55 (m, 2H), 2.92 (t, J=6.8 Hz, 2H). EI-MS m/z: 208 (M$^{+1}$).

Compound Int-TG15 was synthesized via a similar synthetic route as described in Example 6 and Example 37. Yield 75%; EI-MS m/z: 934 (M$^{+1}$).

[Example 44] Preparation of Compound L-2

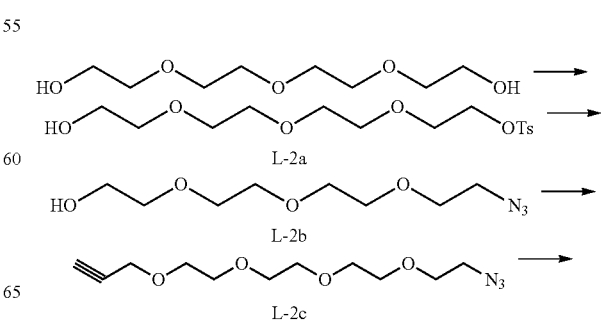

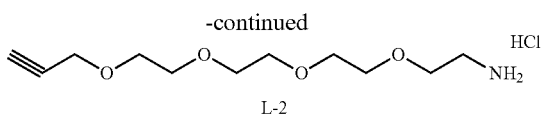

L-2

Compound L-2 was synthesized by a similar synthetic route as described in Journal of Polymer Science, Part A: Polymer Chemistry, 2012, 50(19), 3986-3995, incorporated herein by reference.

Preparation of Compound L-2a
Yield 30%
$^1$H NMR (400 MHz, CDCl$_3$) δ 7.80 (d, J=8.4 Hz, 2H), 7.34 (d, J=8.4 Hz, 2H), 4.16 (t, J=4.8 Hz, 2H), 3.74-3.58 (m, 14H), 2.45 (s, 3H).

Preparation of Compound L-2b
Yield 68%
$^1$H NMR (400 MHz, CDCl$_3$) δ 3.74-3.61 (m, 14H), 3.40 (t, J=4.8 Hz, 2H), 2.45 (t, J=6.0 Hz, 1H).

Preparation of Compound L-2c
Yield 63%
$^1$H NMR (400 MHz, CDCl$_3$) δ 4.21 (d, J=2.4 Hz, 2H), 3.72-3.67 (m, 14H), 3.39 (t, J=5.2 Hz, 2H), 2.43 (t, J=2.4 Hz, 1H).

Preparation of Compound L-2
Yield 76%
$^1$H NMR (400 MHz, CDCl$_3$) δ 4.20 (d, J=2.4 Hz, 2H), 3.71-3.61 (m, 12H), 3.51 (t, J=4.8 Hz, 2H), 2.87 (t, J=5.6 Hz, 2H), 2.43 (t, J=2.4 Hz, 1H).

[Example 45] Preparation of Compound L-3

Compound L-3 was synthesized by a similar synthetic route as described in Journal of Organic Chemistry, 2002, 67, 5032-5035, incorporated herein by reference.

Preparation of Compound L-3a
Yield 92%
$^1$H NMR (400 MHz, CDCl$_3$) δ 10.08 (s, 1H), 7.97 (q, J=8.8 Hz, 8.8 Hz, 4H), 7.16 (brs, 1H), 4.14 (d, J=2.4 Hz, 2H), 3.70-3.62 (m, 16H), 2.41 (t, J=2.4 Hz, 1H). EI-MS m/z: 384 (M$^{+1}$)

Preparation of Compound L-3b
Yield 69%
$^1$H NMR (400 MHz, CDCl$_3$) δ 7.82 (d, J=8.0 Hz, 2H), 7.60 (d, J=7.6 Hz, 2H), 6.88 (brs, 1H), 5.47 (brs, 1H), 4.14 (d, J=2.4 Hz, 2H), 3.70-3.63 (m, 16H), 2.42 (brs, 1H), 2.19 (s, 3H). EI-MS m/z: 404 (M$^{+1}$)

Preparation of Compound L-3
Yield 81%
$^1$H NMR (400 MHz, CDCl$_3$) δ 8.19 (d, J=7.2 Hz, 2H), 7.92 (d, J=7.6 Hz, 2H), 7.07 (brs, 1H), 4.16 (s, 2H), 3.70-3.49 (m, 16H), 2.42 (brs, 1H), 2.19 (s, 3H). EI-MS m/z: 402 (M$^{+1}$)

[Example 46] Preparation of Compound L-4

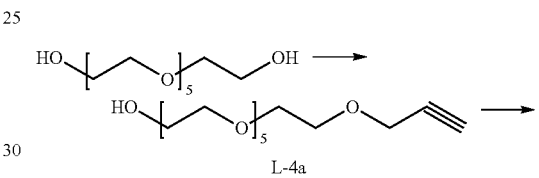

L-4a

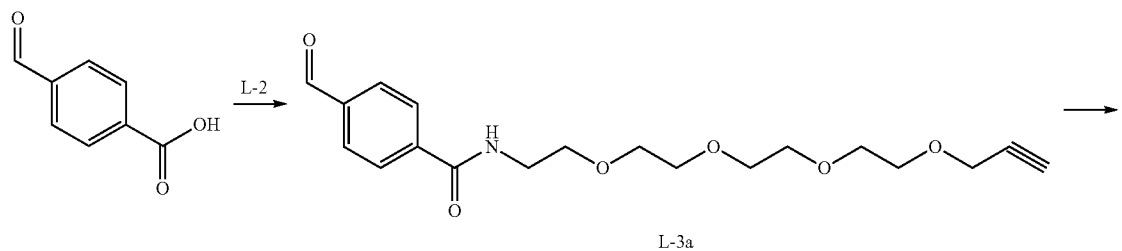

L-3a

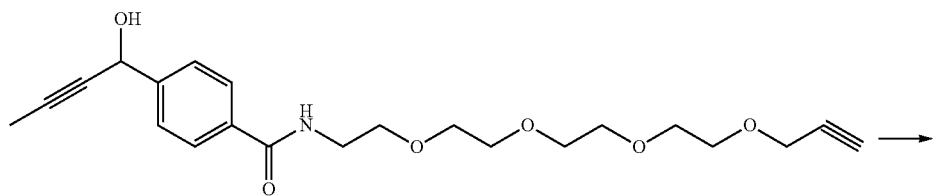

L-3b

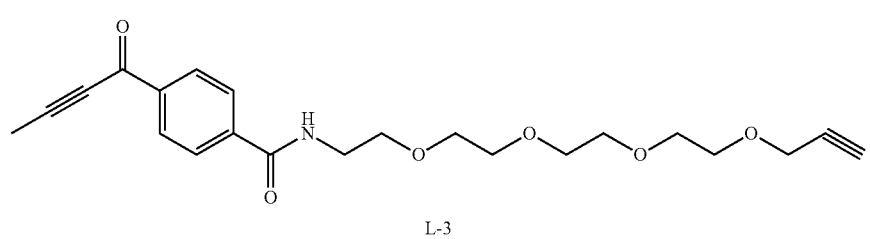

L-3

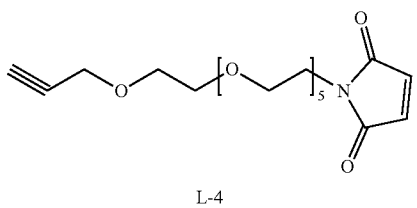

L-4

Compound L-4 was synthesized by a similar synthetic route as described in Journal of Medicinal Chemistry, 52(19), 5816-5825; 2009, incorporated herein by reference.

Preparation of Compound L-4a
Yield 55%
$^1$H NMR (400 MHz, CDCl$_3$) δ 4.21 (d, J=2.0 Hz, 2H), 3.72-3.60 (m, 24H), 2.79 (brs, 1H), 2.43 (t, J=2.4 Hz, 1H).
Preparation of Compound L-4
EI-MS m/z: 400 (M$^{+1}$)

[Example 47] Preparation of Compound MPS-D6

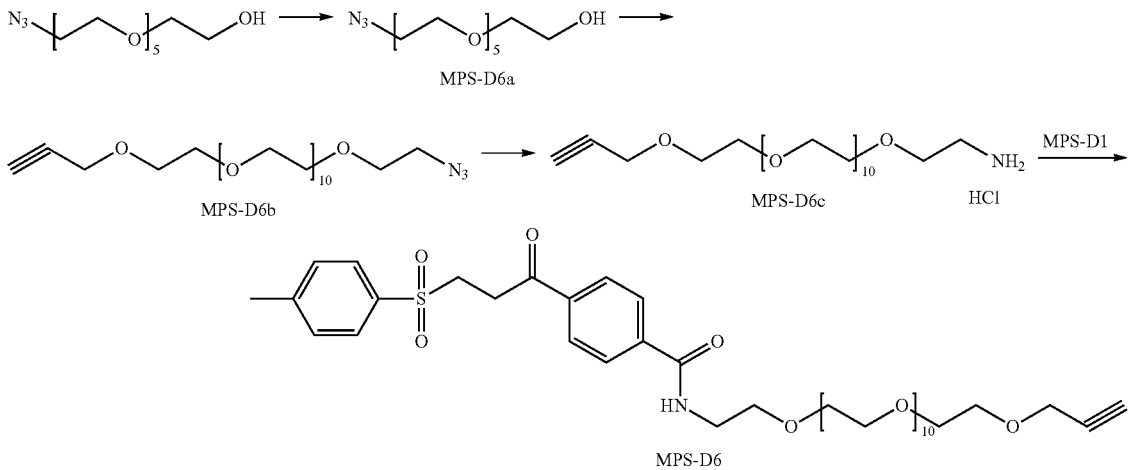

Compound L-5 was synthesized via a similar synthetic route as described in Example 44 and Example 45.

Preparation of Compound MPS-D6a
Yield 91%
1H NMR (400 MHz, CDCl$_3$) δ 7.80 (d, J=8.4 Hz, 2H), 7.35 (d, J=8.4 Hz, 2H), 4.16 (t, J=4.8 Hz, 2H), 3.70-3.61 (m, 20H), 3.39 (t, J=4.8 Hz, 2H), 2.45 (s, 3H). EI-MS m/z: 462 (M$^{+1}$)

Preparation of Compound MPS-D6b
Yield 93%; EI-MS m/z: 610 (M$^{+1}$)
Preparation of Compound MPS-D6c
Yield 54%. EI-MS m/z: 584 (M$^{+1}$)
Preparation of Compound MPS-D6
Yield 72%; EI-MS m/z: 899 (M$^{+1}$)

[Example 48] Preparation of Compound MPS-D7

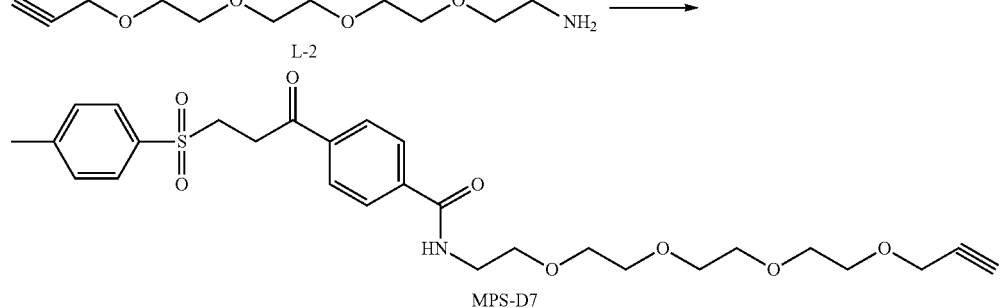

Compound MPS-D7 was synthesized via a similar synthetic route as described in Example 28.

Yield 80%; EI-MS m/z: 546 (M$^{+1}$)

$^1$H NMR (400 MHz, CDCl$_3$) δ 8.11-7.94 (m, 4H), 7.83 (d, J=7.6 Hz, 2H), 7.44 (brs, 1H), 7.38 (d, J=8.0 Hz, 2H), 4.15 (s, 2H), 3.69-3.65 (m, 14H), 3.58-3.48 (m, 4H), 2.80 (s, 1H), 2.46 (s, 3H).

[Example 49] Preparation of Compound Int-TG16

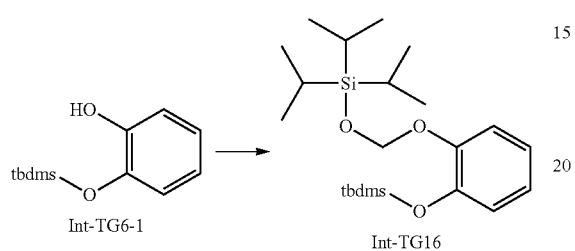

To a solution of compound Int-TG6-1 (300 mg, 1.34 mmol) and TOM-Cl (310 μL, 1.34 mmol) in DCM (2 mL) was added DIPEA (291 μL, 1.67 mmol) under N$_2$ atmosphere. After stirring at room temperature for 2 hours, TOM-Cl (310 μL, 1.34 mmol) and DIPEA (466 μL, 2.67 mmol) were further added thereto. The mixture was stirred overnight at room temperature. After the reaction was completed, the mixture was purified by prep-HPLC to obtain compound Int-TG16 (165 mg, 30%).

$^1$H NMR (400 MHz, CDCl$_3$) δ 7.22-7.20 (m, 1H), 6.92-6.87 (m, 3H), 5.43 (s, 2H), 1.21-1.08 (m, 21H), 1.03 (s, 9H), 0.19 (s, 6H).

[Example 50] Preparation of Compound Int-TG17

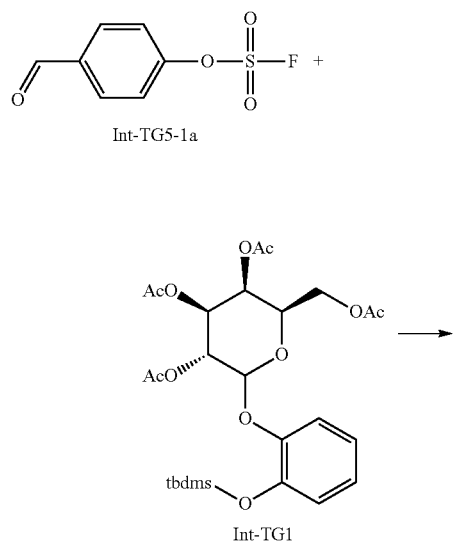

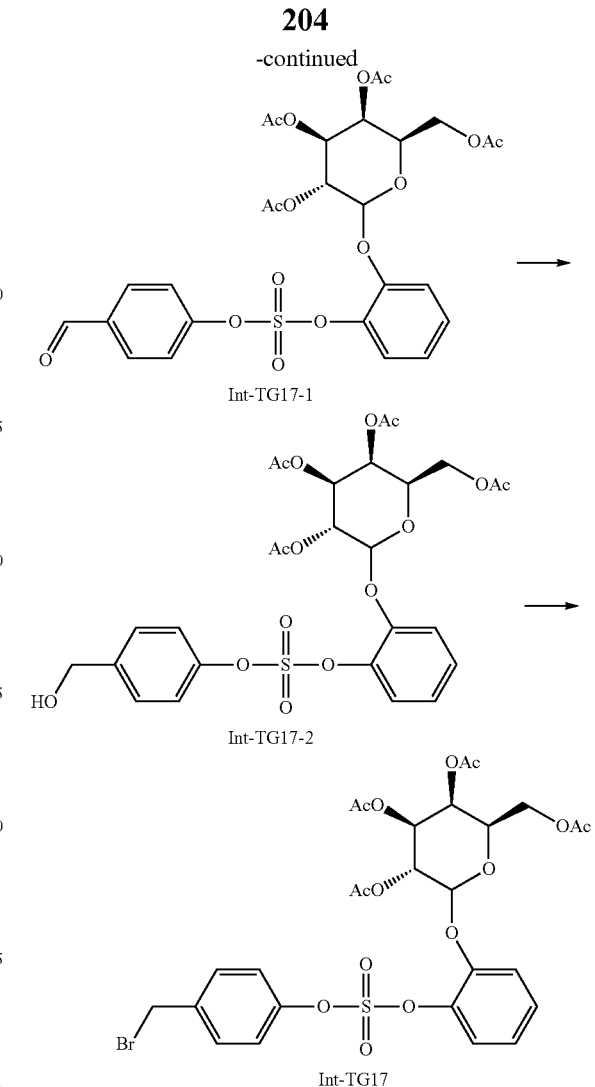

Compound Int-TG17 was synthesized via a similar synthetic route as described in Example 37.

Preparation of Compound Int-TG17-1

Yield 84%; EI-MS m/z: 888 (M$^{+1}$).

$^1$H NMR (400 MHz, CDCl$_3$) δ 10.04 (s, 1H), 7.99-7.97 (m, 1H), 7.56-7.51 (m, 2H), 7.38-7.34 (m, 2H), 7.31-7.27 (m, 2H), 7.15-7.08 (m, 1H), 5.58-5.51 (m, 1H), 5.48-5.45 (m, 1H), 5.12-5.07 (m, 2H), 4.27-4.22 (m, 1H), 4.18-4.13 (m, 1H), 4.08-4.04 (m, 1H), 2.19 (s, 3H), 2.07 (s, 3H), 2.06 (s, 3H), 2.01 (s, 3H).

Preparation of Compound Int-TG17-2

Yield 33% EI-MS m/z: 649 (M$^{+1}$ Na).

$^1$H NMR (400 MHz, CDCl$_3$) δ 7.45-7.41 (m, 3H), 7.35-7.33 (m, 2H), 7.30-7.25 (m, 2H), 7.15-7.10 (m, 1H), 5.51-5.44 (m, 2H), 5.08-5.02 (m, 2H), 4.72 (d, J=5.2 Hz, 2H), 4.26-4.21 (m, 1H), 4.16-4.12 (m, 1H), 4.05-4.01 (m, 1H), 2.22 (s, 3H), 2.05 (s, 3H), 2.04 (s, 3H), 2.00 (s, 3H).

Preparation of Compound Int-TG17

Yield 71% EI-MS m/z: 713 (M$^+$Na).

$^1$H NMR (400 MHz, CDCl3) δ 7.46 (d, J=8.4 Hz, 2H), 7.35-7.32 (m, 3H), 7.28-7.26 (m, 2H), 7.14-7.09 (m, 1H), 5.58-5.54 (m, 1H), 5.46-5.45 (m, 1H), 5.12-5.07 (m, 2H), 4.48 (s, 2H), 4.27-4.23 (m, 1H), 4.17-4.11 (m, 1H), 4.07-4.04 (m, 1H), 2.18 (s, 3H), 2.07 (s, 3H), 2.06 (s, 3H), 2.01 (s, 3H).

[Example 51] Preparation of Compound IntA-Q10

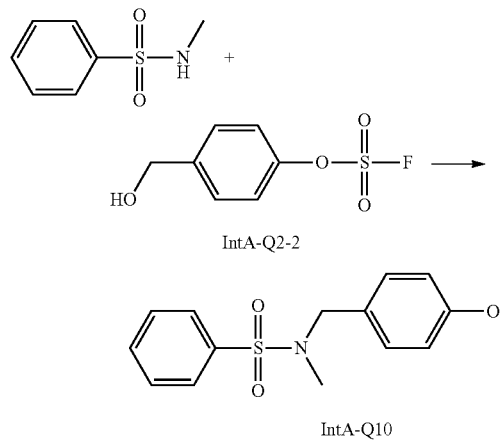

IntA-Q2-2

IntA-Q10

To a solution of N-methyl benzenesulfonamide (208 mg, 1.21 mmol) in THF (5 mL) was added compound IntA-Q2-2 (100 mg, 0.48 mmol) and PPh3 (382 mg, 1.45 mmol) under N$_2$ atmosphere. And then DEAD (221 μL, 1.21 mmol) was added dropwise and the mixture was stirred overnight at room temperature and diluted with EA (50 mL). The organic layer was washed with H$_2$O (40 mL), and brine (40 mL), dried over anhydrous Na$_2$SO$_4$, filtered and concentrated under reduced pressure. The residue was purified by column chromatography to obtain a compound IntA-Q10 (143 mg, 82%).

$^1$H NMR (400 MHz, CDCl$_3$) δ 7.84 (d, J=7.6 Hz, 2H), 7.66-7.63 (m, 1H), 7.60-7.53 (m, 2H), 7.44 (d, J=8.8 Hz, 2H), 7.32 (d, J=8.4 Hz, 2H), 4.19 (s, 2H), 2.65 (s, 3H).

EI-MS m/z: 360 (M$^{+1}$).

[Example 52] Preparation of Compound IntB-Q8

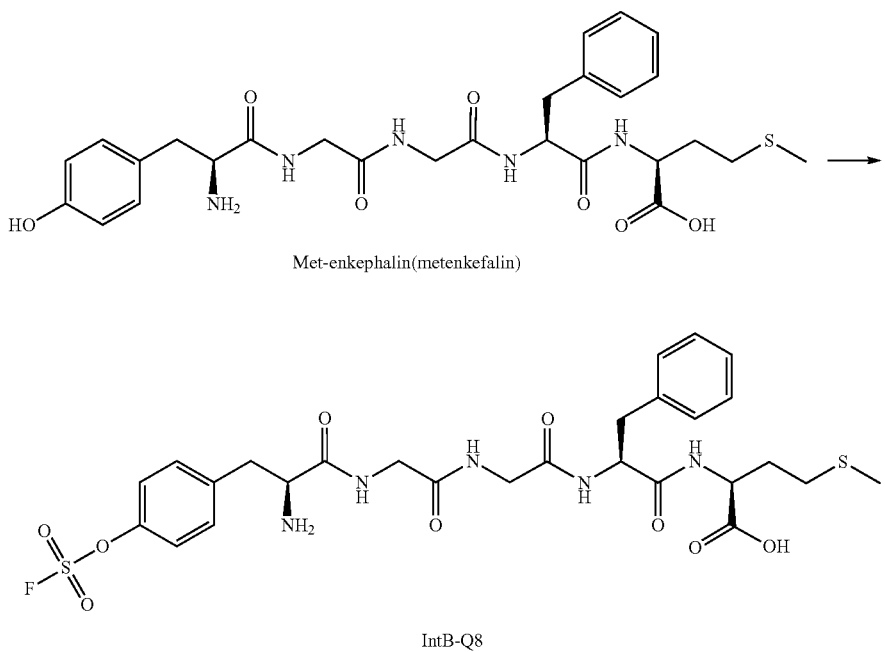

Met-enkephalin(metenkefalin)

IntB-Q8

Compound IntB-Q8 was synthesized via a similar synthetic route as described in Example 12.

Yield 16%; EI-MS m/z: 656 (M$^{+1}$).

[Example 53] Preparation of Compound IntB-Q9

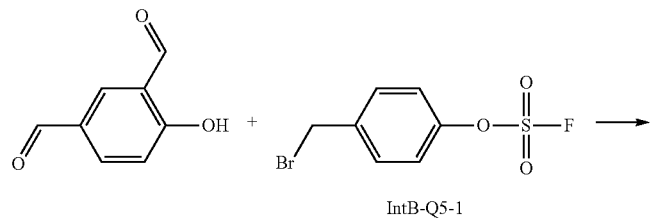

IntB-Q5-1

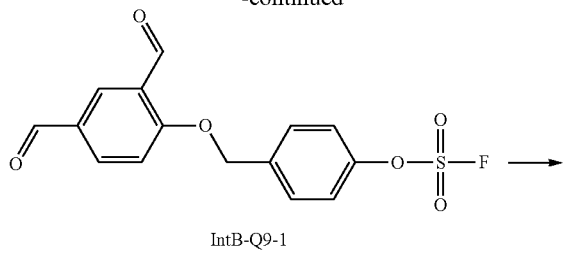

IntB-Q9-1

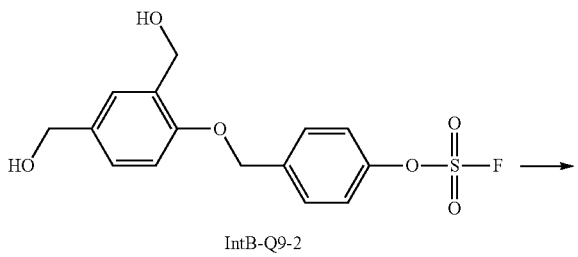

IntB-Q9-2

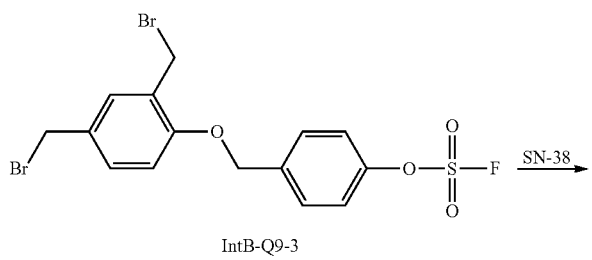

IntB-Q9-3

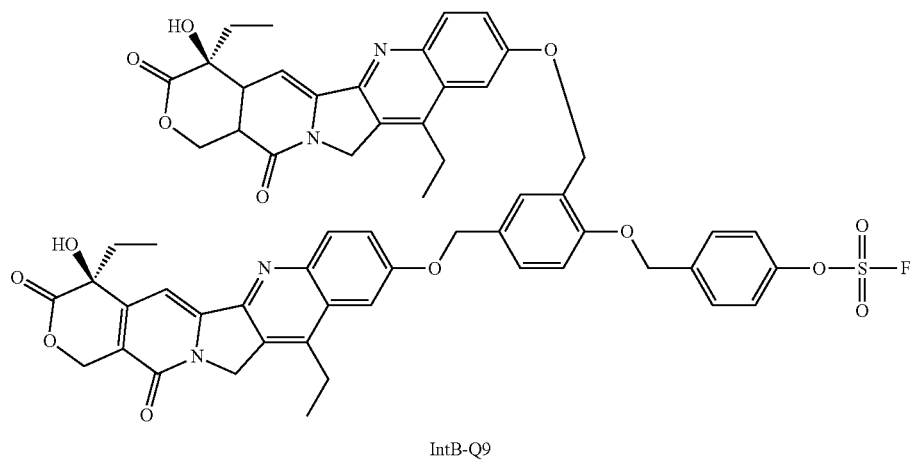

IntB-Q9

Compound IntB-Q9 was synthesized via a similar synthetic route as described in Example 37 and Example 2.

Preparation of Compound IntB-Q9-1

Yield 77%

$^1$H NMR (400 MHz, CDCl3) δ 10.54 (s, 1H), 9.97 (s, 1H), 8.38 (s, 1H), 8.14 (d, J=8.4 Hz, 1H), 7.59 (d, J=8 Hz, 2H), 7.43 (d, J=8.8 Hz, 2H), 7.19 (d, J=8.4 Hz, 1H), 5.33 (s, 2H).

Preparation of Compound IntB-Q9-2

Yield 94%; EI-MS m/z: 365 (M$^+$+Na).

$^1$H NMR (400 MHz, DMSO-d6) δ 7.67-7.61 (m, 4H), 7.37 (s, 1H), 7.12 (d, J=8.8 Hz, 1H), 6.94 (d, J=8.4 Hz, 1H), 5.19 (s, 2H), 5.06-5.02 (m, 2H), 4.56 (d, J=4.8 Hz, 2H), 4.42 (d, J=5.6 Hz, 2H).

Preparation of Compound IntB-Q9-3

Yield 82%

$^1$H NMR (400 MHz, CDCl3) δ 7.62 (d, J=8.4 Hz, 2H), 7.41-7.38 (m, 3H), 7.32 (d, J=8.4 Hz, 1H), 6.86 (d, J=8.8 Hz, 1H), 5.19 (s, 2H), 4.57 (s, 2H), 4.47 (s, 2H).

Preparation of Compound IntB-Q9

EI-MS m/z: 1092 (M$^{+1}$).

[Example 54] Preparation of Compound IntB-Q10

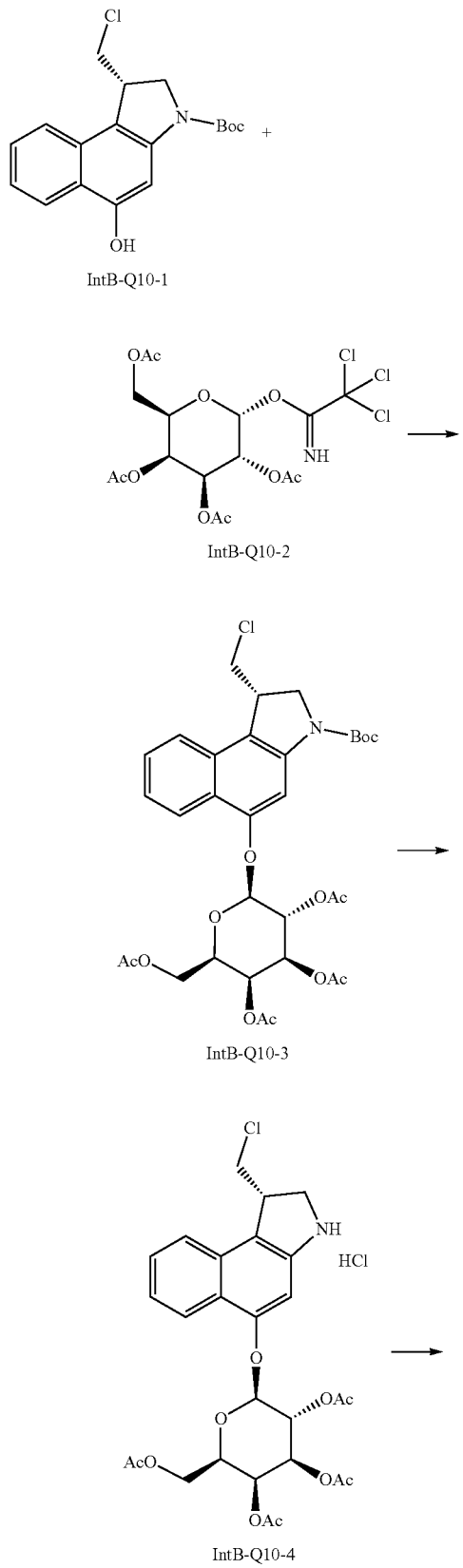

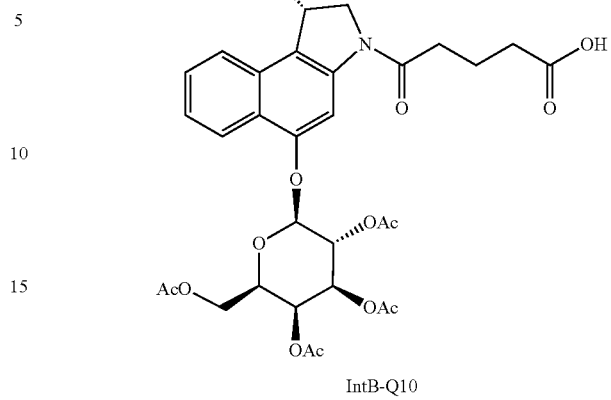

Preparation of Compound IntB-Q10-1

Compound IntB-Q10-1 was synthesized by a similar synthetic route as described in document [see Mol. Pharmaceutics 2015, 12, 1813-1835]

Preparation of Compound IntB-Q10-2

Compound IntB-Q10-2 was synthesized by a similar synthetic route as described in document [see Angew. Chem. Int. Ed. 2010, 49, 7336-7339 and WO2015110935A1]

Preparation of Compound IntB-Q10-3

To a solution of compound IntB-Q10-1 (80 mg, 0.239 mmol) and compound IntB-Q10-2 (118 mg, 0.239 mmol) in DCM (10 mL) was added molecular sieve and $BF_3 \cdot OEt_2$ (14.8 μL, 0.12 mmol) at 0° C. under $N_2$ atmosphere. After stirring for 2 hours, the mixture was filtered through celite and washed with DCM (50 mL) and concentrated under reduced pressure. The residue was purified by column chromatography to obtain compound IntB-Q10-3 (105 mg, 66%) as white foam.

$^1$H NMR (400 MHz, $CDCl_3$) δ 8.12 (d, J=8.0 Hz, 1H), 7.89 (brs, 1H), 7.63 (d, J=8.0 Hz, 1H), 7.50 (m, 1H), 7.35 (m, 1H), 5.70 (m, 1H), 5.51 (s, 1H), 5.33 (m, 1H), 5.20 (m, 1H), 4.23 (m, 3H), 4.11 (m, 2H), 3.93 (m, 2H), 3.42 (t, J=10.8 Hz, 1H), 2.18 (s, 3H), 2.08 (s, 3H), 2.04 (s, 3H), 2.00 (s, 3H), 1.55 (s, 9H). EI-MS m/z: 564.4 ($M^{+1}$).

Preparation of Compound IntB-Q10-4

Compound IntB-Q10-3 (100 mg, 0.15 mmol) was dissolved in DCM (2 mL) and then 4N HCl in 1,4-dioxane (1 mL) was added at 0° C. under $N_2$ atmosphere. After stirring for 4 hours, the reaction was concentrated under reduced pressure.

The reaction mixture was stirred at room temperature for 4 hours under $N_2$. The compound IntB-Q10-3 was used directly in the next step without further purification (90 mg, 99%).

EI-MS m/z: 564.2 ($M^{+1}$).

Preparation of Compound IntB-Q10

To a solution of compound IntB-Q10-3 (90 mg, 0.149 mmol) in THF (5 mL) was added glutaric anhydride (18.8 μL, 0.164 mmol), $Et_3N$ (52 μL, 0.373 mmol) and 4-DMAP (2 mg, 0.015 mmol) at room temperature under $N_2$ atmosphere. The reaction mixture was stirred at room temperature for 2 hours and purified by Prep-HPLC, which obtained compound IntB-Q10 (30 mg, 30%) as white solid.

EI-MS m/z: 678.3 ($M^{+1}$).

[Example 55] Preparation of Compound IntB-Q11 and IntB-Q12

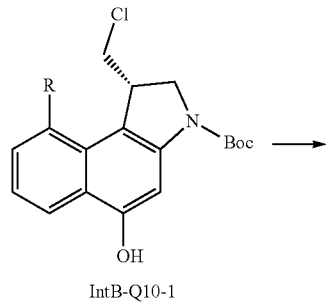

IntB-Q10-1

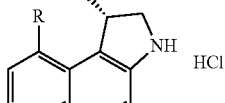

IntB-Q11-1 (R = H)
IntB-Q-12-1 (R = Me)

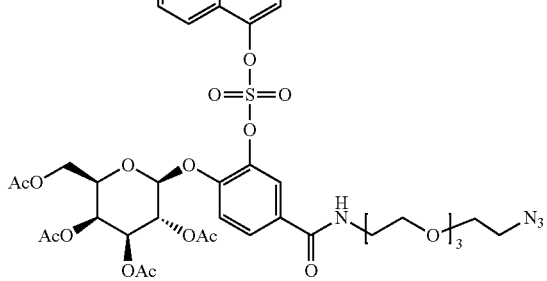

IntB-Q11-2 (R = H)
IntB-Q-12-2 (R = Me)

-continued

IntB-Q11 (R = H)
IntB-Q-12 (R = Me)

Compound IntB-Q11-2 and IntB-Q12-2 were synthesized via a similar synthetic route as described in Example 6 and Example 6.

Preparation of Compound IntB-Q11-1
Yield 98%
1H NMR (400 MHz, CDCl$_3$) δ 8.37 (brs, 1H) 8.02 (d, J=8.8 Hz, 1H), 7.75 (d, J=8.4 Hz, 1H), 7.61 (t, J=7.2 Hz, 1H), 7.51 (t, J=8.0 Hz, 1H), 4.32 (brs, 1H), 4.18 (t, J=8.8, 1H), 4.05 (m, 1H), 3.93 (dd, J=11.2, 2.8 Hz, 1H), 3.52 (t, J=10.8 Hz, 1H), 1.61 (s, 9H). EI-MS m/z: 438.2 (M$^{+1}$+Na).

Preparation of Compound IntB-Q11-2
Yield 79%
$^1$H NMR (400 MHz, CDCl$_3$) δ 8.09 (brs, 1H) 7.77 (m, 3H), 7.57 (t, J=7.2 Hz, 1H), 7.46 (t, J=7.6 Hz, 1H), 7.32 (m, 1H), 6.78 (m, 1H), 5.56 (m, 1H), 5.46 (d, J=2.8 Hz, 1H), 5.22 (d, J=7.6 Hz, 1H), 5.12 (dd, J=10.4, 3.2 Hz, 1H), 4.30 (brs, 1H), 4.25-4.02 (m, 5H), 3.93 (m, 1H), 3.60 (m, 15H), 3.31 (m, 2H), 2.17 (s, 3H), 2.04 (s, 3H), 1.95 (s, 6H), 1.56 (s, 9H). EI-MS m/z: 1080.6 (M$^+$1).

Preparation of Compound IntB-Q11
Compound IntB-11-2 (50 mg, 0.046 mmol) was dissolved in 4N HCl in 1,4-dioxane (1 mL) at 0° C. under N$_2$ atmosphere. After stirring at room temperature for 4 hours, the mixture was diluted with DCM (5 mL) and concentrated. The compound IntB-Q11 was used directly in the next step without further purification (47 mg, 99%).
EI-MS m/z: 980.5 (M$^{+1}$).

Preparation of Compound IntB-Q12-1
Yield 46%; EI-MS m/z: 452.2 (M$^{+1}$+Na).
$^1$H NMR (400 MHz, CDCl$_3$) δ 8.4 (brs, 1H) 7.91 (dd, J=6.8, 2.4 Hz, 1H), 7.38 (m, 2H), 4.34 (m, 1H), 4.23 (m, 1H), 4.05 (m, 1H), 3.62 (d, J=10.4, 1H), 3.30 (t, J=11.2, 1H), 2.83 (s, 1H), 1.61 (s, 9H).

Preparation of Compound IntB-Q12-2
Yield 71%; EI-MS m/z: 1094.4 (M$^{+1}$).
$^1$H NMR (400 MHz, CDCl$_3$) δ 8.33 (brs, 1H) 7.99 (d, J=7.2 Hz, 1H), 7.78 (m, 2H), 7.35 (m, 3H), 6.87 (m, 1H), 5.54 (m, 1H), 5.46 (d, J=2.8 Hz, 1H), 5.22 (d, J=8.0 Hz, 1H), 5.12 (dd, J=10.4, 3.2 Hz, 1H), 4.33 (m, 1H), 4.26-4.01 (m, 5H), 3.61 (m, 14H), 3.32 (m, 3H), 2.83 (s, 1H), 2.21 (s, 3H), 2.07 (s, 3H), 1.99 (s, 6H), 1.57 (s, 9H).

Preparation of Compound IntB-Q12
Yield 99%; EI-MS m/z: 994.5 (M$^{+1}$).

[Example 55a] Preparation of Compound IntB-Q13

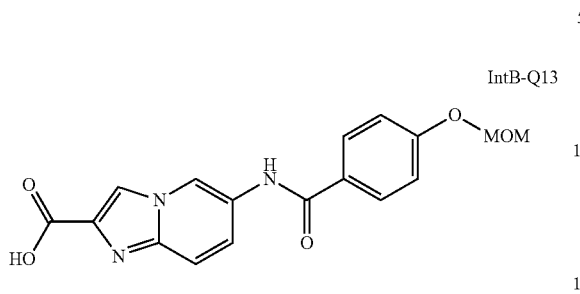

Compound IntB-Q13 was synthesized by a similar synthetic route as described in Mol. Pharmaceutics 2015, 12, 1813-1835, incorporated herein by reference.

[Example 56] Preparation of Compound IntB-Q14

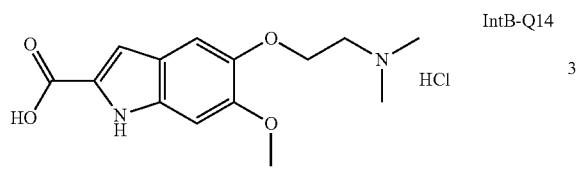

Compound IntB-Q14 was synthesized by a similar synthetic route as described in document WO 2015038426A1, incorporated herein by reference.

[Example 56] Preparation of Compound IntB-Q15

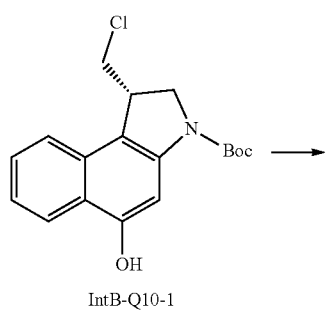

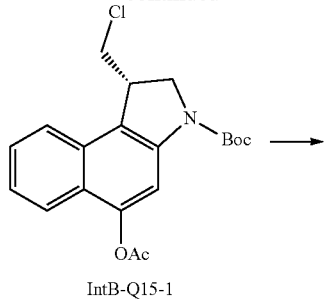

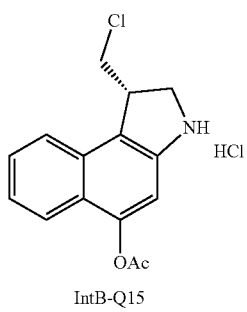

Preparation of Compound IntB-Q15-1

To a solution of compound IntB-Q10-1 (55 mg, 0.016 mmol) in DCM (2 mL) was added acetyl chloride (26.8 µL, 0.032 mmol) and Pyridine (30 µL, 0.032 mmol) at 0° C. under $N_2$ atmosphere. After stirring for 30 minutes, the reaction was warmed up to room temperature and further stirred for 1 hour. The mixture was diluted with EA (20 mL) and washed with $H_2O$ (10 mL). The compound IntB-Q15-1 (50 mg, 80%) as pale yellow foam.

EI-MS m/z: 398.2 ($M^{+1}$+Na).

$^1$H NMR (400 MHz, CDCl$_3$) δ 8.02 (brs, 1H) 7.79 (d, J=8.0 Hz, 1H), 7.72 (t, J=8.8 Hz, 1H), 7.51 (m, 1H), 7.38 (m, 1H), 4.16 (m, 1H), 4.04 (m, 1H), 3.92 (m, 1H), 3.71 (m, 1H), 3.36 (m, 1H), 2.27, (s, 3H), 1.54 (s, 9H).

Preparation of Compound IntB-Q15

Compound IntB-Q15 was synthesized via a similar synthetic route as described in Example 55.

Yield 99%; EI-MS m/z: 276.2 ($M^{+1}$).

[Example 57] Preparation of Compound IntB-Q16

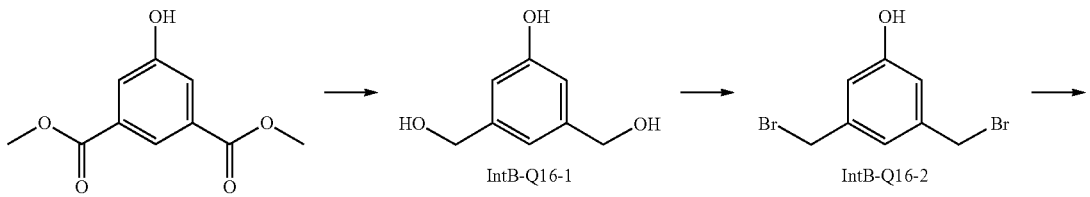

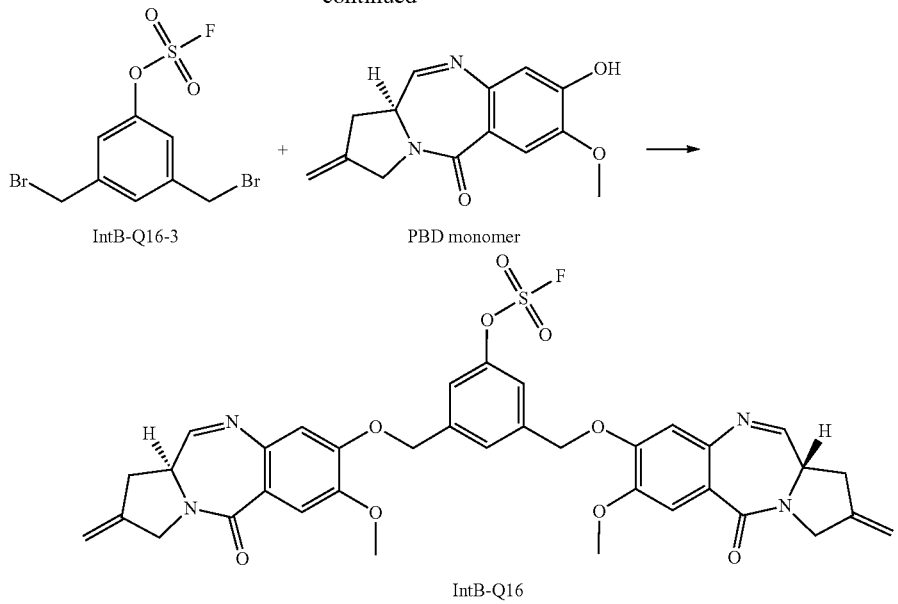

IntB-Q16-3      PBD monomer

IntB-Q16

Preparation of Compound IntB-Q16-1

To a solution of dimethyl 5-hydroxyisophthalate (5.0 g, 23.79 mmol) in THF (300 mL) was added LAH (3.6 g, 95.15 mmol) at 0° C. under a nitrogen atmosphere. After stirring at room temperature for 17 hours, 15% NaOH aqueous solution (10 mL) and distilled water (30 mL) were added. After the mixture was extracted with EA (500 mL), the organic layer was washed with brine (100 mL), dried over $Na_2SO_4$, filtered, and concentrated under reduced pressure, The residue was purified by column chromatography to obtain compound IntB-Q16-1 (3.02 g, 82%).

1H NMR (400 MHz, DMSO-$d_6$) δ 9.21 (s, 1H), 6.66 (s, 1H), 6.58 (s, 2H), 5.07 (t, J=5.6 Hz, 2H), 4.38 (d, J=5.6 Hz, 4H).

Preparation of Compound IntB-Q16-2

To a solution of compound IntB-Q16-1 (881.1 mg, 5.72 mmol) in AcOH (15 mL) was added 33% HBr in AcOH (2.6 mL, 14.29 mmol) at 0° C. under $N_2$ atmosphere. After the mixture was warmed to 65° C. and stirred for 8 hours, and stirred again at room temperature for 2 days. DCM (50 mL) and water (30 mL) were added. The organic layer was washed with $NaHCO_3$ aqueous solution, dried over anhydrous $Na_2SO_4$, filtered and concentrated under reduced pressure. The residue was purified by column chromatogram to obtain a compound IntB-Q16-2 (1.1 g, 71%).

$^1$H NMR (400 MHz, $CDCl_3$) δ 6.99 (s, 1H), 6.81 (s, 2H), 4.85 (s, 1H), 4.41 (s, 4H).

Preparation of Compound IntB-Q16-3

To a solution of compound IntB-Q16-2 (1.0 g, 3.57 mmol) in DCM (35 mL) was added TEA (0.45 mL, 3.21 mmol) at room temperature under $N_2$ atmosphere. The mixture was stirred for 1 hour and DCM (50 mL) and water (30 mL) were added. The organic layer was washed with $NaHCO_3$ aqueous solution, dried over anhydrous $Na_2SO_4$, filtered, and concentrated under reduced pressure. The residue was purified by column chromatography to obtain a compound IntB-Q16-3 (941.7 mg, 73%).

$^1$H NMR (400 MHz, $CDCl_3$) δ 7.47 (s, 1H), 7.32 (s, 2H), 4.46 (s, 4H).

Preparation of Compound IntB-Q16

To a solution of compound IntB-Q16-3 (200 mg, 0.55 mmol) and a PBD monomer (342.3 mg, 1.32 mmol) prepared by a similar method as described in EP 20071813614 A1 in DMF (5 mL) was added $K_2CO_3$ (183.2 mg, 1.32 mmol) at room temperature under $N_2$ atmosphere, The mixture was stirred at room temperature for 2 hours and EA (20 mL) and water (5 mL) were added. The organic layer was dried over anhydrous $Na_2SO_4$, filtered, and concentrated under reduced pressure. The residue was purified by column chromatography to obtain a compound IntB-Q8 (254 mg, 64%).

$^1$H NMR (400 MHz, $CDCl_3$) δ 7.66 (d, J=4.4 Hz, 2H), 7.55 (s, 3H), 7.42 (s, 2H), 6.81 (s, 2H), 5.27-5.17 (m, 8H), 4.29 (s, 4), 3.97 (s, 6H), 3.89-3.85 (m, 2H), 3.15-3.09 (m, 2H), 2.93 (d, J=16 Hz, 2H). EI-MS m/z: 717 ($M^{+1}$).

[Example 58] Preparation of Compound A-1

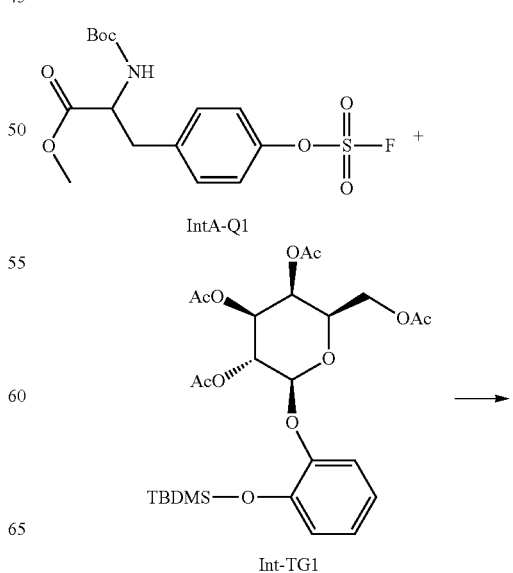

IntA-Q1

Int-TG1

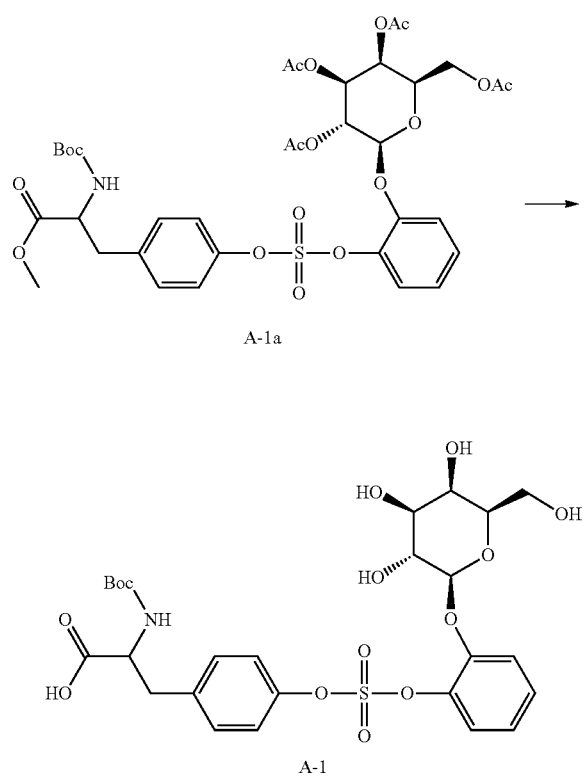

A-1a

A-1

Preparation of Compound A-1a

To a solution of compound IntA-Q1 (46 mg, 0.135 mmol) and compound Int-TG1 (75 mg, 0.135 mmol) in acetonitrile (3 mL) was added DBU (4 μL, 0.027 mmol). The mixture was stirred at room temperature for 12 hours under $N_2$. The mixture was extracted with EA (30 mL×2). The organic layer was washed with water (30 mL), dried over anhydrous $Na_2SO_4$, filtered and concentrated under reduced pressure. The residue was purified by column chromatography to obtain compound A-1a (105 mg, 98%).

$^1$H NMR (400 MHz, $CDCl_3$) δ 7.33-7.26 (m, 5H), 7.21-7.17 (m, 2H), 7.14-7.08 (m, 1H), 5.56 (dd, J=2.4 Hz, 8.0 Hz, 1H), 5.46 (d, J=3.2 Hz, 1H), 5.12-5.08 (m, 2H), 5.06-5.00 (m, 1H), 4.63-4.56 (m, 1H), 4.28-4.23 (m, 1H), 4.18-4.13 (m, 1H), 4.08-4.04 (m, 1H), 3.72 (s, 3H), 3.18-3.03 (m, 2H), 2.19 (s, 3H), 2.07 (s, 3H), 2.06 (s, 3H), 2.01 (s, 3H), 1.42 (s, 9H). EI-MS m/z: 798 ($M^+1$).

Preparation of Compound A-1

To a solution of compound A-1a (100 mg, 0.13 mmol) in THF (4 mL) and methanol (1 mL) was added dropwise LiOH·$H_2O$ (33 mg, 0.79 mmol) dissolved in water (1 mL) at 0° C. After stirring at 0° C. for 2 hours, the reaction was quenched with 1N aqueous hydrochloric acid (3 mL). The mixture was purified by HPLC to obtain compound A-1 (65 mg, 85%).

EI-MS m/z: 616 ($M^{+1}$).

[Example 59] Preparation of Compound A-2

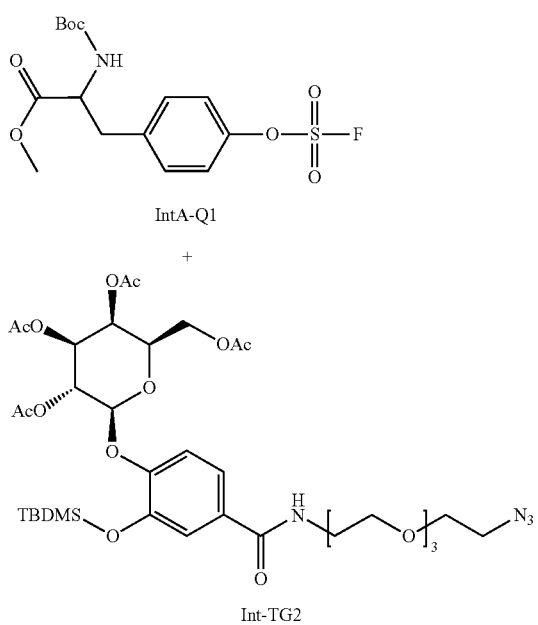

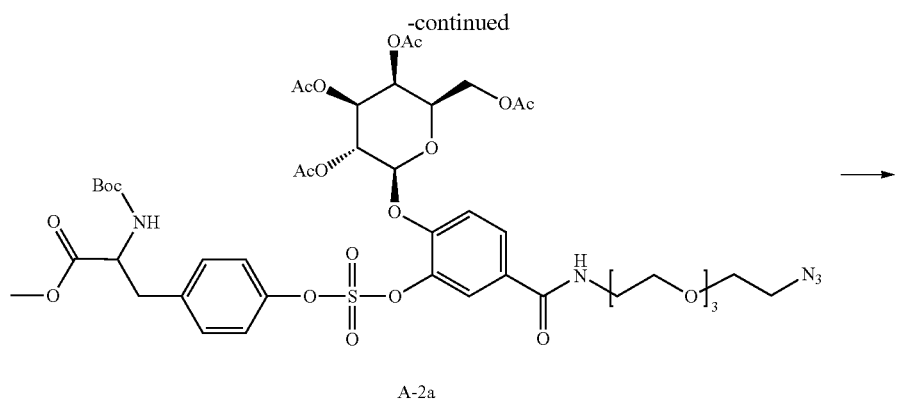
A-2a
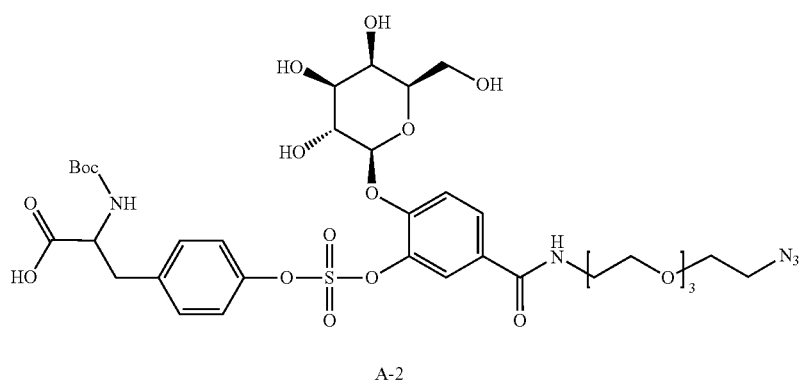
A-2
Compound A-2a was synthesized via a similar synthetic route as described in Example 58.
Yield 95%; EI-MS m/z: 1043 (M$^{+1}$).
$^1$H NMR (400 MHz, CDCl$_3$) δ 7.80 (s, 1H), 7.75 (dd, J=8.0 Hz, 1H), 7.33-7.20 (m, 5H), 7.0 (m, 1H), 5.76 (dd, J=8.0, 10.4 Hz, 1H), 7.47 (d, J=3.2 Hz, 1H), 5.17-5.10 (m, 3H), 4.58 (m, 1H), 4.25-4.08 (m, 3H), 3.72 (s, 3H), 3.66-3.60 (m, 13H), 3.34 (t, J=4.4 Hz, 2H), 2.17 (s, 3H), 2.07 (s, 3H), 2.06 (s, 3H), 2.01 (s, 3H), 1.41 (s, 9H).
Preparation of Compound A-2
Yield 53%; EI-MS m/z: 860 (M$^{+1}$).
[Example 60] Preparation of Compound A-3
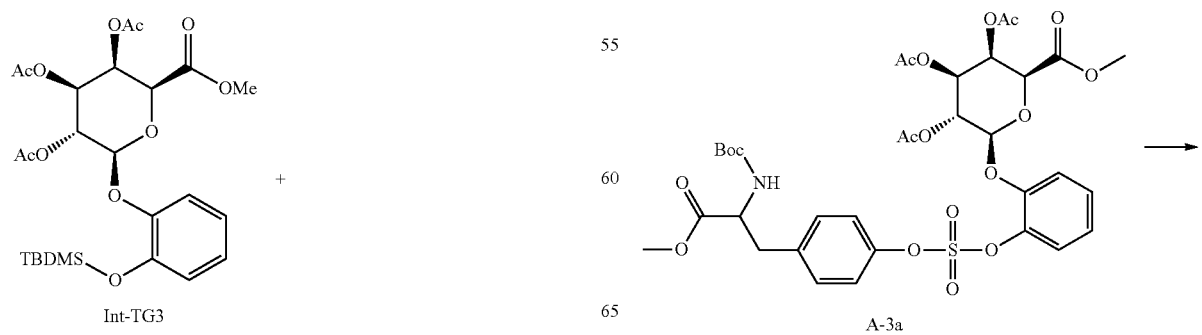

-continued
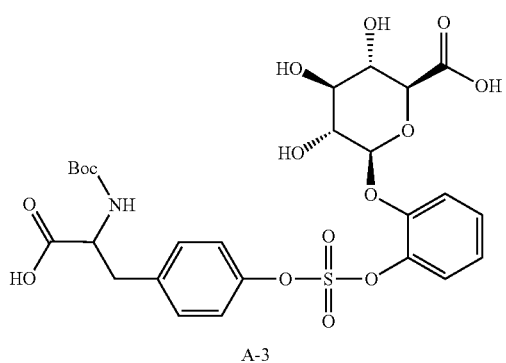
A-3
Compound A-3 was synthesized via a similar synthetic route as described in Example 58.
Preparation of Compound A-3a
EI-MS m/z: 806 (M$^{+1}$+Na).
Preparation of Compound A-3
Yield 33%; EI-MS m/z: 652 (M$^{+1}$+Na).
$^1$H NMR (400 Hz, CD$_3$OD) δ 7.42-7.31 (m, 7H), 7.14-7.10 (m, 1H), 5.13 (d, J=7.2 Hz, 1H), 4.42-4.38 (m, 1H), 4.03 (d, J=10 Hz, 1H), 3.67 (t, J=9.6 Hz, 1H), 3.55-3.43 (m, 2H), 3.27 dd, J=9.2, 5.2 Hz, 1H), 3.16-2.97 (m, 1H), 1.39 (s, 9H).
[Example 61] Preparation of Compound A-4
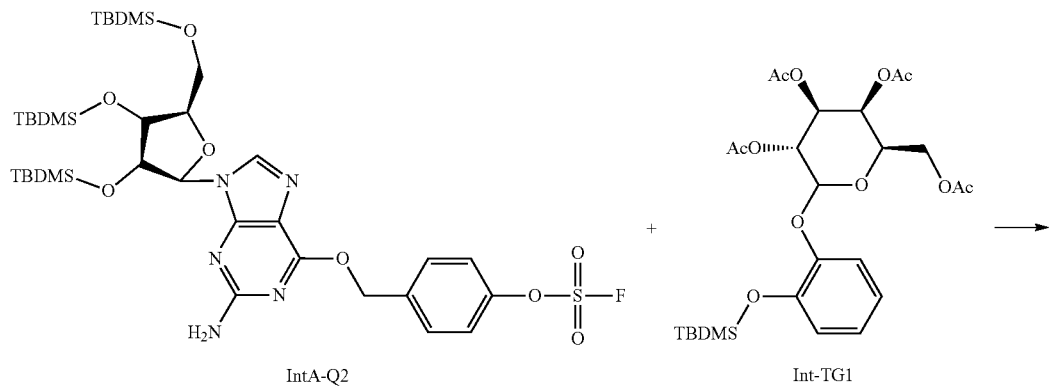
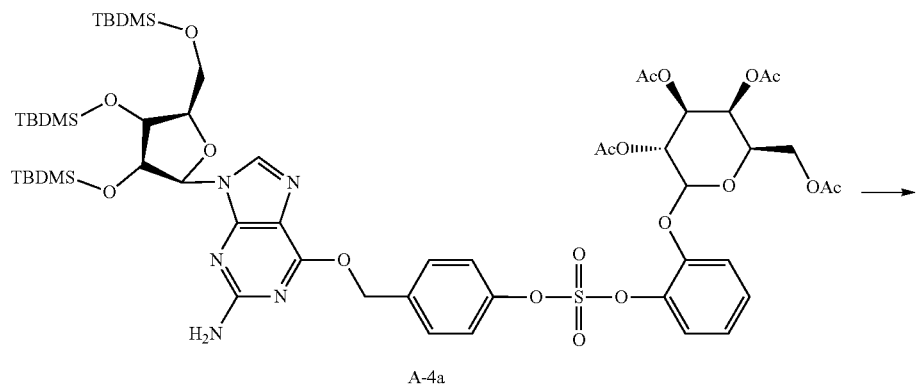
A-4a
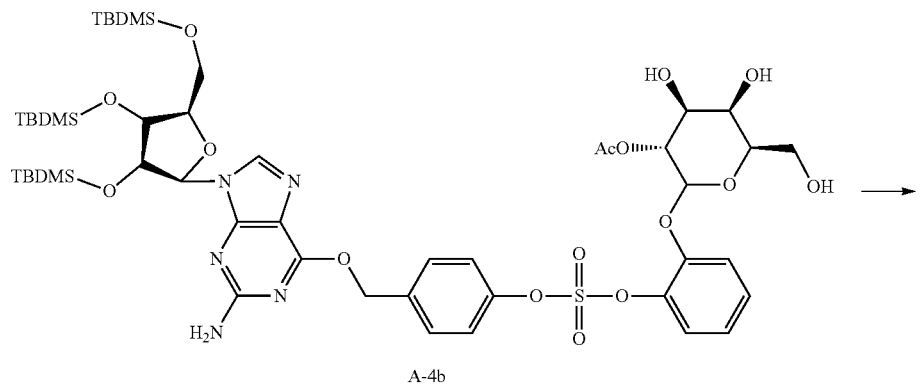
A-4b

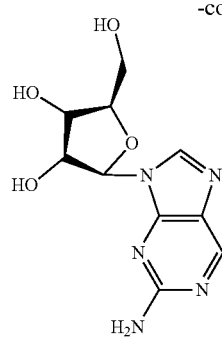
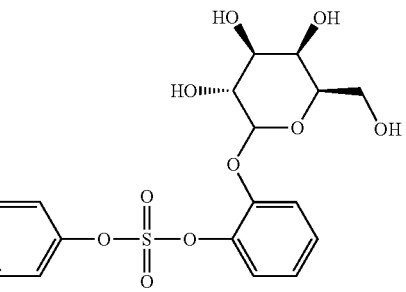

A-4

Preparation of Compound A-4a

Compound A-4a was synthesized via a similar synthetic route as described in Example 58.

EI-MS m/z: 1235 (M$^{+1}$).

Preparation of Compound A-4b

To a solution of compound A-4a (41 mg, 0.03 mmol) in MeOH (2.66 mL) was added K$_2$CO$_3$ (14 mg, 0.10 mmol) at 0° C., and the mixture was stirred at 0° C. for 2 hours. K$_2$CO$_3$ (9 mg, 0.07 mmol) was further added thereto, and the mixture was stirred at 0° C. and diluted with EA (20 mL×2). The organic layer was washed with H$_2$O (20 mL), and brine (20 mL), dried over anhydrous Na$_2$SO$_4$, filtered and concentrated under reduced pressure to produce compound A-4a (35 mg), which was used further purification.

EI-MS m/z: 1067 (M$^{+1}$).

Preparation of Compound A-4

To a solution of compound A-4b (17 mg, 0.02 mmol) in THF (640 µL) was added AcOH (3 µL, 0.05 mmol) and TBAF (48 µL, 0.05 mmol) at 0° C. under N$_2$ atmosphere. After stirring for 1.5 hours, TBAF (48 µL, 0.05 mmol) was further added and stirred at 0° C. for 2 hours. The mixture was purified by prep-HPLC, which produced compound A-4 (3 mg, 22%).

EI-MS m/z: 724 (M$^+$1).

[Example 62] Preparation of Compound A-5

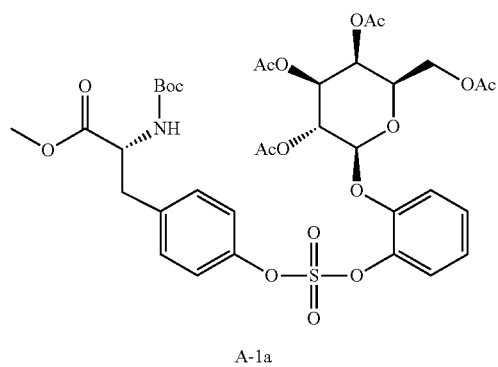

A-1a

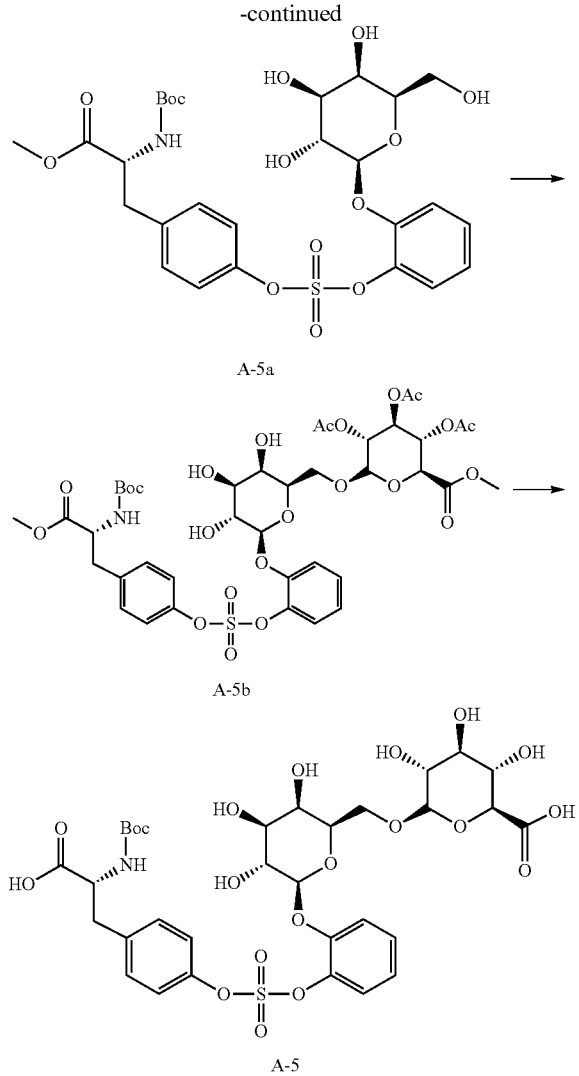

A-5a

A-5b

A-5

Preparation of compound A-5a

Compound A-5a was synthesized via a similar synthetic route as described in Example 58.

Yield 88%; EI-MS m/z: 630 (M$^{+1}$).

Preparation of Compound A-5b

To a solution of compound A-5a (100 mg, 0.16 mmol) and acetobromo-α-D-glucuronic acid methyl ester (64 mg, 0.16 mmol, CAS #21085-72-3) in Et$_2$O (10 mL) was added AgOTf (204 mg, 0.79 mmol) and trimethylpyridine (106 mg, 0.87 mmol) at 0° C. The mixture was stirred at room temperature for 6 hours and diluted with EA (50 mL). It was washed with 2N HCl aqueous solution (10 mL), dried over anhydrous Na$_2$SO$_4$, filtered and concentrated under reduced pressure. The residue was separated and purified by Prep-HPLC to obtain compound A-5b (14 mg, 9%).

EI-MS m/z: 946 (M$^{+1}$).

Preparation of Compound A-5

Compound A-5 was synthesized via a similar synthetic route as described in Example 58.

EI-MS m/z: 792 (M$^{+1}$).

[Example 63] Preparation of Compound A-6

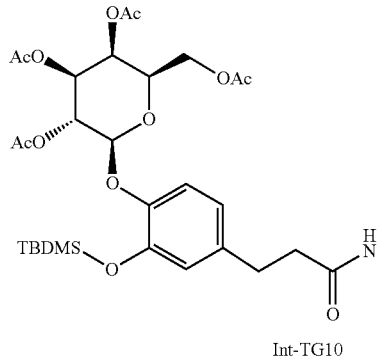
Int-TG10

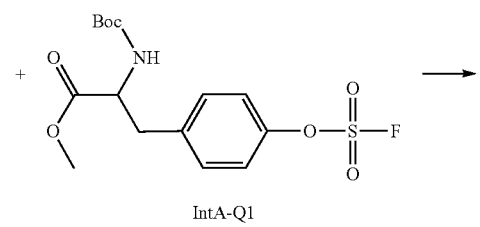
IntA-Q1

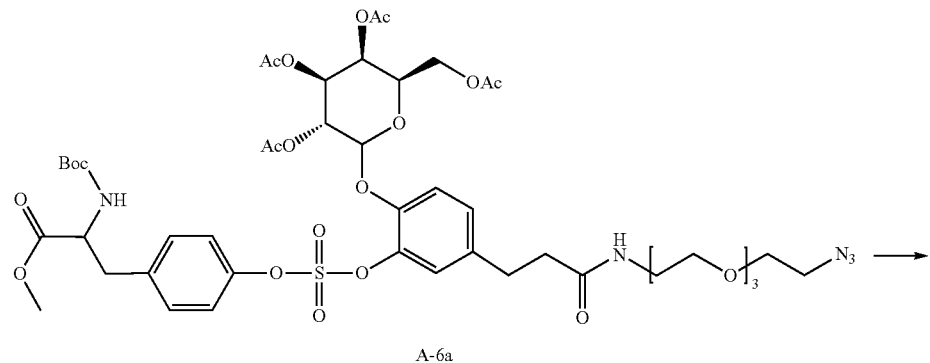
A-6a

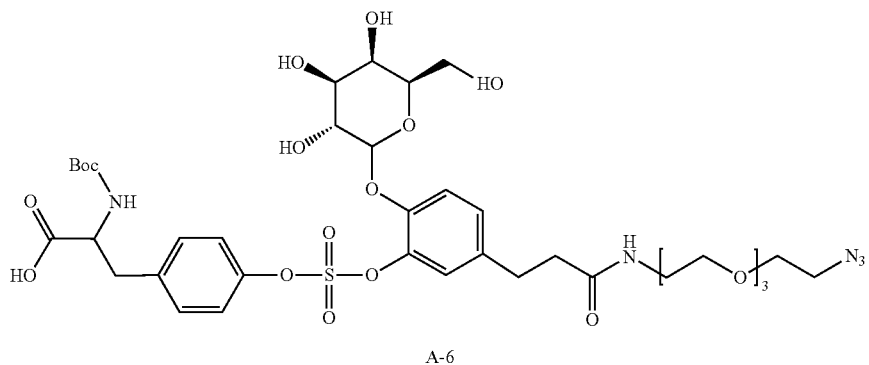
A-6

Compound A-6 was synthesized via a similar synthetic route as described in Example 60.
Preparation of compound A-6a
Yield 53%
EI-MS m/z: 1071 ($M^{+1}$).
Preparation of compound A-6
Yield 16%
EI-MS m/z: 888 ($M^{+1}$).

[Example 64] Preparation of Compound A-7

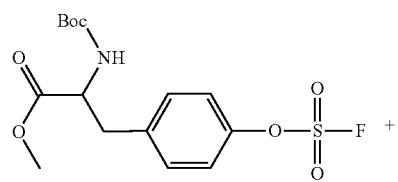

IntA-Q1

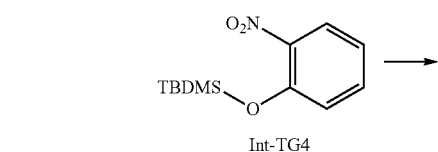

Int-TG4

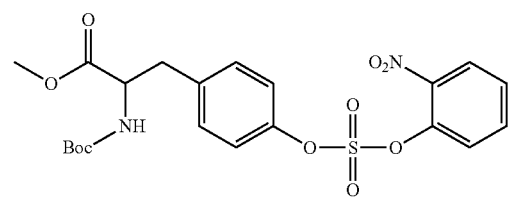

A-7a

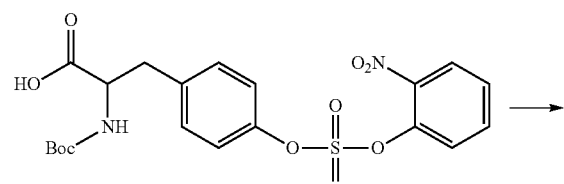

A-7b

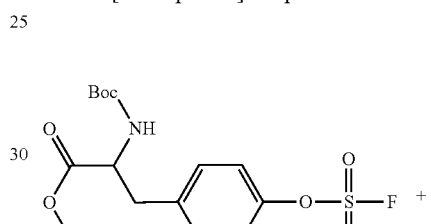

A-7

Preparation of Compound A-7a
To a solution of compound Int-TG4 (73.9 mg, 0.29 mmol) and the compound IntA-Q1 (100 mg, 0.27 mmol) in anhydrous acetonitrile (2 mL) was added BEMP (31 μL, 0.11 mmol) at room temperature under $N_2$ atmosphere. The mixture was stirred at 100° C. for 5 hours under microwave conditions. The mixture was separated and purified by Prep-HPLC to obtain compound A-7a (61.2 mg, 46%).
EI-MS m/z: 519 ($M^{+1}$+Na).
Preparation of Compound A-7b
Compound A-7b was synthesized via a similar synthetic route as described in Example 58.
Yield 64%; EI-MS m/z: 505 ($M^{+1}$+Na).
Preparation of Compound A-7
To a solution of compound A-7b (39 mg, 0.08 mmol) in methanol (2 mL) was added dropwise Zn dust (6.4 mg, 0.10 mmol) and ammonium formate (8.22 mg, 0.13 mmol) at room temperature under $N_2$ atmosphere. The mixture was stirred at room temperature for 2 hours and filtered through celite and washed with MeOH and concentrated. The residue was separated and purified by Prep-HPLC to obtain compound A-7.
EI-MS m/z: 469 ($M^+1$).

[Example 65] Preparation of Compound A-8

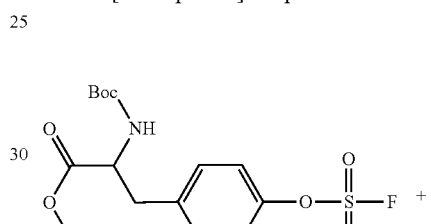

IntA-Q1

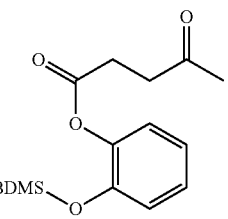

Int-TG6

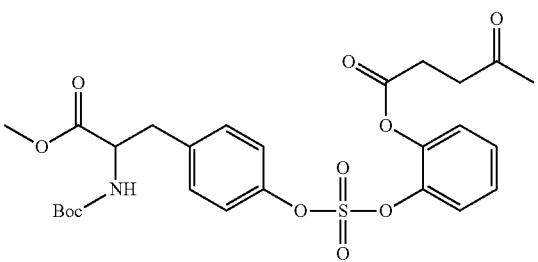

A-8

Compound A-8 was synthesized via a similar synthetic route as described in Example 60.
EI-MS m/z: 588 ($M^{+1}$+Na).

[Example 66] Preparation of Compound A-9
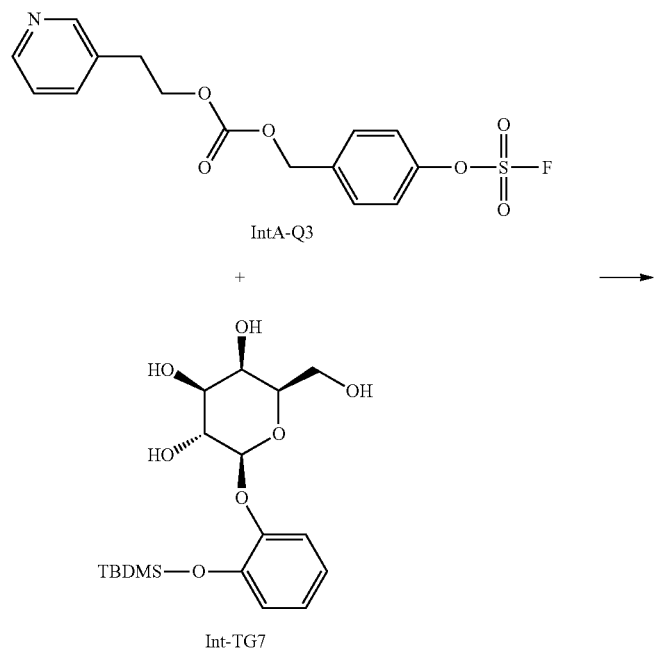
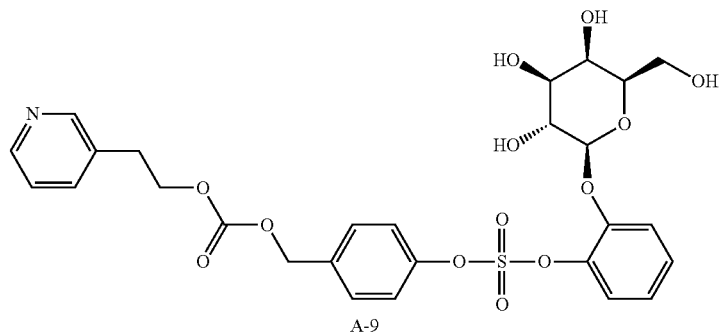
Compound A-9 was synthesized via a similar synthetic route as described in Example 60.
EI-MS m/z: 608 (M$^{+1}$).

[Example 67] Preparation of Compound A-10

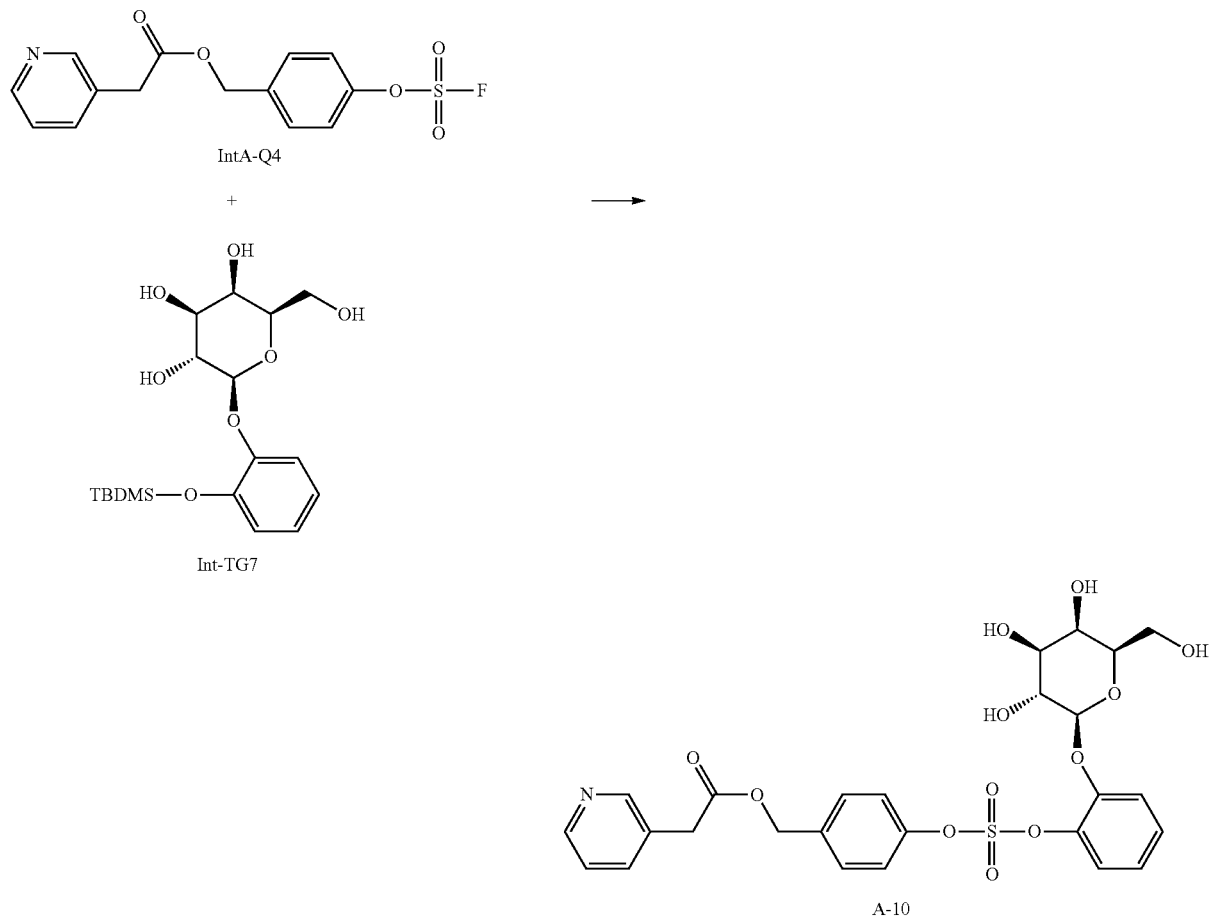

To a solution of compound IntA-Q4 (23 mg, 0.07 mmol) and the compound Int-TG7 (30 mg, 0.08 mmol) in anhydrous acetonitrile (1 mL) was added BEMP (11.2 µL, 0.04 mmol) at room temperature under $N_2$ atmosphere.

The mixture was stirred overnight at room temperature, and separated and purified by Prep-HPLC to obtain compound A-10 (0.3 mg).

EI-MS m/z: 578 ($M^{+1}$).

[Example 68] Preparation of Compound A-11

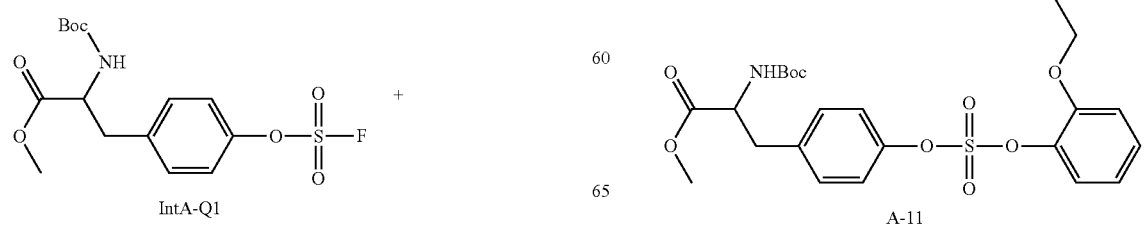

Compound A-11 was synthesized via a similar synthetic route as described in Example 67.

Yield 65%; EI-MS m/z: 603 (M+).

$^1$H NMR (400 MHz, CDCl$_3$) δ 8.19 (dd, J=6.8, 1.2 Hz, 1H), 8.02 (d, J=8.0 Hz, 1H), 7.68 (t, J=6.4 Hz, 1H), 7.49 (t, J=7.2 Hz, 1H), 7.33-7.23 (m, 3H), 7.22 (d, J=8.0 Hz, 1H), 7.17 (d, J=8.8 Hz, 2H), 7.08 (dd, J=7.2, 1.2 Hz, 1H), 7.01 (td, J=6.8, 1.2 Hz, 1H), 5.56 (s, 2H), 4.99 (d, J=8.4 Hz, 1H), 4.59 (q, J=7.2, 6.4 Hz, 1H), 3.14 (dd, J=8.4, 5.6 Hz, 1H), 3.03 (dd, J=7.6, 6.0 Hz, 1H), 1.42 (s, 9H).

[Example 69] Preparation of Compound A-12

Yield 82%; EI-MS m/z: 870 (M+1+Na).

$^1$H NMR (400 MHz, CDCl$_3$) δ 7.80-7.75 (m, 3H), 7.61 (s, 1H), 7.52-7.47 (m, 2H), 7.33 (d, J=8.0 Hz, 2H), 7.21 (d, J=8.1 Hz, 2H), 5.63 (t, J=2.2 Hz, 1H), 5.50 (s, 1H), 5.23 (d, J=7.6 Hz, 1H), 5.15 (d, J=10.4 Hz, 1H), 5.08-4.98 (m, 1H), 4.62-4.54 (m, 1H), 4.36-4.26 (m, 1H), 4.24-4.14 (m, 2H), 3.72 (s, 3H), 3.22-3.02 (m, 2H), 2.20 (s, 3H), 2.08 (s, 6H), 2.02 (s, 3H), 1.42 (s, 9H).

Preparation of Compound A-12

Compound A-12 was synthesized via a similar synthetic route as described in Example 58.

Yield 93%; EI-MS m/z: 688 (M+1+Na).

[Example 70] Preparation of Compound A-13

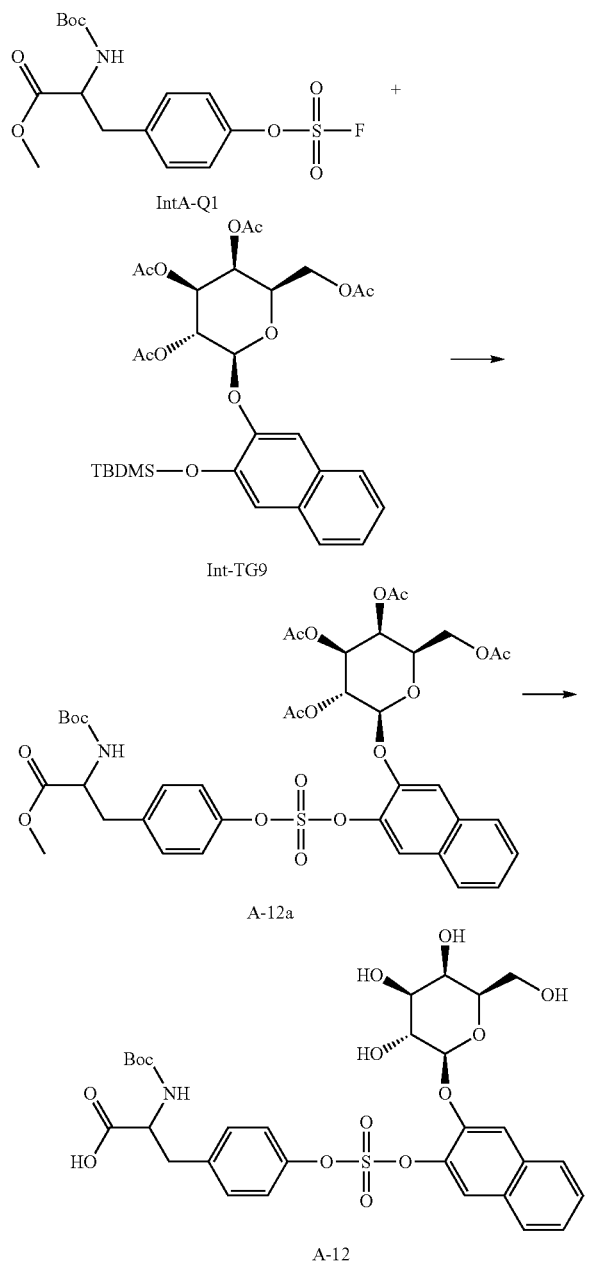

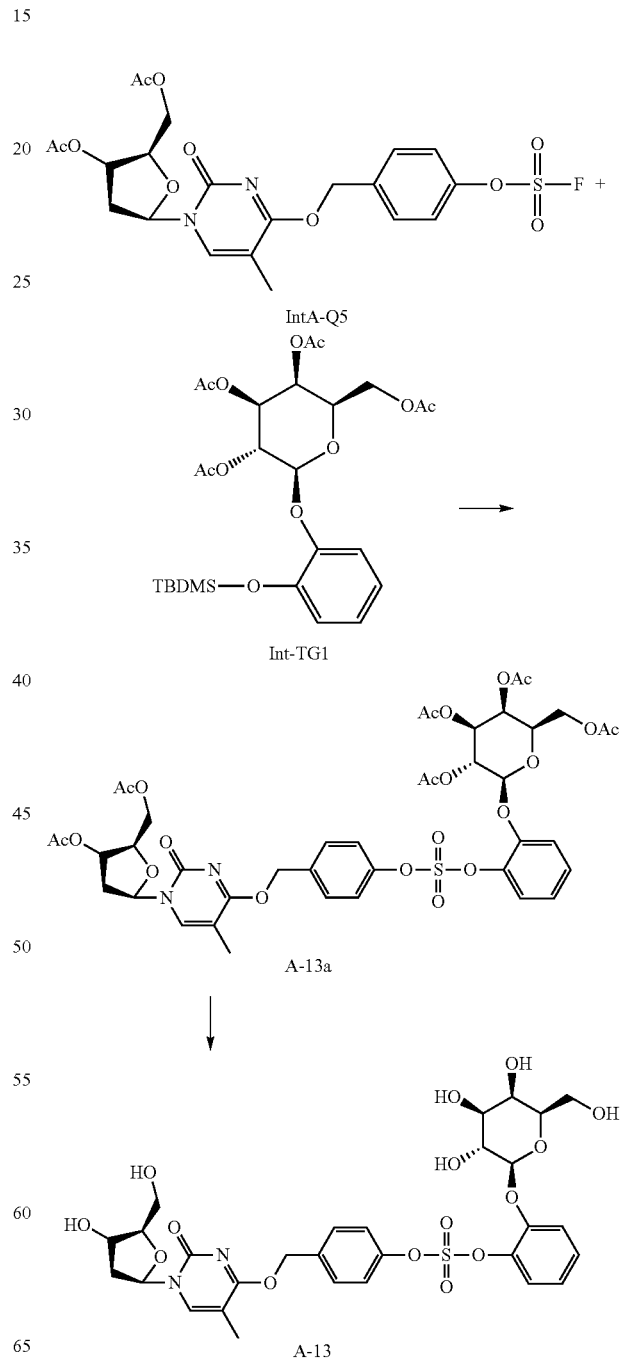

Preparation of Compound A-12a

Compound A-12a was synthesized via a similar synthetic route as described in Example 67.

Preparation of compound A-13a

Compound A-13a was synthesized via a similar synthetic route as described in Example 67.

Yield 43%; EI-MS m/z: 935 ($M^{+1}$).

Preparation of Compound A-13 Compound A-13 was synthesized via a similar synthetic route as described in Example 61.

Yield 61%; EI-MS m/z: 683 ($M^{+1}$).

[Example 71] Preparation of Compound A-14

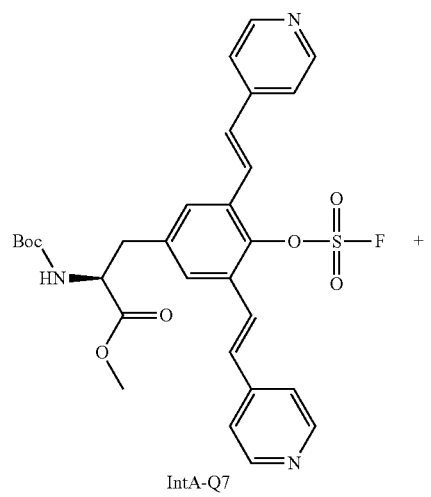

IntA-Q7

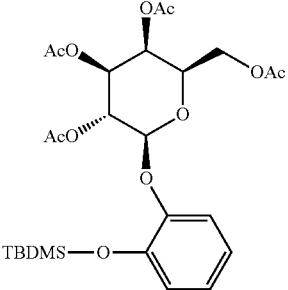

Int-TG1

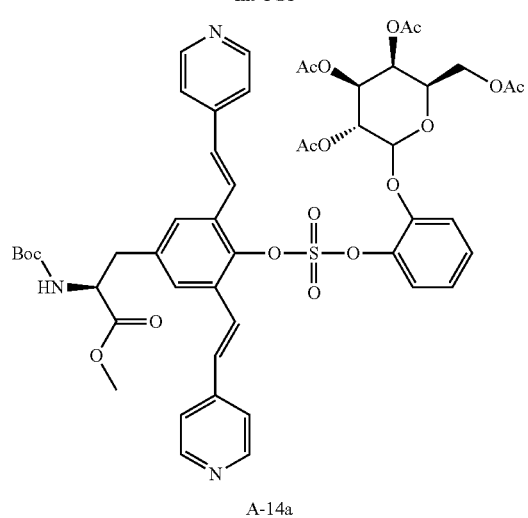

A-14a

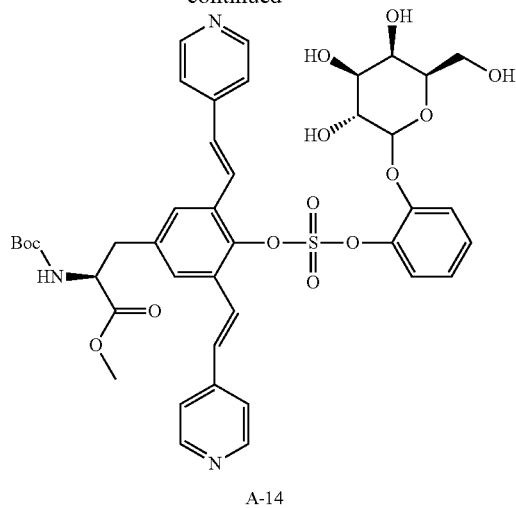

A-14

Preparation of Compound A-14a

Compound A-14a was synthesized via a similar synthetic route as described in Example 66.

Yield quant.; EI-MS m/z: 1004 ($M^{+1}$).

Preparation of Compound A-14

Compound A-14a was synthesized via a similar synthetic route as described in Example 61.

Yield 88%; EI-MS m/z: 836 ($M^{+1}$).

[Example 72] Preparation of Compound A-15

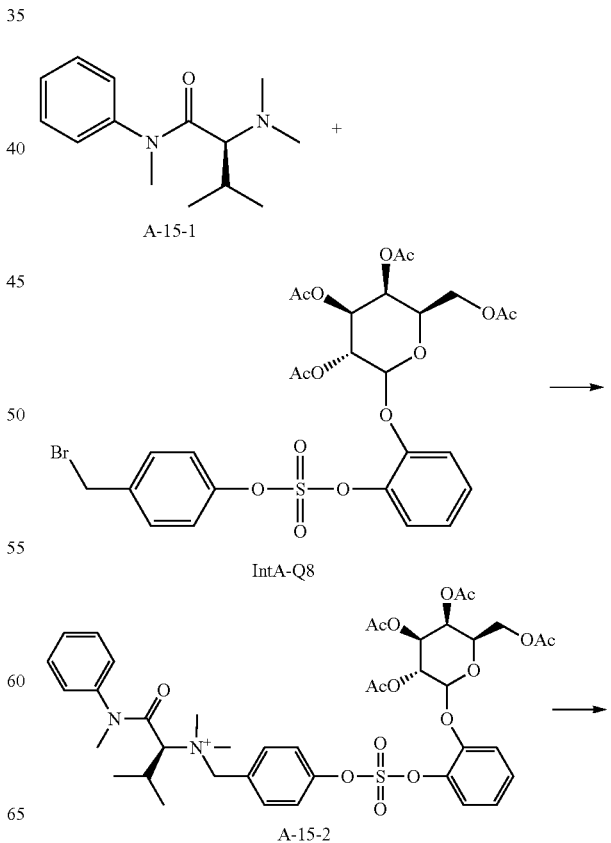

A-15-1

IntA-Q8

A-15-2

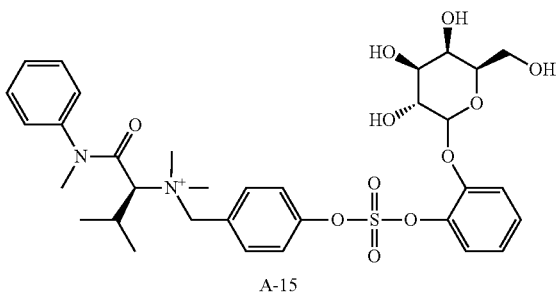

A-15

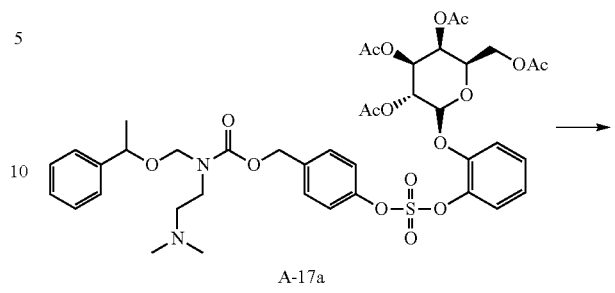

A-17a

Preparation of Compound A-15-2

To a solution of compound A-15-1 (53 mg, 76.9 μmol) and IntA-Q8 (22 mg, 92.3 μmol) in DMF (2 mL) was added dropwise DIPEA (27 μL, 0.15 mmol) under $N_2$ atmosphere. After stirring overnight at room temperature, the mixture was separated and purified by Prep-HPLC to obtain compound A-15-2 (25.9 mg, 40%).

EI-MS m/z: 843 ($M^{+1}$).

Preparation of Compound A-15

Compound A-15 was synthesized via a similar synthetic route as described in Example 61.

Yield 51%; EI-MS m/z: 675 ($M^{+1}$).

[Example 73] Preparation of Compound A-17

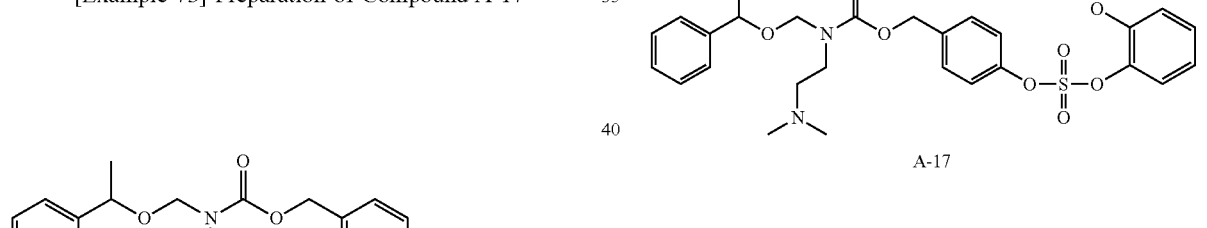

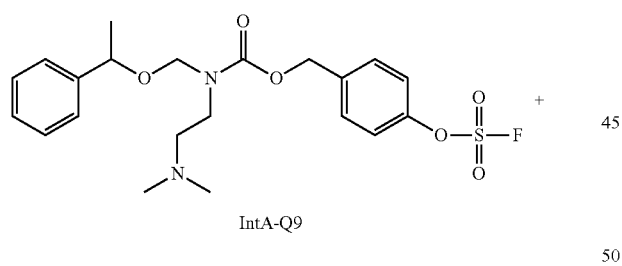

IntA-Q9

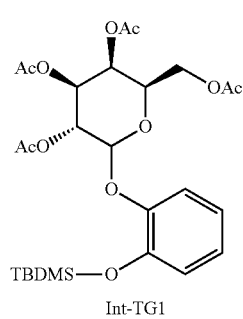

Int-TG1

A-17

Preparation of Compound A-17a

Compound A-17a was synthesized via a similar synthetic route as described in Example 60.

Yield 51%; EI-MS m/z: 875 ($M^{+1}$).

Preparation of Compound A-17

Compound A-17 was synthesized via a similar synthetic route as described in Example 71.

Yield 52.2%; EI-MS m/z: 707 ($M^{+1}$).

[Example 74] Preparation of Compound A-18
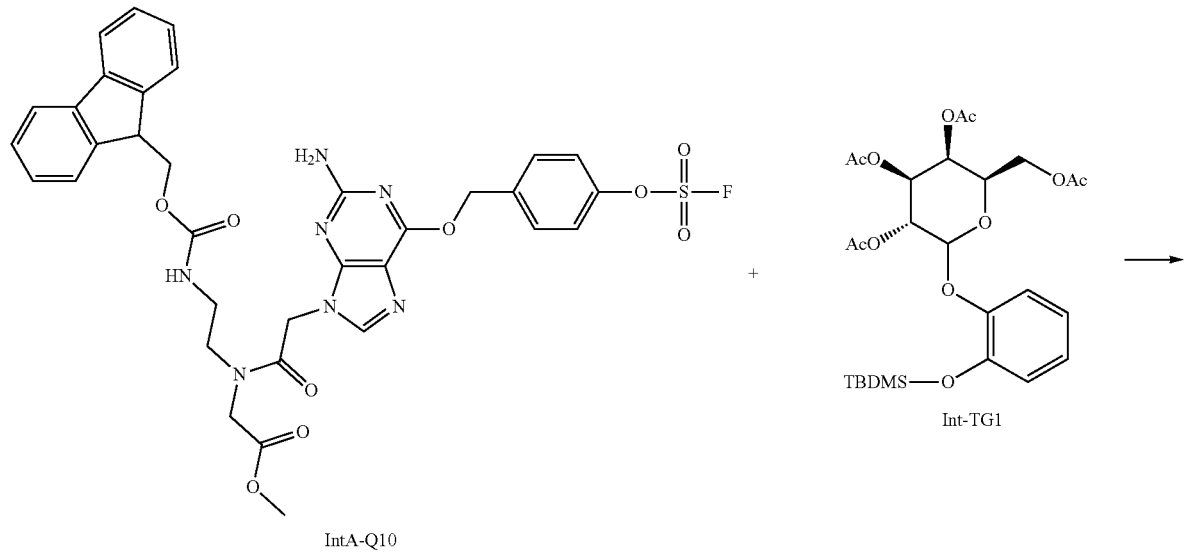
IntA-Q10
Int-TG1
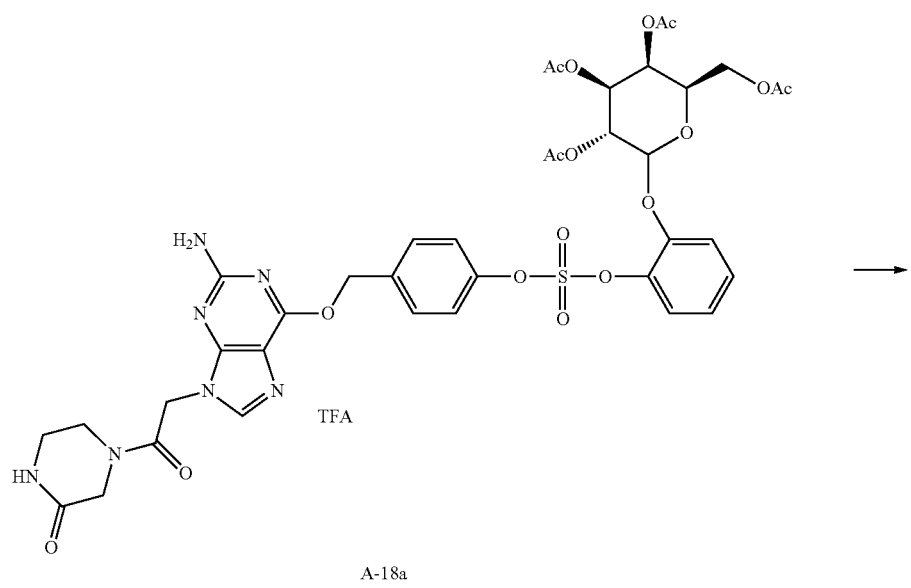
A-18a

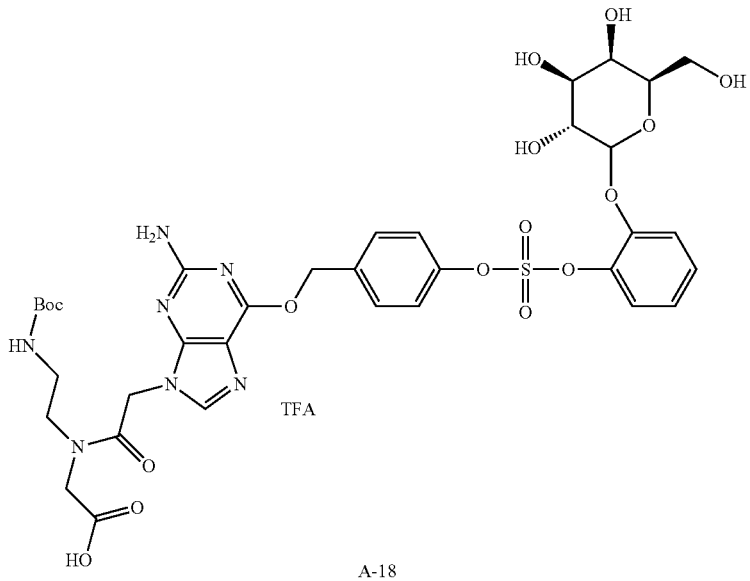

A-18

Preparation of Compound A-18a

To a solution of compound IntA-Q10 (118 mg, 0.16 mmol) and compound Int-TG1 (107 mg, 0.19 mmol) in ACN (2 mL) and DMF (0.2 mL) was added BEMP (23.3 μL, 0.08 mmol) under N₂ atmosphere. After stirring at room temperature for 2.5 minutes, DBU (12 μL, 0.08 mmol) was further added thereto, and the mixture was stirred at room temperature for 2 hours and diluted with EA (30 mL×2). The organic layer was washed with H₂O (30 mL), and brine (20 mL), dried over anhydrous Na₂SO₄, filtered and concentrated under reduced pressure. The residue was separated and purified by Prep-HPLC to obtain compound A-18a (22.5 mg, 14%).

EI-MS m/z: 900 (M$^{+1}$).

Preparation of Compound A-18b

To a solution of compound A-18a (22.5 mg, 0.022 mmol) in ACN (1 mL) was added Boc₂O (14.5 mg, 0.066 mmol) and DMAP (2.7 mg, 0.022 mmol) under N₂ atmosphere. After stirring overnight at room temperature, Boc20 (4.8 mg, 0.022 mmol) and DMAP (1.4 mg, 0.011 mmol) were further added thereto, and the mixture was stirred at room temperature for 5 hours. The mixture was separated and purified by Prep-HPLC to obtain compound A-18 (10 mg, 37%).

EI-MS m/z: 1101 (M$^{+1}$).

Preparation of Compound A-18

Compound A-18 was synthesized via a similar synthetic route as described in Example 58.

EI-MS m/z: 850 (M$^{+1}$).

[Example 75] Preparation of Compound A-19

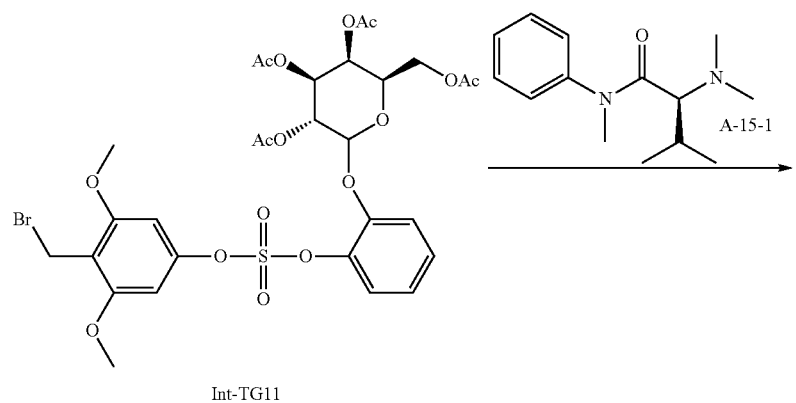

Int-TG11

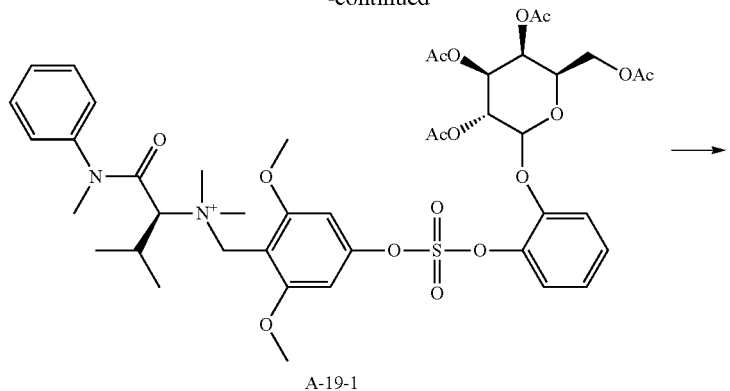
A-19-1
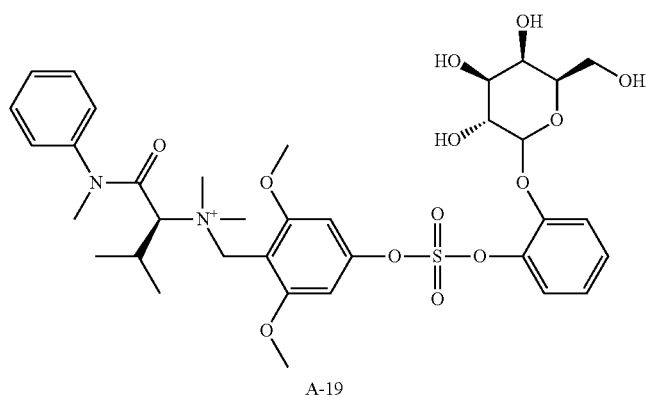
A-19
Compound A-19 was synthesized via a similar synthetic route as described in Example 72.
Preparation of Compound A-19-1
Yield 44%; EI-MS m/z: 904 (M$^{+1}$).
Preparation of Compound A-19
Yield 70%; EI-MS m/z: 736 (M$^{+1}$).
[Example 76] Preparation of Compound A-20
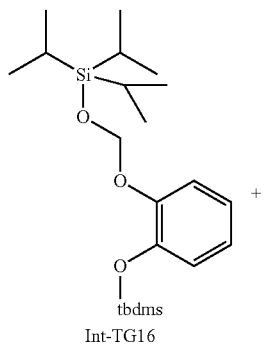
Int-TG16
-continued
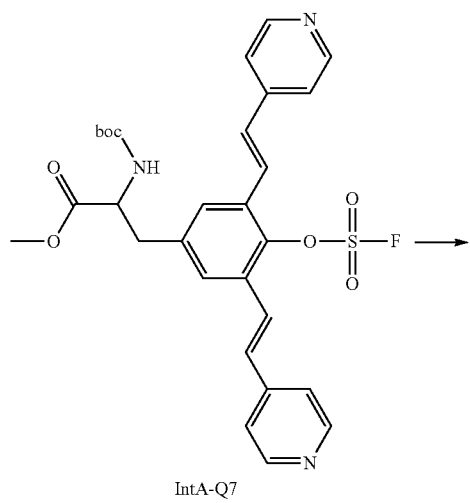
IntA-Q7

245

-continued

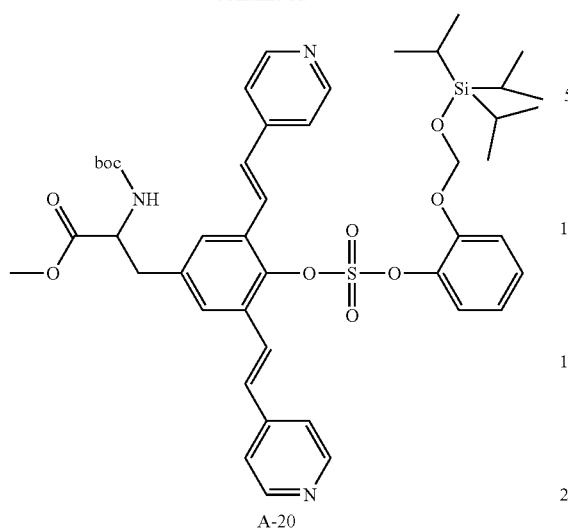

A-20

Compound A-20 was synthesized via a similar synthetic route as described in Example 71.

Yield 68%; EI-MS m/z: 861 (M$^{+1}$).

[Example 77] Preparation of Compound A-21

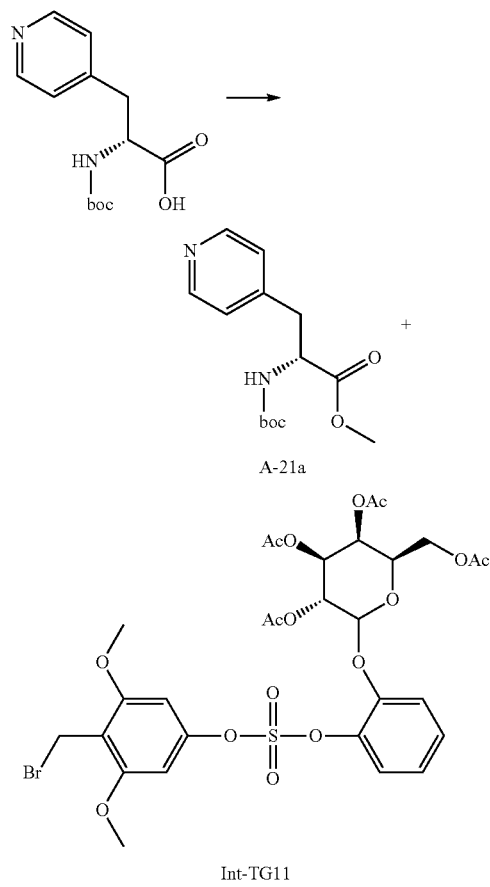

246

-continued

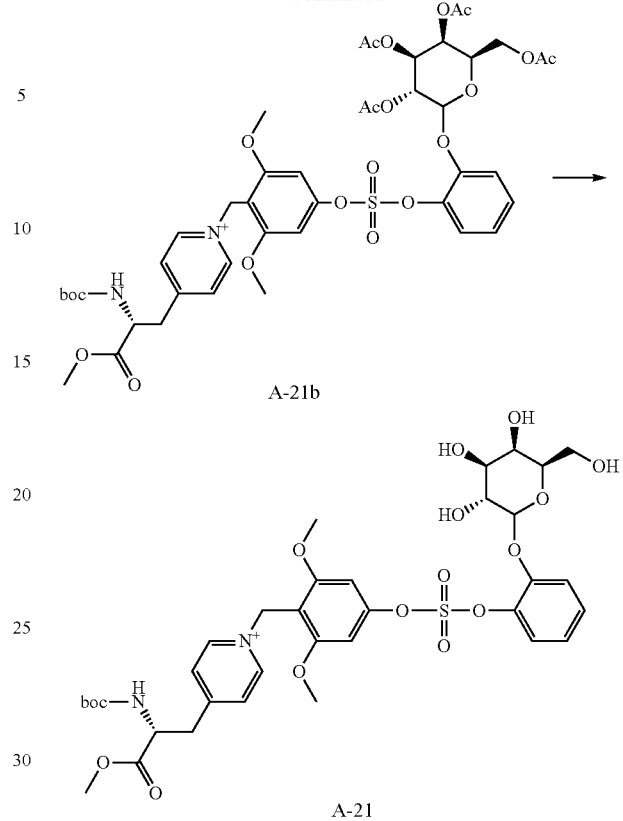

Preparation of Compound A-21a

N-Boc-3-(4-pyridyl)-D-alanine (300 mg, 0.06 mmol) and DMAP (275 mg, 2.25 mmol) were dissolved in MeOH (5 at 0° C. DCC (465 mg, 2.25 mmol) was added at 0° C., the mixture was stirred at 0° C. for 2 hours. The reaction was warmed to room temperature and stirred overnight. The mixture was diluted with EA (30 mL), filtered and concentrated under reduced pressure. The residue was purified by column chromatography to obtain a compound A-21a.

$^1$H NMR (400 MHz, DMSO-d$_6$) δ 8.46 (d, J=5.6 Hz, 2H), 7.37 (d, J=8 Hz, 1H), 7.26 (d, J=5.6 Hz, 2H), 4.29-4.23 (m, 1H), 3.63 (s, 3H), 3.06-3.01 (m, 1H), 2.89-2.83 (in, 1H), 1.31 (s, 9H).

EI-MS m/z: 281 (M$^{+1}$).

Compound A-21 was synthesized via a similar synthetic route as described in Example 72.

Preparation of Compound A-21b

Yield 29%; EI-MS m/z: 950 (M$^{+1}$)

Preparation of compound A-21

Yield 47%; EI-MS m/z: 768 (M$^{+1}$).

[Example 78] Preparation of Compound A-22

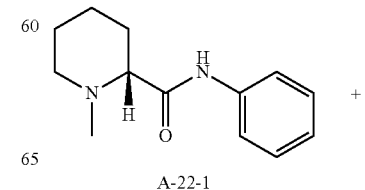

A-22-1

247

-continued

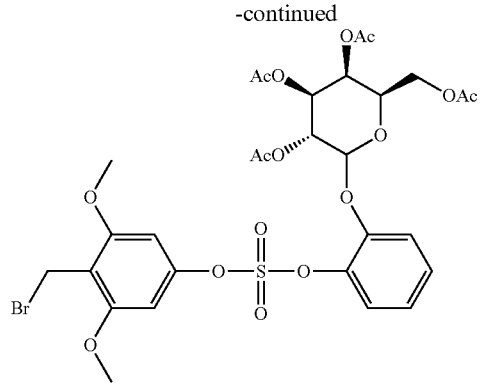

Int-TG11

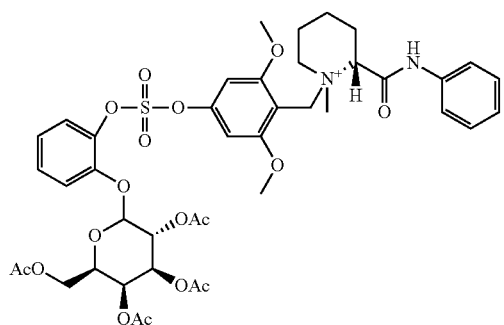

A-22a

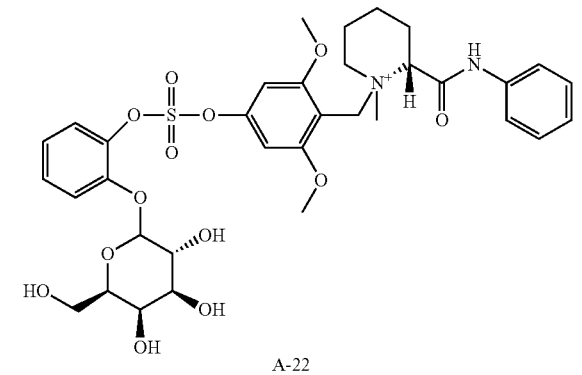

A-22

Compound A-22 was synthesized via a similar synthetic route as described in Example 72.

Preparation of Compound A-22a
Yield 68% EI-MS m/z: 888 (M$^{+1}$).
Preparation of Compound A-22
Yield 56% EI-MS m/z: 720 (M$^{+1}$).

[Example 79] Preparation of Compound A-23

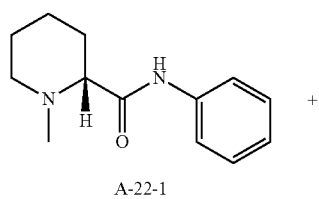

A-22-1

248

-continued

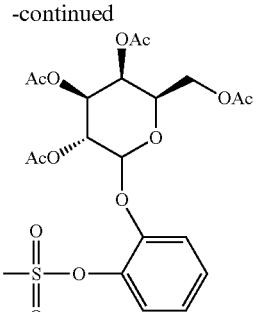

Int-TG17

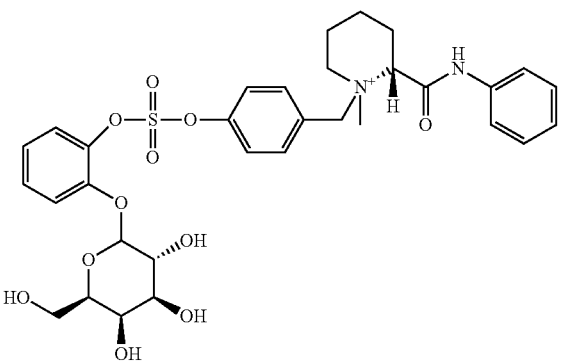

A-23a

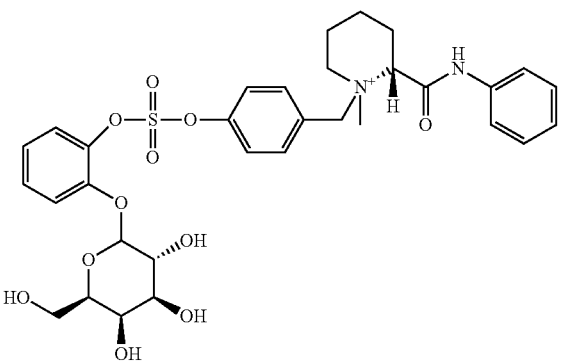

A-23

Compound A-22 was synthesized via a similar synthetic route as described in Example 72.

Preparation of Compound A-22a
Yield 57% EI-MS m/z: 828 (M$^{+1}$).
Preparation of Compound A-22
Yield 72% EI-MS m/z: 660 (M$^{+1}$).

[Example 80] Preparation of Compound A-24
[Example 81] Preparation of Compound A-25
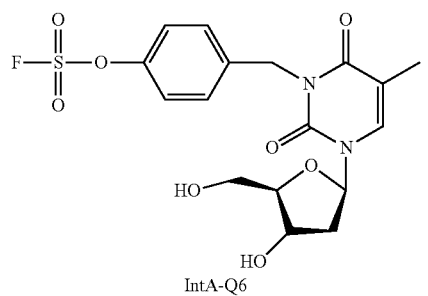
IntA-Q6
+
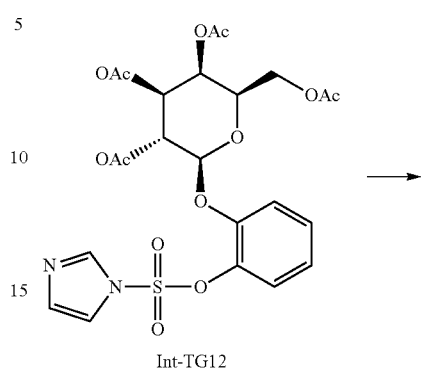
Int-TG12
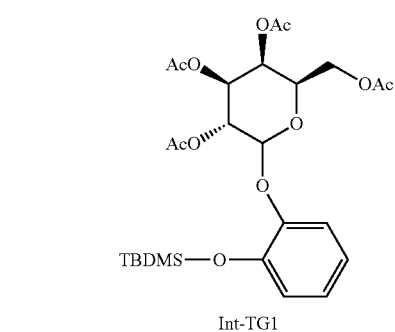
Int-TG1
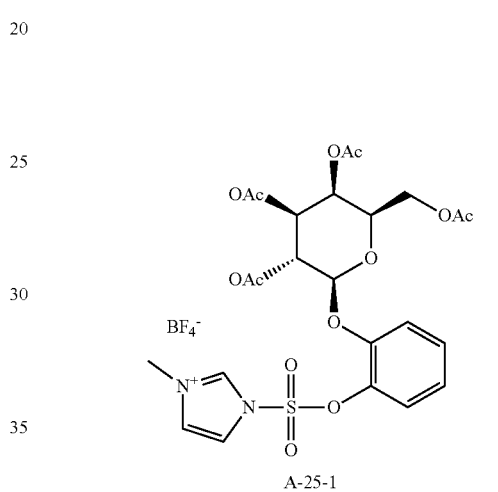
A-25-1
+
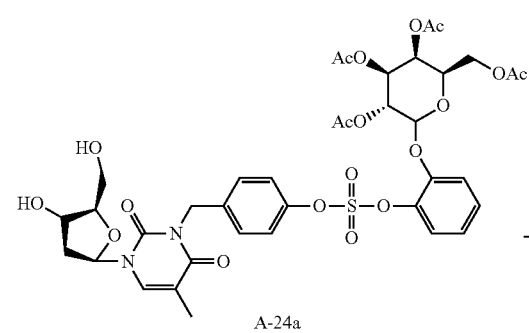
A-24a
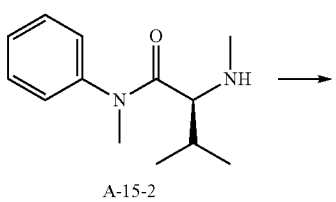
A-15-2
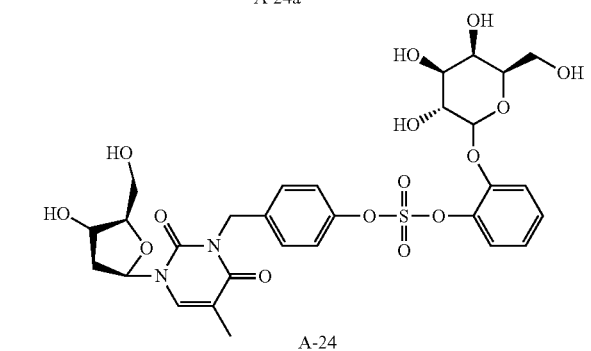
A-24
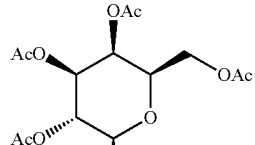
A-25-2
Compound A-24 was synthesized via a similar synthetic route as described in Example 69.
Preparation of Compound A-24a
Yield 33%; EI-MS m/z: 851 (M$^{+1}$).
Preparation of Compound IntA-Q5
Yield 80%; EI-MS m/z: 705 (M$^{+1}$+Na).

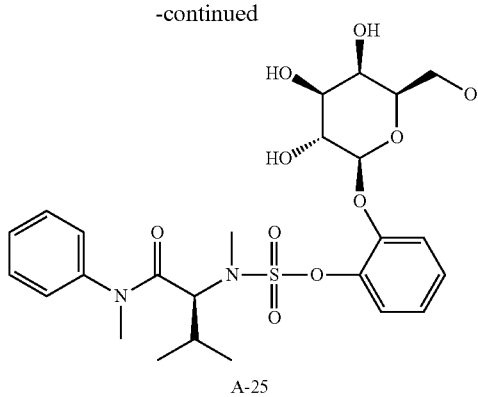

A-25

Preparation of Compound A-25-2

To a solution of compound Int-TG12 (100 mg, 0.175 mmol) in DCM (6 ml) was added Methyl triflate (30 μl, 0.263 mmol) at 0° C. under N$_2$ atmosphere. The mixture was stirred at room temperature for 4 hours and concentrated under reduced pressure. The residue was dissolved in dry ACN (5 mL) and added compound A-15-2 (46 mg, 0.21 mmol) at room temperature. The mixture was heated at 40° C. for 8 hours, quenched with 2 N aq. HCl (8 mL), and extracted with EtOAc (2×10 mL). The organic layer was dried over anhydrous MgSO$_4$, filtered and concentrated. The residue was dissolved in DMSO (1 mL) and purified by prep-HPLC, which produced the compound A-25-2 (43.5 mg, 35%).

EI-MS m/z: 723 (M$^{+1}$).

Preparation of Compound A-25

Compound A-25 was synthesized via a similar synthetic route as described in Example 61.

Yield 60%; EI-MS m/z: 555 (M$^{+1}$).

[Example 82] Preparation of Compound A-26

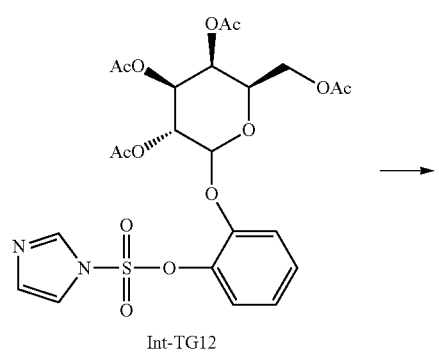

Int-TG12

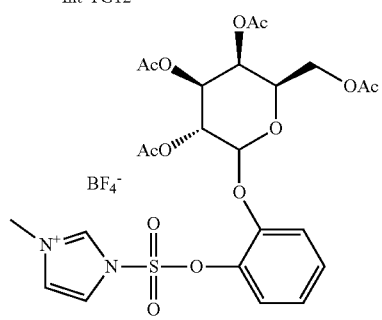

BF$_4^-$

+

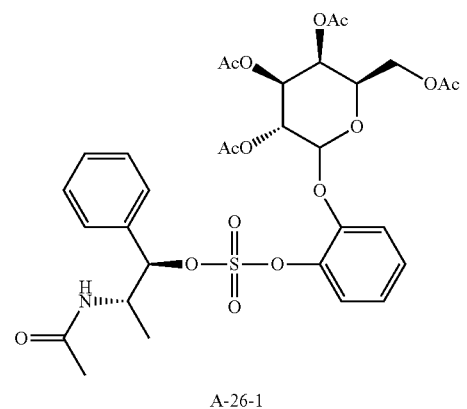

Int-TG13

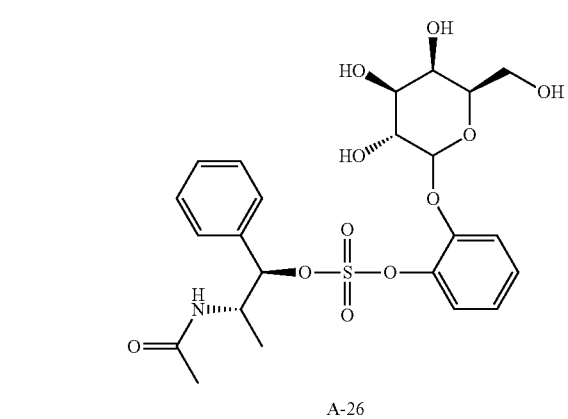

A-26-1

A-26

Compound A-26 was synthesized via a similar synthetic route as described in Example 81.

Preparation of Compound A-26-1

Yield 8%; EI-MS m/z: 696 (M$^{+1}$).

Preparation of Compound A-26

Yield 32%; EI-MS m/z: 528 (M$^{+1}$).

[Example 83] Preparation of Compound A-27

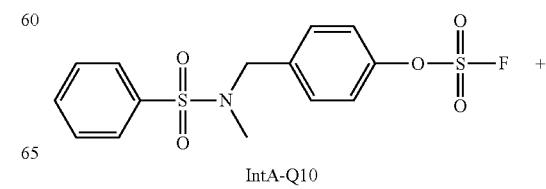

IntA-Q10

+

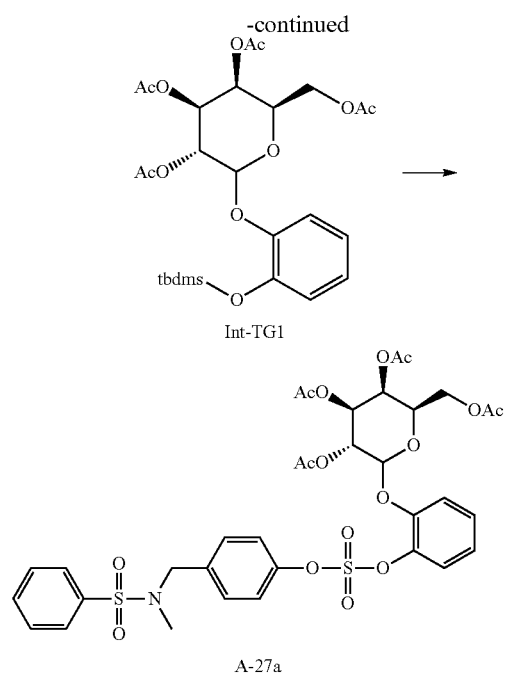
Int-TG1
A-27a
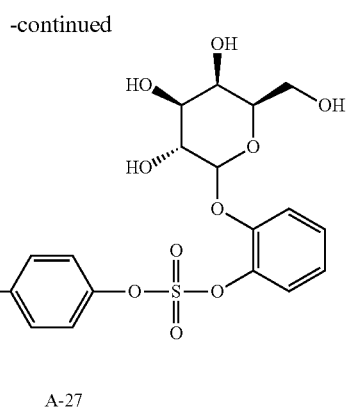
A-27
Compound A-27 was synthesized via a similar synthetic route as described in Example 81.
Preparation of Compound A-26-1
Yield 72%; EI-MS m/z: 802 ($M^{+1}$+Na).
Preparation of Compound A-26
Yield 79%; EI-MS m/z: 634 ($M^{+1}$+Na).
[Example 84] Preparation of Compound B-1
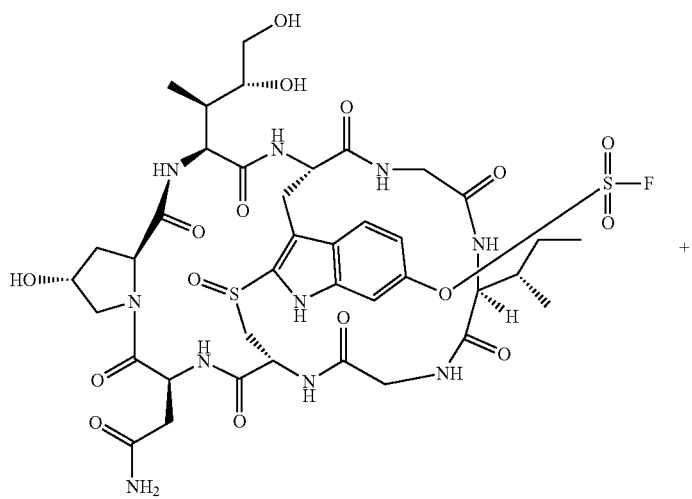
IntB-Q1
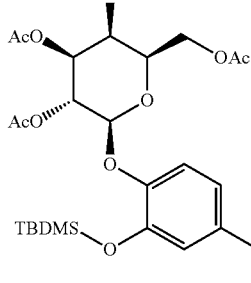
Int-TG2

-continued
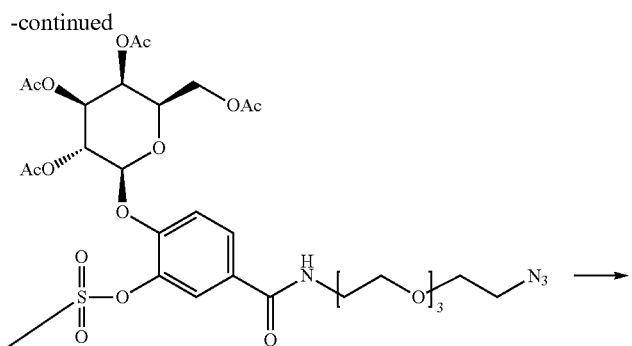
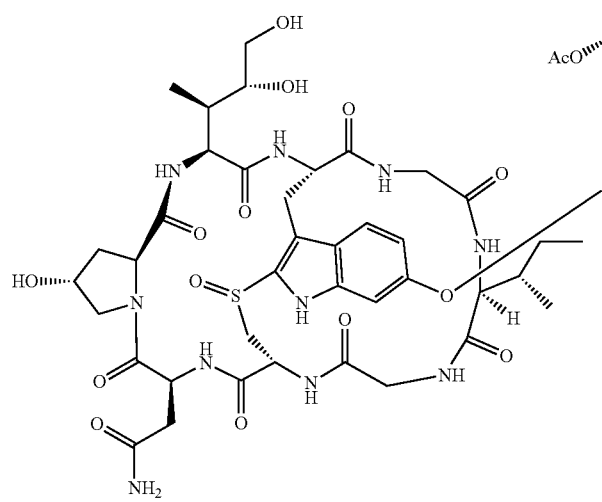
B-1a
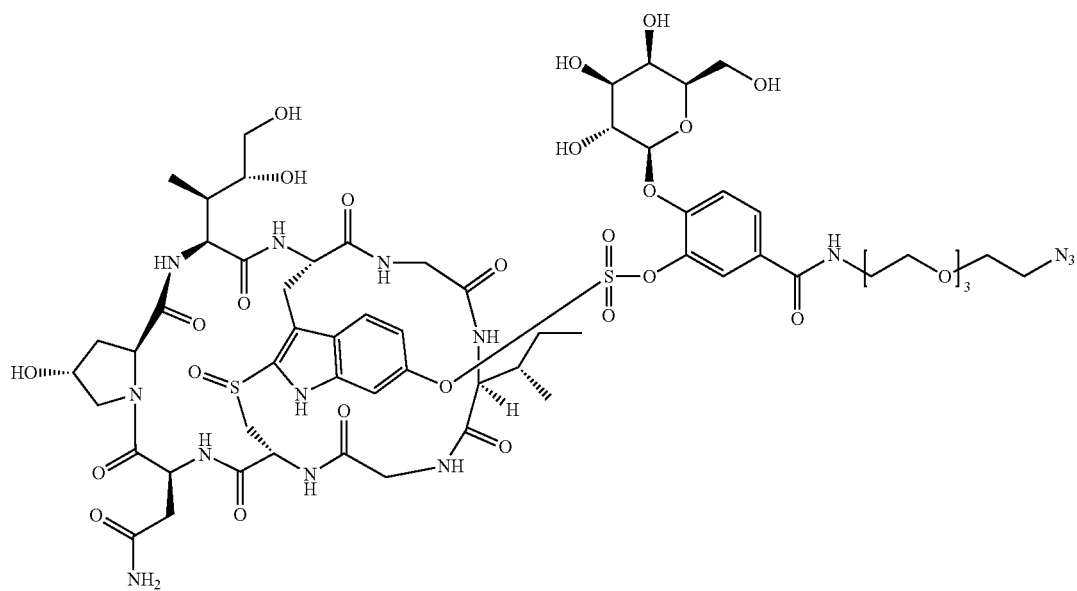
B-1

Compound B-1 was synthesized via a similar synthetic route as described in Example 67 and Example 61
Preparation of Compound B-1a
EI-MS m/z: 1666 (M$^{+1}$).
Preparation of Compound B-1
Yield 19% over 2 steps; EI-MS m/z: 1498 (M$^{+1}$).
[Example 85] Preparation of Compound B-2
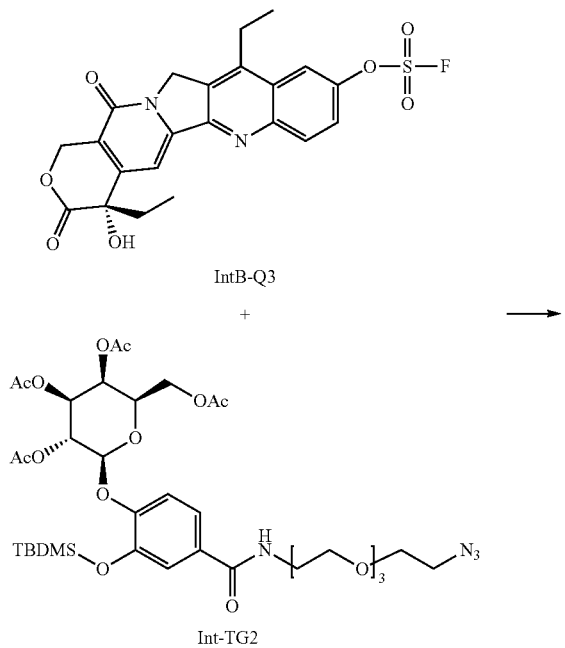
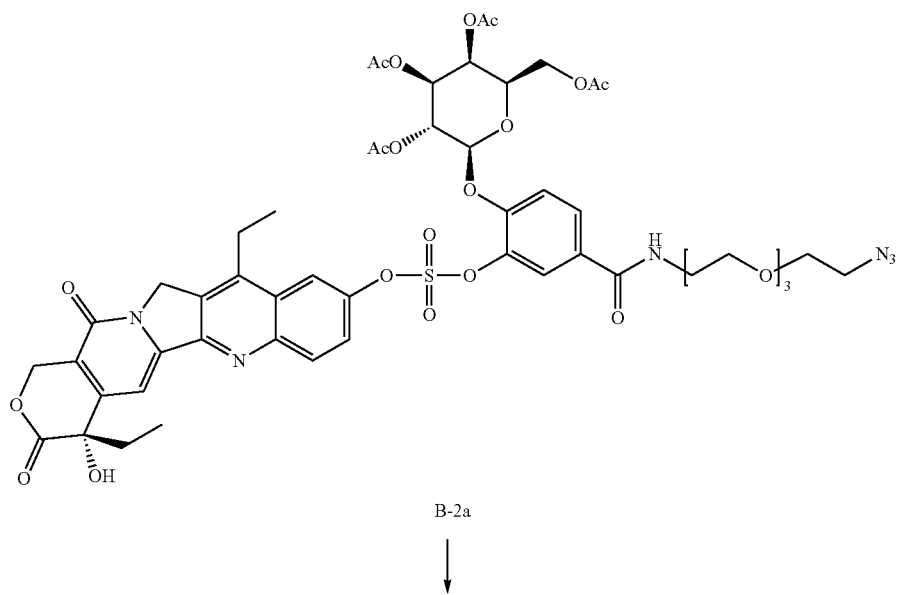

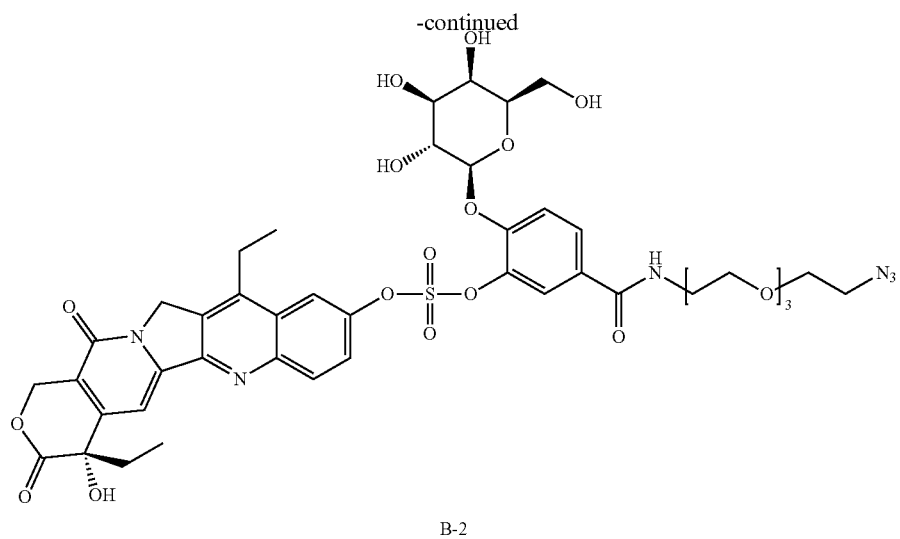
B-2
Compound B-2 was synthesized via a similar synthetic route as described in Example 67 and Example 61.
Preparation of Compound B-2a
Yield 58%; EI-MS m/z: 1140 (M$^+$1).
Preparation of Compound B-2
Yield 76%; EI-MS m/z: 971 (M$^+$1).
[Example 86] Preparation of Compound B-3
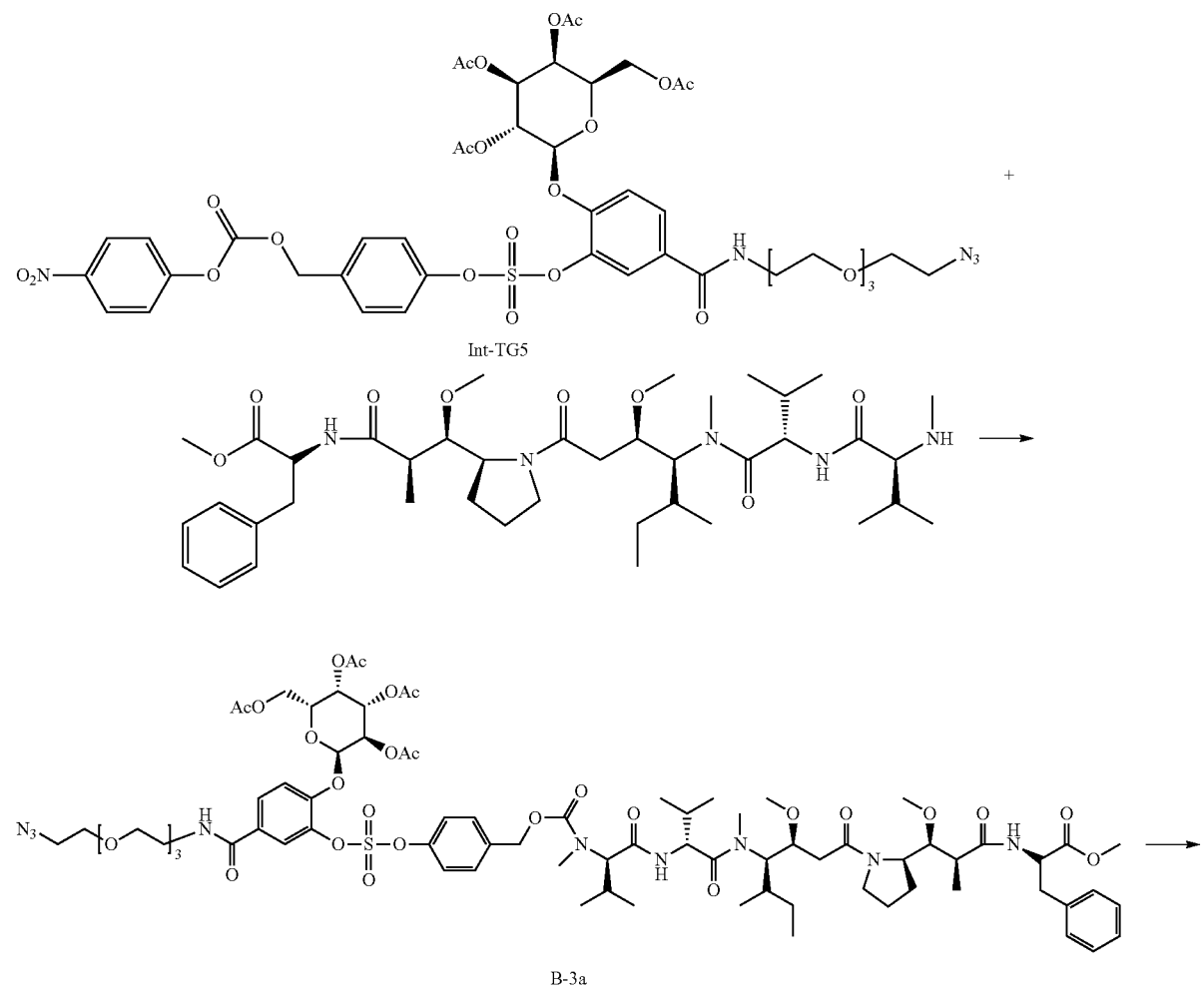

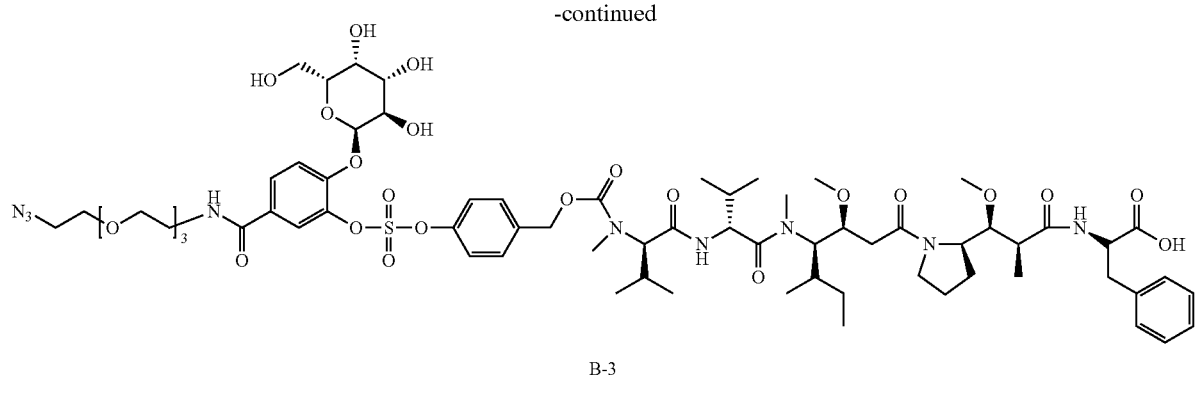

B-3

Preparation of Compound B-3a

To a solution of compound Int-TG5 (65 mg, 0.063 mmol) and MMAF-OMe (52 mg, 0.069 mmol) in DMF (1 mL) was added HOBt (2 mg, 0.013 mmol), DIPEA (12 μL, 0.069 mmol), and pyridine (330 μL) at room temperature under $N_2$ atmosphere. After stirring overnight, the mixture was adjusted to have pH of 2 to 3 with 1N HCl, extracted with EA (8 mL×2). The organic layer was washed distilled water (8 mL) and brine (12 mL, dried over anhydrous $Na_2SO_4$, filtered and concentrated under reduced pressure. The residue was subjected to column chromatography to obtain compound B-3a (73 mg, 71%).

EI-MS m/z: 1644 ($M^{+1}$).

Preparation of Compound B-3

Compound B-3 was synthesized via a similar synthetic route as described in Example 61.

Yield 69%; EI-MS m/z: 1462 ($M^{+1}$).

[Example 87] Preparation of Compound B-4

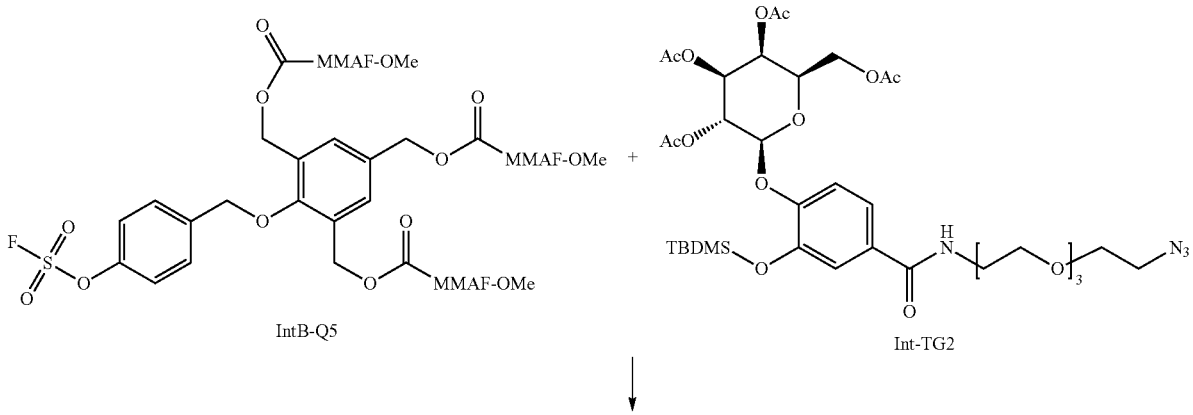

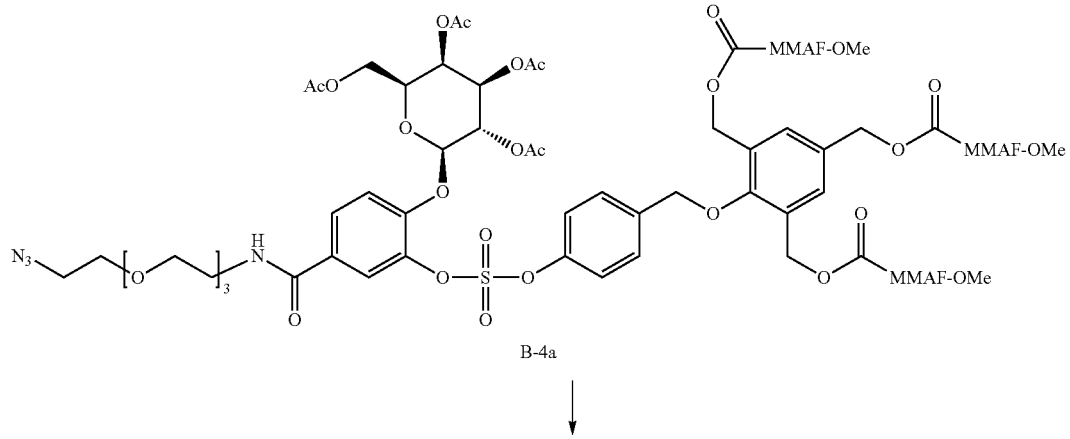

B-4a

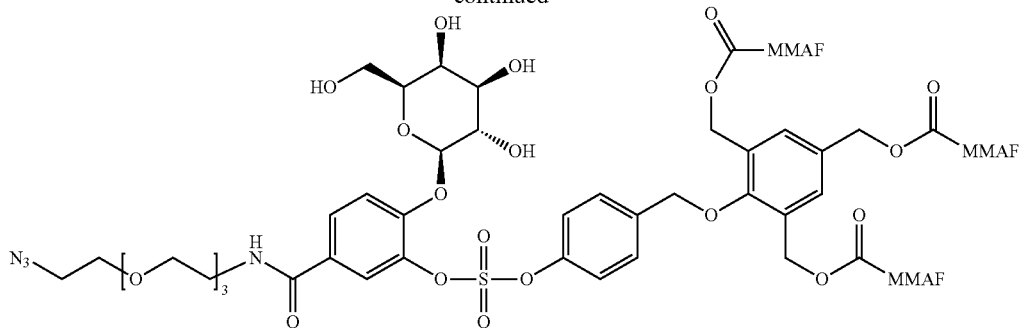
B-4
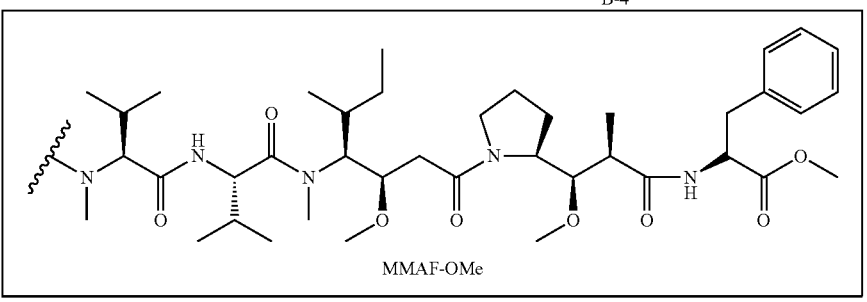
MMAF-OMe
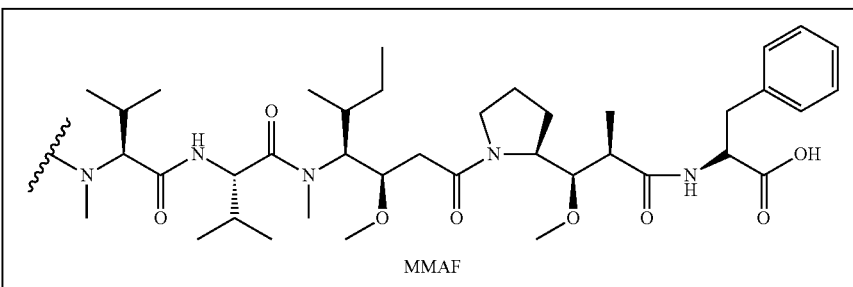
MMAF
Compound B-4 was synthesized via a similar synthetic route as described in Example 67 and Example 61.
Preparation of Compound B-4a
Yield 68%; EI-MS m/z: 1678 (M$^{+1}$/2).
Preparation of Compound B-4
Yield 91%; EI-MS m/z: 1572 (M$^{+1}$/2).
[Example 87] Preparation of Compound B-6
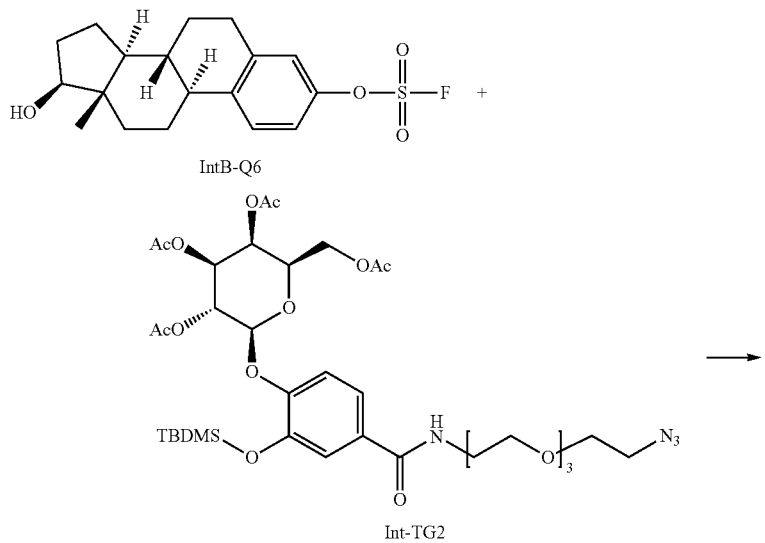
IntB-Q6
Int-TG2

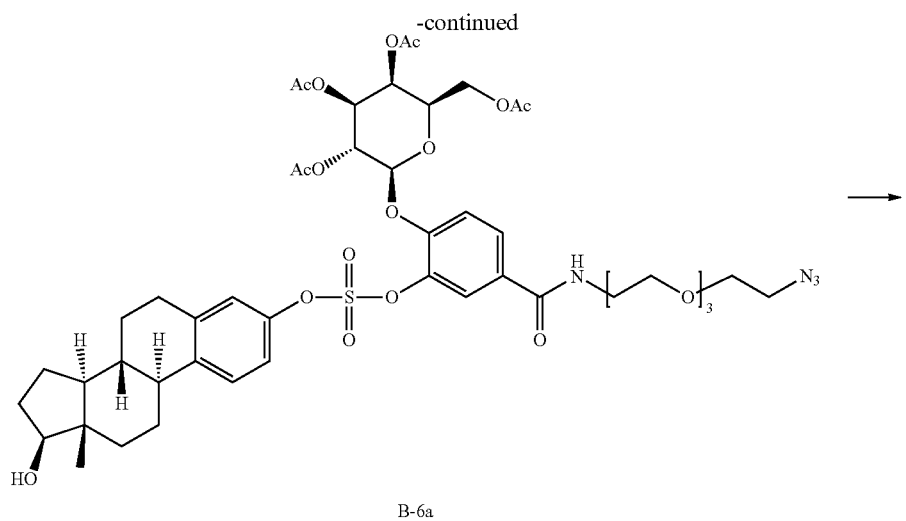
B-6a
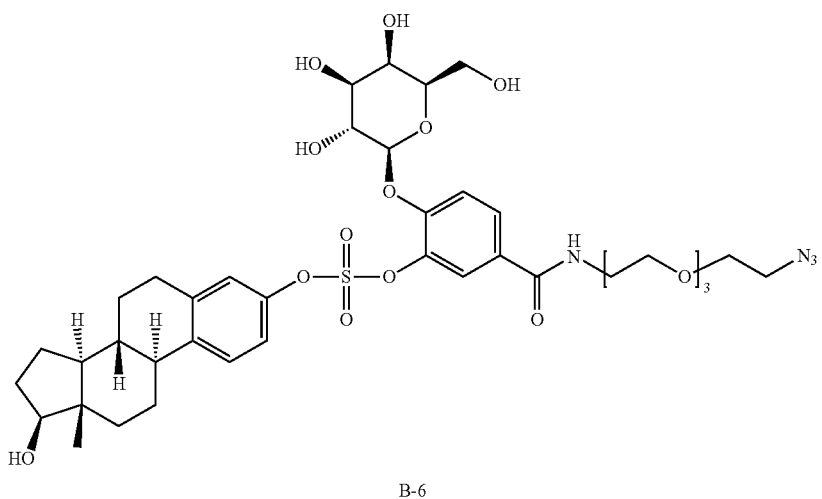
B-6
Compound B-6 was synthesized via a similar synthetic route as described in Example 67 and Example 61
Preparation of Compound B-6a
Yield 100%; crude; EI-MS m/z: 1020 ($M^{+1}$).
Preparation of Compound B-6
Yield 17%;
[Example 87] Preparation of Compound B-7
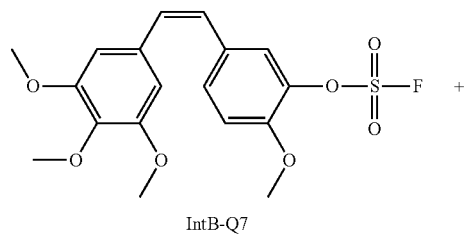
IntB-Q7

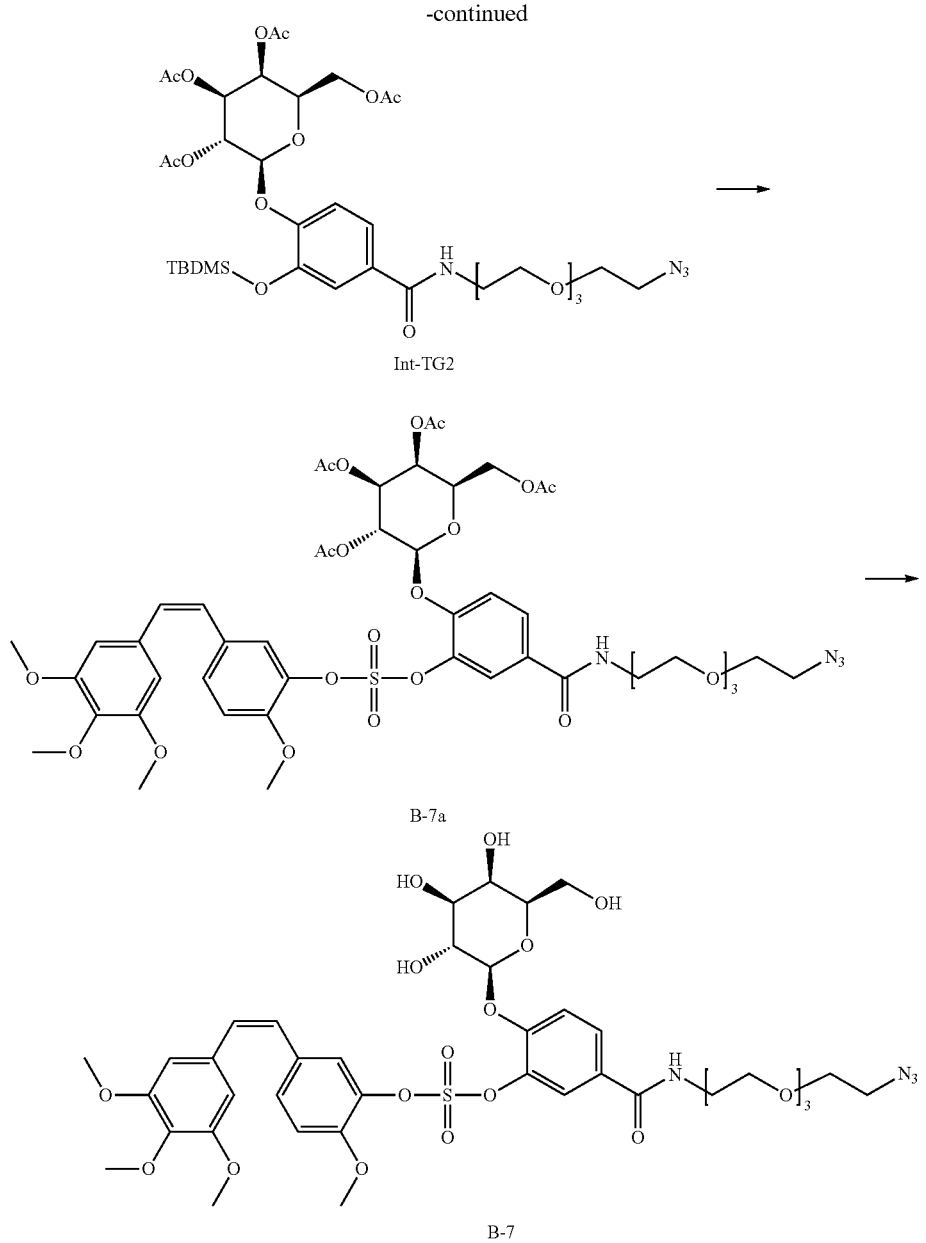
Compound B-7 was synthesized via a similar synthetic route as described in Example 67 and Example 61.
Preparation of Compound B-7a
Yield 99%; EI-MS m/z: 1063 (M$^{+1}$).
Preparation of Compound B-7
EI-MS m/z: 895 (M$^{+1}$).
[Example 89] Preparation of Compound B-8
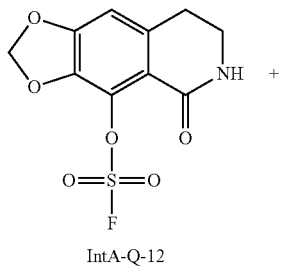

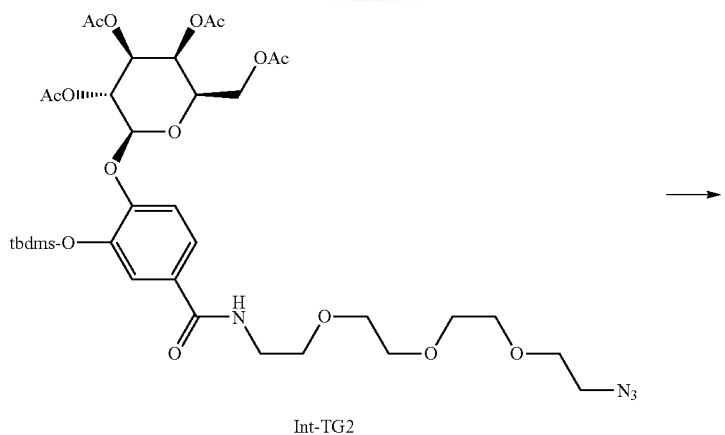
Int-TG2
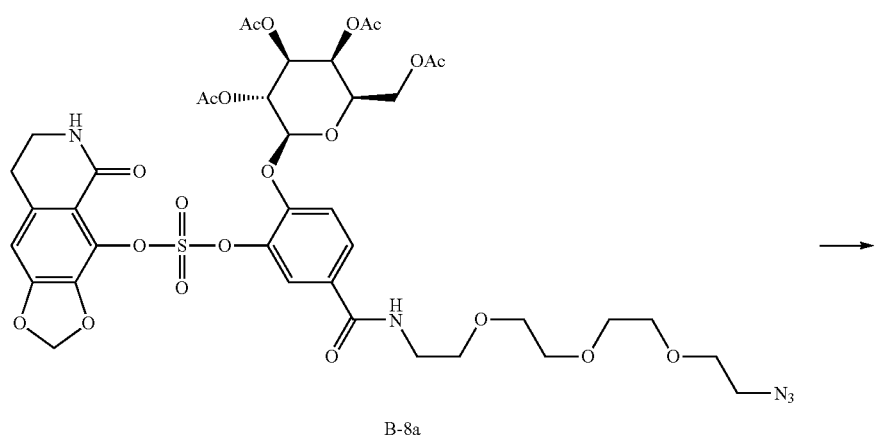
B-8a
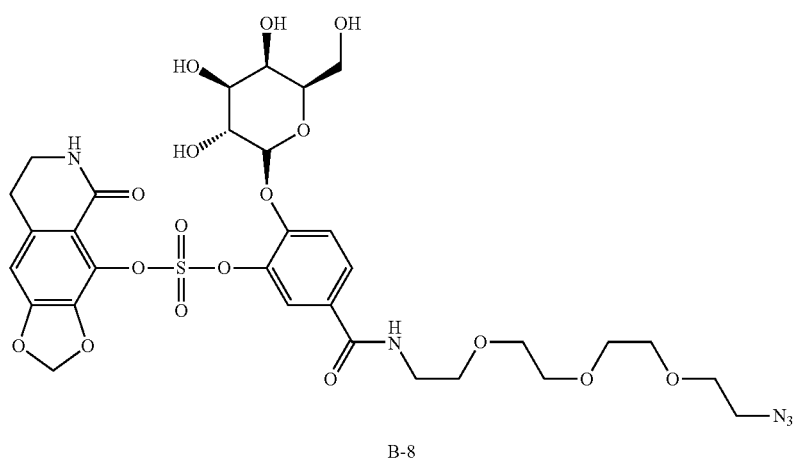
B-8

Preparation of Compound B-8a

Compound B-8a was synthesized via a similar synthetic route as described in Example 67

Yield 16%; EI-MS m/z: 954 (M$^{+1}$), 976 (M$^{+1}$+Na)

Preparation of Compound B-8

To a solution of compound B-8a (3.1 mg, 0.0032 mmol) in methanol (1 mL) was added 25%—NaOMe in MeOH (3 μL, 0.012 mmol) at 0° C. After stirring at room temperature for 1.5 hours, the mixture was neutralized with 2M-HCl aqueous solution and then purified by Prep-HPLC to obtain a compound B-8 as a pink solid (1.2 mg, 47%).

[Example 90] Preparation of Compound B-9

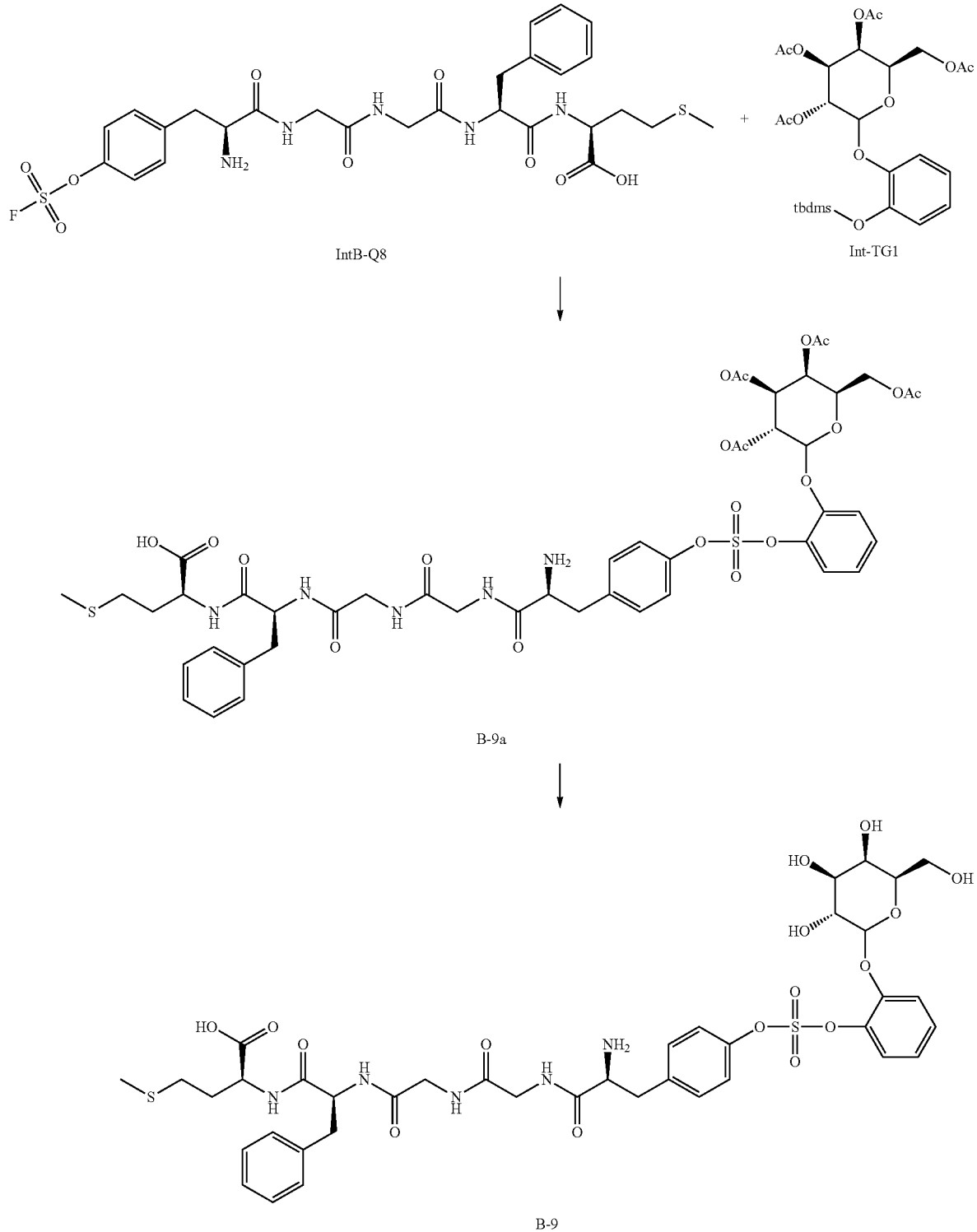

Compound B-9 was synthesized via a similar synthetic route as described in Example 67 and Example 61.
Preparation of Compound B-9a
Yield 50%; EI-MS m/z: 1077 ($M^{+1}$).
Preparation of Compound B-9
Yield 32%; EI-MS m/z: 908 ($M^{+1}$).

[Example 91] Preparation of Compound B-10

NaCNBH$_3$ (21 mg, 0.322 mmol), stirred for 2 hours, and quenched with saturated NaHCO$_3$ (10 mL). EtOAc (20 mL) wad added. The organic layer was dried over anhydrous Na$_2$SO$_4$, filtered and concentrated under reduced pressure. The residue was purified by column chromatography to produce compound AF-OMe (98 mg, 80%). EI-MS m/z: 761 ($M^{+1}$).

Compound B-10 was synthesized via a similar synthetic route as described in Example 72.

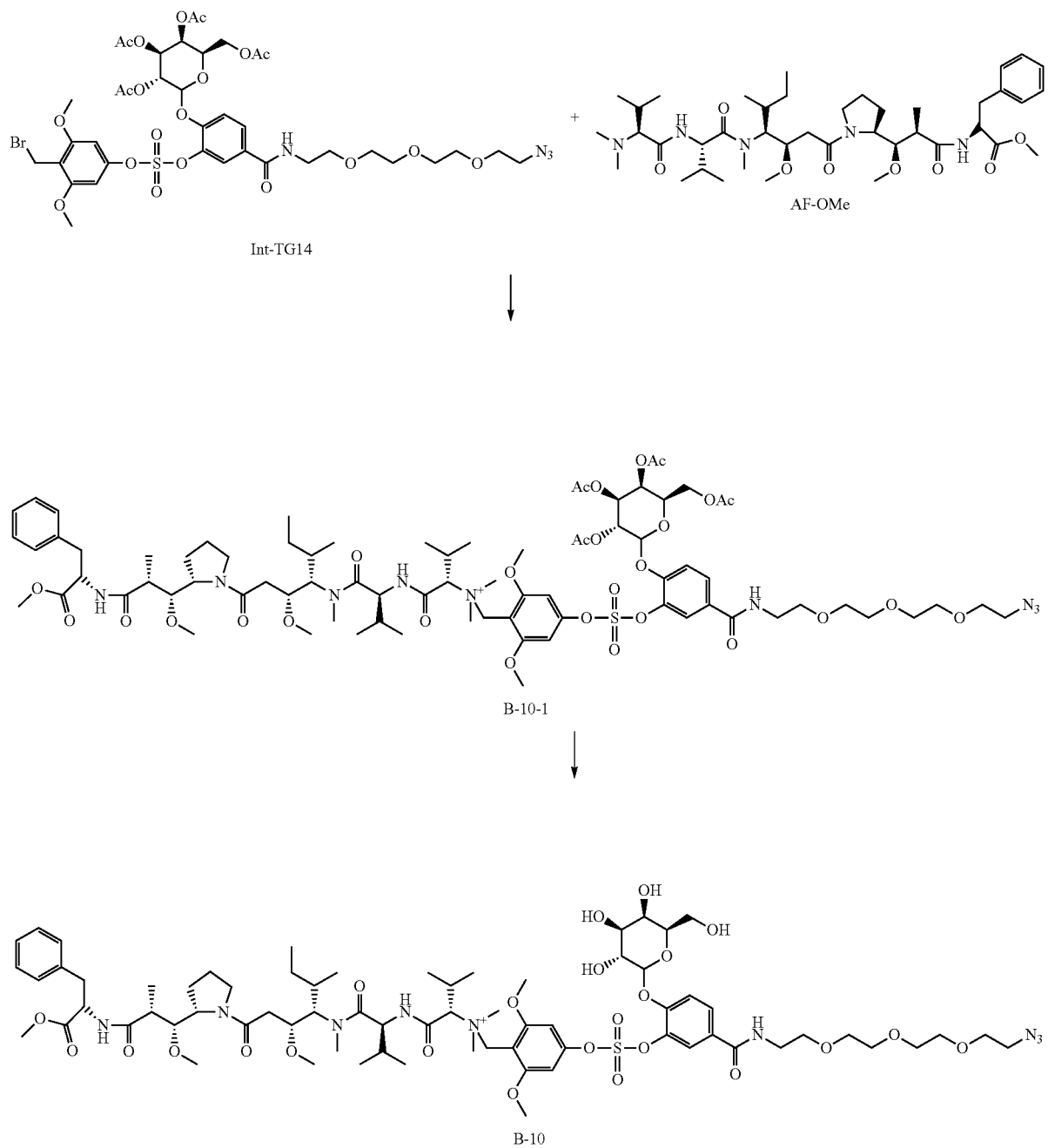

Preparation of Compound AF-OMe
To a solution of compound MMAF-OMe (120 mg, 0.161 mmol) in DMF (4 mL) was added 37% formaldehyde (36 μl, 0.483 mmol) and AcOH (184 μl, 3.22 mmol) at room temperature. After stirring 5 minutes, the mixture was added Preparation of Compound B-10-1
Yield 2700; EI-MS m/z: 1673 ($M^{+1}$).
Preparation of Compound B-10
Yield 81%; EI-MS m/z: 1491 ($M^{+1}$).

[Example 92] Preparation of Compound B-11
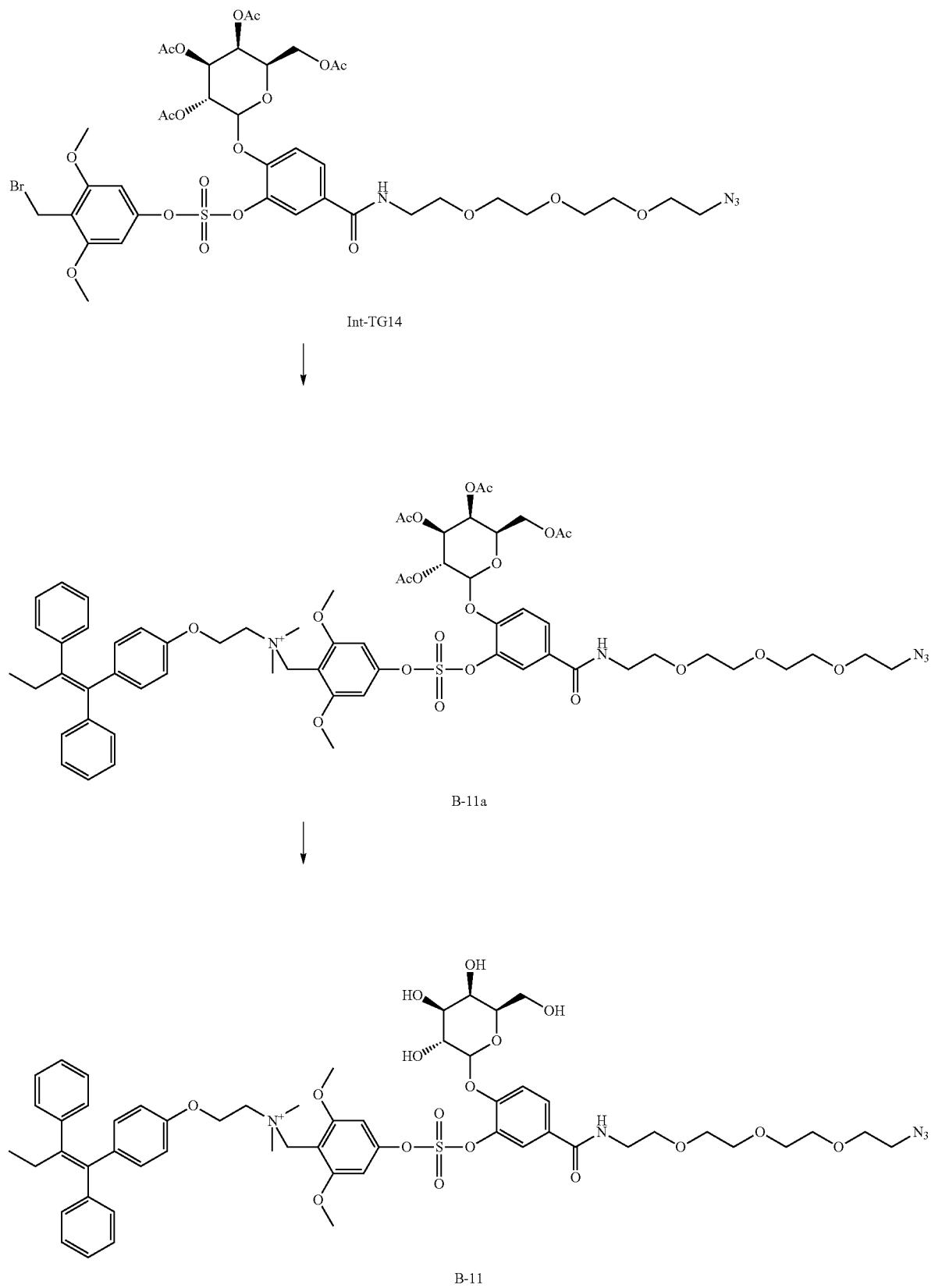

Compound B-11 was synthesized via a similar synthetic route as described in Example 91.
Preparation of Compound B-11a
Yield 87%; EI-MS m/z: 1285 ($M^{+1}$).
Preparation of Compound B-11
Yield 53%; EI-MS m/z: 1117 ($M^+$).
[Example 93] Preparation of Compound B-12
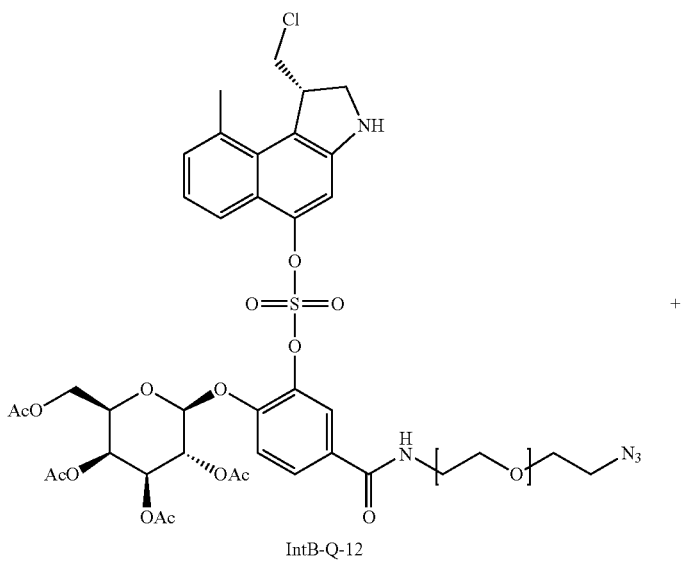
IntB-Q-12
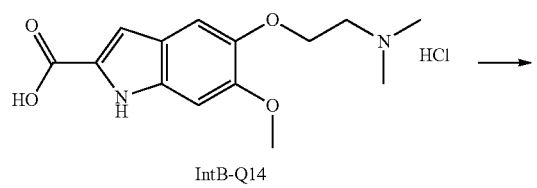
IntB-Q14
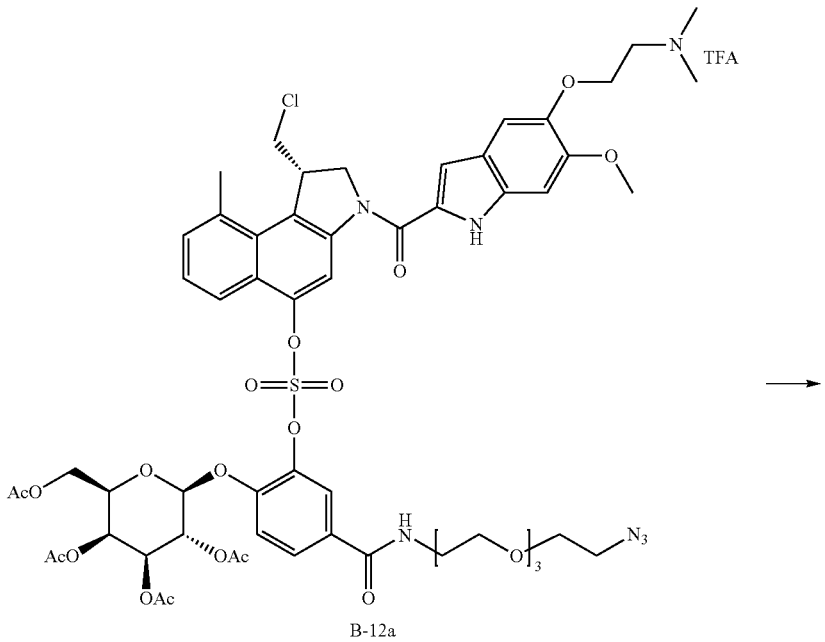
B-12a

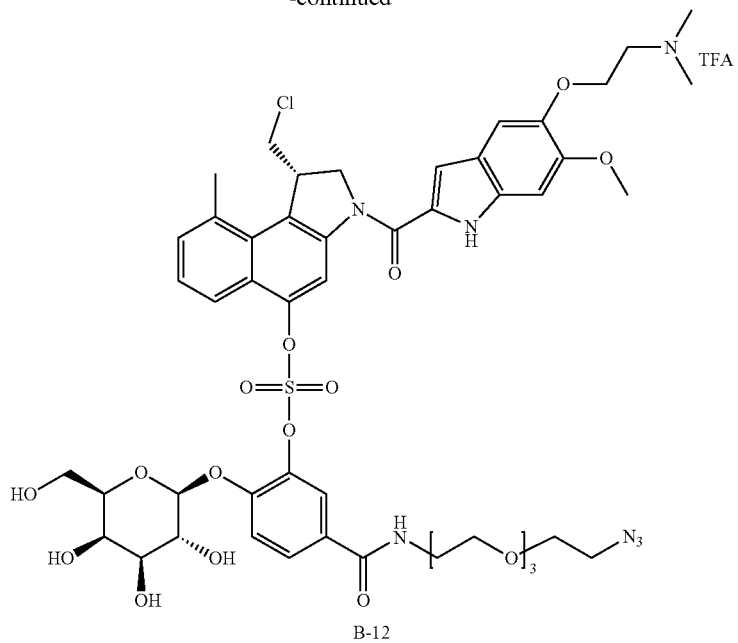
B-12
Compound B-12 was synthesized via a similar synthetic route as described in Example 30 and Example 73.
Preparation of Compound B-12a
Yield 53%; EI-MS m/z: 1254.7 ($M^{+1}$).
Preparation of Compound B-12
Yield 58%; EI-MS m/z: 1086.6 ($M^{+1}$).
[Example 94] Preparation of Compound B-13
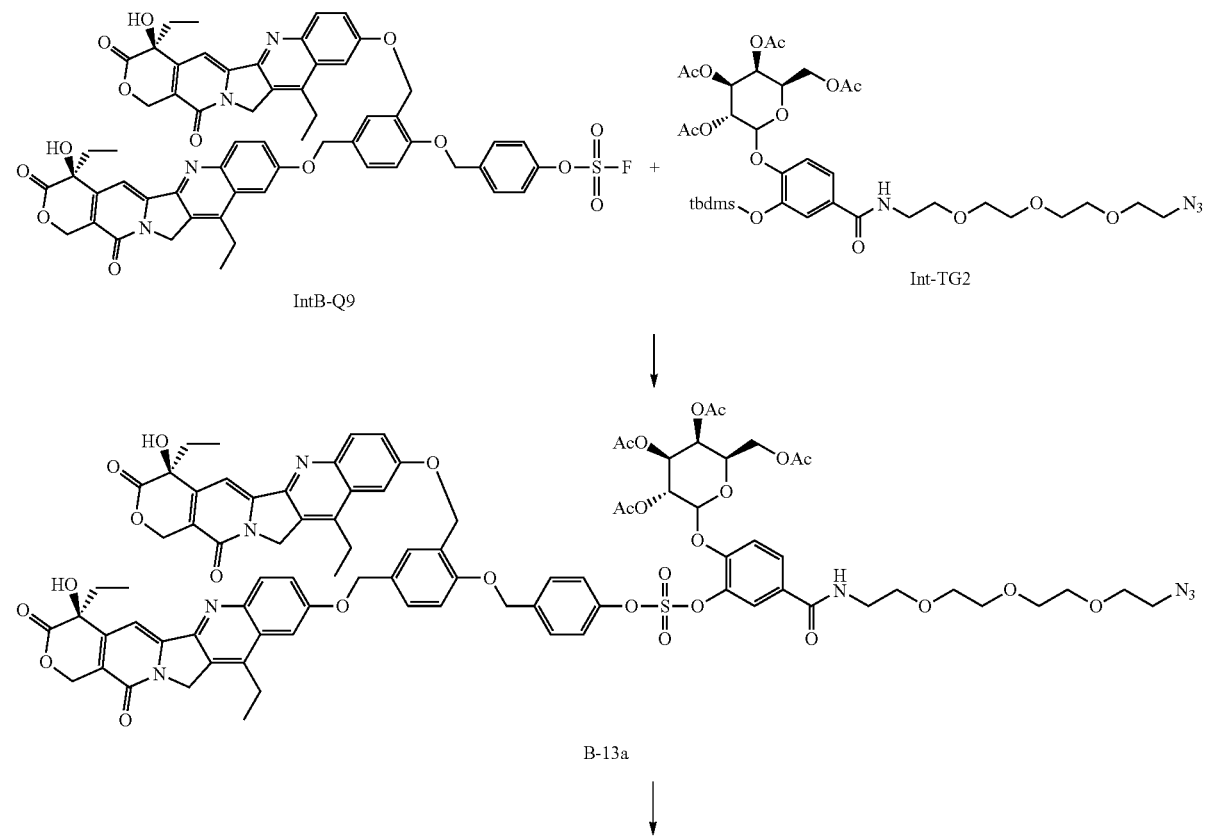
B-13a

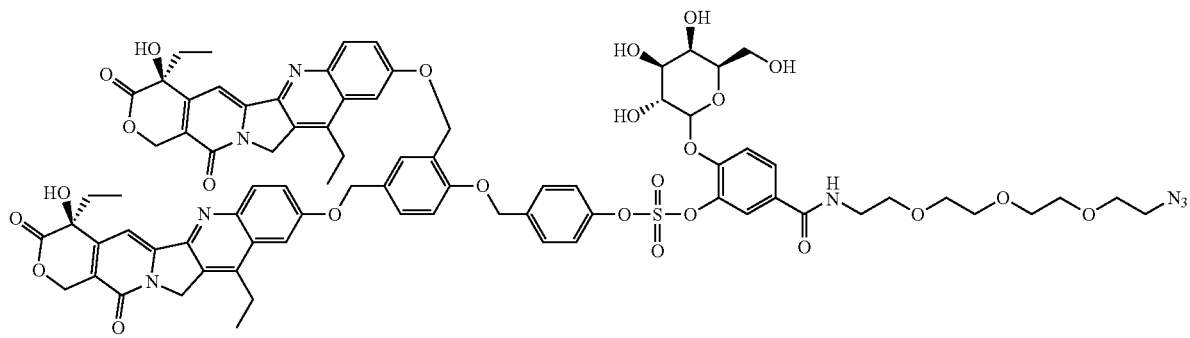
B-13
Compound B-13 was synthesized via a similar synthetic route as described in Example 74.
Preparation of Compound B-13a
Yield 9%; EI-MS m/z: 878 ($M^{+1}/2$).
Preparation of Compound B-13
Yield 33%; EI-MS m/z: 1610 ($M^{+1}$).
[Example 95] Preparation of Compound B-14
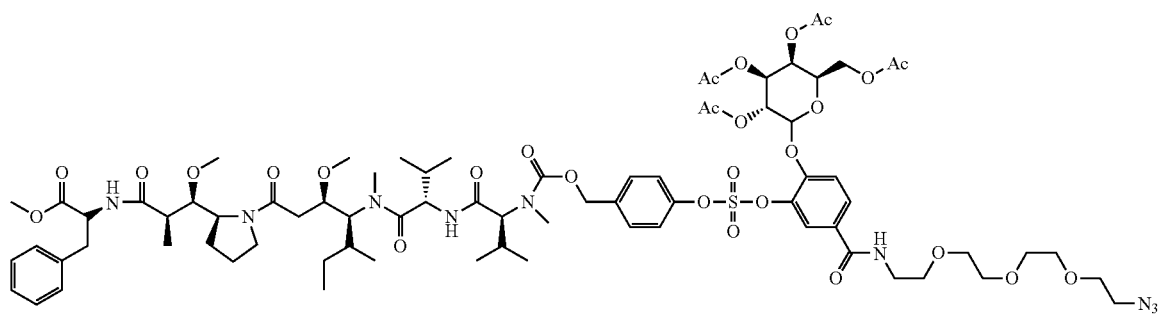
B-3a
↓
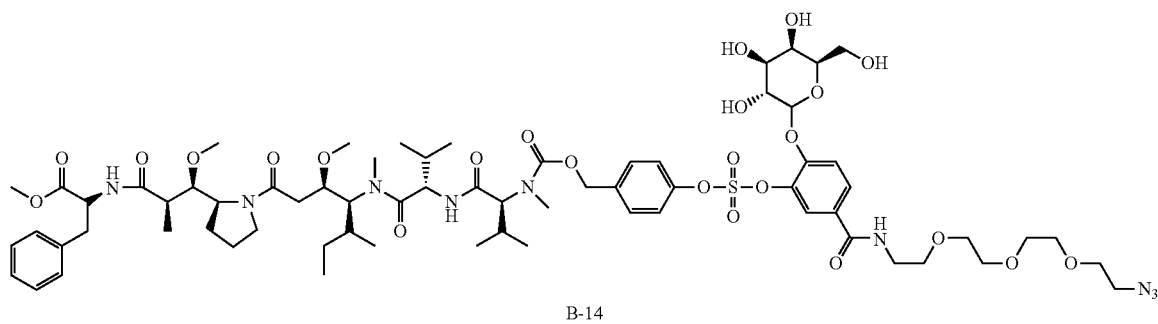
B-14

Compound B-14 was synthesized via a similar synthetic route as described in Example 61.

Yield 3000; EI-MS m/z: 1474 (M$^+$).

[Example 96] Preparation of Compound B-15

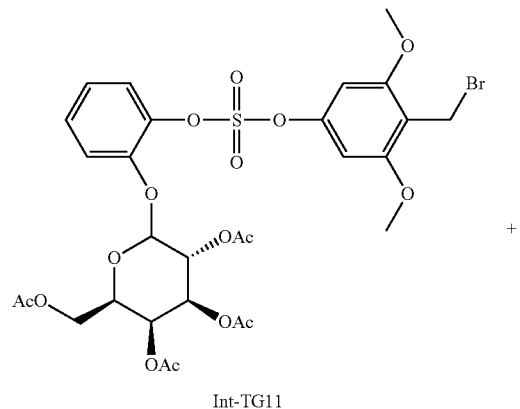

Int-TG11

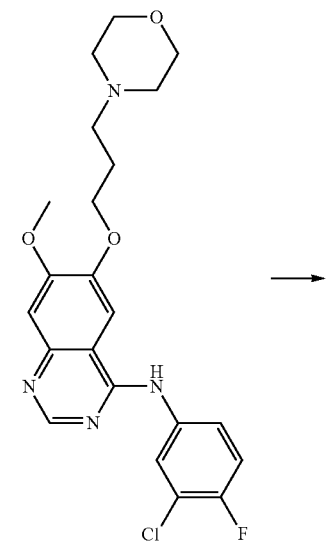

B-15a

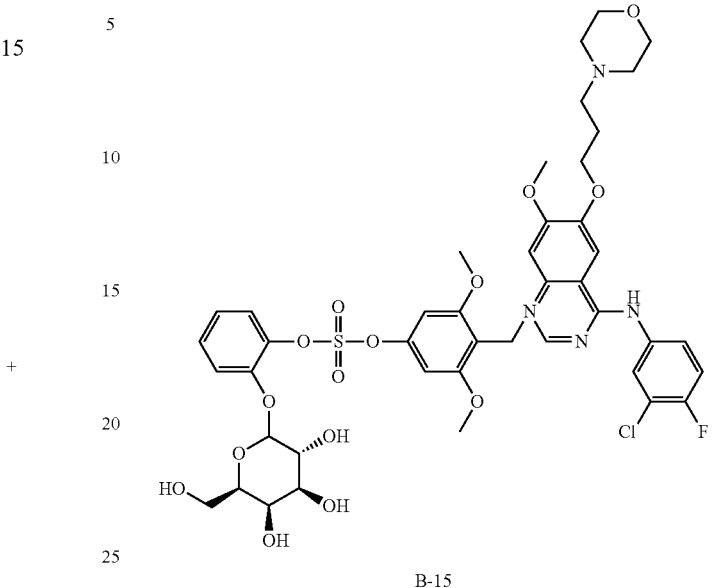

B-15

Compound B-15 was synthesized via a similar synthetic route as described in Example 72.

Preparation of Compound B-15a

Yield 45%; EI-MS m/z: 1116 (M$^+$).

$^1$H NMR (400 MHz, DMSO-d$_6$) δ 8.73 (s, 1H), 8.01 (m, 1H), 7.97 (s, 1H), 7.68 (m, 1H), 7.51 (t, J=9.2 Hz, 1H), 7.45 (d, J=8 Hz, 1H), 7.36 (m, 2H), 7.26 (s, 1H), 7.10-7.07 (m, 1H), 6.89 (s, 2H), 4.97 (d, J=7.2 Hz, 1H), 4.62 (s, 2H), 4.27 (m, 2H), 4.04-3.95 (m, 7H), 3.96 (s, 6H)

Preparation of Compound B-15

Yield 700%; EI-MS m/z: 948 (M$^{+1}$).

[Example 97] Preparation of Compound B-16

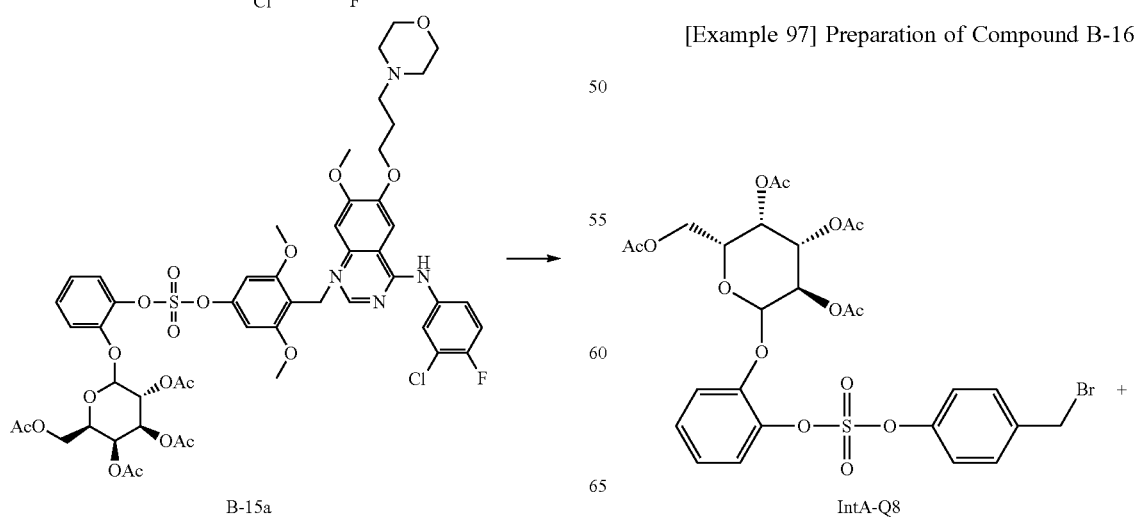

IntA-Q8

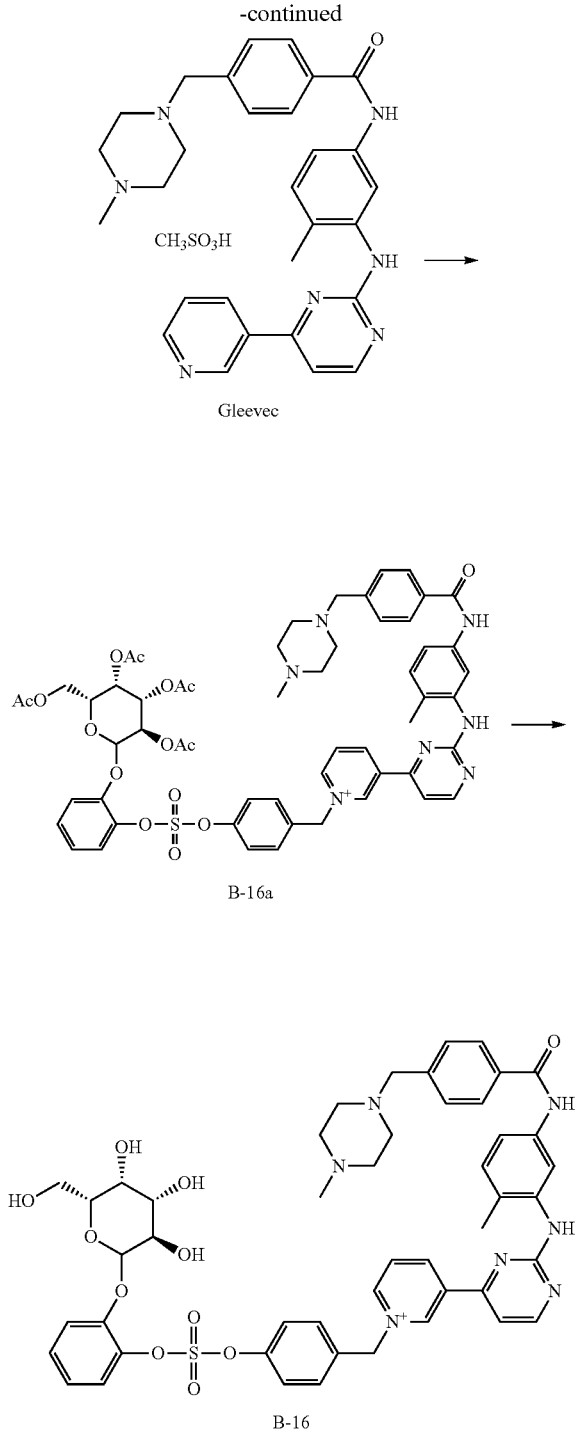

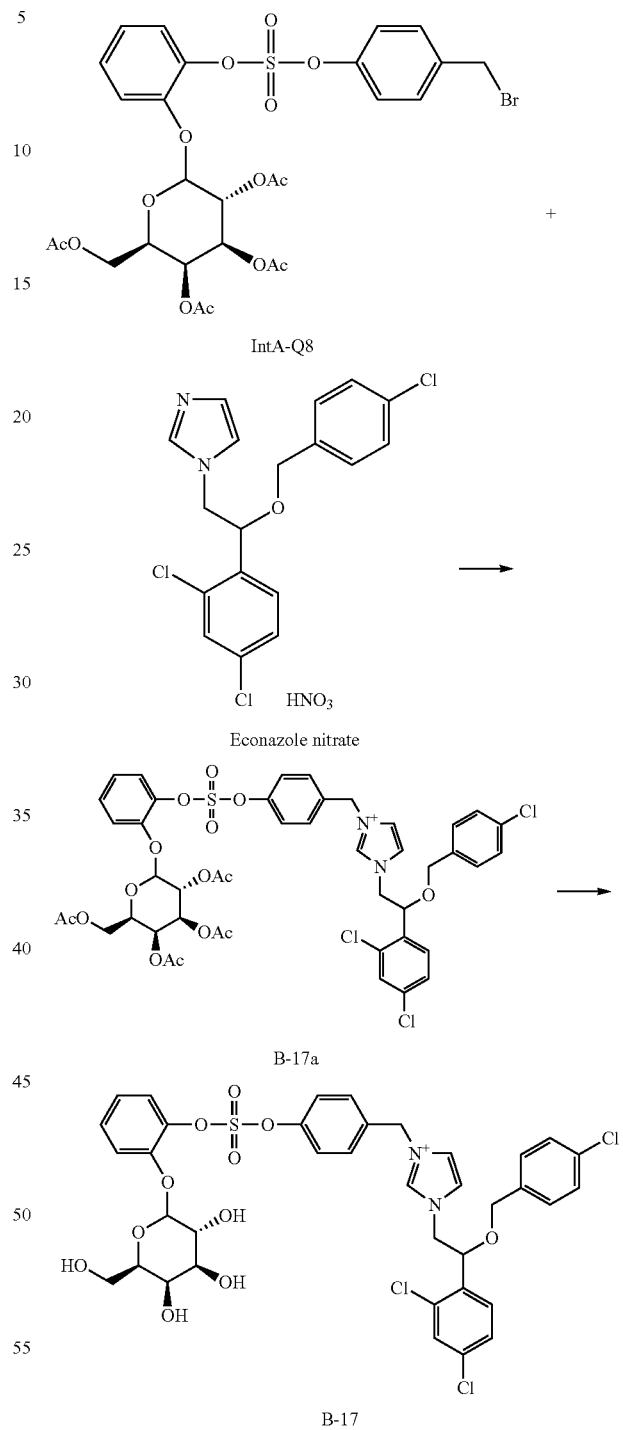

[Example 98] Preparation of Compound B-17

Compound B-16 was synthesized via a similar synthetic route as described in Example 72.
Preparation of Compound B-16a
Yield 99%; EI-MS m/z: 1103 (M$^{+1}$).
Preparation of Compound B-16
Yield 85%; EI-MS m/z: 935 (M$^{+1}$).

Compound B-17 was synthesized via a similar synthetic route as described in Example 72.
Preparation of Compound B-17a
Yield 55%; EI-MS m/z: 991 (M$^{+1}$).
Preparation of Compound B-17
Yield 60%; EI-MS m/z: 823 (M$^{+1}$).

[Example 99] Preparation of Compound B-18
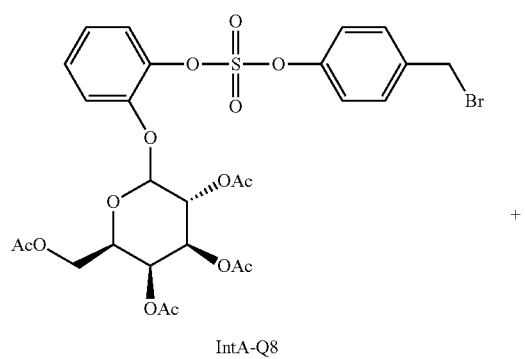
IntA-Q8
+
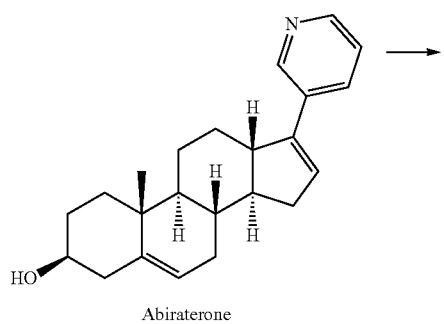
Abiraterone
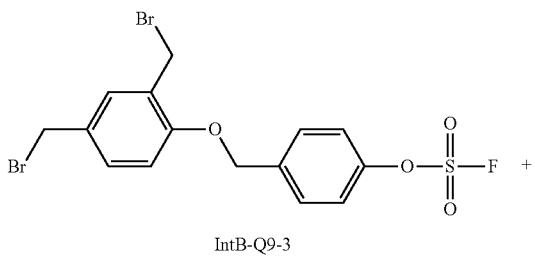
IntB-Q9-3
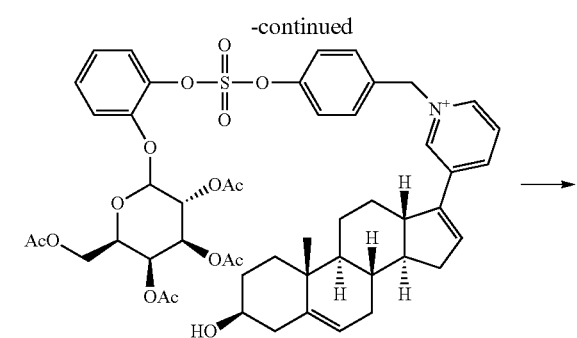
B-18a
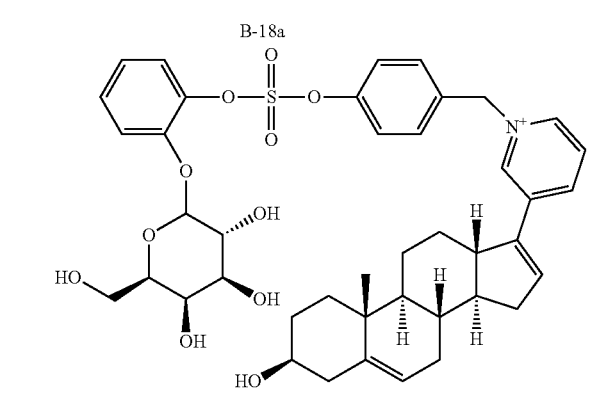
B-18
Compound B-18 was synthesized via a similar synthetic route as described in Example 72.
Preparation of Compound B-18a
Yield 72%; EI-MS m/z: 960 (M$^{+1}$).
Preparation of Compound B-18
Yield 54%; EI-MS m/z: 791 (M$^{+1}$).
[Example 100] Preparation of Compound B-19
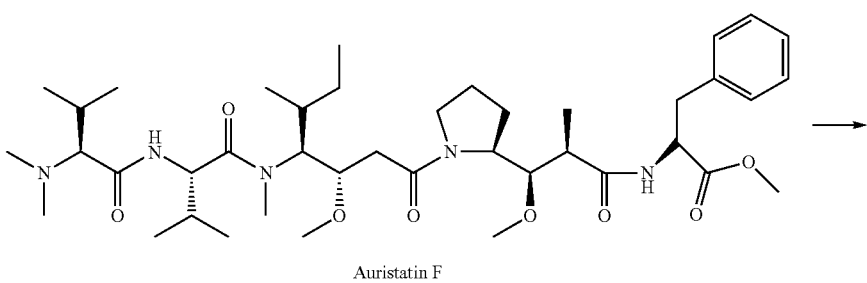
Auristatin F -continued
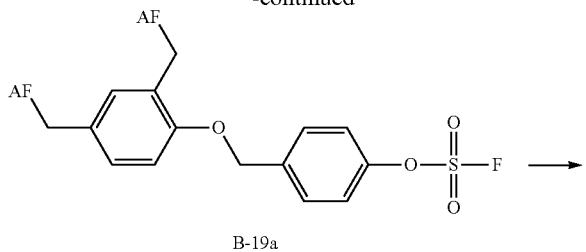
B-19a
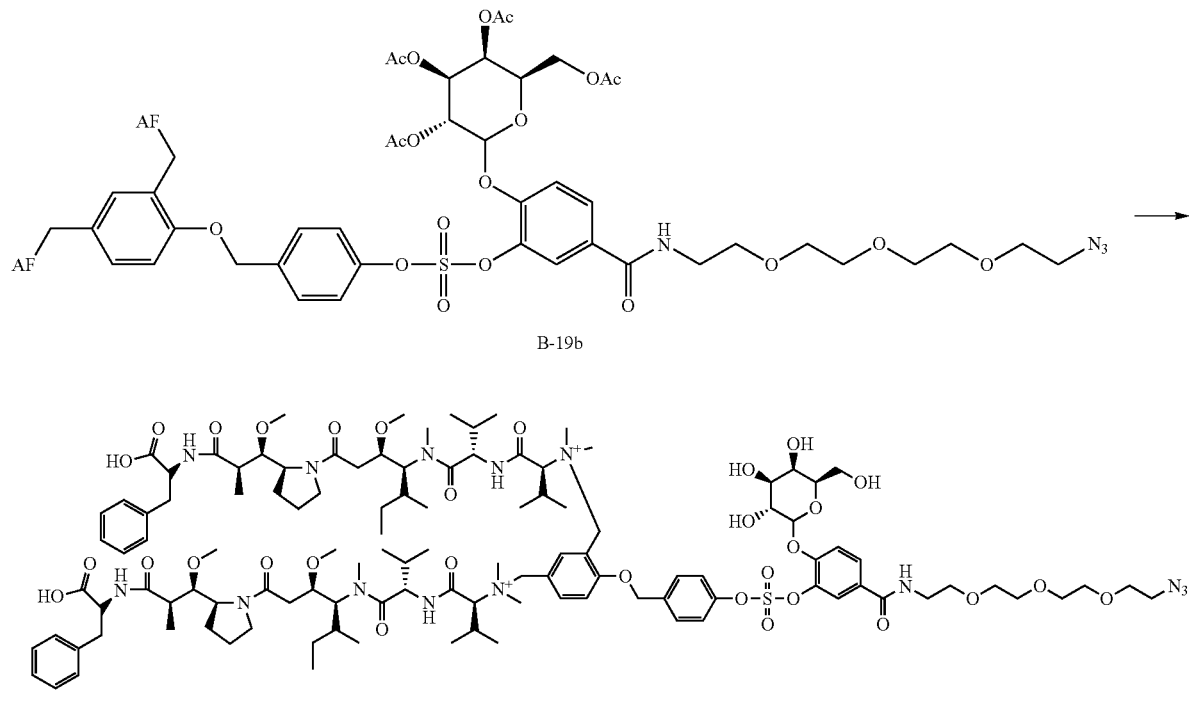
Compound B-19 was synthesized via a similar synthetic route as described in Example 92 and Example 70.
Preparation of Compound B-19a
Yield 38%; EI-MS m/z: 914 (M$^{+1}$/2).
Preparation of Compound B-19b
Yield 60%; EI-MS m/z: 831 (M$^{+}$⅓).
Preparation of Compound B-19
Yield 17%; EI-MS m/z: 1148 (M$^{+1}$/2).
[Example 101] Preparation of Compound B-20
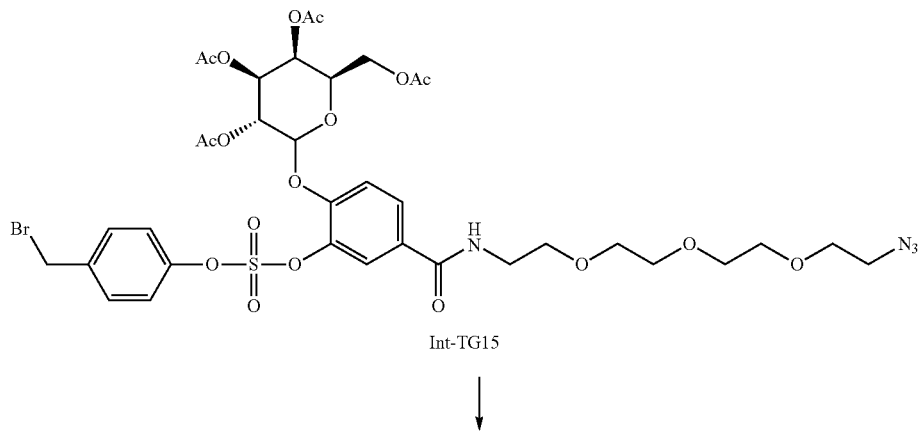
Int-TG15

-continued
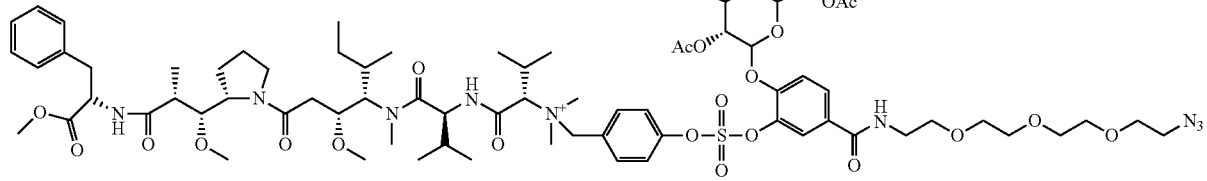
B-20a
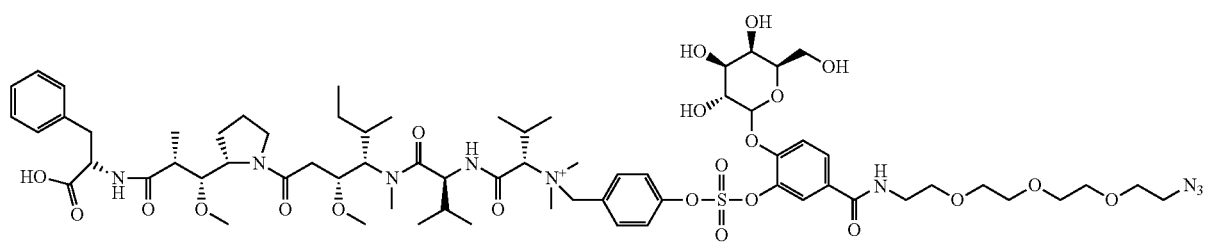
B-20
Compound B-20 was synthesized via a similar synthetic route as described in Example 72.
Preparation of Compound B-20a
Yield 14%; EI-MS m/z: 1614 (M$^{+1}$).
Preparation of Compound B-20
Yield 37%; EI-MS m/z: 1432 (M$^+$).
[Example 102] Preparation of Compound B-21
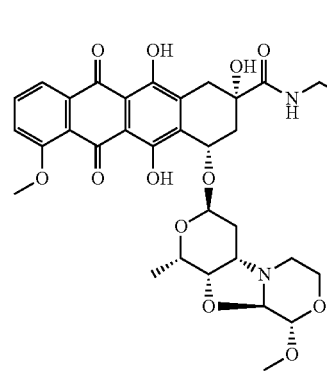
IntQ-11
+
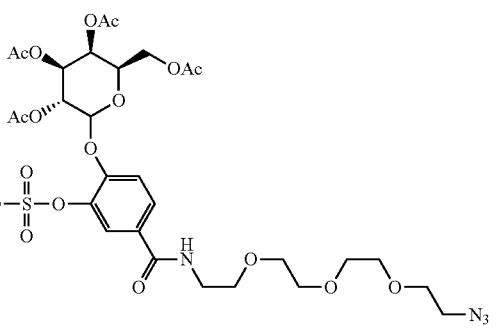
Int-TG14

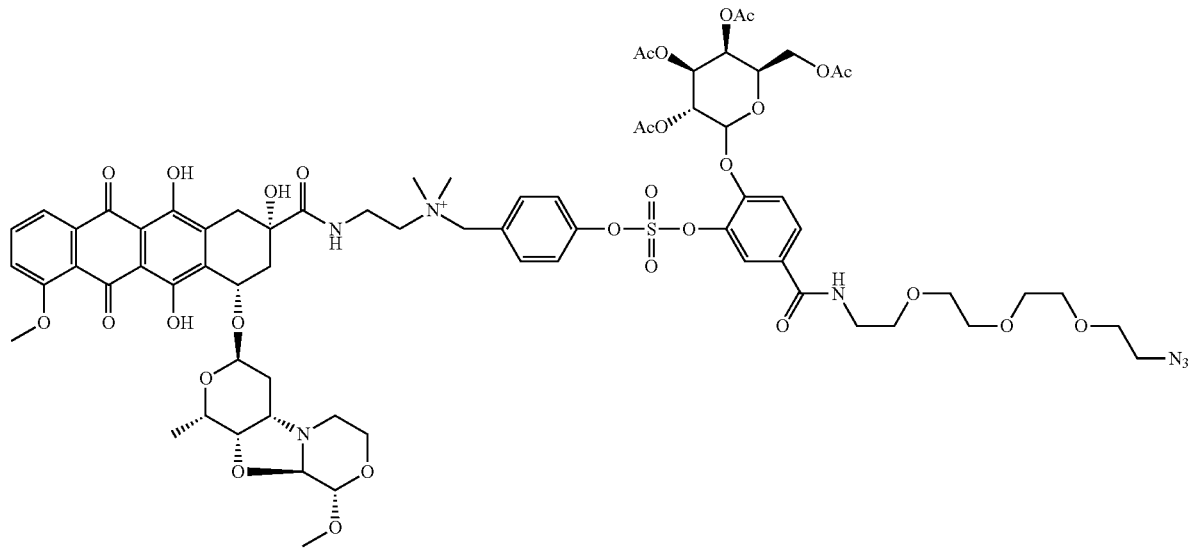
B-21a
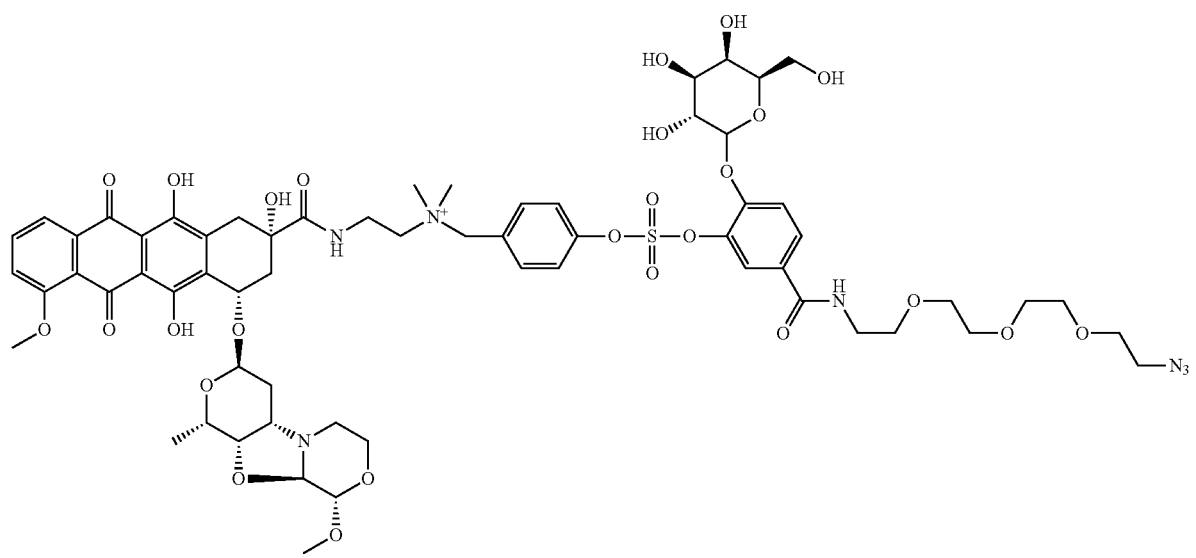
B-21

Compound B-21 was synthesized via a similar synthetic route as described in Example 72.
Preparation of Compound B-21a
Yield 38 EI-MS m/z: 1551 (M$^{+1}$).
Preparation of Compound B-21
Yield 54%; EI-MS m/z: 1383 (M$^{+1}$).
[Example 103] Preparation of Compound B-22
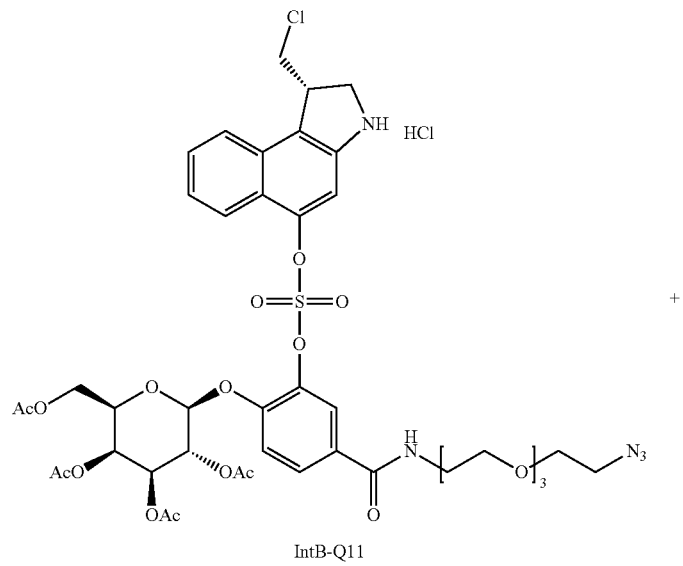
IntB-Q11
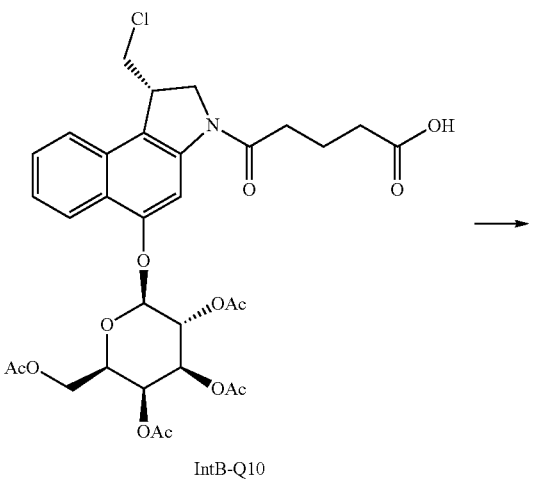
IntB-Q10

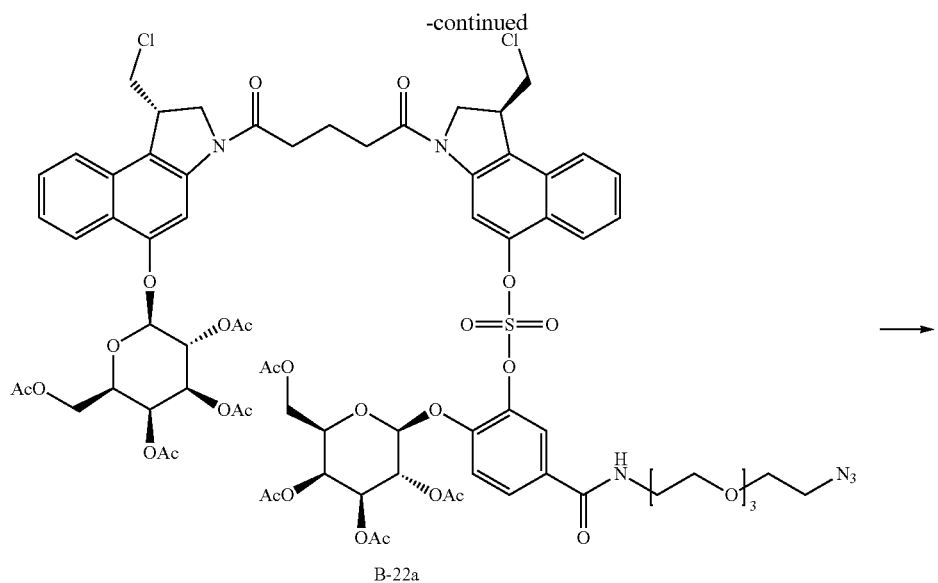

B-22a

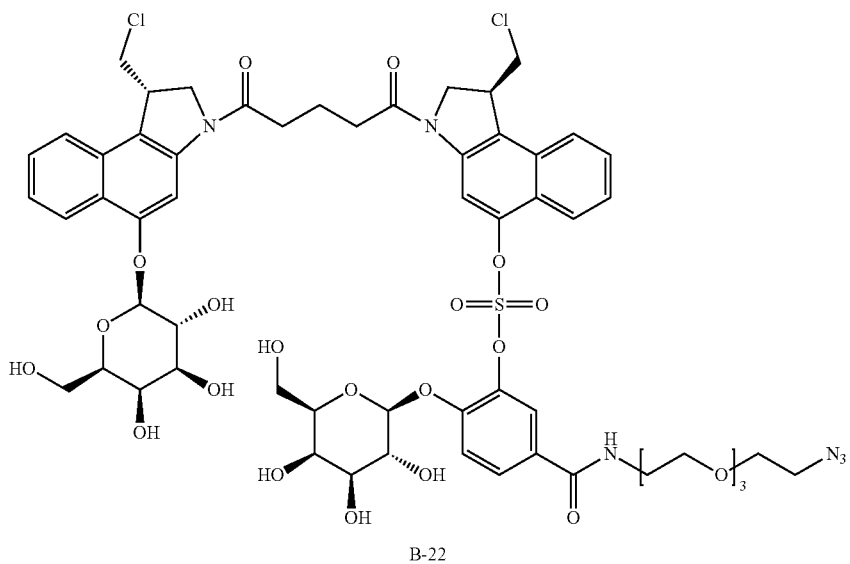

B-22

Preparation of Compound B-22a

To a solution of compound IntB-10 (30 mg, 0.043 mmol) and compound IntB-Q11 (51 mg, 0.05 mmol) in DMF (3 mL) was added EDC-HCl (27.2 mg, 0.142 mmol) at 0° C. under $N_2$ Atmosphere. After stirring for 11 hours, the mixture was purified by Prep-HPLC to obtained compound B-22a (20 mg, 28%) as light brown solid.

EI-MS m/z: 821.7 ($M^{+1}/2$).

Preparation of Compound B-22

To a solution of compound B-22a (10 mg, 0.006 mmol) in MeOH (1.5 mL) was added NaOMe 25% in MeOH (11 μL, 0.048 mmol) at 0° C. under $N_2$ atmosphere. The reaction mixture was stirred at room temperature for 1 hours under $N_2$ atmosphere and adjusted to pH 7 by addition of 5% TFA in ACN solution. The mixture was purified by Prep-HPLC to obtain compound B-22 (5 mg, 63%) as pale yellow solid.

EI-MS m/z: 1305.3 ($M^{+1}$).

[Example 104] Preparation of Compound B-23

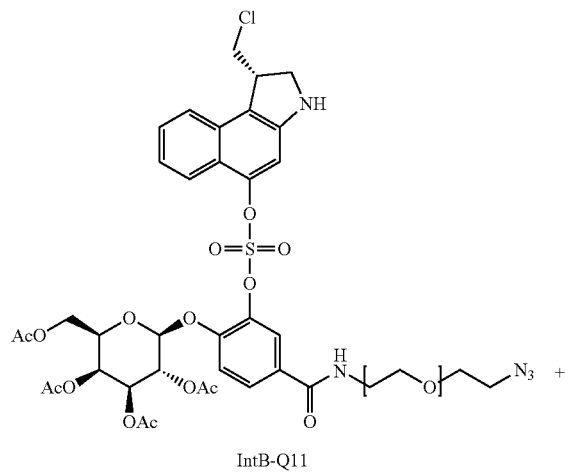

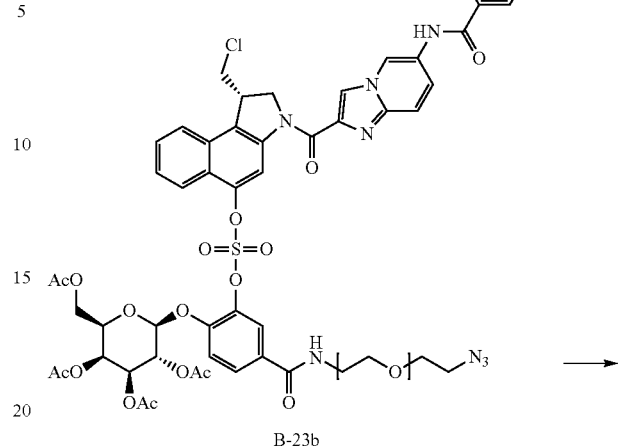

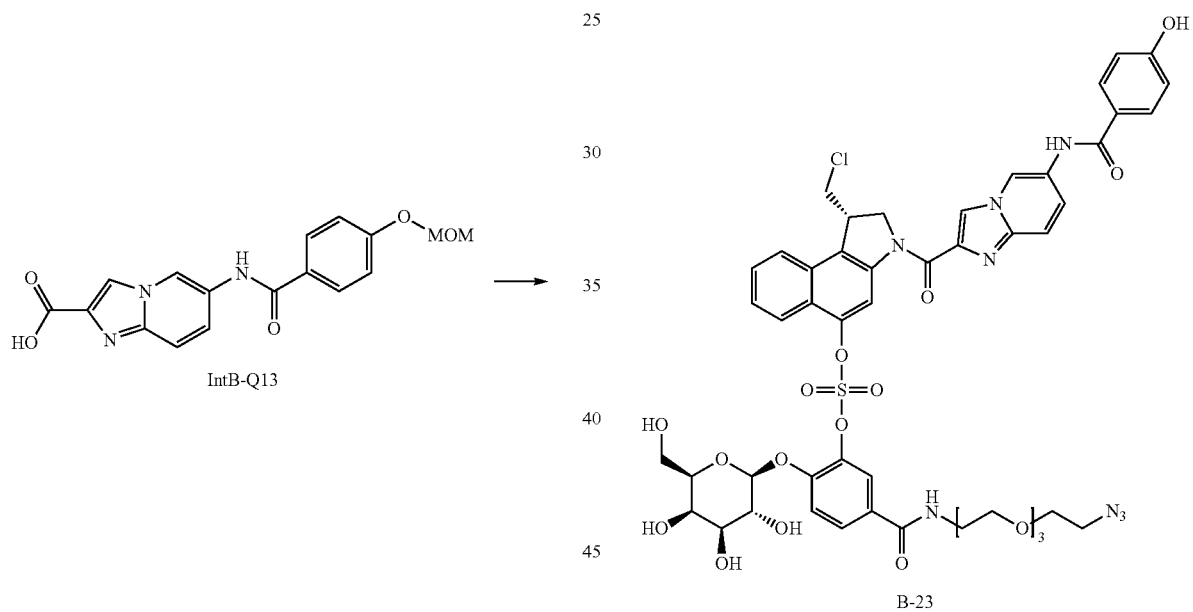

Compound B-23 was synthesized via a similar synthetic route as described in Example 103.

Preparation of Compound B-23a

Yield 53%; EI-MS m/z: 1303.5 ($M^{+1}$).

Preparation of Compound B-23b

To a solution of compound B-23a (30 mg, 0.023 mmol) was added 4N HCl in 1,4-dioxane (1 mL) at room temperature under $N_2$ atmosphere. After stirring for 1 hour, the mixture was diluted with DCM (5 mL) and concentrated. Compound B-23b was used directly in the next step without further purification (28 mg, 97%).

EI-MS m/z: 1259.5 ($M^{+1}$).

Preparation of Compound B-23

Yield 68%; EI-MS m/z: 1259.5 ($M^{+1}$).

[Example 105] Preparation of Compound B-24
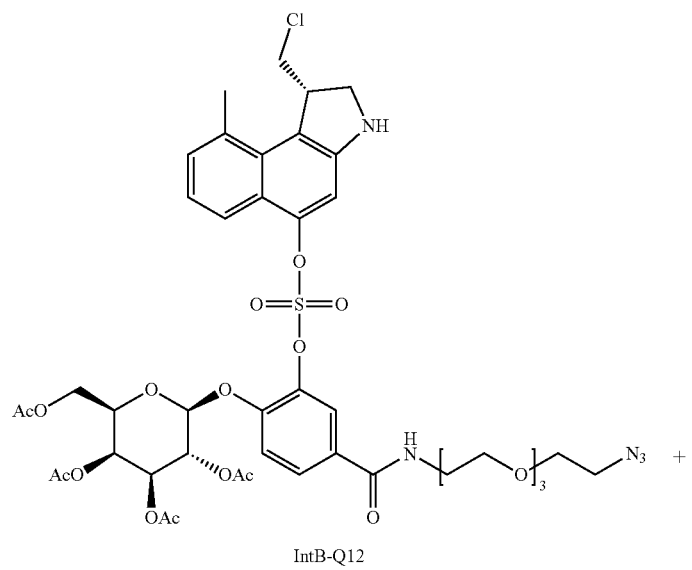
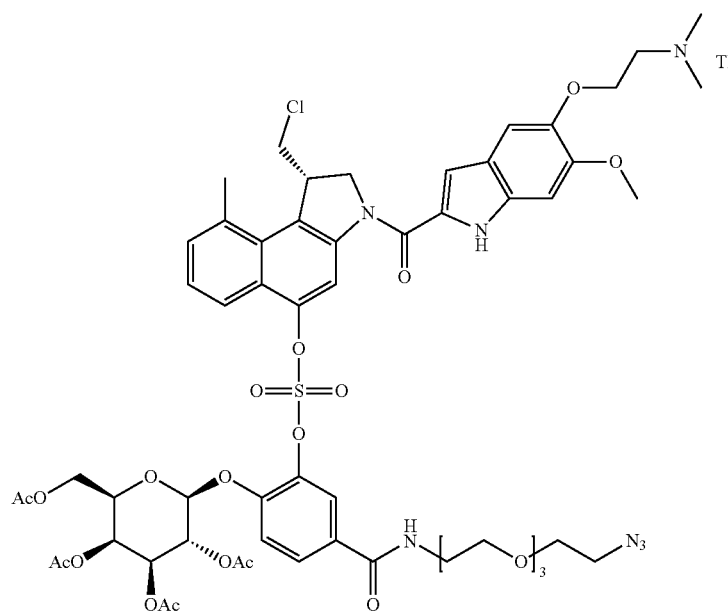

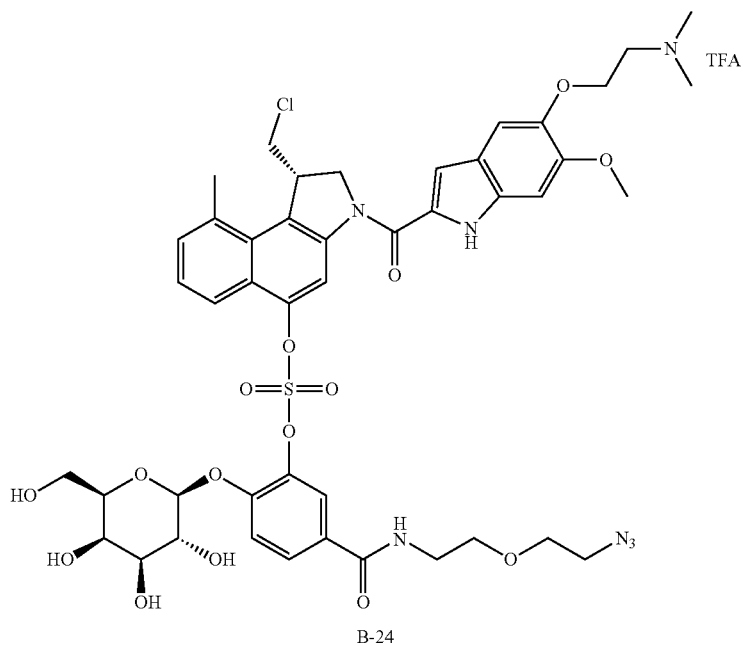
B-24
Compound B-24 was synthesized via a similar synthetic route as described in Example 104.
Preparation of Compound B-24a
Yield 53%; EI-MS m/z: 1254.7 (M$^{+1}$).
Preparation of Compound B-24
Yield 58%; EI-MS m/z: 1086.6 (M$^{+1}$).
[Example 106] Preparation of Compound B-25
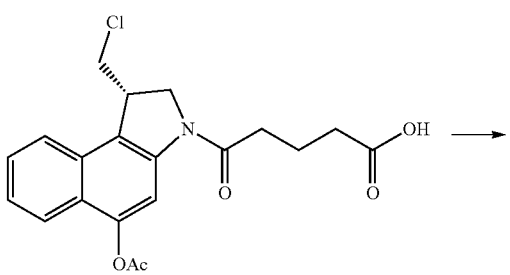
IntB-Q15

-continued
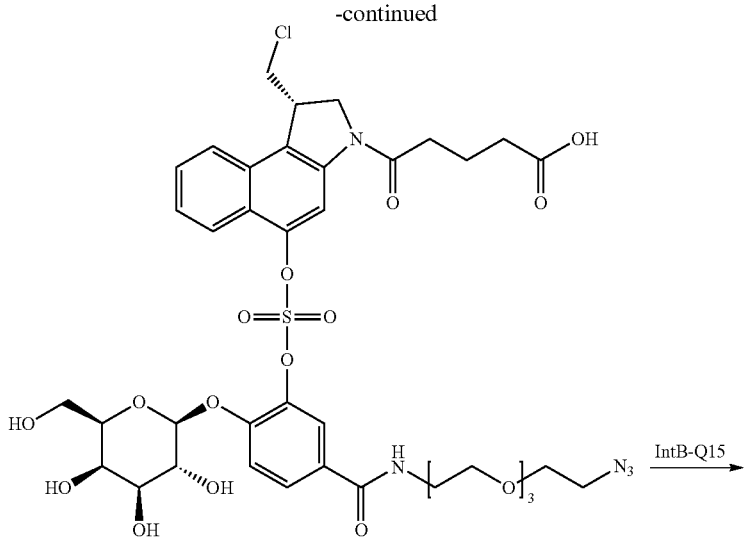
B-25a
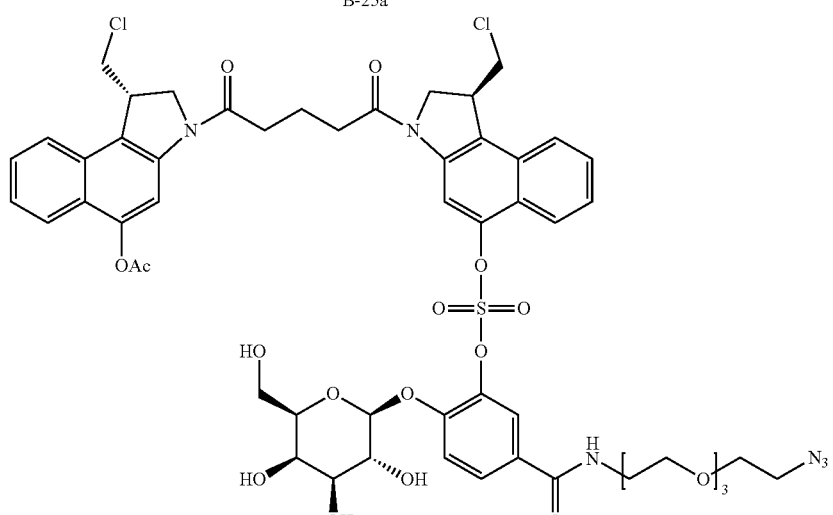
B-25
Compound B-25 was synthesized via a similar synthetic route as described in Example 104.
Preparation of Compound B-25a
Yield 33%; EI-MS m/z: 1094.5 (M$^{+1}$).
Preparation of Compound B-25
Yield 36%; EI-MS m/z: 926.4 (M$^{+1}$).
[Example 107] Preparation of Compound B-26
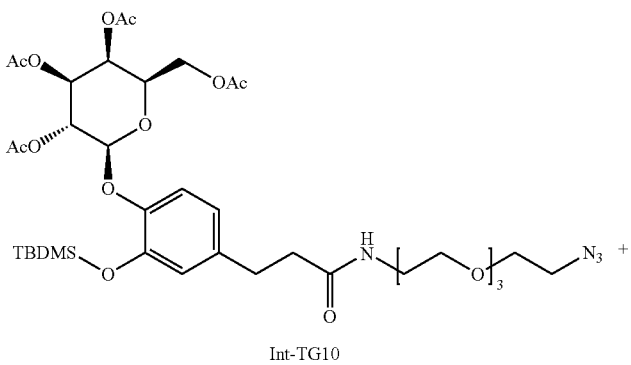
Int-TG10

307
-continued
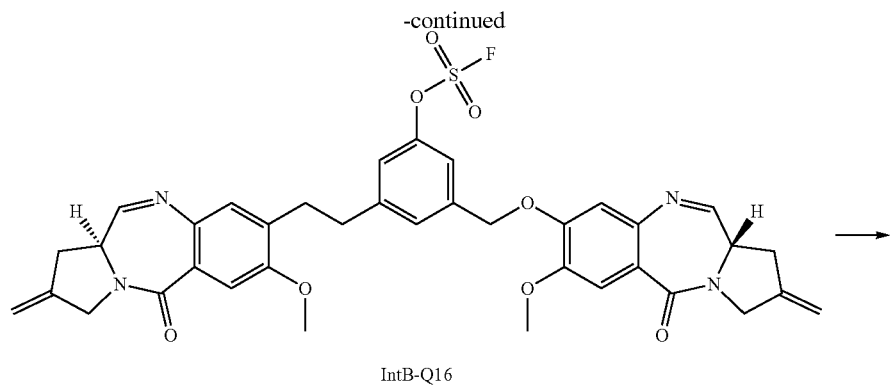
IntB-Q16
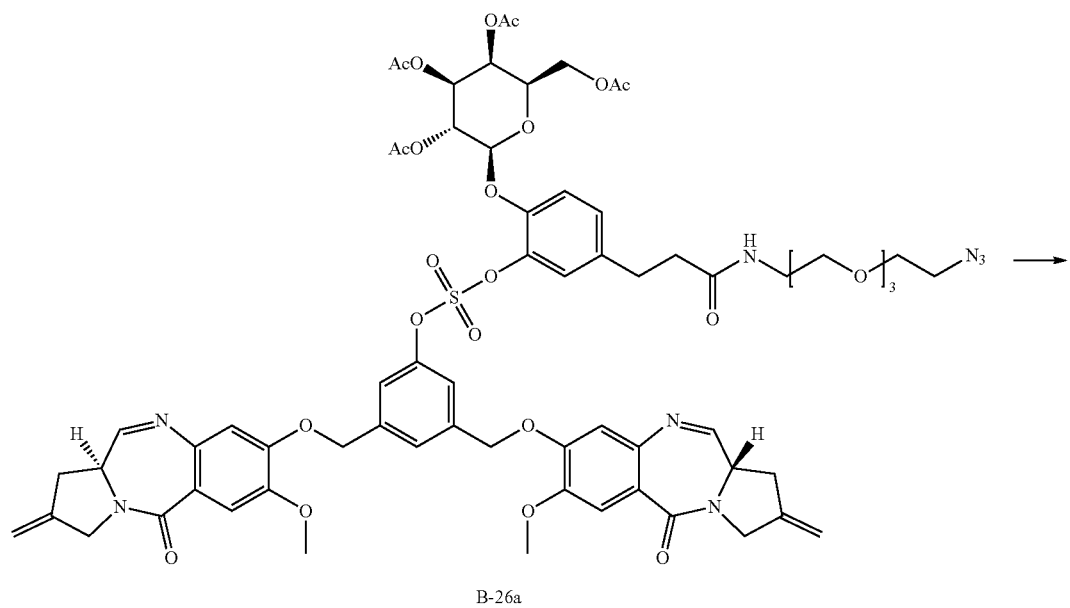
B-26a
308
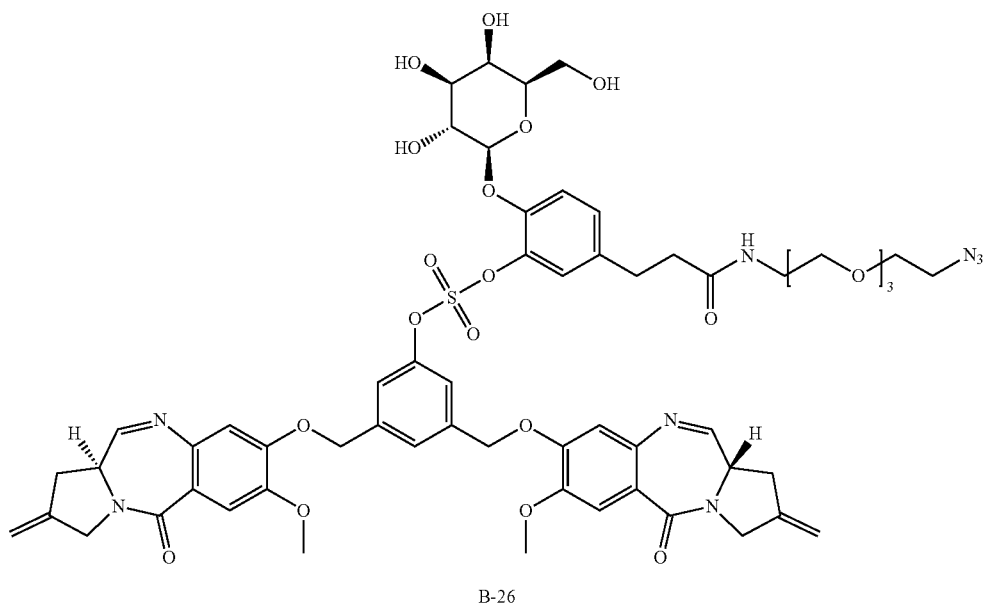
B-26

Compound B-26 was synthesized via a similar synthetic route as described in Example 74.

Preparation of Compound B-26a
Yield 51%; EI-MS m/z: 1382 ($M^{+1}$).

Preparation of Compound B-8
Yield 56%; EI-MS m/z: 1214 ($M^{+1}$).

[Example 108] Preparation of Ligand-Drug Conjugate Compound C-1

311 312
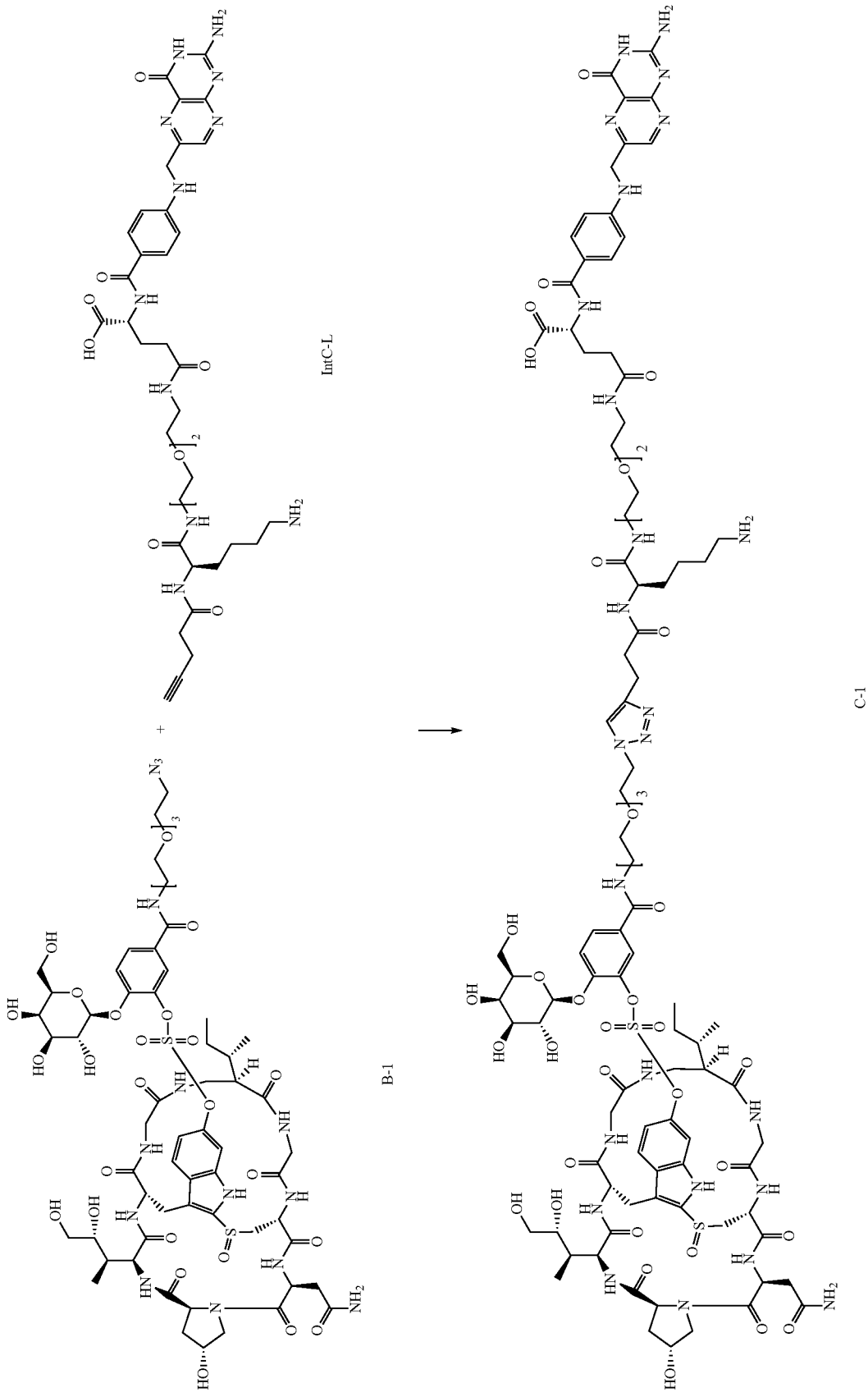

To a solution of compound IntC-L (1.8 mg, 0.0016 mmol) and compound B-1 (1.6 mg, 0.0011 mmol) in EtOH (2 mL) and distilled water (0.5 mL) was added 1 M sodium ascorbate (11 μL, 0.011 mmol) and 0.1 M CuSO$_4$ (21 μL, 0.0021 mmol) at room temperature under N$_2$ nitrogen atmosphere. After stirring for 12 hours, the mixture was separated and purified by Prep-HPLC to obtain compound C-1 (1.7 mg, 61%).

EI-MS m/z: 2278 (M$^{+1}$).

[Example 109] Preparation of Ligand-Drug Conjugate Compound C-2

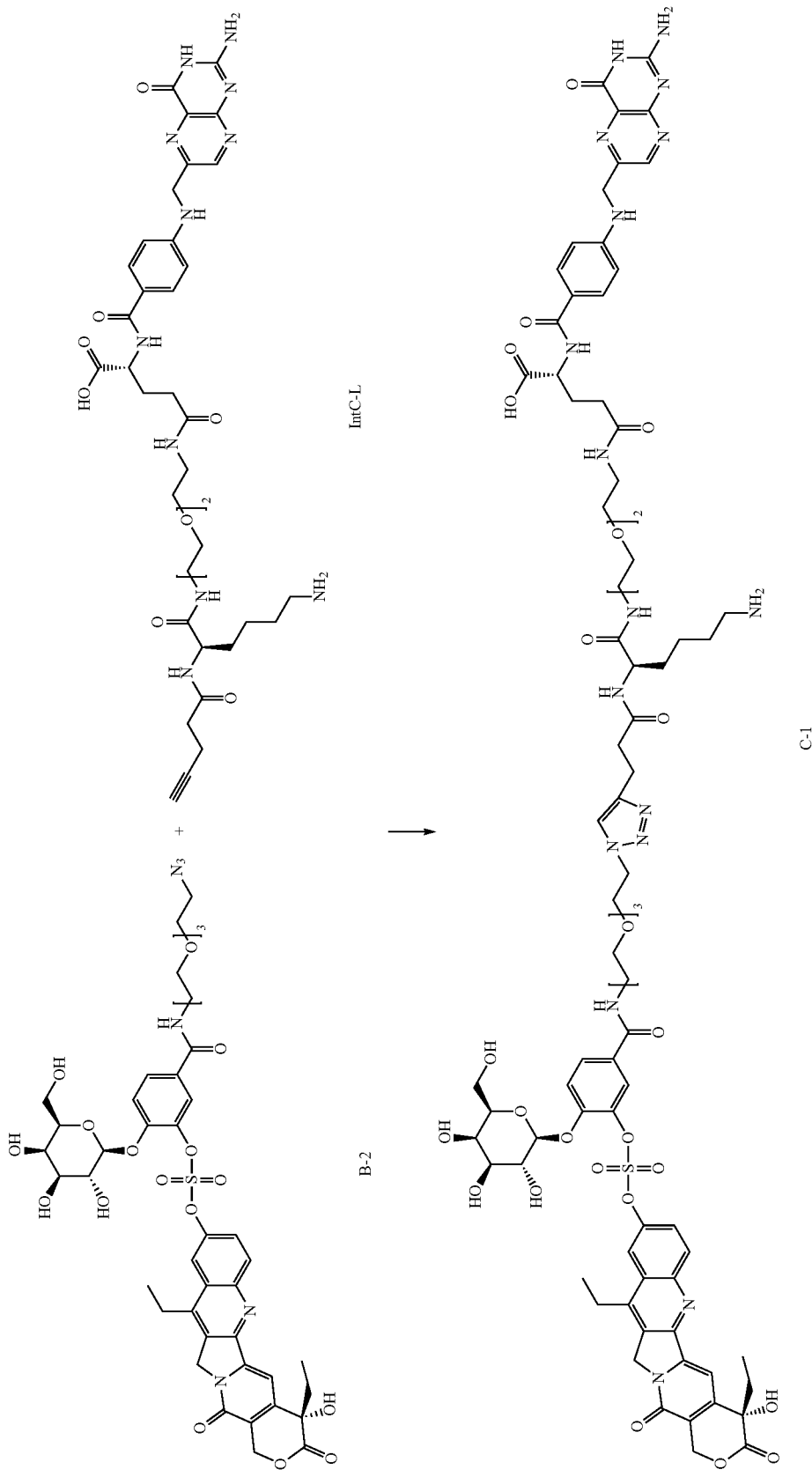

Compound C-2 was synthesized via a similar synthetic route as described in Example 108.

Yield 54%; EI-MS m/z: 1751 (M$^{+1}$)

[Example 110] Preparation of Ligand-Drug Conjugate Compound C-3

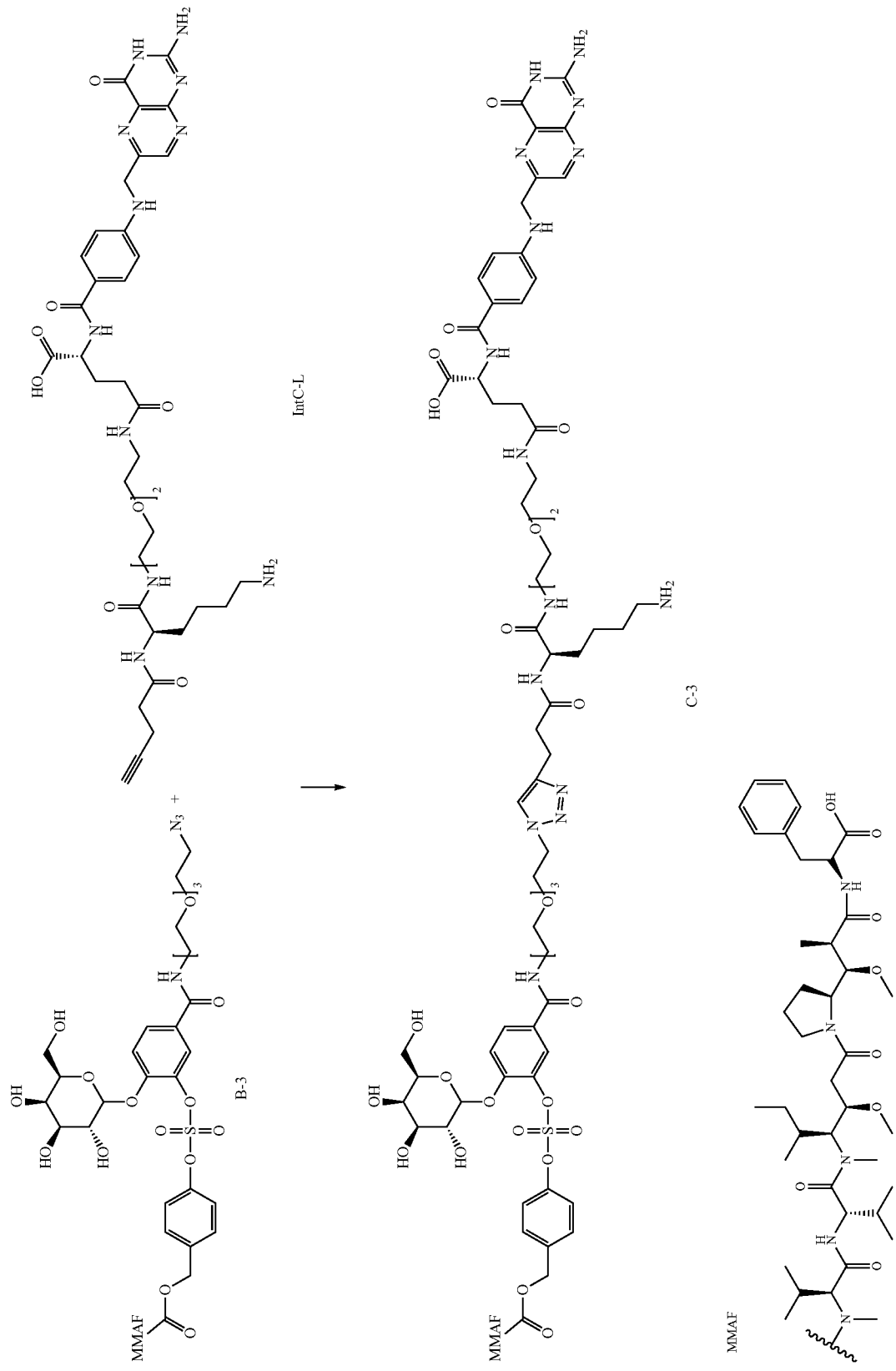

Compound C-3 was synthesized via a similar synthetic route as described in Example 108.

Yield 24%; EI-MS m/z: 2242 (M$^{+1}$)

[Example 111] Preparation of Compound C-4

323 324
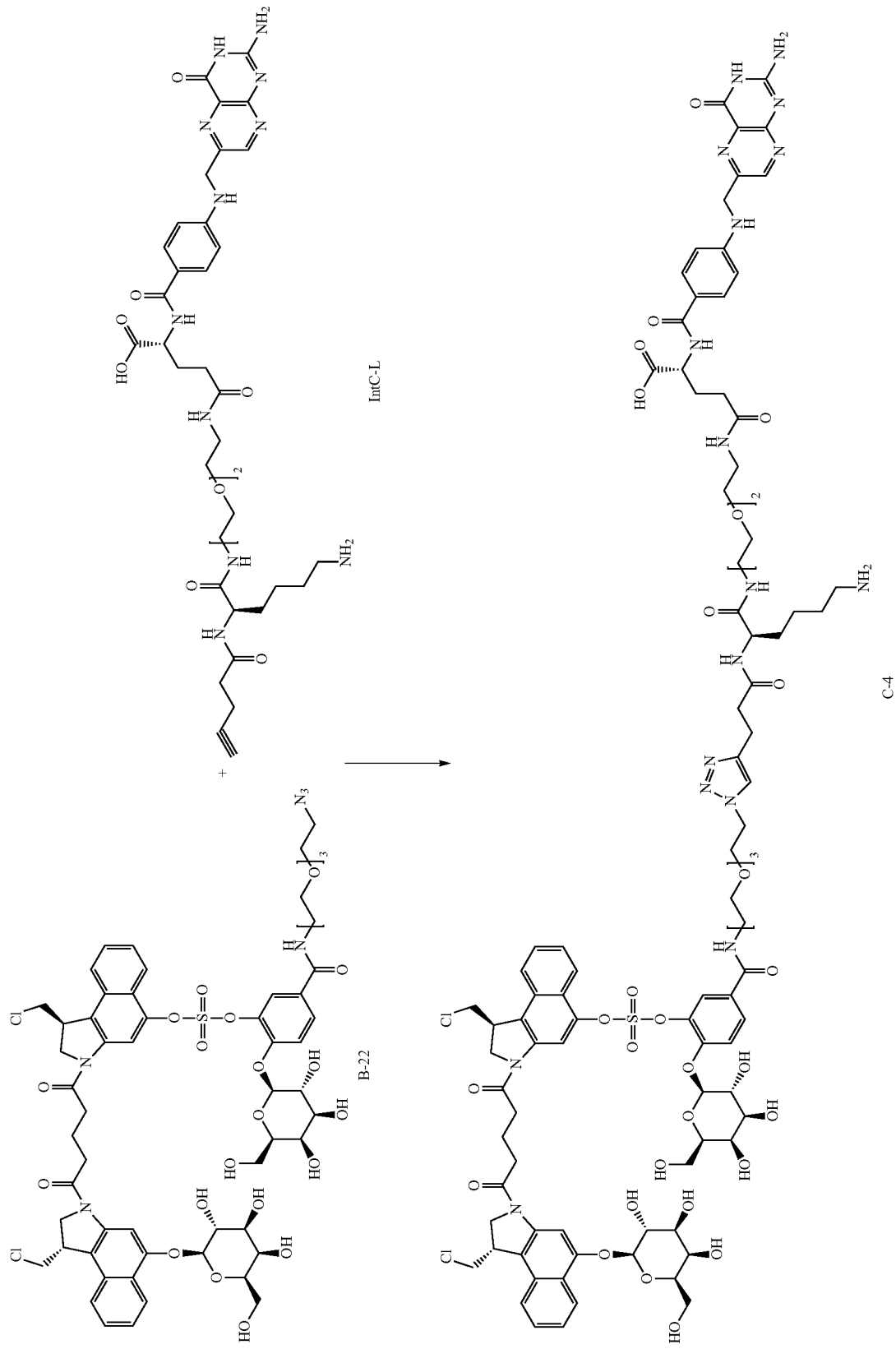

Compound C-4 was synthesized via a similar synthetic route as described in Example 108.
EI-MS m/z: 1043.3 ($M^{+1}/2$).
[Example 112] Preparation of Compound C-5
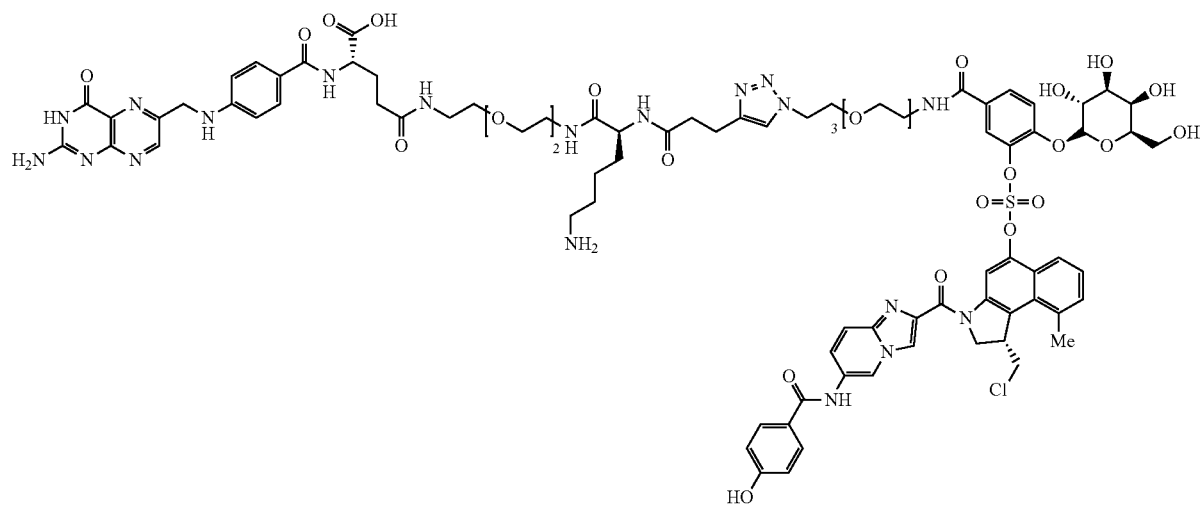
Compound C-6 was synthesized via a similar synthetic route as described in Example 108.
EI-MS m/z: 1886.3 ($M^{+1}$).
[Example 113] Preparation of Compound C-6

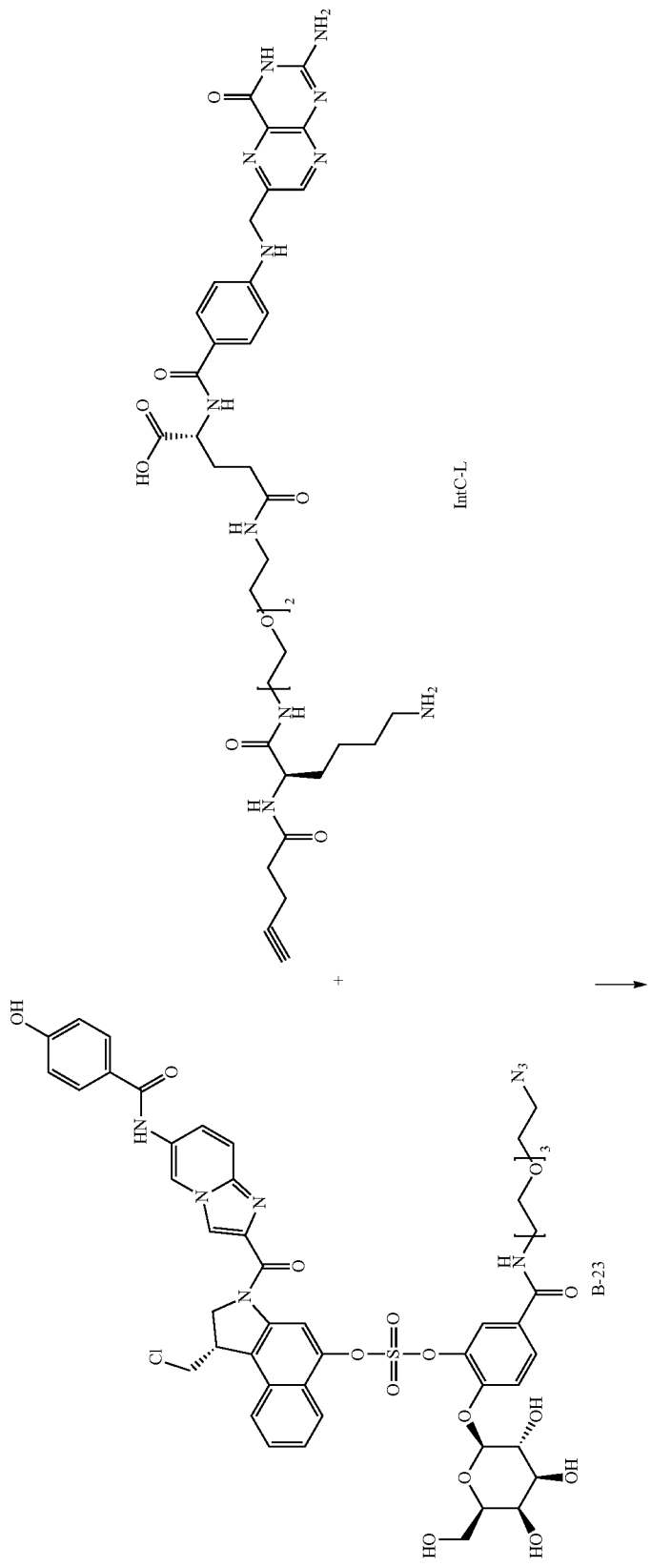

-continued
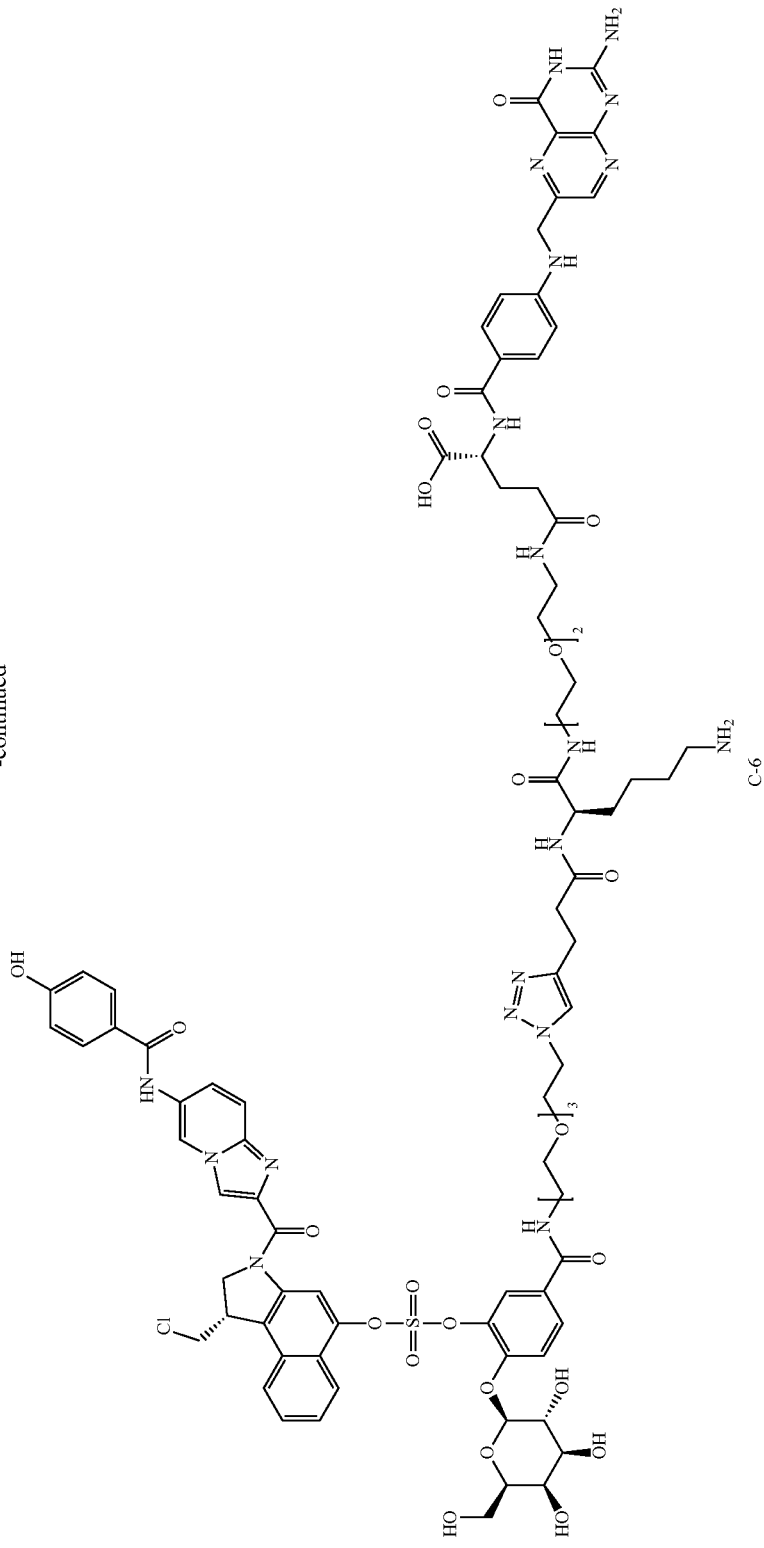
C-6

Compound C-6 was synthesized via a similar synthetic route as described in Example 108.

EI-MS m/z: 936.7 ($M^{+1}/2$).

[Example 114] Preparation of Compound C-7

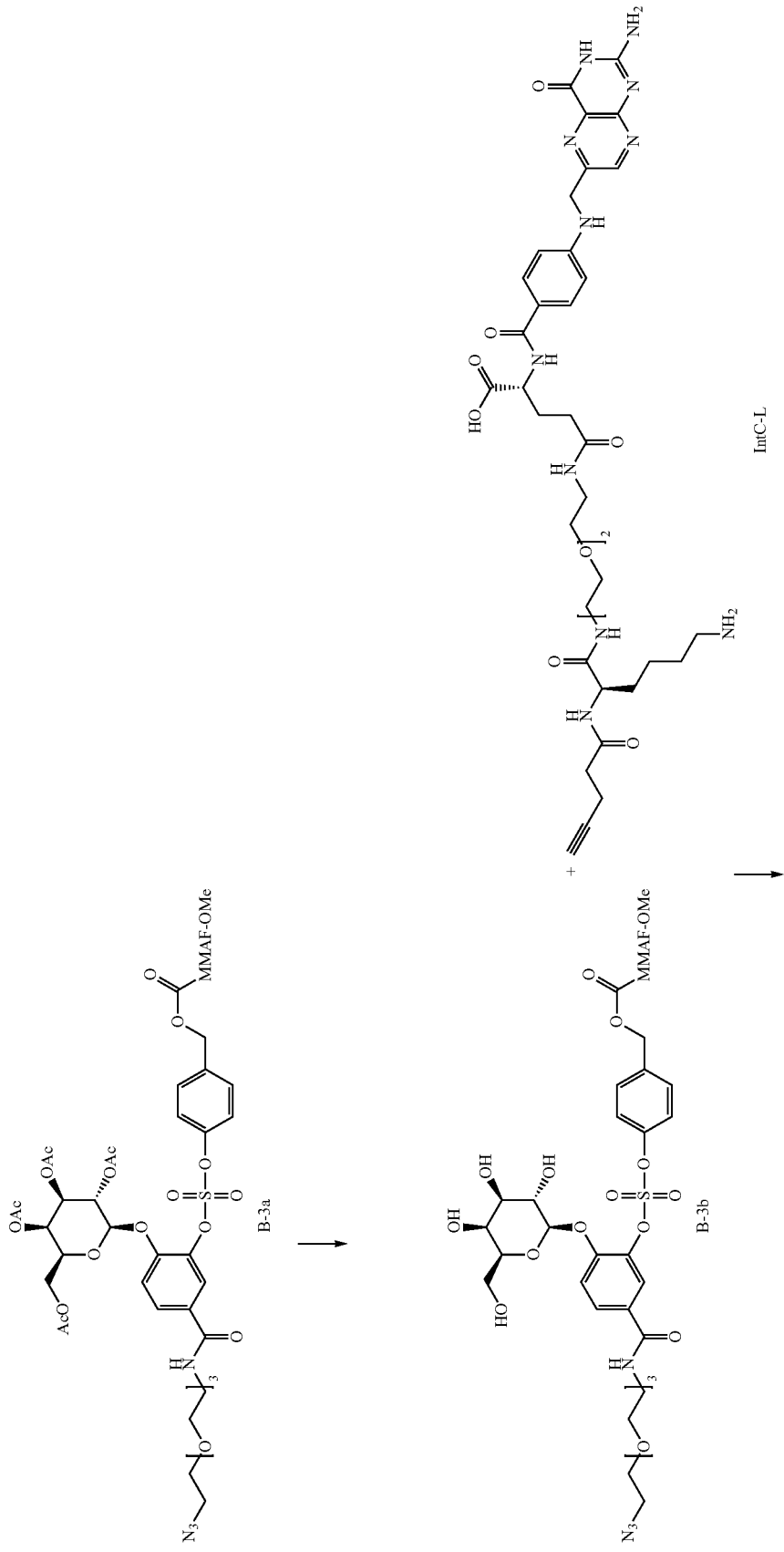

-continued
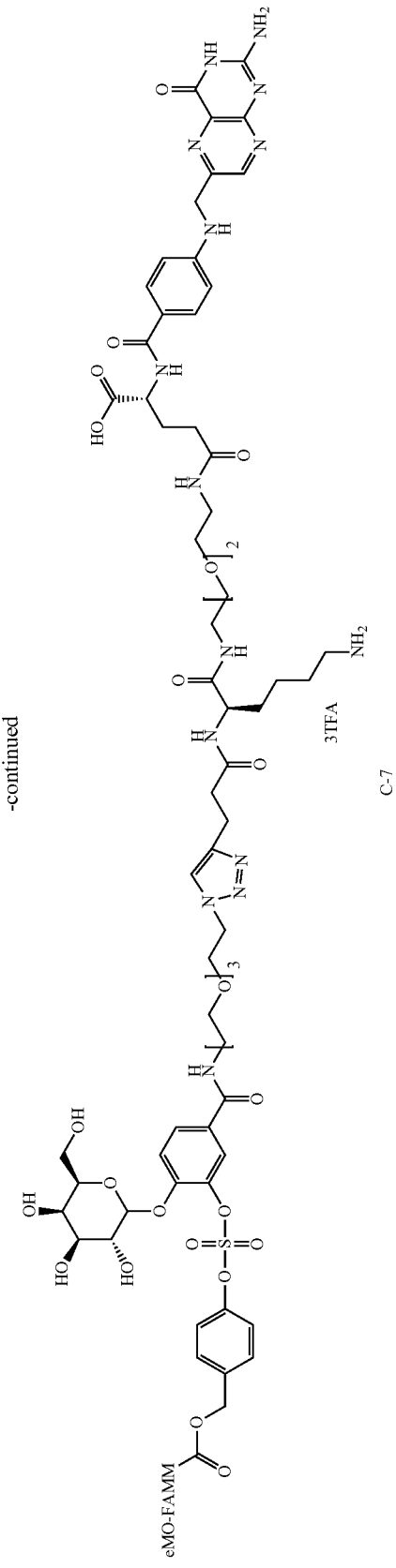
eMO-FAMM
C-7
3TFA
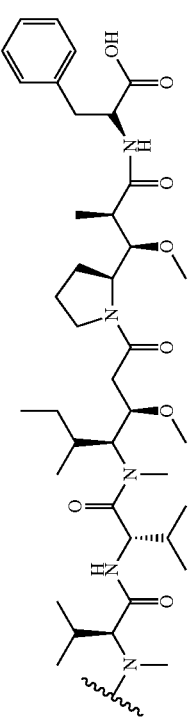
MMAF-OMe

Compound C-7 was synthesized via a similar synthetic route as described in Example 61 and Example 108.
Preparation of Compound B-3b
Yield 30%; EI-MS m/z: 1497 ($M^{+1}$+Na).
Preparation of Compound C-7
Yield 8.7%; EI-MS m/z: 1128 ($M^{+1}$/2).

[Example 115] Preparation of Compound C-8

Compound C-8 was synthesized via a similar synthetic route as described in Example 108.
EI-MS m/z: 934.0 ($M^{+1}$/2).

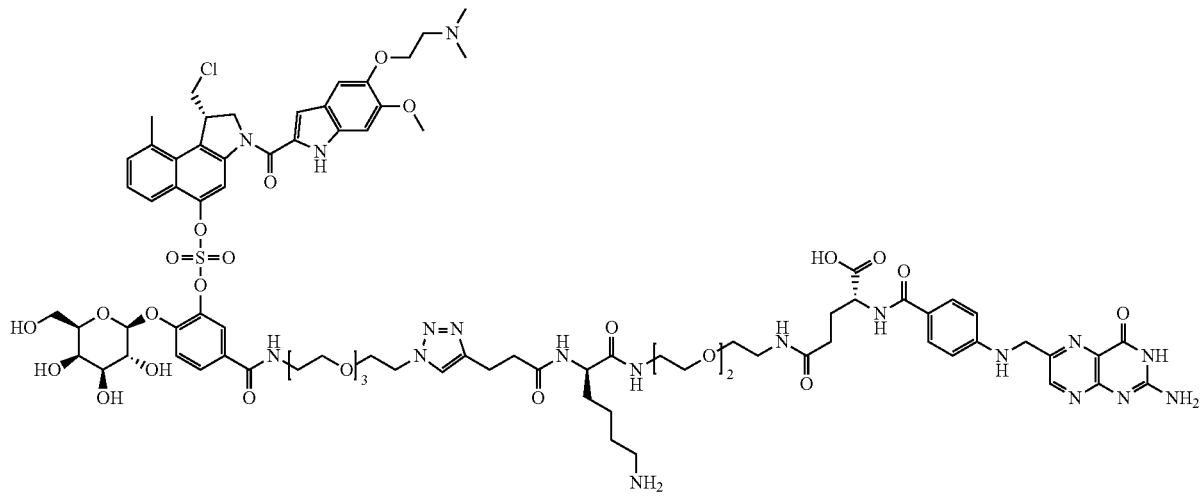

C-8

[Example 116] Preparation of Compound C-9

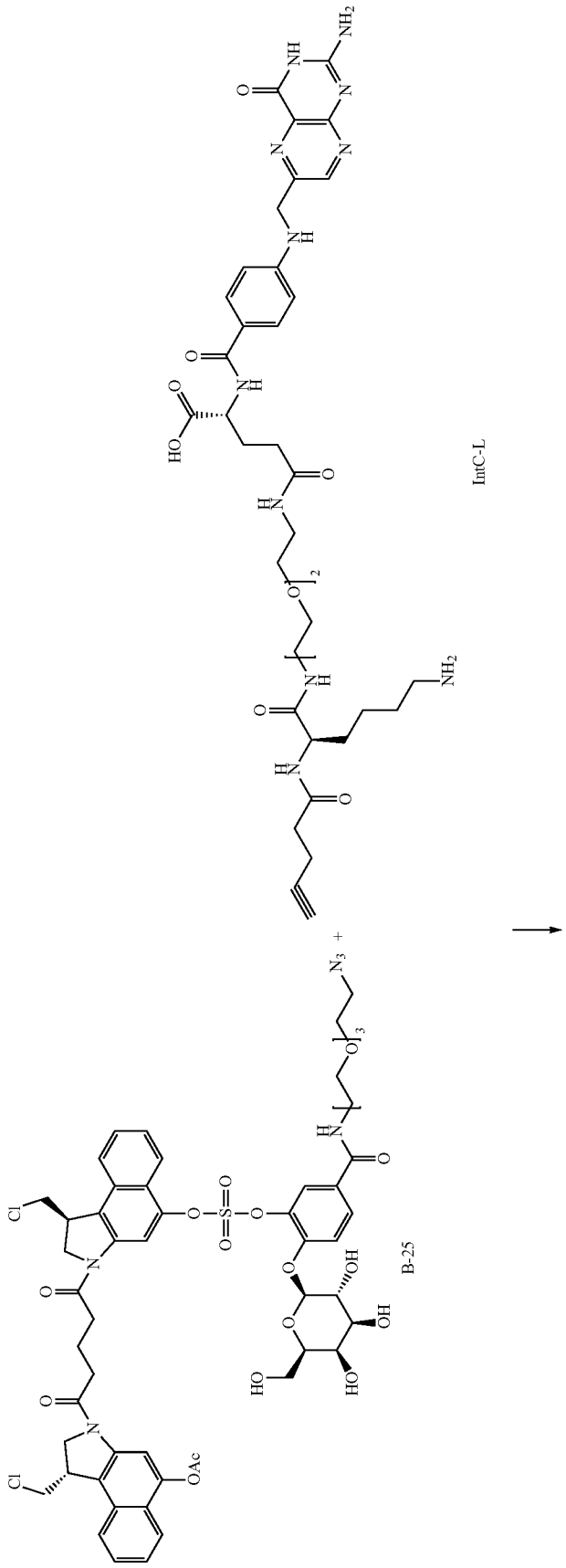

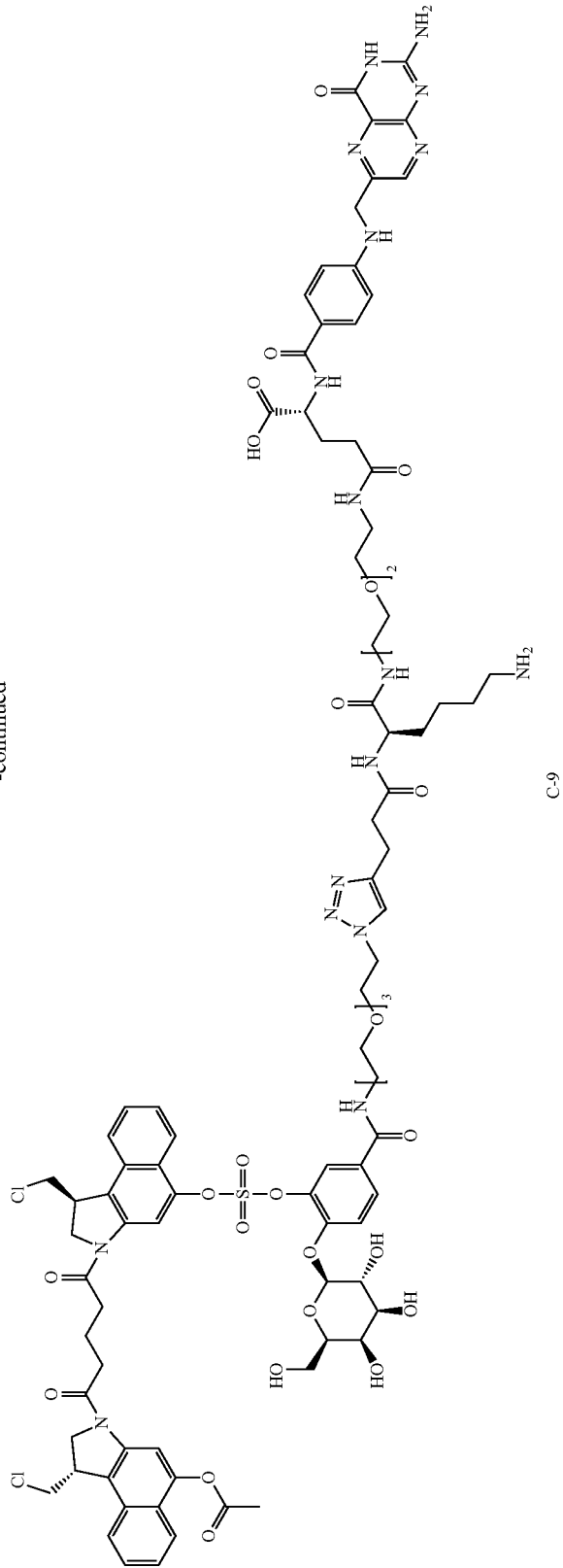

Compound C-9 was synthesized via a similar synthetic route as described in Example 108.

EI-MS m/z: 983.0 (M$^{+1}$)

[Example 117] Preparation of Ligand-Drug Conjugate Compound D-1

345
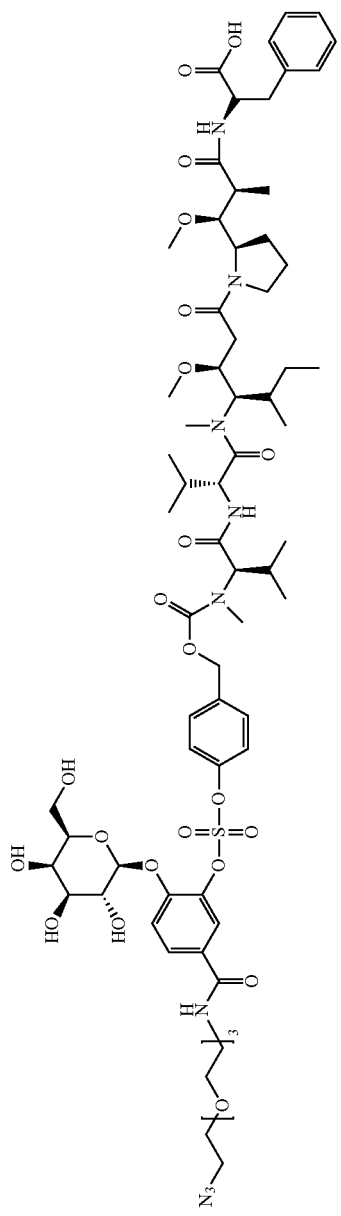
B-3
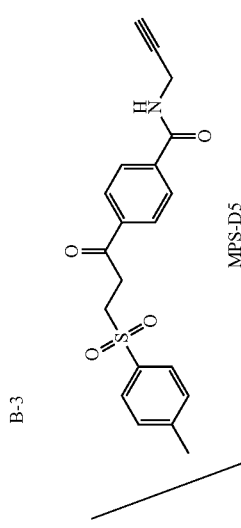
MPS-D5
346
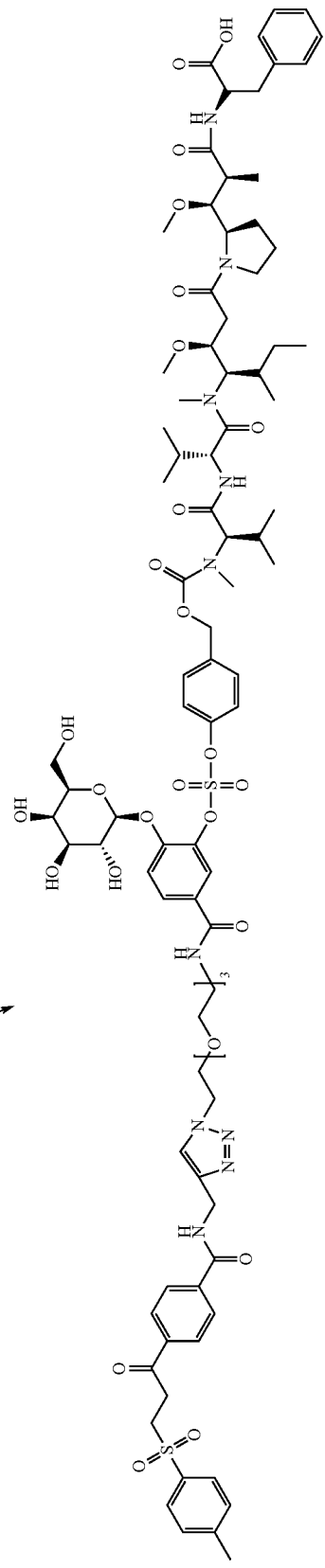
D-1

To a solution of compound B-3 (Example 72, 10 mg, 6.85 μmol) in DMSO (685 μL+7671 μL) was added $(BimC_4A)_3$ (1142 μL) prepared to have concentration of 50 mmol. Then, CuBr prepared to have a concentration of 10 mmol was added thereto in an amount of 685 μL. The mixture was stirred for 2 minutes. The compound MPS-D5 (4.6 mg, 12.3 μmol) was dissolved in DMSO (685 μL) and added thereto, followed by stirring for 10 minutes. After the reaction was completed, the mixed solution was separated and purified by Prep-HPLC to obtain compound D-1 (5.4 mg, 43%).

EI-MS m/z: 916 ($M^{+1}/2$).

[Example 118] Preparation of Ligand-Drug Conjugate Compound D-2

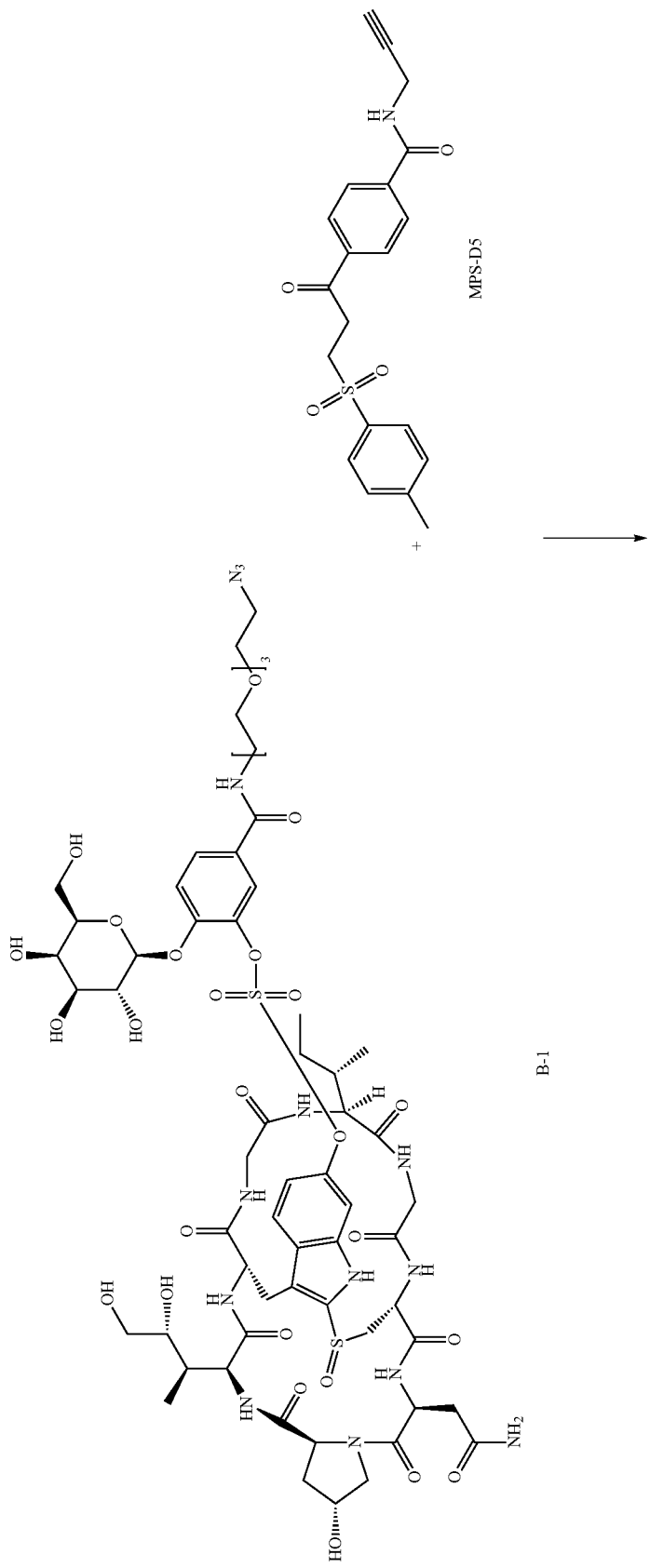

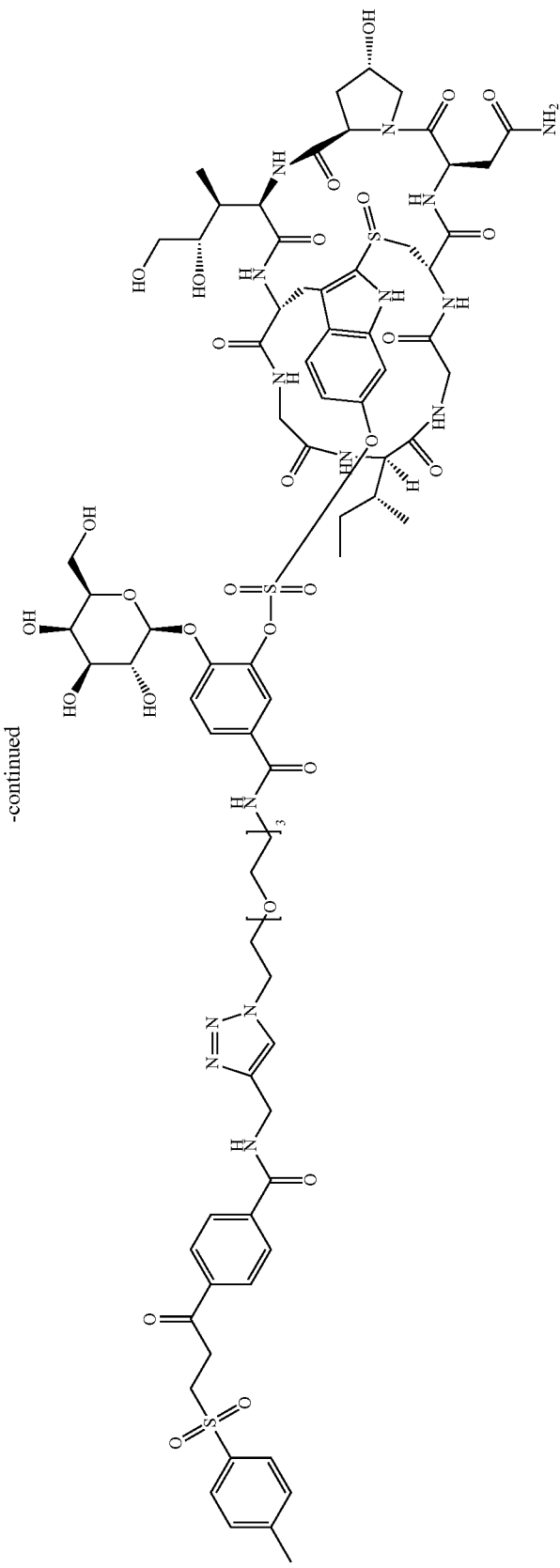
D-2

Compound D-2 was synthesized via a similar synthetic route as described in Example 108.

Yield 35%; EI-MS m/z: 934 ($M^{+1}/2$).

[Example 119] Preparation of Compound D-4

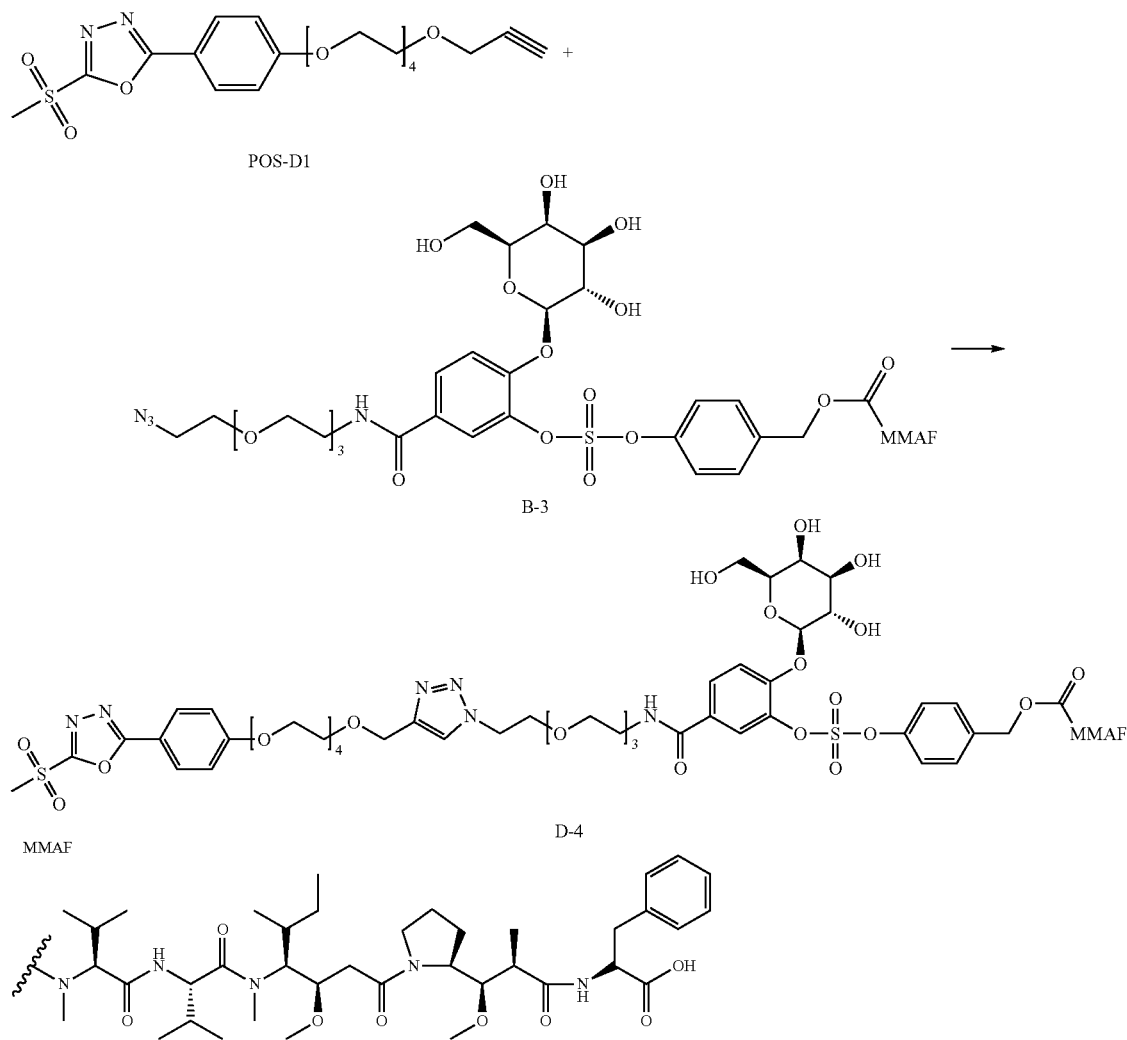

To a solution of compound B-3 (10 mg, 6.85 μmol) in DMSO (685 μL) was added (BimC$_4$A)$_3$ (1142 μL of 50 mmol stock solution) at room temperature under N$_2$ atmosphere. After DMSO (6179 μL) was added, CuBr (685 μL) prepared to have a concentration of 100 mmol was added. Then, the mixture was stirred for 2 minutes. The compound POS-D1 (12.4 mg, 27.4 μmol) was dissolved in DMSO (685 μL) and added thereto, followed by stirring for 10 minutes. After the reaction was completed, the mixed solution was separated and purified by Prep-HPLC to obtain compound D-4 (0.5 mg, 3.8%).

EI-MS m/z: 958 ($M^{+1}/2$).

[Example 120] Preparation of Compound D-5

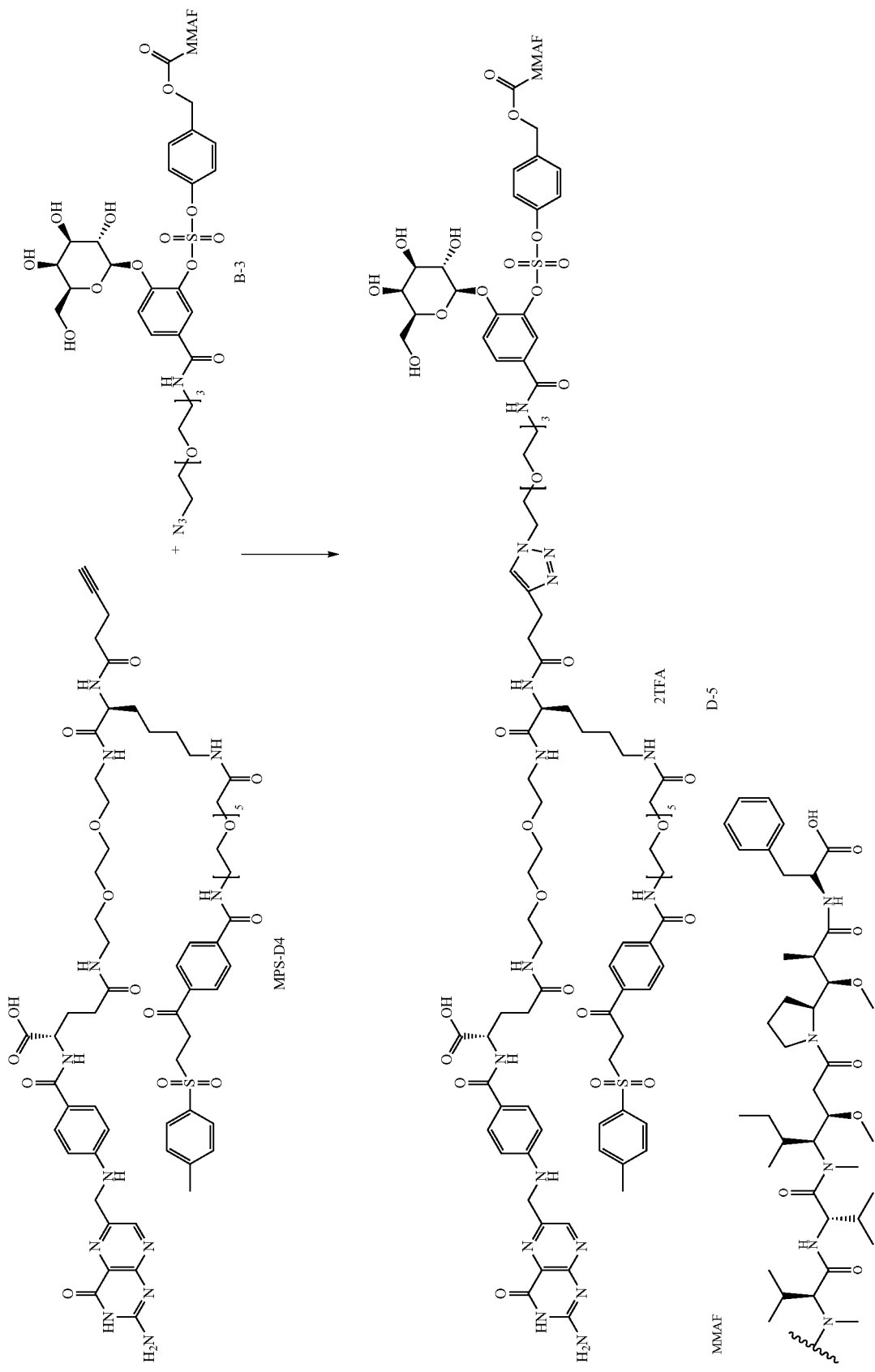

Compound D-5 was synthesized via a similar synthetic route as described in Example 108.

Yield 53%; EI-MS m/z: 1417 ($M^{+1}/2$).

[Example 121] Preparation of Compound D-6

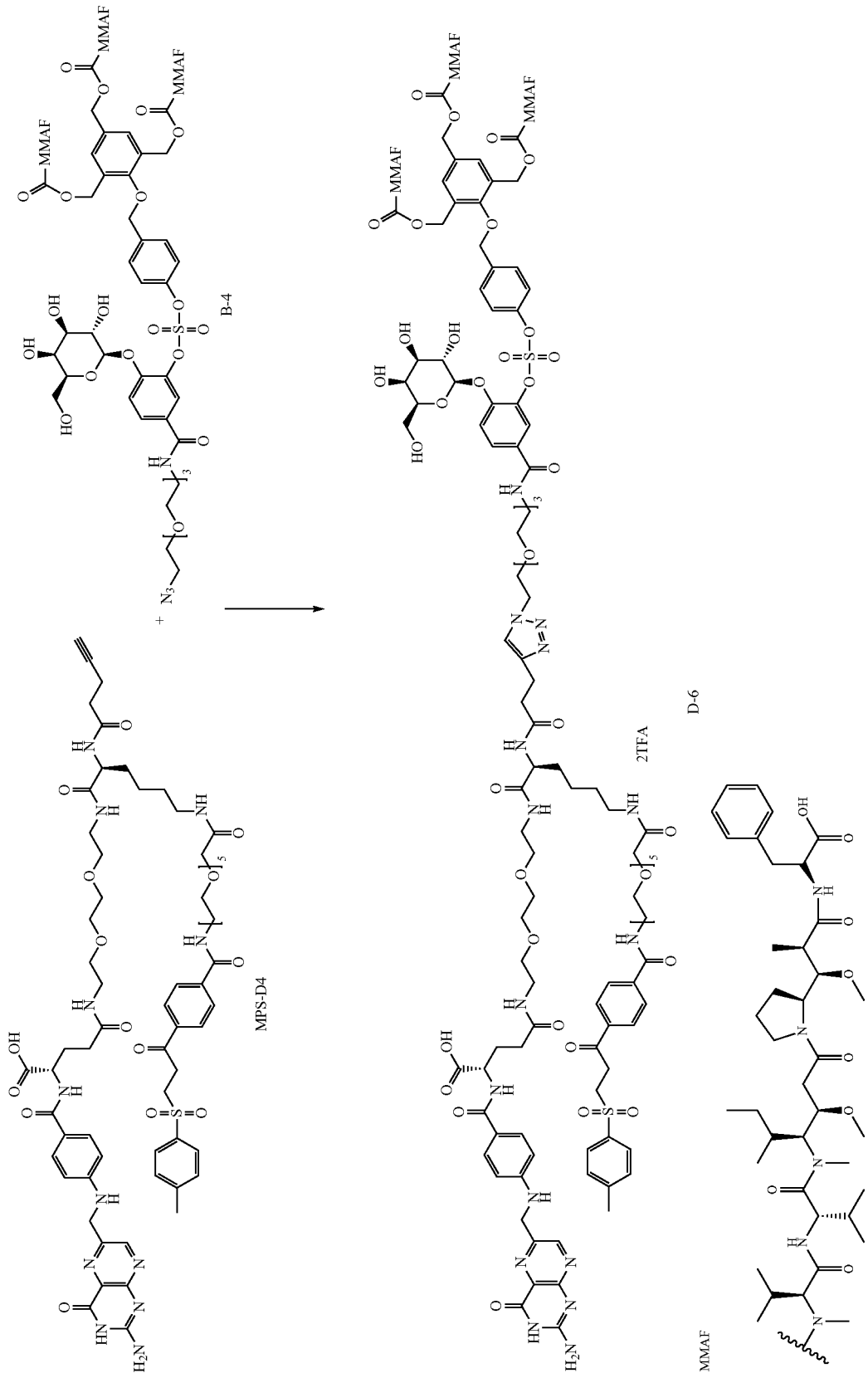

Compound D-6 was synthesized via a similar synthetic route as described in Example 108.
Yield 42%; EI-MS m/z: 4515 (M$^+$), 2258 (M/2$^+$), 1505 (M/3$^+$).
[Example 122] Preparation of Compound D-7
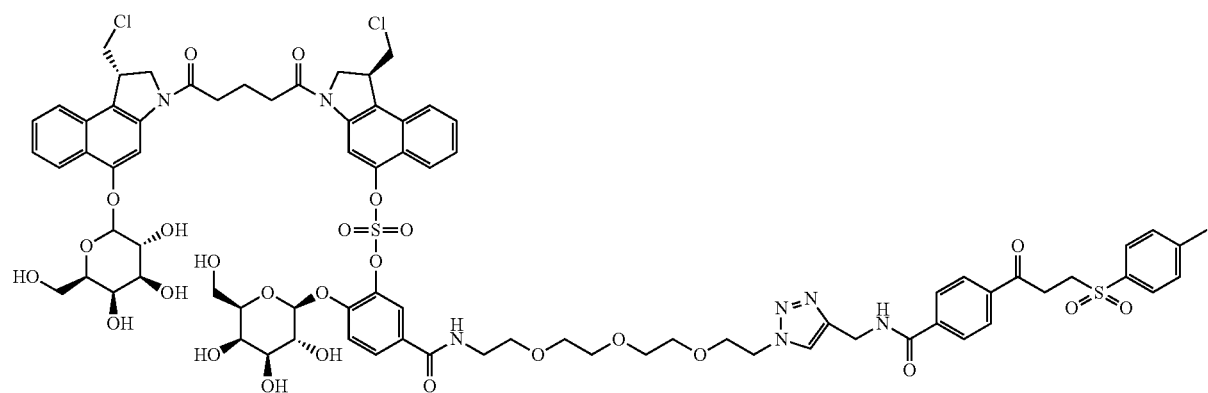 [SMILES: Cc1ccc(S(=O)(=O)CCC(=O)c2ccc(C(=O)NCc3cn(CCOCCOCCOCCNC(=O)c4ccc(O[C@@H]5O[C@H](CO)[C@H](O)[C@H](O)[C@H]5O)c(OS(=O)(=O)Oc5cc6c(c7ccccc57)[C@H](CCl)CN6C(=O)CCCC(=O)N5C[C@@H](CCl)c6c5cc(OC5O[C@H](CO)[C@H](O)[C@H](O)[C@H]5O)c5ccccc65)c4)nn3)cc2)cc1]
Compound D-7 was synthesized via a similar synthetic route as described in Example 108.
EI-MS m/z: 1673.0 (M$^+$).
[Example 123] Preparation of Compound D-8
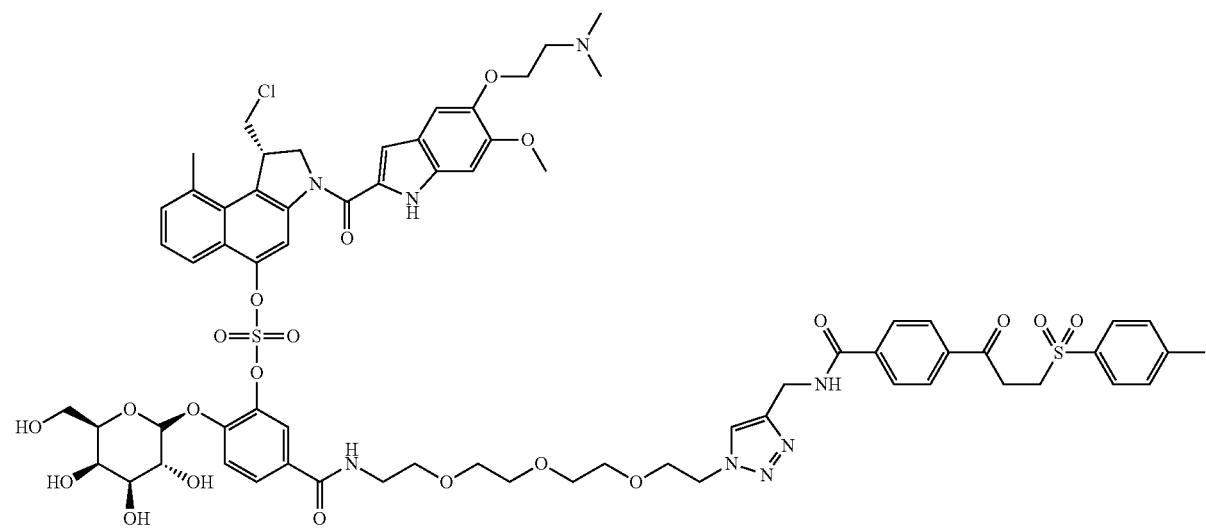

Compound D-8 was synthesized via a similar synthetic route as described in Example 108.
EI-MS m/z: 728.8 (M$^+$/2).
[Example 124] Preparation of Compound D-9
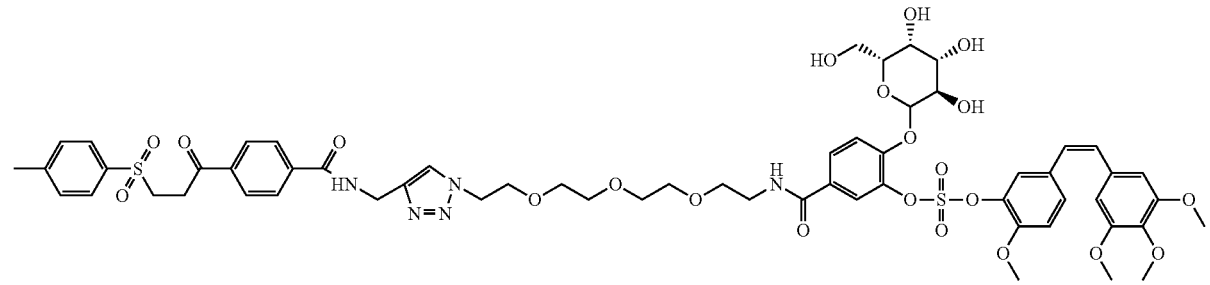
Compound D-9 was synthesized via a similar synthetic route as described in Example 108.
Yield 50%; EI-MS m/z: 1264 (M$^+$).
[Example 125] Preparation of Compound D-10
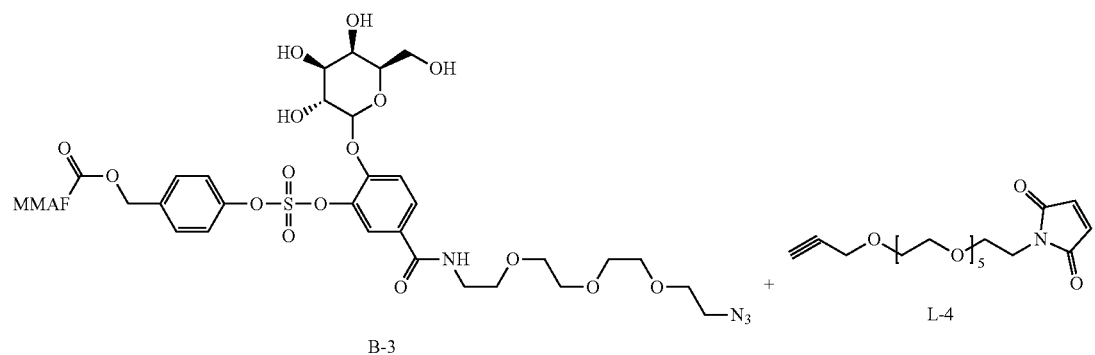
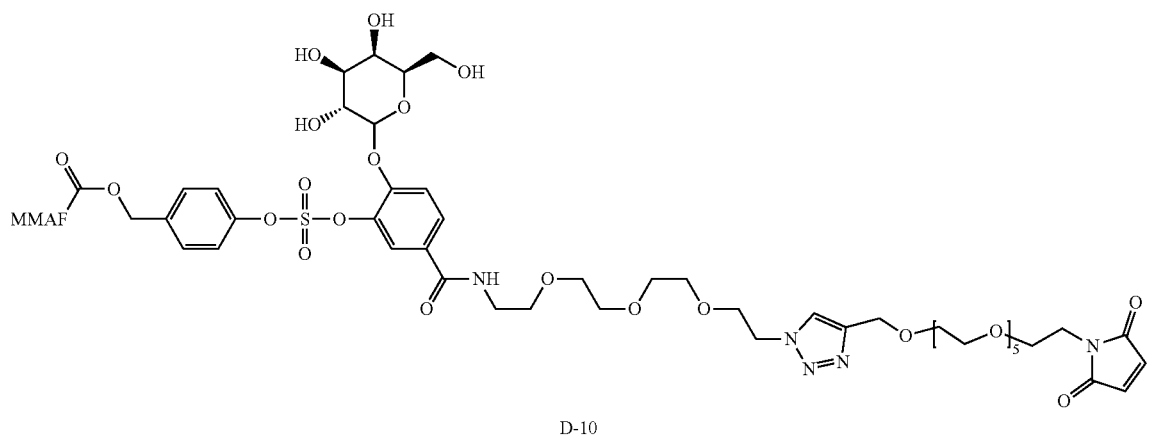

Compound D-10 was synthesized via a similar synthetic route as described in Example 108.
Yield 17%; EI-MS m/z: 1861 (M+).

[Example 126] Preparation of Compound D-11

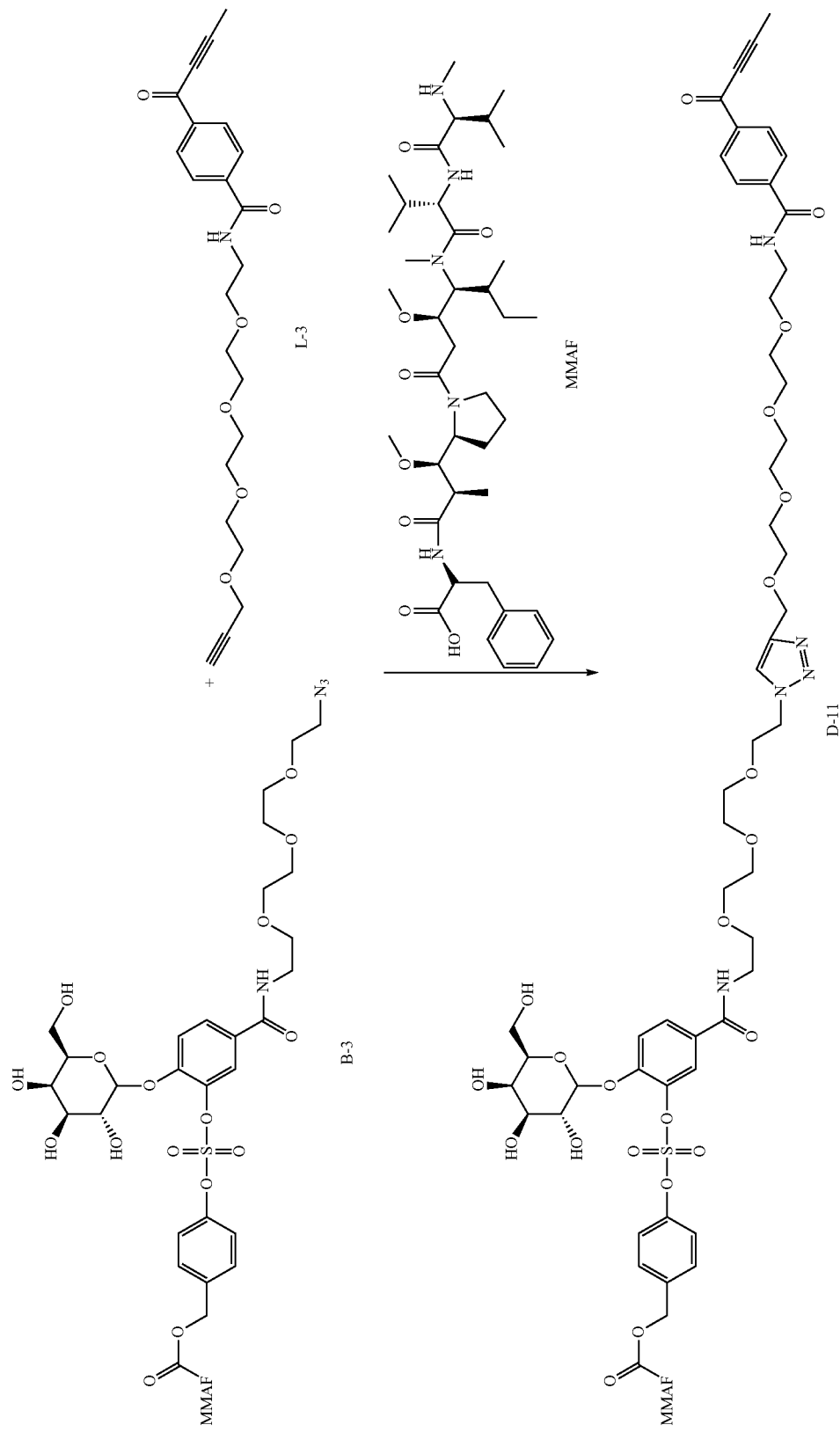

Compound D-11 was synthesized via a similar synthetic route as described in Example 108.

Yield 25%; EI-MS m/z: 1863 (M$^+$).

[Example 127] Preparation of Compound D-12

Compound D-12 was synthesized via a similar synthetic route as described in Example 108.

EI-MS m/z: 1850.8 (M$^+$).

[Example 128] Preparation of Compound D-13

Compound D-13 was synthesized via a similar synthetic route as described in Example 108.

Yield 18%; EI-MS m/z: 930 (M/2$^+$).

[Example 129] Preparation of Compound D-14

-continued
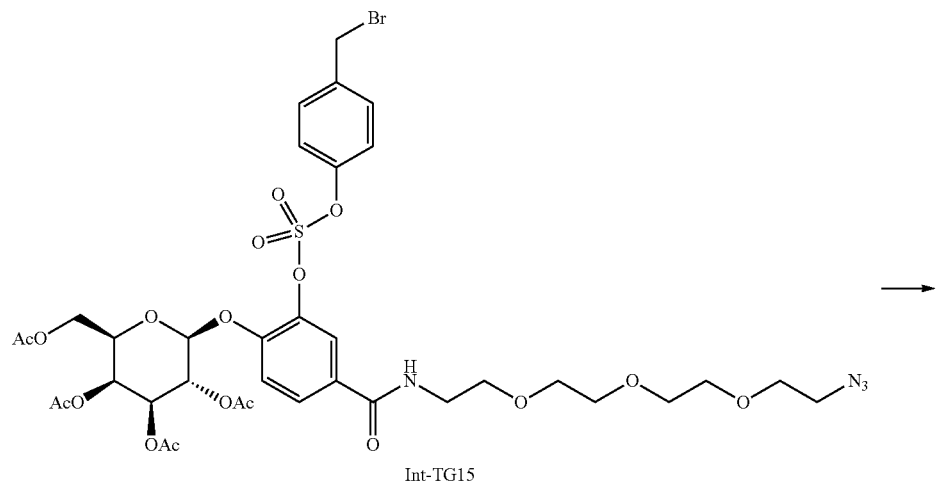
Int-TG15
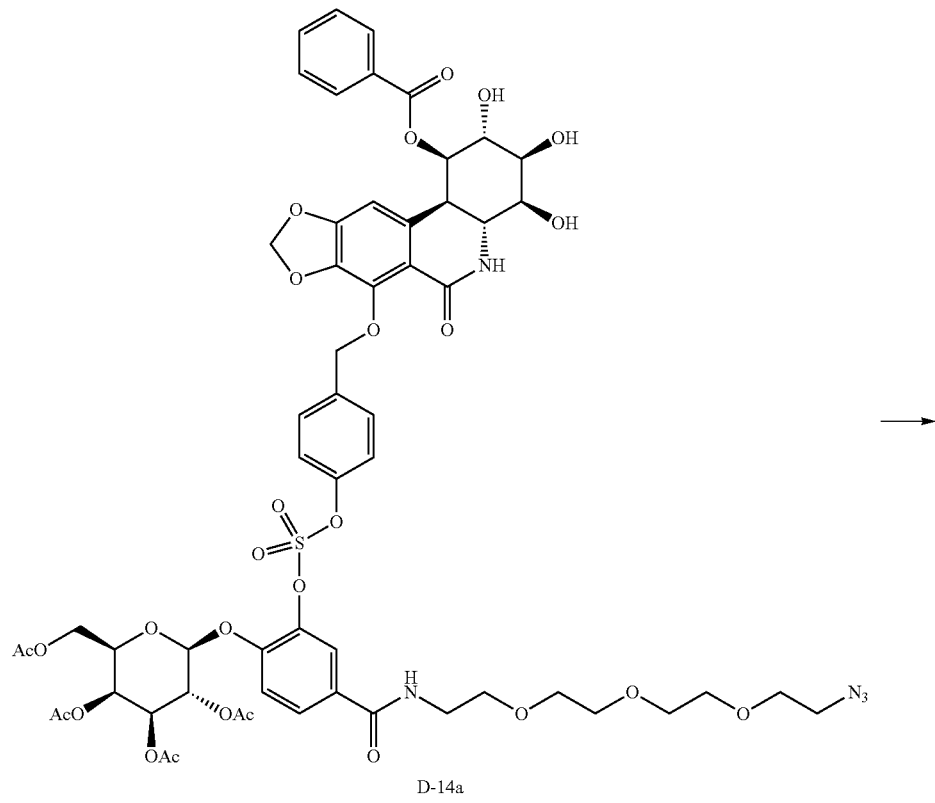
D-14a

-continued

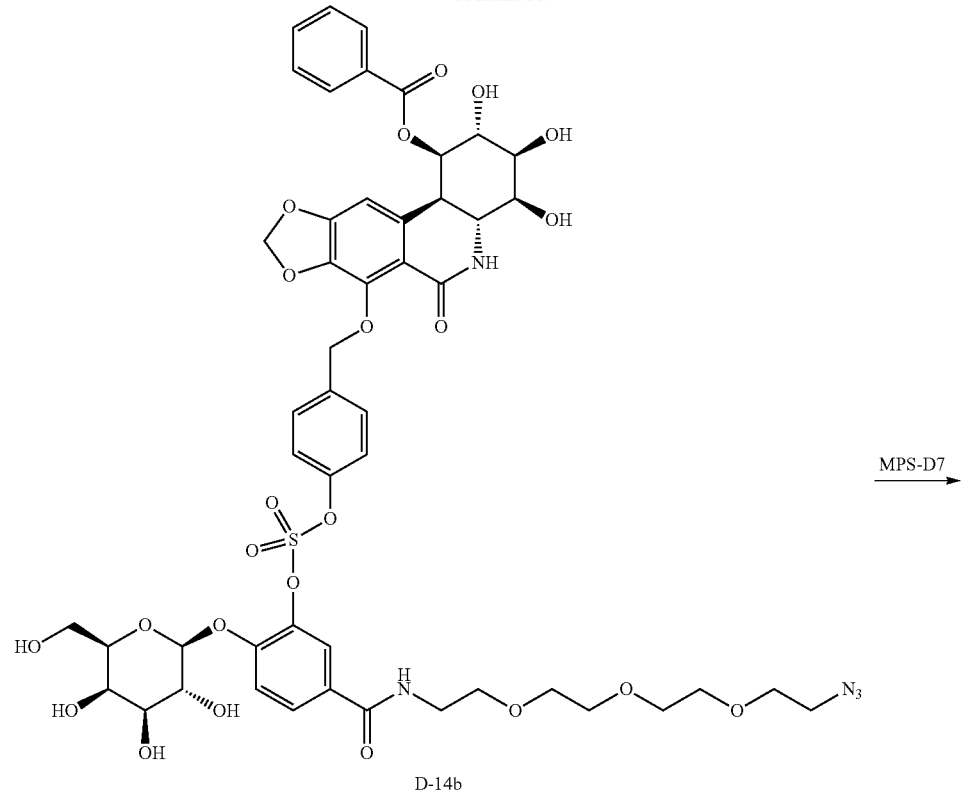

MPS-D7 →

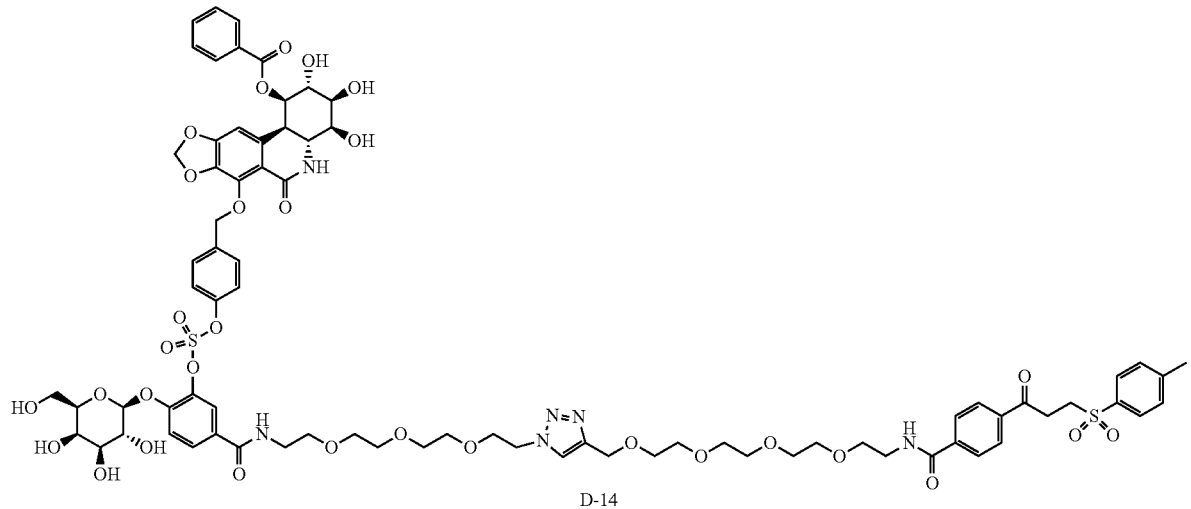

Preparation of Compound (A)

Total synthesis of the Compound (A) was prepared by according to the papers (J. Org. Chem. 2004, 69, 112-121, J. Am. Chem. SOCl. 995, 117, 10143-10144).

Preparation of Compound D-14a

To a solution of compound (A) (10 mg, 0.018 mmol) and compound Int-TG15 (16.8 mg, 0.018 mmol) in ACN (1 mL) was added a molecular sieve (100 mg) under $N_2$ atmosphere. After stirring at room temperature for 10 minutes, $Ag_2O$ (12.5 mg, 0.054 mmol) was added. The mixture was stirred at room temperature for 5 hours and filtered through celite and concentrated under reduced pressure. The residue was purified by prep-HPLC to obtain compound D-14a (18 mg, 71%).

$^1$H NMR (400 MHz, CDCl3) δ 7.99 (m, 2H), 7.85 (s, 1H), 7.77 (d, J=8.8 Hz, 2H), 7.65 (d, J=8.4 Hz, 2H), 7.58 (m, 1H), 7.44-7.40 (m, 2H), 7.36 (J=8.4 Hz, 2H), 7.29 (d, J=8.8 Hz, 1H), 6.94 (m, 1H), 6.46 (s, 1H), 6.11 (s, 1H), 5.94 (m, 2H), 5.80 (s, 1H), 5.56 (m, 1H), 5.50~5.46 (m, 2H), 5.35~5.31 (m, 2H), 5.25-5.22 (m, 2H), 5.15~5.13 (m, 2H), 4.38 (m, 1H), 4.25~4.08 (m, 4H), 3.65~3.59 (m, 15H), 3.54~3.49 (m, 1H), 3.33 (m, 2H), 2.17 (s, 3H), 2.13 (s, 3H), 2.09 (s, 3H), 2.06 (s, 3H), 2.04 (s, 3H), 2.00 (s, 3H), 1.81 (s, 3H). EI-MS m/z: 705 (½M$^+$), 1408 (M$^+$), 1430 (M$^+$Na).

Preparation of Compound D-14b

To a solution of the compound D-14a (16 mg, 0.011 mmol) in DCM (4 mL) was added 1M-NaOMe in methanol (20 μL) at 0° C. After stirring at 0° C. for 20 minutes, the mixture was quenched with 1M-HCl aqueous solution (30 μL) and then purified by prep-HPLC to obtain compound D-14b (4 mg, 32%) EI-MS m/z: 557 (½M$^+$), 1114 (M$^+$), 1136 (M$^+$+Na).

Preparation of Compound D-14

Compound D-14 was synthesized via a similar synthetic route as described in Example 56.

Yield 12%; EI-MS m/z: 830 (M$^{+1}$/2).

[Example 130] Preparation of Compound D-15

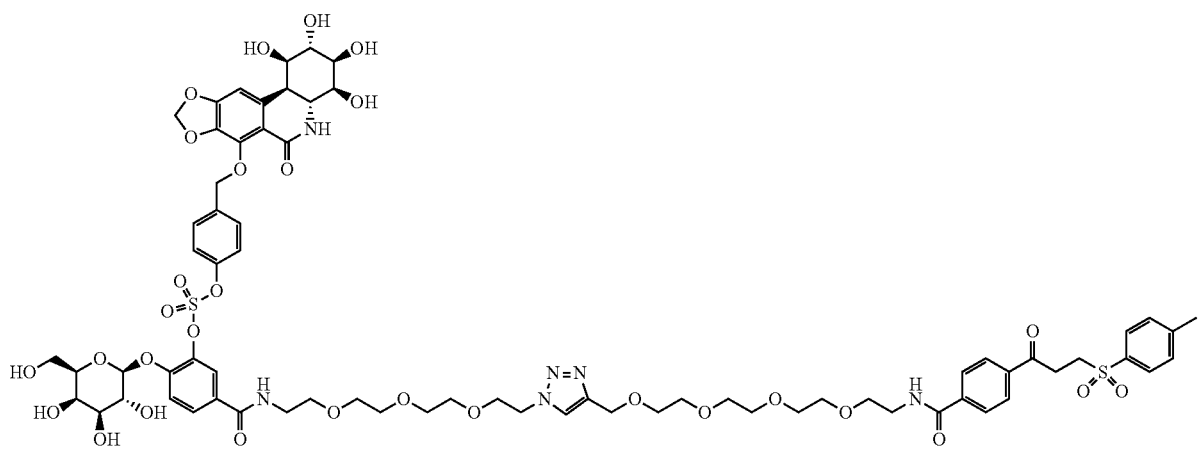 [SMILES: Cc1ccc(S(=O)(=O)CCC(=O)c2ccc(C(=O)NCCOCCOCCOCCOCc3cn(CCOCCOCCOCCNC(=O)c4ccc(O[C@@H]5O[C@H](CO)[C@H](O)[C@H](O)[C@H]5O)c(OS(=O)(=O)Oc5ccc(COc6c7c(cc8c6C(=O)N[C@H]6[C@H](O)[C@H](O)[C@@H](O)[C@H](O)[C@H]86)OCO7)cc5)c4)nn3)cc2)cc1]

Compound D-15 was synthesized via a similar synthetic route as described in Example 119.

Yield 19%; EI-MS m/z: 1556 (M+), 778 (½M+).

[Example 131] Preparation of Compound D-16

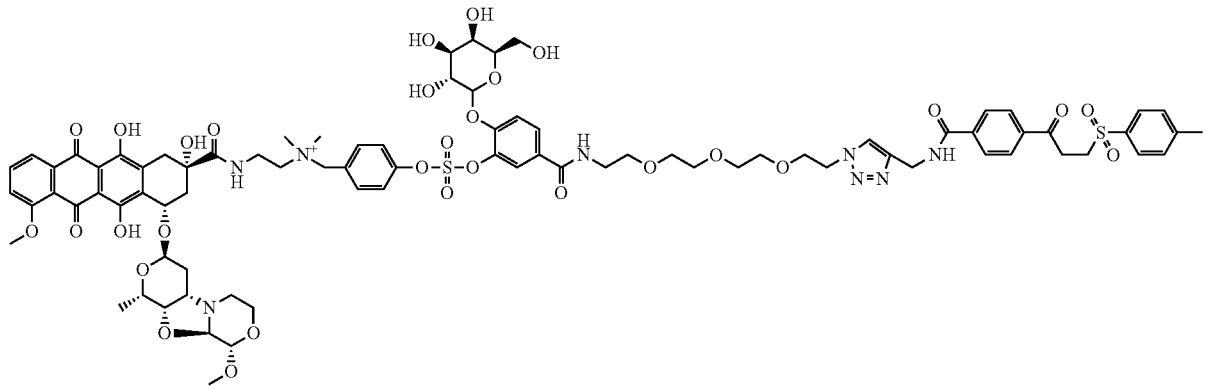 [SMILES: COc1cccc2c1C(=O)c1c(O)c3c(c(O)c1C2=O)C[C@@](O)(C(=O)NCC[N+](C)(C)Cc1ccc(OS(=O)(=O)Oc2cc(C(=O)NCCOCCOCCOCCn4cc(CNC(=O)c5ccc(C(=O)CCS(=O)(=O)c6ccc(C)cc6)cc5)nn4)ccc2OC2O[C@H](CO)[C@H](O)[C@H](O)[C@H]2O)cc1)C[C@@H]3O[C@H]1C[C@H]2[C@H](O[C@@H]3[C@@H](OC)OCCN32)[C@H](C)O1]

Compound D-16 was synthesized via a similar synthetic route as described in Example 108.
Yield 13%; EI-MS m/z: 1753 (M$^+$).
[Example 132] Preparation of Compound D-17
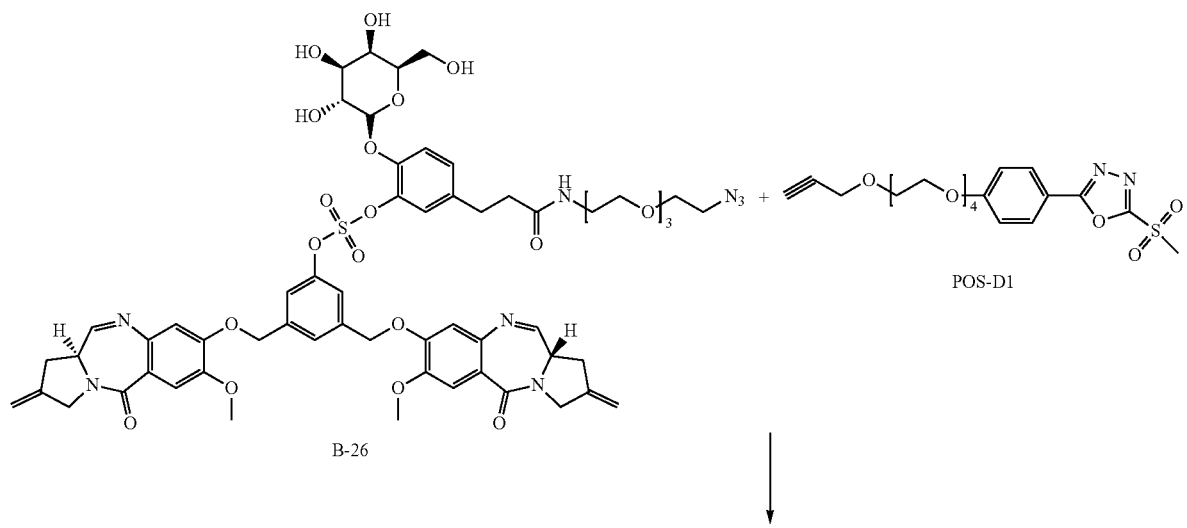
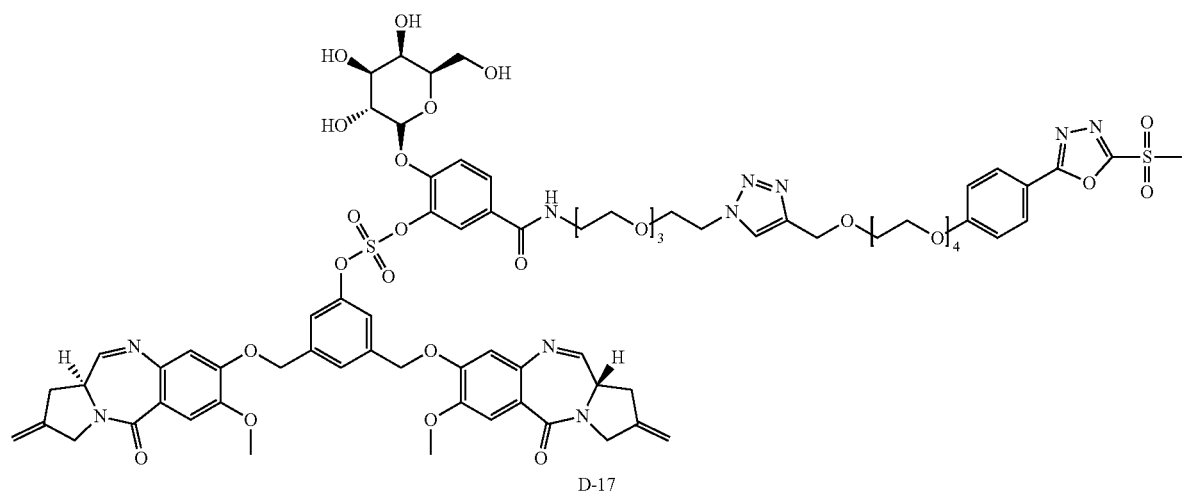

Compound D-17 was synthesized via a similar synthetic route as described in Example 108.
Yield 12%; EI-MS m/z: 1668 (M$^+$).

[Example 133] Preparation of Compound D-18

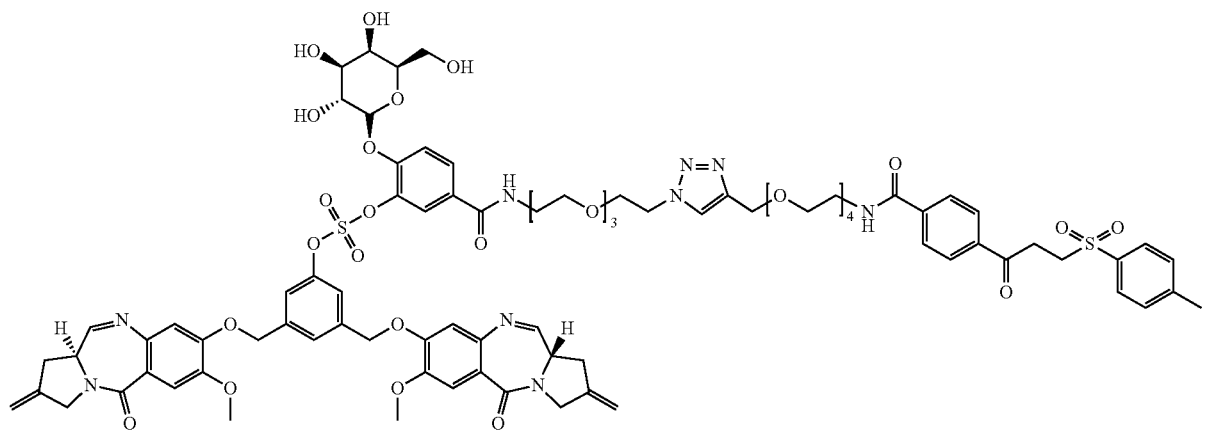

D-18

Compound D-18 was synthesized via a similar synthetic route as described in Example 108.
Yield 7.4%; EI-MS m/z: 1759 (M$^+$).

[Example 134] Preparation of Compound CBI Dimer

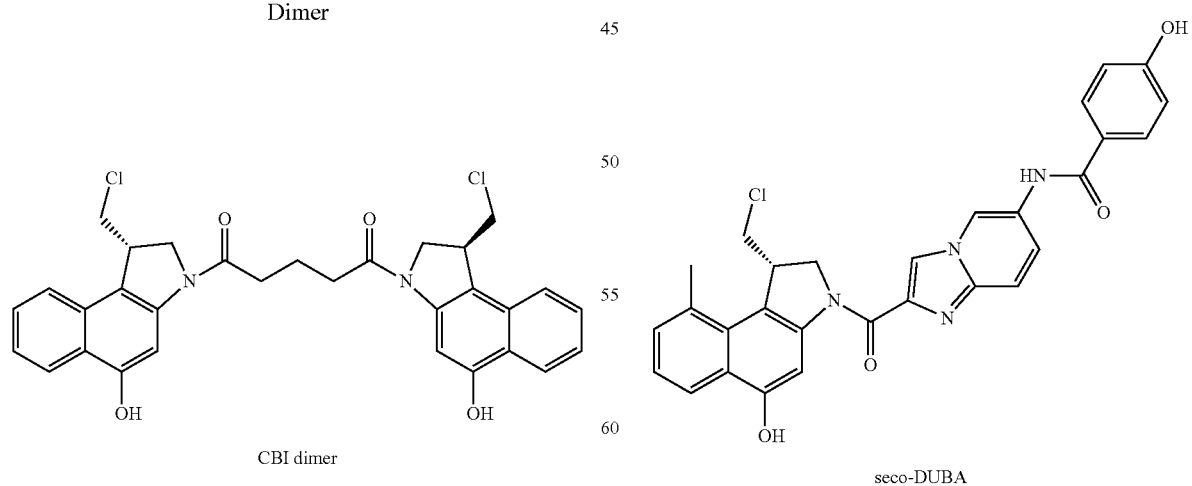

CBI dimer

A CBI dimer was synthesized by a similar synthetic method as described in WO2015110935A.

[Example 135] Preparation of Compound Seco-DUBA seco-DUBA seco-DUBA was synthesized by a similar synthetic method as described in document [see Mol. Pharmaceutics 2015, 12, 1813-1835].

[Example 136] Preparation of Compound Seco-CBI-Indole
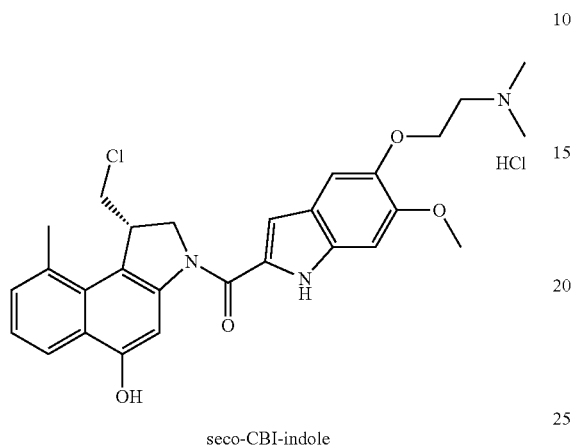
seco-CBI-indole
seco-CBI-indole was synthesized by a similar synthetic method as described in document [see ChemMedChem 2008, 3, 1946-1955].
[Example 137] Preparation of Compound D-3
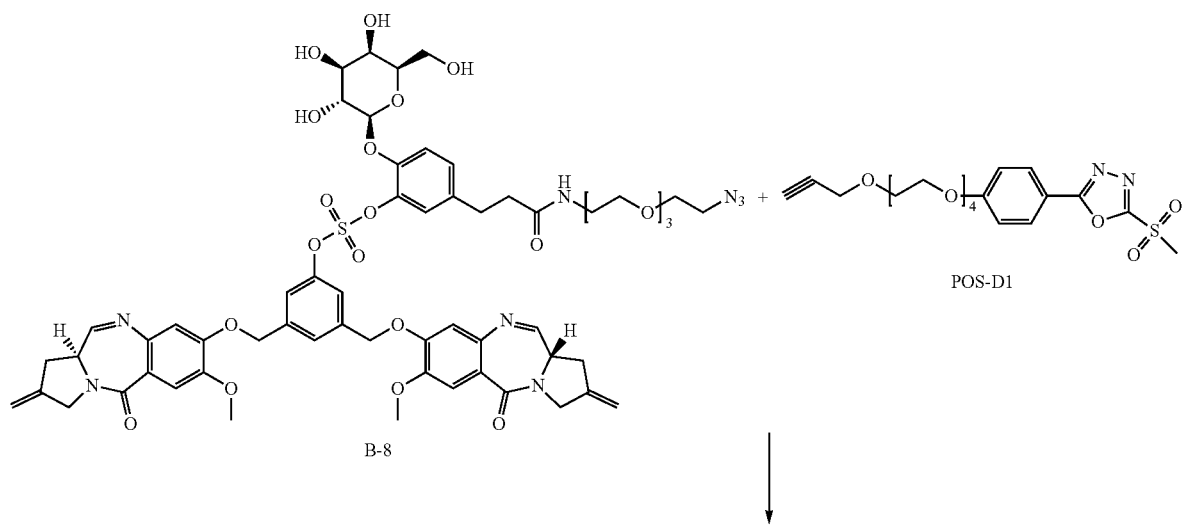

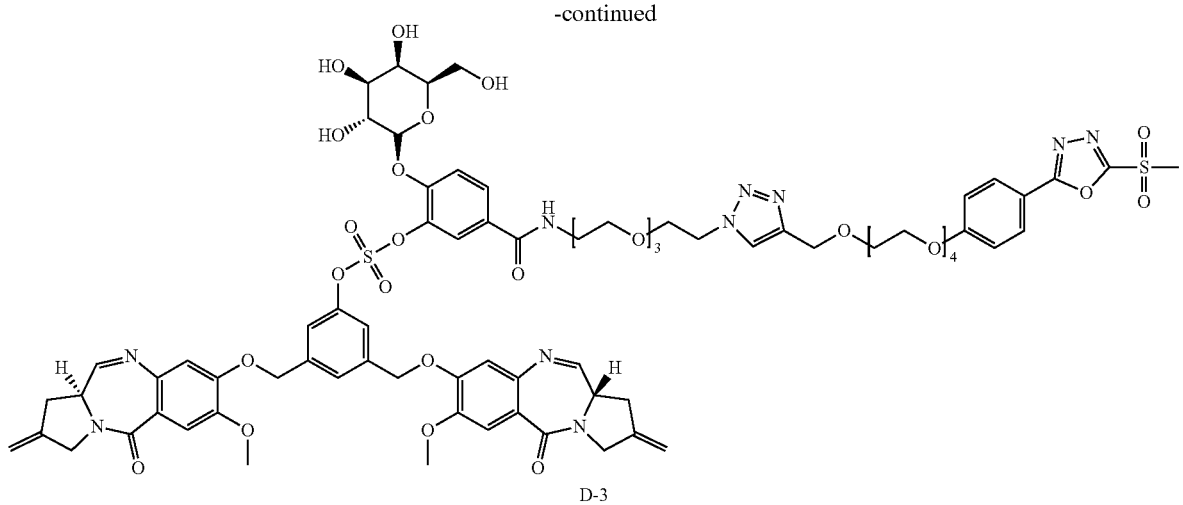

D-3

Compound B-8 (15 mg, 0.01 mmol) was dissolved in DMSO (7 mL) at room temperature under a nitrogen atmosphere, and then (BimC$_4$A)$_3$ (33 mg, 0.04 mmol) dissolved in DMSO (2 mL), CuBr (17 mg, 0.12 mmol) dissolved in DMSO (3 mL), and POS-D1 (Preparation Example 36, 7 mg, 0.01 mmol) dissolved in DMSO (1 mL) were added thereto, followed by stirring for 2 hours. The mixture was separated and purified by Prep-HPLC to obtain a compound D-3 (2.5 mg, 12%).

EI-MS m/z: 1668 (M$^+$).

Biological and Biochemical Studies

[Example 138] Kinetic Study of Enzymatic Cleavage Assay

Method 1) *Escherichia coli* β-galactosidase

The compounds of the present invention (compounds A-2, A-4, A-5, A-6, A-9, A-10, A-12, A-13, A-14, A-15, A-17, A-18, A-19, A-21, A-22, A-23, B-1, B-2, B-3, B-4, B-6, B-7, B-8, B-9, B-10, B-11, B-14, B-15, B-16, B-19 and C-3) were dissolved in DMSO and mixed with PBS buffer solution to prepare 500 μM stock solution (5% DMSO). MPS used as a standard material was dissolved in PBS buffer solution to make 500 μM solution. 406 μL of the PBS buffer solution (pH 7.4) and 140 μL of the compound (500 μM) of the present invention and 140 μL of MPS were mixed. This was followed by the addition of enzyme solution (14 μL of 1 mg/mL). When comparing with human β-galactosidase, 21 μL of enzyme solution (1 mg/mL) was added to achieve the same molar concentration, and the compound of the present invention and MPS each having an amount of 140 μL and 399 μL of the buffer solution (pH 7.4) were mixed. The resulting reaction mixture was incubated at 37° C. *Escherichia coli* β-galactosidase enzyme (Sigma G4155) was used in the reaction mixture. The enzyme reaction solution was aliquoted at 0 min before the reaction and at a predetermined time after the reaction, respectively, wherein each aliquot was 70 μL. Then, the remaining compound of the present invention or MPS, and a material liberated by the enzyme reaction were quantitatively analyzed by HPLC.

Method 2) Human β-galactosidase

The each compound A-3, B-2, and B-10 of the present invention were dissolved in DMSO, and mixed with PBS buffer solution to prepare 500 μM stock solution (5% DMSO). MPS used as a standard material was prepared as a solution to have a concentration of 500 μM in PBS buffer solution. 280 μL of the PBS buffer solution (pH 7.4) and the compound B-2 (500 μM) of the present invention and MPS each having an amount of 140 μL were mixed with each other. Then, 140 μL of 0.1 mg/mL enzyme solution was added thereto, thereby preparing an enzyme reaction solution in a total amount of 700 μL. The reaction mixture was incubated at 37° C. Human β-galactosidase enzyme (R&D 6464-GH-020) was used in the reaction mixture. The enzyme reaction mixture was aliquoted at 0 min before the reaction and at a predetermined time after the reaction, respectively, wherein each aliquot was 70 μL. Then, the remaining compound of the present invention or MPS, and SN38 liberated by the enzyme reaction were quantitatively analyzed by HPLC.

Method 3) *Escherichia coli* β-glucuronidase

The compounds A-1 and A-5 of the present invention were dissolved in DMSO, and mixed with PBS buffer solution to prepare a solution having a concentration of 500 μM (5% DMSO). MPS used as a standard material was prepared as a solution to have a concentration of 500 μM in PBS buffer solution. 406 μL of the PBS buffer solution (pH 7.4) and 140 μL of the compound (500 μM) of the present invention and 140 μL of MPS were mixed. Then, 14 μL of enzyme solution (1 mg/mL) was added thereto, thereby preparing an enzyme reaction solution in a total amount of 700 μL. The reaction mixture was incubated at 37° C. *Escherichia coli* 0-glucuronidase enzyme (Sigma G7396) was used in the reaction mixture. The enzyme reaction mixture was aliquoted at 0 min before the reaction and at a predetermined time after the reaction, respectively, wherein each aliquot was 70 μL. Then, the remaining compound of the present invention or MPS, and a material liberated by the enzyme reaction were quantitatively analyzed by HPLC.

Method 4) *Escherichia coli* β-Galactosidase+β-Glucuronidase

The compound A-5 of the present invention was dissolved in DMSO, and mixed with PBS buffer solution to prepare a solution having a concentration of 500 μM (5% DMSO). MPS used as a standard material was prepared as a solution to have a concentration of 500 μM in PBS buffer solution. 392 μL of the PBS buffer solution (pH 7.4) and 140 μL of the compound A-5 (500 μM) of the present invention and MPS were mixed. Then, 14 μL of 1 mg/mL of 0-galactosidase (Sigma G4155) and 14 µL of 1 mg/mL of β-glucuronidase (Sigma G7396) were added thereto, thereby preparing an enzyme reaction mixture in a total amount of 700 µL. The reaction mixture was incubated at 37° C. The enzyme reaction mixture was aliquoted at 0 min before the reaction and at a predetermined time after the reaction, respectively, wherein each aliquot was 70 µL. Then, the remaining compound of the present invention or MPS, and a material liberated by the enzyme reaction were quantitatively analyzed by HPLC.

TABLE 1

| Compounds of present invention | TG release $t_{1/2}$(min) | Q part release $t_{1/2}$(min) | Experimental method |
|---|---|---|---|
| A-1 | 0.43 ± 0.11 | 36.38 ± 0.39 | Method 3 |
| A-2 | 3.71 ± 0.22 | 123.08 ± 25.96 | Method 1 |
| A-3 | 10.71 | 38.18 | Method 2 |
| A-4 | <5 | 15.3 | Method 1 |
| A-5 | <5 | 70.87 | Method 3 |
|  | <5 | No reaction | Method 1 |
|  | <5 | 139.4 | Method 4 |
| A-6 | 4.60 ± 1.72 | 40.36 ± 8.03 | Method 1 |
| A-9 | <5 | 37.39 | Method 1 |
| A-10 | <5 | 15.24 | Method 1 |
| A-12 | <5 | 14.34 | Method 1 |
| A-13 | <5 | 8.01 | Method 1 |
| A-14 | N/D | 195.2 | Method 1 |
| A-15 | N/D | <5 | Method 1 |
| A-17 | <1 | 6.7 | Method 1 |
| A-18 | <5 | 7.4 | Method 1 |
| A-19 | fast | <5 | Method 1 |
| A-21 | fast | <5 | Method 1 |
| A-22 | fast | <5 | Method 1 |
| A-23 | fast | <5 | Method 1 |
| B-1 | 5.92 | 40.87 | Method 1 |
| B-2 | 0.28 | 1.85 | Method 1/ pH 7.4 |
|  | 5.75 | 46.85 | Method 1/ pH 5.0 |
|  | N/D | 112.2 | Method 2/ pH 7.4 |
|  | 5.33 | 39.41 | Method 2/ pH 5.0 |
| B-3 | <10 | 40.62 | Method 1 |
| B-4 | 20.68 | 312.9 | Method 1 |
| B-6 | <5 | 629.4 | Method 1 |
| B-7 | <5 | 50.23 | Method 1 |
| B-8 | ND | 4.3 | Method 1 |
| B-9 | <5 | 6.82 | Method 1 |
| B-10 | 2.1 | 6.6 | Method 1/ pH 7.4 |
|  | 8.9 | 27.9 | Method 2/ pH 5.0 |
| B-11 | <5 | 6.7 | Method 1 |
| B-14 | ND | 433 | Method 1 |
| B-15 | ND | 2.4 | Method 1 |
| B-16 | ND | 9.0 | Method 1 |
| B-19 | fast | 14.4 | Method 1 |
| C-3 | <5 | 52.03 | Method 1 |

(N/D = not detected under HPLC)

[Example 139] Drug Release Test by Chemical Activation

Method Using Reducing Agent

The compound A-8 obtained by Example 65 was dissolved in DMSO to make a concentration of 10 mM, and mixed with MeOH solution to prepare a solution having a concentration of 300 µM (40% DMSO). MPS used as a standard material was prepared as a solution to have a concentration of 300 µM with PBS buffer solution. NaBH$_4$, a reducing agent, was dissolved in MeOH to have a concentration of 10 mM, and 3.0 equivalents of the compound A-8 was added. Then, the reaction mixture was incubated at 37° C. The reduction reaction mixture was aliquoted at 0 min before the reaction, at 5 min, 10 min and 30 min after the reaction, respectively, wherein each aliquot was 80 µL. Then, the remaining compound A-8 of the present invention or MPS, and BOC-Tyr-OMe liberated by the enzyme reaction were quantitatively analyzed by HPLC.

Method Using Photo-Reaction

The compound A-11 obtained by Example 68 was dissolved in DMSO, and mixed with PBS buffer solution having pH of 7.4 and DMSO solution to prepare a solution having a concentration of 300 µM (50% DMSO). MPS used as a standard material was prepared as a solution to have a concentration of 300 µM in PBS buffer solution.

Then, the reaction was initiated by stirring in a photoreactor of 300 W. The reaction mixture was aliquoted at 0 min before the reaction, at 5 min, 10 min, 30 min, 180 min, 300 min, 420 min, 24 hr, and 48 hr after the reaction, respectively, wherein each aliquot was 80 µL. Then, the remaining compound A-11 of the present invention or MPS, and BOC-Tyr-OH liberated by the photo reaction were quantitatively analyzed by HPLC.

Hydrolysis Condition Under pH 9.2 Buffer (Example of Test According to pH)

The compounds A-7 and A-8 obtained by Examples 63 and 64 were dissolved in DMSO, and mixed with PBS buffer solution having pH of 9.2 to prepare a solution having a concentration of 300 µM (40% DMSO). MPS used as a standard material was prepared as a solution to have a concentration of 300 µM in PBS buffer solution. Then, the reaction was incubated at 37° C. The pH 9.2 reaction mixture of the compound A-7 was aliquoted at 0 min before the reaction, at 5 min, 10 min, 30 min, 60 min, 120 min, and 180 min after the reaction, respectively, wherein each aliquot was 80 µL. Then, the remaining compound A-7 of the present invention or MPS, and BOC-Tyr-OH liberated in the pH 9.2 buffer solution were quantitatively analyzed by HPLC. The pH 9.2 reaction mixture of the compound A-8 was aliquoted at 0 min before the reaction, at 5 min, 10 min, 30 min, 60 min, 120 min, 180 min, 240 min, and 300 min after the reaction, respectively, wherein each aliquot was 80 µL. Then, the remaining compound A-8 of the present invention or MPS, and BOC-Tyr-OMe liberated in the pH 9.2 buffer solution were quantitatively analyzed by HPLC.

Hydrolysis Condition Under pH 5.0 Buffer (Example of Test According to pH)

The compound A-8 obtained by Example 65 was dissolved in DMSO, and mixed with PBS buffer solution having pH of 5.0 and DMSO solution to prepare a solution having a concentration of 300 µM (40% DMSO). MPS used as a standard material was prepared as a solution to have a concentration of 300 µM with PBS buffer solution. Then, the reaction mixture was incubated at 37° C. The pH 5.0 reaction mixture of the compound A-8 was aliquoted at 0 min before the reaction, at 20 min, 180 min, 630 min, and 1 day after the reaction, respectively, wherein each aliquot was 80 µL. Then, the remaining compound A-8 of the present invention or MPS, and BOC-Tyr-OMe liberated in the pH 5.0 buffer solution were quantitatively analyzed by HPLC.

Deprotection Under Fluoro-Ion Concentration

Compound A-20 was dissolved in DMSO to prepare a solution having a concentration of 100 µM (90% DMSO). MPS used as a standard material was prepared as a solution to have a concentration of 100 µM in PBS buffer solution. To a solution of TBAF in THF (100 mM) was added 1.0, 10.0, and 100 equivalents of compound A-20. The reaction mixture was incubated at 37° C., and aliquoted at 0 in before the reaction, at 5 hr, 20 hr, 44 hr, 68 hr and 116 hr after the reaction, respectively, wherein each aliquot was 80 µL. Then, the remaining compound A-20 or MPS liberated in the reaction were quantitatively analyzed by HPLC.

TABLE 2

| Compounds of present invention | Q part release $t_{1/2}$(min) | Experimental method |
|---|---|---|
| A-7 | 19.27 | pH 9.2 |
| A-8 | 41.68 | pH 9.2 |
|  | Not released | pH 5.0 |
|  | 4.42 | Reducing agent |
| A-11 | 52.03 | Photo-reaction |
| A-20 | 2016 | $F^-$ ion(1 eq) |
|  | 672 | $F^-$ ion(10 eq) |
|  | 264 | $F^-$ ion(100 eq) |

[Example 140] In Vitro Analysis of Ligand-Drug Conjugate

KB cancer cells were collected and seeded in 24-well plates at a density of 30,000 cells per well in 2 mL of medium, and cultured for 24 hours. Then, the serial dilutions of compound C-1 obtained in Example 108 were treated from 30 nM to 0.0096 nM, the serial dilutions of compound C-2 obtained in Example 109 were treated from 1000 nM to 0.32 nM, serial dilutions of the compound C-3 obtained in Example 110 and the compound C-7 obtained in Example 114 were treated from 25 nM to 0.0016 nM, and serial dilutions of the drug MMAF-OMe were treated from 10 nM to 0.0097 nM. The serial dilutions of compounds C-5 and C-6 obtained in Example 112 and Example 113 were treated from 100 nM to 0.0001 nM, and the serial dilutions of drug seco-DUBA were treated from 100 nM to 0.001 nM. Serial dilutions of the compounds C-4 and C-9 obtained in Example 111 and Example 116 were treated from 1000 nM to 0.001 nM, and the serial dilutions of drug CBI dimer were treated by from 10 nM to 0.00001 nM. Serial dilutions of the compound C-8 obtained in Example 115 and the drug CBI-indole were treated from 100 nM to 0.0001 nM. After 72 hours, 96 hours, or 144 hours of incubation, 0.2 mL of 3-(4,5-dimethylthiazol-2-yl)-2,5-diphenyltetrazolium bromide (MTT) dye, dissolved in PBS buffer solution (5 mg/mL), was added to each well of the plates. The formazans formed by reduction of the MTT dye by mitochondrial oxidoreductases in the living cells were dissolved in DMSO, and measured using the absorbance at 550 nm. Results thereof are shown in Table 3 below.

TABLE 3

Cell cytotoxicity of ligand-drug conjugate

| Compounds of present invention | KB cell $IC_{50}$(nM) |
|---|---|
| C-1 | 2.31 ± 0.46 |
| C-2 | >500 |
| C-3 | 0.64 ± 0.13 |
| C-4 | 0.02 |
| C-5 | 0.45 |
| C-6 | 0.45 |
| C-7 | 0.82 |
| C-8 | 0.12 |
| C-9 | 0.10 |
| MMAF-OMe | 0.35 ± 0.07 |
| Seco-DUBA | 0.18 |

TABLE 3-continued

Cell cytotoxicity of ligand-drug conjugate

| Compounds of present invention | KB cell $IC_{50}$(nM) |
|---|---|
| CBI dimer | 0.0007 |
| CBI-indole | 0.07 |

[Example 141] Mouse, Rat, Dog and Human Plasma Stability Tests

The compound A-1 obtained in Example 58 and MPS used as a standard material were dissolved in DMSO to make a concentration of 60 mM. Then, each of human plasma (Biochemed 752R-SC-PMG), mouse plasma (Biochemed 029-APSC-MP), rat plasma (Biochemed 031-APSC-MP), and beagle dog plasma (Biochemed 013-APSC-MP) were mixed with the compound and MPS to make a final concentration of 300 µM (final 0.5% DMSO). The resulting plasma mixtures were incubated at 37° C. water bath. Aliquots were taken before the reaction and on 1 day, 2 days, 4 days, and 7 days after the reaction, wherein each aliquot was 300 µL. To complete the reaction, two-fold volumes of acetonitrile was added, followed by brief vortexing, and centrifugation for plasma protein precipitation. Each supernatant obtained after centrifugation was collected and analyzed by HPLC. The compound A-1 was detected and quantitated in the mouse, rat, beagle dog, and human plasma for up to 7 days (>95%). This study demonstrated the excellent stability of β-galactoside linker in plasma.

[Example 142] Chemical Stability

The compound A-1 obtained by Example 58 was dissolved in DMSO, and mixed with PBS (pH 7.4) buffer solution to prepare a solution having a concentration of 500 µM (5% DMSO). MPS used as a standard material was prepared as a solution to have a concentration of 500 µM in PBS buffer solution. 420 µL of the buffer solution, and 140 µL of the compound A-1 solution and 140 µL of MPS solution were mixed, thereby preparing a reaction mixture in a total amount of 700 µL. The reaction mixture was incubated at room temperature while blocking the light. The reaction mixture was aliquoted on 0 day before the reaction and on 1 day, 2 days, 4 days, and 7 days after the reaction, wherein each aliquot amount was 70 µL. Then, the remaining compound A-1, MPS, and liberated tyrosine were quantitated by HPLC analysis. The HPLC analysis confirmed that the compound A-1 was present (>95%) throughout the 7 days incubation period, which was found to be very stable.

[Test Example 6] Preparation of Conjugate (Albumin & Antibody)

The compound D-1 obtained in Example 117, the compound D-2 obtained in Example 118, the compound D-5 obtained in Example 110, and the compound D-6 obtained in Example 111 were used to perform conjugation reaction to a thiol group of engineered cysteine of Trastuzumab (or human serum albumin etc.), thereby preparing D-1-AB, D-2-AB, Albu-D-5, and Albu-D-6 as thiomab drug conjugates (TDC), respectively, with reference to methods presented in document [see Nature Biotechnology, 2008, 26, 925-932, Bioconjugate Chem., 2013, 24, 1256-1263, Bioconjugate Chem., 2016, 27, 1324-1331, Bioconjugate Chem. 2014, 25, 460-469]. The LC/MS analysis confirmed that the molecular weight of the thiomab was 145,450 Da, and a small amount of the glycation form (~146,895 Da) was also present. LC/MS analysis of the prepared antibody drug conjugate D-1-AB revealed the presence of masses about 148,563 Da and about 150,038 Da. These mass shifts were consistent with the conjugation of two molecules of D-1.

[Example 143] In Vitro Analysis of Protein-Drug Conjugate

Figure 12:
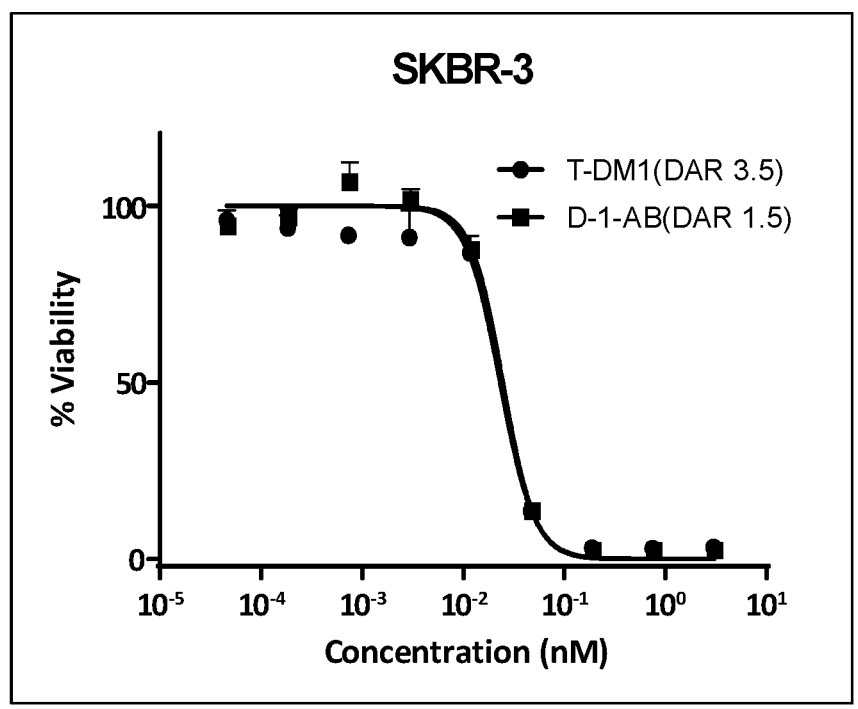
FIG. 12 shows results of in vitro analysis of Compound D-1-AB.
Figure 13:
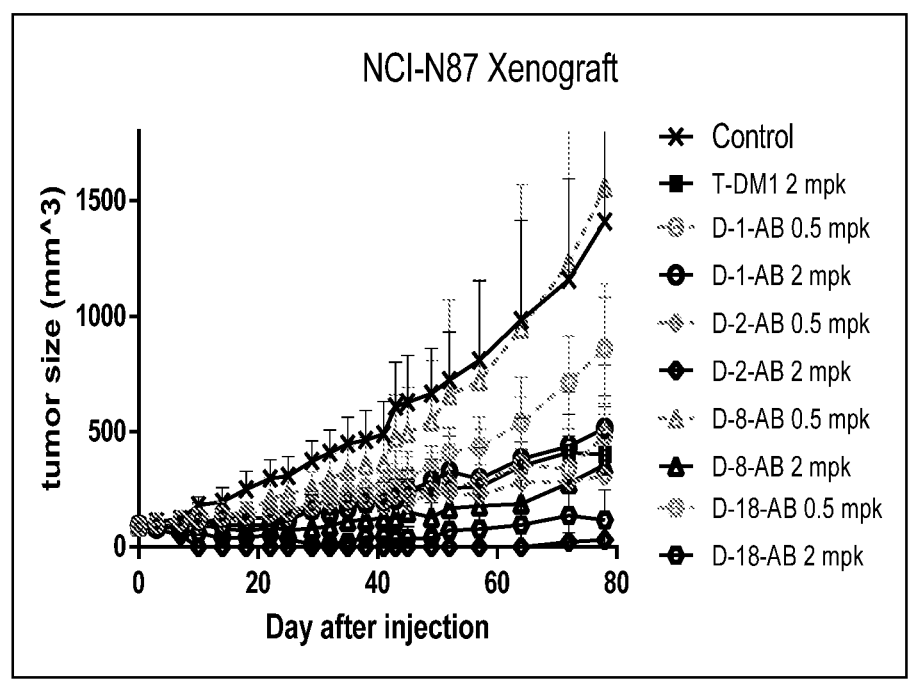
FIG. 13 shows results of in vivo test of Compound D-1-AB, D-2-AB, D-8-AB, and D-16-AB.

KB, SKBR-3, BT-474, NCI-N87 cancer cells were seeded in 96-well plates at a density of 2,000 to 8,000 cells per well in 100 µL of medium, and cultured for 24 hours. The four compounds obtained in Test Example 6 were treated by serial dilutions of 1:4 from 600 nM to 0.009 nM, the drug MMAF-OMe was treated by serial dilutions of 1:4 from 100 nM to 0.0015 nM, and the antibody drug conjugate T-DM1 was treated by serial dilutions of 1:4 from 200 nM to 0.003 nM. Experiments were performed in a similar manner to Test Example 3 to quantify living cells 96 hours later, and results are shown in Tables 4 and 5 below. Further, results of in vitro analysis of Compound D-1-AB were shown in FIG. 12.

TABLE 4

Cell cytotoxicity of protein-drug conjugate

| Compounds of present invention | KB cell $IC_{50}$(nM) |
|---|---|
| Albu-D-5 | 1.08 |
| Albu-D-6 | 0.10* |
| MMAF-OMe | 0.44(0.16*) |

TABLE 5

Cell cytotoxicity of antibody-drug conjugate

| ADCs | DAR | $IC_{50}$(nM) | | |
| | | SKBR-3 | BT-474 | NCI-N87 |
|---|---|---|---|---|
| D-1-AB | 2.0 | 0.02 | 0.10 | 0.21 |
| D-2-AB | 1.71 | 0.01 | 0.08 | 0.14 |
| D-4-AB | mix | | | 0.38 |
| D-7-AB | 0.83 | 0.074 | | |
| D-8-AB | 2.0 | | | 0.056 |
| D-9-AB | 0.99 | >500 | | |
| D-12-AB | 2.0 | | | 0.021 |
| D-13-AB | 1.95 | | | 0.138 |
| D-14-AB | 1.56 | | | 6.01 |
| D-15-AB | 1.87 | | | ~200 |
| D-16-AB | ~0.5 | | | 0.066 |
| D-18-AB | 1.91 | 0.013 | | 0.015 |
| T-DM1 | 3.5 | 0.02 | 0.18 | 0.02 |

(*T-DM1: Roche CAS number; 1018448-65-1)

[Example 144] In Vivo Efficacy

In vivo efficacy of antibody-drug conjugates of the invention was measured by tumor xenograft studies in mice. Male BALB/c nu/nu were injected subcutaneously in the right flank with suspensions of $1 \times 10^6$ of NCI-N87 cells respectively in PBS. Mice were randomized into study groups when tumors reached approximately 100 mm³. T-DM1 (2 mg/kg), D-1-AB, D-2-AB, D-8-AB, and D-18-AB conjugates (0.5 mg/kg or 2 mg/kg) were given i.v. (single injection on treatment day 0). All treatment groups consisted of 6 to 10 animals per group, and tumor size was monitored twice weekly using caliper measurement. The tumor mass was calculated as volume=(width X width X length)/2. Conjugates D-1-AB, D-2-AB, and D-8-AB led to tumor regression within the period of observation, i.e. 80 days from the initiation of the experiment. The control conjugate, T-DM1 was less active than the conjugates of the invention.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A conjugate of Formula (I'):

or a pharmaceutically acceptable salt thereof, wherein:

CB is a targeting moiety;

cb and n are each independently integers having a value of 1 to about 20;

each D-L independently is a group having the structure of Formula (I"):

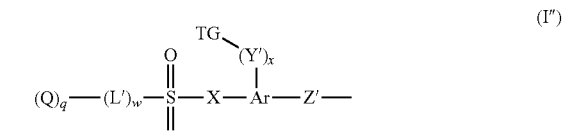

each Q is independently an active agent linked to L' by a heteroatom;

Z' is a linking group;

L' is a spacer moiety attached to the $SO_2$ via a heteroatom selected from O, S, and N, and is selected such that cleavage of the bond between L' and $SO_2$ promotes cleavage of the bond between L' and Q to release the active agent;

X is —O—, —C($R^b$)$_2$—, or —N($R^c$)—;

Ar is aryl, heteroaryl, cycloalkyl, or heterocycloalkyl;

Y' is —($CR^b_2$)$_y$N($R^a$)—, —($CR^b_2$)$_y$O—, or —($CR^b_2$)$_y$S—, positioned such that the N, O, or S atom is attached to TG if y is 1;

X and Y' are positioned on adjacent atoms of Ar;

TG is a triggering group that, when activated, generates an N, O, or S atom capable of reacting with the $SO_2$ to displace (Q)$_q$-(L')$_w$ and form a 5-6-membered ring including X—$SO_2$ and the intervening atoms of Ar;

q is an integer having a value from 1 to about 20;

w, x, and y are each independently an integer having a value of 0 or 1;
each $R^a$ and $R^c$ is independently hydrogen or lower alkyl; and
each $R^b$ is independently hydrogen or lower alkyl; or
two $R^b$, together with the atom to which they are attached, form a 3-5-membered ring;
provided that when w is 0, q is 1.

2. The conjugate of claim 1, wherein X is —O—.

3. The conjugate of claim 1, wherein Ar is aryl.

4. The conjugate of claim 1, wherein Z' is a $C_{10}$-$C_{100}$ linear or branched, saturated or unsaturated alkylene moiety comprising at least two of the following:
   (i) at least one heteroatom selected from —NH—, —C(=O), —O—, —S— and —P—;
   (ii) at least one heteroarylene;
   (iii) at least one amino acid moiety, sugar bond, peptide bond, or amide bond; and
   (iv) one or more substituents selected from the group consisting of $C_1$-$C_{20}$ alkyl, $C_6$-$C_{20}$ aryl $C_1$-$C_8$ alkyl, —$(CH_2)_s$COOH, and —$(CH_2)_p$NH_2, s is an integer having a value of 0 to 10, and p is an integer having a value of 1 to about 10.

5. The conjugate of claim 1, wherein Z' comprises:

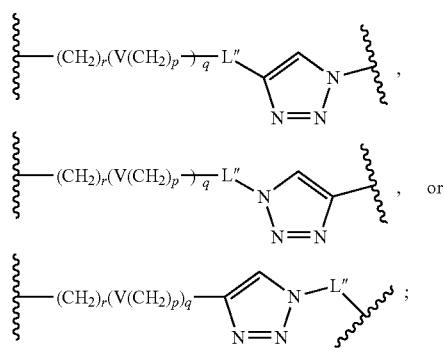

wherein:
each V is independently a single bond, —O—, —S—, —$NR^{21}$—, —C(O)$NR^{22}$—, —$NR^{23}$C(O)—, —$NR^{24}SO_2$—, or —$SO_2NR^{25}$—;
$R^{21}$, $R^{22}$, $R^{23}$, $R^{24}$, and $R^{25}$ are each independently hydrogen, $C_1$-$C_6$alkyl, $C_1$-$C_6$alkyl-$C_6$-$C_{20}$aryl, or $C_1$-$C_6$alkyl-$C_3$-$C_{20}$heteroaryl;
r is an integer having a value of 1 to about 10;
p is an integer having a value of 0 to about 10;
q is an integer having a value of 1 to about 10; and
L" is a single bond.

6. The conjugate of claim 1, wherein Z' is a linking group connecting CB and Ar comprising $(CH_2)_b$, $L^c$, $(P^1)_a$, $W^{a1}$, $W^{a2}$, $W^{a3}$, $W^{b1}$, $W^{b2}$, $Y^1$, and $Y^2$ groups connected to each other in a linear chain by covalent bonds, wherein:
$W^{a1}$, $W^{a2}$, and $W^{a3}$ are each independently —NH—, —C(O)—, or —$CH_2$—;
$W^{b1}$ is an amide bond or triazolylene;
$P^1$ is an amide bond, an amino acid residue, or a peptide;
$L^c$ is alkylene;
$Y^1$ is —$(CH_2)_q$—$(CH_2CH_2X")_o$— or —$(CH_2)_q$—$(X"CH_2CH_2X")_o$—;
X" is —O—, —S—, —NH— or —$CH_2$—;
$Y^2$ is a single bond or a group selected from:

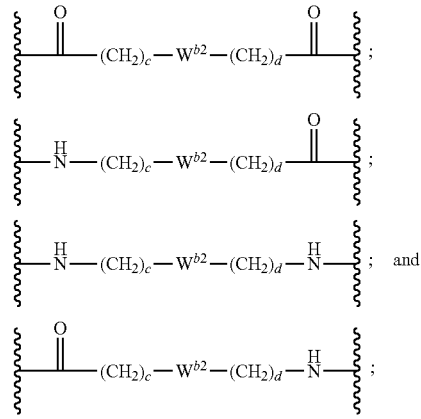

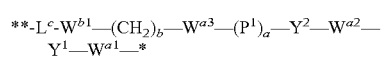

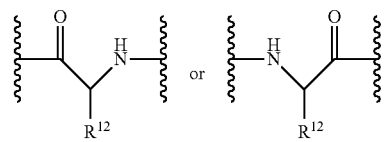

$W^{b2}$ is an amide bond or triazolylene;
a is 0 to 10;
b, c, and d are each independently an integer having a value of 1 to about 10; and
o and q are each independently an integer having a value of 1 to about 10.

7. The conjugate of claim 6, wherein Z' is a linking group of Formula (A):

$$\text{**-}L^c\text{-}W^{b1}\text{—}(CH_2)_b\text{—}W^{a3}\text{—}(P^1)_a\text{—}Y^2\text{—}W^{a2}\text{—}Y^1\text{—}W^{a1}\text{—*}  \quad (A)$$

wherein:
* is the point of attachment to CB; and
** is point of attachment to Ar.

8. The conjugate of claim 6, wherein $P^1$ is

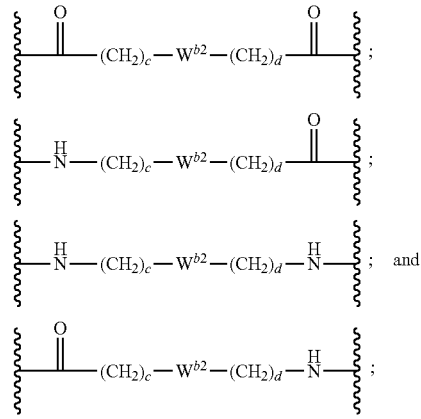

wherein:
$R^{12}$ is hydrogen, alkyl, an amino acid side chain, —$(CH_2)_sC(O)R^{13}$ or —$(CH_2)_pNR^{14}R^{15}$;
p is an integer having a value of 1 to about 10;
s is an integer having a value of 0 to about 10;
$R^{13}$ is OH or —$NH(CH_2)_{s'}(X'''CH_2CH_2)_{s''}Z''$—$(CB)_m$;
$R^{14}$ and $R^{15}$ are each independently hydrogen or —C(O)$(CH_2)_{s'}(X'''CH_2CH_2)_{s''}Z''$—$(CB)_m$;
s" is an integer having a value of 0 to about 10;
s' is an integer having a value of 1 to about 10;
m is an integer having a value of 0 or 1;
X''' is —O—, —S—, —NH—, or —$CH_2$—; and
Z" is a linking group connecting CB to the remainder of $R^{14}$ or $R^{15}$; or Z" is a linking group comprising a reactive group.

9. The conjugate of claim 6, wherein Z' is a linking group of Formula (F'), (G'), (H'), (J'), (K'), (L'), (M'), or (N'):

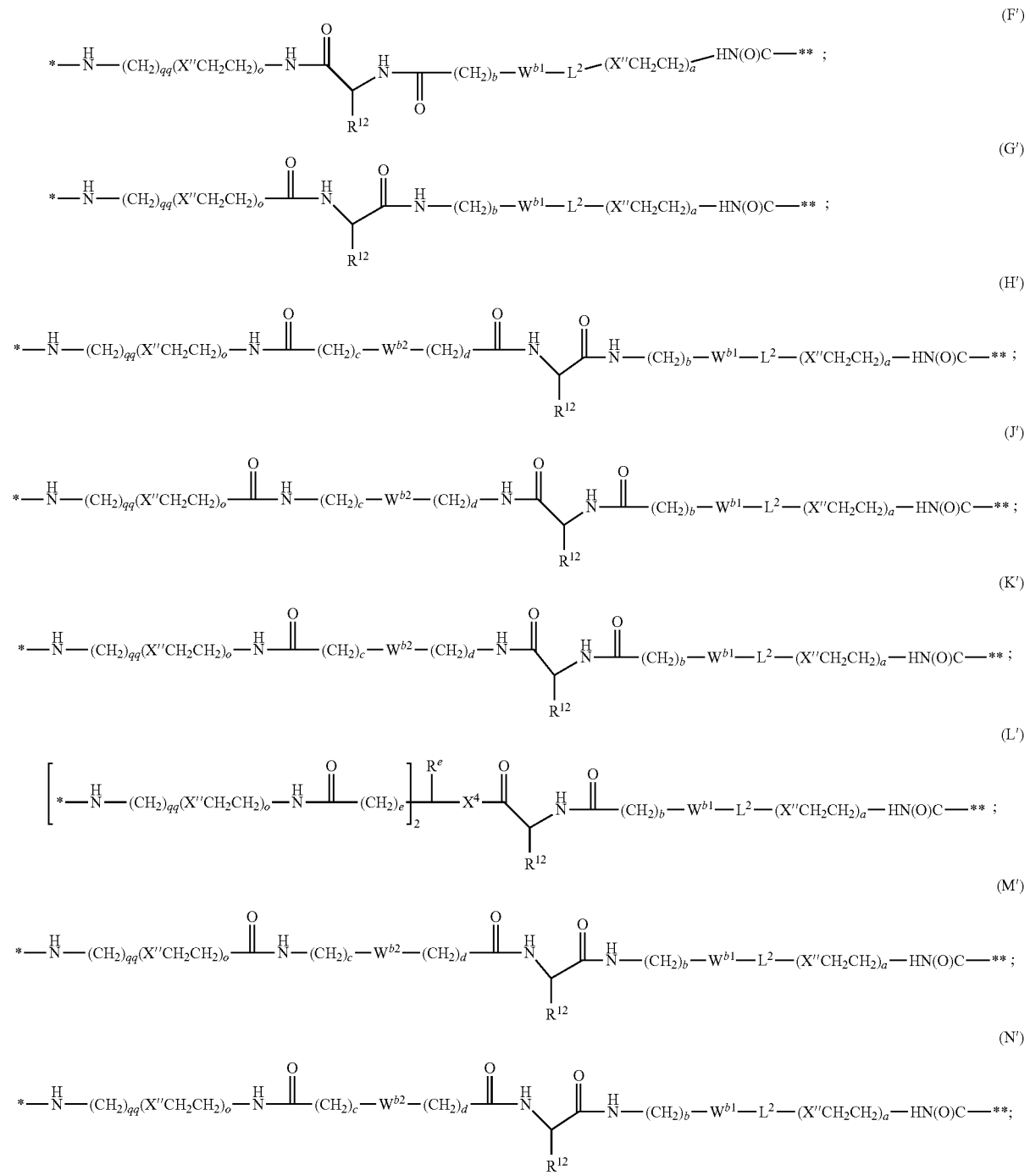

wherein:
$R^e$ is alkyl;
$L^2$ is an optionally present spacer moiety, and may be further substituted with one or more substituents, such as $C_1$-$C_6$ alkyl, $C_5$-$C_{14}$ aryl, and $C_3$-$C_8$ heteroaryl, wherein the alkyl, aryl and heteroaryl are unsubstituted or substituted with one or more substituents selected from $C_1$-$C_{10}$ alkyl, —$(CH_2)_u NH_2$, —$(CH_2)_u NR^{u1} R^{u2}$, —$(CH_2)_u CO_2 H$, —$(CH_2)_u CO_2 R^{u1}$, and —$(CH_2)_u SO_2 R^{u3}$, wherein $R^{u1}$, $R^{u2}$ and $R^{u3}$ are each independently hydrogen, $C_1$-$C_{15}$ alkyl, $C_6$-$C_{20}$ aryl or $C_3$-$C_{10}$ heteroaryl; and u is an integer having a value of 1 to 10;

X" is —O—, —S—, —NH—, or —$CH_2$—;

$X^4$ is —NHC(O)—$(CH_2)_g$—NH— or —C(O)NH—$(CH_2)_h$—NH—;

$W^{b1}$ and $W^{b2}$ are each independently —C(O)NH—, —NHC(O)—,

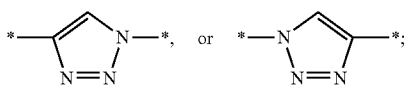

$R^{12}$ is hydrogen, alkyl, an amino acid side chain, —(CH$_2$)$_s$C(O)R$^{13}$ or —(CH$_2$)$_p$NR$^{14}$R$^{15}$;

$R^{13}$ is OH or —NH(CH$_2$)$_s$(X'''CH$_2$CH$_2$)$_{s''}$Z''—(CB)$_m$;

$R^{14}$ and $R^{15}$ are each independently hydrogen or —C(O)(CH$_2$)$_s$(X'''CH$_2$CH$_2$)$_{s''}$Z''—(CB)$_m$;

s and s'' are each independently an integer having a value of 0 to about 10;

m is an integer having a value of 0 or 1;

X''' is —O—, —S—, —NH—, or —CH$_2$—; and

Z'' is a linking group connecting CB to the remainder of $R^{14}$ or $R^5$; or Z'' is a linking group comprising a reactive group; and a, b, c, d, e, g, h, o, p, and qq are each independently an integer having a value of 1 to about 10; and s' is an integer having a value of 1 to about 10.

10. The conjugate of claim 1, wherein TG is a reactive chemical moiety or functional group that can be cleaved by nucleophilic reagent conditions, basic reagent conditions, photo-irradiation, reducing agent conditions, acidic conditions, enzymatic conditions, or oxidative conditions.

11. The conjugate of claim 1, wherein TG is selected from:

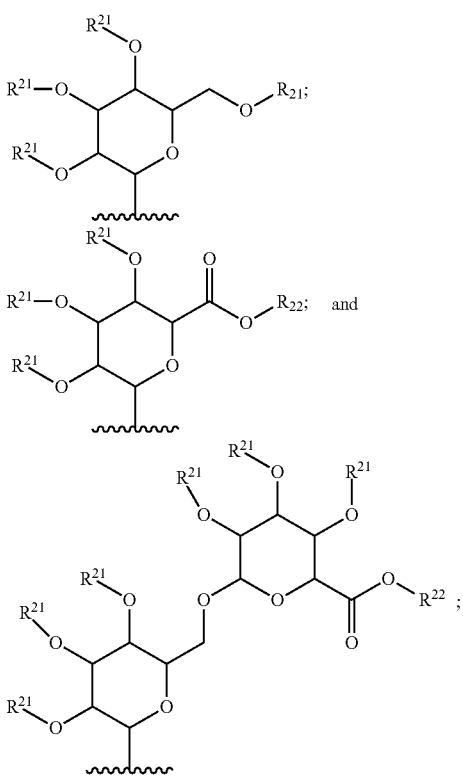

wherein:
each $R^{21}$ is independently hydrogen or acetyl; and
$R^{22}$ is hydrogen or lower alkyl.

12. The conjugate of claim 1, wherein x is 0.

13. The conjugate of claim 12, wherein TG is selected from —NO$_2$, —C(O)—(CH$_2$)$_2$C(O)-alkyl, and nitrobenzyl.

14. The conjugate of claim 1, wherein Q is a chemical factor, a biological factor, a hormone, an oligonucleotide, a toxin, an affinity ligand, a probe for detection, a drug selected from a cytokine, an immunomodulatory compound, an anti-cancer agent, an anti-viral agent, an anti-bacterial agent, an anti-fungal agent, an anthelmintic agent, or a combination thereof.

15. The conjugate of claim 1, wherein (Q)$_q$-(L')$_w$- is selected from:

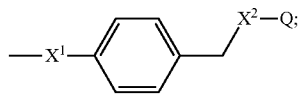

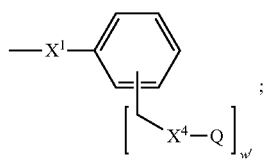

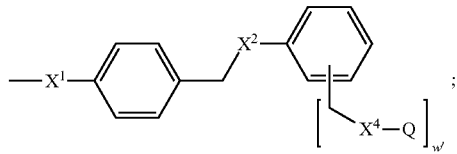

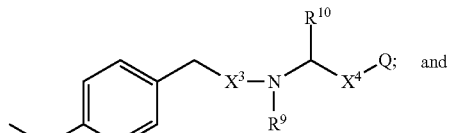

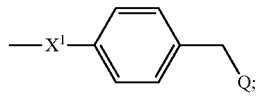

wherein:

$X^1$ is —O— or —NR$^a$—;

$X^2$ and $X^4$ are each independently absent or —C(O)—, or —C(O)O—;

$X^3$ is —OC(=O)—;

w' is an integer having a value of 1, 2, 3, 4, or 5;

$R^9$ and $R^{10}$ are each independently hydrogen, alkyl, aryl, or heteroaryl, wherein alkyl, aryl, and heteroaryl are unsubstituted or substituted with one or more substituents, e.g., selected from alkyl, —(CH$_2$)$_u$NH$_2$, —(CH$_2$)$_u$NR$^{u1}$R$^{u2}$, and —(CH$_2$)$_u$SO$_2$R$^{u3}$;

$R^{u1}$, $R^{u2}$, and $R^{u3}$ are each independently hydrogen, alkyl, aryl, or heteroaryl; and u is an integer having a value of 1 to about 10.

16. The conjugate of claim 15, wherein $(Q)_q\text{-}(L')_w\text{-}$ is selected from:
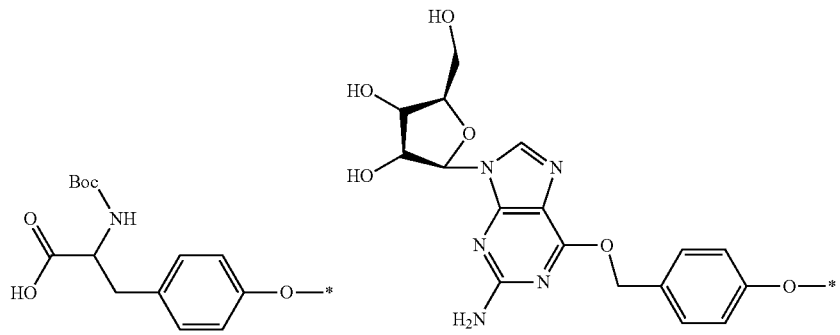
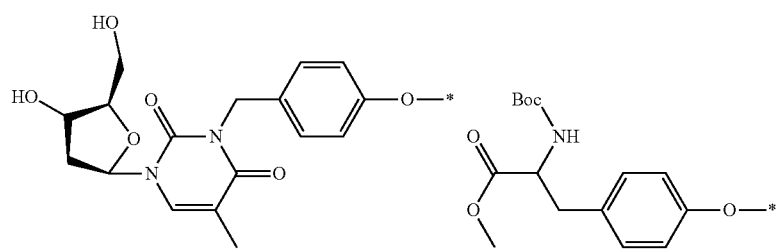
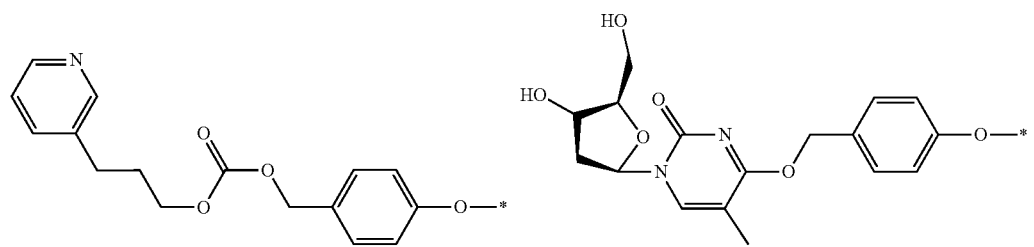
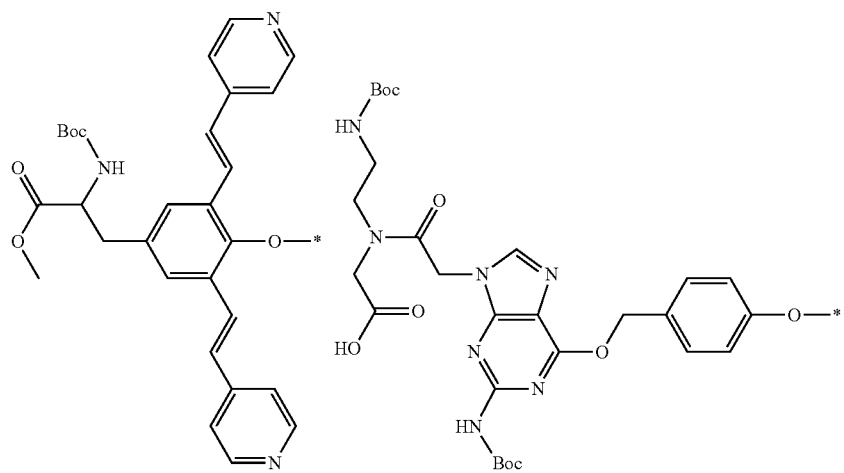
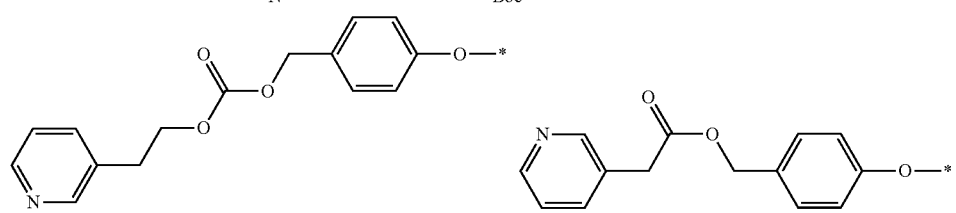

-continued
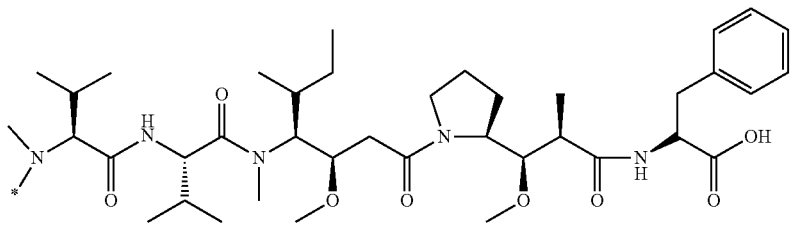
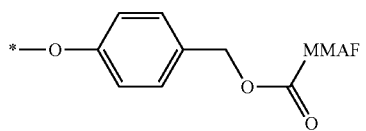
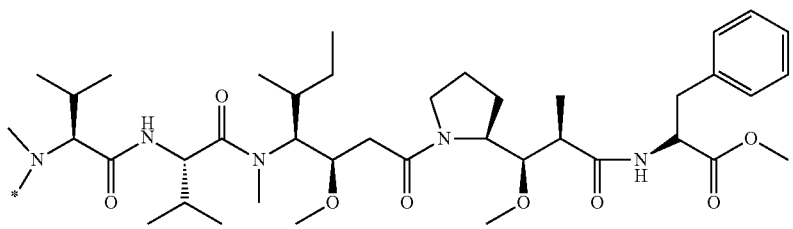
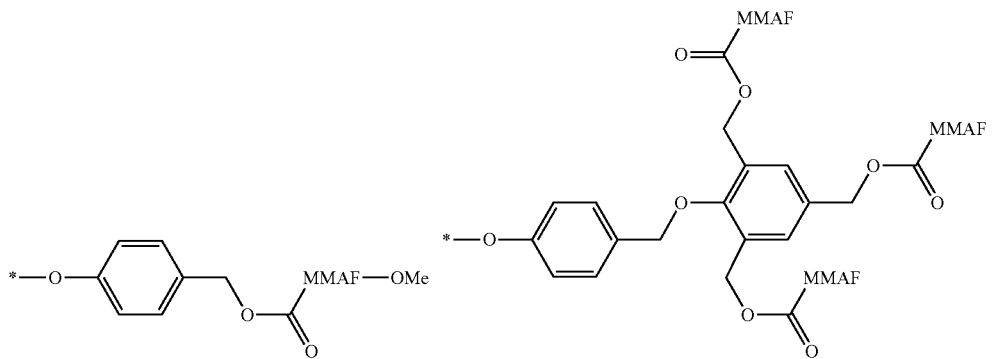
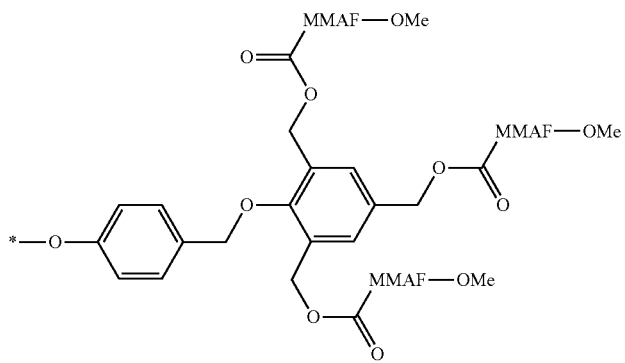

401
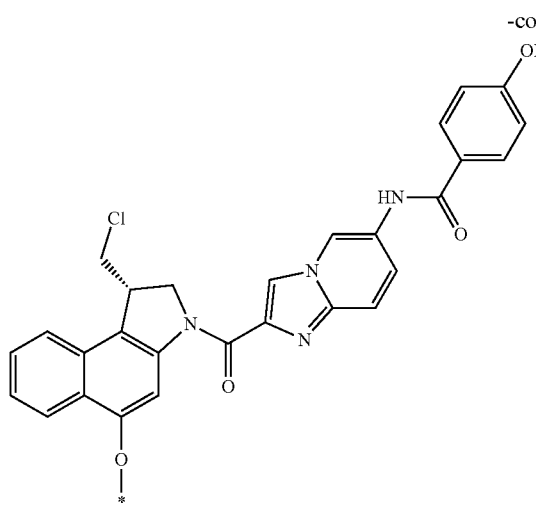
402
-continued
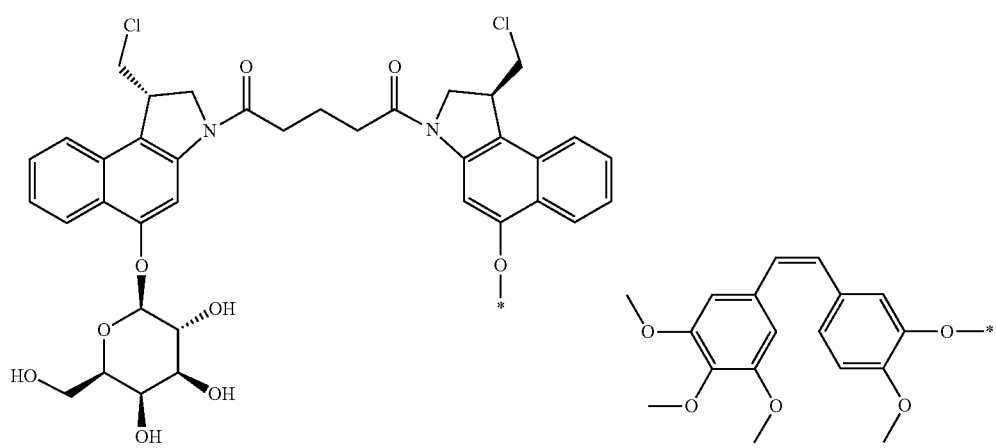
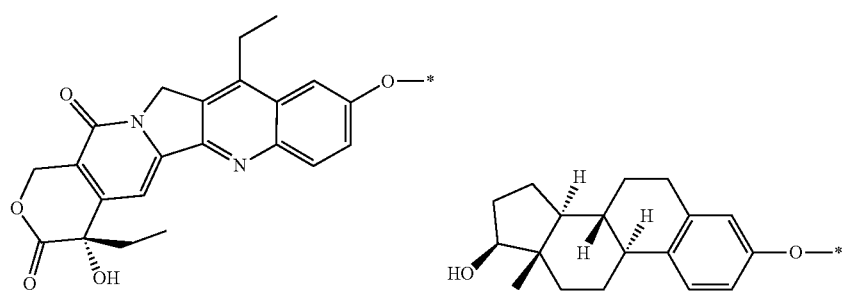

-continued
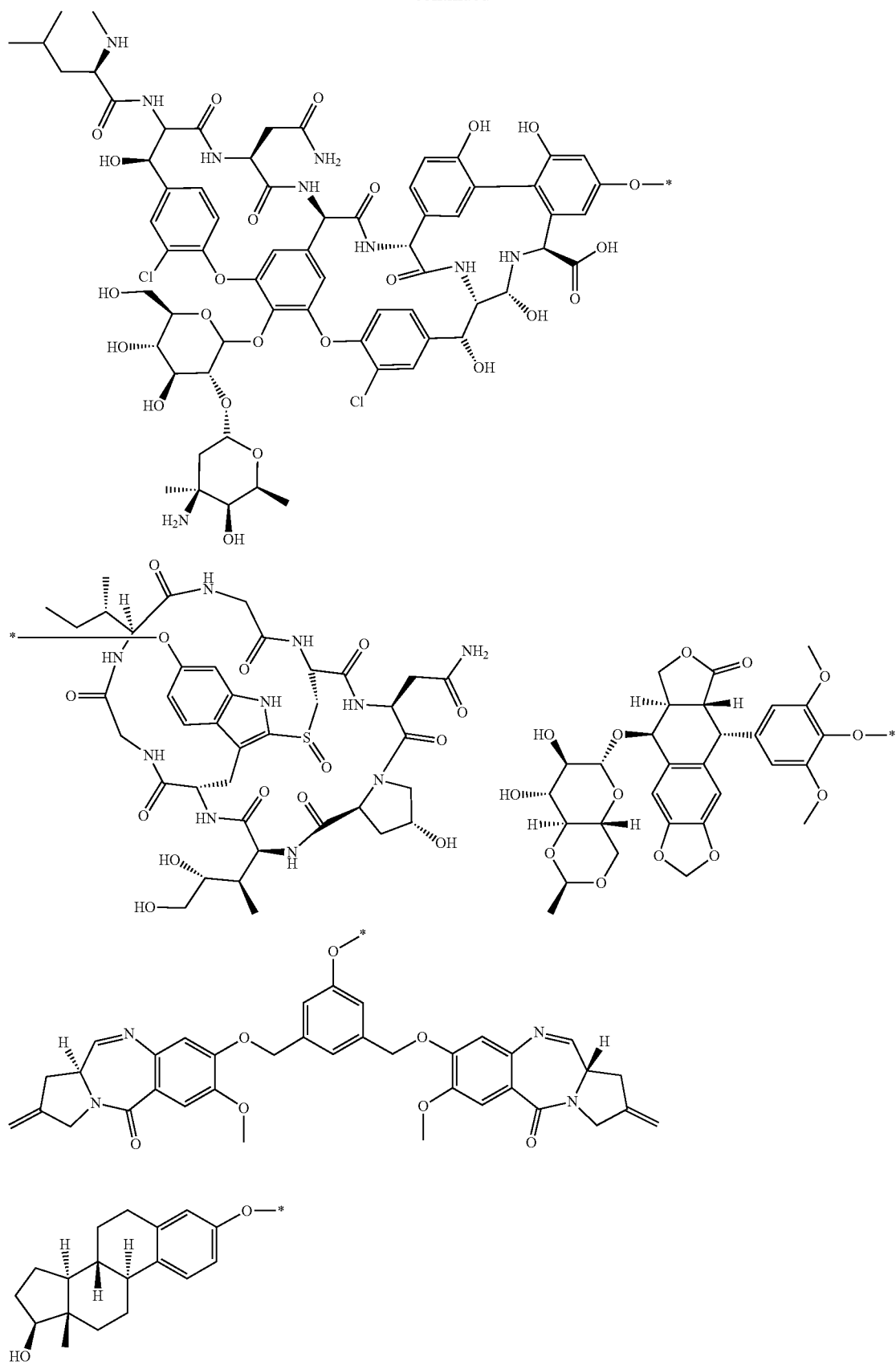

405 406
-continued
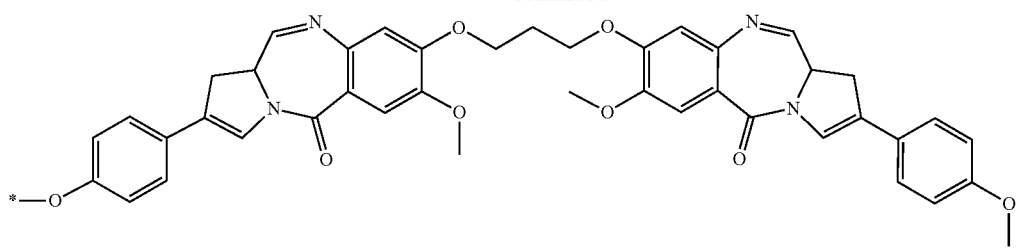
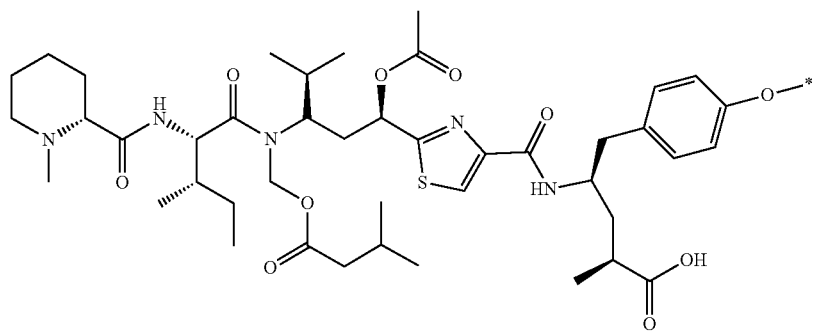
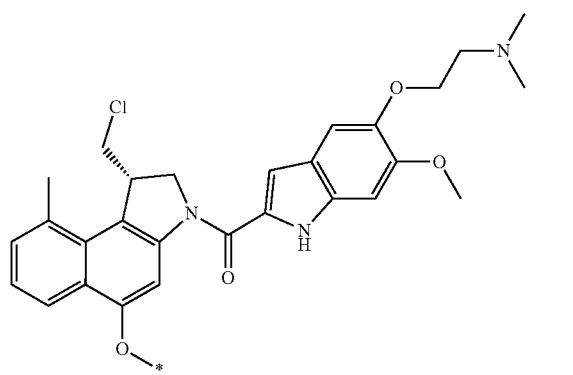
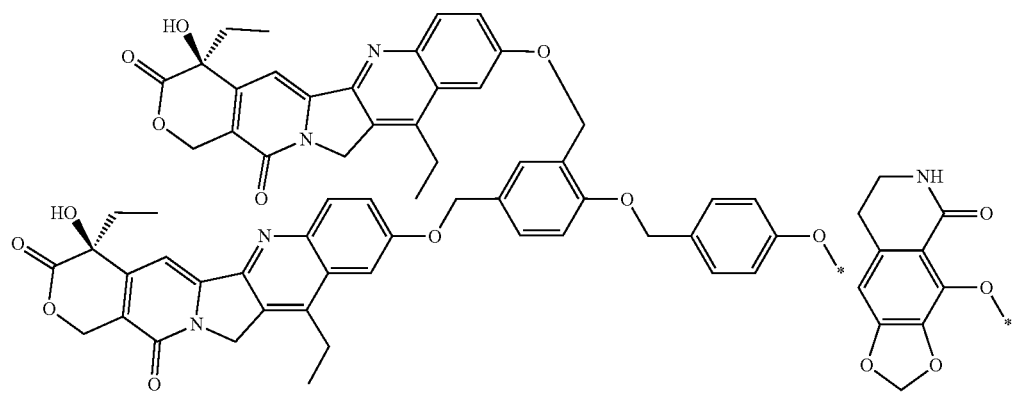
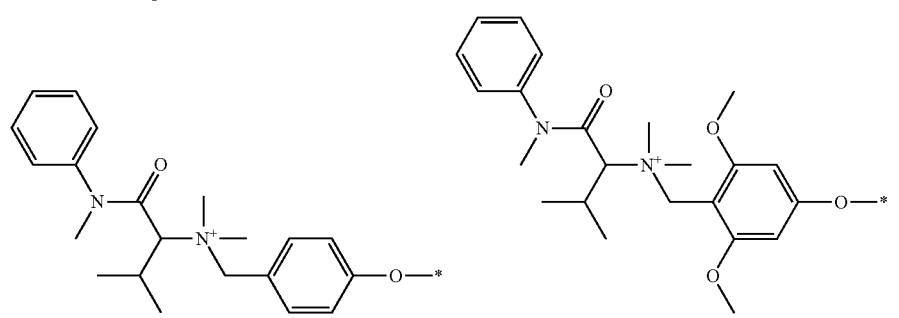

407 408
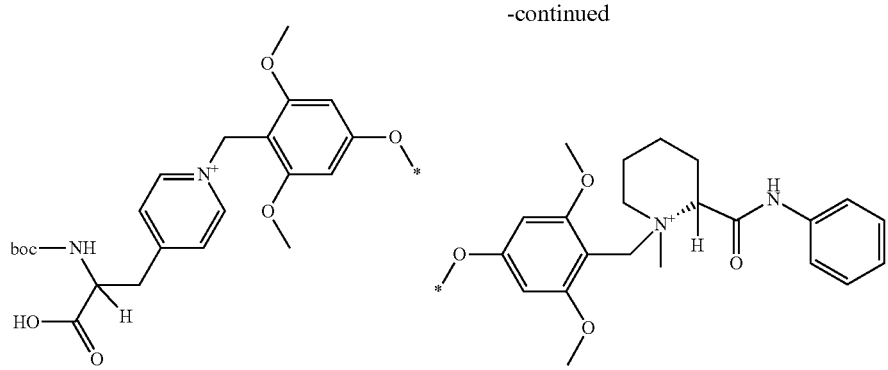
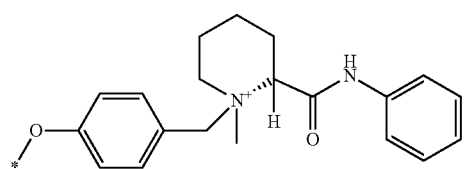
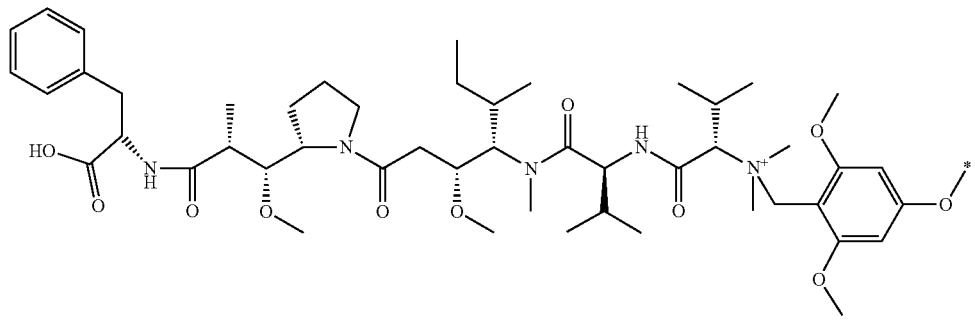
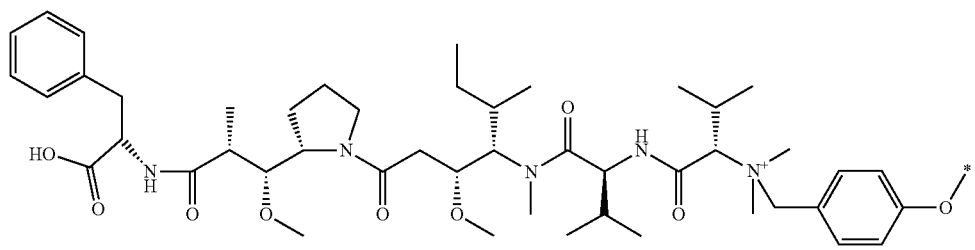
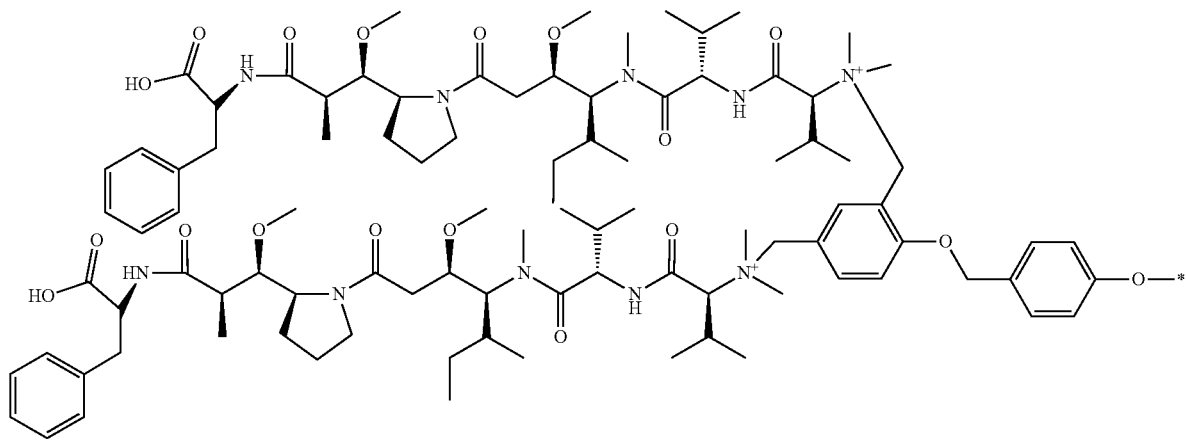

409
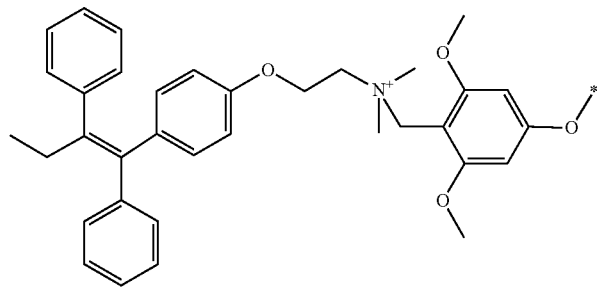
410
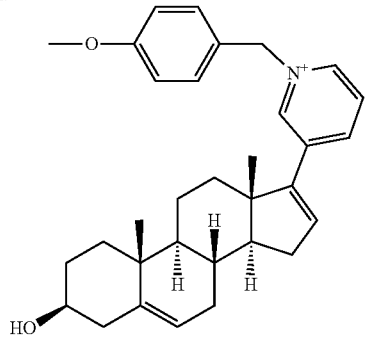
-continued
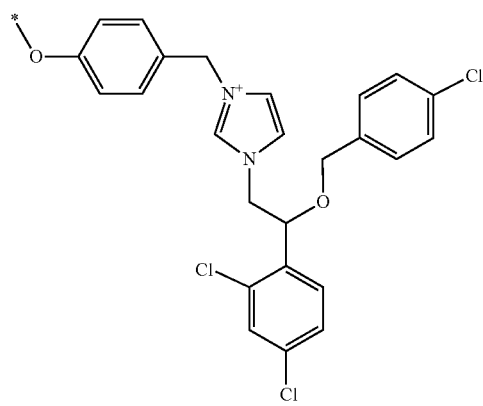
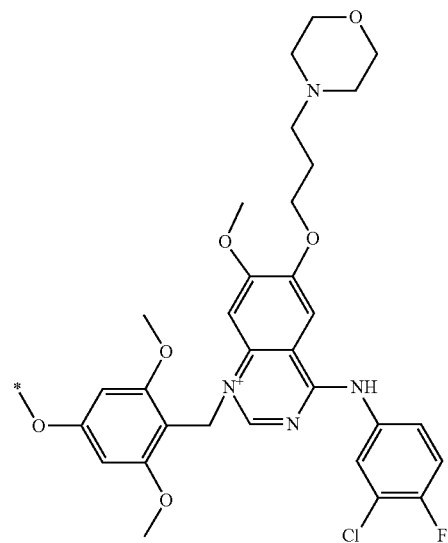
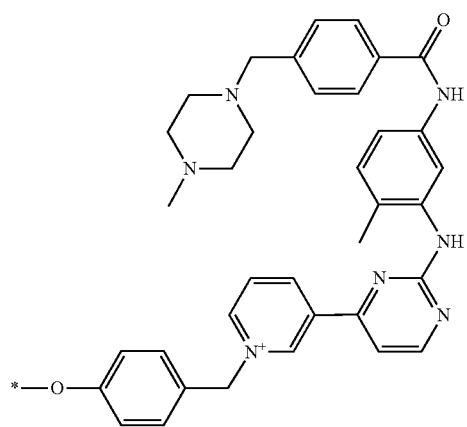

-continued

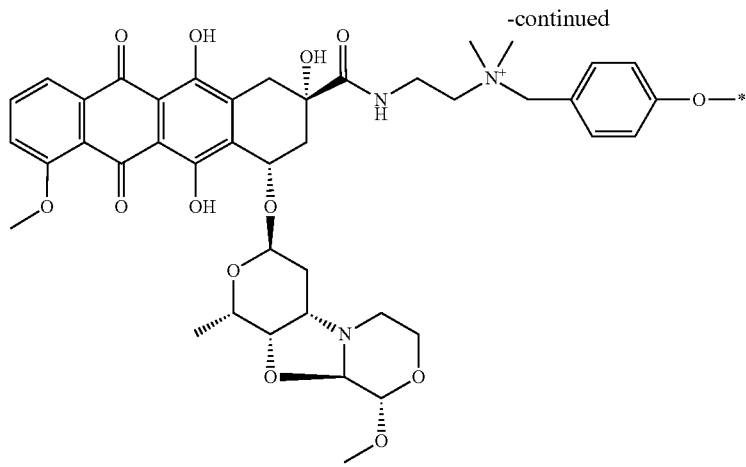

wherein * represents the point of attachment of $(Q)_q$-$(L')_w$ to —SO$_2$—.

17. The conjugate of claim 1, wherein the targeting moiety is a nanoparticle, an immunoglobulin, a nucleic acid, a protein, an oligopeptide, a polypeptide, an antibody, a fragment of an antigenic polypeptide, or a repebody.

18. A pharmaceutical composition comprising a conjugate of claim 1 and a pharmaceutically acceptable carrier or excipient.

19. An imaging composition comprising a conjugate of claim 1.

20. A sensor compound comprising a conjugate of claim 1.

* * * * *

UNITED STATES PATENT AND TRADEMARK OFFICE
CERTIFICATE OF CORRECTION

| | |
|---|---|
| PATENT NO. | : 11,753,431 B2 |
| APPLICATION NO. | : 16/628482 |
| DATED | : September 12, 2023 |
| INVENTOR(S) | : Taekyo Park et al. |

It is certified that error appears in the above-identified patent and that said Letters Patent is hereby corrected as shown below:

In the Specification

At Column 35, Line 21, cancel the text "Also provided herein are compounds of Formula (I):".

At Column 35, Line 24, cancel the text "(I)".

At Column 36, Line 21, cancel the text "-continued".

Signed and Sealed this
Nineteenth Day of November, 2024

Katherine Kelly Vidal
*Director of the United States Patent and Trademark Office*